US010183933B2

(12) United States Patent
Aronov et al.

(10) Patent No.: US 10,183,933 B2
(45) Date of Patent: *Jan. 22, 2019

(54) ISOINDOLINONE INHIBITORS OF PHOSPHATIDYLINOSITOL 3-KINASE

(71) Applicant: Vertex Pharmaceuticals Incorporated, Cambridge, MA (US)

(72) Inventors: Alex Aronov, Newton, MA (US); Jon H. Come, Cambridge, MA (US); Robert J. Davies, Watertown, MA (US); Albert Charles Pierce, Cambridge, MA (US); Philip N. Collier, Cambridge, MA (US); Ronald Lee Grey, Mansfield, MA (US); Hardwin O'Dowd, Boston, MA (US); James A. Henderson, Cambridge, MA (US); Elaine B. Krueger, Cambridge, MA (US); Anne-Laure Grillot, Milton, MA (US); Arnaud Le Tiran, Croissy sur Seine (FR); Yusheng Liao, Lexington, MA (US); David Messersmith, Somerville, MA (US); Jian Wang, Newton, MA (US); Jingrong Cao, Newton, MA (US); Upul Keerthi Bandarage, Lexington, MA (US); Suganthini S. Nanthakumar, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/603,145

(22) Filed: May 23, 2017

(65) Prior Publication Data

US 2017/0260175 A1  Sep. 14, 2017

Related U.S. Application Data

(60) Division of application No. 13/888,960, filed on May 7, 2013, now Pat. No. 9,676,759, which is a continuation of application No. 13/334,868, filed on Jan. 13, 2012, now Pat. No. 8,466,288, which is a continuation of application No. PCT/US2010/061484, filed on Dec. 21, 2010.

(60) Provisional application No. 61/387,582, filed on Sep. 29, 2010, provisional application No. 61/369,201, filed on Jul. 30, 2010, provisional application No. 61/350,631, filed on Jun. 2, 2010, provisional application No. 61/289,003, filed on Dec. 22, 2009.

(51) Int. Cl.
| | | |
|---|---|---|
| C07D 471/02 | (2006.01) |
| C07D 213/04 | (2006.01) |
| C07D 401/00 | (2006.01) |
| C07D 401/02 | (2006.01) |
| C12N 9/99 | (2006.01) |
| A61K 31/437 | (2006.01) |
| C07D 409/14 | (2006.01) |
| C07D 401/04 | (2006.01) |
| C07D 401/14 | (2006.01) |
| C07D 405/14 | (2006.01) |
| C07D 417/14 | (2006.01) |
| C07D 471/04 | (2006.01) |
| C07D 471/20 | (2006.01) |
| C07D 491/20 | (2006.01) |

(52) U.S. Cl.
CPC ........ *C07D 409/14* (2013.01); *C07D 401/04* (2013.01); *C07D 401/14* (2013.01); *C07D 405/14* (2013.01); *C07D 417/14* (2013.01); *C07D 471/04* (2013.01); *C07D 471/20* (2013.01); *C07D 491/20* (2013.01)

(58) Field of Classification Search
None
See application file for complete search history.

(56) References Cited

U.S. PATENT DOCUMENTS 8,466,288 B2   6/2013  Aronov et al.

FOREIGN PATENT DOCUMENTS

| JP | 57134467 | 8/1982 |
|---|---|---|
| WO | 2004108672 A1 | 12/2004 |
| WO | 2006020879 A1 | 2/2006 |
| WO | 2006095159 | 9/2006 |
| WO | 2007000339 A1 | 1/2007 |
| WO | 2007095024 A1 | 8/2007 |
| WO | 2007109211 A2 | 9/2007 |
| WO | 2011087776 A1 | 7/2011 |

OTHER PUBLICATIONS

Organic Chemistry, Thomas Sorrell, University Science Books, Sausalito, 1999.
March's Advanced Organic Chemistry, 5th Ed., Smith, M.B. and March, J., eds. John Wiley & Sons, New York, 2001.
Green and Wuts, Protective Groups in Organic Synthesis, 3rd Ed., John Wiley & Sons, New York, 1999.

(Continued)

*Primary Examiner* — Marcos L Sznaidman
*Assistant Examiner* — Rayna Rodriguez
(74) *Attorney, Agent, or Firm* — Bryan Cave Leighton Paisner LLP

(57) ABSTRACT

The present invention relates to compounds useful as inhibitors of PI3K, particularly of PI3Kγ. The invention also provides pharmaceutically acceptable compositions comprising said compounds and methods of using the compositions in the treatment of various disease, conditions, or disorders.

10 Claims, No Drawings

(56) References Cited

OTHER PUBLICATIONS

Higuchi, T. et al., Pro-drugs as Novel Delivery Systems, vol. 14 of the A.C.S. Symposium Series, Edward B. Roche, ed., Bioreversible Carriers in Drug Design, American Pharmaceutical Association and Pergamon Press, 1987.
Judkins, B.D., et al, Synthetic Communications, A Versatile Synthesis of Amidines from Nitriles Via Amidoximes, 26 (23); 4351-4367, 1996.
Berge, S.M., et al., J. Pharmaceutical Sciences, 66:1-19, 1977.
In Remington, The Science and Practice of Pharmacy, 21st edition, 2005, ed. D.B. Troy, Lippincott Wiliams & Wilkins, Philadelphia.
Encyclopedia of Pharmaceutical Technology, eds., J. Swarbrick and J.C. Boyland, 1988-1999, Marcel Dekker, New York.
Jin, et al., 2010, Biochemical and Biophysical Research Communications, 399: 458-464.
Boronic Acids, ISBN: 3-527-3991-8, Wiley-VCH, 2005, Dennis G. Hall, editor.
Hurst, J., 2-Bromomethylnicotinates: reaction with Nucleophilic Reagents, J. Chem. Soc. 1962, pp. 119-122.
Morrison, J.F., Stone, S.R., (1985), Comments Mol. Cell Biophys., vol. 2: 347-368, 1985.
M. Oki, S. Shimada: "Reaction of 1,2,4-Triazines with N-Phenylmaleimide", Chem. Pharm. Bull., vol. 35, No. 12, 1987, pp. 4705-4710.
HCAPLUS 2005: 115450, Preparation of 2-(1-azabicyclo [2.2.2] OCT-3-yl)-2,3-dihydro indol-1-one and 5-(1-aza bicycle [2.2.2]Oct-3-yl)-5.6-dihydro-furo [2,3-c]pyrrol-4-one derivatives for Thereapeutic use as ligands for the alpha nicotinic Acetyl choline receptor (alpha 7 nAChR), 2005.

ISOINDOLINONE INHIBITORS OF PHOSPHATIDYLINOSITOL 3-KINASE

CROSS-REFERENCE TO RELATED APPLICATIONS

The present application is a divisional application of U.S. application Ser. No. 13/888,960, filed May 7, 2013, which is a continuation of U.S. application Ser. No. 13/349,868, filed on Jan. 13, 2012, which is a continuation of International Patent Application No. PCT/US2010/061484, filed on Dec. 21, 2010, and claims the benefit, under 35 U.S.C. § 120, to U.S. Provisional Application Ser. No. 61/289,003, filed Dec. 22, 2009, U.S. Provisional Application Ser. No. 61/350,631, filed Jun. 2, 2010, U.S. Provisional Application Ser. No. 61/369,201, filed Jul. 30, 2010, and U.S. Provisional Application Ser. No. 61/387,582, filed Sep. 29, 2010; all of which are incorporated by reference in their entireties as if recited in full herein.

TECHNICAL FIELD OF THE INVENTION

The present invention relates to compounds useful as inhibitors of phosphatidylinositol 3-kinase (PI3K). The invention also provides pharmaceutically acceptable compositions comprising the compounds of the invention and methods of using the compositions in the treatment of various disorders.

BACKGROUND OF THE INVENTION

PI3Ks are a family of lipid kinases that catalyze the phosphorylation of the membrane lipid phosphatidylinositol (PI) on the 3'-OH of the inositol ring to produce PI 3-phosphate [PI(3)P, PIP], PI 3,4-bisphosphate [PI(3,4)$P_2$, PIP2] and PI 3,4,5-trisphosphate [PI(3,4,5)$P_3$, PIP3]. PI(3,4)$P_2$ and PI(3,4,5)$P_3$ act as recruitment sites for various intracellular signaling proteins, which in turn form signaling complexes to relay extracellular signals to the cytoplasmic face of the plasma membrane.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain-containing p85 adapter subunit. Class Ia PI3Ks are activated through tyrosine kinase signaling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p101 regulatory subunit. PI3Kγ is regulated by G protein-coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

Although a number of PI3K inhibitors have been developed, there is a need for additional compounds to inhibit PI3Ks for treating various disorders and diseases, especially those affecting the central nervous system (CNS). Accordingly, it would be desirable to develop additional compounds that are useful as inhibitors of PI3K that penetrate the blood-brain barrier (BBB).

SUMMARY OF THE INVENTION

It has been found that compounds of this invention, and pharmaceutically acceptable compositions thereof, are effective as inhibitors of PI3K, particularly PI3Kγ. Accordingly, the invention features compounds having the general formula:

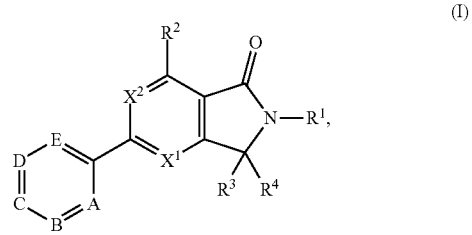

or a pharmaceutically acceptable salt thereof, where each of A, B, C, D, E, $X^1$, $X^2$, $R^1$, $R^2$, $R^3$, and $R^4$ is as defined herein.

The invention also provides pharmaceutical compositions that include a compound of formula I and a pharmaceutically acceptable carrier, adjuvant, or vehicle. These compounds and pharmaceutical compositions are useful for treating or lessening the severity of a variety of disorders, including autoimmune diseases and inflammatory diseases of the CNS.

The compounds and compositions provided by this invention are also useful for the study of PI3K in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

Compounds that have been drawn with stereochemical centers defined are stereochemically pure, but with the absolute stereochemistry still undefined. Such compounds can have either the R or S configuration. In those cases where such an absolute assignment has been determined, the chiral center(s) will be labeled R or S in the drawing.

As described herein, compounds of the invention may optionally be substituted with one or more substituents, such as are illustrated generally above, or as exemplified by particular classes, subclasses, and species of the invention. It will be appreciated that the phrase "optionally substituted"

is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 3 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 3 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl or heteroaryl group include: halogen; $C_{1-4}$aliphatic, —OH; —OR°; —SH°; —SR°; 1,2-methylenedioxy; 1,2-ethylenedioxy; phenyl (Ph); —O(Ph); —$(CH_2)_{1-2}$(Ph); —CH═CH(Ph); —$NO_2$; —CN; —$NH_2$; —NH(R°); —N(R°)$_2$; —NHC(O)R°; —NR°C(O)R°; —NHC(S)R°; —NR°C(S)R°; —NHC(O)$NH_2$; —NHC(O)NH(R°); —NHC(O)N(R°)$_2$; —NR°C(O)NH(R°); —NR°C(O)N(R°)$_2$; —NHC(S)$NH_2$; —NHC(S)N(R°)$_2$; —NHC(S)NH(R°); —NR°C(S)NH(R°); —NR°C(S)N(R°)$_2$; —NHC(O)OR°; —NR°C(O)OR°; —C(O)OH; —C(O)OR°; —C(S)R°; —C(O)$NH_2$; —C(O)NH(R°); —C(O)N(R°)$_2$; —C(S)$NH_2$; —C(S)NH(R°); —C(S)N(R°)$_2$; —OC(O)$NH_2$; —OC(O)NH(R°); —OC(O)N(R°)$_2$; —OC(O)R°; —C(NOR°)H; —C(NOR°)R°; —S(O)$_2$R°; —S(O)$_3$R°; —S(O)$_3$H; —S(O)$_2$$NH_2$; —S(O)$_2$NH(R°); —S(O)$_2$N(R°)$_2$; —S(O)R°; —NHS(O)$_2$R°; —NR°S(O)$_2$R°; —N(OR°)R°; —$(CH_2)_{0-2}$NHC(O)R°; -L-R°; -L-N(R°)$_2$; -L-SR°; -L-OR°; -L-($C_{3-10}$ cycloaliphatic), -L-($C_{6-10}$ aryl), -L-(5-10 membered heteroaryl), -L-(5-10 membered heterocyclyl), oxo, $C_{1-4}$ haloalkoxy, $C_{1-4}$ haloalkyl, -L-$NO_2$, -L-CN, -L-OH, -L-$CF_3$; or two substituents, on the same carbon or on different carbons, together with the carbon or intervening carbons to which they are bound, form a 5-7 membered saturated, unsaturated, or partially saturated ring, wherein L is a $C_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(═N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each occurrence of R° is independently selected from optionally substituted $C_{1-6}$ aliphatic, an unsubstituted 5 to 6 membered heteroaryl or heterocyclic ring, phenyl, or —$CH_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Non-limiting optional substituents on the aliphatic group of R° include —$NH_2$, —NH($C_{1-4}$ aliphatic), —N($C_{1-4}$ aliphatic)$_2$, halogen, $C_{1-4}$ aliphatic, —OH, —O($C_{1-4}$ aliphatic), —$NO_2$, —CN, —C(O)OH, —C(O)O($C_{1-4}$ aliphatic), —O(halo$C_{1-4}$ aliphatic), or halo$C_{1-4}$ aliphatic, wherein each of the foregoing $C_{1-4}$ aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHC(O)O (alkyl), ═NNHS(O)$_2$(alkyl), or ═NR*, where each R* is independently selected from hydrogen or an optionally substituted $C_{1-8}$ aliphatic. Optional substituents on the aliphatic group of R* are selected from —$NH_2$, —NH($C_{1-4}$ aliphatic), —N($C_{1-4}$ aliphatic)$_2$, halogen, $C_{1-4}$ aliphatic, —OH, —O($C_{1-4}$ aliphatic), —$NO_2$, —CN, —C(O)OH, —C(O)O($C_{1-4}$ aliphatic), —C(O)$NH_2$, —C(O)NH($C_{1-4}$ aliphatic), —C(O)N($C_{1-4}$ aliphatic)$_2$, —O(halo-$C_{1-4}$ aliphatic), and halo($C_{1-4}$ aliphatic), where each of the foregoing $C_{1-4}$ aliphatic groups of R* is unsubstituted; or two R* on the same nitrogen are taken together with the nitrogen to form a 5-8 membered heterocyclyl or heteroaryl ring having 1-3 heteroatoms independently selected from nitrogen, oxygen, and sulfur.

In some embodiments, optional substituents on the nitrogen of a non-aromatic heterocyclic ring include —R$^+$, —N(R$^+$)$_2$, —C(O)R$^+$, —C(O)OR$^+$, —C(O)C(O)R$^+$, —C(O)$CH_2$C(O)R$^+$, —S(O)$_2$R$^+$, —S(O)$_2$N(R$^+$)$_2$, —C(═S)N(R$^+$)$_2$, —C(═NH)—N(R$^+$)$_2$, or —NR$^+$S(O)$_2$R$^+$; wherein R$^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH═CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from —$NH_2$, —NH($C_{1-4}$ aliphatic), —N($C_{1-4}$ aliphatic)$_2$, halogen, $C_{1-4}$ aliphatic, —OH, —O($C_{1-4}$ aliphatic), —$NO_2$, —CN, —C(O)OH, —C(O)O ($C_{1-4}$ aliphatic), —O(halo($C_{1-4}$ aliphatic)), or halo($C_{1-4}$ aliphatic), wherein each of the foregoing $C_{1-4}$ aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

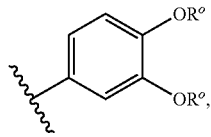

these two occurrences of R° are taken together with the oxygen atoms to which they are bound to form a fused 6-membered oxygen containing ring:

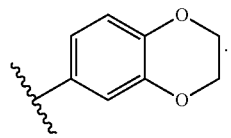 [SMILES: *c1ccc2c(c1)OCCO2]

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)$_2$NR°—, —NR°S(O)$_2$—, —NR°C(O)NR°—, —OC(O)NR°—, —NR°S(O)$_2$NR°—, —S(O)—, or —S(O)$_2$—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

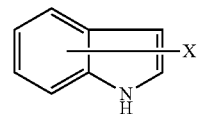

Structure a

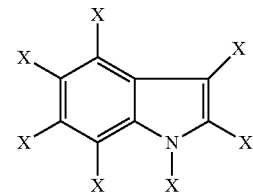

Structure b

This also applies to multiple ring systems fused to optional ring systems (which would be represented by dotted lines). For example, in Structure c, X is an optional substituent both for ring A and ring B.

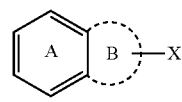

Structure c

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

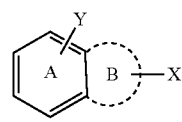

Structure d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4- dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in biological assays, or as PI3K inhibitors with improved therapeutic profile.

Description of Compounds of the Invention

In one aspect, the invention features compounds having formula I:

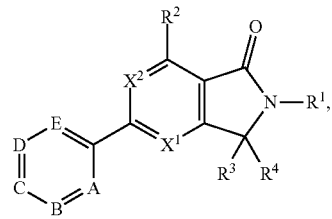

or a pharmaceutically acceptable salt thereof, wherein:
$X^1$ is N or CH;
$X^2$ is N, CH, or C—CH$_3$;
$R^1$ is selected from a phenyl ring, a 5-6 membered heteroaryl ring, a pyridone ring, or a 9-10 membered fused bicyclic heteroaryl or heterocyclic ring system wherein each of said rings or ring systems is optionally substituted with 1 or 2 independent occurrences of $R^{1a}$ and each of said heteroaryl or heterocyclic rings has 1, 2, or 3 heteroatoms selected from nitrogen, oxygen, or sulfur;
$R^{1a}$ is chloro, fluoro, $C_{1-8}$aliphatic, —(CH$_2$)$_{0-2}$C$_{3-6}$cycloaliphatic, —(CH$_2$)$_{0-2}$-5-6 membered heterocyclic having up to two heteroatoms selected from nitrogen, oxygen, or sulfur, —CN, —C(O)C$_{1-4}$aliphatic, —C(O)NH(C$_{1-4}$aliphatic), —C(O)N(C$_{1-4}$aliphatic)$_2$, —C(O)OC$_{1-4}$aliphatic, —S(O)$_2$NH(C$_{1-4}$aliphatic), —S(O)$_2$N(C$_{1-4}$aliphatic)$_2$, or —S(O)$_2$C$_{1-4}$aliphatic, wherein up to 3 non-adjacent carbon atoms of said aliphatic or cycloaliphatic of $R^{1a}$ can be substituted for by —O—, —S—, or —N($R^{1b}$)— and wherein each of said aliphatic, cycloaliphatic, or heterocyclic of $R^{1a}$ is optionally and independently substituted with up to 4 occurrences of $J^R$;
each $J^R$ is independently fluoro, oxo, —(CH$_2$)$_{0-2}$CN, —(CH$_2$)$_{0-2}$CF$_3$, —C(O)R$^{1b}$, —C(O)N(R$^{1b}$)$_2$, —C(O)O(R$^{1b}$), —N(R$^{1b}$)$_2$, —N(R$^{1b}$)C(O)R$^{1b}$, —(CH$_2$)$_{0-2}$OR$^{1b}$, phenyl, or a 5-6 membered heteroaryl, 4-6 heterocyclyl, or 9-11 fused bicyclic heteroaryl or heterocyclyl, each of said heteroaryl or heterocyclyl rings having up to 3 atoms selected from nitrogen, oxygen, or sulfur, wherein each of said cycloaliphatic, phenyl, heteroaryl, or heterocyclyl is optionally substituted with up to 2 $R^{1c}$;
each $R^{1b}$ is, independently, selected from hydrogen, $C_{1-8}$aliphatic, —(CH$_2$)$_{0-1}$C$_{3-6}$cycloaliphatic, —(CH$_2$)$_{0-1}$C$_{4-6}$heterocyclic having up to two heteroatoms selected from N or O, or two $R^{1b}$ together with the atom to which they are bonded form a 5-6 membered heterocyclic ring, wherein each aliphatic, cycloaliphatic, or heterocyclic is optionally substituted with up to three F atoms or up to two —OH, —C$_{1-2}$alkyl, or —OC$_{1-2}$alkyl groups;
each $R^{1c}$ is, independently, fluoro, chloro, C$_{1-4}$aliphatic, —(CH$_2$)$_{0-2}$OH, —CN, —C(O)C$_{1-4}$aliphatic, or —C(O)OC$_{1-4}$aliphatic;
$R^2$ is hydrogen, F, Cl, CF$_3$, C$_{1-2}$aliphatic, C$_{3-4}$cycloaliphatic, —N(CH$_3$)$_2$, —N(CH$_2$)$_3$, —OCF$_3$, —OCHF$_2$, or —OC$_{1-2}$aliphatic;
$R^3$ is hydrogen, C$_{1-6}$aliphatic, C$_{3-6}$ cycloaliphatic, C$_{4-7}$ heterocyclyl having 1 or 2 atoms selected from N or O, —(CH$_2$)$_{0-1}$CF$_3$, —OH, —OC$_{1-6}$aliphatic, —OC$_{3-6}$cycloaliphatic, —OC$_{3-6}$heterocyclyl having one oxygen atom, —O(CH$_2$)$_2$OC$_{1-2}$aliphatic, or —OC$_{1-2}$alkylC(O)OC$_{1-3}$aliphatic, or benzyl; and
$R^4$ is hydrogen or C$_{1-6}$alkyl; or $R^3$ and $R^4$ together with the carbon to which they are bonded form a 3-6 membered cycloaliphatic ring, a 3-6 membered heterocyclic ring having up to two atoms selected from N or O, or a C₂alkenyl, wherein each of said aliphatic, cycloaliphatic, or heterocyclyl of $R^3$, $R^4$, or $R^3$ and $R^4$ together is optionally substituted with up to three F atoms, or up to two $C_{1-2}$alkyl, —C(O)$C_{1-4}$alkyl, —C(O)O$C_{1-4}$alkyl, —OH, or —O$C_{1-2}$alkyl groups;

A is N or $CR^A$;
B is N or $CR^B$, or A=B is a sulfur atom;
C is N or $CR^C$;
D is N or $CR^D$;
E is N or $CR^E$ wherein no more than two of A, B, C, D, or E is N;
$R^A$ is hydrogen, CH₃, or OCH₃;
$R^B$ is hydrogen, F, Cl, $C_{1-3}$aliphatic, —(CH₂)$_{0-1}$CF₃, —(CH₂)$_{0-1}$CHF₂, or —O(CH₂)$_{0-1}$CF₃;
$R^C$ is hydrogen, F, Cl, $C_{1-3}$aliphatic, —(CH₂)$_{0-1}$CF₃, —(CH₂)$_{0-1}$CHF₂, N($R^{1b}$)₂, —OH, —O(CH₂)$_{0-1}$CF₃, or —O$C_{1-8}$aliphatic, wherein up to 2 non-adjacent carbon atoms of said aliphatic can be substituted for by —O—;
$R^D$ is hydrogen, fluoro, chloro, $C_{1-4}$aliphatic, —C(O)OH, —C(O)O$C_{1-4}$aliphatic, —C(O)N($R^{1b}$)₂, —CN, —C($R^{D1}$)=N—O$R^{1b}$, —N($R^{1b}$)₂, —N($R^{D1}$)C(O)$C_{1-4}$aliphatic, —N($R^{D1}$)C(O)phenyl, —N($R^{D1}$)S(O)₂$C_{1-4}$aliphatic, —N($R^{D1}$)S(O)₂N($R^{1b}$)₂, —N($R^{D1}$)S(O)₂phenyl-OH, —O$C_{1-8}$aliphatic, —O(CH₂)$_{0-1}$$C_{3-6}$cycloaliphatic, —S$C_{1-4}$aliphatic, —S(O)$C_{1-4}$aliphatic, —S(O)₂$C_{1-4}$aliphatic, or —S(O)₂N($R^{1b}$)₂; wherein up to 2 non-adjacent carbon atoms of said aliphatic, cycloaliphatic, or heterocyclic of $R^D$ can be substituted for by —O— and each of said aliphatic, cycloaliphatic, or phenyl of $R^D$ can be substituted with up to 5 fluorine atoms; or $R^D$ and $R^C$ together with the atoms to which they are attached form a phenyl or pyridyl ring;
each $R^{D1}$ is, independently, hydrogen or $C_{1-2}$alkyl; and
$R^E$ is hydrogen, F, Cl, —NHC(O)$C_{1-8}$aliphatic, —OH, —O$C_{1-2}$aliphatic, —(CH₂)$_{0-1}$CF₃, —(CH₂)$_{0-1}$CHF₂, $C_{1-3}$aliphatic, $C_{3-4}$cycloaliphatic, N($R^{1b}$)₂, azetidin-1-yl.

In one embodiment, compounds have formula I and $R^D$ is hydrogen, fluoro, chloro, $C_{1-4}$aliphatic, —(CH₂)$_{0-1}$CF₃, —C(O)N($R^{1b}$)₂, —CN, —N($R^{1b}$)₂, —NHC(O)$C_{1-8}$aliphatic, —OH, —O(CH₂)$_{0-1}$CF₃, —O(CH₂)$_{0-1}$CHF₂, —O(CH₂)$_{0-1}$CH₂F, —O$C_{1-8}$aliphatic, —O(CH₂)$_{0-1}$$C_{3-6}$cycloaliphatic, —S$C_{1-8}$aliphatic, —S(O)₂$C_{1-8}$aliphatic, —S(O)₂N($R^{1b}$)₂; wherein up to 2 non-adjacent carbon atoms of said aliphatic, cycloaliphatic, or heterocyclic of $R^D$ can be substituted for by —O—, or $R^D$ and $R^C$ together with the atoms to which they are attached form a phenyl or pyridyl ring; $R^3$ is hydrogen, $C_{1-6}$alkyl, $C_{3-6}$ cycloalkyl, —(CH₂)$_{0-1}$CF₃, —OH, —O$C_{1-6}$alkyl, —O$C_{3-6}$cycloalkyl, —O$C_{3-6}$heterocyclyl having one oxygen atom, —O(CH₂)₂O$C_{1-2}$alkyl, or —O$C_{1-2}$alkylC(O)O$C_{1-3}$alkyl, or benzyl; and $R^4$ is hydrogen or $C_{1-6}$alkyl; or $R^3$ and $R^4$ together with the carbon to which they are bonded form a 3-6 membered cycloalkyl ring, a 3-6 membered heterocyclic ring having one oxygen atom, wherein each of said alkyl, cycloalkyl, or heterocyclyl of $R^3$, $R^4$ or $R^3$ and $R^4$ together is optionally substituted with up to two F, $C_{1-2}$alkyl or —O$C_{1-2}$alkyl.

In another embodiment, compounds have formula I and each $R^{1b}$ is, independently, selected from hydrogen, $C_{1-4}$ aliphatic, or $C_{3-6}$ cycloaliphatic; $R^B$ is hydrogen, F, Cl, —OCF₃, —O$C_{1-2}$aliphatic, —CF₃, or $C_{1-2}$aliphatic; $R^C$ is hydrogen, F, Cl, $C_{1-3}$aliphatic, —(CH₂)$_{0-1}$CF₃, —N($R^{1b}$)₂, —OH, —OCF₃, or —O$C_{1-8}$aliphatic; $R^D$ is hydrogen, fluoro, chloro, $C_{1-4}$aliphatic, (CH₂)$_{0-1}$CF₃, —C(O)NH$C_{1-8}$aliphatic, —CN, —N($R^{1b}$)₂, —NHC(O)$C_{1-8}$aliphatic, —OH, —OCF₃, —OCHF₂, —O$C_{1-8}$aliphatic, —O(CH₂)$_{0-1}$$C_{3-6}$cycloaliphatic, —S$C_{1-8}$aliphatic, —S(O)₂$C_{1-8}$aliphatic, —S(O)₂N($R^{1b}$)₂; wherein up to 2 non-adjacent carbon atoms of said aliphatic or cycloaliphatic of $R^D$ can be substituted for by —O—, or $R^D$ and $R^C$ together with the atoms to which they are attached form a phenyl or pyridyl ring; $R^E$ is hydrogen, F, Cl, —NHC(O)$C_{1-8}$aliphatic, —OH, —OCF₃, —O$C_{1-2}$aliphatic, CF₃, $C_{1-2}$aliphatic, $C_{3-4}$cycloaliphatic, N(CH₃)₂, azetidin-1-yl; $R^2$ is hydrogen, F, Cl, CF₃, $C_{1-2}$aliphatic, $C_{3-4}$cycloaliphatic, —N(CH₃)₂, —N(CH₂)₃, —OCF₃, or —O$C_{1-2}$aliphatic; and $R^3$ is hydrogen, $C_{1-2}$alkyl, —OH, —O$C_{1-2}$alkyl, —O(CH₂)₂O$C_{1-2}$alkyl, or —O$C_{1-2}$alkylC(O)O$C_{1-2}$alkyl; and $R^4$ is hydrogen or $C_{1-2}$alkyl.

In one embodiment, compounds have formula II:

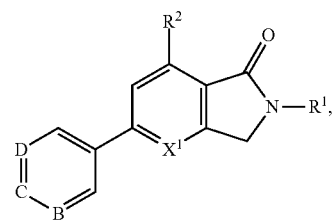

(II)

or a pharmaceutically acceptable salt thereof, wherein:
$X^1$ is CH or N;
$R^1$ is selected from a phenyl ring, a 5-membered heteroaryl ring, a 6-membered heteroaryl ring, or a 9- or 10-membered fused bicyclic heteroaryl or heterocyclic ring system wherein each of said rings or ring systems is optionally substituted with 1 or 2 independent occurrences of $R^{1a}$ and each of said heteroaryl or heterocyclic rings has 1, 2, or 3 heteroatoms selected from nitrogen, oxygen, or sulfur;
$R^{1a}$ is chloro, fluoro, $C_{1-6}$aliphatic, $C_{3-6}$cycloaliphatic, —CN, —C(O)$R^{1b}$, —C(O)N($R^{1b}$)₂, —C(O)O($R^{1b}$), or —O$R^{1b}$, wherein each of said aliphatic or cycloaliphatic is optionally substituted with up to 3 occurrences of $J^R$;
each $J^R$ is independently fluoro, oxo, —CN, —C(O)$R^{1b}$, —C(O)N($R^{1b}$)₂, —C(O)O($R^{1b}$), —N($R^{1b}$)₂, —N($R^{1b}$)C(O)$R^{1b}$, —O$R^{1b}$, or a 5-membered heteroaryl or heterocyclyl having up to 3 atoms selected from nitrogen, oxygen, or sulfur;
each $R^{1b}$ is independently selected from hydrogen, $C_{1-4}$ aliphatic, or $C_{3-6}$ cycloaliphatic;
$R^2$ is hydrogen, F, Cl, CF₃, or CH₃;
B is N;
C is $CR^C$, wherein $R^C$ is hydrogen, fluoro, chloro, $C_{1-3}$aliphatic, CF₃, —OCF₃, or —O$C_{1-2}$aliphatic; and
D is $CR^D$, wherein $R^D$ is fluoro, chloro, $C_{1-3}$aliphatic, CF₃, —OCF₃, or —O$C_{1-2}$aliphatic.

In one embodiment of compounds of formula II, $X^1$ is N.
In one embodiment of compounds of formula II, $R^2$ is CH₃.

In a further embodiment,

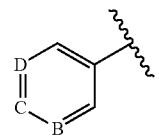

is a substituted pyridine-3-yl.

In another aspect, the invention features compounds having formula I-A:

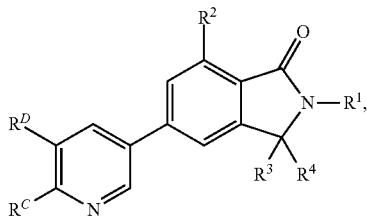

(I-A)

or a pharmaceutically acceptable salt thereof, wherein $R^1$ is

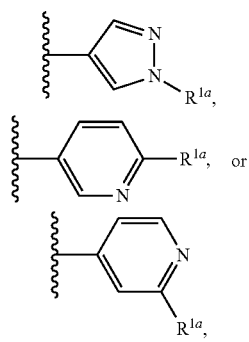

wherein
$R^{1a}$ is —$C_{1-4}$alkyl, optionally and independently substituted with —CN, up to three F atoms, or up to two $CH_3$, —$OC_{1-2}$alkyl, or —OH groups;
$R^2$ is $C_{1-2}$alkyl;
$R^3$ is hydrogen, —OH, —$OC_{1-4}$ alkyl, or $C_{1-4}$alkyl optionally substituted with up to two —OH groups;
$R^4$ is hydrogen or $CH_3$, or $R^3$ and $R^4$ together form a $C_{3-6}$cycloalkyl ring optionally substituted with up to two OH groups, or a 4-6 membered heterocyclic ring having one oxygen or a nitrogen atom optionally substituted with $C_{1-4}$alkyl, —C(O)$C_{1-4}$alkyl, or C(O)O $C_{1-4}$alkyl;
$R^C$ is hydrogen, F, $C_{1-2}$alkyl, or —$OC_{1-2}$alkyl; and
$R^D$ is —$OR^{D1}$, —C(O)N($R^{D1}$)$R^{D2}$, —S(O)$^2$N($R^{D1}$)$R^{D2}$, —S(O)$_{1-2}R^{D2}$, —N($R^{D1}$)S(O)$_2R^{D2}$, or —N($R^{D1}$)S(O)$_2$N($R^{D1}$)$R^{D2}$, wherein
$R^{D1}$ is hydrogen or $C_{1-2}$alkyl, and $R^{D2}$ is $C_{1-4}$alkyl, —(CH$_2$)$_{0-1}C_{3-6}$cycloalkyl, or —(CH$_2$)$_{0-1}C_{4-6}$heterocyclyl having up to two oxygen or nitrogen atoms, each alkyl, cycloalkyl, or heterocyclyl optionally substituted with up to three F atoms or up to two —OH groups.

In one embodiment, $R^{1a}$ is $C_{1-2}$alkyl, optionally substituted with up to 3 fluorine atoms.

In another embodiment, $R^{1a}$ is $C_{1-4}$alkyl, optionally substituted with CN.

In another embodiment, $R^2$ is $CH_3$.

In another embodiment, at least one of $R^3$ and $R^4$ is not hydrogen.

In a further embodiment, each of $R^3$ and $R^4$ is $CH_3$.

In another further embodiment, $R^3$ and $R^4$ together form a 4-6 membered heterocyclic ring having one oxygen or a nitrogen atom optionally substituted with $C_{1-4}$alkyl, —C(O)$C_{1-4}$alkyl, or —C(O)O$C_{1-4}$alkyl.

In another embodiment for any of the compounds of formulae I, II, or I-A, $R^1$ is a 5-membered heteroaryl ring having 1-3 heteroatoms selected from N, O, or S and optionally substituted with 1 or 2 $R^{1a}$ groups. Examples include optionally substituted pyrazol-4-yl, pyrazol-3-yl, imidazol-4-yl, 1,2,3-triazol-4-yl, 1,2,4-triazol-3-yl, 1,2,5-triazol-3-yl, 1,3-thiazol-4-yl, 1,3-thiazol-2-yl, 1,2-thiazol-5-yl, 1,2-isoxazol-3-yl ring systems.

In another embodiment $R^1$ is selected from

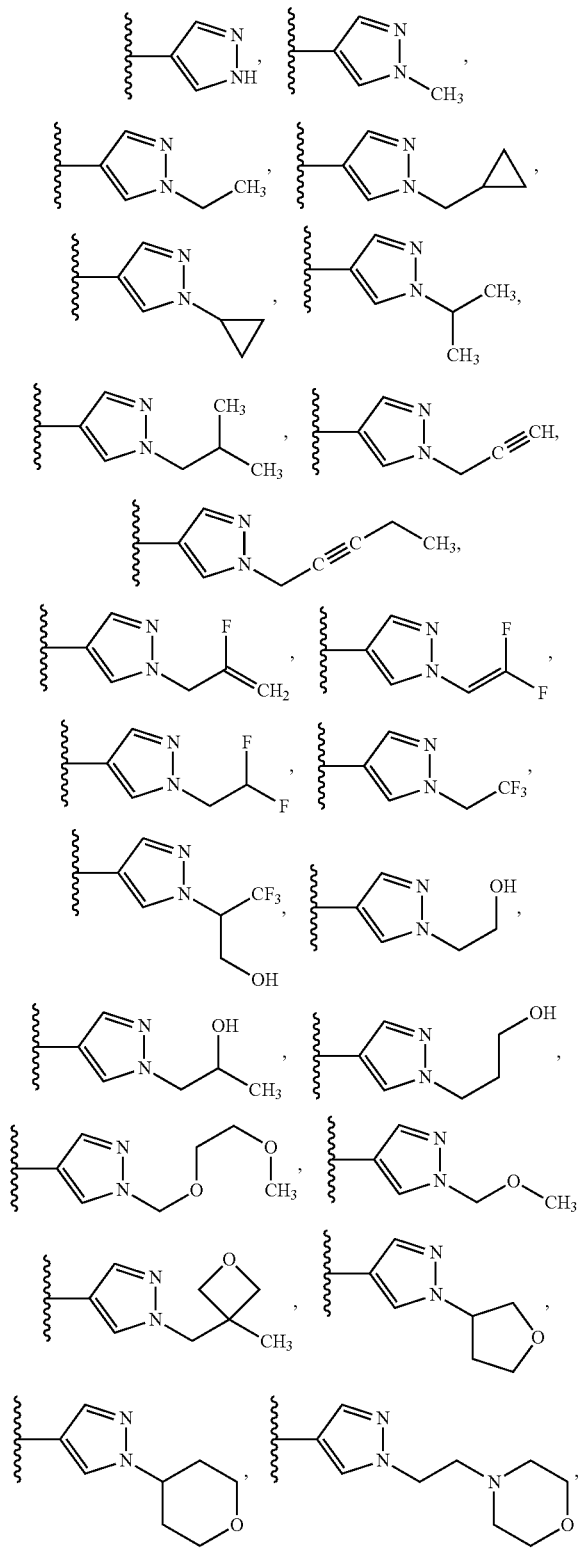

-continued
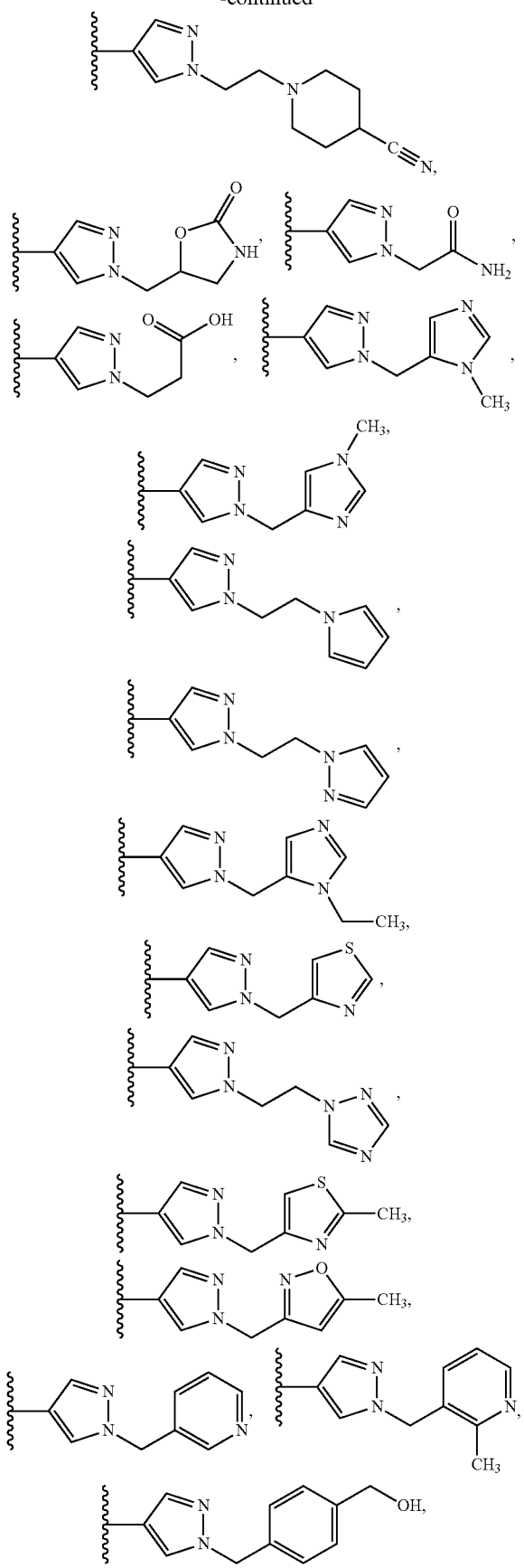
-continued
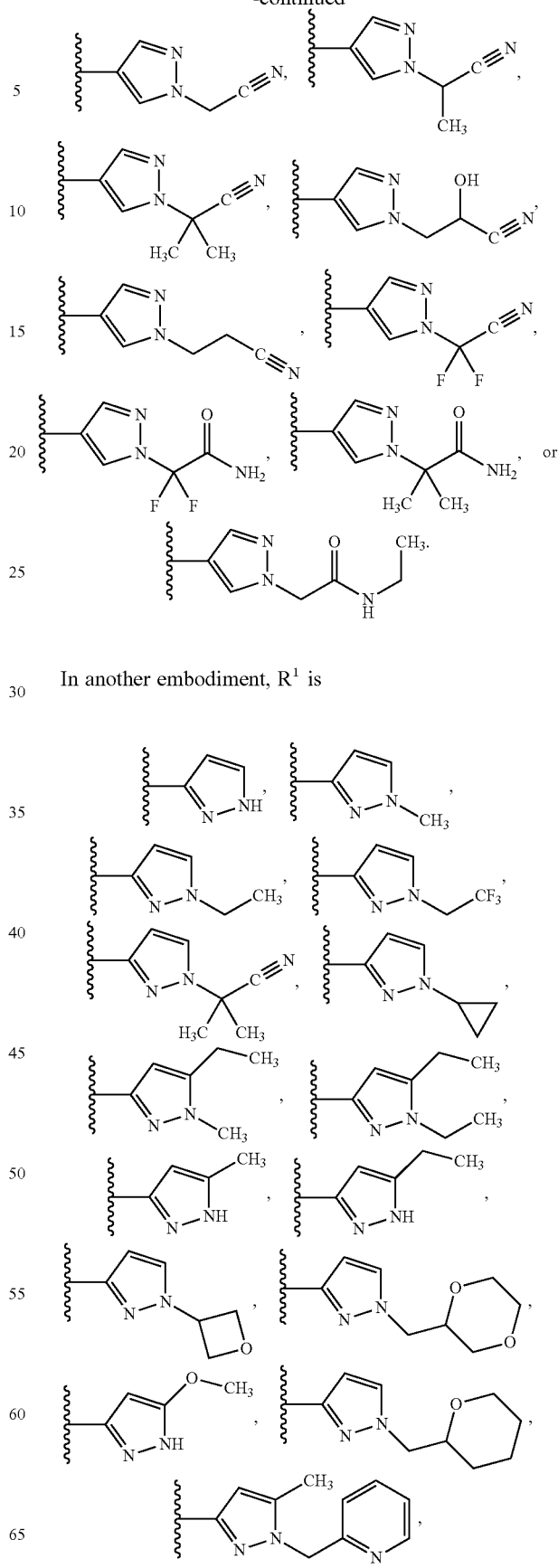
In another embodiment, R¹ is

-continued
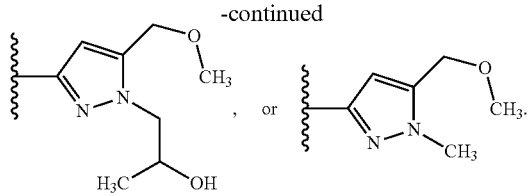
In yet another embodiment, R¹ is
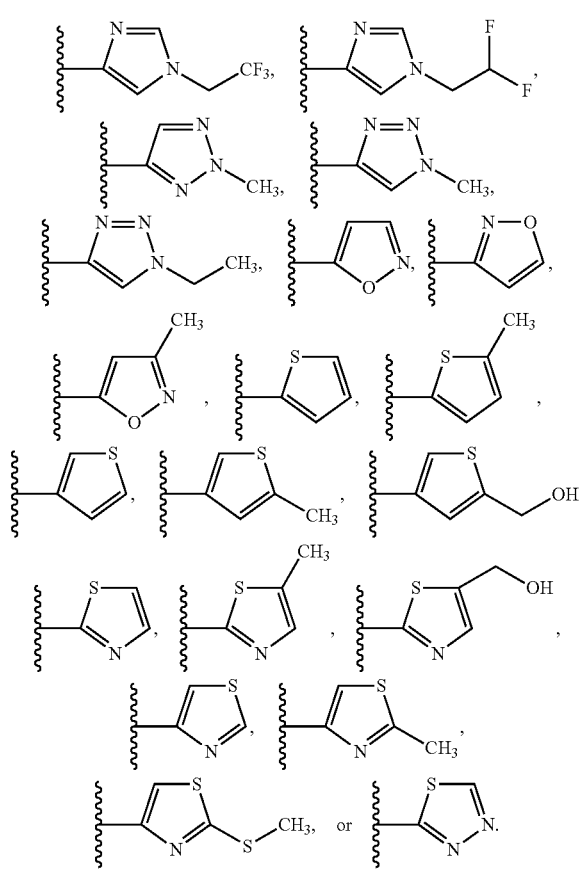
In another embodiment, R¹ is selected from
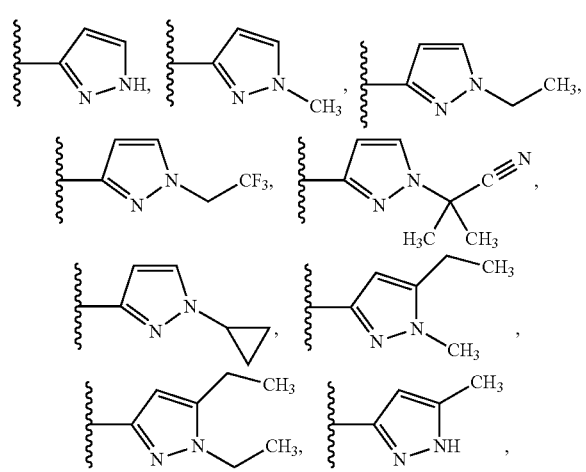
-continued
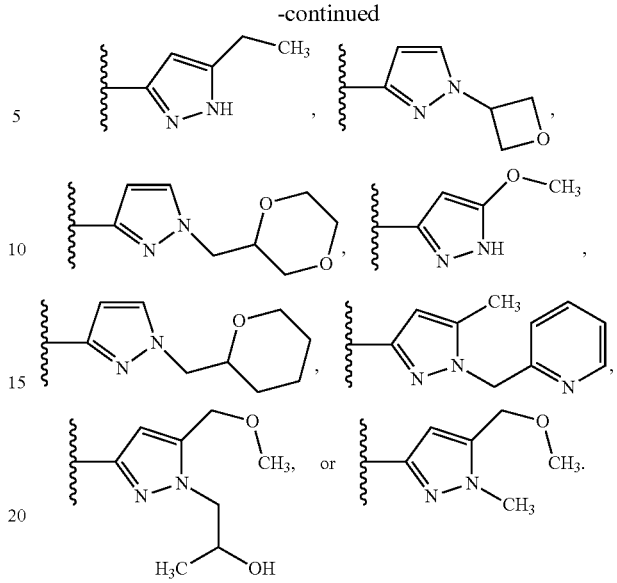
In yet another embodiment, R¹ is
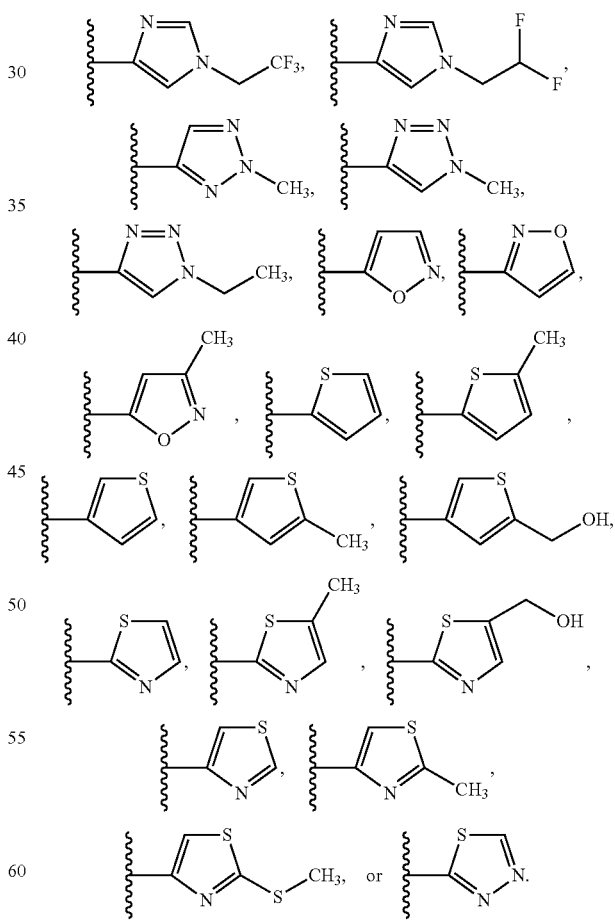
In one embodiment for any of the compounds of formulae I, II, or I-A, $R^1$ is

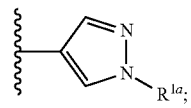

$R^2$ is $CH_3$;
$R^3$ is hydrogen, $C_{1-2}$alkyl, OH, or $OCH_3$;
$R^4$ is hydrogen or $CH_3$;
$R^C$ is hydrogen; and
$R^D$ is $-OC_{1-2}$alkyl or $-OC_{3-5}$cycloalkyl, each optionally substituted with up to 3 fluorine atoms.

In a further embodiment, $R^1$ is 1-(2,2-difluoroethyl)-1H-pyrazol-4-yl or 1-(2,2,2-trifluoroethyl)-1H-pyrazol-4-yl.

In one embodiment for any of the compounds of formulae I, II, or I-A, $R^1$ is a 6-membered heteroaryl ring having 1-3 nitrogens and optionally substituted with 1 or 2 $R^{1a}$ groups. In a further embodiment, $R^1$ is an optionally substituted pyridyl ring.

In a further embodiment,
$R^1$ is

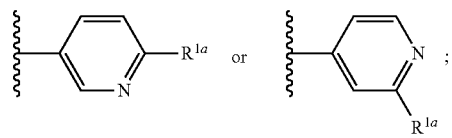

$R^2$ is $CH_3$;
$R^3$ is hydrogen, $C_{1-2}$alkyl, OH, or $OCH_3$;
$R^4$ is hydrogen or $CH_3$;
$R^C$ is hydrogen, F, Cl, $C_{1-3}$aliphatic, $(CH_2)_{0-1}CF_3$, $-OCF_3$, or $-OC_{1-8}$aliphatic; and
$R^D$ is $-C(O)NHC_{1-8}$aliphatic.

In a another embodiment, $R^1$ is selected from

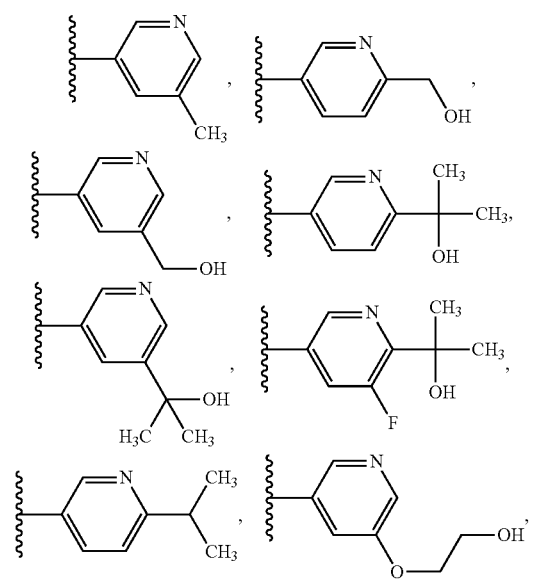

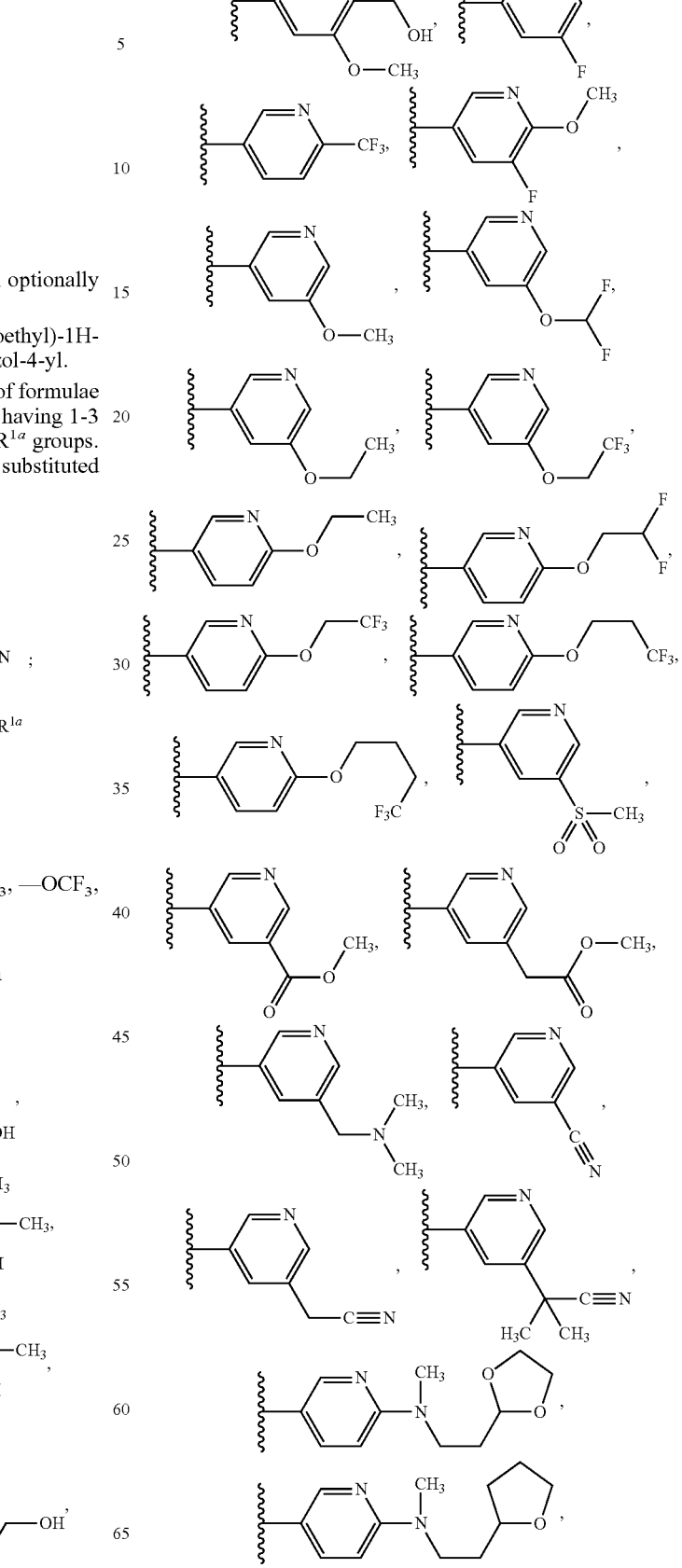

-continued

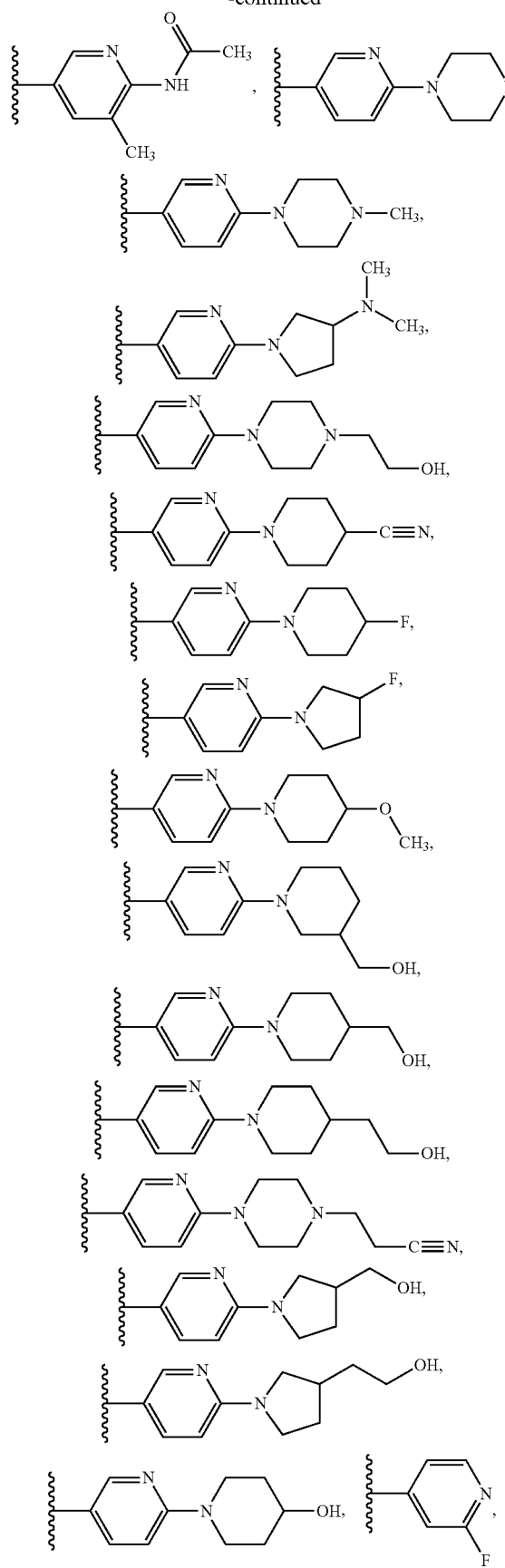

-continued

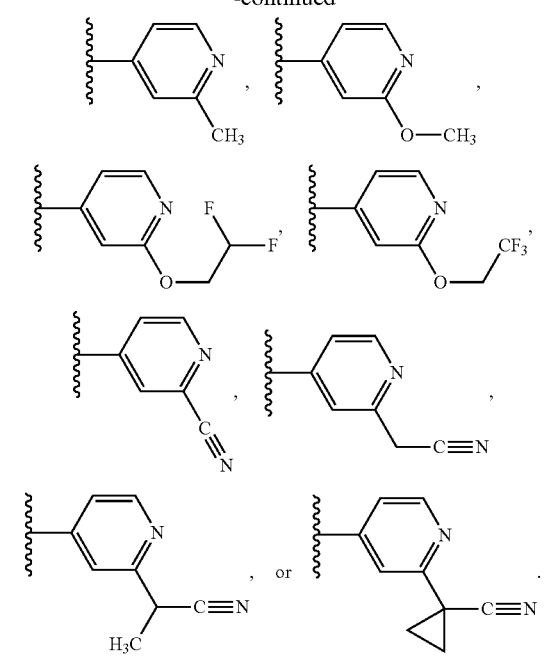

In one embodiment for any of the compounds of formulae I, II, or I-A, $R^D$ is —C(O)OH, —C(O)N($R^{1b}$)$_2$, —CN, —S(O)$_2$C$_{1-8}$aliphatic, or —S(O)$_2$N($R^{1b}$)$_2$.

In another embodiment, each of $R^C$ and $R^D$ is, independently, hydrogen, fluoro, chloro, C$_{1-3}$aliphatic, CF$_3$, —OCF$_3$, —OCHF$_2$, or —OC$_{1-2}$aliphatic, wherein at least one of $R^C$ and $R^D$ is not hydrogen.

In another embodiment, $R^C$ is hydrogen and $R^D$ is —OC$_{1-3}$alkyl, optionally substituted with up to 3 F atoms. In a further embodiment, $R^C$ is hydrogen and $R^D$ is —OCH$_3$, —OCH$_2$CH$_3$, —OCF$_3$, —OCH$_2$CF$_3$, OCHF$_2$, or OCH$_2$CHF$_2$.

In another embodiment, each of $R^C$ and $R^D$ is —OCH$_3$.

In one embodiment,

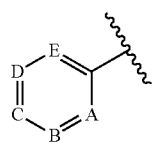

is selected from:

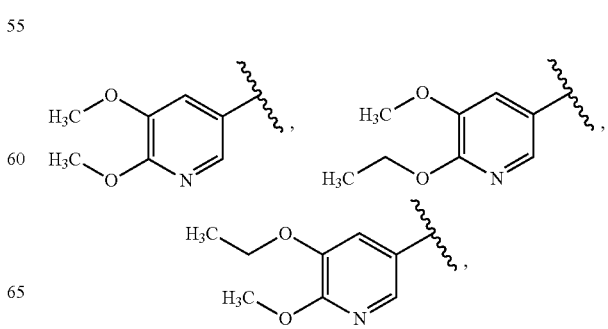

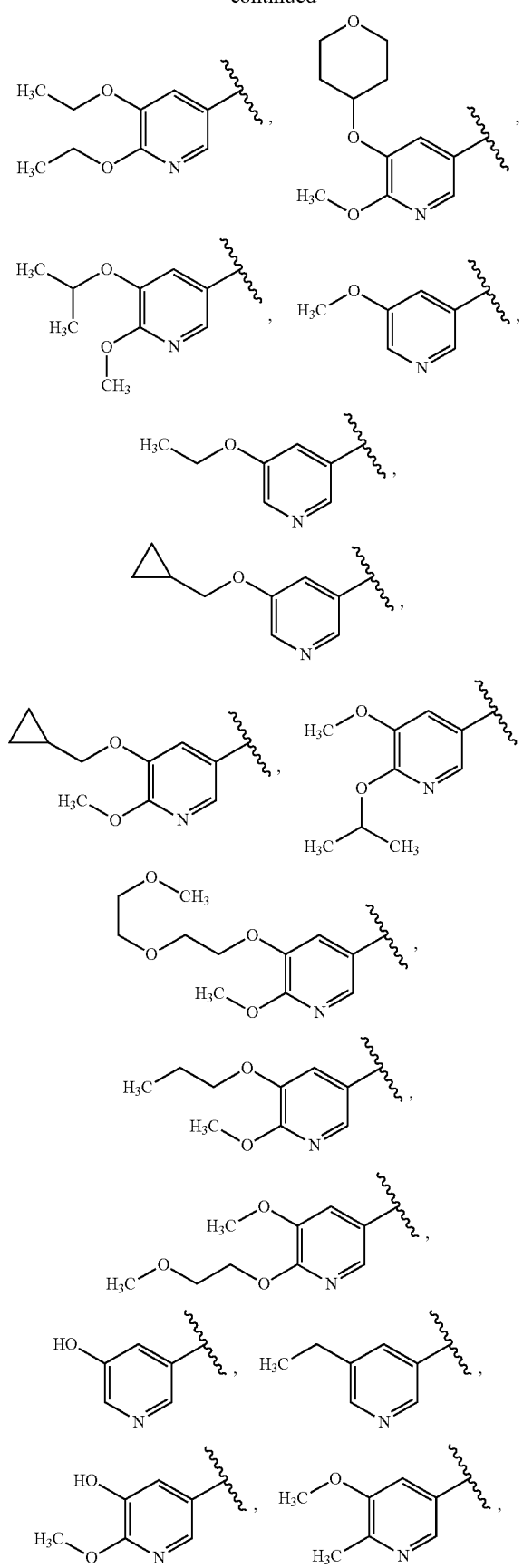
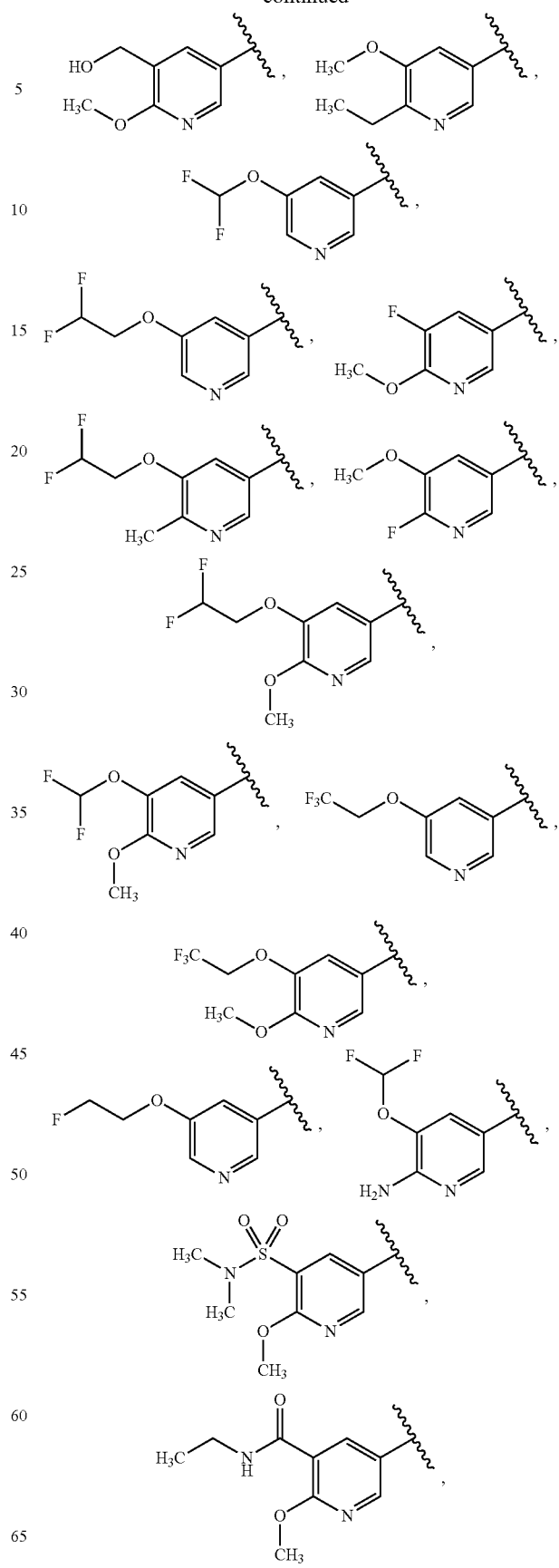

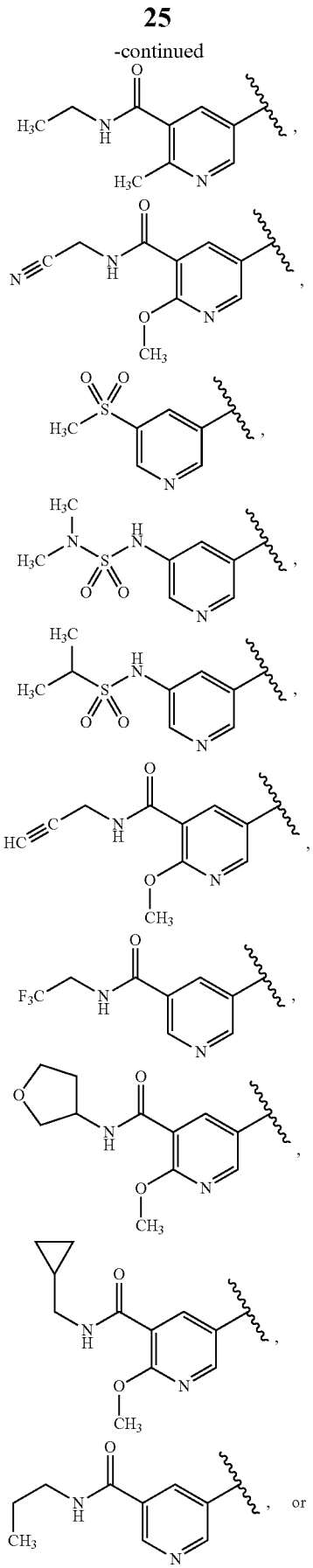

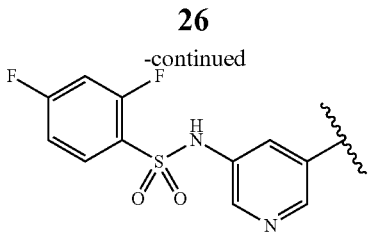

In another embodiment $R^3$ and $R^4$, together with the intervening carbon atom, form a 4-6 membered heterocyclic ring having one atom selected from N or O.

In another embodiment, the invention features a compound selected from the group of compounds listed in Table 1.

The invention also features a pharmaceutical composition comprising a compound of the invention and a pharmaceutically acceptable carrier, adjuvant, or vehicle.

In one embodiment, the composition includes a therapeutic agent selected from an agent for treating multiple sclerosis, an anti-inflammatory agent, an immunomodulatory agent, or an immunosuppressive agent. Examples of such additional therapeutic agents include beta interferon, glatiramir, natalizumab, or mitoxantrone.

In another embodiment, the invention features a method of inhibiting PI3K kinase activity in a patient by administering to the patient a compound of formula I, II, or I-A, or a pharmaceutical composition thereof. In a further embodiment PI3K-gamma is selectively inhibited over PI3K-alpha, PI3K-beta, or PI3K-gamma. In a further embodiment, PI3K-gamma is selectively inhibited over PI3K-alpha, PI3K-beta, and PI3K-gamma In another embodiment, the invention features a method of treating or lessening the severity of a disease or condition selected from an autoimmune disease or an inflammatory disease of the brain or spinal cord selected from multiple sclerosis, epilepsy, Parkinson's Disease, Alzheimer's Disease, Huntington's Disease, or amyotrophic lateral sclerosis in a patient by administering to the patient a compound of formula I, II, or I-A, or a pharmaceutical composition thereof.

In a further embodiment, the disease or disorder is multiple sclerosis.

In another embodiment, the method of treatment includes administering to a patient a compound or composition of the invention and an additional therapeutic agent, wherein the additional therapeutic agent is appropriate for the disease being treated and is administered together with the compound or composition as a single dosage form, or separately as part of a multiple dosage form. Examples of such additional therapeutic agents are those useful for treating multiple sclerosis, such as beta interferon, glatiramir, natalizumab, or mitoxantrone.

The invention also features a non-therapeutic method of inhibiting PI3K-gamma kinase activity in a biological sample in vitro comprising contacting said biological sample with a compound of formulae I, II, or I-A, or a composition containing said compound.

Compositions, Formulations, and Administration of Compounds of the Invention

In another embodiment, the invention provides a pharmaceutical composition comprising a compound of any of the formulae or classes described herein. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a PI3K, particularly PI3Kγ, in a biological sample or in a patient. In another embodiment, the amount of compound in the compositions of this invention is such that is effective to measurably inhibit PI3Kα. In one embodiment, the composition of this invention is formulated for administration to a patient in need of such composition. In a further embodiment, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of PI3K.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one aspect of the invention, the invention features a method of treating or lessening the severity of a PI3K-mediated condition or disease in the brain or spinal cord of a patient. The term "PI3K-mediated disease", as used herein means any disease or other deleterious condition in which a PI3K isoform is known to play a role. In one embodiment, the PI3K isoform is PI3Kγ.

Accordingly, in one embodiment, the invention features a method of treating a PI3Kγ-mediated disease of the central nervous system. Such conditions include, without limitation, inflammatory diseases and autoimmune-related diseases of the central nervous system. Accordingly, the invention provides a method of treating or lessening the severity of a disease of condition selected from an autoimmune disease or an inflammatory disease of the central nervous system of a patient, comprising administering to said patient a compound or composition of the invention.

In a further embodiment, the compound of the invention is selective for the inhibition of the PI3Kγ-isoform. In one embodiment, compounds of the invention are selective for the inhibition of the PI3K gamma isoform over the PI3K alpha isoform in an in vitro assay by at least 20-fold. In another embodiment, the PI3Kγ-selective compounds of the invention inhibit the gamma isoform over each of the alpha, beta, and delta isoforms in an in vitro assay by at least 3-fold. In another embodiment, the PI3Kγ-selective compounds of the invention inhibit the gamma isoform over each of the alpha, beta, and delta isoforms in an in vitro assay by at least 5-fold. In yet another embodiment, the PI3Kγ-selective compounds of the invention inhibit the gamma isoform over each of the alpha, beta, and delta isoforms in an in vitro assay by at least 10-fold.

In another embodiment, the invention provides a method of treating or lessening the severity of an inflammatory or autoimmune disease or disorder of the central nervous system. In another embodiment, the invention provides a method of treating or lessening the severity of a symptom of an inflammatory or autoimmune disease or disorder of the central nervous system. In a further embodiment, the invention provides a method of treating neuroinflammation. Such diseases or disorders include, without limitation, multiple sclerosis, transverse myelitis, progressive multifocal leukoencephalopathy, meningitis, encephalitis, myelitis, encephalomyelitis, intracranial or intraspinal abscess, phlebitis or thrombophlebitis of intracranial venous sinuses, Parkinson's Disease, Alzheimer's Disease, Huntington's Disease, Pick's Disease, amyotrophic lateral sclerosis, HIV type-I dementia, frontotemporal lobe dementia, or traumatic brain or spinal cord injury.

PI3Kγ has also been reported to be important in diseases or disorders characterized by the activation of resident cells such as microglia. See Jin et al., 2010, *Biochemical and Biophysical Research Communications* 399:458-464. Microglia may potentiate damage to blood-brain barrier (BBB) integrity and endanger neuronal survaival through the release of reactive oxygen species or pro-inflammatory cytokines and other neurotoxins. Inhibition of microglial activation may protect the brain after ischemic stroke, as well as other neurovascular disorders such as multiple sclerosis.

Compounds or compositions of the invention may be administered with one or more additional therapeutic agents, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month, or 2 months.

Non-limiting examples of chemotherapeutic agents or other anti-proliferative agents that may be combined with the compounds of this invention include taxanes, aromatase inhibitors, anthracyclines, microtubule targeting drugs, topoisomerase poison drugs, targeted monoclonal or polyclonal antibodies, inhibitors of a molecular target or enzyme (e.g., a kinase inhibitor), or cytidine analogues. In one embodiment, the additional chemotherapeutic agent is amsacrine, anastrozole, asparaginase, Avastin™ (bevacizumab) azathioprine, bicalutamide, bleomycin, camptothecin, carmustine, chlorambucil, cyclophosphamide, cytarabine (araC), daunonibicin, dactinomycin, doxorubicin (adriamycin), epirubicin, epothilone, etoposide, exemestane, fludarabine, 5-fluorouracil (5-FU), flutamide, Gemzar™ (gemcitabine), Gleevec™ (imatanib), Herceptin™ (trastuzumab), idarubicin, ifosfamide, an interferon, an interleukin, irinotecan, letrozole, leuprolide, lomustine, lovastatin, mechlorethamine, megestrol, melphalan, 6-mercaptopurine, methotrexate (MTX), minosine, mitomycin, mitoxantrone, navelbine, nocodazole, platinum derivatives such as cisplatin, carboplatin and oxaliplatin, raloxifene, tamoxifen, Taxotere™ (docetaxel), Taxol™ (paclitaxel), teniposide, topotecan, tumor necrosis factor (TNF), vinblastin, vincristin, vindesine, vinorelbine, or Zoladex™ (goserelin). Another chemotherapeutic agent can also be a cytokine such as G-CSF (granulocyte colony stimulating factor). In yet another embodiment, a compound of the present invention, or a pharmaceutically acceptable salt, prodrug, metabolite, analog or derivative thereof, may be administered in combination with surgery, radiation therapy, or with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

Additional therapeutic agents also include those useful for treating multiple sclerosis (MS), such as, for example, beta interferon (e.g., Avonex® and Rebif®), glatiramir (Copaxone®), Tysabri® (natalizumab), Betaseron® (IFN-beta), and mitoxantrone.

The invention provides a method of inhibiting PI3K kinase activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly PI3K kinase activity, in a biological sample is useful for a variety of purposes known to one of skill in the art. Examples of such purposes include, but are not limited to, biological specimen storage and biological assays. In one embodiment, the method of inhibiting PI3K kinase activity in a biological sample is limited to non-therapeutic methods.

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C. American Chemical Society, 1997. The following definitions describe terms and abbreviations used herein:

ATP adenosine triphosphate
Brine a saturated NaCl solution in water
Cp*RuCl(cod) chloro(pentamethylcyclopentadienyl)(cyclooctadiene)ruthenium(II)
DCM dichloromethane
DIEA diisopropylethylamine
DMA dimethylacetamide
DMAP 4-dimethylaminopyridine
DMF dimethylformamide
DMSO methylsulfoxide
dppfPdCl$_2$ 1,1'-bis(diphenylphosphino)-ferrocene dichloropalladium.dichloromethane
DTT dithiothreitol
EDCl 1-ethyl-3-(3-dimethylaminopropyl)carbodiimide
ESMS electrospray mass spectrometry
Et$_2$O ethyl ether
EtOAc ethyl acetate
EtOH ethyl alcohol
HATU 2-(7-aza-1H-benzotriazole-1-yl)-1,1,3,3-tetramethyluronium hexafluorophosphate
HEPES 4-(2-hydroxyethyl)-1-piperazineethanesulfonic acid
HPLC high performance liquid chromatography
LC-MS liquid chromatography-mass spectrometry
m-CPBA meta-chloroperbenzoic acid
Me methyl
MeOH methanol
MTBE methyl t-butyl ether
MC methyl cellulose
NMP N-methylpyrrolidine
PBS phosphate buffered saline
Pd(Cy)$_3$Cl$_2$ dichloro-bis(tricyclohexylphosphoranyl)palladium(II)
Ph phenyl
RT or rt room temperature (between 20° C. and 25° C.)
tBu tertiary butyl
TCA trichloroacetic acid
THF tetrahydrofuran
TEA triethylamine General Synthetic Procedures In general, the compounds of this invention may be prepared by methods described herein or by other methods known to those skilled in the art.

Example 1. General Preparation of the Compounds of Formula I

Compounds of formula I can be prepared as shown in Scheme 1, Routes A to K, wherein each of A, B, C, D, E, X$^1$, X$^2$, R$^1$, and R$^2$ is as described elsewhere in the description and each of R$^3$ and R$^4$ is H. As shown in Route A of the scheme, for compounds of formula I where X is CH, the aryl halide of formula A1 is treated with N-bromosuccinimide (NBS) to produce bromoalkyl compounds of formula of formula A2. Subsequent reaction of the bromoalkyl compounds with amines of formula A3 produce 5-haloisoindolinones of formula A4. Reaction of a compound of formula A4 with a boronic acid or boronate of formula A5 in the presence of an appropriate palladium catalyst produces compounds of formula I, wherein each of X$^1$ and X$^2$ is CH. Procedures for preparing a boronate or boronic acid from aryl or heteroaryl halides are described in *Boronic Acids*, ISBN: 3-527-30991-8, Wiley-VCH, 2005 (Dennis G. Hall, editor). In one example, the halogen is bromine and the boronate is prepared by reacting the aryl or heteroaryl bromide with 4,4,5,5-tetramethyl-2-(4,4,5,5-tetramethyl-1,3,2-dioxaborolan-2-yl)-1,3,2-dioxaborolane. In subsequent coupling reactions, boronates or boronic acids so formed can be reacted with aryl or heteroaryl halides in the presence of 1,1'-bis(diphenylphosphino)-ferrocene dichloro-palladium-.dichloromethane (dppfPdCl$_2$).

As shown in Route B, the sequence of steps outlined above can be changed such that compounds of formula A1 are first reacted with compounds of A5, followed by formation of alkyl bromides A7 and then reacting the alkyl bromides with amines of formula A3 to produce compounds of formula I, wherein X is CH and R$^5$ is hydrogen.

Scheme 1, Routes A & B

Route A

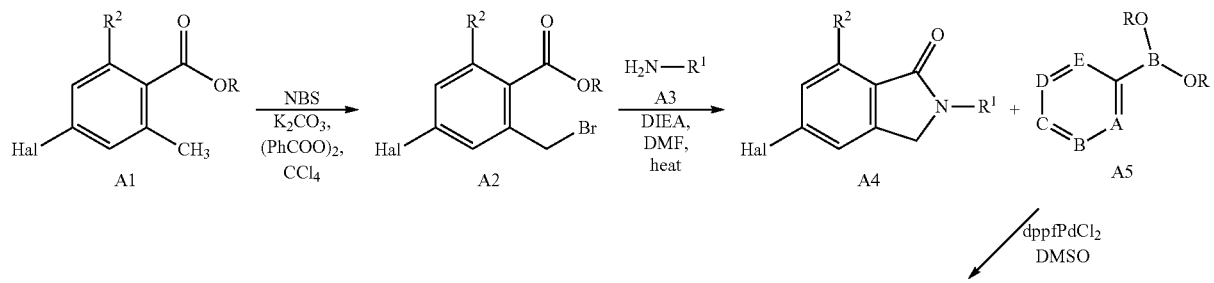

Route B

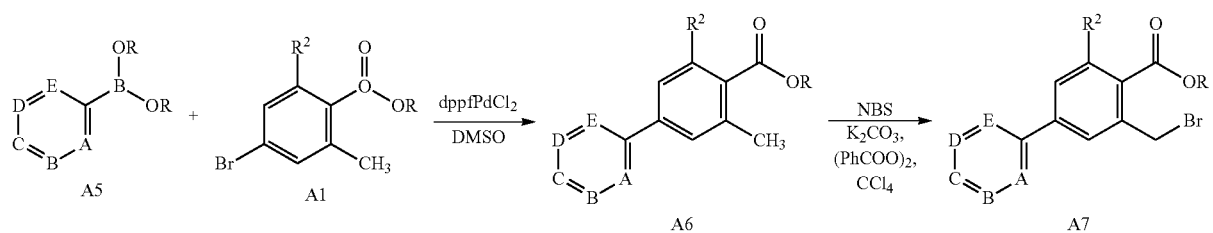

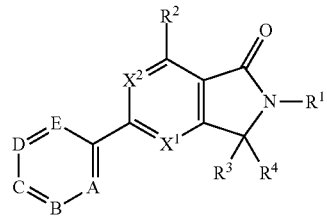

(I): $X^1$ & $X^1$ = CH,
$R^3$ & $R^4$ = H

As shown in Route C, in order to prepare compounds of formula I, wherein $X^1$ is N, compounds for formula A8 can be reacted with 1,3,5-trichloro-1,3,5-triazinane-2,4,6-trione to form chloroalkyl compounds of formula A9. Compounds of formula A9 are then treated with oxidizing agents such as meta-chloroperbenzoic acid to form the N-oxides of formula A10, which are subsequently treated with phosphorus oxychloride to produce pyridyl chlorides of formula A11. Reaction of a compound of formula A11 with an amine of formula A3 produces a 5-chloroazaisoindolinone of formula A12. Reaction of a compound of formula A12 with a boronic acid or boronate of formula A5 in the presence of an appropriate palladium catalyst produces a compound of formula I, wherein $X^1$ is N and $X^2$ is CH or C—$CH_3$.

Scheme 1, Route C

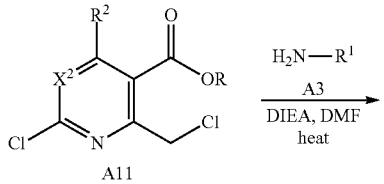

(I): $X^1$ = N, $X^2$ = CH or C—$CH_3$,
$R^3$ & $R^4$ = H

Compounds of formula I, wherein $X^1$ is CH or N, $X^2$ is N and each of $R^3$ and $R^4$ is hydrogen can be also be prepared in a manner similar to that described for Route C, as shown in Route D.

Scheme 1, Route D

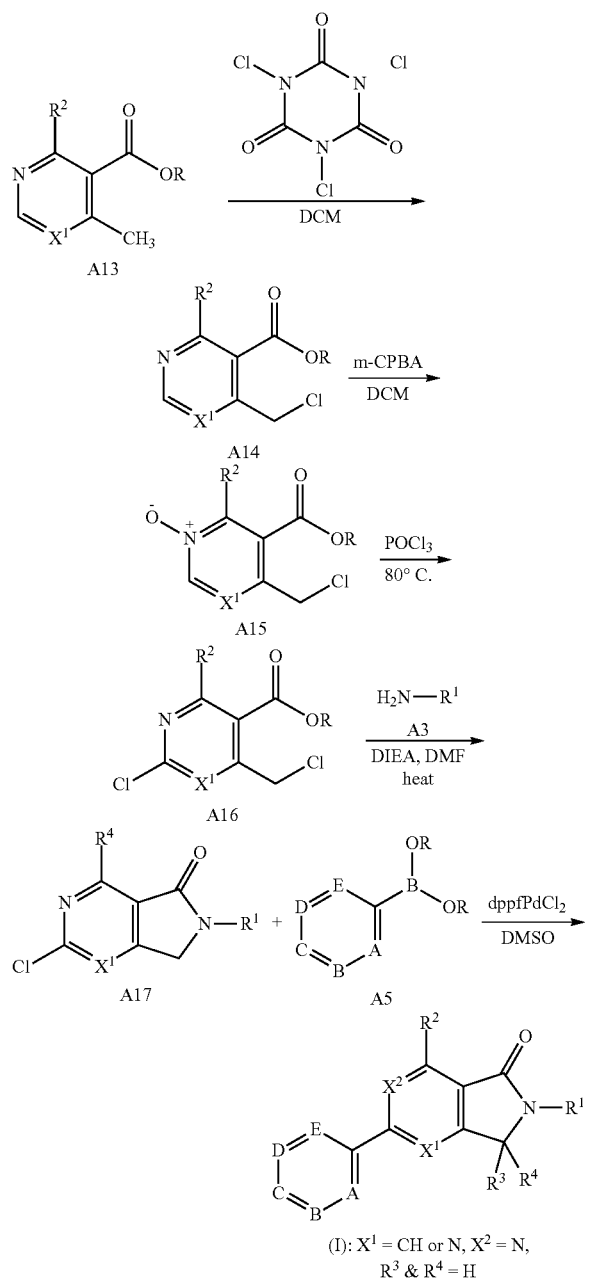

Scheme 1, Route E

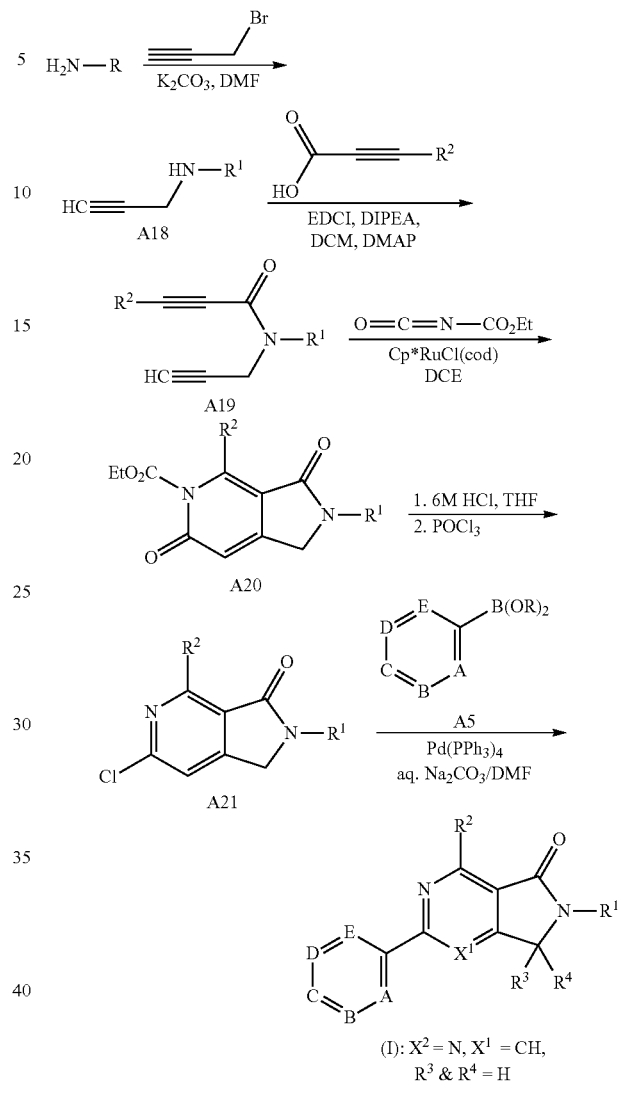

Compounds of formula I, wherein $X^1$ is CH, $X^2$ is N and each of $R^3$ and $R^4$ is hydrogen can be prepared as shown in as shown in Route E. Accordingly, amines of formula $R^1$—$NH_2$ are reacted with halomethylacetylene to produce compounds of formula A18, which can then be reacted with carboxyacetylenes to produce compounds of formula A19. Reaction with ethyl carbonisocyanatidate in the presence of chloro(pentamethylcyclopentadienyl)(cyclooctadiene)ruthenium(II) produce compounds of formula A20. Acidic hydrolysis and decarboxylation of the ethoxyester followed by formation of chloropyridine via phosphorous oxychloride produces compounds of formula A21. Reaction with boronates of formula A4 under catalytic cross-coupling conditions produce compounds of formula I.

Compounds of formula I, wherein an aryl or heteroaryl halide is used to introduce $R^1$, can be prepared as shown in as shown in Route F. Accordingly, amides of formula A23 (prepared by the aminolysis of compounds of formula A22) are reacted with aryl chlorides, aryl bromides, aryl iodides, or aryl triflates in the presence of a copper or palladium catalyst to produce compounds of formula I.

Scheme 1, Route F

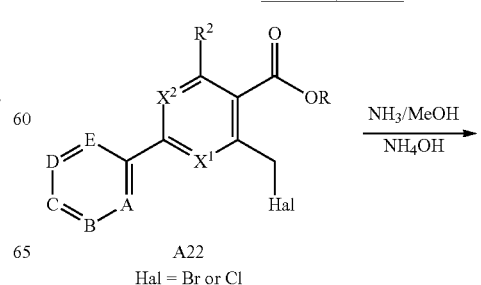

Hal = Br or Cl

-continued

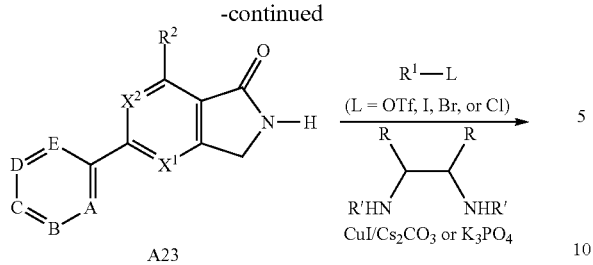

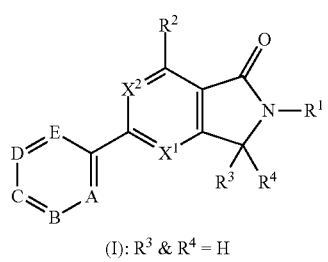

As shown in Route G, compounds of formula I, where $R^1$ is a substituted pyrazole, can also be prepared by reacting compounds of formula A25 under basic conditions with an alkylating agent of formula $R^{1a}$—X, where X is a halide or sulfonate leaving group.

Scheme 1, Route G

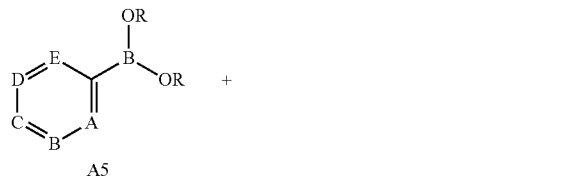

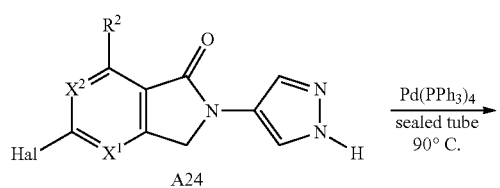

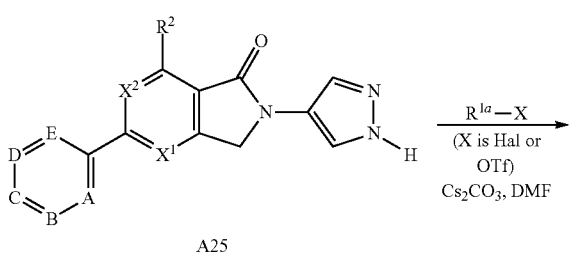

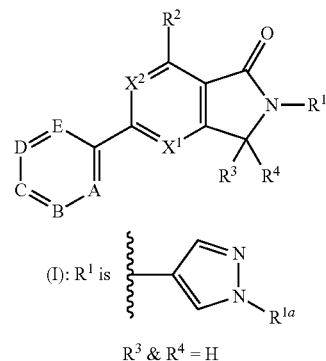

As shown in Route H, reaction of pyrrolopyridine diones of formula A26 with a reducing agent, such as Zn/acetic acid, produces alcohols of formula A27. These alcohols can be subsequently alkylated with an alkylating agent (e.g., L is a leaving group such as sulfonate or halide and $R^{3'}$ is an aliphatic, cycloaliphatic, or heterocyclic group) in the presence of a base to product compounds of formula A28. Compounds of formula A28 are then treated with oxidizing agents such as meta-chloroperbenzoic acid to form the N-oxides of formula A29, which are subsequently treated with phosphorus oxychloride to produce pyridyl chlorides of formula A30. Reaction with boronates or boronic acids of formula A5 in a Pd-mediated cross coupling reaction produce compounds of formula I, where $R^3$ is an ether-linked moiety and $R^4$ is hydrogen. When a mixture of enantiomers or diastereomers is present, such mixtures can be separated by resolution methods such as supercritical fluid chromatography.

Scheme 1, Route H

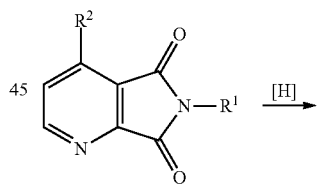

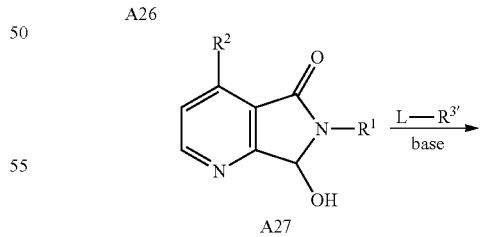

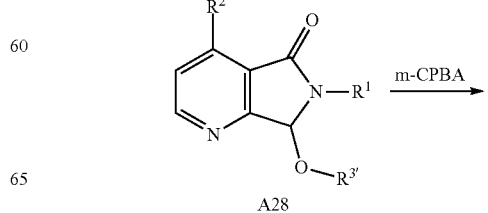

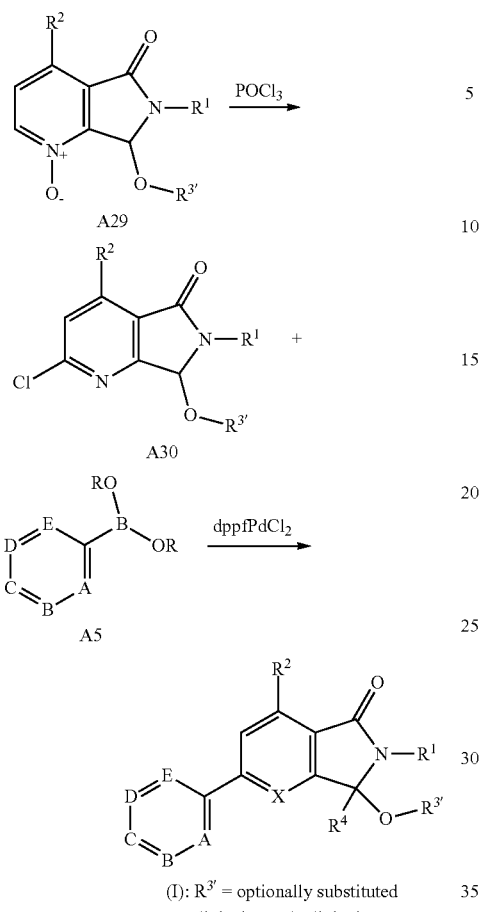
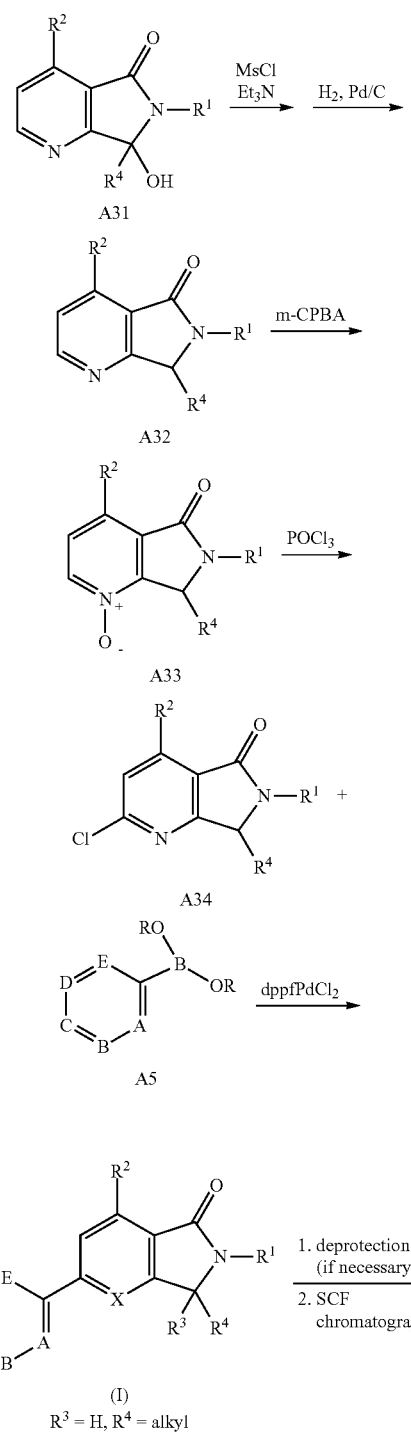

As shown in Route I, reaction of pyrrolopyridine diones of formula A26 with a Grignard reagent, followed by dehydration and hydrogenation of the intermediate compound having formula A31, produce compounds of formula A32. Compounds of formula A32 are then treated with oxidizing agents such as meta-chloroperbenzoic acid to form the N-oxides of formula A33, which are subsequently treated with phosphorus oxychloride to produce pyridyl chlorides of formula A34. Reaction with boronates or boronic acids of formula A5 in a Pd-mediated cross coupling reaction produce compounds of formula I as a mixture of enantiomers. Such mixtures can be separated by resolution methods such as supercritical fluid chromatography.

Scheme 1, Route I

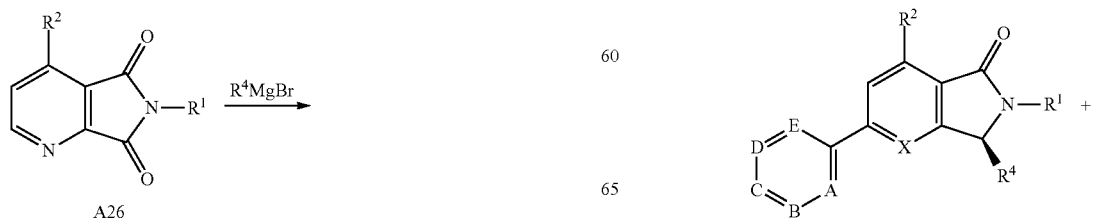

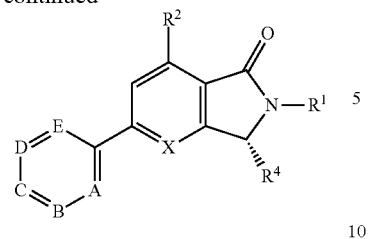

As shown in Route J, compounds of formula I where neither R³ or R⁴ is hydrogen can be prepared by treatment of compounds of formula A35 with strong non-nucleophilic base followed by reaction with at least two equivalents of alkylating agent.

Scheme 1, Route J

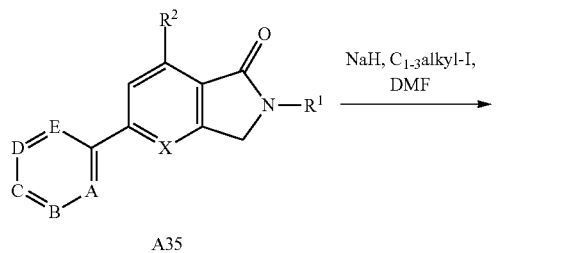

As shown in Scheme 1, Route K, compounds of formula I where R³ and R⁴ and the intervening carbon form a ring can be prepared by treatment of compounds of formula A35 with strong non-nucleophilic base followed by reaction with an equivalent of a bis-alkylating agent.

Scheme 1, Route K

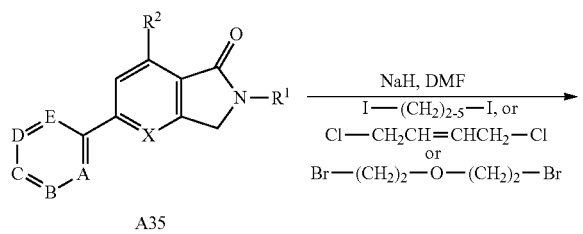

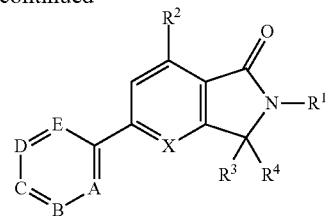

(I)
R³ & R⁴ = (CH₂)₂₋₅
or
(CH₂CH═CHCH₂)
or
CH₂(CH₂OCH₂)CH₂

The following representative examples provide details for the preparation of the compounds of the invention.

Example 2. Preparation of 3-ethoxy-2-methoxy-5-bromopyridine (Compound 2004)

As shown in step 2-i of Scheme 2, to NaH (4.0 g, 60% in mineral oil, 0.1 mol) in a 100 mL DMF suspension was added 10 mL of an absolute ethyl alcohol (4.6 g, 0.1 mol)/DMF solution at RT. After the evolution of hydrogen gas, the reaction mixture was stirred at RT for 30 minutes and the resulting ethoxide solution transferred to a solution of 3,5-dibromopyridine (11.84 g, 0.05 mol, obtained from Aldrich Chemical Co.) in 100 mL DMF at 60° C. The reaction was stirred at 60° C. for 4 hours and then allowed to come to RT. Brine and ethyl acetate were added and the organics were partitioned, dried over MgSO₄, filtered, and the volatiles removed under reduced pressure. The resulting crude material was purified by silica gel chromatography, with the desired product eluting with 20% ethyl acetate/hexanes to give 3-bromo-5-ethoxypyridine (Compound 2001, 4.25 g, 42% yield): ¹H NMR (CDCl₃) δ 8.3 (dd, 2H), 7.4 (d, 1H), 4.12 (q, 2H), 1.45 (t, 3H). 3-Benzyloxy-5-bromopyridine was prepared by an analogous procedure: ¹H NMR (CDCl₃) δ 8.33 (d, 2H), 7.5-7.35 (m, 6H), 5.15 (s, 2H).

Alternatively, as shown in step 2-ii of Scheme 2, 3-bromo-5-hydroxypyridine (100 mg, 0.57 mmol, obtained from Aldrich Chemical Co.) was diluted with DMF (3 mL). Potassium carbonate (158.8 mg, 1.15 mmol) was added, followed by the addition of bromoethane (62.6 mg, 42.6 µL, 0.57 mmol). The mixture was warmed to 60° C. and stirred overnight. After cooling, the mixture was dissolved in ethyl acetate and washed with 2 M NaOH, followed by water. The organics were dried over sodium sulfate, filtered, and the volatiles removed under reduced pressure. The resulting crude 3-bromo-5-ethoxypyridine (Compound 2001) was used without further purification. The following compounds were made by analogous procedures: 3-bromo-5-propoxypyridine, ESMS (M+H) 218.19/216.19; 3-bromo-5-butylpyridine, ESMS (M+H) 230.22/232.22; 3-bromo-5-(cyclohexylmethoxy)pyridine, ESMS (M+H) 270.2/272.22; 3-(2-fluoroexthoxy)-5-bromopyridine, ESMS (M+H) 220.14/222.14; 3-(2,2-difluoroexthoxy)-5-bromopyridine; and 3-(2-ethylbutoxy)-5-bromopyridine, ESMS (M+H) 258.33/256.33.

As shown in step 2-iii of Scheme 2, 3-chloroperoxybenzoic acid (9.426 g, 42.06 mmol) was added to 3-bromo-5-methoxypyridine (4.25 g, 21 mmol) in 200 mL of DCM at RT. The reaction was stirred overnight and the mixture was washed with 200 mL of 2 N NaOH and 2×200 mL brine. The organic phase was dried over MgSO$_4$, filtered and the volatiles removed under reduced pressure to provide 3-bromo-5-ethoxypyridine, 1-oxide (Compound 2002, 4.4 g): $^1$H NMR (CDCl$_3$): δ 8.05 (s, 1H), 7.9 (s, 1H), 7.0 (s, 1H), 4.12 (q, 2H), 1.45 (t, 3H).

As shown in step 2-iv of Scheme 2, phosphorous oxychloride (48.02 g, 403.6 mmol) was added to 3-bromo-5-ethoxypyridine, 1-oxide (4.4 g, 20.18 mmol) in 700 mL of DCM at RT. The reaction mixture was stirred at RT overnight. After the addition of brine, the organics were partitioned, dried over MgSO$_4$, filtered, and the filtrate concentrated under reduced pressure. The product was purified by filtering the concentrate through a pad of silica gel and eluting the pad with ethyl acetate. The volatiles were removed under reduced pressure to provide 5-bromo-2-chloro-3-ethoxypyridine (Compound 2003, 4.3 g, 85.6%): $^1$H NMR (CDCl$_3$) δ 8.1 (s, 1H), 7.32 (s, 1H), 4.15 (q, 2H), 1.6 (t, 3H).

As shown in step 2-v of Scheme 2, 40.51 mL of a 25% MeONa/MeOH solution was added to 5-bromo-2-chloro-3-ethoxypyridine (4.3 g, 17.27 mmol). The reaction mixture was refluxed for 2 hours. After cooling, ethyl acetate and brine were added to the mixture. The organic phase was dried with MgSO$_4$, filtered, and evaporated under reduced pressure. After purification via silica gel chromatography, 5-bromo-3-ethoxy-2-methoxypyridine (Compound 2004, 2.1 g, 50% yield) was obtained: $^1$H NMR (CDCl$_3$) δ 7.8 (s, 1H), 7.15 (s, 1H), 4.1 (q, 2H), 4.0 (s, 3H), 1.5 (t, 3H). The following compounds were synthesized by an analogous procedure: 5-Bromo-3-isopropoxy-2-methoxypyridine: $^1$H NMR (CDCl$_3$) δ 7.7 (s, 1H), 7.1 (s, 1H), 4.55-4.5 (m, 1H), 3.9 (s, 3H), 1.3 (d, 6H); 5-bromo-2-ethoxy-3-methoxypyridine: ESMS (M+H) 232, 234; 5-bromo-3-methoxy-2-propoxypyridine: ESMS (M+H) 246, 248; 5-bromo-2-isopropoxy-3-methoxypyridine: ESMS (M+H) 246, 248; 5-bromo-2-(2,2-difluoroethoxy)-3-methoxypyridine: ESMS (M+H) 268, 270; 5-bromo-2,3-diethoxypyridine: ESMS (M+H) 246, 248; 5-bromo-2-(2,2-difluoroethoxy)-3-ethoxypyridine: ESMS (M+H) 282, 284; 5-bromo-3-ethoxy-2-propoxypyridine: ESMS (M+H) 260, 262; 5-bromo-3-ethoxy-2-isopropoxypyridine: ESMS (M+H) 260, 262; 5-bromo-3-(2-fluoroethoxy)-2-methoxypyridine: ESMS (M+H) 250, 252; 5-bromo-2-methoxy-3-propoxypyridine: ESMS (M+H) 246, 248; 5-bromo-2-methoxy-3-(2-methoxyethoxy)pyridine: ESMS (M+H) 262, 264; 5-bromo-3-(2,2-difluoroethoxy)-2-methoxypyridine: $^1$H NMR (CDCl$_3$) δ 7.9 (d, 1H), 7.2 (d, 1H), 6.1 (tt, 1H), 4.4 (q, 2H), 4.2 (td, 2H), 1.4 (t, 3H); 5-bromo-2-ethoxy-3-isopropoxypyridine: $^1$H NMR (CDCl$_3$) δ 7.7 (d, 1H), 7.1 (d, 1H), 4.4 (m, 1H), 4.3 (q, 2H), 1.3 (m, 9H); 5-bromo-3-butoxy-2-methoxypyridine: ESMS (M+H) 260, 262; 5-bromo-2-methoxy-3-(2,2,2-trifluoroethoxy)pyridine: ESMS (M+H) 286, 288; and 5-bromo-2-ethoxy-3-(2,2,2-trifluoroethoxy) pyridine: ESMS (M+H) 300, 302.

Also prepared by a procedure analogous to that shown in Scheme 2 were 5-methoxy-3-bromopyridine, 5-difluoromethoxy-3-bromopyridine, 2-amino-3-difluoromethoxy-5-bromopyridine, 2,3-dimethoxy-5-bromopyridine, 2-ethoxy-3-methoxy-5-bromopyridine, 2-(2-methoxyethoxy)-3-methoxy-5-bromopyridine, 2-(2-ethoxyethoxy)-3-methoxy-5-bromopyridine, 2-(2-propyloxyethoxy)-3-methoxy-5-bromopyridine, 2-(2-ethoxybutoxy)-3-methoxy-5-bromopyridine, 2-(2-(2-methoxyethoxy)ethoxy)-3-methoxy-5-bromopyridine, 2,3-diethoxy-5-bromopyridine, 2-methoxy-3-propoxy-5-bromopyridine, 2-methoxy-3-(2-methoxyethoxy)-5-bromopyridine, 2-methoxy-3-(2-butoxyethoxy)-5-bromopyridine, 2-methoxy-3-(3-methoxypropyloxy)-5-bromopyridine, 2-methoxy-3-(tetrahydro-2H-pyran-4-yloxy)-5-bromopyridine, and 2-methoxy-3-(tetrahydro-2H-pyran-4-yloxy)-5-bromopyridine.

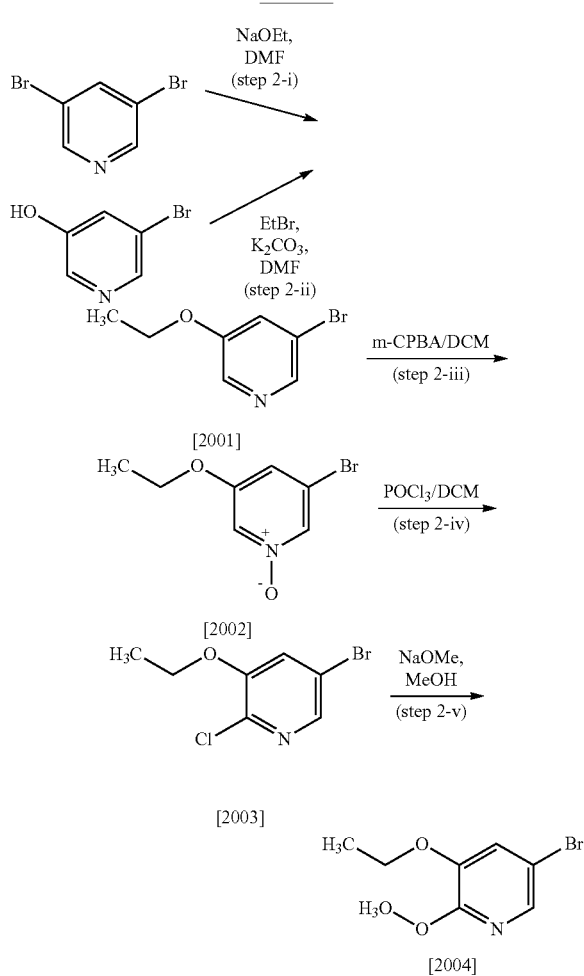

Scheme 2

Example 3(a). Preparation of 5-bromo-3-(difluoromethoxy)-2-methoxypyridine (Compound 2010)

As shown in step 3(a)-i of Scheme 3(a), 2-chloro-3-hydroxypyridine (Compound 2005, 2.0 g, 15.4 mmol, obtained from Aldrich Chemical Co.) was dissolved in 40 mL of DMF and 5.0 mL of water along with sodium chlorodifluoroacetate (4.71 g, 30.9 mmol, obtained from Lancaster Synthesis, Inc.) and anhydrous potassium carbonate (2.56 g; 18.5 mmol). The reaction mixture was heated in an oil bath at 100° C. for 2 hours. Another equivalent of sodium chlorodifluoroacetate and 1.2 equiv. of potassium carbonate were added and heating continued for an additional 2.0 hours. After this time, the reaction was cooled and the volatiles removed under reduced pressure. The residue was partitioned between brine and ethyl acetate and the organics washed once more with brine, dried over Na$_2$SO$_4$, filtered, and the volatiles removed under reduced pressure. The product was purified by silica gel chromatography, eluting with a hexanes/DCM to DCM gradient, to produce 2-chloro-3-(difluoromethoxy)pyridine as a white solid (Compound 2006, 2.0 g, 72% yield): ESMS (M+H) 180; $^1$H NMR (CDCl$_3$) δ 8.05 (m, 1H), 7.45 (m, 1H), 6.90 (m, 1H), 6.60 (t, 1H; J=75 Hz), 4.01 (s, 3H).

As shown in step 3(a)-ii of Scheme 3(a), an excess of sodium metal was dissolved into 20 mL anhydrous methanol and 2-chloro-3-(difluoromethoxy)pyridine (2.0 g, 11.1 mmol) in anhydrous methanol was added. The reaction mixture was stirred in a sealed vessel at 100° C. for 6 hours. The volatiles were removed under reduced pressure and the residue was partitioned between EtOAc and brine. The brine was extracted with EtOAc and the combined organics were dried over Na$_2$SO$_4$, filtered, and the volatiles removed under reduced pressure. The product was purified by silica gel chromatography (DCM) to yield 3-(difluoromethoxy)-2-methoxypyridine as a colorless oil (Compound 2007, 1.1 g, 56% yield: ESMS (M+H) 176.

As shown in step 3(a)-iii of Scheme 3(a), 3-(difluoromethoxy)-2-methoxypyridine (270 mg, 1.54 mmol) was dissolved in 5 mL of DCM and BBr$_3$ (540 μL; 1275 mg; 4.10 mmol) in heptane was added. The reaction mixture was stirred for 10 minutes at RT under an atmosphere of nitrogen, brought to reflux, and then stirred an additional 4 hours. The mixture was cooled and water was added to quench the reaction. The pH was adjusted to 7-8 with sodium bicarbonate, the organics partitioned, and the aqueous layer saturated with NaCl and extracted twice more with DCM. The combined organics were dried over Na$_2$SO$_4$, filtered, and the volatiles removed under reduced pressure. The product was purified by silica gel chromatography (DCM to 5% MeOH/DCM gradient) to yield 3-(difluoromethoxy)pyridin-2-ol as a white solid (Compound 2008, 986 mg, 97% yield): ESMS (M+H) 162.

As shown in step 3(a)-iv of Scheme 3(a), 3-(difluoromethoxy)pyridin-2-ol (986 mg; 6.12 mmol) was dissolved in 25 mL of glacial acetic acid and sodium acetate (79 mg; 9.6 mmol) was added. The mixture was cooled in an ice bath and bromine (780 μL; 1.63 g; 10.22 mmol) in 10 mL of glacial acetic acid was added over 10 minutes. The reaction was stirred for 30 minutes at 10-15° C. The volatiles were removed under reduced pressure and the residue was partitioned between brine/saturated sodium carbonate solution and ethyl acetate. After the evolution of gas ceased, the organic and aqueous layers were separated and the aqueous solution extracted three additional times with EtOAc. The combined organics were dried over Na$_2$SO$_4$, filtered, and the volatiles removed under reduced pressure. The residue was purified twice by silica gel chromatography (first a DCM to 10% MeOH/DCM gradient then 1:1 EtOAc/hexanes) to provide 5-bromo-3-(difluoromethoxy)pyridin-2-ol as a light yellow powder (Compound 2009, 810 mg, 55% yield): ESMS (M+H) 241.9/243.9; $^1$H NMR (CDCl$_3$) δ 13.2 (br m, 1H), 7.44 (d, 1H, J=2.1 Hz), 7.18 (d, 1H, J=2.1 Hz), 6.92 (t, 1H, J=75 Hz).

As shown in step 3(a)-v of Scheme 3(a), 5-bromo-3-(difluoromethoxy)pyridin-2-ol (300 mg; 1.25 mmol) was dissolved in 5 mL of chloroform. Silver carbonate (690 mg; 2.5 mmol) and methyl iodide (780 μL; 1.77 g; 12.5 mmol) were added and the mixture stirred at RT overnight. The reaction mixture was filtered through diatomaceous earth, which was washed with additional CHCl$_3$. The filtrates were concentrated under reduced pressure to yield an oil which was purified by silica gel chromatography to yield 5-bromo-3-(difluoromethoxy)-2-methoxypyridine as a white solid (Compound 2010, 250 mg, 78% yield): ESMS (M+H) 254/256; $^1$H NMR (CDCl$_3$) δ 8.08 (d, 1H, J=2.1 Hz), 7.56 (d, 1H, J=2.1 Hz), 6.60 (t, 1H, J=75 Hz), 3.98 (s, 3H).

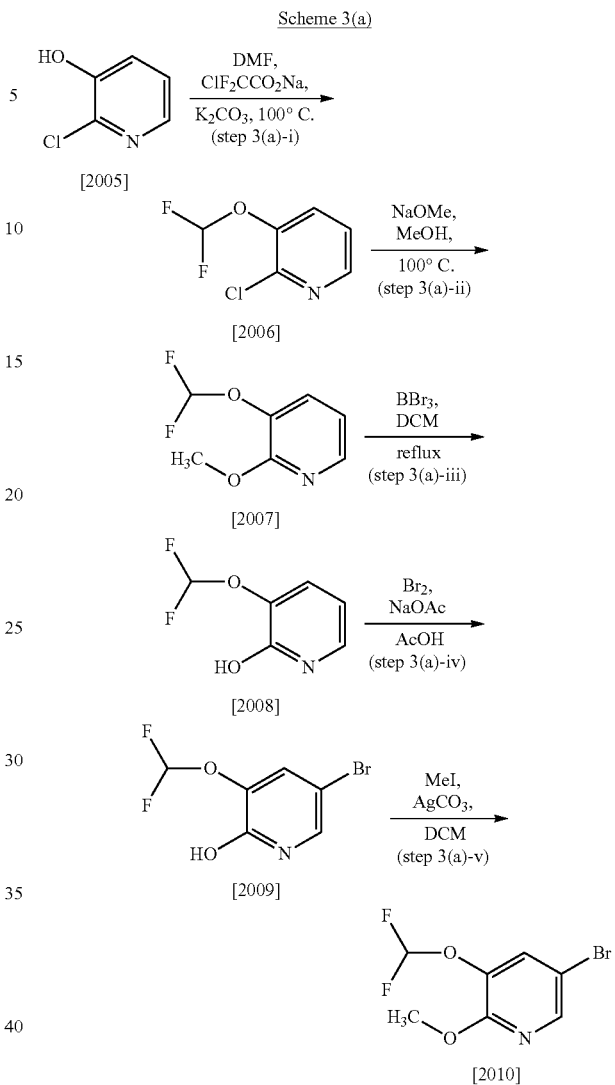

Example 3(b). Preparation of 5-bromo-2-ethoxy-3-methoxypyridine (Compound 2011) and 5-bromo-2,3-dimethoxypyridine (Compound 2012)

As shown in step 3(b)-i of Scheme 3(b), 5-bromo-2-chloro-3-methoxypyridine (1.0 g, 4.5 mmol, prepared in the same manner as Compound 2003 in Example 2 starting with 3-bromo-5-methoxypyridine) was treated with a sodium ethoxide/ethanol solution (5.05 mL, 21% w/v, 13.5 mmol) and the reaction mixture microwave irradiated at 100° C. for 20 minutes. Water was added and the ethanol evaporated under reduced pressure. The resulting aqueous solution was extracted with DCM and ether, followed by drying the combined extracts over MgSO4. After filtration, removal of the volatiles under reduced pressure provided 5-bromo-2-ethoxy-3-methoxypyridine (Compound 2011), 0.72 g, 69% yield): ESMS (M+H) 232.32/234.23. As shown in step 3(b)-ii of Scheme 3(b), Compound 2012 (ESMS (M+H) 218.32/220.23) was prepared in the same manner as Compound 2011, using sodium methoxide in methanol instead of sodium ethoxide in ethanol.

Scheme 3(b)

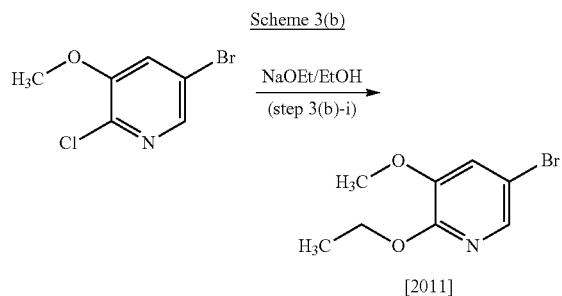

[2011]

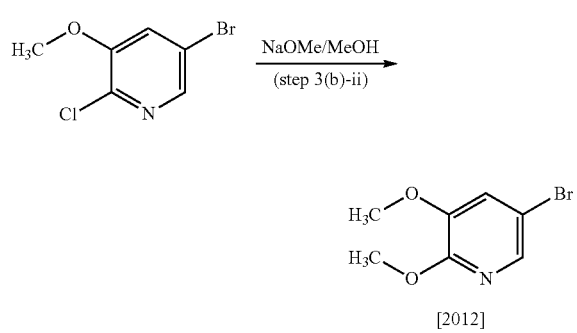

[2012]

Scheme 4(a)

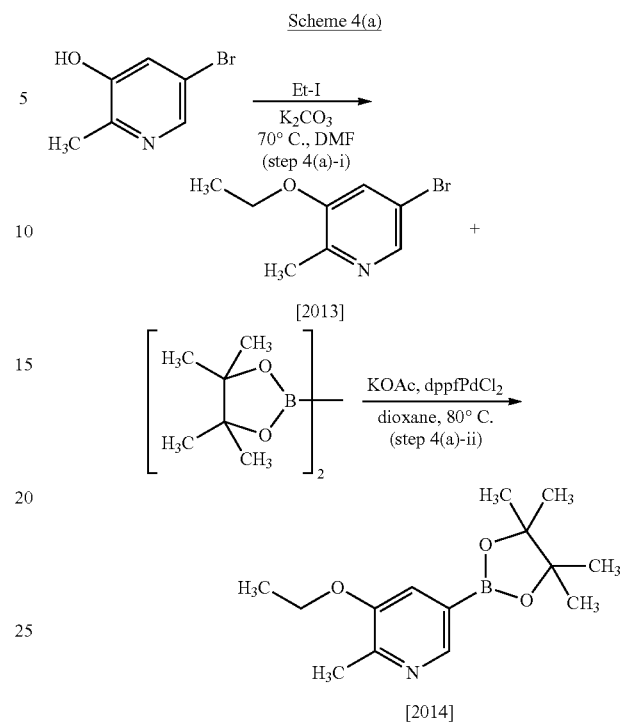

[2014]

Example 4(a). Preparation of 3-ethoxy-2-methyl-5-(4,4,5,5-tetramethyl-1,3,2-dioxaborolan-2-yl)pyridine (Compound 2014)

As shown in step 4(a)-i of Scheme 4(a), iodoethane (13.69 g, 7.021 mL, 87.75 mmol) was added to 5-bromo-2-methylpyridin-3-ol (5.5 g, 29.25 mmol) and $K_2CO_3$ (12.13 g, 87.75 mmol) in 200 mL DMF. The mixture was stirred at 70° C. overnight and sat'd NaHCO3 was added to the mixture. The mixture was extracted with EtOAc (3×) and the combined organics were washed with water (3×) and brine. After drying over sodium sulfate, the mixture was filtered and concentrated under reduced pressure. The residue was purified by medium pressure silica gel chromatography (30% EtOAc in hexane) to yield 5-bromo-3-ethoxy-2-methylpyridine (Compound 2013, 4.6 g, 65% yield): ESMS (M+H) 216.18; $^1$H NMR (CDCl$_3$) δ 8.14 (d, J=1.9 Hz, 1H), 7.20 (d, J=1.8 Hz, 1H), 4.03 (q, J=7.0 Hz, 2H), 2.43 (s, 3H), 1.47 (t, J=7.0 Hz, 3H)

As shown in step 4(a)-ii of Scheme 4(a), 5-bromo-3-ethoxy-2-methylpyridine (4.16 g, 19.25 mmol), 4,4,5,5-tetramethyl-2-(4,4,5,5-tetramethyl-1,3,2-dioxaborolan-2-yl)-1,3,2-dioxaborolane (5.866 g, 23.10 mmol) and KOAc (5.668 g, 57.75 mmol) were mixed in 200 mL dioxane. The mixture was degassed for 1 h with $N_2$, then 1,1'-bis(diphenylphosphino)-ferrocene dichloro-palladium.dichloromethane (162.6 mg, 0.1925 mmol) was added and the mixture was heated at 80° C. under $N_2$ for 16 hours. After cooling to RT, MTBE was added to the mixture, which was then was through Florisil®. The solvent was removed under reduced pressure to obtain a grey solid, which was triturated with hexanes to afford 3-ethoxy-2-methyl-5-(4,4,5,5-tetramethyl-1,3,2-dioxaborolan-2-yl)pyridine (Compound 2014, 4.05 g, 80% yield): $^1$H NMR (CDCl$_3$) δ 8.43 (d, J=1.1 Hz, 1H), 7.40 (s, 1H), 4.03 (d, J=7.0 Hz, 2H), 2.51 (s, 3H), 1.46 (t, J=7.0 Hz, 3H), 1.37 (s, 12H).

Example 4(b). Preparation of N-ethyl-2-methoxy-5-(4,4,5,5-tetramethyl-1,3,2-dioxaborolan-2-yl)nicotinamide (Compound 2016)

As shown in step 4(b)-i of Scheme 4(b), HATU (8.194 g, 2.55 mmol) and DIPEA (5.570 g, 7.507 mL, 43.10 mmol) was added to a solution of 5-bromo-2-methoxypyridine-3-carboxylic acid (5 g, 21.55 mmol) in DMF (50 mL). The resulting solution was stirred for 10 minutes followed by the addition of ethanamine hydrochloric acid (1.757 g, 2.196 mL, 21.55 mmol). The resulting solution was stirred at room temperature for 5 hours. To the reaction mixture was added water (100 mL) and ethyl acetate (100 mL). The organic layer was separated and dried over anhydrous sodium sulfate, filtered, and concentrated under reduced pressure. The crude residue was purified by silica gel chromatography (0-2% methanol in dichloromethane gradient) to produce 5-bromo-N-ethyl-2-methoxynicotinamide as off white solid (Compound 2015, 3.4 g): $^1$H NMR (DMSO-d$_6$) δ 8.41 (d, J=2.5 Hz, 1H), 8.31 (s, 1H), 8.20-8.13 (m, 1H), 3.95 (s, 3H), 3.35-3.23 (m, 2H), 1.11 (t, J=7.2 Hz, 3H).

As shown in step 4(b)-ii of Scheme 4(b), a sealed tube was charged with Bis(dipinacolato)diboron (3.332 g, 13.12 mmol), dichloro-bis(tricyclohexylphosphoranyl)palladium (484.2 mg, 0.6560 mmol), KOAc (3.863 g, 39.36 mmol), and 2-methyltetrahydrofuran (52.46 mL). The mixture was degassed for 10 min then heated in an oil bath for 12 h at 125° C. The reaction was deemed complete by HPLC. Workup by filtration through florisil and concentration in vacuo. Triturated the yellow oil with hexanes causing ppt'n of off white solid. Collected under vacuum filtration and dried under high vacuum to constant mass (4.7 g). 1H NMR (300 MHz, DMSO) d 8.43 (d, J=2.0 Hz, 1H), 8.27 (d, J=2.0 Hz, 1H), 8.23 (d, J=5.5 Hz, 1H), 3.98 (s, 3H), 3.35-3.25 (m, 2H), 1.26 (s, 12H), 1.12 (t, J=7.2 Hz, 3H)

Scheme 4(b)

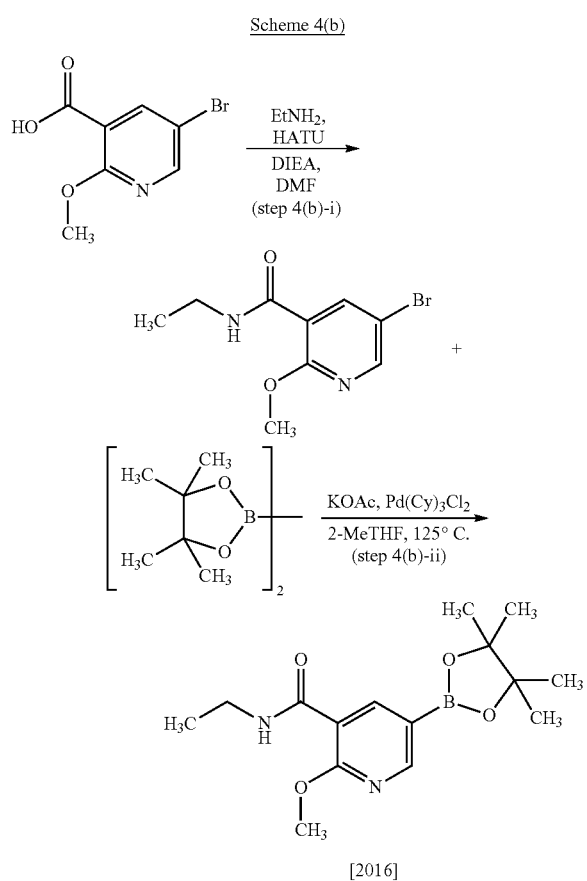

Example 5. Preparation of 2-[4-[5-(5,6-dimethoxy-3-pyridyl)-1-oxo-isoindolin-2-yl]pyrazol-1-yl]acetonitrile (Compound 3)

As shown in step 5-i of Scheme 5, methyl 4-bromo-2-(bromomethyl)benzoate (Compound 2018, 2.08 g, 6.75 mmol; prepared by reacting 1-(4-bromo-2-methylphenyl)ethanone with NBS), 1H-pyrazol-4-amine (561 mg, 6.75 mmol), and DIEA (873 mg, 1.18 mL, 6.75 mmol) were combined in DMF (7.78 mL) and heated at 110° C. for 90 min. The reaction mixture was diluted with MeOH (60 mL) and the resulting white crystalline solid was collected by filtration and dried under vacuum to give 5-bromo-2-(1H-pyrazol-4-yl)isoindolin-1-one (Compound 2019, 1.21 g, 4.35 mmol, 64% yield): ESMS (M+H) 279.99.

As shown in step 5-ii of Scheme 5, 5-bromo-2-(1H-pyrazol-4-yl)isoindolin-1-one (1.2 g, 4.32 mmol) was combined with cesium carbonate (1.69 g, 5.18 mmol) in DMF (10 mL) in a sealable tube and nitrogen gas was bubbled through the solution for 5 minutes. 2-Iodoacetonitrile (1.08 g, 468 µL, 6.47 mmol) was added and the tube was sealed and heated to 110° C. in an oil bath for 18 hours. Additional iodoacetonitrile added (0.5 mL) and the reaction mixture was heated for an additional 24 hours. The reaction mixture was poured into H$_2$O/EtOAc and the resulting dark brown solid was collected by filtration. The solid was washed with MeOH and then diethyl ether to provide 2-[4-(5-bromo-1-oxo-isoindolin-2-yl)pyrazol-1-yl]acetonitrile (Compound 2020, 920 mg, 2.9 mmol, 67% yield): ESMS (M+H) 319.04; $^1$H NMR (DMSO-d$_6$) δ 8.35 (s, 1H), 7.92 (m, 2H), 7.70 (m, 2H), 5.53 (s, 2H), 4.88 (s, 2H).

As shown in step 5-iii of Scheme 5, 2,3-dimethoxy-5-(4,4,5,5-tetramethyl-1,3,2-dioxaborolan-2-yl)pyridine [Compound 2021, 376 mg, 1.42 mmol; prepared by reacting 5-bromo-2,3-dimethoxypyridine with 4,4,5,5-tetramethyl-2-(4,4,5,5-tetramethyl-1,3,2-dioxaborolan-2-yl)-1,3,2-dioxaborolane], 2-[4-(5-bromo-1-oxo-isoindolin-2-yl)pyrazol-1-yl]acetonitrile (450 mg, 1.42 mmol), and cesium carbonate (925 mg, 2.84 mmol) were taken up in DMSO (7.5 mL) in a sealable tube. Nitrogen gas was bubbled through the solution for 5 minutes, dppfPdCl$_2$ (141 mg, 0.17 mmol) added, and the vessel sealed. The reaction mixture was heated to 100° C. for 50 min. After cooling, the mixture was poured into EtOAc/H$_2$O, the resulting dark solid material filtered off, and the organics passed through a plug of florisil. The filtrate was concentrated to a solid under reduced pressure, the residue was suspended in MeOH, and the solid collected by filtration to give 2-[4-[5-(5,6-dimethoxy-3-pyridyl)-1-oxo-isoindolin-2-yl]pyrazol-1-yl]acetonitrile as a solid (Compound 3, 323 mg, 57% yield): ESMS (M+H) 376.28; $^1$H NMR (DMSO-d$_6$) δ 8.37 (s, 1H), 8.11 (d, J=1.8 Hz, 1H), 7.99 (s, 1H), 7.95 (s, 1H), 7.84 (m, 2H), 7.64 (d, J=1.7 Hz, 1H), 5.55 (s, 2H), 4.93 (s, 2H), 3.93 (s, 3H), 3.91 (s, 3H).

Scheme 5

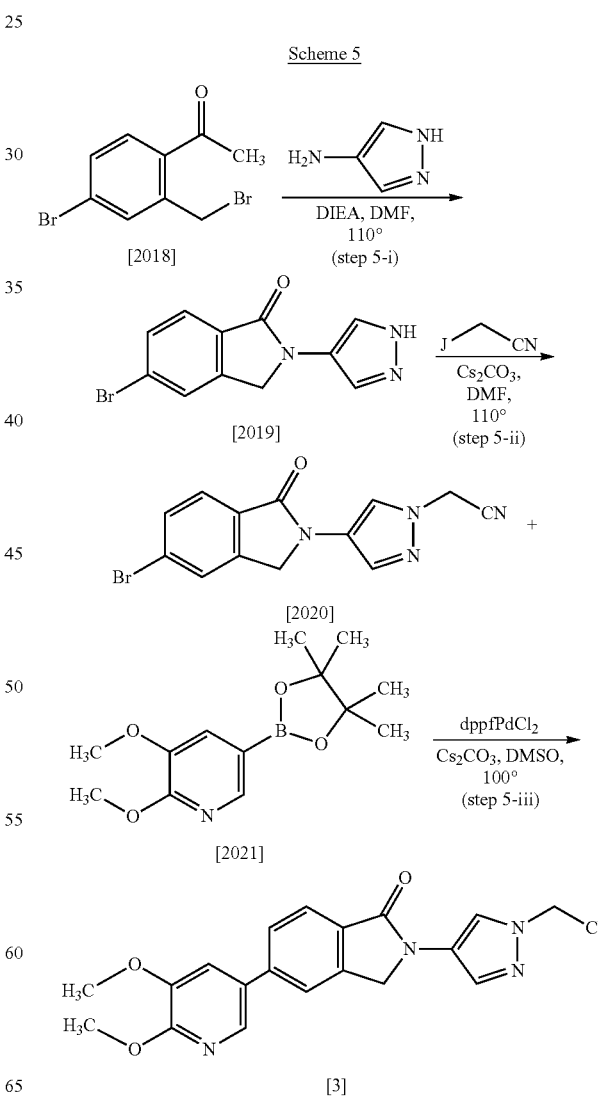

Example 6. Preparation of 2-(4-(5-(5,6-dimethoxy-pyridin-3-yl)-7-methyl-1-oxoisoindolin-2-yl)-1H-pyrazol-1-yl)acetonitrile (Compound 48)

As shown in step 6-i of Scheme 6, 2,3-dimethoxy-5-(4,4,5,5-tetramethyl-1,3,2-dioxaborolan-2-yl)pyridine (Compound 2021, 920 mg, 3.47 mmol), methyl 4-bromo-2,6-dimethyl-benzoate (844 mg, 3.47 mmol), and $Cs_2CO_3$ (2.26 g, 6.94 mmol) were taken up in DMSO (12 mL) in a sealable tube. Nitrogen gas was bubbled through the solution for 5 minutes, dppfPdCl$_2$ (141 mg, 0.174 mmol) added, and the vessel sealed. The reaction mixture was heated at 90° C. for 60 minutes under an atmosphere of nitrogen. After cooling, the mixture was poured into EtOAc/water. The organics were washed with water, brine, passed through a plug of Florisil®, and concentrated under reduced pressure to give a solid. The solid was suspended in MeOH and collected by filtration to provide methyl 4-(5,6-dimethoxy-3-pyridyl)-2,6-dimethyl-benzoate (Compound 2022, 310 mg). The filtrate was concentrated and purified by silica gel chromatography (0 to 50% EtOAc/hex) to provide an additional 400 mg of Compound 2022 (total yield 710 mg, 2.4 mmol, 68% yield). This compound was used in subsequent reactions as is.

As shown in step 6-ii of Scheme 6, Compound 2022 (710 mg, 2.36 mmol) was dissolved in $CCl_4$ (20 mL) and $K_2CO_3$ (651 mg, 4.71 mmol), NBS (461 mg, 2.59 mmol), and benzoyl peroxide (57 mg, 0.24 mmol) were added. The reaction mixture was heated to reflux for 4 hours. After cooling to room temperature, the reaction mixture was filtered and the solid washed with $CCl_4$. The filtrate was concentrated to an oil under reduced pressure and purified by silica gel chromatography to provide methyl 2-(bromomethyl)-4-(5,6-dimethoxy-3-pyridyl)-6-methyl-benzoate (Compound 2023, 685 mg, about 70% pure). This compound was used in subsequent reactions as is.

As shown in step 6-iii of Scheme 6, 1H-pyrazol-4-amine (149 mg, 1.79 mmol), methyl 2-(bromomethyl)-4-(5,6-dimethoxy-3-pyridyl)-6-methyl-benzoate (680 mg, 1.79 mmol) and DIEA (231 mg, 312 µL, 1.79 mmol) were combined in DMF (5 mL), heated to 90° C. for 6 hours, and allowed to cool to room temperature over 16 hours. The reaction mixture was taken up in EtOAc/water and the organic layer washed with water, brine, dried, and concentrated under reduced pressure to yield a foam. The foam was recrystallized in DCM/MeOH. The resulting solid was collected by filtration, washed with DCM, and dried under vacuum to provide 5-(5,6-dimethoxy-3-pyridyl)-7-methyl-2-(1H-pyrazol-4-yl)isoindolin-1-one (Compound 2024, 115 mg). The filtrate from the recrystallization was concentrated under reduced pressure and the residue purified by silica gel chromatography (20 to 100% EtOAc/hex) to yield an additional 88 mg of Compound 2024 (total yield 203 mg, 0.66 mmol, 32% yield): ESMS (M+H) 351.26; $^1$H NMR (DMSO-d$_6$) δ 12.83 (s, 1H), 8.10 (m, 2H), 7.88 (s, 1H), 7.74 (s, 1H), 7.61 (s, 2H), 4.83 (s, 2H), 3.92 (s, 3H), 3.91 (s, 3H), 2.72 (s, 3H).

As shown in step 6-iv of Scheme 6, 5-(5,6-dimethoxy-3-pyridyl)-7-methyl-2-(1H-pyrazol-4-yl)isoindolin-1-one (88 mg, 0.25 mmol) was dissolved in DMF (2 mL) with $Cs_2CO_3$ (123 mg, 0.38 mmol). 2-Bromoacetonitrile (45 mg, 0.38 mmol) was added and the reaction mixture stirred overnight at room temperature. The reaction mixture was diluted with MeOH/H$_2$O/EtOAc and the resulting white solid was collected by filtration; washed sequentially with water, MeOH, and Et$_2$O; and dried under vacuum to provide 2-(4-(5-(5,6-dimethoxypyridin-3-yl)-7-methyl-1-oxoisoindolin-2-yl)-1H-pyrazol-1-yl)acetonitrile (Compound 48, 30 mg, 0.077 mmol, 29% yield): ESMS (M+H) 390.29; $^1$H NMR (DMSO-d$_6$) δ 8.34 (s, 1H), 8.10 (d, J=1.8 Hz, 1H), 7.95 (s, 1H), 7.76 (s, 1H), 7.68-7.53 (m, 2H), 5.53 (s, 2H), 4.85 (s, 2H), 3.92 (s, 3H), 3.91 (s, 3H), 2.72 (s, 3H).

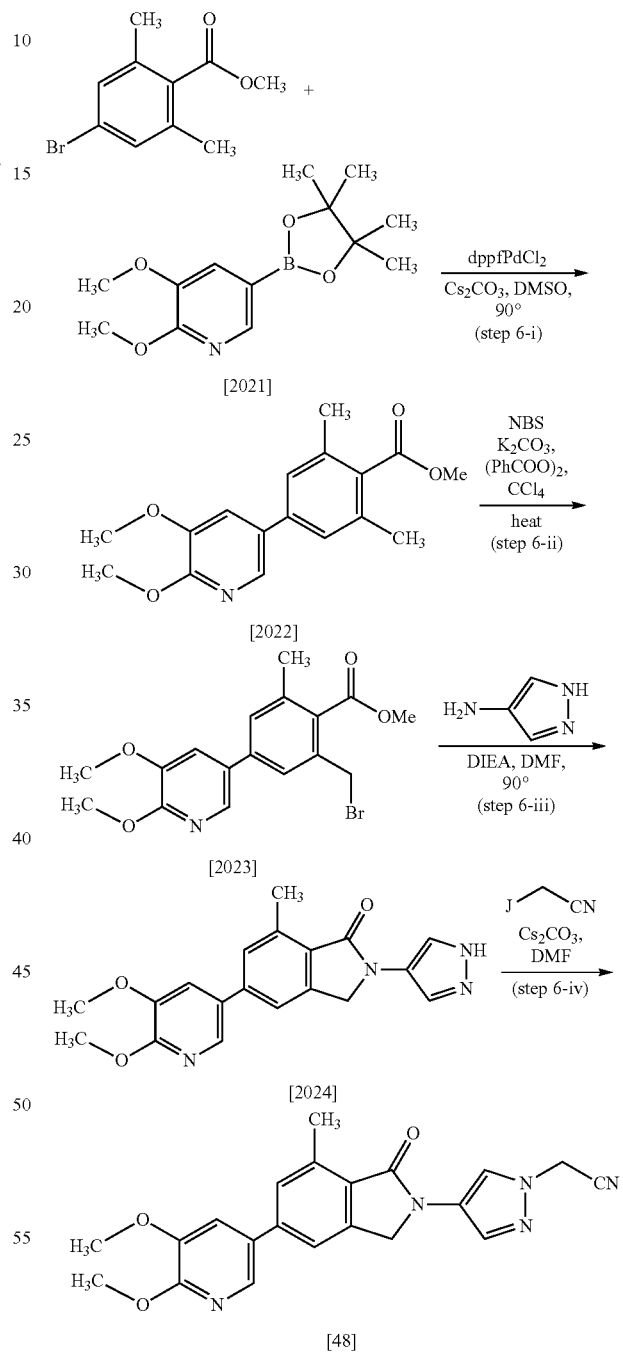

Scheme 6

Example 7. Preparation of 2-(4-(7-chloro-5-(5,6-dimethoxypyridin-3-yl)-1-oxoisoindolin-2-yl)-1H-pyrazol-1-yl)acetonitrile (Compound 58)

As shown in step 7-i of Scheme 7, 2,3-dimethoxy-5-(4,4,5,5-tetramethyl-1,3,2-dioxaborolan-2-yl)pyridine (503 mg, 1.9 mmol), methyl 4-bromo-2-chloro-6-methyl-benzoate (500 mg, 1.9 mmol), and Cs$_2$CO$_3$ (1.24 g, 3.8 mmol) were combined in DMSO (7 mL) in a sealable tube. Nitrogen gas was bubbled through the solution for 5 minutes, dppfPdCl$_2$ (78 mg, 0.1 mmol) added, and the vessel sealed. The reaction mixture was heated at 90° C. for 60 minutes under an atmosphere of nitrogen. After cooling, the mixture was poured into EtOAc/water. The organic layer washed with water, brine, passed through a plug of Florisil®, and concentrated under reduced pressure. The resulting oil which was purified by silica gel chromatography (0 to 50% EtOAc/hexanes) to provide methyl 2-chloro-4-(5,6-dimethoxy-3-pyridyl)-6-methyl-benzoate (Compound 2025, 367 mg, 1.14 mmol, 60% yield): ESMS (M+H) 322.12.

As shown in step 7-ii of Scheme 7, methyl 2-chloro-4-(5,6-dimethoxy-3-pyridyl)-6-methyl-benzoate (365 mg, 1.13 mmol) was dissolved in CCl$_4$ (20 mL) and NBS (162 mg, 0.907 mmol) added. The reaction mixture heated to reflux for 3 hours, at which time K$_2$CO$_3$ (150 mg) and additional NBS (60 mg) were added. The reaction mixture was heated an additional 6 hours. At this time, HPLC analysis indicated that about 30% of the starting material (Compound 2025) had been converted to Compound 2026. Additional NBS (60 mg) was added and the reaction mixture refluxed for an additional 6 hours, followed by allowing the mixture to stand at room temperature overnight. At this time, HPLC analysis indicated that about 50% of the starting material had been converted to product. The reaction mixture was filtered, washed with CCl$_4$, and the filtrate concentrated under reduced pressure to give crude 2-(4-(7-chloro-5-(5,6-dimethoxypyridin-3-yl)-1-oxoisoindolin-2-yl)-1H-pyrazol-1-yl)acetonitrile (Compound 2026) as an oil, which was used in subsequent reactions as is.

As shown in step 7-iii of Scheme 7, Compound 2026 obtained from step 7-ii was dissolved in DMF (5 mL) and 2-(4-aminopyrazol-1-yl)acetonitrile (100 mg, 0.82 mmol) and DIEA (226 mg, 304 µL, 1.75 mmol) were added. The reaction mixture was heated to 80° C. for 4 hours, cooled to room temperature, and allowed to stand overnight. The mixture was poured into EtOAc/water (1:1 160 mL). The organic layer was washed with water, dried, and concentrated under reduced pressure to a yield a residue which solidified when treated with MeOH (20 mL). The solid was collected by filtration, taken up in EtOAc (30 mL), and heated to reflux. After cooling to room temperature, the crystalline product was collected by filtration dried in vacuo to provide 2-(4-(7-chloro-5-(5,6-dimethoxypyridin-3-yl)-1-oxoisoindolin-2-yl)-1H-pyrazol-1-yl)acetonitrile (Compound 58, 68 mg, 0.17 mmol, 15% yield): ESMS (M+H) 410.3; $^1$H NMR (DMSO-d$_6$) δ 8.36 (s, 1H), 8.16 (d, J=1.8 Hz, 1H), 7.97 (m, 2H), 7.92 (s, 1H), 7.69 (s, 1H), 5.56 (s, 2H), 4.90 (s, 2H), 3.93 (s, 3H), 3.92 (s, 3H).

Scheme 7

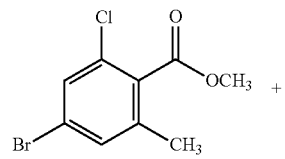

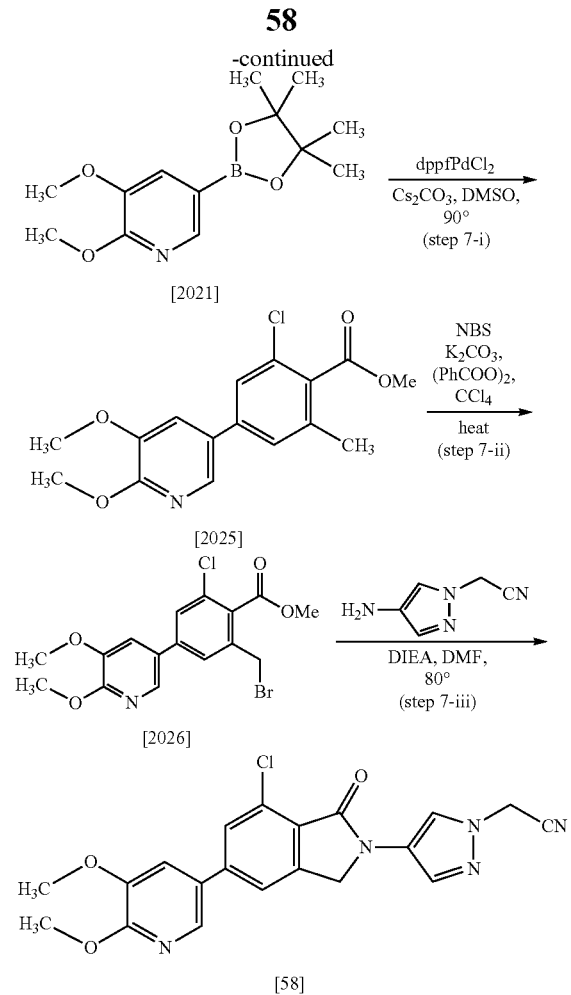

Example 8. Preparation of 2-(4-(2-(5,6-dimethoxypyridin-3-yl)-5-oxo-5H-pyrrolo[3,4-b]pyridin-6(7H)-yl)-1H-pyrazol-1-yl)acetonitrile (Compound 25)

As shown in step 8-i of Scheme 8, according to the procedure of International Patent Application Publication No. WO2006/095159, a mixture of ethyl 2-methyl-6-oxo-1,6-dihydropyridine-3-carboxylate (5.92 g, 32.6 mmol) in phosphorous oxychloride (45 mL) was heated at 90° C. for 1 hour. After cooling, the reaction mixture was concentrated under reduced pressure and ice water was added to the residue, followed by addition 28% ammonium hydroxide to adjust the pH to 7. The resulting white solid was collected by filtration, washed with ice water, and dried under high vacuum to give ethyl 6-chloro-2-methylnicotinate (Compound 2027, 6.18 g, 94.7% yield): ESMS (M+1) 200.19; $^1$H NMR (CDCl$_3$) δ 8.18 (d, J=8.2 Hz, 1H), 7.27 (d, J=8.2 Hz, 1H), 4.40 (q, J=7.1 Hz, 2H), 2.84 (s, 3H), 1.42 (t, J=7.4, 3H).

As shown in step 8-ii of Scheme 8, a mixture of ethyl 6-chloro-2-methylpyridine-3-carboxylate (Compound 2027, 4.0 g, 20 mmol), 2,3-dimethoxy-5-(4,4,5,5-tetramethyl-1,3,2-dioxaborolan-2-yl)pyridine (Compound 2021, 5.84 g, 22 mmol), Pd(PPh$_3$)$_4$ (1.15 g, 1 mmol), and sodium carbonate (6.37 g, 60 mmol) in a mixture of acetonitrile/water (3:1, 90 mL) was heated at 90° C. under an atmosphere of nitrogen for 4 hours. After cooling, the volatiles were removed under reduced pressure and the residue dissolved in DCM. After washing with water, the organic phase was dried (Na$_2$SO$_4$), filtered, and concentrated under reduced pressure. The residue was purified by silica gel chromatography (0-20% EtOAc/hexanes) to give ethyl 5',6'-dimethoxy-6-methyl-2,3'-bipyridine-5-carboxylate (Compound 2028, 5.8 g, 95.7% yield): ESMS (M+1) 303.41; $^1$H NMR (CDCl$_3$) δ 8.27 (d, J=1.8 Hz, 1H), 8.17 (d, J=8.2 Hz, 1H), 7.83 (d, J=1.8 Hz, 1H), 7.52 (d, J=8.3 Hz, 1H), 4.32 (q, J=7.1 Hz, 2H), 4.01 (s, 2H), 3.93 (s, 3H), 2.83 (s, 3H), 1.34 (t, J=7.1 Hz, 3H).

As shown in step 8-iii of Scheme 8, to a solution of Compound 2029 (4.4 g, 14.6 mmol) in CCl$_4$ (75 mL) was added 2,2'-azobis(isobutyronitrile) (AIBN, 239 mg, 1.46 mmol) and NBS (1.7 g, 9.55 mmol). The mixture was stirred at 80° C. for 1.5 hours under an atmosphere of nitrogen. The reaction mixture was filtered and concentrated. The residue was purified by silica gel chromatography (20% EtOAc/hexanes) to give a mixture of starting material and ethyl 5',6'-dimethoxy-6-bromomethyl-2,3'-bipyridine-5-carboxylate (Compound 2029, 4.44 g, about 60% pure): ESMS (M+1) 381.4, 383.19. The product was used as is in subsequent reactions.

As shown in step 8-iv of Scheme 8, a solution of the above mixture (Compound 2029, 2.2 g, about 60% pure) in DMF (40 mL) at 0° C. was added dropwise over 2 hours to a suspension of 2-(4-amino-1H-pyrazol-1-yl)acetonitrile (844 mg, 6.9 mmol) and sodium carbonate (732 mg, 6.9 mmol) in DMF (20 mL). After addition was complete, the reaction mixture was stirred at 0° C. for 2 hours and heated at 80° C. for 15 hours. Additional sodium carbonate (732 mg) was added and the reaction mixture was heated at 90° C. for an additional 7 hours. After cooling, the mixture was poured into water and a precipitate formed. The solid was collected by filtration, washed with methyl t-butyl ether, and dried under high vacuum to provide 2-(4-(2-(5,6-dimethoxypyridin-3-yl)-5-oxo-5H-pyrrolo[3,4-b]pyridin-6(7H)-yl)-1H-pyrazol-1-yl)acetonitrile (Compound 25, 450 mg).

Scheme 8

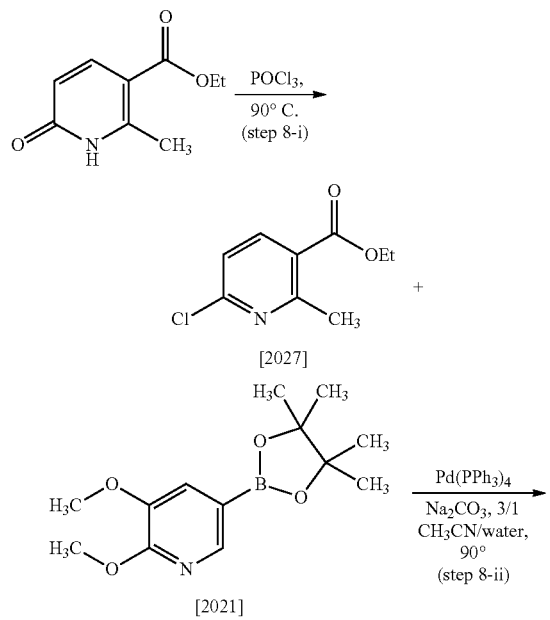

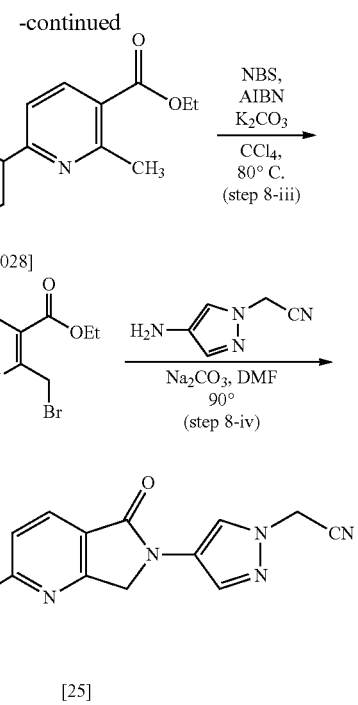

Example 9. Preparation of 2-(5,6-dimethoxypyridin-3-yl)-4-methoxy-6-(1-(2,2,2-trifluoroethyl)-1H-pyrazol-4-yl)-6,7-dihydro-5H-pyrrolo[3,4-b]pyridin-5-one (Compound 88)

As shown in step 9-i of Scheme 9, ethyl 4,6-dihydroxy-2-methylpyridine-3-carboxylate (Accla Biochem Inc.) was suspended in 50 mL of POCl$_3$ and heated to 90° C. under a nitrogen atmosphere for 5 hours. The reaction mixture was cooled and concentrated under reduced pressure. Ice was added to the dark oil with stirring followed by the addition of ethyl acetate and water. The organics were washed with water, brine, and dried over sodium sulfate. After filtration, the volatiles were removed under reduced pressure and the crude product purified by silica gel chromatography to yield ethyl 4,6-dichloro-2-methylnicotinate as a pale yellow oil (Compound 2030, 62% yield): ESMS (M+H) 234/236/238; $^1$H NMR (CDCl$_3$) δ 7.27 (s, 1H), 4.4 (quart, 2H), 2.55 s, 3H), 1.41 (t, 3H).

As shown in step 9-ii of Scheme 9, Compound 2030 (500 mg, 2.14 mmol) and of 2,3-dimethoxy-5-(4,4,5,5-tetramethyl-1,3,2-dioxaborolan-2-yl)pyridine (Compound 2021, 566 mg, 2.14 mmol) were dissolved into 10 mL of DME and flushed with nitrogen for 5 minutes. Tetrakistriphenylphosphine palladium(0) (250 mg, 0.2136 mmol) was added while continuing the flow of nitrogen. A solution of saturated aqueous 2M K$_2$CO$_3$ (2.2 mL) (flushed with nitrogen) was added and the mixture was heated to 70° C. for 1.5 hours. The volatiles were removed under reduced pressure and the residue treated with water and 2 mL of 1.0N HCl. A precipitate formed which was partitioned between EtOAc and water. The organics were washed with water, brine, dried over sodium sulfate, and the volatiles removed under reduced pressure. The crude product was purified by silica gel chromatography (DCM—25% EtOAc/DCM) to provide ethyl 4-chloro-5',6'-dimethoxy-6-methyl-2,3'-bipyridine-5-carboxylate (Compound 2031, 650 mg, 90% yield) of a white-beige solid: ESMS (M+1) 337/339; $^1$H NMR (CDCl$_3$)

δ 8.26 (d, 1H J=2 Hz), 7.77 (d, 1H, J=2 Hz), 7.56 (s, 1H), 4.48 (quart, 2H), 4.08 (s, 3H), 4.00 (s, 3H), 2.63 (s, 3H), 1.43 (t, 3H).

As shown in step 9-iii of Scheme 9, Compound 2031 (650 mg, 1.93 mmol) was dissolved in anhydrous methanol and to it was added 3.0 mL of freshly made 2.54M sodium methoxide. The reaction was heated under a nitrogen atmosphere at 60° C. for 16 hours. After cooling to room temperature, the volatiles were removed under reduced pressure and the residue was partitioned between water and EtOAc. The organics were washed with water, brine, dried over sodium sulfate, filtered, and the volatiles removed under reduced pressure. Purification by silica gel chromatography provided ethyl 4,5',6'-trimethoxy-6-methyl-2,3'-bipyridine-5-carboxylate (Compound 2032, 200 mg, 32% yield) as a of white solid: ESMS (M+1) 319; $^1$H NMR (CDCl$_3$) δ 8.23 (d, 1H, J=2 Hz), 7.8 (d, 1H, J=2 Hz), 7.06 (s, 1H), 4.07 (s, 3H), 3.99 (s, 3H), 3.94 (s, 3H).

As shown in step 9-iv of Scheme 9, Compound 2032 (200 mg, 0.628 mmol) and NBS (112 mg, 0.63 mmol) were added to 15 mL of CCl$_4$ and the solution purged with nitrogen for 5 minutes. Benzoyl peroxide (20 mole %) was added and the reaction mixture heated at 65° C. under nitrogen for 16 hours. An additional equivalent of NBS and 0.3 equivalents of benzoyl peroxide were added and heating continued for an additional hour. Potassium carbonate (1.0 g) was added as an acid scavenger and heating continued for an additional 24 hours. The reaction mixture was cooled and filtered through a cotton plug and the volatiles removed under reduced pressure. The residue was taken up in DCM and passed through a plug of silica gel, which was eluted with additional DCM. Elution with EtOAc recovered crude product, which was further purified by silica gel chromatography (DCM—1:1 EtOAc/DCM to give ethyl 6-(bromomethyl)-4,5',6'-trimethoxy-2,3'-bipyridine-5-carboxylate (Compound 2033, 87 mg of white solid: ESMS (M+1) 397/399.

As shown in step 9-v of Scheme 9, Compound 2033 (100 mg, 0.252 mmol), 1-(2,2,2-trifluoroethyl)-4-aminopyrazole (42 mg, 0.25 mmol), and DIEA (65 mg, 0.5 mmol) were dissolved in 4 mL of DMF and heated for 3 hours at 110° C. The reaction mixture was cooled, diluted with water, and extracted with EtOAc. The organics were washed with water, brine, dried over sodium sulfate, and solvent removed under reduced pressure. The crude product was passed through a plug of silica gel, which was eluted with 5% EtOH/EtOAc. Purification of the filtrate by silica gel chromatography (5% MeOH/DCM—7.5% MeOH/DCM) gave 2-(5,6-dimethoxypyridin-3-yl)-4-methoxy-6-(1-(2,2,2-trifluoroethyl)-1H-pyrazol-4-yl)-6,7-dihydro-5H-pyrrolo[3,4-b]pyridin-5-one (Compound 88, 11 mg, 9% yield) as a beige solid: ESMS (M+1) 450.

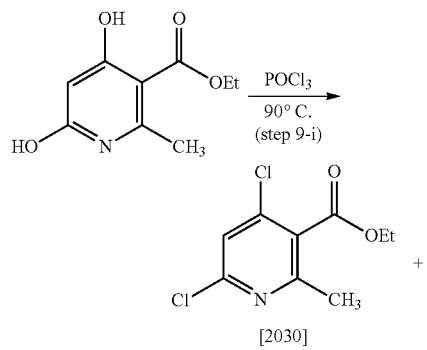

Scheme 9

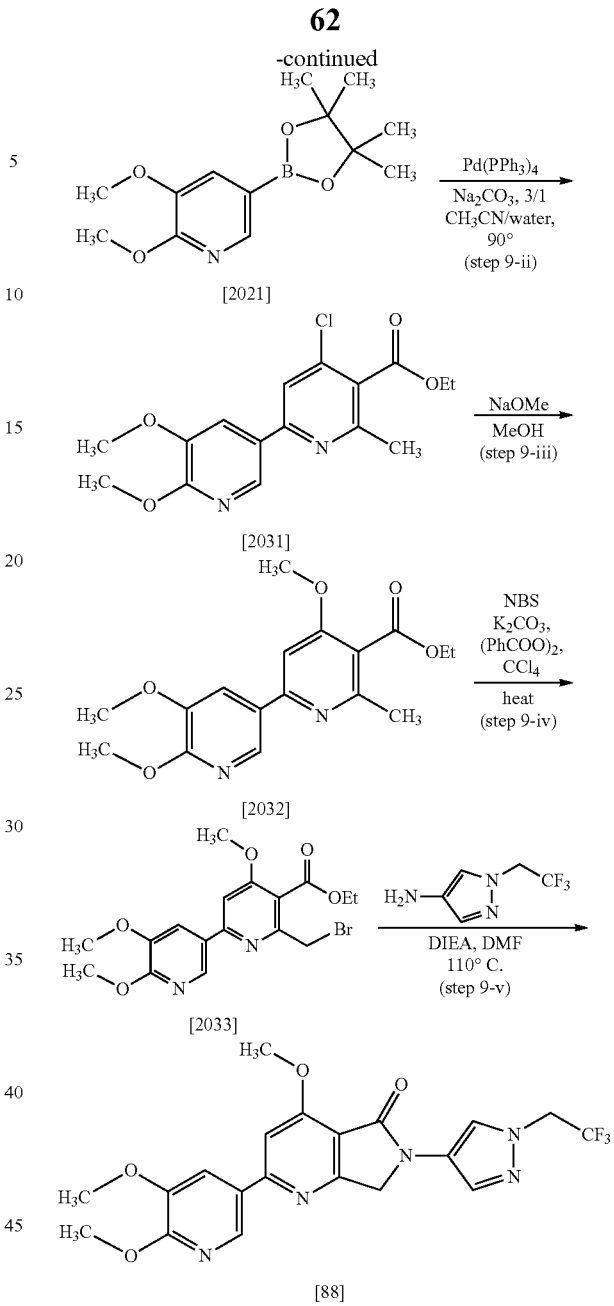

Example 10. Preparation of 4-chloro-2-(5,6-dimethoxypyridin-3-yl)-6-(1-(2,2,2-trifluoroethyl)-1H-pyrazol-4-yl)-6,7-dihydro-5H-pyrrolo[3,4-b]pyridin-5-one (Compound 82) and 2-(5,6-dimethoxypyridin-3-yl)-4-ethyl-6-(1-(2,2,2-trifluoroethyl)-1H-pyrazol-4-yl)-6,7-dihydro-5H-pyrrolo[3,4-b]pyridin-5-one (Compound 182)

As shown in steps 10-i and 10-ii of Scheme 10, Compound 2031 was converted to Compound 82 in a manner similar to that in the conversion of Compound 2032 to Compound 88.

As shown in step 10-iii Scheme 10, 4-Chloro-2-(5,6-dimethoxypyridin-3-yl)-6-(1-(2,2,2-trifluoroethyl)-1H-pyrazol-4-yl)-6,7-dihydro-5H-pyrrolo[3,4-b]pyridin-5-one (Compound 82, 75 mg, 0.165 mmol and a degassed solution of 2M aqueous sodium carbonate (826 uL, 1.65 mmol] were suspended in 10 mL of toluene. The reaction mixture was purged with nitrogen for 5 minutes and tetrakistriphenylphosphine palladium(0) (38 mg, 0.033 mmol] was added, followed by the addition of 2 M triethylborate solution in THF (992 µL, 1.0 mmol). The reaction vessel was sealed and heated for 14 hours at 80° C. The reaction mixture was cooled and the volatiles removed under reduced pressure. The residue was dissolved in EtOAc/DCM 1:1 and filtered. The filtrate was concentrated under reduced pressure. The product was purified by preparative thin layer chromatography produced 2-(5,6-dimethoxypyridin-3-yl)-4-ethyl-6-(1-(2,2,2-trifluoroethyl)-1H-pyrazol-4-yl)-6,7-dihydro-5H-pyrrolo[3,4-b]pyridin-5-one (Compound 182, 1.1 mg): ESMS (M+1) 448.

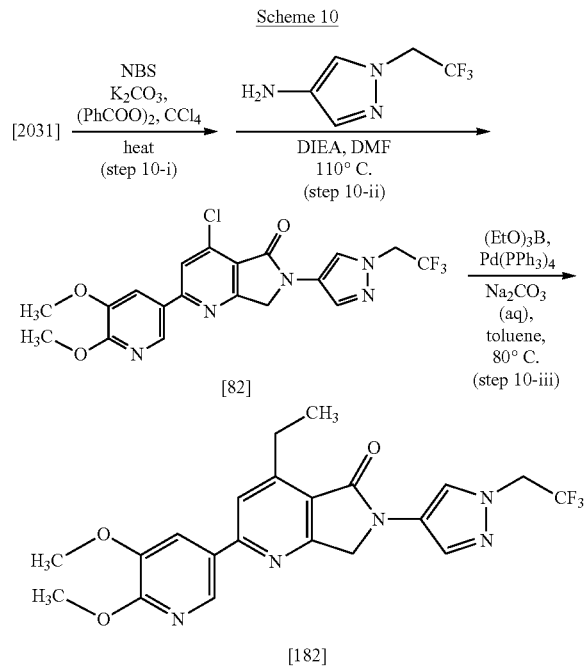

Example 11. Preparation of 2-(5,6-dimethoxypyridin-3-yl)-3-methyl-6-(1H-pyrazol-4-yl)-6,7-dihydro-5H-pyrrolo[3,4-b]pyridin-5-one (Compound 238)

As shown in step 11-i of Scheme 11, 2,5-dimethylnicotinic acid (Compound 2034, 519 mg, 3.43 mmol) was dissolved in 1,1,1-triethoxyethane (5.57 g, 6.29 mL, 34.3 mmol) in a microwave vial. The reaction mixture was heated to 150° C. for 5 minutes. After dilution with 30 mL of DCM, the organics were washed with 10 mL of saturated NaHCO$_3$. The organic layer was passed through a phase separator and then concentrated under reduced pressure to give ethyl 2,5-dimethylnicotinate (Compound 2035, 390 mg, 63% yield) as a yellow oil: ESMS (M+1) 179.89; $^1$H NMR (300 MHz, DMSO-d$_6$) δ 8.46 (d, J=1.9 Hz, 1H), 7.98 (d, J=1.9 Hz, 1H), 4.31 (q, J=7.1 Hz, 2H), 2.65 (s, 3H), 2.31 (s, 3H), 1.32 (t, J=7.1 Hz, 3H).

As shown in step 11-ii of Scheme 11, Compound 2035 (354 mg, 1.98 mmol) and 1,3,5-trichloro-1,3,5-triazinane-2,4,6-trione (689 mg, 2.96 mmol) were combined in DCM (1.8 mL). After stirring 18 hours at room temperature, the mixture was diluted with 20 mLs each of saturated sodium carbonate and dichloromethane. The organics were separated, washed with saturated sodium carbonate, washed with brine, dried over sodium sulfate, filtered, and concentrated under reduced pressure to give ethyl 2-(chloromethyl)-5-methylnicotinate (Compound 2036, 465 mg) as a pale yellow oil: ESMS (M+1) 213.86.

As shown in step 11-iii of Scheme 11, Compound 2036 (465 mg, 2.18 mmol) was placed in a 40 ml vial, diluted with DCM (4.35 mL), and 3-chlorobenzenecarboperoxoic acid (m-CPBA, 551 mg, 2.39 mmol) was added at room temperature with stirring. After 18 hours, the mixture was diluted with 30 mL of DCM, washed with saturated sodium carbonate (3×5 mL), and washed with brine. The organics were passed through a phase separator and concentrated to dryness under reduced pressure to give ethyl 2-(chloromethyl)-3-(ethoxycarbonyl)-5-methylpyridine 1-oxide (Compound 2037, 318 mg, 1.38 mmol, 63% yield): ESMS (M+1) 230.14. This material was used as is in subsequent reactions.

As shown in step 11-iv of Scheme 11, Compound 2037 (318 mg, 1.385 mmol) was dissolved in phosphorus oxychloride (4.25 g, 2.58 mL, 27.7 mmol). The reaction mixture was heated to 90° C. under an atmosphere of nitrogen for 18 hours. The mixture was concentrated to dryness under reduced pressure, diluted with 5 mL of DCM, and washed with 5 mL of water. The organics were passed through a phase separator and the volatiles removed under reduced pressure. Purification by silica gel chromatography gave ethyl 6-chloro-2-(chloromethyl)-5-methylnicotinate (Compound 2038, 78 mg, 0.314 mmol, 22.7%): ESMS (M+1) 248.17; $^1$H NMR (300 MHz, DMSO-d$_6$) δ 8.29 (s, 1H), 5.00 (s, 2H), 4.51-4.23 (m, 2H), 2.38 (s, 3H), 1.35 (t, J=7.1 Hz, 3H).

As shown in step 11-v of Scheme 11, Compound 2038 (76 mg, 0.306 mmol) was dissolved in 1 mL of DMF and added dropwise to a stirring solution of 1H-pyrazol-4-amine (63.6 mg, 0.766 mmol) and DIEA (59.4 mg, 801 µL, 0.46 mmol) in 1 mL of DMF. The reaction was stirred at room temperature for 2 hours and then heated overnight at 80° C. After the addition of 10 mL of methanol, the mixture was allowed to cool to produce a solid. The solid was collected by filtration and washed with 3 mL of methanol. The solid was dried overnight under high vacuum to give 2-chloro-3-methyl-6-(1H-pyrazol-4-yl)-6,7-dihydro-5H-pyrrolo[3,4-b]pyridin-5-one (Compound 2039, 35 mg, 0.141 mmol, 46% yield). ESMS (M+1) 249.08.

As shown in step 11-vi of Scheme 11, 2,3-dimethoxy-5-(4,4,5,5-tetramethyl-1,3,2-dioxaborolan-2-yl)pyridine (Compound 2028, 45 mg, 0.169 mmol), 1 M sodium carbonate (281 µL, 0.281 mmol), and Compound 2039 (35 mg, 0.141 mmol) were taken up in 3 mL DMF as a slurry. The mixture was degassed with nitrogen for 30 minutes and Pd(PPh$_3$)$_4$ (32.5 mg, 0.028 mmol) was added. The mixture was degassed with nitrogen for another 5 minutes and then heated for 18 hours at 80° C. in a sealed vial. Additional methanol was added followed by dilution with DCM. The organics were washed with a solution of saturated Na$_2$CO$_3$, passed through a phase separator, and concentrated under reduced pressure to dryness. The product was purified by reversed-phase HPLC (10-90% acetonitrile/water) to give 2-(5,6-dimethoxypyridin-3-yl)-3-methyl-6-(1H-pyrazol-4-yl)-6,7-dihydro-5H-pyrrolo[3,4-b]pyridin-5-one (Compound 238, 18.8 mg, 0.052 mmol, 37% yield); ESMS (M+1) 352.26; $^1$H NMR (300 MHz, CDCl$_3$) δ 8.10 (d, J=11.8 Hz, 3H), 7.97 (d, J=1.9 Hz, 1H), 7.34 (d, J=1.8 Hz, 1H), 4.83 (s, 2H), 4.10 (s, 3H), 3.96 (s, 3H), 2.54 (s, 3H).

Scheme 11

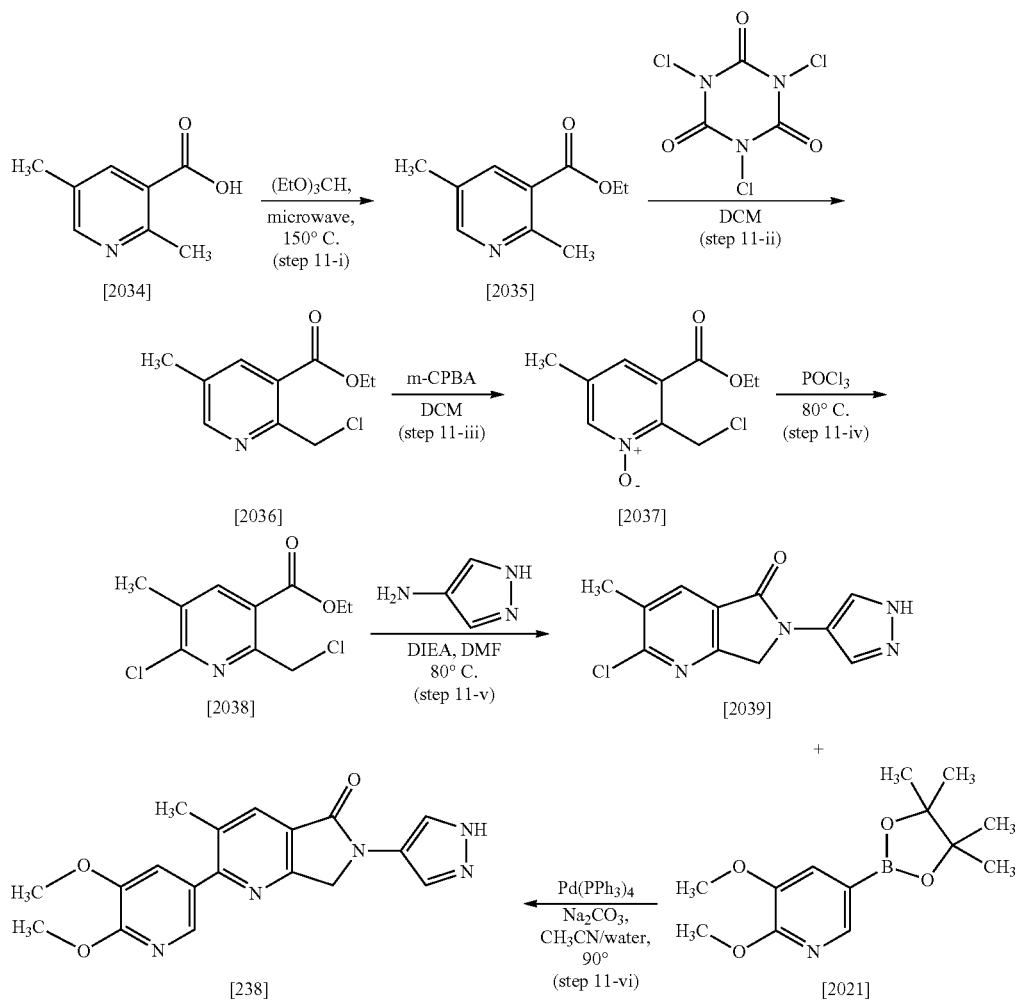

Example 12. Preparation of 2-(5,6-dimethoxypyridin-3-yl)-4-methyl-6-(1H-pyrazol-4-yl)-6,7-dihydro-5H-pyrrolo[3,4-b]pyridin-5-one (Compound 135)

As shown in step 12-i of Scheme 12, to a degassed mixture of Compound 2021 (111 mg, 0.42 mmol), sodium carbonate (97 mg, 0.91 mmol) and 2-chloro-4-methyl-6-(1H-pyrazol-4-yl)-6,7-dihydro-5H-pyrrolo[3,4-b]pyridin-5-one (Compound 2040, 104 mg, 0.42 mmol; prepared from ethyl 6-chloro-2-(chloromethyl)-4-methylnicotinate in a manner similar to that of the preparation of Compound 2039 in step 11-v of Example 11) in DMF/acetonitrile/water (1:1:0.5) was added Pd(PPh$_3$)$_4$ (50 mg, 0.04 mmol). The reaction mixture was heated in a sealed tube at 90° C. for 48 hours. Water (5 mL) was added and the mixture stirred at RT for 30 minutes. After filtration, the collected solid was washed with MeOH and EtOAc, sonicated in EtOAc, then collected by filtration to give 2-(5,6-dimethoxypyridin-3-yl)-4-methyl-6-(1H-pyrazol-4-yl)-6,7-dihydro-5H-pyrrolo[3,4-b]pyridin-5-one (Compound 135, 100 mg, 66% yield) as a pale green solid: ESMS (M+H) 352.4; $^1$H NMR (300 MHz, DMSO-d$_6$) δ 12.88 (s, 1H), 8.54 (d, J=1.9 Hz, 1H), 8.29-7.66 (m, 4H), 4.90 (s, 2H), 3.93 (d, J=10.5 Hz, 6H), 2.72 (s, 3H).

Scheme 12

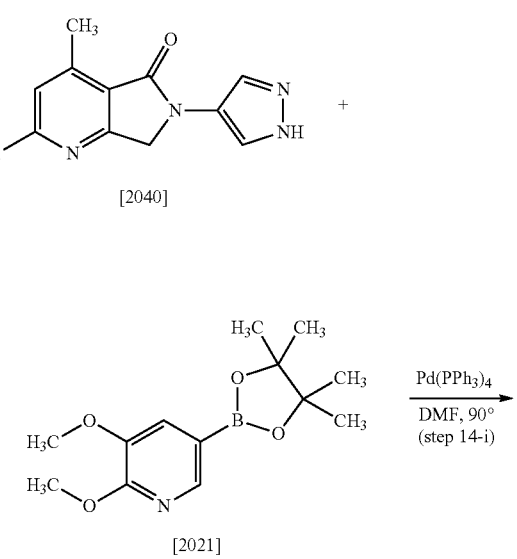

-continued

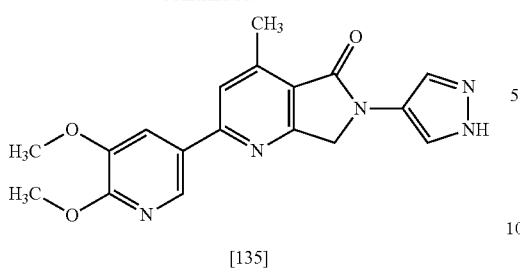

[135]

Example 13. Preparation of 2-(5,6-dimethoxypyridin-3-yl)-4-methyl-6,7-dihydro-5H-pyrrolo[3,4-b]pyridin-5-one (Compound 2043)

As shown in step 13-i of Scheme 13, ethyl 6-chloro-2-(chloromethyl)-4-methylnicotinate (Compound 2041, 5.11 g, 20.6 mmol; prepared from 2,5-dimethylnicotinic acid in a manner similar to the preparation of Compound 2038 in Example 11) was dissolved in methanol (30.6 mL). 7M ammonia/MeOH (21.3 mL, 149 mmol) was added followed by the addition of ammonium hydroxide (18.7 g, 20.8 mL, 533 mmol). The reaction mixture was stirred overnight at room temperature and the precipitate that had formed was collected by filtration and dried under high vacuum to provide 2-chloro-4-methyl-6,7-dihydro-5H-pyrrolo[3,4-b]pyridin-5-one (Compound 2042, 2.6 g, 14.2 mmol, 69% yield): ESMS (M+1) 183.29; $^1$H NMR (300 MHz, CDCl$_3$) δ 8.74 (s, 1H), 7.44 (d, J=0.5 Hz, 1H), 4.35 (s, 2H), 2.60 (s, 3H).

As shown in step 13-ii of Scheme 13, 2-chloro-4-methyl-6,7-dihydropyrrolo[3,4-b]pyridin-5-one (2.54 g, 13.91 mmol), 1M sodium carbonate (27.82 mmol), and 2,3-dimethoxy-5-(4,4,5,5-tetramethyl-1,3,2-dioxaborolan-2-yl)pyridine (4.43 g, 16.7 mmol) were slurried in DMF (216 mL). The reaction mixture was flushed with nitrogen for 30 minutes. Pd(PPh$_3$)$_4$ (1.607 g, 1.391 mmol) was added and the nitrogen flush was continued for another 5 minutes. The reaction mixture was then heated at 80° C. for 16 hours. The mixture was diluted with 1 L ethyl acetate and 350 mL saturated NaHCO$_3$. A precipitate formed in the separatory funnel which was collected by filtration and washed with EtOAc, water, and ethyl ether. Drying the solid overnight under high vacuum gave 2-(5,6-dimethoxy-3-pyridyl)-4-methyl-6,7-dihydropyrrolo[3,4-b]pyridin-5-one (Compound 2043, 3.82 g, 13.38 mmol, 96% yield): ESMS (M+H) 286.29; $^1$H NMR (300 MHz, DMSO-d$_6$) δ 8.63 (s, 1H), 8.49 (d, J=1.9 Hz, 1H), 8.06-7.82 (m, 2H), 4.41 (s, 2H), 3.94 (s, 3H), 3.90 (s, 3H), 2.67 (s, 3H).

Scheme 13

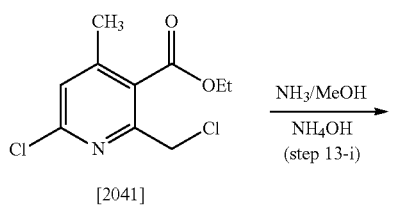

[2041]

-continued

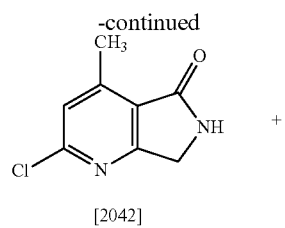

[2042]

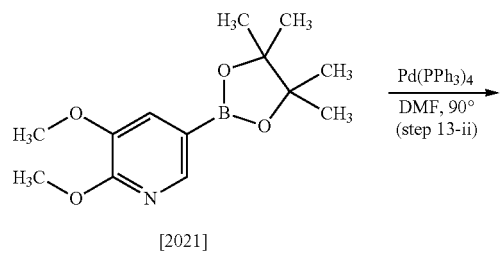

[2021]

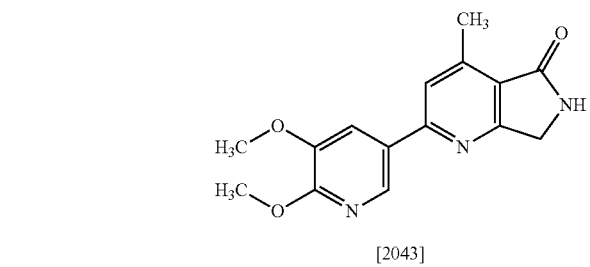

[2043]

Example 14. Preparation of 2-(5,6-dimethoxypyridin-3-yl)-6-(5-methylthiophen-2-yl)-6,7-dihydro-5H-pyrrolo[3,4-b]pyridin-5-one (Compound 252)

As shown in step 14-i of Scheme 14, 2-(5,6-dimethoxy-3-pyridyl)-6,7-dihydropyrrolo[3,4-b]pyridin-5-one (Compound 2044, 100 mg, 0.37 mmol; prepared via the aminolysis of Compound 2029 as shown in step 13-i of Example 13), 2-iodo-5-methyl-thiophene (99 mg, 54 µL, 0.44 mmol), and cesium carbonate (240 mg, 0.737 mmol) were weighed into a small screw top tube. The reaction mixture was flushed with nitrogen for 15 minutes. CuI (14.0 mg, 0.074 mmol) and N,N'-dimethylethane-1,2-diamine (6.5 mg, 7.8 µL, 0.073 mmol) were added and the nitrogen flush was continued for another 5 minutes. The tube was sealed and the contents heated at 100° C. for 18 hours. After cooling to room temperature, the reaction mixture was diluted with 20 mL water and the precipitate collected by filtration. The solid was washed with water, washed with methanol, and then taken up in 6 mL DMSO. Purification by reversed-phase HPLC provided 2-(5,6-dimethoxypyridin-3-yl)-6-(5-methylthiophen-2-yl)-6,7-dihydro-5H-pyrrolo[3,4-b]pyridin-5-one (Compound 252, 31.6 mg, 0.084 mmol, 23% yield): ESMS (M+H) 368.01; $^1$H NMR (300 MHz, DMSO-d$_6$) δ 8.56 (d, J=2.0 Hz, 1H), 8.30-8.12 (m, 2H), 7.99 (d, J=2.0 Hz, 1H), 6.73 (d, J=3.7 Hz, 1H), 6.67 (dd, J=3.7, 1.1 Hz, 1H), 5.09 (s, 2H), 3.96 (s, 3H), 3.92 (s, 3H), 2.42 (d, J=0.7 Hz, 3H).

Scheme 14

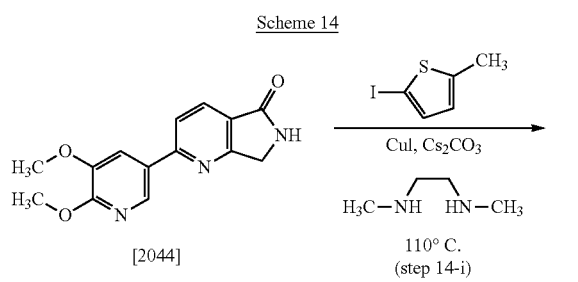

[2044]

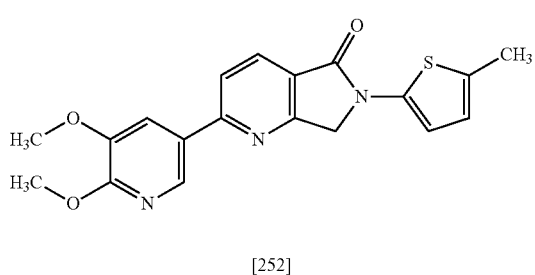

[252]

Example 15. Preparation of 2-(5,6-dimethoxypyridin-3-yl)-7,7-dimethyl-6-(1-(2,2,2-trifluoroethyl)-1H-pyrazol-4-yl)-6,7-dihydro-5H-pyrrolo[3,4-b]pyridin-5-one (Compound 311)

As shown in step 15-i of Scheme 15, to a solution of 2-(5,6-dimethoxypyridin-3-yl)-6-(1-(2,2,2-trifluoroethyl)-1H-pyrazol-4-yl)-6,7-dihydro-5H-pyrrolo[3,4-b]pyridin-5-one (Compound 115, 20 mg, 0.047 mmol, prepared by reacting compound 2029 with 1-(2,2,2-trifluoroethyl)-1H-pyrazol-4-amine in a manner similar to that shown in Example 8) in DMF (500 µL) was added iodomethane (17 mg, 0.119 mmol) followed by NaH (6 mg, 60% w/w in mineral oil). The reaction was stirred at room temperature for 2 hours, quenched with a saturated aqueous solution of NaHCO$_3$ (1 mL) and extracted with DCM (3×2 mL). The organics were concentrated and the crude residue was purified by preparative silica gel thin layer chromatography (100% EtOAc) to provide 2-(5,6-dimethoxypyridin-3-yl)-7,7-dimethyl-6-(1-(2,2,2-trifluoroethyl)-1H-pyrazol-4-yl)-6,7-dihydro-5H-pyrrolo[3,4-b]pyridin-5-one (Compound 346, 11.2 mg, 50% yield) as a white solid: ESMS (M+H) 447.87; $^1$H NMR (300 MHz, CDCl$_3$) δ 8.45 (d, J=1.9 Hz, 1H), 8.24-8.08 (m, 2H), 7.84 (dd, J=19.0, 4.1 Hz, 3H), 4.75 (q, J=8.3 Hz, 2H), 4.08 (t, J=17.3 Hz, 6H), 1.72 (s, 6H).

Scheme 15

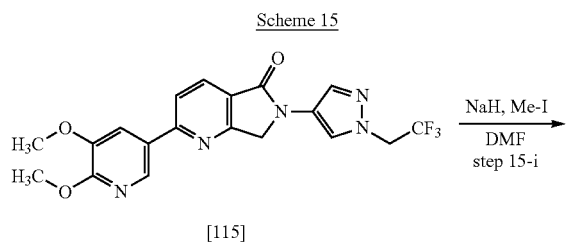

[115]

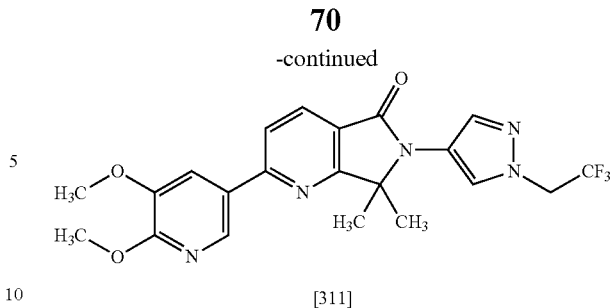

[311]

Example 16. Preparation of (S)-2-(6-ethoxy-5-methoxypyridin-3-yl)-7-methyl-6-(1-(2,2,2-trifluoroethyl)-1H-pyrazol-4-yl)-6,7-dihydro-5H-pyrrolo[3,4-b]pyridin-5-one (Compound 354) and (R)-2-(6-ethoxy-5-methoxypyridin-3-yl)-7-methyl-6-(1-(2,2,2-trifluoroethyl)-1H-pyrazol-4-yl)-6,7-dihydro-5H-pyrrolo[3,4-b]pyridin-5-one (Compound 355)

As shown in step 16-i of Scheme 16, to a solution of 2,2,2-trifluoroethanol (26.54 g, 19.33 mL, 265 mmol) and pyridine (20.99 g, 21.46 mL, 265 mmol) in DCM (120 mL) at 0° C. was added a solution of trifluoromethylsulfonyl trifluoromethanesulfonate (74.85 g, 44.6 mL, 265 mmol) in DCM (150 mL) via addition funnel over the course of 45 minutes. The reaction mixture was stirred an additional 15 minutes after completion of addition then quenched with water (400 mL). The organics were washed with water (400 mL), dried over MgSO$_4$, and filtered to produce 2,2,2-trifluoroethyl trifluoromethanesulfonate (Compound 2045), which was used as is. As shown in step 16-ii of Scheme 16, the solution of Compound 2045 was added over the course of 25 min to a solution of 4-nitro-1H-pyrazole (25 g, 221.1 mmol) in DMF (200 mL) with K$_2$CO$_3$ (61.11 g, 442.2 mmol) cooled in an ice-water bath. Once addition was complete, the cooling bath was removed and the reaction mixture stirred at 23° C. for 16 hours. The organics were washed with water (500 mL) and the aqueous wash was extracted with DCM (150 mL). The combined organics were dried over MgSO$_4$, filtered, and concentrated under reduced pressure. The resulting DMF-containing concentrate was diluted with 1:1 EtOAc:hexanes (500 mL), washed with water (3×250 mL), brine (200 mL), dried (MgSO$_4$), filtered, and concentrated under reduced pressure to give 4-nitro-1-(2,2,2-trifluoroethyl)pyrazole (Compound 2046, 40.4 g, 207.1 mmol, 93.65% yield) as a tan solid: $^1$H NMR (CDCl$_3$, 300 MHz) δ 8.31 (s, 1H), 8.17 (s, 1H), 4.79 (q, J=9 Hz, 2H).

As shown in step 16-iii of Scheme 16, to a solution of Compound 2046 (40.4 g, 207.1 mmol) in EtOH (600 mL) in a Parr bottle was added palladium (10 g, 9.397 mmol) (Pd/C, 10 wt % dry basis, wet, Degussa type). The mixture was placed under 50 p.s.i. of hydrogen gas and shaken at 23° C. for 40 minutes. The reaction mixture was through a Corning 0.22 µm PES membrane and the filtrate was concentrated to give 1-(2,2,2-trifluoroethyl)pyrazol-4-amine (Compound 2047, 33.94 g, 205.6 mmol, 99.24% yield) as a clear reddish oil: $^1$H NMR (CDCl$_3$, 300 MHz) δ 7.26 (s, 1H), 7.10 (s, 1H), 4.59 (q, J=9 Hz, 2H), 2.95 (br s, 2H). ESMS (M+H) 165.97.

As shown in step 16-iv of Scheme 16, to Compound 2047 (7.16 g, 43.36 mmol) in THF (204.6 mL) at 23° C. was added furo[3,4-b]pyridine-5,7-dione (6.465 g, 43.36 mmol) followed by the addition of DMAP (52.97 mg, 0.4336 mmol). The reaction mixture was stirred at 50° C. After 3 hours, acetic anhydride (8.853 g, 8.182 mL, 86.72 mmol) was added and the reaction mixture heated at 70° C. for another 1.5 hours. After cooling, the reaction mixture was concentrated and the residue partitioned between DCM and saturated aqueous NaHCO₃ (100 mL each). The aqueous layer was extracted with DCM (50 mL) and the combined organics were washed with saturated aqueous NaHCO3 (100 mL), dried (MgSO₄), filtered, and concentrated under reduced pressure. The residue was recrystallized from hot EtOAc/hexanes to give 6-(1-(2,2,2-trifluoroethyl)-1H-pyrazol-4-yl)-5H-pyrrolo[3,4-b]pyridine-5,7(6H)-dione (Compound 2048, 6.07 g, 20.49 mmol, 47.27%) as yellow needles: ESMS (M+H) 297.23; ¹H NMR (CDCl₃, 300 MHz) δ 9.05 (m, 1H), 8.32 (s, 1H), 8.31 (s, 1H), 8.26 (m, 1H), 7.70 (m, 1H), 4.79 (q, J=9 Hz, 2H).

As shown in step 16-v of Scheme 16, to Compound 2048 (5.69 g, 19.21 mmol) in THF (500 mL) at −78° C. under an atmosphere of nitrogen was slowly added methyl magnesium bromide (16.95 g, 16.46 mL of 1.4 M solution in 1:3 THF:toluene, 23.05 mmol). After stirring for 1 hour at −78° C. the reaction was warmed to 0° C. and stirred an additional 1 hour. The reaction was quenched with saturated aqueous NH₄Cl (100 mL). After stirring for 15 minutes, the mixture was partially concentrated under reduce pressure and partitioned between water (150 mL) and EtOAc (200 mL). The organics were washed with brine (150 mL), dried (MgSO₄), filtered, and concentrated to give 7-hydroxy-7-methyl-6-(1-(2,2,2-trifluoroethyl)-1H-pyrazol-4-yl)-6,7-dihydro-5H-pyrrolo[3,4-b]pyridin-5-one (Compound 2049, 5.77 g, 18.48 mmol, 96.2% yield) as a yellow solid: ESMS (M+H) 313.23; ¹H NMR (CDCl₃, 300 MHz) δ 8.73 (m, 1H), 8.10 (s, 1H), 8.01 (s, 1H), 8.00 (m, 1H), 7.40 (m, 1H), 4.73 (q, J=9 Hz, 2H), 1.84 (s, 3H).

As shown in step 16-vi of Scheme 16, to Compound 2049 (5.77 g, 18.48 mmol) in DCM (170 mL) at 23° C. was added Et₃N (7.48 g, 10.30 mL, 73.9 mmol) followed by methanesulfonyl chloride (MsCl, 3.18 g, 2.15 mL, 27.7 mmol). After stirring for 20 minutes, EtOH (6 mL) was added and stirring continued for 10 minutes in order to quench any excess MsCl. The reaction mixture was partitioned between saturated aqueous NaHCO₃ (300 mL) and DCM (50 mL). The aqueous layer was extracted with DCM (150 mL) and the combined organics were dried (MgSO₄), filtered, and combined with EtOH (200 mL). The resulting solution (containing 7-methylene-6-(1-(2,2,2-trifluoroethyl)-1H-pyrazol-4-yl)-6,7-dihydro-5H-pyrrolo[3,4-b]pyridin-5-one, Compound 2050) was concentrated under reduced pressure to approximately 100 mL and diluted with additional EtOH (250 mL). Pd/C (10 wt % dry basis, wet, Degussa type, 2.85 g) was added and the reaction mixture stirred under an atmosphere of hydrogen for 1 hour as shown in step 16-vii of Scheme 16. Analysis showed incomplete conversion of starting material to product so the mixture was filtered, treated with fresh catalyst (3.0 g), then stirred under an atmosphere of hydrogen for 90 minutes at 23° C. The catalyst was removed by filtration and the resulting solution concentrated under reduce pressure to give 7-methyl-6-(1-(2,2,2-trifluoroethyl)-1H-pyrazol-4-yl)-6,7-dihydro-5H-pyrrolo[3,4-b]pyridin-5-one (Compound 2051, 5.532 g, 18.67 mmol, 100% yield): ESMS (M+H) 297.23; ¹H NMR (CDCl₃, 300 MHz) δ 8.80 (m, 1H), 8.28 (s, 1H), 8.19 (m, 1H), 7.76 (s, 1H), 7.47 (m, 1H), 4.98 (q, J=6 Hz, 1H), 4.76 (q, J=9 Hz, 2H), 1.70 (d, J=6 Hz, 3H). NMR analysis show a minor amount of over-reduced material but the crude product was used as is in subsequent reactions.

As shown in step 16-viii of Scheme 16, to a solution of Compound 2051 (5.532 g, 18.67 mmol) in CHCl₃ (58.20 mL) was added m-CPBA (6.903 g, 28.00 mmol). The reaction mixture was stirred at 23° C. for 2 days. The reaction mixture was partitioned between saturated aqueous NaHCO₃ and DCM (100 mL each) and the aqueous layer extracted with DCM (100 mL). The combined organics were dried (MgSO₄), filtered, and concentrated under reduced pressure. The residue was purified by medium pressure silica gel chromatography (0-15% MeOH in DCM) to give 7-methyl-5-oxo-6-(1-(2,2,2-trifluoroethyl)-1H-pyrazol-4-yl)-6,7-dihydro-5H-pyrrolo[3,4-b]pyridine 1-oxide (Compound 2052, 3.47 g, 11.11 mmol, 59.5% yield) as a white solid: ESMS (M+H) 313.23; ¹H NMR (CD₃OD, 300 MHz) δ 8.50 (dd, J=3, 6 Hz, 1H), 8.30 (s, 1H), 7.97 (s, 1H), 7.94 (d, J=9 Hz, 1H), 7.69 (t, J=6 Hz, 1H), 5.36 (q, J=6 Hz, 1H), 5.00 (q, J=9 Hz, 2H), 1.74 (d, J=6 Hz, 3H).

As shown in step 16-ix of Scheme 16, to Compound 2052 (3.47 g, 11.11 mmol) in CHCl₃ (10 mL) at 85° C. was added POCl₃ (17.04 g, 10.36 mL, 111 mmol). After 2.5 hours at 85° C., the reaction mixture was treated with toluene (30 mL) and then concentrated to give a dark purple glassy oil, which was partitioned between DCM and saturated aqueous NaHCO₃ (300 mL each). An insoluble dark material was observed. The aqueous layer was extracted with DCM (3×150 mL) and the combined organics dried (MgSO₄), filtered, and concentrated under reduced pressure. The residue was purified by medium pressure silica gel chromatography (0-80% EtOAc in hexanes) to give 2-chloro-7-methyl-6-(1-(2,2,2-trifluoroethyl)-1H-pyrazol-4-yl)-6,7-dihydro-5H-pyrrolo[3,4-b]pyridin-5-one (Compound 2053, 1.20 g, 3.64 mmol, 32.8% yield) as a tan solid: ESMS (M+H) 331.19; ¹H NMR (CDCl₃, 300 MHz) δ 8.26 (s, 1H), 8.13 (d, J=9 Hz, 1H), 7.74 (s, 1H), 7.50 (d, J=9 Hz, 1H), 4.95 (q, J=6 Hz, 1H), 4.75 (q, J=9 Hz, 2H), 1.70 (d, J=6 Hz, 3H).

As shown in step 16-x of Scheme 16, to Compound 2053 (366 mg, 1.107 mmol), 2-ethoxy-3-methoxy-5-(4,4,5,5-tetramethyl-1,3,2-dioxaborolan-2-yl)pyridine (371 mg, 1.328 mmol), Na₂CO₃ (352 mg, 3.32 mmol), and Pd(PPh₃)₄ (64 mg, 0.055 mmol) was added DMF (12 mL) followed by water (3 mL). The reaction vessel was evacuated, placed under an atmosphere of hydrogen, and warmed to 100° C. (sand bath). After 18 hours, the reaction mixture was partitioned between EtOAc and water (100 mL each). The organics were washed with water (2×80 mL), brine (80 mL) dried (MgSO₄), filtered, and concentrated under reduced pressure. The residue was dissolved in hot EtOAc (20 mL) then treated with hexanes (20 mL). After standing at 23° C. for 2.5 h the resulting precipitate was collected by filtration and dried in vacuo to give a mixture of (S)-2-(6-ethoxy-5-methoxypyridin-3-yl)-7-methyl-6-(1-(2,2,2-trifluoroethyl)-1H-pyrazol-4-yl)-6,7-dihydro-5H-pyrrolo[3,4-b]pyridin-5-one (Compound 354) and (R)-2-(6-ethoxy-5-methoxypyridin-3-yl)-7-methyl-6-(1-(2,2,2-trifluoroethyl)-1H-pyrazol-4-yl)-6,7-dihydro-5H-pyrrolo[3,4-b]pyridin-5-one (Compound 355) (347 mg, 0.7583 mmol, 68.50%) as off-white needles: ESMS (M+H) 448.39; ¹H NMR (CDCl₃, 300 MHz) δ 8.44 (d, J=3 Hz, 1H), 8.31 (s, 1H), 8.22 (d, J=9 Hz, 1H), 7.93 (d, J=3 Hz, 1H), 7.86 (d, J=9 Hz, 1H), 7.77 (s, 1H), 5.03 (q, J=6 Hz, 1H), 4.77 (q, J=9 Hz, 2H), 4.61 (q, J=6 Hz, 2H), 4.04 (s, 3H), 1.76 (d, J=6 Hz, 3H), 1.52 (t, J=6 Hz, 3H). These two compounds were separated by supercritical fluid chromatography on a Whelk-O-1® (Regis Technologies, Inc.) column using DMF as modifier to give the individual enantiomers.

Scheme 16

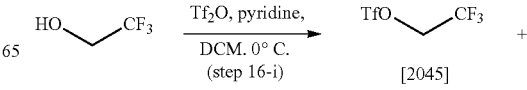

[2045]

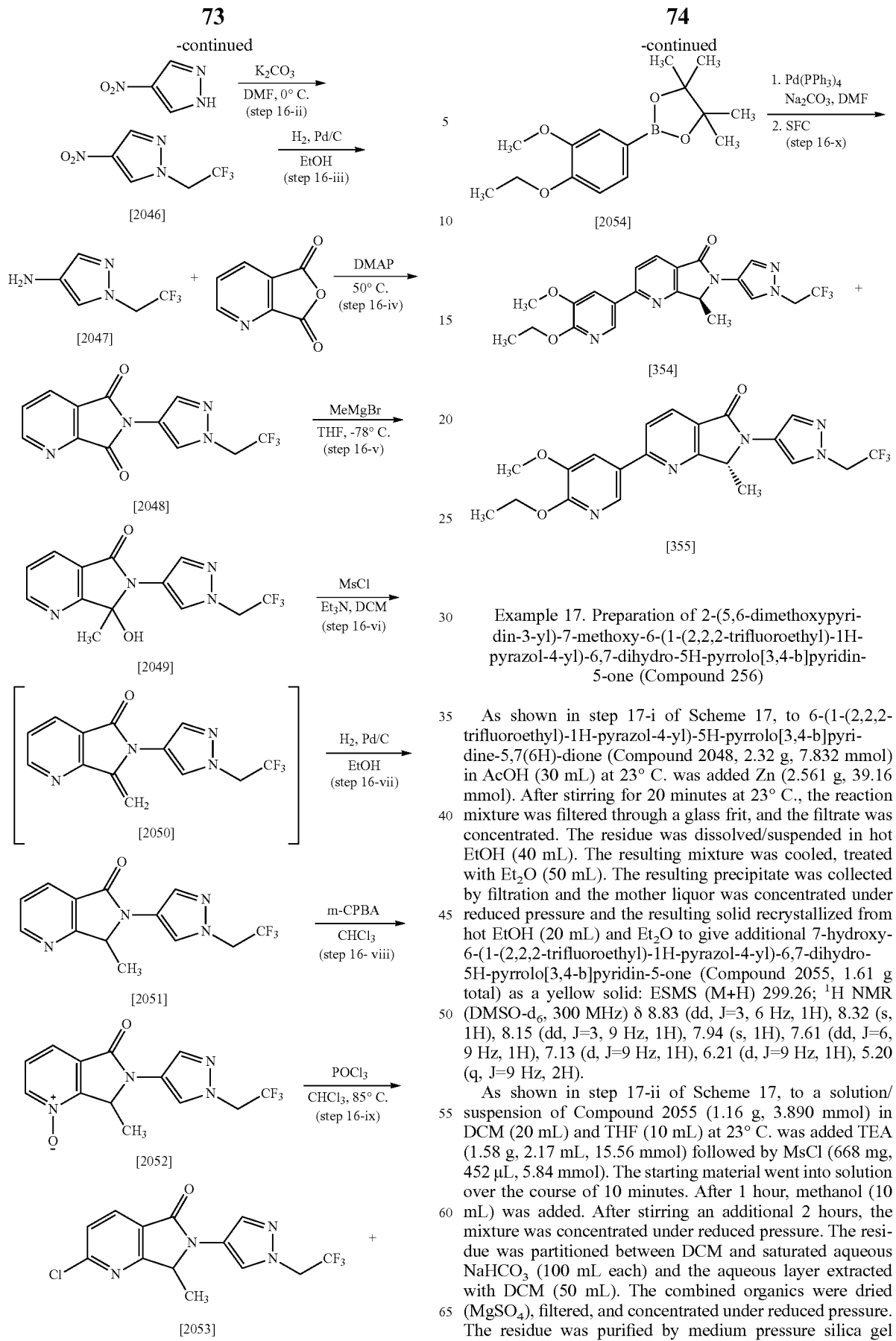

Example 17. Preparation of 2-(5,6-dimethoxypyridin-3-yl)-7-methoxy-6-(1-(2,2,2-trifluoroethyl)-1H-pyrazol-4-yl)-6,7-dihydro-5H-pyrrolo[3,4-b]pyridin-5-one (Compound 256)

As shown in step 17-i of Scheme 17, to 6-(1-(2,2,2-trifluoroethyl)-1H-pyrazol-4-yl)-5H-pyrrolo[3,4-b]pyridine-5,7(6H)-dione (Compound 2048, 2.32 g, 7.832 mmol) in AcOH (30 mL) at 23° C. was added Zn (2.561 g, 39.16 mmol). After stirring for 20 minutes at 23° C., the reaction mixture was filtered through a glass frit, and the filtrate was concentrated. The residue was dissolved/suspended in hot EtOH (40 mL). The resulting mixture was cooled, treated with Et$_2$O (50 mL). The resulting precipitate was collected by filtration and the mother liquor was concentrated under reduced pressure and the resulting solid recrystallized from hot EtOH (20 mL) and Et$_2$O to give additional 7-hydroxy-6-(1-(2,2,2-trifluoroethyl)-1H-pyrazol-4-yl)-6,7-dihydro-5H-pyrrolo[3,4-b]pyridin-5-one (Compound 2055, 1.61 g total) as a yellow solid: ESMS (M+H) 299.26; $^1$H NMR (DMSO-d$_6$, 300 MHz) δ 8.83 (dd, J=3, 6 Hz, 1H), 8.32 (s, 1H), 8.15 (dd, J=3, 9 Hz, 1H), 7.94 (s, 1H), 7.61 (dd, J=6, 9 Hz, 1H), 7.13 (d, J=9 Hz, 1H), 6.21 (d, J=9 Hz, 1H), 5.20 (q, J=9 Hz, 2H).

As shown in step 17-ii of Scheme 17, to a solution/suspension of Compound 2055 (1.16 g, 3.890 mmol) in DCM (20 mL) and THF (10 mL) at 23° C. was added TEA (1.58 g, 2.17 mL, 15.56 mmol) followed by MsCl (668 mg, 452 μL, 5.84 mmol). The starting material went into solution over the course of 10 minutes. After 1 hour, methanol (10 mL) was added. After stirring an additional 2 hours, the mixture was concentrated under reduced pressure. The residue was partitioned between DCM and saturated aqueous NaHCO$_3$ (100 mL each) and the aqueous layer extracted with DCM (50 mL). The combined organics were dried (MgSO$_4$), filtered, and concentrated under reduced pressure. The residue was purified by medium pressure silica gel chromatography (0-100% EtOAc in hexanes) to give 7-methoxy-6-(1-(2,2,2-trifluoroethyl)-1H-pyrazol-4-yl)-6,7-dihydro-5H-pyrrolo[3,4-b]pyridin-5-one (Compound 2056, 0.82 g, 2.63 mmol, 67.5% yield) as a white solid: ESMS (M+H) 313.29; $^1$H NMR (CDCl$_3$, 300 MHz) δ 8.89 (dd, J=3, 6 Hz, 1H), 8.26 (s, 1H), 8.19 (dd, J=3, 9 Hz, 1H), 8.05 (s, 1H), 7.54 (dd, J=6, 9 Hz, 1H), 6.15 (s, 1H), 4.76 (q, J=9 Hz, 2H), 3.12 (s, 3H).

As shown in step 17-iii of Scheme 17, to a solution of Compound 2056 (0.82 g, 2.63 mmol) in CHCl$_3$ (10 mL) was added mCPBA (777 mg, 3.15 mmol). The reaction was stirred at 23° C. for 5 minutes, warmed to 59° C. (sand bath), stirred at 59° C. for 24 hours, then at 23° C. for an additional 3 days. Purification by medium pressure silica gel chromatography (0-15% MeOH in DCM) gave 7-methoxy-5-oxo-6-(1-(2,2,2-trifluoroethyl)-1H-pyrazol-4-yl)-6,7-dihydro-5H-pyrrolo[3,4-b]pyridine 1-oxide (Compound 2057, 628 mg, 1.91 mmol, 73% yield) as a white solid: ESMS (M+H) 329.23; $^1$H NMR (CDCl$_3$, 300 MHz) δ 8.49 (dd, J=2, 6 Hz, 1H), 8.31 (s, 1H), 7.89 (s, 1H), 7.71 (m, 2H), 6.52 (s, 1H), 5.21 (q, J=9 Hz, 2H), 3.18 (s, 3H).

As shown in step 17-iv of Scheme 17, to Compound 2057 (620 mg, 1.89 mmol) was added CHCl$_3$ (3.5 mL) followed by the addition of POCl$_3$ (5.79 g, 3.52 mL, 37.8 mmol). The reaction mixture was heated to 90° C. (sand bath). After 1.8 hours, toluene (10 mL) was added then the solution was concentrated under reduced pressure to remove excess POCl$_3$. The residue was partitioned between DCM and saturated aqueous NaHCO$_3$ (100 mL each) and the aqueous layer was extracted with DCM (50 mL). The combined organics were dried (MgSO$_4$), filtered, concentrated under reduced pressure, and the residue purified by medium pressure silica gel chromatography (0-65% EtOAc in hexanes) to give 2-chloro-7-methoxy-6-(1-(2,2,2-trifluoroethyl)-1H-pyrazol-4-yl)-6,7-dihydro-5H-pyrrolo[3,4-b]pyridin-5-one (Compound 2058, 275 mg, 0.79 mmol, 42% yield) as a clear oil: ESMS (M+H) 347.18; $^1$H NMR (CDCl$_3$, 300 MHz) δ 8.23 (s, 1H), 8.13 (d, J=9 Hz, 1H), 8.02 (s, 1H), 7.57 (d, J=9 Hz, 1H), 6.08 (s, 1H), 4.76 (q, J=9 Hz, 2H), 3.18 (s, 3H).

As shown in step 17-v of Scheme 17, to Compound 2058 (293 mg, 0.85 mmol), 2,3-dimethoxy-5-(4,4,5,5-tetramethyl-1,3,2-dioxaborolan-2-yl)pyridine (269 mg, 1.01 mmol), Na$_2$CO$_3$ (179 mg, 1.69 mmol), and Pd(PPh$_3$)$_4$ (98 mg, 0.085 mmol) was added DMF (10 mL), followed by the addition of water (2 mL). The reaction vessel was evacuated, placed under an atmosphere of nitrogen, then warmed to 110° C. (sand bath). After 16 hours the reaction mixture was partitioned between EtOAc and water (100 mL each). The organics were washed with water (70 mL), brine (70 mL), dried (MgSO$_4$), filtered, and concentrated under reduced pressure. The residue was dissolved/suspended in EtOAc (7 mL) and heated with swirling in a water bath at 50° C. for 40 minutes. The resulting mixture was treated with hexanes (5 mL) and swirled an additional 5 minutes at 50° C. After cooling to 23° C., the resulting solid was collected by filtration and washed with 1:1 (EtOAc:hexanes, 5 mL) to give 2-(5,6-dimethoxypyridin-3-yl)-7-methoxy-6-(1-(2,2,2-trifluoroethyl)-1H-pyrazol-4-yl)-6,7-dihydro-5H-pyrrolo[3,4-b]pyridin-5-one (Compound 256) as a mixture of enantiomers: ESMS (M+H) 450.44; $^1$H NMR (CDCl$_3$, 300 MHz) δ 8.57 (d, J=3 Hz, 1H), 8.35 (s, 2H), 8.27 (s, 2H), 7.99 (d, J=3 Hz, 1H), 7.93 (s, 1H), 6.40 (s, 1H), 5.22 (q, J=9 Hz, 2H), 3.96 (s, 3H), 3.93 (s, 3H), 3.13 (s, 3H).

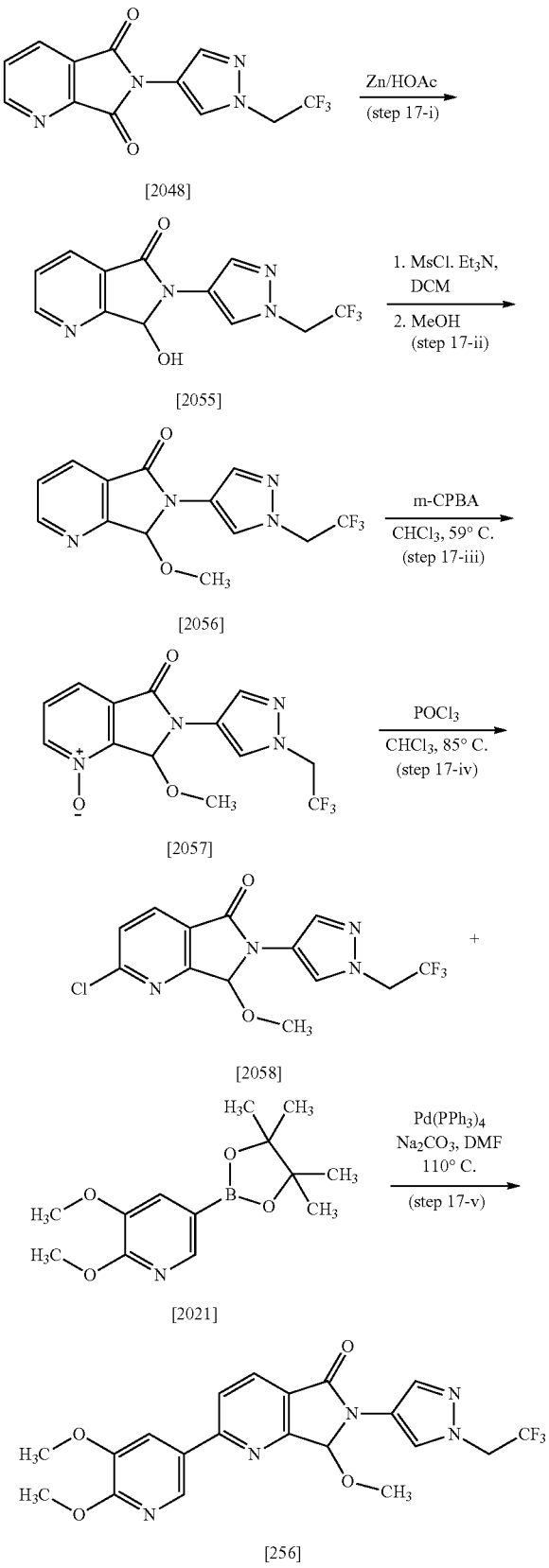

Example 18. Preparation of 2-(5,6-dimethoxypyridin-3-yl)-7-(2-methoxyethoxy)-6-(1-(2,2,2-trifluoroethyl)-1H-pyrazol-4-yl)-6,7-dihydro-5H-pyrrolo[3,4-b]pyridin-5-one (Compound 336)

As shown in step 18-i of Scheme 18, to 7-hydroxy-6-(1-(2,2,2-trifluoroethyl)-1H-pyrazol-4-yl)-6,7-dihydro-5H-pyrrolo[3,4-b]pyridin-5-one (Compound 2055, 4.35 g, 14.6 mmol) in CHCl$_3$ (80 mL) and MeOH (40 mL) was added mCPBA (5.39 g, 21.9 mmol). After stirring for 24 hours, additional mCPBA (1.26 g, 7.30 mmol) was added. After stirring an additional 16 hours, the resulting precipitate was collected by filtration and washed with DCM (10 mL) and Et$_2$O (20 mL) to give 7-hydroxy-5-oxo-6-(1-(2,2,2-trifluoroethyl)-1H-pyrazol-4-yl)-6,7-dihydro-5H-pyrrolo[3,4-b]pyridine 1-oxide (Compound 2059, 2.49 g) as a white solid: ESMS (M+H) 315.25; $^1$H NMR (DMSO-d$_6$, 300 MHz) δ 8.44 (d, J=6 Hz, 1H), 8.31 (s, 1H), 7.89 (s, 1H), 7.65 (m, 2H), 7.43 (d, J=9 Hz, 1H), 6.41 (d, J=9 Hz, 1H), 5.20 (q, J=9 Hz, 2H).

As shown in step 18-ii of Scheme 18, to Compound 2059 (312 mg, 0.99 mmol) in MeCN (10 mL) was added K$_2$CO$_3$ (686 mg, 4.96 mmol) followed by the addition of POCl$_3$ (761 mg, 463 µL, 4.96 mmol). The reaction mixture was refluxed under an atmosphere of nitrogen for 24 hours and then filtered through a glass frit. The filtrate was concentrated under reduced pressure then partitioned between DCM (60 mL), water (10 mL), and saturated aqueous NaHCO$_3$ (50 mL). The aqueous layer was extracted with DCM (50 mL) and the combined organics were dried (MgSO$_4$), filtered, and concentrated under reduced pressure. The residue was purified by medium pressure silica gel chromatography (0-60% EtOAc in hexanes) to give 2,7-dichloro-6-(1-(2,2,2-trifluoroethyl)-1H-pyrazol-4-yl)-6,7-dihydro-5H-pyrrolo[3,4-b]pyridin-5-one (Compound 2060, 150 mg, 0.43 mmol, 43%) as a white solid: $^1$H NMR (CDCl$_3$, 300 MHz) δ 8.14 (s, 1H), 8.07 (d, J=9 Hz, 1H), 7.89 (s, 1H), 7.51 (d, J=9 Hz, 1H), 6.50 (s, 1H), 4.69 (q, J=9 Hz, 2H).

As shown in step 18-ii of Scheme 18, to Compound 2060 (180 mg, 0.5127 mmol) in DMF (6 mL) was added 2,3-dimethoxy-5-(4,4,5,5-tetramethyl-1,3,2-dioxaborolan-2-yl)pyridine (Compound 2021, 163 mg, 0.62 mmol), Na$_2$CO$_3$ (217 mg, 2.05 mmol), Pd(PPh$_3$)$_4$ (30 mg, 0.026 mmol), and 2-methoxyethanol (1.5 mL, 19.0 mmol). The reaction vessel was evacuated, placed under an atmosphere of nitrogen, then warmed to 100° C. (sand bath). After 16 hours, the reaction mixture was partitioned between EtOAc and water (100 mL each). The organics were concentrated under reduced pressure and the residue dissolved in DMSO (5 mL) and purified by reversed-phase HPLC (10-90% aqueous MeCN with 0.1% TFA buffer) to give 2-(5,6-dimethoxypyridin-3-yl)-7-(2-methoxyethoxy)-6-(1-(2,2,2-trifluoroethyl)-1H-pyrazol-4-yl)-6,7-dihydro-5H-pyrrolo[3,4-b]pyridin-5-one (Compound 336, 55 mg) as a white lyophilizate: ESMS (M+H) 494.39; $^1$H NMR (CD$_3$OD, 300 MHz) δ 8.50 (d, J=3 Hz, 1H), 8.33 (s, 1H), 8.22 (d, J=9 Hz, 1H), 8.13 (d, J=9 Hz, 1H), 8.08 (d, J=3 Hz, 1H), 8.00 (s, 1H), 6.29 (s, 1H), 4.99 (q, J=9 Hz, 2H), 4.03 (s, 3H), 3.97 (s, 3H), 3.66 (m, 1H), 3.53 (m, 3H), 3.29 (s, 3H).

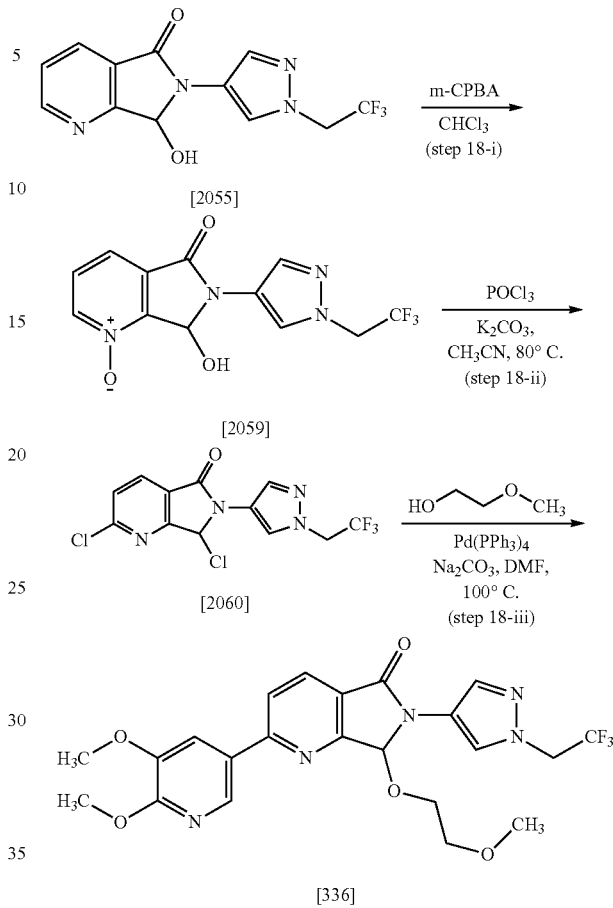

Scheme 18

Example 19. Preparation of methyl 2-(2-(5,6-dimethoxypyridin-3-yl)-5-oxo-6-(1-(2,2,2-trifluoroethyl)-1H-pyrazol-4-yl)-6,7-dihydro-5H-pyrrolo[3,4-b]pyridin-7-yl)acetate (Compound 307)

As shown in step 19-i of Scheme 19, to 7-hydroxy-6-(1-(2,2,2-trifluoroethyl)-1H-pyrazol-4-yl)-6,7-dihydro-5H-pyrrolo[3,4-b]pyridin-5-one (Compound 2055, 1.75 g, 5.87 mmol) and methyl 2-triphenylphosphoranylideneacetate (2.06 g, 6.16 mmol) was added toluene (23 mL) and THF (12 mL). The reaction mixture was heated to reflux and held there for 2.5 hours. After cooling, the reaction mixture was concentrated under reduced pressure and the residue purified by medium pressure silica gel chromatography (0-7.5% EtOH in DCM) to give methyl 2-(5-oxo-6-(1-(2,2,2-trifluoroethyl)-1H-pyrazol-4-yl)-6,7-dihydro-5H-pyrrolo[3,4-b]pyridin-7-yl)acetate (Compound 2061, 2.25 g, 6.35 mmol) as a clear oil: ESMS (M+H) 355.29. The product contained a small amount of triphenylphosphine oxide but was used in subsequent reactions as is.

As shown in step 19-ii of Scheme 19, to Compound 2061 (2.08 g, 5.89 mmol) in CHCl$_3$ (32 mL) was added mCPBA (2.17 g, 8.80 mmol) and the reaction mixture refluxed for 2 hours, cooled, and concentrated under reduced pressure. The resulting residue was purified by medium pressure silica gel chromatography (0-12% EtOH in DCM) to give 7-(2-methoxy-2-oxoethyl)-5-oxo-6-(1-(2,2,2-trifluoroethyl)-1H- pyrazol-4-yl)-6,7-dihydro-5H-pyrrolo[3,4-b]pyridine 1-oxide (Compound 2062, 1.31 g, 3.55 mmol, 60% yield) as a white solid: ESMS (M+H) 371.35; $^1$H NMR (DMSO-$d_6$, 300 MHz) δ 8.48 (d, J=6 Hz, 1H), 8.30 (s, 1H), 7.91 (s, 1H), 7.75 (d, J=6 Hz, 1H), 7.63 (t, J=3 Hz, 1H), 5.63 (m, 1H), 5.21 (q, J=9 Hz, 2H), 3.56 (dd, J=3, 15 Hz, 1H), 3.36 (s, 3H), 3.16 (dd, J=6, 15 Hz, 1H).

As shown in step 19-iii of Scheme 19, to Compound 2062 (1.06 g, 2.86 mmol) was added $POCl_3$ (13.17 g, 8.00 mL, 85.9 mmol). The reaction mixture was heated at 90° C. (sand bath) for 2.5 hours, followed by the removal of $POCl_3$ under reduced pressure. The residue was partitioned between saturated aqueous $NaHCO_3$ and DCM (100 mL each) and the aqueous layer was extracted with DCM (50 mL). The combined organics were dried ($MgSO_4$), filtered, and concentrated under reduced pressure. The residue was purified by medium pressure silica gel chromatography (0-100% EtOAc in hexanes to give methyl 2-(2-chloro-5-oxo-6-(1-(2,2,2-trifluoroethyl)-1H-pyrazol-4-yl)-6,7-dihydro-5H-pyrrolo[3,4-b]pyridin-7-yl)acetate (Compound 2063, 378 mg, 0.97 mmol, 34% yield) as a white solid: ESMS (M+H) 389.33; $^1$H NMR ($CDCl_3$, 300 MHz) δ 8.13 (d, J=9 Hz, 1H), 8.12 (s, 1H), 7.75 (s, 1H), 7.51 (d, J=9 Hz, 1H), 5.30 (m, 1H), 4.76 (q, J=9 Hz, 2H), 3.62 (s, 3H), 3.10 (m, 2H).

As shown in step 19-iv of Scheme 19, to Compound 2063 (375 mg, 0.965 mmol), 2,3-dimethoxy-5-(4,4,5,5-tetramethyl-1,3,2-dioxaborolan-2-yl)pyridine (Compound 2021, 307 mg, 1.16 mmol), $Na_2CO_3$ (205 mg, 1.93 mmol), $Pd(PPh_3)_4$ (112 mg, 0.0965 mmol) was added DMF (12 mL) followed by the addition of water (2.5 mL). The reaction vessel was evacuated, placed under an atmosphere of nitrogen, then warmed to 110° C. (sand bath). After 18 hours, the reaction mixture was cooled and partitioned between EtOAc and water (100 mL each). The organics were washed with brine (50 mL), dried ($MgSO_4$), filtered and concentrated under reduced pressure. The residue was suspended in hot EtOAc (20 mL) and swirled for 45 min at 60° C. to give a uniform suspension, which was allowed to stand at 23° C. for 24 hours. The resulting solid was collected by filtration, dissolved in warm DMSO (50 mL), and filtered through a 0.45 micron PTFE membrane (syringe filter). The filtrate was treated with water (5 mL) and the resulting precipitate collected by filtration, washed with water (10 mL), suspended in warm MeCN (5 mL) and treated with water (5 mL). The resulting suspension was frozen and lyophilized to give methyl 2-(2-(5,6-dimethoxypyridin-3-yl)-5-oxo-6-(1-(2,2,2-trifluoroethyl)-1H-pyrazol-4-yl)-6,7-dihydro-5H-pyrrolo[3,4-b]pyridin-7-yl)acetate (Compound 307, 195 mg, 0.38 mmol, 39% yield) as a white solid: ESMS (M+H) 491.86; $^1$H NMR (DMSO-$d_6$, 300 MHz) δ 8.56 (d, J=3 Hz, 1H), 8.30 (s, 1H), 8.23 (d, J=9 Hz, 1H), 8.19 (d, J=9 Hz, 1H), 7.99 (d, J=3 Hz, 1H), 7.89 (s, 1H), 5.51 (m, 1H), 5.21 (q, J=9 Hz, 2H), 3.96 (s, 3H), 3.92 (s, 3H), 3.46 (s, 3H), 3.26 (dd, J=3, 15 Hz, 1H), 3.03 (dd, J=6, 15 Hz, 1H).

Scheme 19

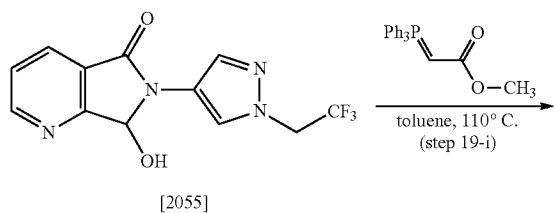

[2055]

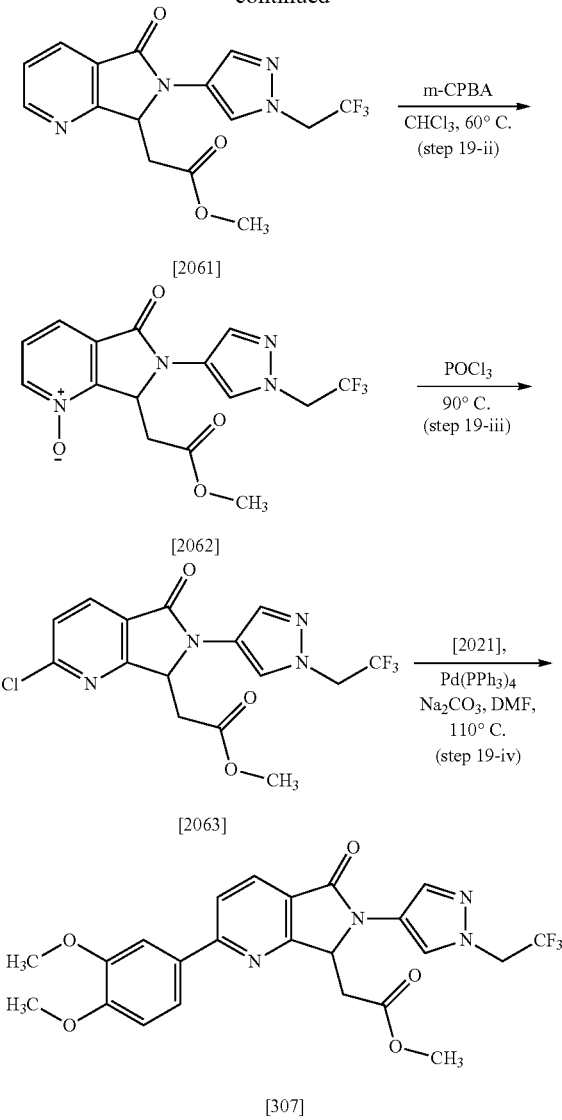

Example 20. Preparation of 6-(1-(2-(1H-pyrazol-1-yl)ethyl)-1H-pyrazol-4-yl)-2-(5,6-dimethoxypyridin-3-yl)-6,7-dihydro-5H-pyrrolo[3,4-b]pyridin-5-one (Compound 171)

As shown in step 20-i of Scheme 20, 2-(5,6-dimethoxypyridin-3-yl)-6-(1H-pyrazol-4-yl)-6,7-dihydro-5H-pyrrolo[3,4-b]pyridin-5-one [Compound 70, 100 mg, 0.2964 mmol, prepared from 2-chloro-6-(1H-pyrazol-4-yl)-6,7-dihydro-5H-pyrrolo[3,4-b]pyridin-5-one and 2,3-dimethoxy-5-(4,4,5,5-tetramethyl-1,3,2-dioxaborolan-2-yl)pyridine (Compound 2021) in a manner similar to the preparation of compound 135 as shown in Example 12], and cesium carbonate (193 mg, 0.593 mmol), were weighed into a conical microwave vial equipped with a stir bar. DMF (1.05 mL) was added followed by the addition of 1-(2-chloroethyl)pyrazole (77 mg, 0.593 mmols). The vial was sealed and heated at 120° C. for 15 minutes. Water (3 mL) was added and the resulting precipitate collected by filtration and washed with 5 mL of water. The filtrate was concentrated under reduced pressure. Each of the collected solid and the residue from concentration of the filtrate was diluted with DMSO until solubilized and purified by reversed-phase HPLC to give 6-(1-(2-(1H-pyrazol-1-yl)ethyl)-1H-pyrazol-4-yl)-2-(5,6-dimethoxypyridin-3-yl)-6,7-dihydro-5H-pyrrolo[3,4-b]pyridin-5-one (Compound 171, 22 mg, 0.05 mmol, 17% yield): ESMS (M+H) 432.0; $^1$H NMR (DMSO-$d_6$, 300 MHz) δ 8.47 (d, J=2.0 Hz, 1H), 8.10 (s, 2H), 7.95-7.87 (m, 2H), 7.75 (s, 1H), 7.45 (d, J=2.2 Hz, 1H), 7.40 (d, J=1.3 Hz, 1H), 6.12 (t, J=2.0 Hz, 1H), 4.84 (s, 2H), 4.50 (s, 4H), 3.88 (s, 3H), 3.85 (s, 3H).

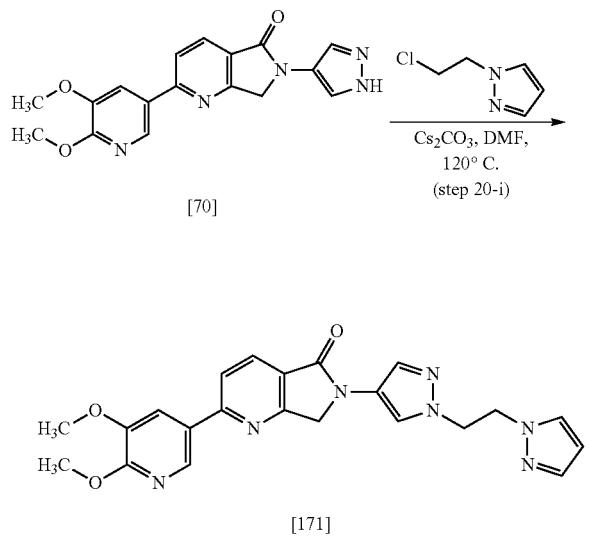

Example 21. Preparation of 6-(5,6-dimethoxypyridin-3-yl)-4-methyl-2-(1-(2,2,2-trifluoroethyl)-1H-pyrazol-4-yl)-1H-pyrrolo[3,4-c]pyridin-3(2H)-one (Compound 243)

As shown in step 21-i of Scheme 21, to a round-bottomed flask containing 1-(2,2,2-trifluoroethyl)pyrazol-4-amine (2.01 g, 12.2 mmol) and potassium carbonate (3.364 g, 24.34 mmol) under an atmosphere of nitrogen was added DMF (15 mL), followed by the addition of 3-bromoprop-1-yne (1.45 g, 1.09 mL, 12.2 mmol). The reaction mixture was stirred at RT for 18 hours. Water and EtOAc were added and the aqueous layer extracted with EtOAc. The combined organics were washed with brine, water, dried (sodium sulfate), filtered, and concentrated under reduced pressure. Purification by silica gel chromatography (petroleum ether: EtOAc, 1:1) gave N-(prop-2-ynyl)-1-(2,2,2-trifluoroethyl)-1H-pyrazol-4-amine (Compound 2064, 1.19 g, 48% yield) as an orange solid: $^1$H NMR (CDCl$_3$, 300 MHz) δ 7.32 (1H, s), 7.16 (1H, s), 4.62 (2H, q), 3.81 (2H, dd), 3.20 (1H, t), 2.27 (1H, t).

As shown in step 21-ii of Scheme 21, to a solution of Compound 2064 (1.19 g, 5.88 mmol) in DCM (20 mL) was added DIEA (2.28 g, 3.07 mL, 17.6 mmol), but-2-ynoic acid (544 mg, 6.47 mmol) and DMAP (36 mg, 0.29 mmol). The reaction mixture was cooled in ice-bath, EDCl (1.05 g, 6.76 mmol) was added, and the cold bath removed after 3 minutes.

After stirring the reaction mixture for 18 hours at RT, water and DCM were added and the layers separated. The aqueous layer was extracted with DCM and the combined organics were washed with brine, water, dried (sodium sulfate), filtered and concentrated under reduced pressure. Purification by silica gel chromatography (petroleum ether: EtOAc, 1:1) gave N-(prop-2-ynyl)-N-(1-(2,2,2-trifluoroethyl)-1H-pyrazol-4-yl)but-2-ynamide (Compound 2065, 650 mg, 41% yield) as a white solid: $^1$H NMR (CDCl$_3$, 300 MHz) δ 8.18 (1H, s), 7.77 (1H, s), 7.71 (1H, s), 7.69 (1H, s), 4.78 (2H, d), 4.76-4.63 (2H, m), 4.46 (2H, d), 2.40 (1H, t), 2.27 (1H, t), 2.13 (2H, s), 1.83 (2H, s).

As shown in step 21-iii of Scheme 21, to a solution of ethyl N-(oxomethylene)carbamate (385 mg, 345 µL, 3.34 mmol) and Cp*RuCl(cod) (21 mg, 0.056 mmol) in dry 1,2-dichloroethane (3 mL) was added a solution of Compound 2065 (303 mg, 1.11 mmol) in 1,2-dichloroethane (6 mL) over 25 min under nitrogen at rt. The reaction mixture was heated at 65° C. for 1 hr then concentrated under reduced pressure. Purification by silica gel chromatography (petroleum ether:EtOAc, 1/1 gradient to 0/1) gave ethyl 4-methyl-3,6-dioxo-2-(1-(2,2,2-trifluoroethyl)-1H-pyrazol-4-yl)-2,3-dihydro-1H-pyrrolo[3,4-c]pyridine-5(6H)-carboxylate (Compound 2066, 179 mg, 41% yield) as a white solid: $^1$H NMR (DMSO-$d_6$, 300 MHz) δ 8.28 (1H, s), 7.84 (1H, d), 6.52 (1H, s), 5.18 (2H, q), 4.75 (2H, s), 4.51 (2H, q), 2.67 (2H, s), 1.36 (2H, t).

As shown in step 21-iv of Scheme 21, to a solution of Compound 2066 (614 mg, 1.58 mmol) in THF (10 mL) was added HCl (6 M, 10 mL) at rt. The reaction mixture was heated at reflux overnight and then concentrated under reduced pressure. To the residue was added phosphorus oxychloride (15 mL, 161 mmol) and the reaction mixture was heated at 95° C. for 3 hours under an atmosphere of nitrogen. After cooling and concentrating the mixture under reduced pressure, ice was added followed by the addition of EtOAc 30 minutes later. The aqueous layer was extracted with EtOAc and the combined organics washed with brine, dried (sodium sulfate), filtered, and concentrated under reduced pressure. Purification by silica gel chromatography (petroleum ether:EtOAc, 1:1) gave 6-chloro-4-methyl-2-(1-(2,2,2-trifluoroethyl)-1H-pyrazol-4-yl)-1H-pyrrolo[3,4-c]pyridin-3(2H)-one (Compound 2067, 356 mg, 68%) as a white solid: ESMS (M+H) 330.90.

As shown in step 21-iv of Scheme 21, Compound 2067 (129 mg, 0.390 mmol) and Compound 2021 (134 mg, 0.51 mmol) were taken up in DMF and sodium carbonate (1 M, 0.780 mmol) and nitrogen passed through the solution for 30 minutes. Tetrakistriphenylphosphine palladium(0) (23 mg, 0.020 mmol) was added and the reaction mixture flushed with nitrogen for an additional 5 min, then heated at 110° C. overnight. After cooling the reaction to room temperature, EtOAc and water were added. The aqueous layer was extracted with EtOAc and the combined organics were dried (sodium sulfate), filtered through diatomaceous earth, and concentrated under reduced pressure. Purification by silica gel chromatography (EtOAc) gave 6-(5,6-dimethoxypyridin-3-yl)-4-methyl-2-(1-(2,2,2-trifluoroethyl)-1H-pyrazol-4-yl)-1H-pyrrolo[3,4-c]pyridin-3(2H)-one (Compound 243, 137 mg; 77% yield) as a white solid.

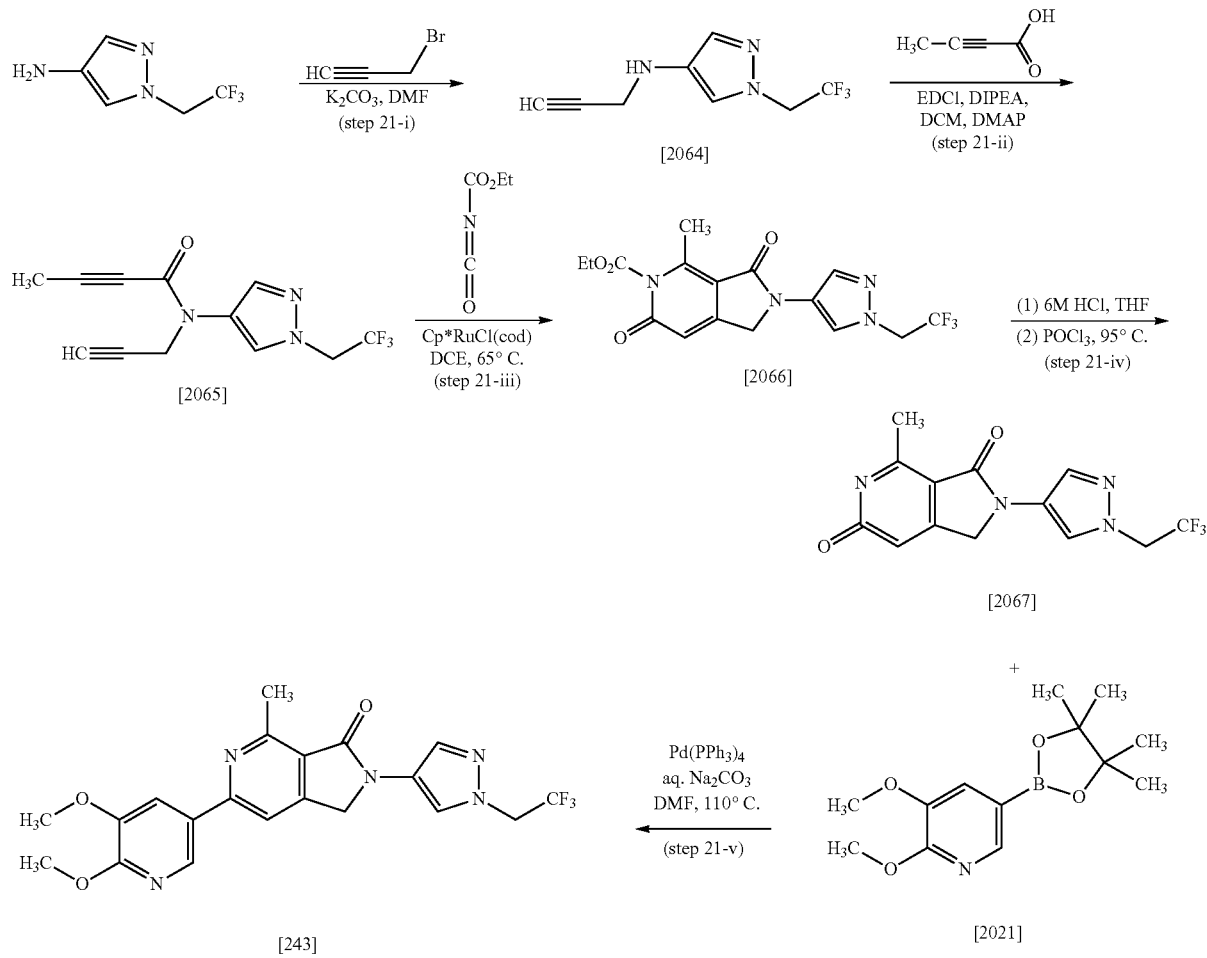

Example 22. Preparation of 2-(5,6-dimethoxypyridin-3-yl)-7-methyl-6-(1-(2,2,2-trifluoroethyl)-1H-pyrazol-4-yl)-6,7-dihydro-5H-pyrrolo[3,4-b]pyridin-5-one (Compound 254)

As shown in step 22-i of Scheme 22, a 1 L round bottom flask fitted with a condenser was charged with 2,6-dichloropyridine-3-carboxylic acid (10.0 g, 52.1 mmol), 2,3-dimethoxy-5-(4,4,5,5-tetramethyl-1,3,2-dioxaborolan-2-yl)pyridine (Compound 2021, 13.81 g, 52.1 mmol), Pd(PPh$_3$)$_4$ (3.01 g, 2.60 mmol), Na$_2$CO$_3$ (16.56 g, 156 mmol), dioxane (250 mL) and water (100 mL). The flask was evacuated for 1 minute and the mixture placed under an atmosphere of N$_2$. The mixture was heated at 110° C. for 16 hours, after which time a precipitate formed. The reaction mixture was cooled and transferred to a separatory funnel. Na$_2$CO$_3$ (200 mL 10 wt % aqueous) was added, followed by water (100 mL) and EtOAc (500 mL). The precipitate/emulsion persisted, mostly localized in the aqueous layer. The aqueous layer was separated, washed with EtOAc (300 mL), and then carefully acidified with concentrated HCl (~50 mL) to a pH of 2. The resulting precipitate was collected via filtration and washed with water (50 mL). The wet solid was transferred to a 1 L flask with aid of EtOH (200 mL) then evaporated to dryness. The solid residue was dissolved/suspended in EtOAc (120 mL) then treated with hexanes (120 mL). The resulting solid was collected via filtration, washed with hexanes (50 mL), and dried under reduced pressure to give 2-chloro-6-(5,6-dimethoxy-3-pyridyl)pyridine-3-carboxylic acid (Compound 2068, 11.99 g, 78% yield) as a an off-white solid: ESMS (M+H) 295.27; $^1$H NMR (DMSO-d$_6$, 300 MHz) δ 13.72 (s, 1H), 8.49 (d, J=1.98, 1H), 8.30 (d, J=8.08, 1H), 8.15 (d, J=8.11, 1H), 7.88 (d, J=1.98, 1H), 3.95 (s, 3H), 3.91 (s, 3H).

As shown in step 22-ii of Scheme 22, to a solution of 1-(2,2,2-trifluoroethyl)pyrazol-4-amine (Compound 2047, 5.78 g, 35.0 mmol), 2-chloro-6-(5,6-dimethoxy-3-pyridyl)pyridine-3-carboxylic acid (Compound 2068, 9.38 g, 31.8 mmol) and HBTU (13.28 g, 35.0 mmol) in DMF (150 mL) at 23° C. was added DIEA (12.35 g, 16.64 mL, 95.52 mmol). The reaction mixture was stirred for 2 h and then partitioned between EtOAc (400 mL) and water (400 mL). The organic layer was separated, washed with water (400 mL), 10% aqueous Na$_2$CO$_3$ (300 mL), brine (300 mL), combined brine and 2 N HCl (300 mL, 20 mL), and brine (300 mL). The organic layer was then diluted with EtOAc (150 mL) and EtOH (70 mL) and warmed to 75° C. with swirling to give a clear solution. The solution was treated with MgSO$_4$ and filtered while still warm. After concentration under reduced pressure, the residue was dissolved/suspended in EtOAc (200 mL) and spun at 80° C. for 1 h to give a uniform suspension. Hexanes (200 mL) were added and the resulting suspension was left standing at 23° C. for 14 h. The precipitate was collected via filtration, washed with hexanes (100 mL) to provide 2-chloro-6-(5,6-dimethoxy-3-pyridyl)-N-[1-(2,2,2-trifluoroethyl)pyrazol-4-yl]pyridine-3-carboxamide (Compound 2069, 11.32 g, 80% yield) as a white solid after drying in vacuo: ESMS (M+H) 442.50; $^1$H NMR (DMSO-$d_6$, 300 MHz) δ 10.86 (s, 1H), 8.49 (d, J=1.89, 1H), 8.25 (s, 1H), 8.16 (m, 2H), 7.88 (d, J=1.89, 1H), 7.66 (s, 1H), 5.16 (q, J=9.10, 2H), 3.95 (s, 3H), 3.92 (s, 3H).

As shown in step 22-iii of Scheme 22, a 250 mL Parr vessel was charged with 2-chloro-6-(5,6-dimethoxy-3-pyridyl)-N-[1-(2,2,2-trifluoroethyl)pyrazol-4-yl]pyridine-3-carboxamide (Compound 2069, 5.00 g, 11.32 mmol), $PdCl_2$ ($CH_3CN)_2$ (147 mg, 0.566 mmol), and dicyclohexyl-[2-(2,4,6-triisopropylphenyl)phenyl]phosphane (378 mg, 0.792 mmol). Nitrogen was bubbled through mixture for 3 min then triethylamine (5.727 g, 7.888 mL, 56.60 mmol) was added followed by ethynyl(trimethyl)silane (3.34 g, 4.80 mL, 34.0 mmol) were added. The vessel was sealed and warmed to 100° C. After 14 hours, the reaction mixture was cooled to 23° C. and partitioned between EtOAc (300 mL) and water (300 mL). The organic layer was separated, washed with water (300 mL), saturated aqueous $NaHCO_3$ (200 mL), brine (300 mL), dried ($MgSO_4$), filtered, and concentrated under reduced pressure. The residue was purified by medium pressure silica gel chromatography: 0-100% EtOAc in hexanes to provide 3.7 g of a tan solid. The solid was dissolved in EtOAc (15 mL, hot, 70° C.) then treated with hexanes (30 mL). The resulting suspension was spun and cooled via an ice-water bath for 40 min then the precipitate was collected via filtration, washed with hexanes (30 mL) to give 6-(5,6-dimethoxy-3-pyridyl)-N-[1-(2,2,2-trifluoroethyl)pyrazol-4-yl]-2-(2-trimethylsilylethynyl)pyridine-3-carboxamide (Compound 2070, 3.14 g, 55%) as a pale yellow solid: ESMS (M+H) 504.63; $^1$H NMR (CDCl$_3$, 300 MHz) δ 9.69 (s, 1H), 8.54 (d, J=8.44, 1H), 8.36 (d, J=1.96, 1H), 8.28 (s, 1H), 7.87 (d, J=1.93, 1H), 7.83 (d, J=8.48 Hz, 1H), 7.62 (s, 1H), 4.71 (q, J=8.33, 2H), 4.11 (s, 3H), 4.03 (s, 3H).

As shown in step 22-iv of Scheme 22, to a solution of 6-(5,6-dimethoxy-3-pyridyl)-N-[1-(2,2,2-trifluoroethyl)pyrazol-4-yl]-2-(2-trimethylsilylethynyl)pyridine-3-carboxamide (Compound 2070, 540 mg, 1.07 mmol) in EtOH (18.5 mL) at 23° C. was added dropwise EtONa (165 µL of a 1.3 M solution in EtOH, 0.214 mmol). After 25 min, the resulting slurry was cooled to 0° C. and, after stirring for 10 min at 0° C., the slurry was filtered, and the collected solid was washed with ice-cold EtOH (3×10 mL) to give 2-(5,6-dimethoxy-3-pyridyl)-7-methylene-6-[1-(2,2,2-trifluoroethyl)pyrazol-4-yl]pyrrolo[3,4-b]pyridin-5-one (Compound 2071, 436 mg, 93%) as a pale yellow solid after drying in vacuo: ESMS (M+H) 432.52; $^1$H NMR (CDCl$_3$, 300 MHz) δ 8.38 (d, J=1.96, 1H), 8.15 (d, J=8.13, 1H), 7.88 (d, J=1.98, 1H), 7.84 (s, 1H), 7.82 (d, J=8.16 Hz, 1H), 7.74 (s, 1H), 5.86 (d, J=1.89, 1H), 5.11 (d, J=1.89, 1H), 4.72 (q, J=8.32, 2H), 4.05 (s, 3H), 3.96 (s, 3H).

As shown in step 22-v of Scheme 22, to a solution of 2-(5,6-dimethoxy-3-pyridyl)-7-methylene-6-[1-(2,2,2-trifluoroethyl)pyrazol-4-yl]pyrrolo[3,4-b]pyridin-5-one (Compound 2071, 436 mg, 1.01 mmol) in THF (20 mL) was added Pd/C (200 mg, 10 wt % dry basis, wet, Degussa type). The reaction vessel was evacuated and then placed under an atmosphere of $H_2$ (balloon). After stirring for 2.5 h, the reaction mixture was filtered through a pad of silica and washed with THF (80 mL). The resulting filtrate was concentrated under reduced pressure and the residue treated with EtOAc (6 mL). After heating to reflux to give a uniform suspension, hexanes (10 mL) were added. The resulting suspension was cooled to 0° C. (ice-water bath), held at 0° C. for 5 min, and the precipitate collected via filtration to give 2-(5,6-dimethoxy-3-pyridyl)-7-methyl-6-[1-(2,2,2-trifluoroethyl)pyrazol-4-yl]-7H-pyrrolo[3,4-b]pyridin-5-one (Compound 254, 300 mg, 68%) as a pale tan-colored solid: ESMS (M+H) 434.44; $^1$H NMR (DMSO-$d_6$, 300 MHz) δ 8.57 (d, J=3 Hz, 1H), 8.39 (s, 1H), 8.23 (d, J=9 Hz, 1H), 8.18 (d, J=9 Hz, 1H), 8.00 (d, J=3 Hz, 1H), 7.97 (s, 1H), 5.22 (m, 3H), 3.96 (s, 3H), 3.93 (s, 3H), 1.60 (d, J=6 Hz, 3H).

Scheme 22

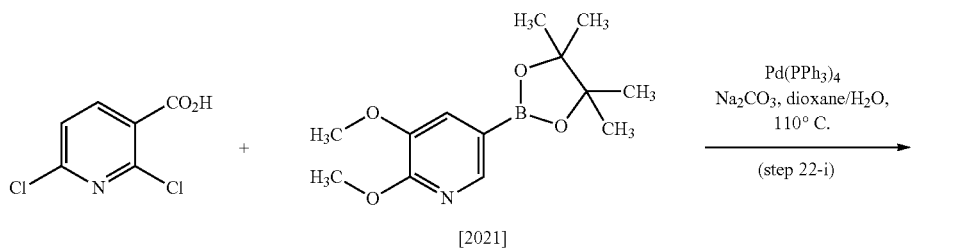

[2021]

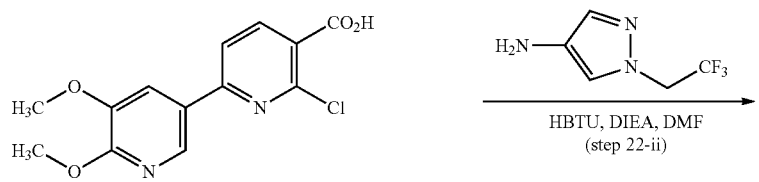

[2068]

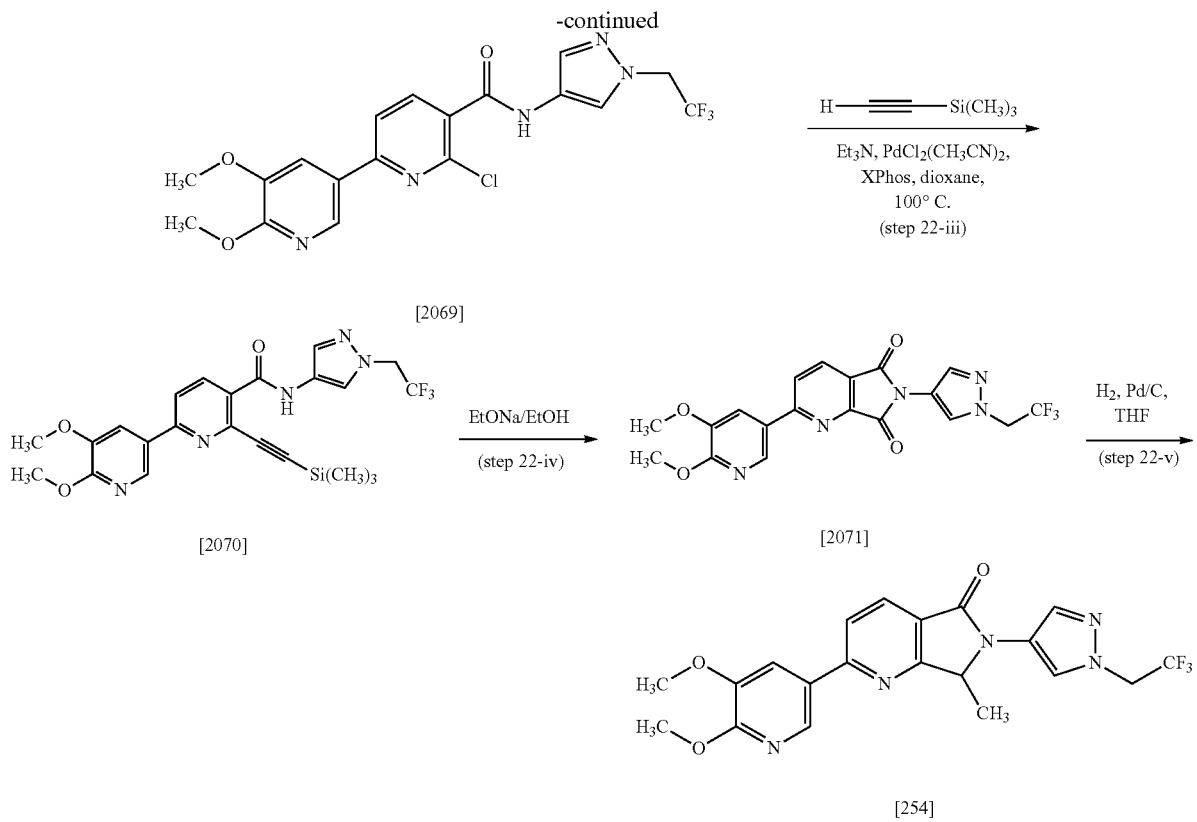

Example 23. Preparation of 2'-(5-methoxypyridin-3-yl)-4'-methyl-6'-(1-(2,2,2-trifluoroethyl)-1H-pyrazol-4-yl)spiro[cyclopropane-1,7'-pyrrolo[3,4-b]pyridin]-5'(6'H)-one (Compound 651)

As shown in step 23-i of Scheme 23, 1,2-dibromoethane (369.3 mg, 169.4 µL, 1.966 mmol) was added to a stirring solution of 2-chloro-4-methyl-6-[1-(2,2,2-trifluoroethyl)pyrazol-4-yl]-7H-pyrrolo[3,4-b]pyridin-5-one (500 mg, 1.512 mmol, prepared from the reaction of 1-(2,2,2-trifluoroethyl)-4-aminopyrazole with Compound 2041) in DMF (12 mL) at RT, followed by the addition of NaH (133 mg, 3.326 mmol, 60 wt % dispersion in mineral oil). The reaction mixture was stirred for 30 min at RT, cooled to 0° C. and quenched with sat'd NaHCO₃ (10 mL). The reaction mixture was extracted with DCM (3×10 mL) and the combined organics were dried over Na₂SO₄, filtered, and concentrated under reduced pressure. The crude residue was purified by medium pressure silica gel chromatography (0-50% EtOAc/hexanes) to provide 2'-chloro-4'-methyl-6'-(1-(2,2,2-trifluoroethyl)-1H-pyrazol-4-yl)spiro[cyclopropane-1,7'-pyrrolo[3,4-b]pyridin]-5'(6'H)-one (Compound 2073, 250 mg, 47% yield): ESMS (M+H) 358.0.

As shown in step 23-ii of Scheme 23, Potassium acetate (20.64 mg, 0.2103 mmol) and Pd(PPh₃)₄ (16.20 mg, 0.01402 mmol) were added to a solution of Compound 2073 (50 mg, 0.1402 mmol) and 3-methoxy-5-(4,4,5,5-tetramethyl-1,3,2-dioxaborolan-2-yl)pyridine (Compound 2074, 49.44 mg, 0.2103 mmol) in DMF (383.6 µL) and H₂O (127.9 µL). The solution was degassed and then heated to 100° C. in a microwave for 1 hour. The reaction was concentrated and the residue was purified by medium pressure silica gel chromatography (0-100% EtOAc/hexanes) to provide 2'-(5-methoxypyridin-3-yl)-4'-methyl-6'-(1-(2,2,2-trifluoroethyl)-1H-pyrazol-4-yl)spiro[cyclopropane-1,7'-pyrrolo[3,4-b]pyridin]-5'(6'H)-one (Compound 651, 30 mg, 47% yield) as a white solid: ESMS (M+H) 430.59.

Using the appropriate intermediates, protected if so required, Compounds 832, 833, 957, and 966 were also prepared by a similar procedure. This procedure was also used as an alternative to the procedure described in Example 15 for the preparation of Compound 311.

Scheme 23

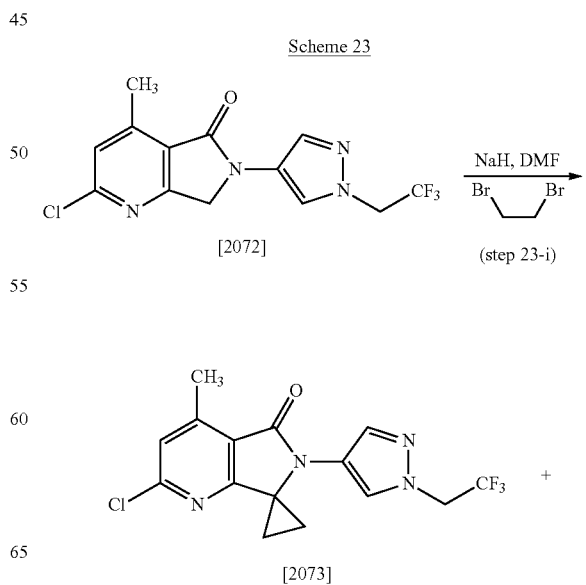

-continued

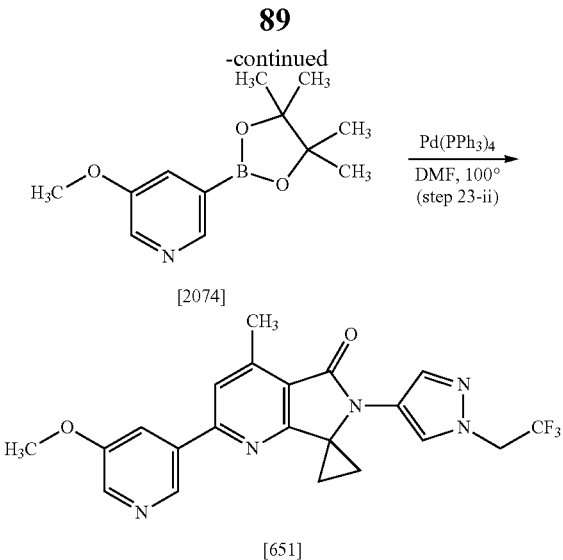

Example 24. Preparation of 2-(5-methoxy-3-pyridyl)-4-methyl-6-[1-(2,2,2-trifluoroethyl)pyrazol-4-yl]spiro[pyrrolo[3,4-b]pyridine-7,3'-tetrahydrofuran]-5-one (Compound 972)

As shown in step 24-i of Scheme 24, trimethylsilylcyanide (4.241 g, 5.700 mL, 42.75 mmol) was added to a solution of 1-(2,2,2-trifluoroethyl)pyrazol-4-amine (7.059 g, 42.75 mmol) and tetrahydrofuran-3-one (3.68 g, 42.75 mmol) in AcOH (45 mL) at 0° C. via syringe over 30 seconds. The reaction mixture was slowly warmed to 23° C. After stirring for 16 hours, the mixture was added to 1:1 ammonium hydroxide:ice (200 mL) and extracted with DCM (2×200 mL). The organics were dried (magnesium sulfate) filtered and concentrated. The residue was purified by medium pressure silica gel chromatography (0-100% EtOAc in hexanes to provide 3-[[1-(2,2,2-trifluoroethyl)pyrazol-4-yl]amino]tetrahydrofuran-3-carbonitrile (Compound 2075, 3.66 g, 14.07 mmol, 32.91% yield) as a brown oil: ESMS (M+H) 261.32; $^1$H NMR (CDCl$_3$, 300 MHz) δ 7.47 (s, 1H), 7.46 (s, 1H), 4.68 (q, J=9, 2H), 4.06 (m, 4H), 2.42 (m, 3H).

As shown in step 24-ii of Scheme 24, to a solution of but-2-ynoic acid (833.6 mg, 9.915 mmol) in DCM (12 mL) at 0° C. was added 1-chloro-N,N,2-trimethyl-prop-1-en-1-amine (1.325 g, 1.312 mL, 9.915 mmol). After stirring for 40 minutes, the reaction mixture was cooled to –78° C. and a solution of 3-[[1-(2,2,2-trifluoroethyl)pyrazol-4-yl]amino]tetrahydrofuran-3-carbonitrile (Compound 2075, 1.72 g, 6.610 mmol) and DIEA (2.563 g, 3.454 mL, 19.83 mmol) in DCM (12 mL) was added. The reaction mixture was warmed to 0° C. (ice-water bath), and after 1 hour the mixture was warmed to 23° C. After 30 min at 23° C., the reaction mixture was partitioned between water and EtOAc (100 mL each). The organics were separated (insoluble precipitate is present), washed with water then brine (100 mL each), dried (magnesium sulfate), filtered, and concentrated under reduced pressure. The residue was purified by medium pressure silica gel chromatography (0-80% EtOAc/hexanes) to provide N-(3-cyanotetrahydrofuran-3-yl)-N-[1-(2,2,2-trifluoroethyl)pyrazol-4-yl]buta-2,3-dienamide (Compound 2076, 1.48 g) as a yellow oil: ESMS (M+H) 327.20; $^1$H NMR (CDCl$_3$, 300 MHz) δ 7.70 (s, 1H), 7.63 (s, 1H), 5.57 (t, J=6, 1H), 5.19 (d, J=6, 2H), 4.77 (q, J=9, 2H), 4.00 (m, 4H), 2.50 (m, 1H), 2.30 (m, 1H).

As shown in step 24-iii of Scheme 24, to a solution of ditert-butyl propanedioate (3.579 g, 3.705 mL, 16.55 mmol) in THF (50 mL) at 23° C. was added NaH (496.4 mg, 12.41 mmol). After stirring for 20 minutes, a solution of Compound 2076 (2.70 g, 8.275 mmol) in THF (50 mL) was added. After 1 hour, the reaction was quenched with saturated aqueous ammonium chloride (100 mL) and partitioned between water and EtOAc (150 mL each). The organics were separated, washed with brine (200 mL) containing 1 N HCl (10 mL aq), washed with brine (150 mL), dried (magnesium sulfate), filtered and concentrated under reduced pressure. The residue was purified by medium pressure silica gel chromatography (0-100% EtOAc in hexanes) to provide intermediate tert-butyl 4'-methyl-2',5'-dioxo-6'-(1-(2,2,2-trifluoroethyl)-1H-pyrazol-4-yl)-1',2',4,5,5',6'-hexahydro-2H-spiro[furan-3,7'-pyrrolo[3,4-b]pyridine]-3'-carboxylate (2.03 g, 4.334 mmol) as a pale yellow solid: ESMS (M+H) 469.31; $^1$H NMR (DMSO-d$_6$, 300 MHz) δ 12.80 (br s, 1H), 8.16 (s, 1H), 7.80 (s, 1H), 5.17 (q, J=9, 2H), 4.18 (d, J=12, 1H), 3.90 (m, 2H), 3.75 (m, 1H), 2.45 (m, 1H), 2.44 (s, 3H), 2.33 (m, 1H), 1.52 (s, 9H).

As shown in step 24-iv of Scheme 24, tert-butyl 4'-methyl-2',5'-dioxo-6'-(1-(2,2,2-trifluoroethyl)-1H-pyrazol-4-yl)-1',2',4,5,5',6'-hexahydro-2H-spiro[furan-3,7'-pyrrolo[3,4-b]pyridine]-3'-carboxylate (2.00 g, 4.270 mmol) was taken up in DCM (25 mL) at 23° C. and TFA (25 mL) was added. After 30 minutes, the reaction mixture was treated with toluene (80 mL) and concentrated under reduced pressure to provide 4'-methyl-2',5'-dioxo-6'-(1-(2,2,2-trifluoroethyl)-1H-pyrazol-4-yl)-1',2',4,5,5',6'-hexahydro-2H-spiro[furan-3,7'-pyrrolo[3,4-b]pyridine]-3'-carboxylic acid (Compound 2077, 1.776 g, 4.307 mmol, 52.37% overall yield) as an off-white solid: ESMS (M+H) 413.32; $^1$H NMR (DMSO-d$_6$, 300 MHz) δ 13.50 (br s, 1H), 8.16 (s, 1H), 7.79 (s, 1H), 5.17 (q, J=9, 2H), 4.15 (d, J=12, 1H), 3.99 (m, 2H), 3.85 (m, 1H), 2.63 (s, 3H), 2.55 (m, 1H), 2.35 (m, 1H).

As shown in step 24-v of Scheme 24, to a suspension of Compound 2077 (1.77 g, 4.293 mmol) in MeCN (10 mL) was added LiOH dihydrate (270.2 mg, 6.440 mmol) followed by water (10 mL). After stirring for 5 minutes, NBS (802.4 mg, 4.508 mmol) was added. After a total of 40 min following the addition of NBS, the reaction mixture was partitioned between EtOAc and water (100 mL each). The aqueous layer was treated with 1 N aq HCl (8 mL) to give a white precipitate. The resulting suspension was concentrated and the residue digested in hot EtOH (25 mL) to give a suspension, which was treated with water (25 mL) and left standing at 23° C. for 2 h. The precipitate was then collected via filtration and washed with water (20 mL). Drying the solid under reduced pressure provided 3'-bromo-4'-methyl-6'-(1-(2,2,2-trifluoroethyl)-1H-pyrazol-4-yl)-4,5-dihydro-2H-spiro[furan-3,7'-pyrrolo[3,4-b]pyridine]-2',5'(1'H,6'H)-dione (Compound 2078, 1.65 g, 3.690 mmol, 85.94% yield) as an off-white solid: ESMS (M+H) 447.17; $^1$H NMR (DMSO-d$_6$, 300 MHz) δ 13.20 (br s, 1H), 8.14 (s, 1H), 7.78 (s, 1H), 5.17 (q, J=9, 2H), 4.14 (d, J=9, 1H), 3.98 (m, 2H), 3.83 (m, 1H), 2.59 (s, 3H), 2.49 (m, 1H), 2.32 (m, 1H).

As shown in step 24-vi of Scheme 24, to a suspension of Compound 2078 (1.65 g, 3.690 mmol) in EtOH (50 mL) at 23° C. was added triethylamine (1.120 g, 1.543 mL, 11.07 mmol), followed by the addition of Pd/C (430 mg, 0.4041 mmol) (10 wt % dry basis, Degussa type, wet). The reaction vessel was evacuated and the reaction atmosphere replaced with hydrogen gas. After stirring for 16 hours, the reaction mixture was treated with MeOH and DCM (50 mL each) and then filtered through diatomaceous earth, which was subsequently washed with 4:1 DCM:MeOH (100 mL). The combined filtrate was concentrated under reduced pressure to provide 4-methyl-6-[1-(2,2,2-trifluoroethyl)pyrazol-4-yl]spiro[1H-pyrrolo[3,4-b]pyridine-7,3'-tetrahydrofuran]-2,5-dione as a white solid (Compound 2079, 2 g, triethylamine impurity), which was used as is in subsequent reactions: ESMS (M+H) 369.30; $^1$H NMR (DMSO-$d_6$, 300 MHz) δ 8.16 (s, 1H), 7.80 (s, 1H), 6.34 (br s, 1H), 5.17 (q, J=9, 2H), 4.13 (d, J=12, 1H), 3.93 (m, 3H), 2.45 (s, 3H), 2.30 (m, 2H).

As shown in step 24-vii of Scheme 24, To a solution/suspension of Compound 2079 (1.359 g, 3.69 mmol, estimated mass of starting material based on 100% conversion in step 24-vi) in DCM (30 mL) was added DIEA (1.431 g, 1.929 mL, 11.07 mmol) followed by the addition of N-(5-chloro-2-pyridyl)-1,1,1-trifluoro-N-(trifluoromethylsulfonyl)-methanesulfonamide (Commin's reagent, 1.594 g, 4.059 mmol). The reaction mixture becomes homogenous in <10 minutes. After stirring for 3 h, additional Commin's reagent (400 mg) was added and the reaction mixture stirred an additional 90 minutes. The mixture was concentrated, loaded directly onto a silica gel chromatography column in DCM (15 mL), and purified by medium pressure silica gel chromatography (0-50% EtOAc in hexanes). The recovered product was contaminated with Commin's reagent so it was dissolved in DCM (100 mL), washed with saturated aqueous sodium bicarbonate (100 mL), dried (magnesium sulfate), filtered, and concentrated under reduced pressure to provide 4'-methyl-5'-oxo-6'-(1-(2,2,2-trifluoroethyl)-1H-pyrazol-4-yl)-4,5,5',6'-tetrahydro-2H-spiro[furan-3,7'-pyrrolo[3,4-b]pyridine]-2'-yl trifluoromethanesulfonate (Compound 2080, 1.757 g, 3.436 mmol, 93.14%) as a yellow oil: ESMS (M+H) 501.24; $^1$H NMR (DMSO-$d_6$, 300 MHz) δ 8.29 (s, 1H), 7.90 (s, 1H), 7.64 (s, 1H), 5.22 (q, J=9, 2H), 4.24 (d, J=12, 1H), 4.07 (m, 1H), 3.90 (m, 2H), 2.74 (s, 3H), 2.39 (m, 2H).

As shown in step 24-viii of Scheme 24, a microwave reaction vessel was charged with Compound 2080, 3-methoxy-5-(4,4,5,5-tetramethyl-1,3,2-dioxaborolan-2-yl)pyridine (121.4 mg, 0.5164 mmol), sodium carbonate (136.8 mg, 1.291 mmol), DMF (5 mL), and water (2.5 mL). A stream of nitrogen was passed through the reaction mixture for 5 min, then Pd(PPh$_3$)$_4$ (24.87 mg, 0.02152 mmol) was added. Nitrogen gas was bubbled though mixture for a further 3 minutes and then the reaction vessel was sealed with a septum and heated to 105° C. (sand bath). After 16 hours at this temperature, the reaction mixture was partitioned between EtOAc and water (100 mL each). The organics were separated, washed with brine (50 mL), dried (magnesium sulfate), filtered, and concentrated. The residue was purified by medium pressure silica gel chromatography (0-8% EtOH in DCM) to yield a crude product, which was dissolved/suspended in hot EtOAc (2 mL), treated with hexanes (3 mL), and left standing at 23° C. for 30 minutes. The resulting precipitate was collected by filtration and dried under reduced pressure to provide 2-(5-methoxy-3-pyridyl)-4-methyl-6-[1-(2,2,2-trifluoroethyl)pyrazol-4-yl]spiro[pyrrolo[3,4-b]pyridine-7,3'-tetrahydrofuran]-5-one (Compound 972, 87 mg, 0.1866 mmol, 43% yield) as an off-white solid: ESMS (M+H) 460.35; $^1$H NMR (DMSO-$d_6$, 300 MHz) δ 8.93 (d, J=3, 1H), 8.36 (d, J=3, 1H), 8.26 (s, 1H), 8.04 (s, 1H), 8.01 (dd, J=3, 3, 1H), 7.88 (s, 1H), 5.16 (q, J=9, 2H), 4.19 (d, J=9, 1H), 4.05 (m, 3H), 3.88 (s, 3H), 2.66 (s, 3H), 2.36 (m, 2H).

Using the appropriate intermediates, Compounds 978 and 989 were produced by a similar procedure.

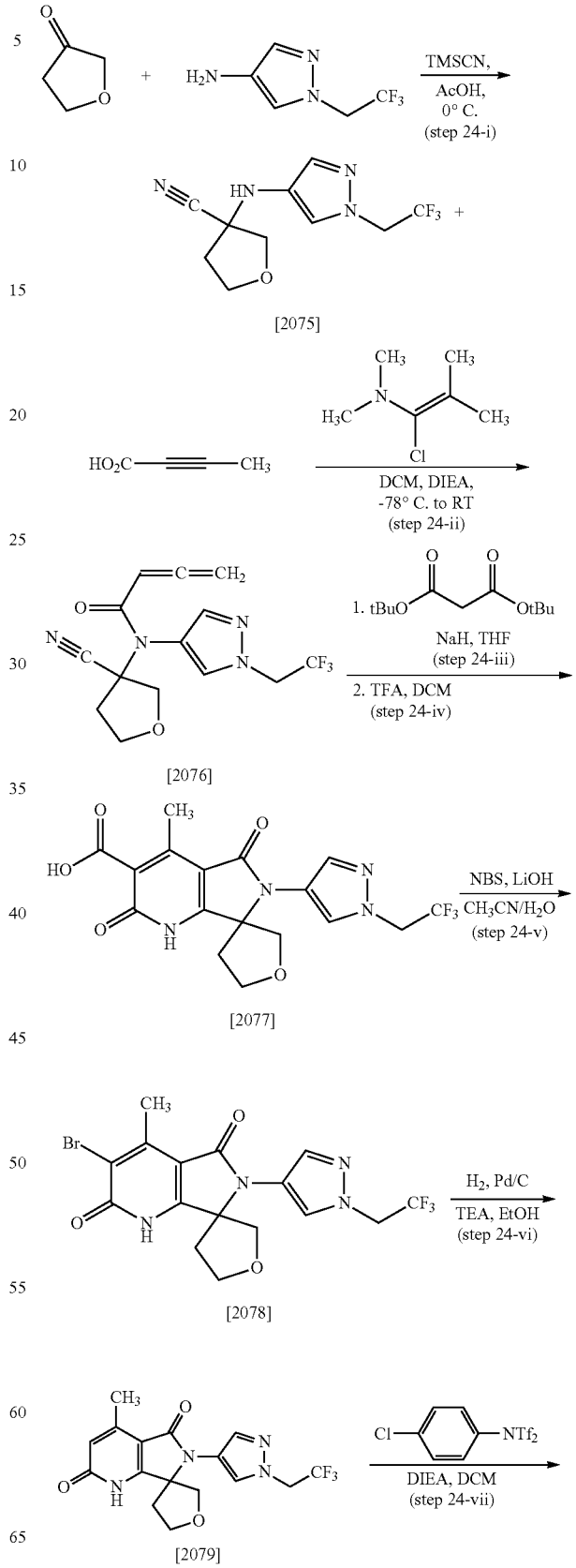

Scheme 24

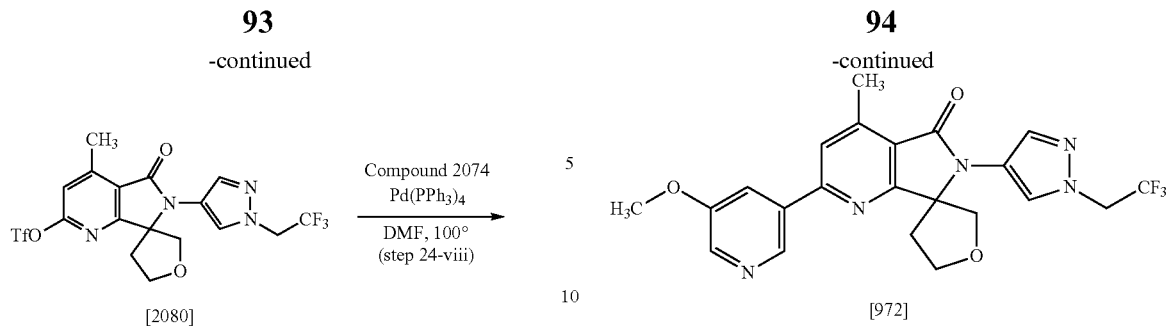

Table 1 provides analytical characterization data for compounds of formula I (blank cells indicate that the test was not performed).

TABLE 1

| Cmpd No. | Structure | ESMS (M + H) | ¹H NMR (300 MHz, unless indicated otherwise) |
|---|---|---|---|
| 1 | 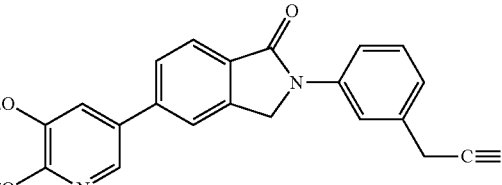 | 386.30 | (DMSO-$d_6$) δ 8.12 (d, J = 1.9 Hz, 1H), 8.02 (d, J = 8.2 Hz, 2H), 7.88 (m, 3H), 7.65 (d, J = 1.9 Hz, 1H), 7.49 (t, J = 8.0 Hz, 1H), 7.18 (d, J = 7.7 Hz, 1H), 5.09 (s, 2H), 4.11 (s, 2H), 3.94 (s, 3H) and 3.92 (s, 3H) |
| 2 | 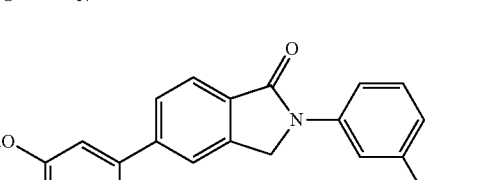 | 400.65 | (CDCl$_3$) δ 8.10-7.81 (m, 3H), 7.73 (d, J = 8.1 Hz, 1H), 7.61 (d, J = 6.6 Hz, 2H), 7.39 (t, J = 8.0 Hz, 1H), 7.28-7.05 (m, 2H), 4.89 (s, 2H), 4.03 (s, 3H), 3.85 (s, 3H), 1.63 (d, J = 7.3 Hz, 3H) |
| 3 | 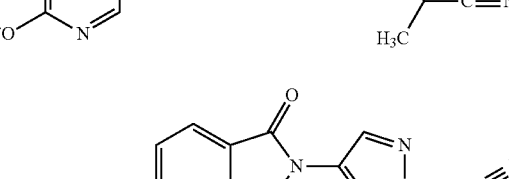 | 376.14 | (DMSO-$d_6$) δ 8.37 (s, 1H), 8.11 (d, J = 2.0 Hz, 1H), 7.97 (m, 2H), 7.84 (m, 2H), 7.64 (d, J = 2.0 Hz, 1H), 5.55 (s, 2H), 4.93 (s, 2H), 3.93 (s, 3H), 3.91 (s, 3H) |
| 4 | 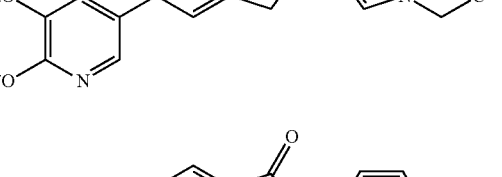 | 412.22 | (CDCl$_3$) δ 8.01-7.81 (m, 3H), 7.73-7.60 (m, 3H), 7.36 (t, J = 10.5 Hz, 1H), 7.22 (m, 1H), 7.10 (m, 1H), 4.88 (s, 2H), 4.02 (s, 3H), 3.91 (s, 3H), 1.70 (m, 2H), 1.44 (m, 2H) |
| 5 | 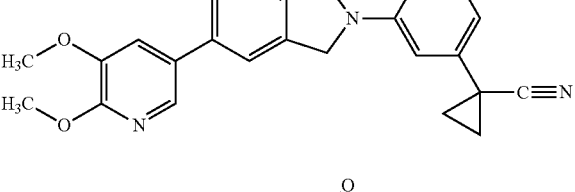 | 372.18 | (DMSO-$d_6$) δ 8.40 (s, 1H), 8.28 (d, J = 7.7 Hz, 1H), 8.13 (d, J = 1.8 Hz, 1H), 8.01 (s, 1H), 7.97-7.83 (m, 2H), 7.79-7.54 (m, 3H), 5.13 (s, 2H), 3.94 (s, 3H), 3.92 (s, 3H) |

TABLE 1-continued

| Cmpd No. | Structure | ESMS (M + H) | ¹H NMR (300 MHz, unless indicated otherwise) |
|---|---|---|---|
| 6 | 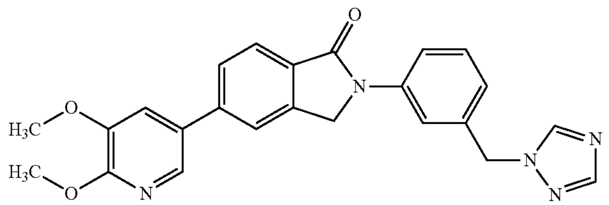 [SMILES: COc1cc(-c2ccc3c(c2)CN(c2cccc(Cn4cncn4)c2)C3=O)cnc1OC] | 428.25 | (DMSO-d$_6$) δ 8.69 (s, 1H), 8.12 (d, J = 1.9 Hz, 1H), 8.05-7.76 (m, 6H), 7.64 (d, J = 2.0 Hz, 1H), 7.45 (t, J = 7.9 Hz, 1H), 7.08 (d, J = 7.8 Hz, 1H), 5.48 (s, 2H), 5.06 (s, 2H), 3.92 (s, 3H). 3.91 (s, 3H) |
| 7 | 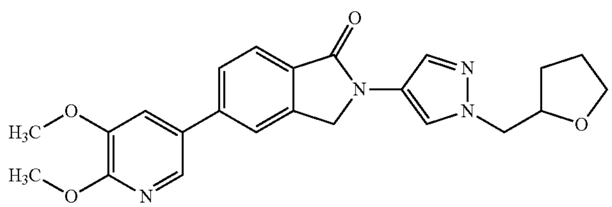 [SMILES: COc1cc(-c2ccc3c(c2)CN(c2cnn(CC4CCCO4)c2)C3=O)cnc1OC] | 421.27 | (DMSO-d$_6$) δ 8.18 (s, 1H), 8.11 (d, J = 1.9 Hz, 1H), 7.97 (s, 1H), 7.84 (m, 3H), 7.64 (d, J = 1.9 Hz, 1H), 4.90 (s, 2H), 4.18 (m, 3H), 3.92 (s, 3H), 3.91 (s, 3H), 3.78 (m, 1H), 3.65 (m, 1H), 2.03-1.47 (m, 4H) |
| 8 | 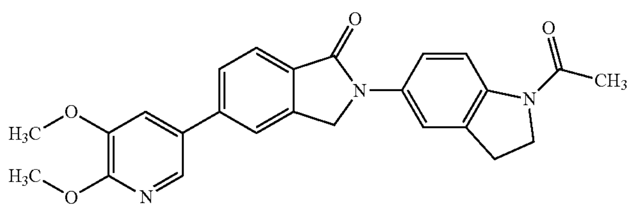 [SMILES: COc1cc(-c2ccc3c(c2)CN(c2ccc4c(c2)CCN4C(C)=O)C3=O)cnc1OC] | 430.26 | (DMSO-d$_6$) δ 8.09 (m, 2H), 7.98 (s, 1H), 7.85 (m, 3H), 7.63 (m, 2H), 5.04 (s, 2H), 4.13 (t, J = 8.4 Hz, 2H), 3.93 (s, 3H), 3.91 (s, 3H) 3.19 (t, J = 8.4 Hz, 2H), 2.17 (s, 3H) |
| 9 | 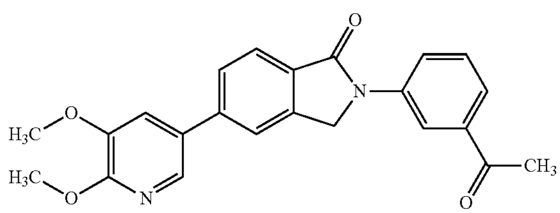 [SMILES: COc1cc(-c2ccc3c(c2)CN(c2cccc(C(N)=O)c2)C3=O)cnc1OC] | 389.21 | (DMSO-d$_6$) δ 8.48 (s, 1H), 8.22 (d, J = 8.4 Hz, 1H), 8.13 (s, 1H), 8.02 (s, 1H), 7.96-7.72 (m, 3H), 7.71-7.45 (m, 2H), 5.16 (s, 2H), 3.93 (s, 3H) 3.91 (s, 3H), 2.64 (s, 3H) |
| 10 | 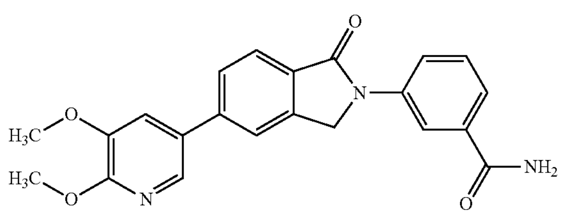 | 390.22 | (DMSO-d$_6$) δ 8.28 (s, 1H), 8.22 (d, J = 8.1 Hz, 1H), 8.13 (d, J = 2.0 Hz, 1H), 8.01 (s, 2H), 7.88 (m, 2H), 7.67 (m, 2H), 7.53 (t, J = 7.9 Hz, 1H), 7.42 (s, 1H), 5.13 (s, 2H), 3.93 (m, 3H). 3.91(m, 3H) |
| 11 | 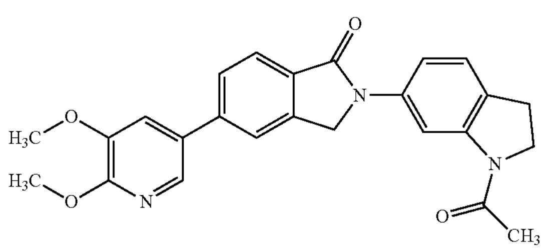 [SMILES: COc1cc(-c2ccc3c(c2)CN(c2ccc4c(c2)N(C(C)=O)CC4)C3=O)cnc1OC] | 430.26 | (DMSO-d$_6$) δ 8.56 (s, 1H), 8.11 (d, J = 1.8 Hz, 1H), 8.01 (s, 1H), 7.84 m, 2H), 7.64 (m, 2H), 7.28 (d, J = 7.6 Hz, 1H), 5.01 (s, 2H), 4.14 (t, J = 8.5 Hz, 2H), 3.93 (s, 3H), 3.91 (s, 3H), 3.15(m, 2H), 2.19 (s, 3H) |
| 12 | 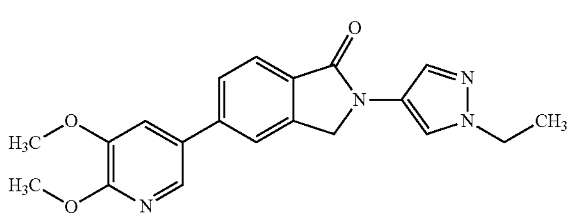 [SMILES: CCn1cc(N2Cc3cc(-c4cnc(OC)c(OC)c4)ccc3C2=O)cn1] | 365.20 | (DMSO-d$_6$) δ 8.19 (s, 1H), 8.11 (s, 1H), 7.97 (s, 1H), 7.84 (m, 3H), 7.64 (s, 1H), 4.89 (s, 2H), 4.32-4.06 (m, 2H), 3.92 (s, 3H), 3.91 (s, 3H), 1.39 (t, J = 7.2 Hz, 3H). |

TABLE 1-continued

| Cmpd No. | Structure | ESMS (M + H) | ¹H NMR (300 MHz, unless indicated otherwise) |
|---|---|---|---|
| 13 | 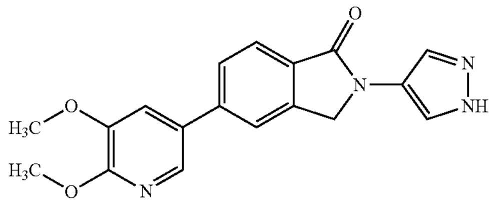 [SMILES: COc1cc(-c2ccc3c(c2)CN(c2cn[nH]c2)C3=O)cnc1OC] | 337.26 | |
| 14 | 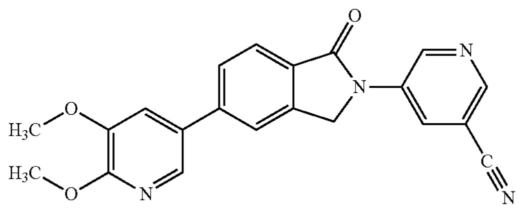 [SMILES: COc1cc(-c2ccc3c(c2)CN(c2cncc(C#N)c2)C3=O)cnc1OC] | 373.00 | (CDCl$_3$) δ 9.08 (d, 1H), 8.84 (t, 1H), 8.6 (m, 1H), 7.95 (m, 2H), 7.65 (m2H), 7.21 (d, 1H), 4.91 (s, 2H), 4.02 (s, 3H0, 3.91 (s, 3H). |
| 15 | 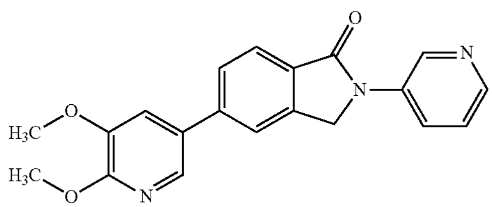 [SMILES: COc1cc(-c2ccc3c(c2)CN(c2cccnc2)C3=O)cnc1OC] | 348.20 | (DMSO-d$_6$) δ 9.14 (d, J = 2.6 Hz, 1H), 8.38 (m, 2H), 8.13 (d, J = 1.9 Hz, 1H), 8.03 (s, 1H), 7.89 (m, 2H), 7.66 (d, J = 1.8 Hz, 1H), 7.50 (dd, J = 8.4, 4.6 Hz, 1H), 5.14 (s, 2H), 3.94 (s, 3H), 3.92 (s, 3H) |
| 16 | 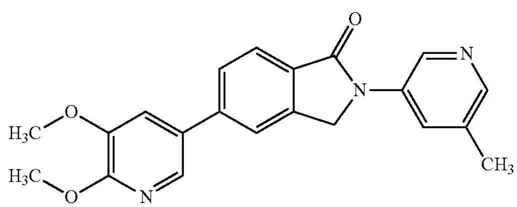 | 362.30 | (CDCl$_3$) δ 8.75 (s, 1H), 8.42 (s, 1H), 8.31 (s, 1H), 8.02 (m, 2H), 7.71 m, 2H), 7.31 (m, 1H), 4.98 (s, 2H), 4.11 (s, 3H), 4.00 (s, 3H), 2.44 (s, 3H) |
| 17 | 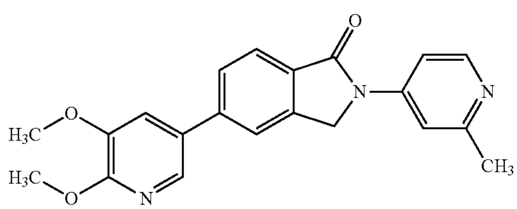 | 362.33 | (CDCl$_3$) δ 8.42 (d, J = 5.8 Hz, 1H), 8.06-7.82 (m, 2H), 7.77-7.40 (m, 3H), 7.34-7.11 (m, 2H), 4.83 (s, 2H), 4.02 (s, 3H), 3.91 (s, 3H), 2.53 (s, 3H) |
| 18 | 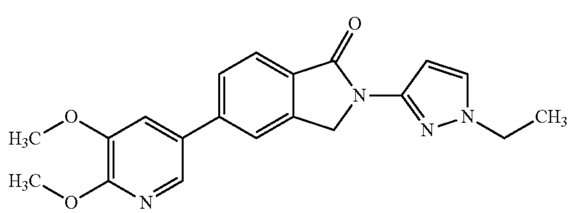 [SMILES: CCn1ccc(N2Cc3cc(-c4cnc(OC)c(OC)c4)ccc3C2=O)n1] | 365.39 | (DMSO-d$_6$) δ 8.10 (d, J = 2.0 Hz, 1H), 7.99 (s, 1H), 7.90-7.77 (m, 2H), 7.75 (d, J = 2.3 Hz, 1H), 7.63 (d, J = 2.0 Hz, 1H), 6.78 (d, J = 2.3 Hz, 1H), 4.97 (s, 2H), 4.12 (q, J = 7.3 Hz, 2H), 3.92 (d, J = 5.8 Hz, 5H), 3.30 (s, 4H), 2.50 (dt, J = 3.5, 1.7 Hz, 6H), 1.40 (t, J = 7.2 Hz, 3H) |
| 19 | 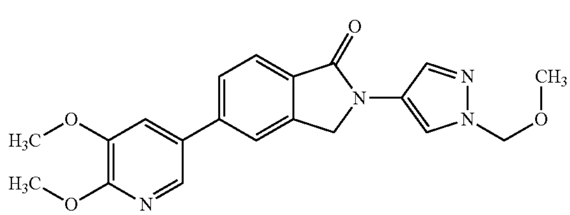 | 381.36 | (DMSO-d$_6$) δ 8.34 (s, 1H), 8.11 (d, J = 2.0 Hz, 1H), 7.96 (d, J = 13.0 Hz, 2H), 7.85 (dt, J = 16.3, 8.0 Hz, 2H), 7.64 (d, J = 2.0 Hz, 1H), 5.42 (s, 2H), 4.93 (s, 2H), 3.92 (d, J = 5.1 Hz, 6H), 3.30 (s, 3H), 3.27 (s, 3H), 2.50 (dt, J = 3.5, 1.7 Hz, 4H) |

TABLE 1-continued

| Cmpd No. | Structure | ESMS (M + H) | ¹H NMR (300 MHz, unless indicated otherwise) |
|---|---|---|---|
| 20 | 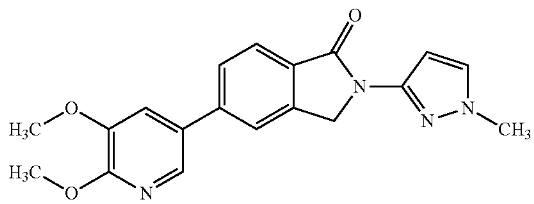 | 351.37 | (DMSO-d₆) δ 8.10 (d, J = 2.0 Hz, 1H), 7.99 (s, 1H), 7.93-7.74 (m, 2H), 7.70 (d, J = 2.2 Hz, 1H), 7.63 (d, J = 2.0 Hz, 1H), 6.78 (d, J = 2.2 Hz, 1H), 4.96 (s, 2H), 3.92 (d, J = 5.4 Hz, 6H), 3.83 (s, 3H), 3.30 (s, 1H), 2.50 (dt, J = 3.5, 1.7 Hz, 4H) |
| 21 | 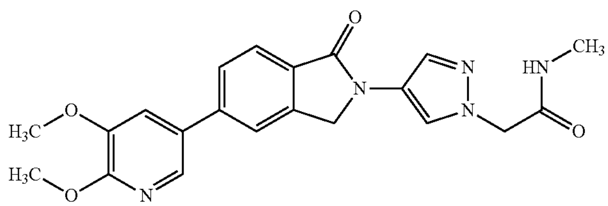 [SMILES: CNC(=O)Cn1cc(N2Cc3cc(-c4cnc(OC)c(OC)c4)ccc3C2=O)cn1] | 408.41 | (DMSO-d₆) δ 8.21 (s, 1H), 8.11 (d, J = 2.0 Hz, 1H), 7.98 (s, 2H), 7.84 (dt, J = 7.9, 6.0 Hz, 3H), 7.64 (d, J = 2.0 Hz, 1H), 4.90 (s, 2H), 4.80 (s, 2H), 3.92 (d, J = 5.4 Hz, 5H), 3.30 (s, 3H), 2.63 (d, J = 4.6 Hz, 3H), 2.50 (dt, J = 3.5, 1.8 Hz, 10H) |
| 22 | 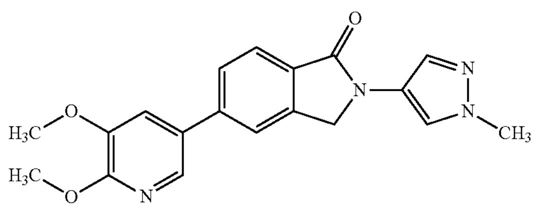 | 351.36 | (DMSO-d₆) δ 8.15 (s, 1H), 8.10 (d, J = 2.0 Hz, 1H), 7.97 (s, 1H), 7.91-7.72 (m, 3H), 7.63 (d, J = 2.0 Hz, 1H), 4.88 (s, 2H), 3.92 (d, J = 5.3 Hz, 6H), 3.88 (s, 3H), 3.30 (s, 1H), 2.50 (dt, J = 3.5, 1.8 Hz, 5H) |
| 23 | 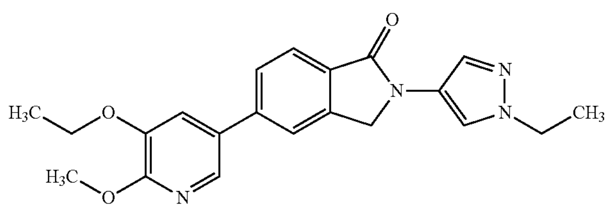 [SMILES: CCOc1cc(-c2ccc3c(c2)CN(c2cnn(CC)c2)C3=O)cnc1OC] | 379.41 | (DMSO-d₆) δ 8.19 (s, 1H), 8.10 (d, J = 2.0 Hz, 1H), 7.96 (s, 1H), 7.90-7.71 (m, 3H), 7.61 (d, J = 2.0 Hz, 1H), 4.88 (s, 2H), 4.27-4.07 (m, 4H), 3.93 (s, 3H), 3.30 (s, 3H), 2.50 (dt, J = 3.5, 1.7 Hz, 10H), 1.39 (td, J = 7.1, 3.5 Hz, 5H) |
| 24 | 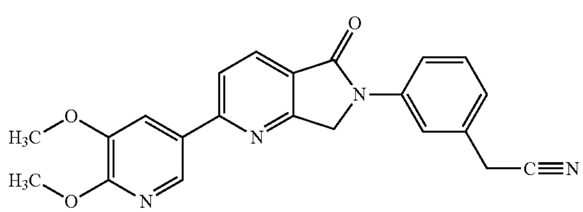 [SMILES: COc1cc(-c2ccc3c(n2)CN(c2cccc(CC#N)c2)C3=O)cnc1OC] | 401.23 | (CDCl₃) δ 8.43 (d, J = 1.6 Hz, 1H), 8.26 (d, J = 8.1 Hz, 1H), 8.01 (s, 1H), 7.96 (s, 1H), 7.89 (d, J = 8.1 Hz, 1H), 7.81 (d, J = 9.6 Hz, 1H), 7.50 (t, J = 8.0 Hz, 1H), 7.23 (m, 1H), 5.02 (s, 2H), 4.29 (q, J = 6.9 Hz, 2H), 4.15 (s, 3H), 3.85 (s, 2H), 1.56 (t, J = 6.9 Hz, 3H) |
| 25 | 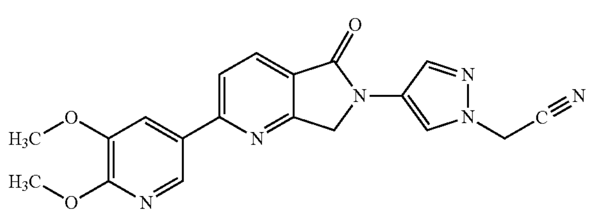 [SMILES: COc1cc(-c2ccc3c(n2)CN(c2cnn(CC#N)c2)C3=O)cnc1OC] | 377.30 | (DMSO-d₆) δ 8.56 (s, 1H), 8.39 (s, 1H), 8.22 (m, 2H), 7.98 m (s, 2H), 5.55 (s, 2H), 5.00 (s, 2H), 3.95 (s, 3H), 3.93 (s, 3H) |
| 26 | 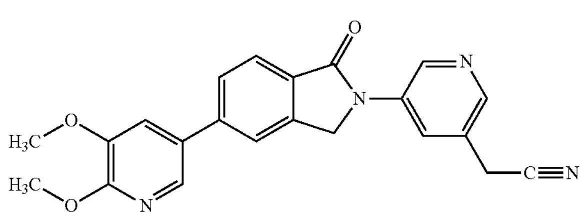 [SMILES: COc1cc(-c2ccc3c(c2)CN(c2cncc(CC#N)c2)C3=O)cnc1OC] | 387.25 | (DMSO-d₆) δ 9.08 (d, J = 2.1 Hz, 1H), 8.56 (s, 1H), 8.42 (s, 1H), 8.14 (d, J = 1.9 Hz, 1H), 8.04 (s, 1H), 7.91 (m, 2H), 7.66 (d, J = 1.8 Hz, 1H), 5.16 (s, 2H), 4.22 (s, 2H), 3.94 (s, 3H), 3.92 (s, 3H) |

TABLE 1-continued

| Cmpd No. | Structure | ESMS (M + H) | ¹H NMR (300 MHz, unless indicated otherwise) |
|---|---|---|---|
| 27 | 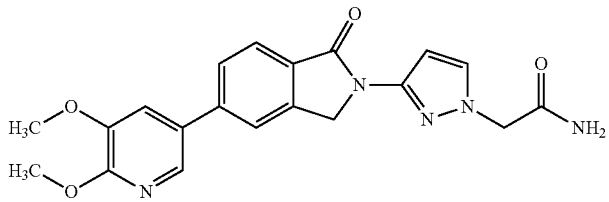 [SMILES: COc1cc(-c2ccc3c(c2)CN(c2ccn(CC(N)=O)n2)C3=O)cnc1OC] | 394.39 | (DMSO-d₆) δ 8.10 (d, J = 1.8 Hz, 1H), 7.98 (s, 1H), 7.85 (q, J = 8.0 Hz, 2H), 7.73 (d, J = 2.3 Hz, 1H), 7.63 (d, J = 1.9 Hz, 1H), 7.45 (s, 1H), 7.26 (s, 1H), 6.82 (d, J = 2.3 Hz, 1H), 4.97 (d, J = 9.1 Hz, 2H), 4.74 (s, 2H), 3.92 (d, J = 5.8 Hz, 6H), 3.30 (s, 2H), 3.17 (s, 1H), 2.89 (s, 0H), 2.73 (s, 0H), 2.60-2.42 (m, 6H) |
| 28 | 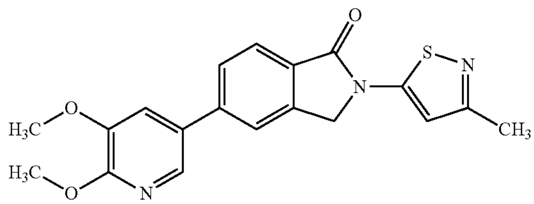 | 368.35 | |
| 29 | 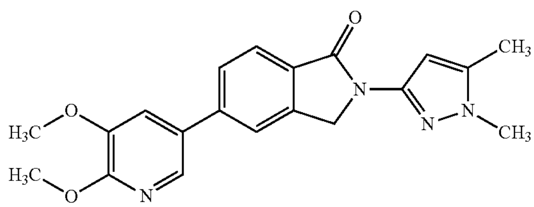 | 365.42 | (DMSO-d₆) δ 8.09 (d, J = 1.8 Hz, 1H), 7.97 (s, 1H), 7.83 (q, J = 8.0 Hz, 2H), 7.65 (m, 1H), 7.4 (m, 1H), 7.25 (dd, J = 9.2, 5.4 Hz, 1H), 6.62 (s, 1H), 4.91 (s, 2H), 3.92 (d, J = 5.6 Hz, 6H), 3.70 (s, 3H), 3.30 (s, 2H), 2.50 (s, 4H), 2.28 (s, 3H) |
| 30 | 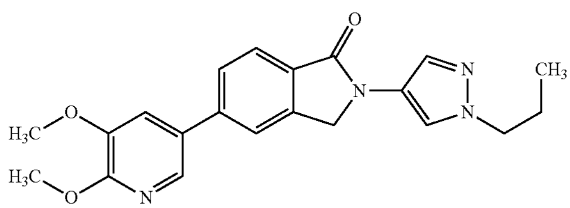 [SMILES: CCCn1cc(N2Cc3cc(-c4cnc(OC)c(OC)c4)ccc3C2=O)cn1] | 379.35 | (DMSO-d₆) δ 8.18 (s, 1H), 8.10 (m, 1H), 7.97 (s, 1H), 7.92-7.71 (m, 3H), 7.63 (m, 1H), 4.87 (s, 2H), 4.09 (t, J = 6.9 Hz, 2H), 3.91 (t, J = 7.0 Hz, 6H), 2.50 (s, 10H), 1.81 (dd, J = 14.4, 7.2 Hz, 2H), 0.86 (t, J = 7.3 Hz, 3H) |
| 31 | 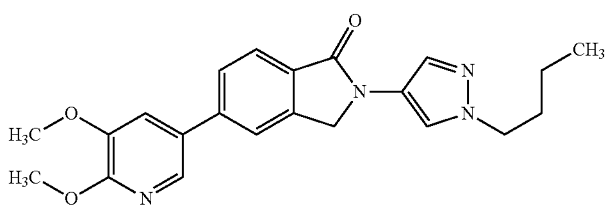 | 393.36 | (DMSO-d₆) δ 8.18 (s, 1H), 8.11 (d, J = 2.0 Hz, 1H), 7.97 (s, 1H), 7.83 (m, 3H), 7.64 (d, J = 2.0 Hz, 1H), 4.89 (s, 2H), 4.13 (t, J = 7.0 Hz, 2H), 3.92 (d, J = 5.4 Hz, 6H), 2.50 (dt, J = 3.6, 1.8 Hz, 11H), 1.95-1.64 (m, 2H), 1.27 (dd, J = 14.9, 7.4 Hz, 2H), 0.90 (t, J = 7.4 Hz, 3H) |
| 32 | 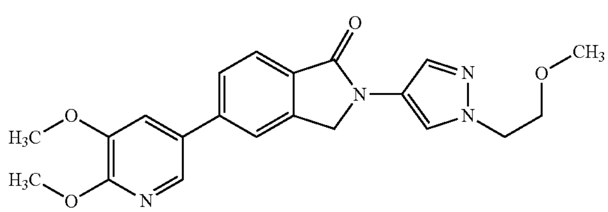 | 395.35 | (DMSO-d₆) δ 8.19 (s, 1H), 8.10 (d, J = 2.0 Hz, 1H), 7.96 (s, 1H), 7.90-7.73 (m, 3H), 7.63 (d, J = 2.0 Hz, 1H), 4.89 (s, 2H), 4.30 (t, J = 5.3 Hz, 2H), 3.92 (d, J = 5.4 Hz, 6H), 3.71 (t, J = 5.3 Hz, 2H), 3.25 (s, 3H), 2.50 (dt, J = 3.6, 1.8 Hz, 3H) |
| 33 | 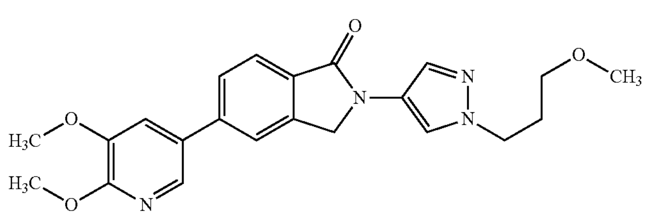 | 409.36 | |

TABLE 1-continued

| Cmpd No. | Structure | ESMS (M + H) | ¹H NMR (300 MHz, unless indicated otherwise) |
|---|---|---|---|
| 34 | 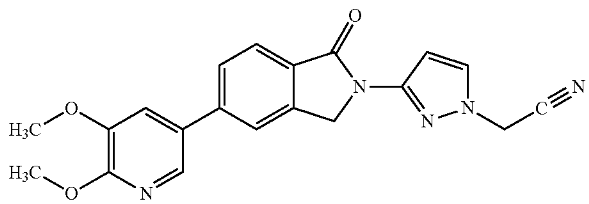 [SMILES: COc1cc(-c2ccc3c(c2)CN(c2ccn(CC#N)n2)C3=O)cnc1OC] | 376.28 | (DMSO-d$_6$) δ 8.10 (d, J = 1.9 Hz, 1H), 8.01 (s, 1H), 7.92-7.81 (m, 3H), 7.63 (d, J = 1.9 Hz, 1H), 6.92 (d, J = 2.4 Hz, 1H), 5.48 (s, 2H), 4.99 (s, 2H), 3.90 (dd, J = 11.6, 4.7 Hz, 6H), 2.57-2.35 (m, 15H) |
| 35 | 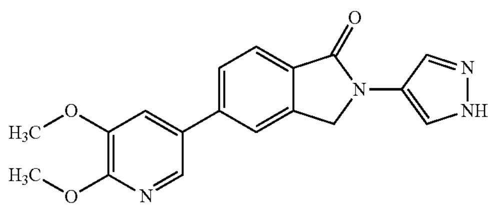 [SMILES: COc1cc(-c2ccc3c(c2)CN(c2cn[nH]c2)C3=O)cnc1OC] | 337.19 | (DMSO-d$_6$) δ 12.86 (s, 1H), 8.22-8.04 (m, 2H), 7.97 (s, 1H), 7.91-7.72 (m, 3H), 7.63 (s, 1H), 4.91 (s, 2H), 3.93 (s, 3H), 3.91 (s, 3H), 2.50 (s, 5H) |
| 36 | 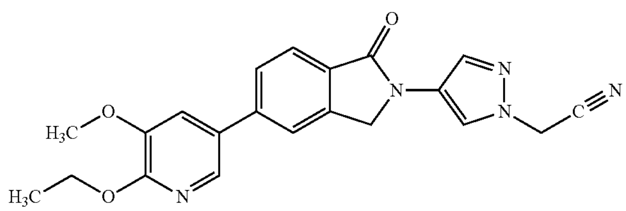 [SMILES: CCOc1ncc(-c2ccc3c(c2)CN(c2cnn(CC#N)c2)C3=O)cc1OC] | 390.29 | (DMSO-d$_6$) δ 8.37 (s, 1H), 8.09 (d, J = 2.0 Hz, 1H), 7.97 (m, 2H), 7.92-7.76 (m, 2H), 7.63 (d, J = 2.0 Hz, 1H), 5.54 (s, 2H), 4.93 (s, 2H), 4.39 (q, J = 7.0 Hz, 2H), 3.91 (s, 3H), 1.36 (t, J = 7.0 Hz, 3H) |
| 37 | 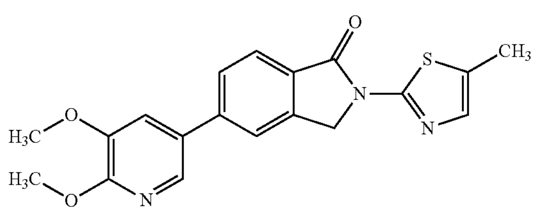 | 368.20 | |
| 38 | 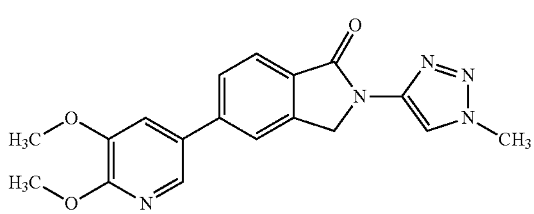 | 366.30 | (DMSO-d$_6$) δ 8.48 (s, 1H), 8.12 (d, J = 1.8 Hz, 1H), 8.06 (s, 1H), 7.95-7.78 (m, 2H), 7.64 (s, 1H), 5.10 (s, 2H), 4.46 (q, J = 7.3 Hz, 2H), 3.93 (m, 3H), 3.91 (m, 3H), 1.47 (t, J = 7.3 Hz, 3H) |
| 39 | 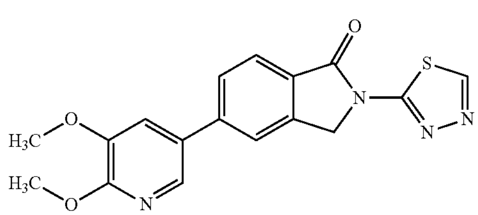 [SMILES: COc1cc(-c2ccc3c(c2)CN(c2nncs2)C3=O)cnc1OC] | 355.23 | |
| 40 | 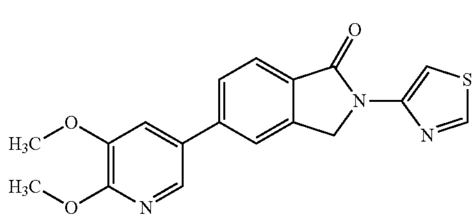 [SMILES: COc1cc(-c2ccc3c(c2)CN(c2cscn2)C3=O)cnc1OC] | 354.27 | (DMSO-d$_6$) δ 9.12 (d, J = 2.2 Hz, 1H), 8.12 (d, J = 2.0 Hz, 1H), 8.05 (s, 1H), 7.98 (d, J = 2.2 Hz, 1H), 7.89 (m, 2H), 7.65 (d, J = 2.0 Hz, 1H), 5.18 (s, 2H), 3.92 (d, J = 5.1 Hz, 6H), 3.30 (s, 4H), 2.50 (dt, J = 3.5, 1.7 Hz, 9H) |

TABLE 1-continued

| Cmpd No. | Structure | ESMS (M + H) | ¹H NMR (300 MHz, unless indicated otherwise) |
|---|---|---|---|
| 41 | 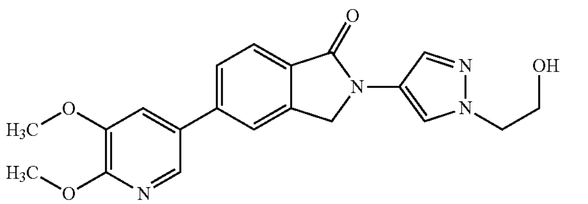 [SMILES: COc1cc(-c2ccc3c(c2)CN(c2cnn(CCO)c2)C3=O)cnc1OC] | 381.34 | |
| 42 | 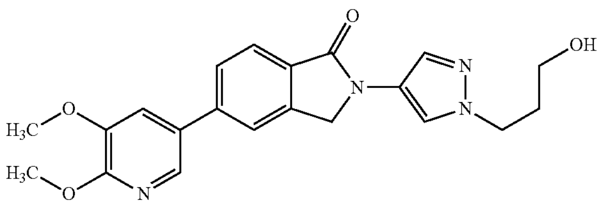 [SMILES: COc1cc(-c2ccc3c(c2)CN(c2cnn(CCCO)c2)C3=O)cnc1OC] | 395.35 | |
| 43 | 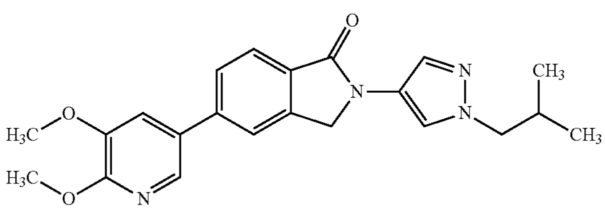 [SMILES: COc1cc(-c2ccc3c(c2)CN(c2cnn(CC(C)C)c2)C3=O)cnc1OC] | 393.35 | (DMSO-d₆) δ 8.17 (s, 1H), 8.11 (d, J = 2.0 Hz, 1H), 7.97 (s, 1H), 7.83 (dd, J = 19.0, 7.5 Hz, 3H), 7.64 (d, J = 2.0 Hz, 1H), 4.90 (s, 2H), 3.93 (m, 8H), 2.50 (dt, J = 3.5, 1.8 Hz, 7H), 2.13 (dt, J = 13.5, 6.8 Hz, 1H), 0.87 (d, J = 6.7 Hz, 6H) |
| 44 | 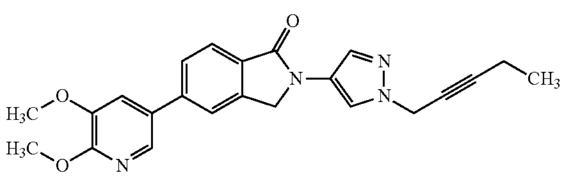 [SMILES: CCC#CCn1cc(N2Cc3cc(-c4cnc(OC)c(OC)c4)ccc3C2=O)cn1] | 403.35 | (DMSO-d₆) δ 8.25 (s, 1H), 8.11 (d, J = 2.0 Hz, 1H), 7.97 (s, 1H), 7.84 (q, J = 7.8 Hz, 3H), 7.64 (d, J = 1.9 Hz, 1H), 5.03 (t, J = 2.1 Hz, 2H), 4.91 (s, 2H), 3.93 (s,, 3H), 3.91 (s, 3H), 2.60-2.42 (m, 7H), 2.33-2.12 (m, 2H), 1.08 (t, J = 7.5 Hz, 3H) |
| 45 | 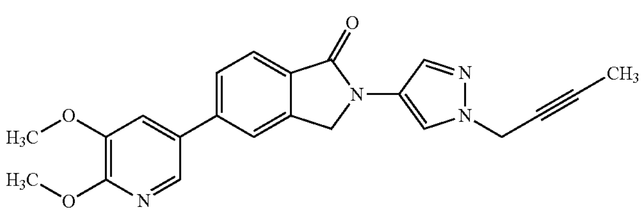 [SMILES: CC#CCn1cc(N2Cc3cc(-c4cnc(OC)c(OC)c4)ccc3C2=O)cn1] | 389.34 | (DMSO-d₆) δ 8.25 (s, 1H), 8.11 (d, J = 2.0 Hz, 1H), 7.97 (s, 1H), 7.90-7.70 (m, 3H), 7.64 (d, J = 2.0 Hz, 1H), 5.01 (d, J = 2.4 Hz, 2H), 4.91 (s, 2H), 3.93 (s, 3H), 3.91 (s, 3H), 2.50 (dt, J = 3.5, 1.7 Hz, 9H), 1.85 (t, J = 2.4 Hz, 3H) |
| 46 | 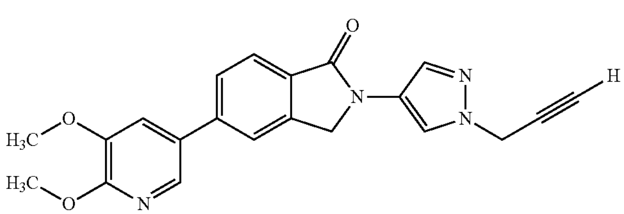 [SMILES: C#CCn1cc(N2Cc3cc(-c4cnc(OC)c(OC)c4)ccc3C2=O)cn1] | 375.32 | |
| 47 | 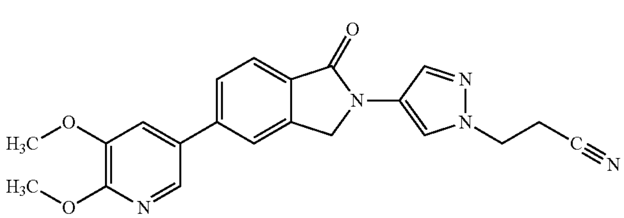 [SMILES: COc1cc(-c2ccc3c(c2)CN(c2cnn(CCC#N)c2)C3=O)cnc1OC] | 390.38 | (DMSO-d₆) δ 8.33 (s, 1H), 8.11 (d, J = 2.0 Hz, 1H), 7.98 (s, 1H), 7.84 (q, J = 7.8 Hz, 3H), 7.64 (d, J = 2.0 Hz, 1H), 4.91 (s, 2H), 4.44 (t, J = 6.4 Hz, 2H), 3.93 (s, 3H), 3.91 (s, 3H), 3.09 (t, J = 6.4 Hz, 2H), 2.50 (dt, J = 3.5, 1.7 Hz, 8H) |

TABLE 1-continued

| Cmpd No. | Structure | ESMS (M + H) | ¹H NMR (300 MHz, unless indicated otherwise) |
|---|---|---|---|
| 48 | 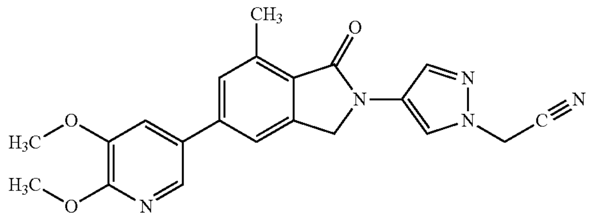 [SMILES: COc1cc(-c2cc(C)c3c(c2)CN(c2cnn(CC#N)c2)C3=O)cnc1OC] | 390.30 | (DMSO-d$_6$) δ 8.34 (s, 1H), 8.10 (d, J = 1.8 Hz, 1H), 7.95 (s, 1H), 7.76 (s, 1H), 7.68-7.53 (m, 2H), 5.53 (s, 2H), 4.85 (s, 2H), 3.92 (s, 3H), 3.91 (s, 3H), 2.72 (s, 3H) |
| 49 | 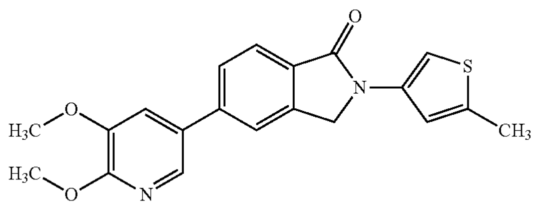 | 367.29 | |
| 50 | 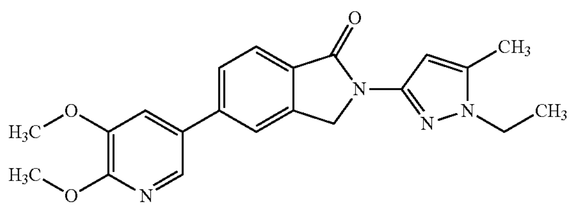 [SMILES: CCn1nc(N2Cc3cc(-c4cnc(OC)c(OC)c4)ccc3C2=O)cc1C] | 379.36 | |
| 51 | 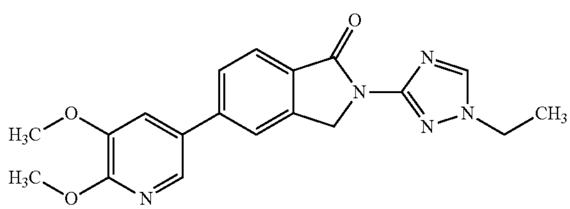 [SMILES: CCn1cnc(N2Cc3cc(-c4cnc(OC)c(OC)c4)ccc3C2=O)n1] | 366.36 | |
| 52 | 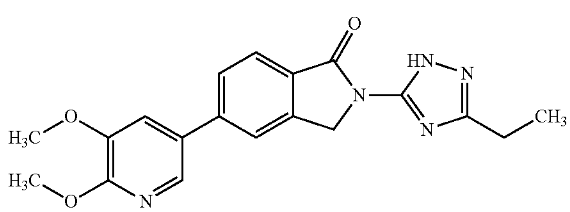 [SMILES: CCc1n[nH]c(N2Cc3cc(-c4cnc(OC)c(OC)c4)ccc3C2=O)n1] | 366.30 | (DMSO-d$_6$) δ 13.41 (s, 1H), 8.11 (d, J = 1.8 Hz, 1H), 8.02 (s, 1H), 7.93-7.77 (m, 2H), 7.64 (d, J = 1.7 Hz, 1H), 5.03 (s, 2H), 3.93 (s, 3H), 3.91 (s, 3H), 2.68 (q, J = 7.6 Hz, 2H), 1.25 (t, J = 7.6 Hz, 3H) |
| 53 | 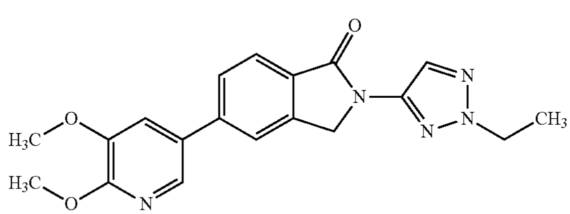 [SMILES: CCn1ncc(N2Cc3cc(-c4cnc(OC)c(OC)c4)ccc3C2=O)n1] | 366.30 | (DMSO-d$_6$) δ 8.21-8.06 (m, 2H), 8.03 (s, 1H), 7.96-7.79 (m, 2H), 7.64 (d, J = 1.9 Hz, 1H), 5.01 (s, 2H), 4.44 (q, J = 7.3 Hz, 2H), 3.93 (s, 3H), 3.91 (s, 3H), 1.48 (t, J = 7.3 Hz, 3H) |
| 54 | 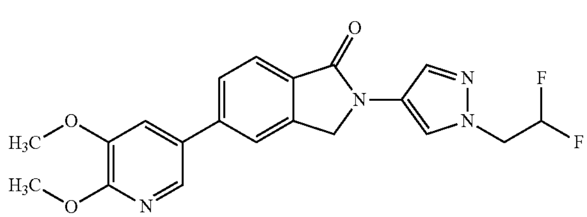 [SMILES: COc1cc(-c2ccc3c(c2)CN(c2cnn(CC(F)F)c2)C3=O)cnc1OC] | 401.30 | (DMSO-d$_6$) δ 8.31 (s, 1H), 8.11 (d, J = 1.9 Hz, 1H), 7.98 (s, 1H), 7.84 (dd, J = 16.1, 7.0 Hz, 3H), 7.64 (d, J = 1.9 Hz, 1H), 6.57 (d, J = 3.6 Hz, .25H), 6.38 (t, J = 3.7 Hz, .5H), 6.20 (t, J = 3.6 Hz, .25H), 4.92 (s, 2H), 4.68 (td, J = 15.1, 3.7 Hz, 2H), 3.93 (s, 3H), 3.91 (s, 3H) |

TABLE 1-continued

| Cmpd No. | Structure | ESMS (M + H) | $^1$H NMR (300 MHz, unless indicated otherwise) |
|---|---|---|---|
| 55 | 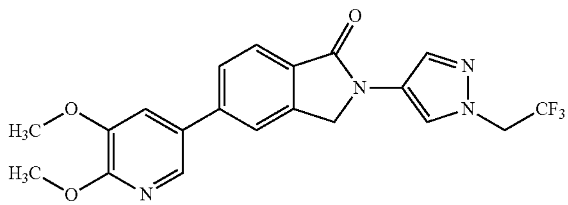 [SMILES: COc1cc(-c2ccc3c(c2)CN(c2cnn(CC(F)(F)F)c2)C3=O)cnc1OC] | 419.28 | (DMSO-d$_6$) δ 8.38 (s, 1H), 8.11 (d, J = 2.0 Hz, 1H), 7.98 (s, 1H), 7.93 (s, 1H), 7.84 (dd, J = 11.9, 4.6 Hz, 2H), 7.64 (d, J = 2.0 Hz, 1H), 5.18 (t, J = 9.2 Hz, 2H), 4.94 (s, 2H), 3.93 (s, 3H), 3.91 (s, 3H) |
| 56 | 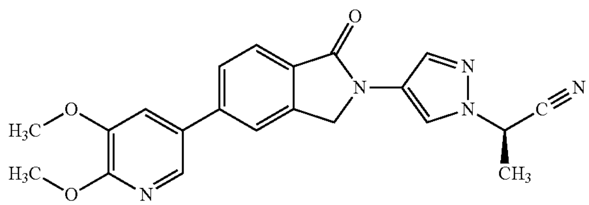 [SMILES: COc1cc(-c2ccc3c(c2)CN(c2cnn([C@H](C)C#N)c2)C3=O)cnc1OC] | 390.29 | |
| 57 | 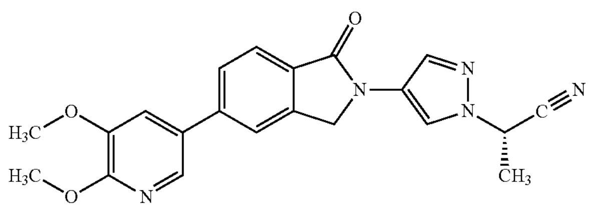 [SMILES: COc1cc(-c2ccc3c(c2)CN(c2cnn([C@@H](C)C#N)c2)C3=O)cnc1OC] | 390.29 | |
| 58 | 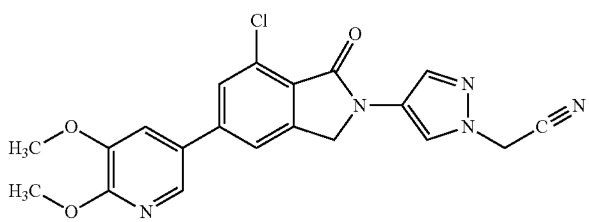 [SMILES: COc1cc(-c2cc(Cl)c3c(c2)CN(c2cnn(CC#N)c2)C3=O)cnc1OC] | 410.30 | (DMSO-d$_6$) δ 8.36 (s, 1H), 8.16 (d, J = 1.8 Hz, 1H), 7.97 (m, 2H), 7.92 (s, 1H), 7.69 (s, 1H), 5.56 (s, 2H), 4.90 (s, 2H), 3.93 (s, 3H)3.92 (s, 3H) |
| 59 | 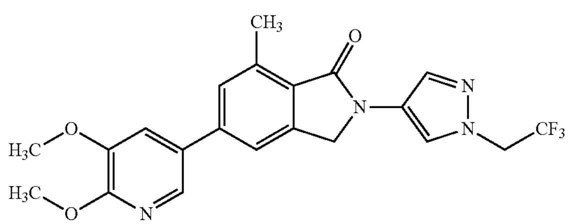 [SMILES: COc1cc(-c2cc(C)c3c(c2)CN(c2cnn(CC(F)(F)F)c2)C3=O)cnc1OC] | 432.90 | (DMSO-d$_6$) δ 8.36 (s, 1H), 8.10 (s, 1H), 7.92 (s, 1H), 7.76 (s, 1H), 7.63 (m, 2H), 5.18 (m, 2H), 4.86 (s, 2H), 3.91 (s, 3H), 3.92 (s, 3H), 2.72 (s, 3H) |
| 60 | 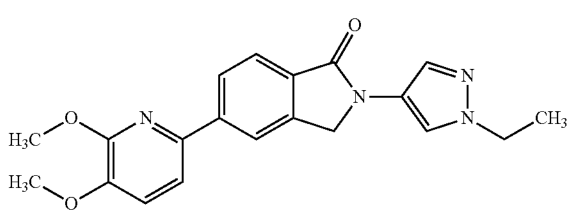 [SMILES: CCn1cc(N2Cc3cc(-c4ccc(OC)c(OC)n4)ccc3C2=O)cn1] | 365.4 | |
| 61 | 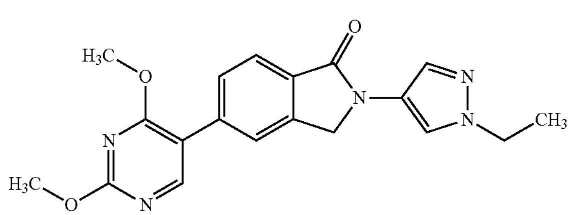 [SMILES: CCn1cc(N2Cc3cc(-c4cnc(OC)nc4OC)ccc3C2=O)cn1] | 366.42 | |

TABLE 1-continued

| Cmpd No. | Structure | ESMS (M + H) | ¹H NMR (300 MHz, unless indicated otherwise) |
|---|---|---|---|
| 62 | 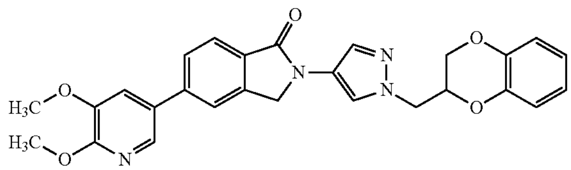 [SMILES: COc1cc(-c2ccc3c(c2)CN(c2cnn(CC4COc5ccccc5O4)c2)C3=O)cnc1OC] | 485.12 | |
| 63 | 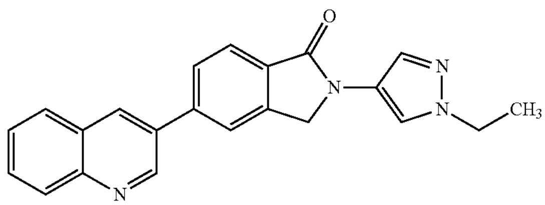 [SMILES: CCn1cc(N2Cc3cc(-c4cnc5ccccc5c4)ccc3C2=O)cn1] | 355.4 | |
| 64 | 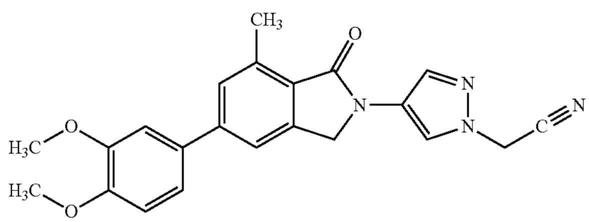 [SMILES: COc1ccc(-c2cc(C)c3c(c2)CN(c2cnn(CC#N)c2)C3=O)cc1OC] | 388.94 | (DMSO-d₆) δ 8.33 (s, 1H), 7.94 (s, 1H), 7.71 (s, 1H), 7.58 (s, 1H), 7.30 (m, 2H), 7.07 (d, J = 9.0 Hz, 1H), 5.54 (s, 2H), 4.83 (s, 2H), 3.87 (s, 3H), 3.81 (s, 3H), 2.71 (s, 3H) |
| 65 | 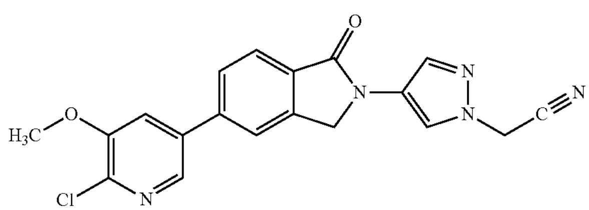 [SMILES: COc1cc(-c2ccc3c(c2)CN(c2cnn(CC#N)c2)C3=O)cnc1Cl] | 379.99 | |
| 66 | 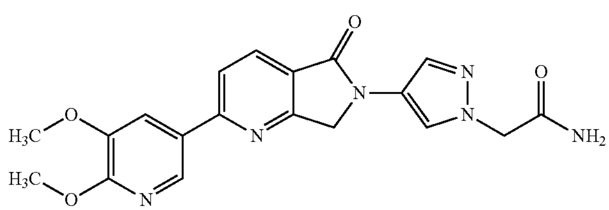 [SMILES: COc1cc(-c2ccc3c(n2)CN(c2cnn(CC(N)=O)c2)C3=O)cnc1OC] | 395.38 | (DMSO-d₆) δ 8.56 (d, J = 1.9Hz, 1H), 8.22 (s, 1H), 8.20 (s, 1H), 8.19 (s, 1H), 7.99 (d, J = 1.9Hz, 1H), 7.82 (s, 1H), 7.49 (br. s, 1H), 7.25 (br. s, 1H), 4.98 (s, 2H), 4.81 (s, 2H), 3.96 (s, 3H), 3.92 (s, 3H) |
| 67 | 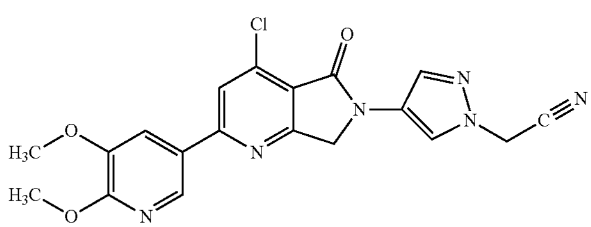 [SMILES: COc1cc(-c2cc(Cl)c3c(n2)CN(c2cnn(CC#N)c2)C3=O)cnc1OC] | 411.31 | (DMSO-d₆) δ 8.61 (d, J = 1.7 Hz, 1H), 8.37 (s, 1H), 8.32 (s, 1H), 8.00 (s, 1H), 7.98 (s, 1H), 5.56 (s, 2H), 4.97 (s, 2H), 3.96 (s, 3H), 3.92 (s, 3H) |
| 68 | 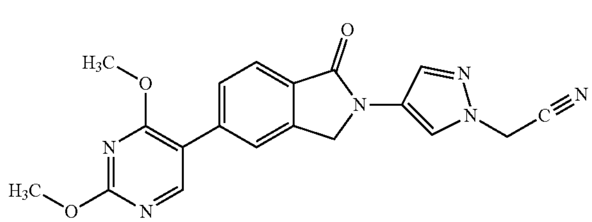 [SMILES: COc1ncc(-c2ccc3c(c2)CN(c2cnn(CC#N)c2)C3=O)c(OC)n1] | 377.3 | |

TABLE 1-continued

| Cmpd No. | Structure | ESMS (M + H) | ¹H NMR (300 MHz, unless indicated otherwise) |
|---|---|---|---|
| 69 | 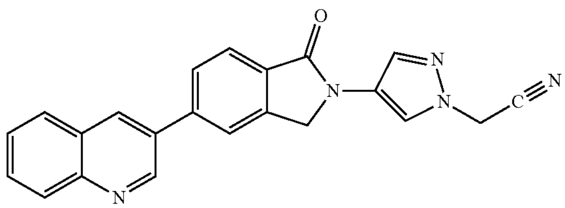 [SMILES: N#CCn1cc(N2Cc3cc(-c4cnc5ccccc5c4)ccc3C2=O)cn1] | 365.96 | (CDCl₃) δ 8.33 (s, 2H), 8.13 (d, J = 8.6 Hz, 1H), 8.01 (d, J = 7.8 Hz, 1H), 7.85 (dd, J = 17.5, 8.5 Hz, 3H), 7.77-7.66 (m, 2H), 7.63-7.52 (m, 1H), 5.07 (s, 2H), 4.81 (s, 2H) |
| 70 | 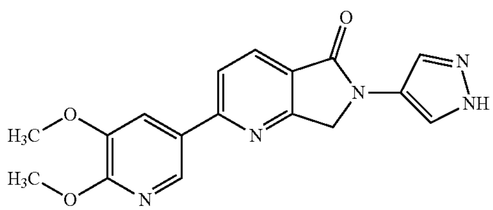 [SMILES: COc1cc(-c2ccc3c(n2)CN(c2cn[nH]c2)C3=O)cnc1OC] | 338.31 | (DMSO-d₆) δ 12.86 (s, 1H), 8.55 (d, J = 1.9Hz, 1H), 8.18 (s, 2H), 8.10-7.93 (m, 3H), 4.98 (s, 2H), 3.96 (s, 3H), 3.93 (s, 3H), 2.50 (dt, J = 3.6, 1.8 Hz, 7H) |
| 71 | 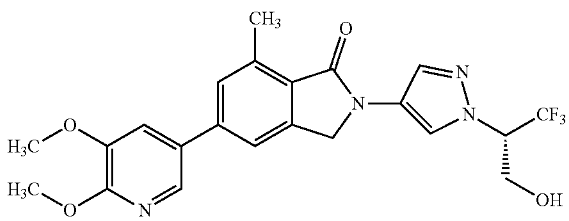 [SMILES: COc1cc(-c2cc(C)c3c(c2)CN(c2cnn([C@@H](CO)C(F)(F)F)c2)C3=O)cnc1OC] | 462.82 | (DMSO-d₆) δ 8.26 (s, 1H), 8.09 (d, J = 2.0 Hz, 1H), 7.85 (s, 1H), 7.75 (s, 1H), 7.62 (m, 2H), 6.70 (s, 1H), 4.82 (s, 2H), 4.51-4.17 (m, 3H), 3.92 (s, 3H), 3.91 (s, 3H), 2.72 (s, 3H) |
| 72 | 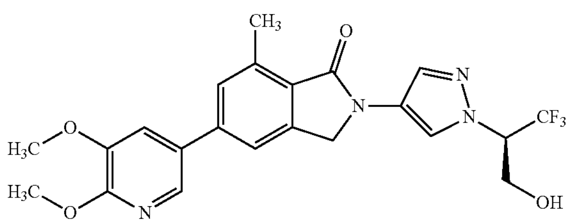 [SMILES: COc1cc(-c2cc(C)c3c(c2)CN(c2cnn([C@H](CO)C(F)(F)F)c2)C3=O)cnc1OC] | 462.82 | (DMSO-d₆) δ 8.26 (s, 1H), 8.09 (d, J = 2.0 Hz, 1H), 7.85 (s, 1H), 7.75 (s, 1H), 7.62 (m, 2H), 6.70 (s, 1H), 4.82 (s, 2H), 4.51-4.17 (m, 3H), 3.92 (s, 3H), 3.91 (s, 3H), 2.72 (s, 3H) |
| 73 | 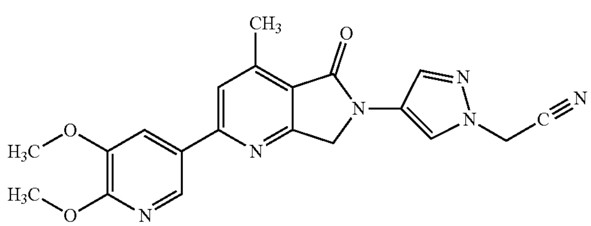 | 391.25 | (DMSO-d₆) δ 8.55, 8.54, 8.35, 7.97, 5.55, 4.92, 3.95, 3.92, 3.30, 2.72. |
| 74 | 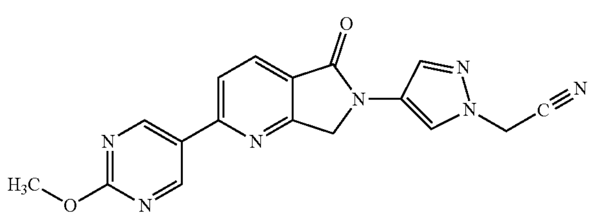 [SMILES: COc1ncc(-c2ccc3c(n2)CN(c2cnn(CC#N)c2)C3=O)cn1] | 348.03 | (DMSO-d₆) δ 9.36 (s, 2H), 8.40 (s, 1H), 8.28 (d, J = 8.1 Hz, 1H), 8.20 (d, J = 8.3 Hz, 1H), 7.98 (s, 1H), 5.56 (s, 2H), 5.01 (s, 2H), 4.02 (s, 3H) |
| 75 | 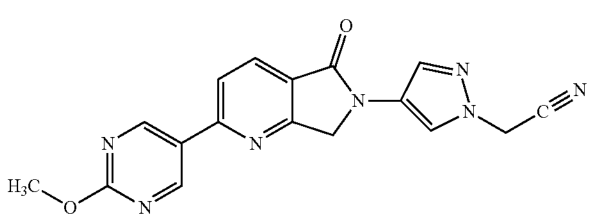 [SMILES: COc1ncc(-c2ccc3c(n2)CN(c2cnn(CC#N)c2)C3=O)cn1] | 384.21 | |

TABLE 1-continued

| Cmpd No. | Structure | ESMS (M + H) | ¹H NMR (300 MHz, unless indicated otherwise) |
|---|---|---|---|
| 76 | 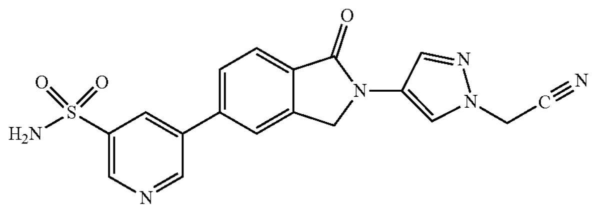 [SMILES: N#CCn1cc(N2Cc3cc(-c4cncc(S(N)(=O)=O)c4)ccc3C2=O)cn1] | 395.22 | 1H NMR (300 MHz, CD3CN) d 9.11 (dd, J = 14.7, 2.2 Hz, 2H), 8.48 (s, 1H), 8.28 (d, J = 0.6 Hz, 1H), 8.03-7.75 (m, 4H), 5.92 (s, 2H), 5.21 (s, 2H), 4.89 (s, 2H) |
| 77 | 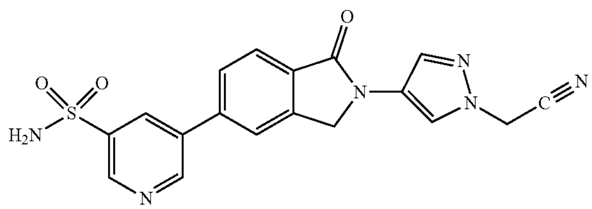 [SMILES: N#CCn1cc(N2Cc3cc(-c4cncc(S(N)(=O)=O)c4)ccc3C2=O)cn1] | 404.14 | |
| 78 | 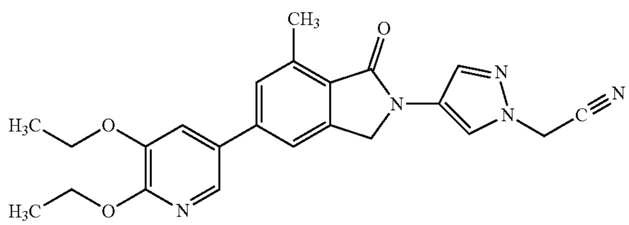 [SMILES: CCOc1cc(-c2cc(C)c3c(c2)CN(c2cnn(CC#N)c2)C3=O)cnc1OCC] | 418.46 | (CDCl3) δ 8.34 (s, 1H), 7.97 (d, J = 2.1 Hz, 1H), 7.74 (s, 1H), 7.44 (s, 1H), 7.38 (s, 1H), 7.26 (s, 1H), 5.09 (s, 2H), 4.73 (s, 2H), 4.52 (q, J = 7.0 Hz, 2H), 4.19 (q, J = 7.0 Hz, 2H), 2.81 (s, 3H), 1.62-1.38 (m, 6H) |
| 79 | 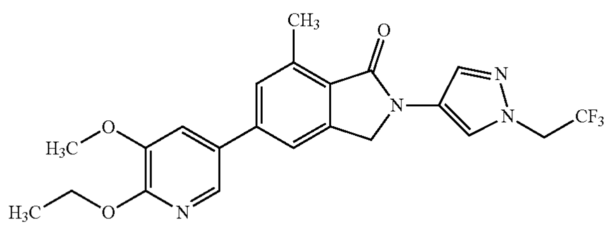 [SMILES: CCOc1ncc(-c2cc(C)c3c(c2)CN(c2cnn(CC(F)(F)F)c2)C3=O)cc1OC] | 447.46 | |
| 80 | 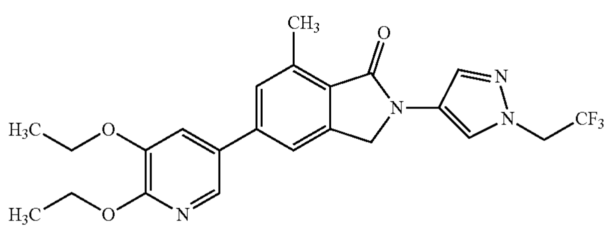 [SMILES: CCOc1cc(-c2cc(C)c3c(c2)CN(c2cnn(CC(F)(F)F)c2)C3=O)cnc1OCC] | 461.51 | |
| 81 | 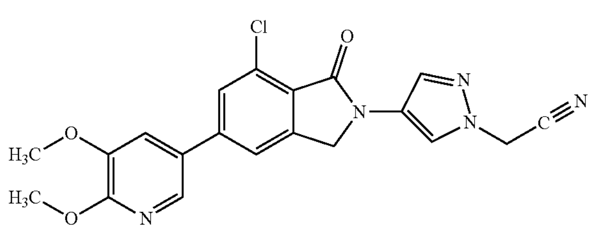 [SMILES: COc1cc(-c2cc(Cl)c3c(c2)CN(c2cnn(CC#N)c2)C3=O)cnc1OC] | 410.38 | (DMSO-d6) δ 8.36 (s, 1H), 8.21 (s, 1H), 7.97 (s, 1H), 7.91-7.67 (m, 2H), 7.11 (d, J = 8.6 Hz, 1H), 5.56 (s, 2H), 4.94 (s, 2H), 3.87 (d, J = 10.8 Hz, 6H) |
| 82 | 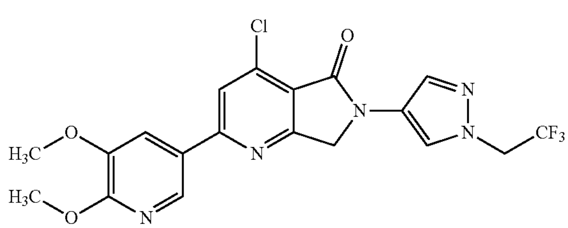 [SMILES: COc1cc(-c2cc(Cl)c3c(n2)CN(c2cnn(CC(F)(F)F)c2)C3=O)cnc1OC] | 454.33 | (DMSO-d6) δ 8.61 (s, 1H), 8.39 (s, 1H), 8.31 (s, 1H), 8.00 (s, 1H), 7.95 (s, = 1H), 5.21 (dd, J = 18.1, 8.8 Hz, 2H), 4.98 (s, 2H), 3.96 (s, 3H), 3.92 (s, 3H) |

TABLE 1-continued
| Cmpd No. | Structure | ESMS (M + H) | ¹H NMR (300 MHz, unless indicated otherwise) |
|---|---|---|---|
| 83 | 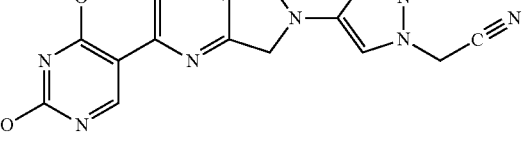 | 377.85 | (DMSO-d₆) δ 9.07 (s, 1H), 8.49 (s, 1H), 8.32 (d, J = 8.2 Hz, 1H), 8.17 (d, J = 7.9 Hz, 1H), 8.07 (s, 1H), 5.65 (s, 2H), 5.08 (s, 2H), 4.17 (s, 3H), 4.10 (s, 3H) |
| 84 | 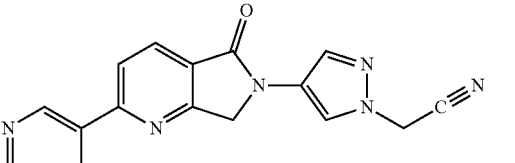 | 332.95 | (DMSO-d₆) δ 9.04 (s, 2H), 8.37 (s, 1H), 8.16 (d, J = 8.1 Hz, 1H), 8.04 (d, J = 8.2 Hz, 1H), 7.96 (s, 1H), 7.17 (s, 2H), 5.55 (s, 2H), 4.95 (s, 2H) |
| 85 | 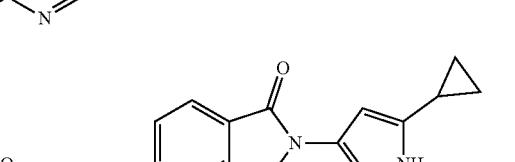 | 378.26 | |
| 86 | 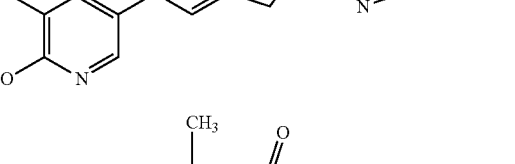 | 390.29 | (DMSO-d₆) δ 8.34, 7.96, 7.93, 7.80, 7.78, 7.63, 7.59, 7.57, 7.12, 7.09, 5.54, 4.90, 3.88, 3.84, 3.30, 2.71 |
| 87 | 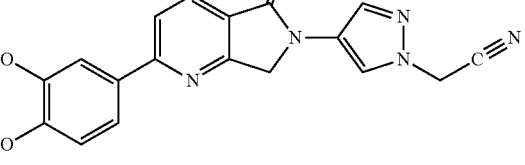 | 388.43 | (DMSO-d₆) δ 9.06 (br. s, 1H), 8.60 (d, J = 1.9 Hz, 2H), 8.41 (s, 1H), 8.28 (d, J = 8.2 Hz, 1H), 8.22 (d, J = 8.2 Hz, 1H), 8.00 (d, J = 1.9 Hz, 1H), 5.20 (s, 2H), 4.20 (s, 2H), 3.96 (s, 3H), 3.93 (s, 3H) |
| 88 | 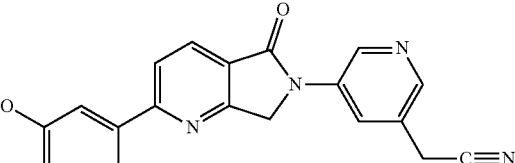 | 407 | |
| 89 | 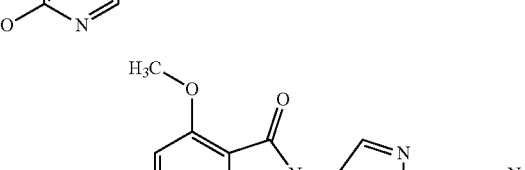 | 380.6 | |

TABLE 1-continued
| Cmpd No. | Structure | ESMS (M + H) | ¹H NMR (300 MHz, unless indicated otherwise) |
|---|---|---|---|
| 90 | 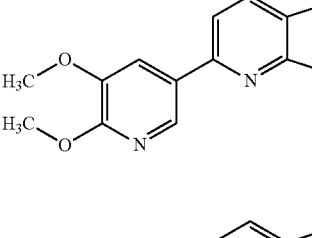 | 391.6 | (DMSO-d₆) δ 8.56 (d, J = 2.0 Hz, 1H), 8.36 (s, 1H), 8.21 (t, J = 5.8 Hz, 2H), 7.99 (d, J = 2.0 Hz, 1H), 7.88 (s, 1H), 4.99 (s, 2H), 4.45 (t, J = 6.4 Hz, 2H), 3.96 (s, 2H), 3.92 (s, 3H), 3.09 (t, J = 6.4 Hz, 2H) |
| 91 | 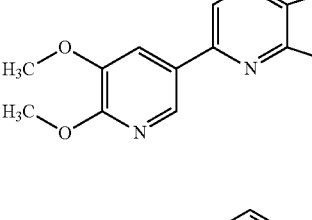 | 382.6 | |
| 92 | 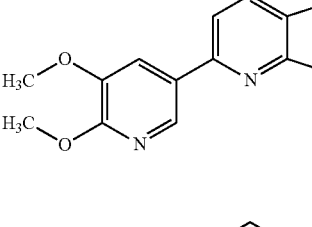 | 421.6 | (DMSO-d₆) δ 8.56 (d, J = 1.9 Hz, 1H), 8.37 (s, 1H), 8.19 (d, J = 3.1 Hz, 2H), 7.99 (d, J = 1.9 Hz, 1H), 7.90 (s, 1H), 5.22 (s, 1H), 4.99 (s, 2H), 4.68 (s, 1H), 3.96 (s, 3H), 3.92 (s, 3H), 3.73 (t, J = 5.8 Hz, 2H), 3.19-3.06 (m, 2H) |
| 93 | 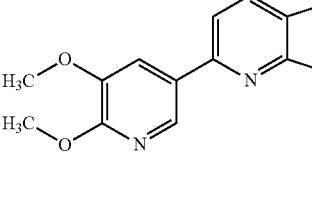 | 396.6 | |
| 94 | 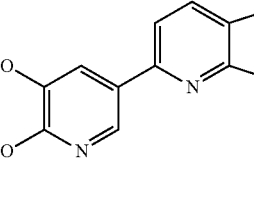 | 402.6 | |
| 95 | 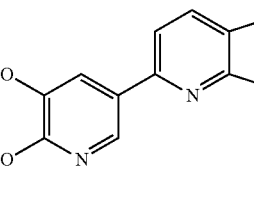 | 396.6 | |
| 96 | 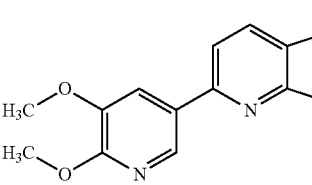 | 391.6 | (DMSO-d₆) δ 8.56 (d, J = 1.9 Hz, 1H), 8.42 (s, 1H), 8.20 (q, J = 8.2 Hz, 2H), 8.04-7.96 (m, 2H), 5.95 (d, J = 7.1 Hz, 1H), 5.00 (s, 2H), 3.96 (s, 3H), 3.92 (s, 3H), 1.83 (d, J = 7.1 Hz, 3H) |

TABLE 1-continued

| Cmpd No. | Structure | ESMS (M + H) | ¹H NMR (300 MHz, unless indicated otherwise) |
|---|---|---|---|
| 97 | 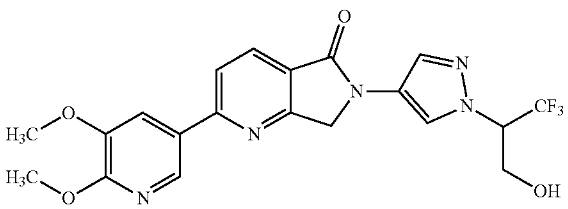 [SMILES: COc1cc(-c2ccc3c(n2)CN(c2cnn(C(CO)C(F)(F)F)c2)C3=O)cnc1OC] | 450.2 | |
| 98 | 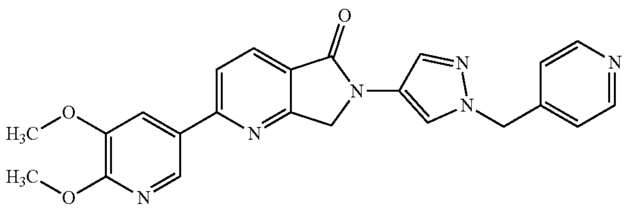 [SMILES: COc1cc(-c2ccc3c(n2)CN(c2cnn(Cc4ccncc4)c2)C3=O)cnc1OC] | 430 | |
| 99 | 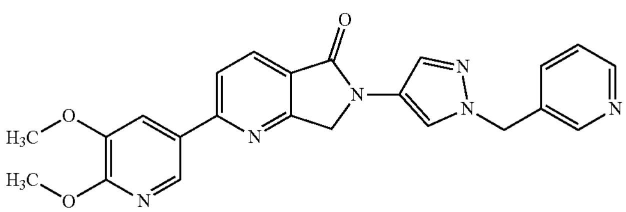 [SMILES: COc1cc(-c2ccc3c(n2)CN(c2cnn(Cc4cccnc4)c2)C3=O)cnc1OC] | 429.3 | |
| 100 | 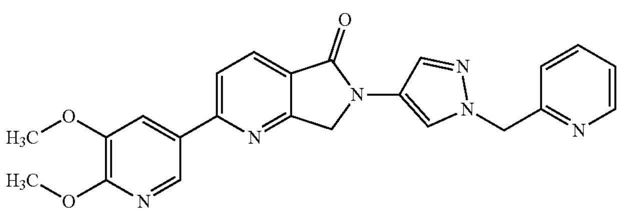 [SMILES: COc1cc(-c2ccc3c(n2)CN(c2cnn(Cc4ccccn4)c2)C3=O)cnc1OC] | 429.8 | |
| 101 | 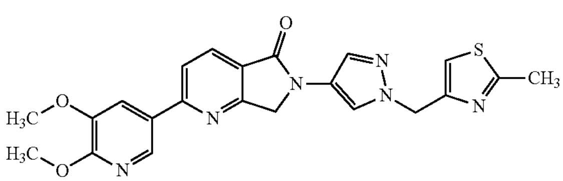 | 449.3 | (DMSO-d$_6$) δ 8.55 (s, 1H), 8.28 (s, 1H), 8.25-8.13 (m, 2H), 7.98 (s, 1H), 7.82 (s, 1H), 7.38 (s, 1H), 5.40 (s, 2H), 4.97 (s, 2H), 3.96 (s, 3H), 3.92 (s, 3H), 2.63 (d, J = 1.2 Hz, 3H) |
| 102 | 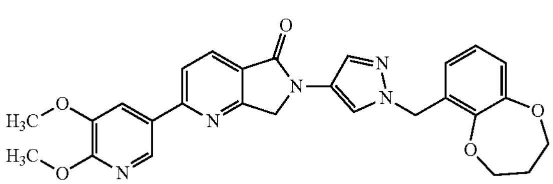 [SMILES: COc1cc(-c2ccc3c(n2)CN(c2cnn(Cc4cccc5c4OCCCO5)c2)C3=O)cnc1OC] | 500.7 | |
| 103 | 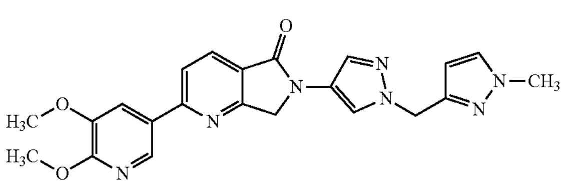 | 432.6 | (DMSO-d$_6$) δ 8.55 (d, J = 2.0 Hz, 1H), 8.19 (d, J = 7.0 Hz, 3H), 7.98 (d, J = 1.9 Hz, 1H), 7.80 (d, J = 0.6 Hz, 1H), 7.63 (d, J = 2.2 Hz, 1H), 6.17 (d, J = 2.2 Hz, 1H), 5.27 (s, 2H), 4.95 (s, 2H), 3.95 (s, 3H), 3.90 (s, 3H), 3.81 (s, 3H) |

TABLE 1-continued

| Cmpd No. | Structure | ESMS (M + H) | ¹H NMR (300 MHz, unless indicated otherwise) |
|---|---|---|---|
| 104 | 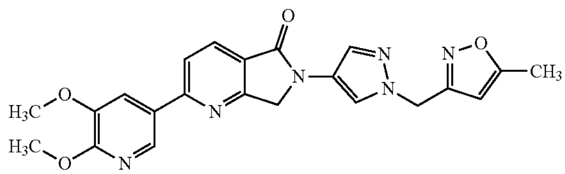 | 433.3 | (DMSO-d₆) δ 8.55 (s, 1H), 8.35 (s, 1H), 8.28-8.11 (m, 2H), 7.99 (s, 1H), 7.87 (s, 1H), 6.12 (s, 1H), 5.45 (d, J = 8.1 Hz, 2H), 4.98 (s, 2H), 3.96 (s, 3H), 3.92 (s, 3H), 2.39 (s, 3H) |
| 105 | 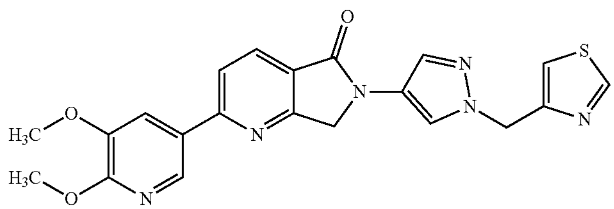 [SMILES: COc1cc(-c2ccc3c(n2)CN(c2cnn(Cc4cscn4)c2)C3=O)cnc1OC] | 435.6 | |
| 106 | 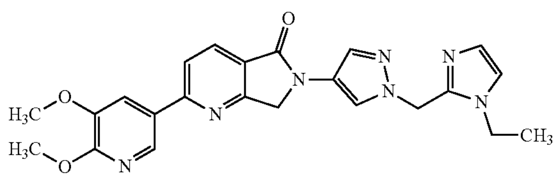 [SMILES: CCn1ccnc1Cn1cc(N2Cc3nc(-c4cnc(OC)c(OC)c4)ccc3C2=O)cn1] | 446.6 | (DMSO-d₆) δ 8.55 (s, 1H), 8.43 (s, 1H), 8.20 (d, J = 8.0 Hz, 2H), 7.98 (s, 1H), 7.83 (s, 1H), 7.21 (s, 1H), 6.88 (s, 1H), 5.46 (s, 2H), 4.96 (s, 2H), 4.06 (q, J = 7.5 Hz, 2H), 3.96 (s, 3H), 3.92 (s, 3H), 1.21 (t, J = 7.0 Hz, 3H) |
| 107 | 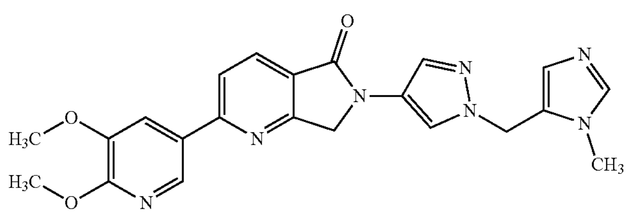 [SMILES: COc1cc(-c2ccc3c(n2)CN(c2cnn(Cc4cncn4C)c2)C3=O)cnc1OC] | 432.6 | |
| 108 | 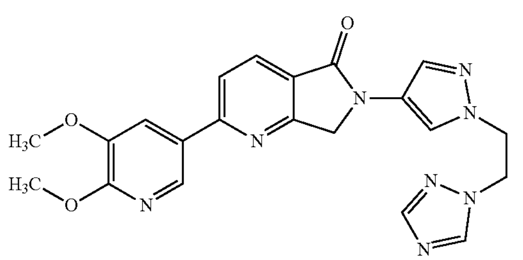 [SMILES: COc1cc(-c2ccc3c(n2)CN(c2cnn(CCn4cncn4)c2)C3=O)cnc1OC] | 433.6 | |
| 109 | 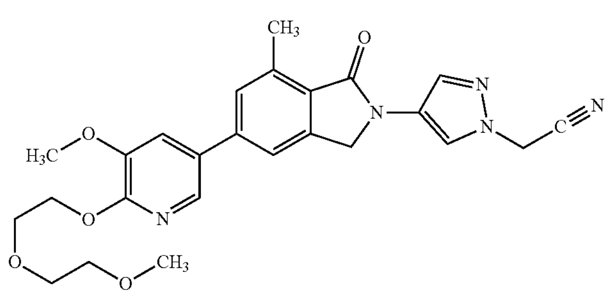 [SMILES: COCCOCCOc1ncc(-c2cc(C)c3c(c2)CN(c2cnn(CC#N)c2)C3=O)cc1OC] | 478.51 | |

TABLE 1-continued
| Cmpd No. | Structure | ESMS (M + H) | ¹H NMR (300 MHz, unless indicated otherwise) |
|---|---|---|---|
| 110 | 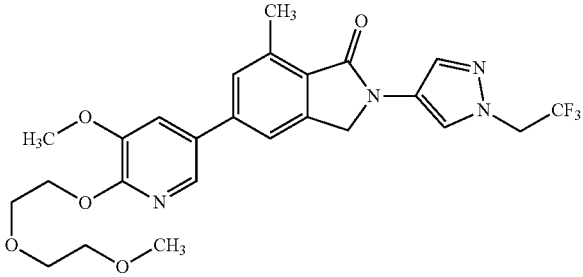 [SMILES: COCCOCCOc1ncc(-c2cc(C)c3c(c2)CN(c2cnn(CC(F)(F)F)c2)C3=O)cc1OC] | 521.62 | |
| 111 | 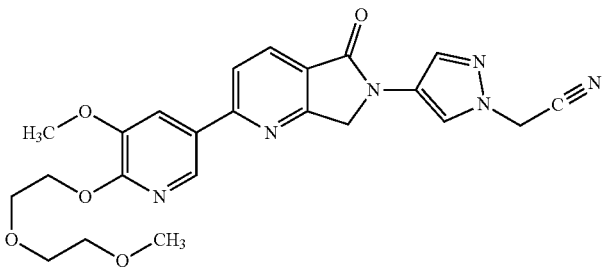 [SMILES: COCCOCCOc1ncc(-c2ccc3c(n2)CN(c2cnn(CC#N)c2)C3=O)cc1OC] | 465.54 | |
| 112 | 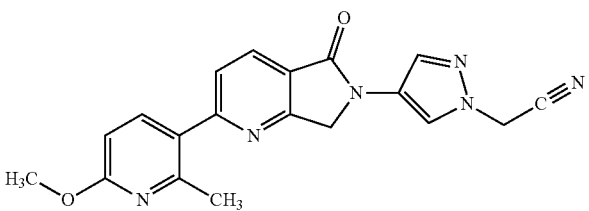 [SMILES: COc1ccc(-c2ccc3c(n2)CN(c2cnn(CC#N)c2)C3=O)c(C)n1] | 361.24 | (DMSO-d₆) δ 8.50 (s, 1H), 8.33 (d, J = 8.0 Hz, 1H), 8.08 (s, 1H), 7.98 (d, J = 8.5 Hz, 1H), 7.84 (d, J = 8.0 Hz, 1H), 6.91 (d, J = 8.5 Hz, 1H), 5.66 (s, 2H), 5.09 (s, 3H), 4.02 (s, 3H), 2.65 (s, 3H) |
| 113 | 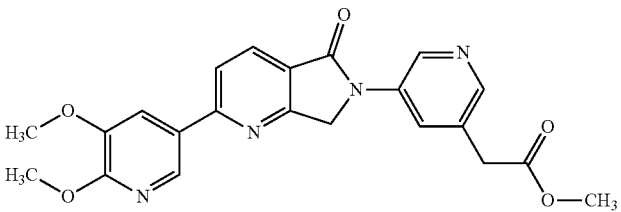 | 421.43 | (DMSO-d₆) δ 9.02 (d, J = 2.4 Hz, 1H), 8.57 (d, J = 2.0 Hz, 1H), 8.37 (dd, J = 7.8, 5.5 Hz, 1H), 8.34 (s, 1H), 8.26 (d, J = 8.2 Hz, 1H), 8.21 (d, J = 8.3 Hz, 1H), 8.00 (d, J = 1.9 Hz, 1H), 5.18 (s, 2H), 3.96 (s, 3H), 3.92 (s, 3H), 3.83 (s, 2H), 3.67 (s, 3H) |
| 114 | 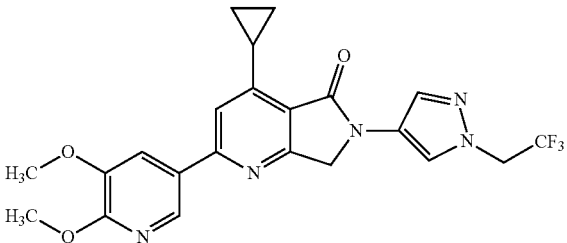 [SMILES: COc1cc(-c2cc(C3CC3)c3c(n2)CN(c2cnn(CC(F)(F)F)c2)C3=O)cnc1OC] | 460.39 | (CDCl₃) δ 8.24 (s, 1H), 8.20 (s, 1H), 7.74 (s, 1H), 7.70 (s, 1H), 7.02 (s, 1H), 4.71 (s, 2H), 4.65 (m, 2H), 4.02 (s, 3H), 3.93 (s, 3H), 3.29 (m, 1H), 1.27 (m, 1H), 0.92 (m, 1H), 0.76-0.70 (m, 2H) |
| 115 | 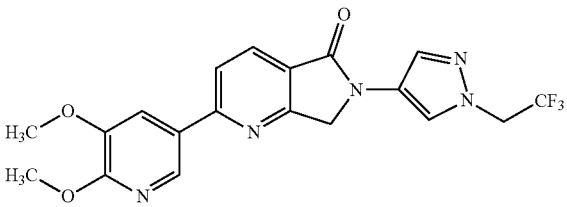 [SMILES: COc1cc(-c2ccc3c(n2)CN(c2cnn(CC(F)(F)F)c2)C3=O)cnc1OC] | 420.42 | (DMSO-d₆) δ 8.56 (d, J = 1.9 Hz, 1H), 8.40 (s, 1H), 8.21 (t, J = 6.1 Hz, 2H), 7.99 (d, J = 1.9 Hz, 1H), 7.95 (s, 1H), 5.21 (d, J = 9.1 Hz, 2H), 5.01 (s, 2H), 3.96 (s, 3H), 3.92 (s, 3H) |

TABLE 1-continued
| Cmpd No. | Structure | ESMS (M + H) | ¹H NMR (300 MHz, unless indicated otherwise) |
|---|---|---|---|
| 116 | 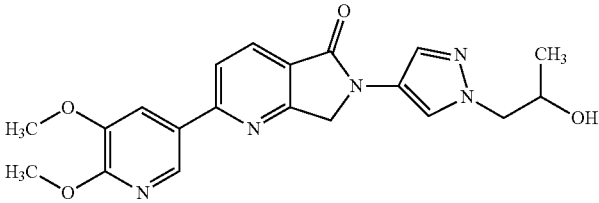 | 396.44 | (DMSO-d$_6$) δ 8.55 (d, J = 1.9 Hz, 1H), 8.30-8.02 (m, 3H), 7.98 (d, J = 1.9 Hz, 1H), 7.80 (s, 1H), 5.02-4.90 (m, 3H), 4.09-3.98 (m, 3H), 3.95 (s, 3H), 3.92 (s, 3H), 1.06 (d, J = 5.8 Hz, 3H) |
| 117 | 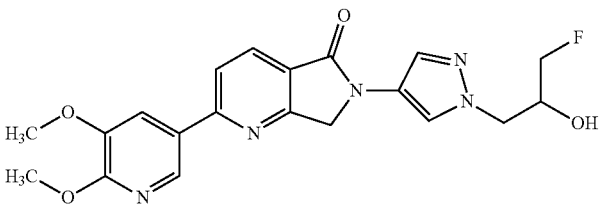 [SMILES: COc1cc(-c2ccc3c(n2)CN(c2cnn(CC(O)CF)c2)C3=O)cnc1OC] | 414.4 | (DMSO-d$_6$) δ 8.56 (d, J = 1.9 Hz, 1H), 8.27 8.14 (m, 3H), 7.99 (d, J = 1.9 Hz, 1H), 7.84 (s, 1H), 5.51 (d, J = 5.3 Hz, 1H), 4.97 (s, 2H), 4.53-4.02 (m, 5H), 3.95 (s, 3H), 3.92 (s, 3H) |
| 118 | 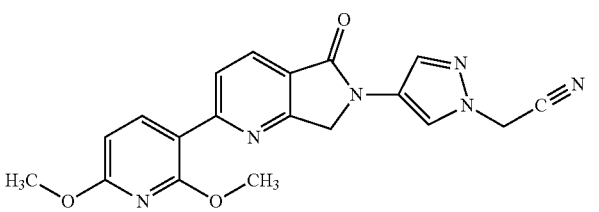 [SMILES: COc1ccc(-c2ccc3c(n2)CN(c2cnn(CC#N)c2)C3=O)c(OC)n1] | 376.81 | (DMSO-d$_6$) δ 8.51-8.34 (m, 2H), 8.18 (s, 2H), 7.96 (s, 2H), 6.60 (d, J = 8.3 Hz, 1H), 5.56 (s, 2H), 4.95 (s, 2H), 4.04 (s, 3H), 3.96 (s, 3H) |
| 119 | 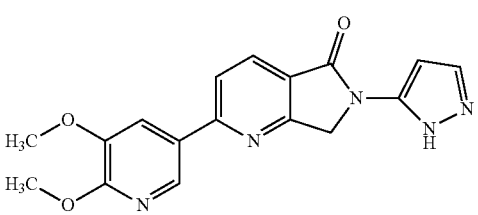 [SMILES: COc1cc(-c2ccc3c(n2)CN(c2ccn[nH]2)C3=O)cnc1OC] | 338.26 | (DMSO-d$_6$) δ 12.65 (br.s, 1H), 8.56 (d, J = 1.8 Hz, 1H), 8.23 (d, J = 8.1 Hz, 1H), 8.18 (d, J = 8.2 Hz, 1H), 8.00 (d, J = 1.9 Hz, 1H), 7.78 (d, J = 2.3 Hz, 1H), 6.83 (d, J = 2.3 Hz, 1H), 5.04 (s, 2H), 3.96 (s, 3H), 3.92 (s, 3H) |
| 120 | 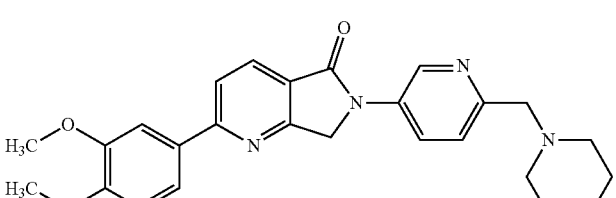 | 448.55 | (DMSO-d$_6$) δ 10.47 (br. s, 1H), 9.29 (d, J = 2.6 Hz, 1H), 8.60 (d, J = 1.9 Hz, 1H), 8.51 (dd, J = 8.5, 2.7 Hz, 1H), 8.29 (d, J = 8.2 Hz, 1H), 8.25 (d, J = 8.3 Hz, 1H), 8.01 (d, J = 1.9 Hz, 1H), 7.67 (d, J = 8.6 Hz, 1H), 5.24 (s, 2H), 4.52 (s, 2H), 3.96 (s, 3H), 3.91 (s, 3H), 3.86 (s, 4H), 3.29 (s, 4H). |
| 121 | 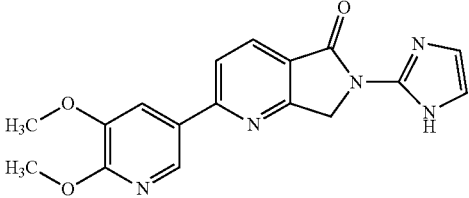 [SMILES: COc1cc(-c2ccc3c(n2)CN(c2ncc[nH]2)C3=O)cnc1OC] | 338.2 | |

TABLE 1-continued

| Cmpd No. | Structure | ESMS (M + H) | ¹H NMR (300 MHz, unless indicated otherwise) |
|---|---|---|---|
| 122 | 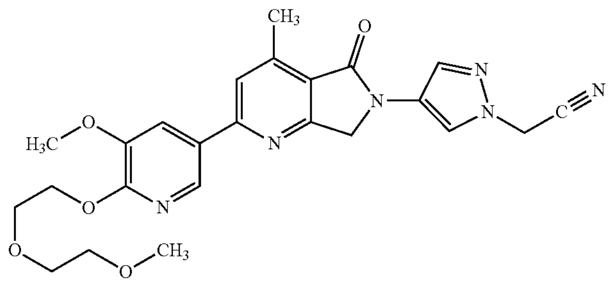 [SMILES: COCCOCCOc1ncc(-c2cc(C)c3c(n2)CN(c2cnn(CC#N)c2)C3=O)cc1OC] | 479.53 | |
| 123 | 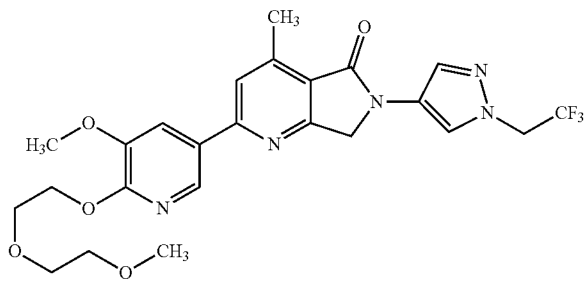 [SMILES: COCCOCCOc1ncc(-c2cc(C)c3c(n2)CN(c2cnn(CC(F)(F)F)c2)C3=O)cc1OC] | 521.88, 522.52 | (CDCl₃) δ 8.41-8.29 (m, 2H), 7.85 (d, J = 1.8 Hz, 2H), 7.78 (s, 1H), 7.58 (s, 1H), 4.86-4.45 (m, 6H), 4.10-3.93 (m, 5H), 3.76 (dd, J = 5.6, 3.8 Hz, 2H), 3.61 (dd, J = 5.6, 3.7 Hz, 2H), 3.41 (s, 3H), 2.82 (s, 3H) |
| 124 | 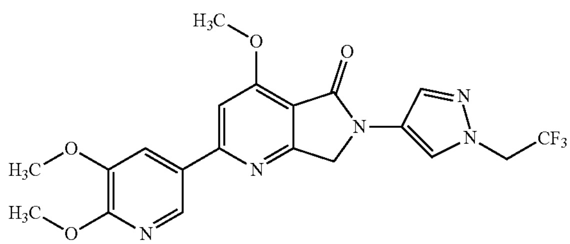 [SMILES: COc1cc(-c2cc(OC)c3c(n2)CN(c2cnn(CC(F)(F)F)c2)C3=O)cnc1OC] | 450 | |
| 125 | 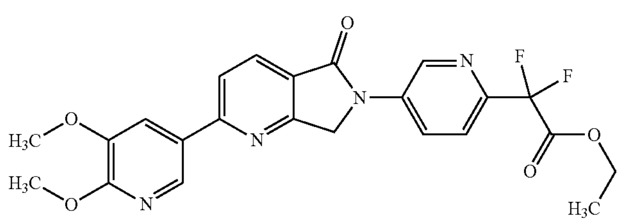 [SMILES: CCOC(=O)C(F)(F)c1ccc(N2Cc3nc(-c4cnc(OC)c(OC)c4)ccc3C2=O)cn1] | 471.4 | (DMSO-d₆) δ 9.18 (d, J = 2.1 Hz, 1H), 8.71 (dd, J = 8.8, 2.4 Hz, 1H), 8.59 (d, J = 1.5 Hz, 1H), 8.31 (d, J = 8.1 Hz, 1H), 8.25 (d, J = 8.1 Hz, 1H), 8.05-7.99 (m, 1H), 7.97 (d, J = 8.8 Hz, 1H), 5.24 (s, 2H), 4.36 (q, J = 7.1 Hz, 2H), 3.96 (s, 3H), 3.93 (s, 3H), 1.30-1.19 (m, 3H) |
| 126 | 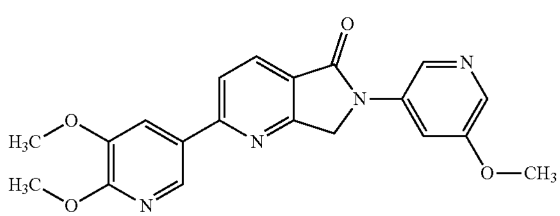 | 379.46 | |
| 127 | 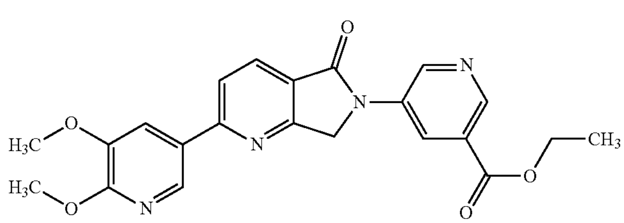 [SMILES: CCOC(=O)c1cncc(N2Cc3nc(-c4cnc(OC)c(OC)c4)ccc3C2=O)c1] | 421.44 | (DMSO-d₆) δ 9.23 (d, J = 2.6 Hz, 1H), 8.99-8.93 (m, 1H), 8.88 (d, J = 1.7 Hz, 1H), 8.54 (d, J = 1.8 Hz, 1H), 8.23 (d, J = 8.2 Hz, 1H), 8.19 (d, J = 8.3 Hz, 1H), 7.95 (d, J = 1.8 Hz, 1H), 5.18 (s, 2H), 4.39 (q, J = 7.1 Hz, 2H), 3.94 (s, 3H), 3.92 (s, 3H), 1.37 (t, J = 7.1 Hz, 3H) |

TABLE 1-continued
| Cmpd No. | Structure | ESMS (M + H) | ¹H NMR (300 MHz, unless indicated otherwise) |
|---|---|---|---|
| 128 | 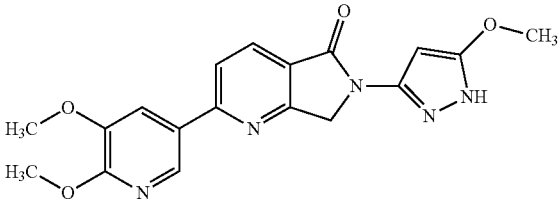 | 368.34 | |
| 129 | 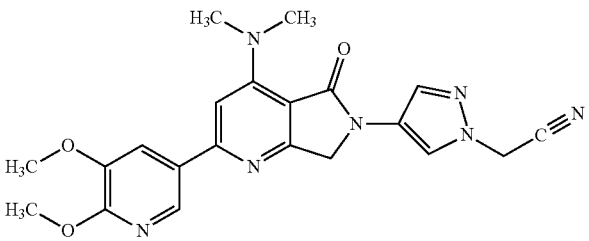 [SMILES: COc1cc(-c2cc(N(C)C)c3c(n2)CN(c2cnn(CC#N)c2)C3=O)cnc1OC] | 420.4 | (CDCl₃) δ 8.24-8.02 (m, 1H), 7.73 (s, 0H), 7.67 (s, 1H), 6.84 (s, 1H), 5.02 (s, 1H), 4.71 (s, 1H), 4.04 (d, J = 12.6 Hz, 1H), 3.94 (s, 1H), 3.30 (s, 2H) |
| 130 | 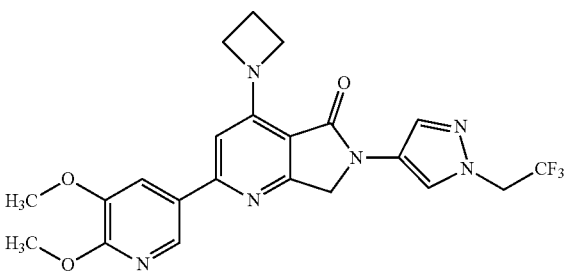 [SMILES: COc1cc(-c2cc(N3CCC3)c3c(n2)CN(c2cnn(CC(F)(F)F)c2)C3=O)cnc1OC] | 475.47 | (CDCl₃) δ 8.20 (d, J = 1.9 Hz, 1H), 8.14 (s, 1H), 7.87-7.79 (s, 1H), 7.76 (s, 1H), 6.43 (s, 1H), 4.82 (s, 2H), 4.72 (m, J = 6.0 Hz, 2H), 4.55 (m, 4H), 4.10 (s, 3H), 4.01 (s, 3H), 2.54(m, 2H) |
| 131 | 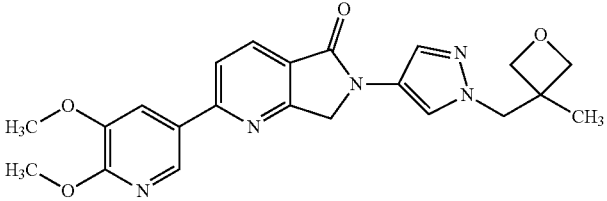 | 422.7 | (DMSO-d₆) δ 8.56 (d, J = 2.0 Hz, 1H), 8.27 (s, 1H), 8.19 (s, 2H), 7.99 (d, J = 2.0 Hz, 1H), 7.84 (s, 1H), 4.98 (s, 2H), 4.62 (d, J = 5.8 Hz, 2H), 4.38 (s, 2H), 4.23 (d, J = 5.9 Hz, 2H), 3.96 (s, 3H), 3.92 (s, 3H), 1.17 (s, 3H) |
| 132 | 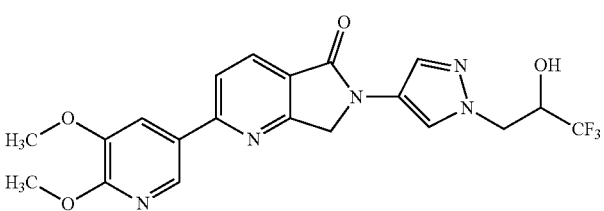 [SMILES: COc1cc(-c2ccc3c(n2)CN(c2cnn(CC(O)C(F)(F)F)c2)C3=O)cnc1OC] | 450.5 | |
| 133 | 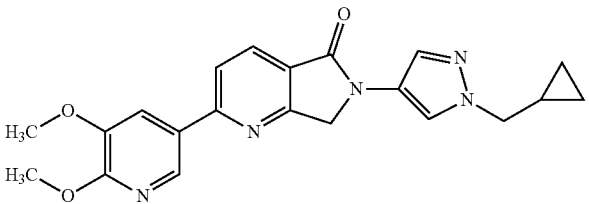 [SMILES: COc1cc(-c2ccc3c(n2)CN(c2cnn(CC4CC4)c2)C3=O)cnc1OC] | 392.6 | |

TABLE 1-continued

| Cmpd No. | Structure | ESMS (M + H) | ¹H NMR (300 MHz, unless indicated otherwise) |
|---|---|---|---|
| 134 | 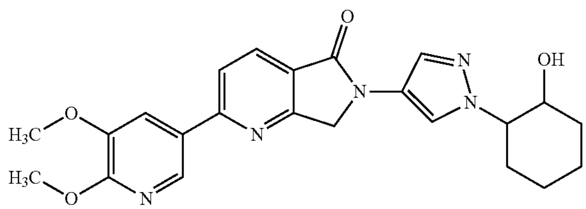 [SMILES: COc1cc(-c2ccc3c(n2)CN(c2cnn(C4CCCCC4O)c2)C3=O)cnc1OC] | 436.9 | |
| 135 | 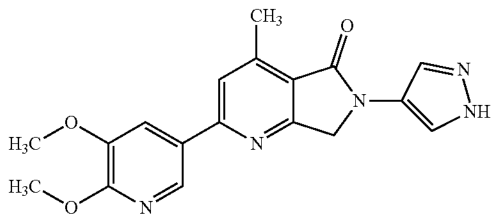 [SMILES: COc1cc(-c2cc(C)c3c(n2)CN(c2cn[nH]c2)C3=O)cnc1OC] | 352.4 | (DMSO-d₆) δ 12.88 (s, 1H), 8.54 (d, J = 1.9 Hz, 1H), 8.29-7.66 (m, 4H), 4.90 (s, 2H), 3.93 (d, J = 10.5 Hz, 6H), 2.72 (s, 3H) |
| 136 | 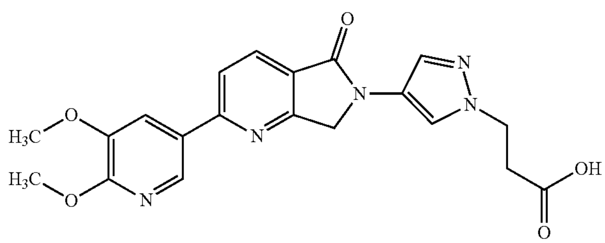 [SMILES: COc1cc(-c2ccc3c(n2)CN(c2cnn(CCC(=O)O)c2)C3=O)cnc1OC] | 410.42 | (DMSO-d₆) δ 8.55 (s, 1H), 8.27-8.11 (m, 3H), 7.98 (s, 1H), 7.81 (s, 1H), 4.95 (s, 2H), 4.35 (t, J = 6.7 Hz, 2H), 3.96 (s, 3H), 3.93 (s, 3H), 2.79 (t, J = 6.7 Hz, 2H) |
| 137 | 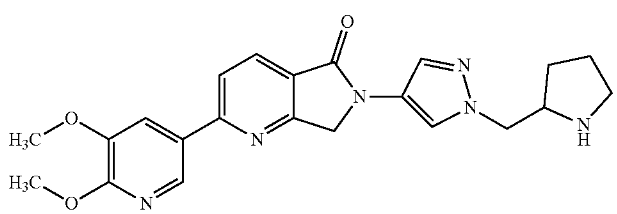 [SMILES: COc1cc(-c2ccc3c(n2)CN(c2cnn(CC4CCCN4)c2)C3=O)cnc1OC] | 421.26 | |
| 138 | 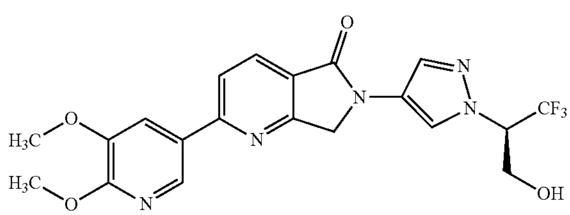 [SMILES: COc1cc(-c2ccc3c(n2)CN(c2cnn([C@H](CO)C(F)(F)F)c2)C3=O)cnc1OC] | 450.24 | |
| 139 | 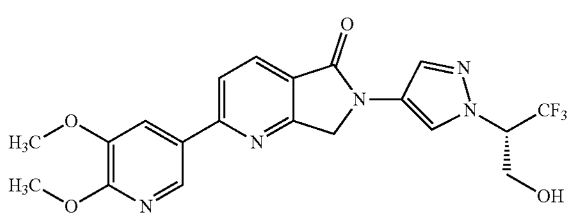 [SMILES: COc1cc(-c2ccc3c(n2)CN(c2cnn([C@@H](CO)C(F)(F)F)c2)C3=O)cnc1OC] | 450.24 | |
| 140 | 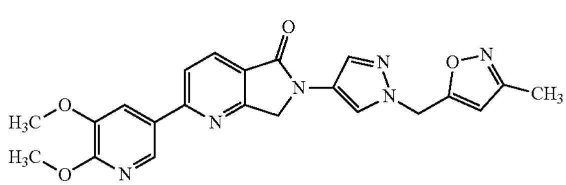 | 433.6 | |

TABLE 1-continued

| Cmpd No. | Structure | ESMS (M + H) | ¹H NMR (300 MHz, unless indicated otherwise) |
|---|---|---|---|
| 141 | 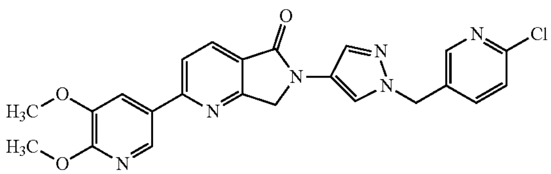 [SMILES: COc1cc(-c2ccc3c(n2)CN(c2cnn(Cc4ccc(Cl)nc4)c2)C3=O)cnc1OC] | 463.3 | |
| 142 | 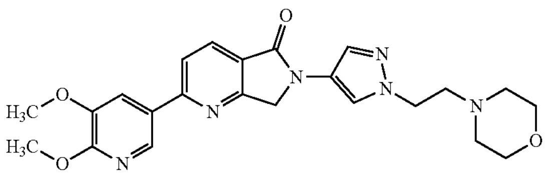 [SMILES: COc1cc(-c2ccc3c(n2)CN(c2cnn(CCN4CCOCC4)c2)C3=O)cnc1OC] | 451.6 | (DMSO-d$_6$) δ 8.55 (d, J = 1.9 Hz, 1H), 8.25 (s, 1H), 8.19 (d, J = 1.4 Hz, 2H), 7.99 (d, J = 1.9 Hz, 1H), 7.80 (s, 1H), 4.97 (s, 2H), 4.27 (t, J = 6.5 Hz, 2H), 3.96 (s, 3H), 3.92 (s, 3H), 3.60-3.52 (m, 3H), 2.73 (s, 2H), 2.43 (s, 4H), 2.27 (s, 1H) |
| 143 | 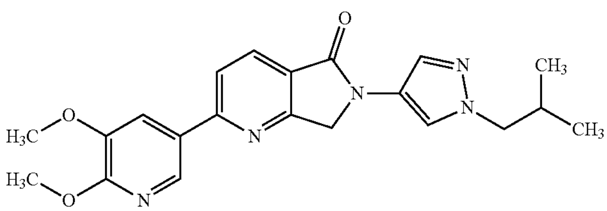 [SMILES: COc1cc(-c2ccc3c(n2)CN(c2cnn(CC(C)C)c2)C3=O)cnc1OC] | 394.3 | |
| 144 | 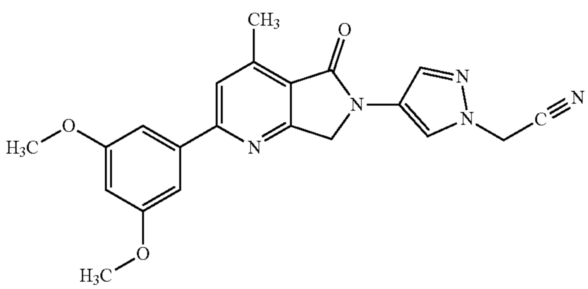 [SMILES: COc1cc(OC)cc(-c2cc(C)c3c(n2)CN(c2cnn(CC#N)c2)C3=O)c1] | 390.9 | |
| 145 | 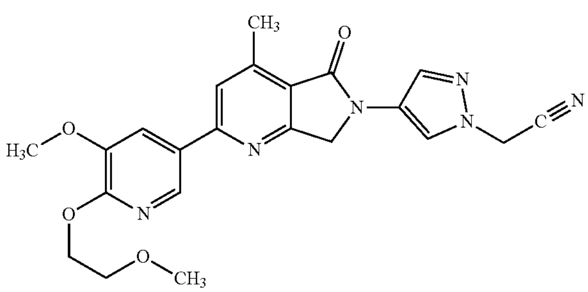 [SMILES: COCCOc1ncc(-c2cc(C)c3c(n2)CN(c2cnn(CC#N)c2)C3=O)cc1OC] | 435.53 | (DMSO-d$_6$) δ 8.52 (d, J = 1.9 Hz, 1H), 8.35 (s, 1H), 7.98 (dd, 2H), 5.54 (s, 2H), 4.91 (s, 2H), 4.59-4.32 (m, 2H), 3.92 (s, 3H), 3.79-3.47 (m, 2H), 3.29 (s, 3H), 2.72 (s, 3H) |
| 146 | 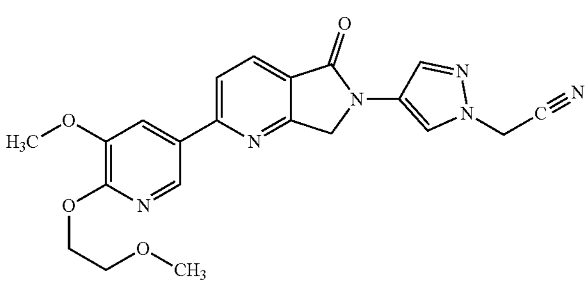 [SMILES: COCCOc1ncc(-c2ccc3c(n2)CN(c2cnn(CC#N)c2)C3=O)cc1OC] | 421.46 | |

TABLE 1-continued

| Cmpd No. | Structure | ESMS (M + H) | ¹H NMR (300 MHz, unless indicated otherwise) |
|---|---|---|---|
| 147 | 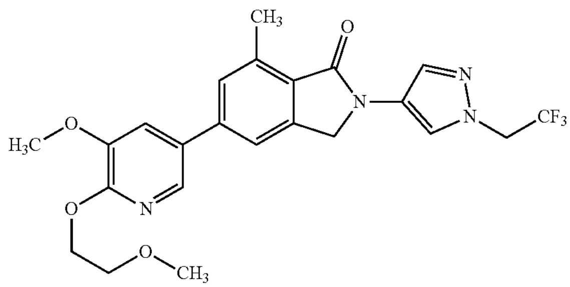 [SMILES: COCCOc1ncc(-c2cc(C)c3c(c2)CN(c2cnn(CC(F)(F)F)c2)C3=O)cc1OC] | 477.48 | |
| 148 | 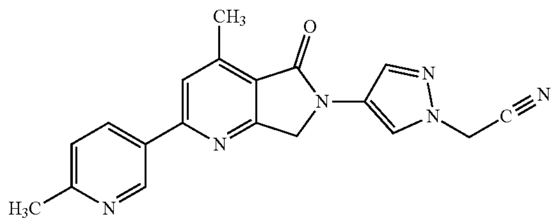 [SMILES: Cc1ccc(-c2cc(C)c3c(n2)CN(c2cnn(CC#N)c2)C3=O)cn1] | 344.94 | |
| 149 | 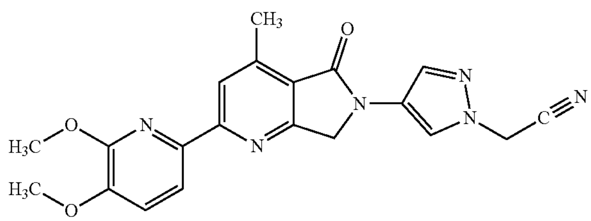 [SMILES: COc1ccc(-c2cc(C)c3c(n2)CN(c2cnn(CC#N)c2)C3=O)nc1OC] | 391.5 | |
| 150 | 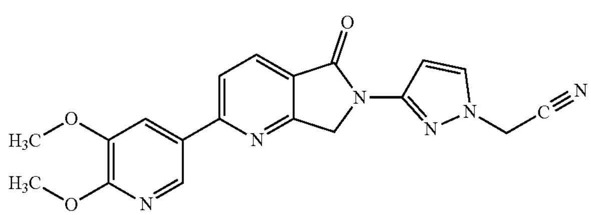 [SMILES: COc1cc(-c2ccc3c(n2)CN(c2ccn(CC#N)n2)C3=O)cnc1OC] | 377.3 | |
| 151 | 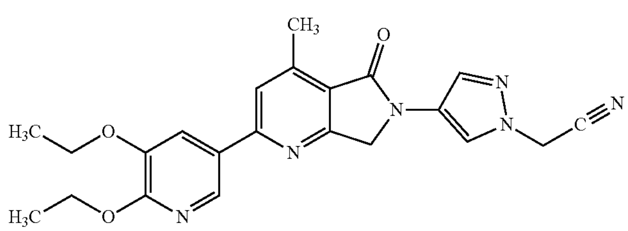 [SMILES: CCOc1cc(-c2cc(C)c3c(n2)CN(c2cnn(CC#N)c2)C3=O)cnc1OCC] | 419.48 | (CDCl$_3$) δ 8.36 (d, J = 1.9 Hz, 1H), 8.33 (s, 1H), 7.84 (d, J = 1.9 Hz, 1H), 7.78 (s, 1H), 7.57 (s, 1H), 5.14 (d, J = 11.0 Hz, 2H), 4.78 (s, 2H), 4.56 (q, J = 7.1 Hz, 2H), 4.25 (q, J = 7.0 Hz, 2H), 2.81 (s, 3H), 1.65- 1.41 (m, 6H) |
| 152 | 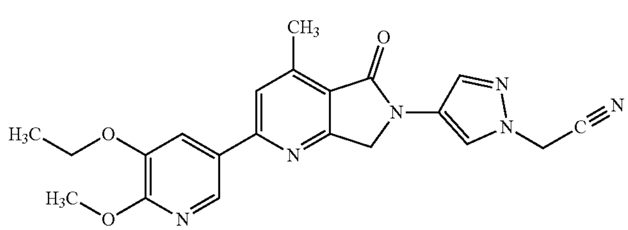 [SMILES: CCOc1cc(-c2cc(C)c3c(n2)CN(c2cnn(CC#N)c2)C3=O)cnc1OC] | 405.43 | (CDCl$_3$) δ 8.36 (d, J = 2.0 Hz, 1H), 8.31 (s, 1H), 7.83 (d, J = 2.0 Hz, 1H), 7.76 (s, 1H), 7.55 (s, 1H), 5.10 (s, 2H), 4.76 (s, 2H), 4.24 (q, J = 7.0 Hz, 2H), 4.10 (d, J = 4.6 Hz, 3H), 2.80 (s, 3H), 1.54 (dd, J = 8.3, 5.7 Hz, 3H) |

TABLE 1-continued
| Cmpd No. | Structure | ESMS (M + H) | ¹H NMR (300 MHz, unless indicated otherwise) |
|---|---|---|---|
| 153 | 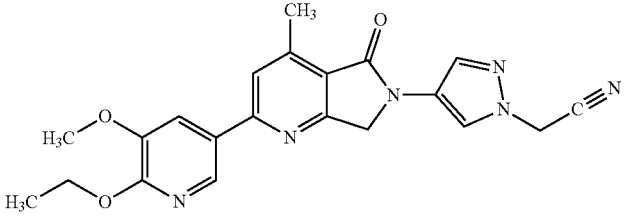 [SMILES: CCOc1ncc(-c2cc(C)c3c(n2)CN(c2cnn(CC#N)c2)C3=O)cc1OC] | 405.43 | (CDCl₃) δ 8.37 (d, J = 2.0 Hz, 1H), 8.33 (s, 1H), 7.86 (d, J = 2.0 Hz, 1H), 7.79 (s, 1H), 7.59 (s, 1H), 5.12 (s, 2H), 4.79 (s, 2H), 4.57 (q, J = 7.1 Hz, 2H), 4.03 (s, 3H), 2.82 (s, 4H), 1.51 (t, J = 7.1 Hz, 3H) |
| 154 | 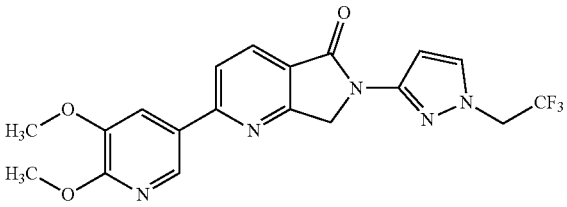 [SMILES: COc1cc(-c2ccc3c(n2)CN(c2ccn(CC(F)(F)F)n2)C3=O)cnc1OC] | 420.36 | |
| 155 | 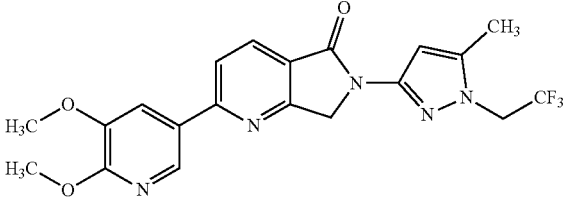 [SMILES: COc1cc(-c2ccc3c(n2)CN(c2cc(C)n(CC(F)(F)F)n2)C3=O)cnc1OC] | 434.44 | |
| 156 | 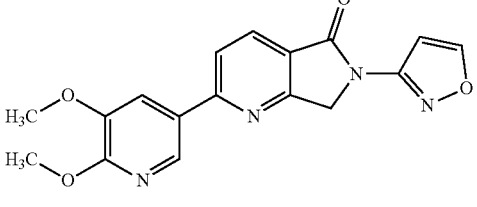 | 339.22 | |
| 157 | 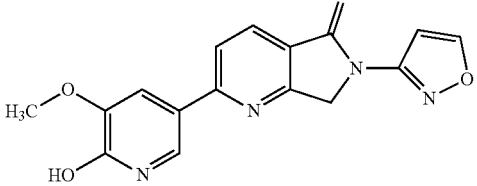 | 325.18 | |
| 158 | 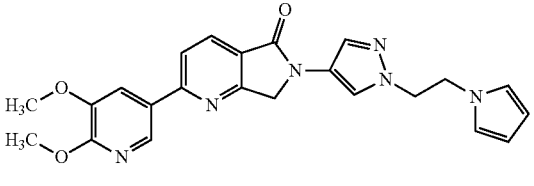 [SMILES: COc1cc(-c2ccc3c(n2)CN(c2cnn(CCn4cccc4)c2)C3=O)cnc1OC] | 431.34 | (DMSO-d₆) δ 8.55 (d, J = 2.0 Hz, 1H), 8.18 (m, 2H), 8.03 (s, 1H), 7.98 (d, J = 2.0 Hz, 1H), 7.84 (s, 1H), 6.63 (t, J = 2.1 Hz, 2H), 5.95 (t, J = 2.1 Hz, 2H), 4.93 (s, 2H), 4.47 (t, J = 6.1 Hz, 2H), 4.34 (t, J = 6.1 Hz, 2H), 3.96 (s, 3H), 3.92 (s, 3H) |
| 159 | 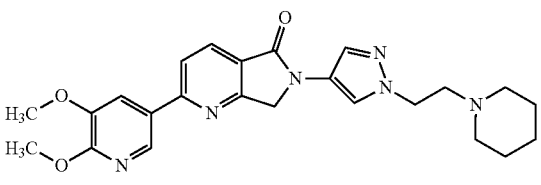 [SMILES: COc1cc(-c2ccc3c(n2)CN(c2cnn(CCN4CCCCC4)c2)C3=O)cnc1OC] | 449.7 | |

TABLE 1-continued

| Cmpd No. | Structure | ESMS (M + H) | ¹H NMR (300 MHz, unless indicated otherwise) |
|---|---|---|---|
| 160 | 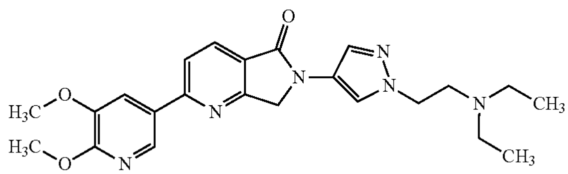 [SMILES: CCN(CC)CCn1cc(N2Cc3nc(-c4cnc(OC)c(OC)c4)ccc3C2=O)cn1] | 437.7 | (DMSO-d$_6$) δ 8.55 (d, J = 2.0 Hz, 1H), 8.19 (m, 3H), 7.99 (d, J = 1.9 Hz, 1H), 7.80 (s, 1H), 4.96 (s, 2H), 4.18 (t, J = 6.6 Hz, 2H), 3.96 (s, 3H), 3.92 (s, 3H), 2.81 (t, J = 6.6 Hz, 2H), 2.59-2.51 (m, 4H), 0.94 (t, J = 7.1 Hz, 6H) |
| 161 | 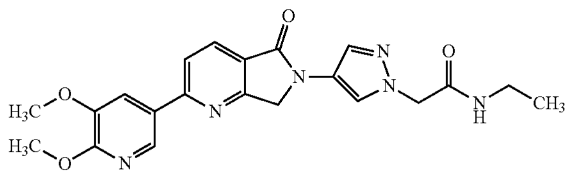 [SMILES: CCNC(=O)Cn1cc(N2Cc3nc(-c4cnc(OC)c(OC)c4)ccc3C2=O)cn1] | 423.6 | |
| 162 | 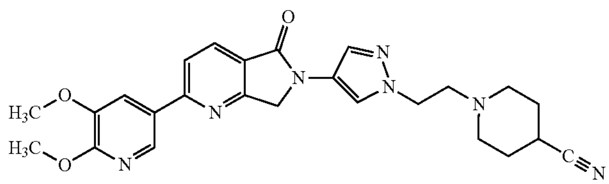 [SMILES: COc1cc(-c2ccc3c(n2)CN(c2cnn(CCN4CCC(C#N)CC4)c2)C3=O)cnc1OC] | 474.7 | |
| 163 | 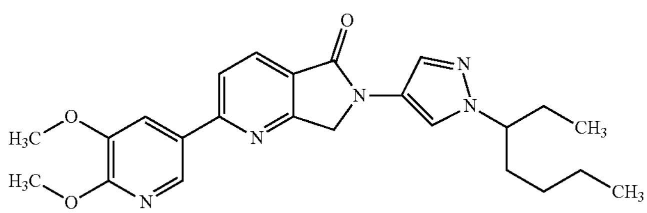 [SMILES: CCCCC(CC)n1cc(N2Cc3nc(-c4cnc(OC)c(OC)c4)ccc3C2=O)cn1] | 436.7 | |
| 164 | 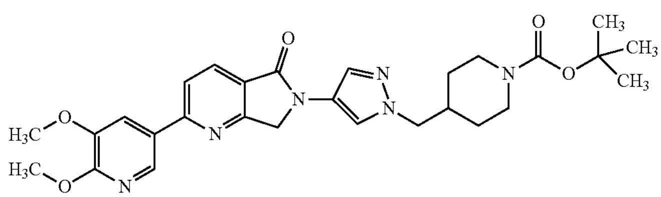 [SMILES: COc1cc(-c2ccc3c(n2)CN(c2cnn(CC4CCN(C(=O)OC(C)(C)C)CC4)c2)C3=O)cnc1OC] | 535.9 | |
| 165 | 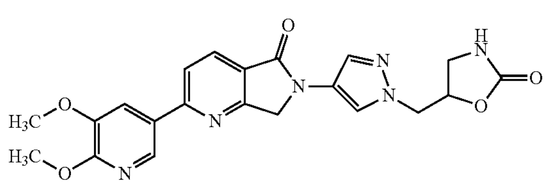 [SMILES: COc1cc(-c2ccc3c(n2)CN(c2cnn(CC4CNC(=O)O4)c2)C3=O)cnc1OC] | 437.9 | |
| 166 | 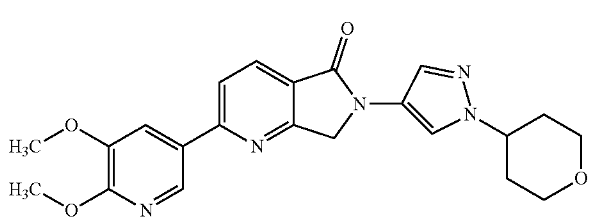 [SMILES: COc1cc(-c2ccc3c(n2)CN(c2cnn(C4CCOCC4)c2)C3=O)cnc1OC] | 422.6 | |
| 167 | 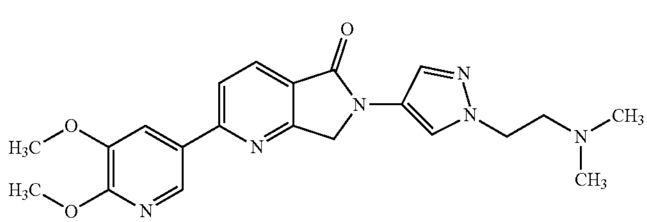 | 409.6 | |

TABLE 1-continued

| Cmpd No. | Structure | ESMS (M + H) | ¹H NMR (300 MHz, unless indicated otherwise) |
|---|---|---|---|
| 168 | 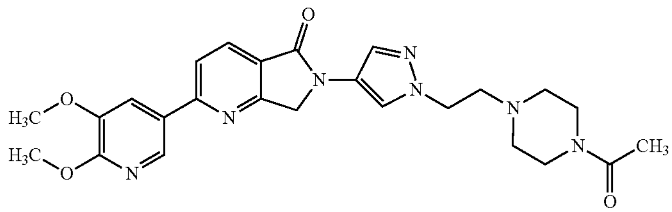 [SMILES: COc1cc(-c2ccc3c(n2)CN(c2cnn(CCN4CCN(C(C)=O)CC4)c2)C3=O)cnc1OC] | 492.7 | (DMSO-d$_6$) δ 8.55 (d, J = 2.0 Hz, 1H), 8.26 (s, 1H), 8.19 (m, 2H), 7.99 (d, J = 1.9 Hz, 1H), 7.81 (s, 1H), 4.97 (s, 2H), 4.28 (s, 2H), 3.96 (s, 3H), 3.92 (s, 3H), 3.40 (s, 4H), 2.76 (s, 2H), 2.40 (m, 4H), 1.98 (s, 3H) |
| 169 | 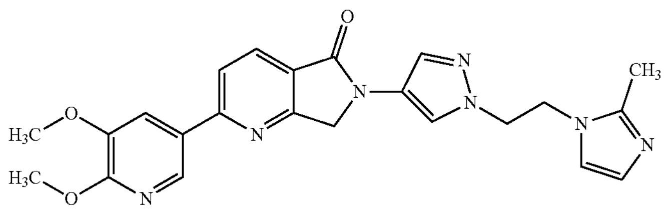 [SMILES: COc1cc(-c2ccc3c(n2)CN(c2cnn(CCn4ccnc4C)c2)C3=O)cnc1OC] | 446.6 | |
| 170 | 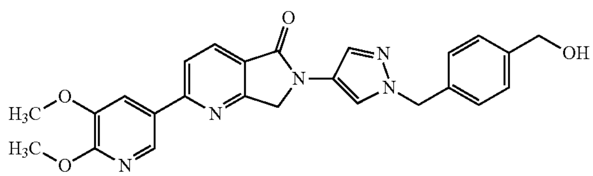 [SMILES: COc1cc(-c2ccc3c(n2)CN(c2cnn(Cc4ccc(CO)cc4)c2)C3=O)cnc1OC] | 458.43 | (DMSO-d$_6$) δ 8.55 (d, J = 2.0 Hz, 1H), 8.29 (s, 1H), 8.18 (m, 2H), 7.98 (d, J = 1.9 Hz, 1H), 7.83 (s, 1H), 7.27 (m, 4H), 5.35 (s, 2H), 4.96 (s, 2H), 4.47 (s, 2H), 3.95 (s, 3H), 3.91 (s, 3H) |
| 171 | 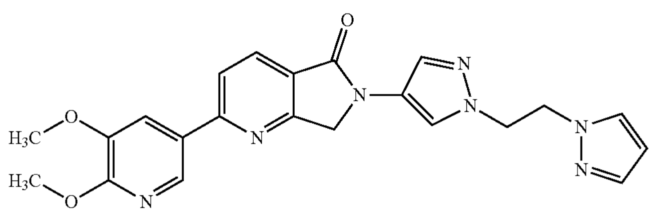 [SMILES: COc1cc(-c2ccc3c(n2)CN(c2cnn(CCn4cccn4)c2)C3=O)cnc1OC] | 432 | (DMSO-d$_6$) δ 8.47 (d, J = 2.0 Hz, 1H), 8.10 (s, 2H), 7.95-7.87 (m, 2H), 7.75 (s, 1H), 7.45 (d, J = 2.2 Hz, 1H), 7.40 (d, J = 1.3 Hz, 1H), 6.12 (t, J = 2.0 Hz, 1H), 4.84 (s, 2H), 4.50 (s, 4H), 3.88 (s, 3H), 3.85 (s, 3H) |
| 172 | 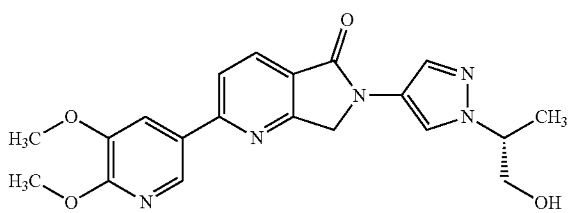 [SMILES: COc1cc(-c2ccc3c(n2)CN(c2cnn([C@H](C)CO)c2)C3=O)cnc1OC] | 396.3 | (DMSO-d$_6$) δ 8.55 (d, J = 2.0 Hz, 1H), 8.19 (m, 3H), 7.98 (d, J = 1.9 Hz, 1H), 7.80 (s, 1H), 4.96 (s, 2H), 4.08-3.97 (m, 3H), 3.96 (s, 3H), 3.92 (s, 3H), 1.06 (d, J = 5.9 Hz, 3H) |
| 173 | 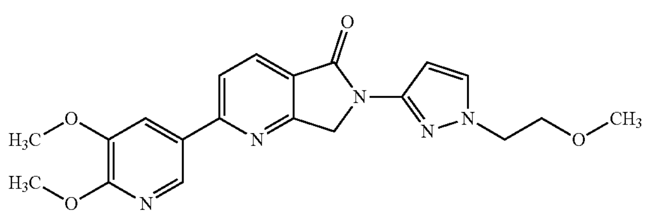 | 396 | (DMSO-d$_6$) δ 8.56 (d, J = 2.0 Hz, 1H), 8.20 (q, J = 8.2 Hz, 2H), 7.99 (d, J = 1.9 Hz, 1H), 7.74 (d, J = 2.3 Hz, 1H), 6.78 (d, J = 2.3 Hz, 1H), 5.00 (s, 2H), 4.25 (t, J = 5.3 Hz, 2H), 3.94 (d, J = 11.1 Hz, 6H), 3.71 (t, J = 5.3 Hz, 2H), 3.26 (s, 3H) |
| 174 | 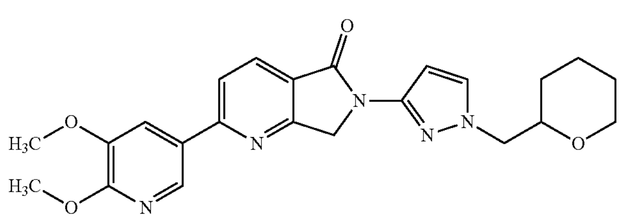 [SMILES: COc1cc(-c2ccc3c(n2)CN(c2ccn(CC4CCCCO4)n2)C3=O)cnc1OC] | 436 | (DMSO-d$_6$) δ 8.56 (d, J = 1.9 Hz, 1H), 8.20 (d, J = 5.6 Hz, 2H), 7.99 (d, J = 1.9 Hz, 1H), 7.70 (d, J = 2.3 Hz, 1H), 6.77 (d, J = 2.3 Hz, 1H), 4.99 (s, 2H), 4.09 (d, J = 5.7 Hz, 2H), 3.94 (d, J = 11.2 Hz, 6H), 3.86 (d, J = 11.9 Hz, 1H), 3.74-3.60 (m, 2H), 1.78 (s, 1H), 1.47 (s, 4H), 1.24 (s, 1H) |

TABLE 1-continued

| Cmpd No. | Structure | ESMS (M + H) | ¹H NMR (300 MHz, unless indicated otherwise) |
|---|---|---|---|
| 175 | 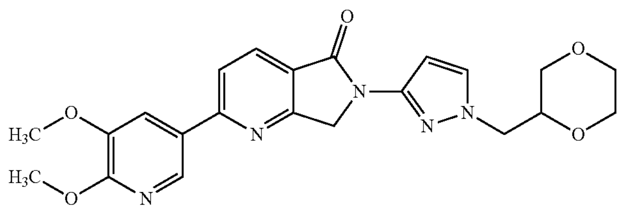 [SMILES: COc1cc(-c2ccc3c(n2)CN(c2ccn(CC4COCCO4)n2)C3=O)cnc1OC] | 438 | (DMSO-d₆) δ 8.56 (d, J = 2.0 Hz, 1H), 8.20 (d, J = 5.7 Hz, 2H), 8.00 (d, J = 2.0 Hz, 1H), 7.73 (d, J = 2.3 Hz, 1H), 6.79 (d, J = 2.3 Hz, 1H), 5.00 (s, 2H), 4.14 (d, J = 5.9 Hz, 2H), 3.94 (d, J = 11.3 Hz, 6H), 3.33 (d, J = 15.8 Hz, 9H (masked by solvent peak)) |
| 176 | 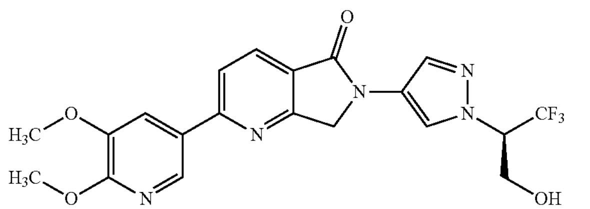 [SMILES: COc1cc(-c2ccc3c(n2)CN(c2cnn([C@H](CO)C(F)(F)F)c2)C3=O)cnc1OC] | 396.61 | (DMSO-d₆) δ 8.55 (d, J = 2.0 Hz, 1H), 8.24-8.12 (m, 3H), 7.98 (d, J = 1.9 Hz, 1H), 7.80 (s, 1H), 4.96 (s, 2H), 4.10-3.98 (m, 4H), 3.96 (s, 3H), 3.92 (s, 3H), 1.06 (d, J = 5.9 Hz, 3H) |
| 177 | 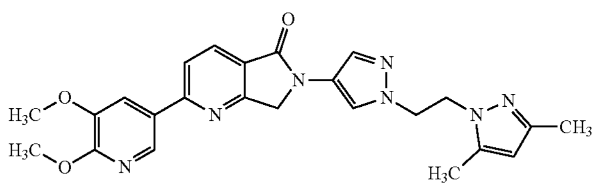 | 460.67 | (DMSO-d₆) δ 8.54 (d, J = 1.9 Hz, 1H), 8.19 (d, J = 8.3 Hz, 2H), 8.01-7.92 (m, 2H), 7.84 (s, 1H), 5.73 (s, 1H), 4.91 (s, 2H), 4.49 (t, J = 5.8 Hz, 2H), 4.32 (t, J = 5.8 Hz, 2H), 3.95 (s, 3H), 3.92 (s, 3H), 2.11 (s, 3H), 1.91 (s, 3H) |
| 178 | 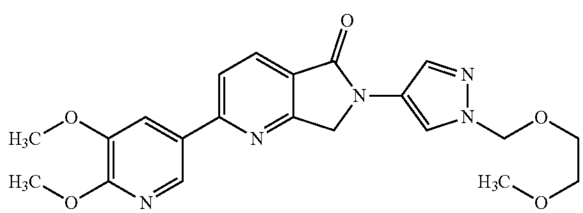 [SMILES: COCCOCn1cc(N2Cc3nc(-c4cnc(OC)c(OC)c4)ccc3C2=O)cn1] | 426 | |
| 179 | 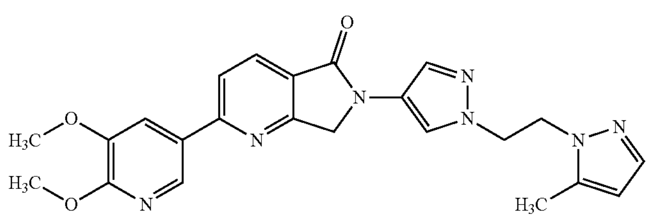 [SMILES: COc1cc(-c2ccc3c(n2)CN(c2cnn(CCn4nccc4C)c2)C3=O)cnc1OC] | 446.77 | (DMSO-d₆) δ 8.54 (d, J = 2.0 Hz, 1H), 8.17 (s, 2H), 7.98 (d, J = 2.0 Hz, 1H), 7.90 (s, 1H), 7.84 (s, 1H), 7.36 (d, J = 1.6 Hz, 1H), 5.95 (d, J = 0.9 Hz, 1H), 4.90 (s, 2H), 4.53 (t, J = 5.6 Hz, 2H), 4.42 (t, J = 5.5 Hz, 2H), 3.95 (s, 3H), 3.92 (s, 3H), 1.99 (s, 3H) |
| 180 | 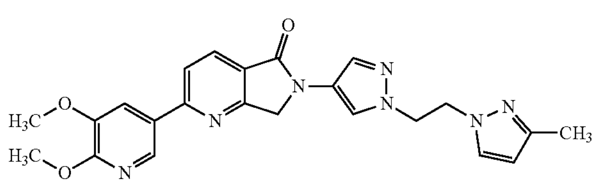 | 446.12 | (DMSO-d₆) δ 8.55 (d, J = 2.0 Hz, 1H), 8.18 (d, J = 1.0 Hz, 2H), 8.03 (s, 1H), 7.98 (d, J = 2.0 Hz, 1H), 7.83 (s, 1H), 7.36 (d, J = 2.1 Hz, 1H), 5.95 (d, J = 2.2 Hz, 1H), 4.92 (s, 2H), 4.53 (d, J = 5.4 Hz, 2H), 4.47 (d, J = 5.4 Hz, 2H), 3.96 (s, 3H), 3.92 (s, 3H), 2.16 (s, 3H) |
| 181 | 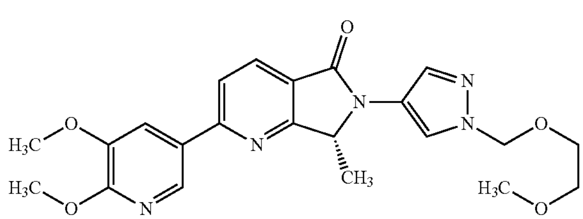 [SMILES: COCCOCn1cc(N2C(=O)c3ccc(-c4cnc(OC)c(OC)c4)nc3[C@H]2C)cn1] | 440 | |

TABLE 1-continued

| Cmpd No. | Structure | ESMS (M + H) | ¹H NMR (300 MHz, unless indicated otherwise) |
|---|---|---|---|
| 182 | (structure) | 448 | |
| 183 | (structure) | 443.27 | (DMSO-d₆) δ 8.57 (t, J = 4.7 Hz, 2H), 8.41 (s, 1H), 8.20 (d, J = 1.0 Hz, 2H), 7.99 (d, J = 1.9 Hz, 1H), 7.91 (s, 1H), 7.69 (s, 1H), 7.64-7.51 (m, 1H), 5.57 (s, 2H), 4.99 (s, 2H), 3.95 (s, 3H), 3.92 (s, 3H), 2.66 (s, 3H) |
| 184 | (structure) | 433 | (DMSO-d₆) δ 8.57 (d, J = 1.9 Hz, 1H), 8.34-8.16 (m, 3H), 8.00 (d, J = 1.9 Hz, 2H), 7.53 (d, J = 2.3 Hz, 1H), 6.71 (d, J = 2.3 Hz, 1H), 4.99 (s, 2H), 4.71-4.62 (m, 2H), 4.53 (t, J = 5.5 Hz, 2H), 3.94 (d, J = 9.2 Hz, 6H) |
| 185 | (structure) | 352.35 | |
| 186 | (structure) | | (DMSO-d₆) δ 9.33 (s, 2H), 8.37 (d, J = 0.6 Hz, 1H), 8.04 (s, 1H), 7.97 (d, J = 0.6 Hz, 1H), 5.55 (s, 2H), 4.92 (s, 2H), 4.01 (s, 3H), 2.72 (s, 3H) |
| 187 | (structure) | 457.6 | |
| 188 | (structure) | 449 | |

TABLE 1-continued

| Cmpd No. | Structure | ESMS (M + H) | $^1$H NMR (300 MHz, unless indicated otherwise) |
|---|---|---|---|
| 189 | 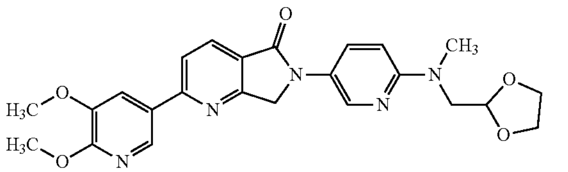 | 463.2 | |
| 190 | 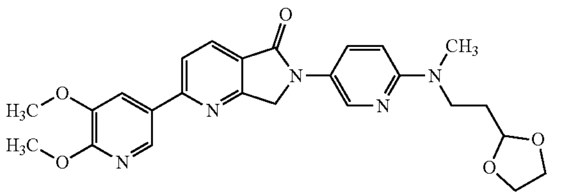 [SMILES: COc1cc(-c2ccc3c(n2)CN(c2ccc(N(C)CCC4OCCO4)nc2)C3=O)cnc1OC] | 478.3 | |
| 191 | 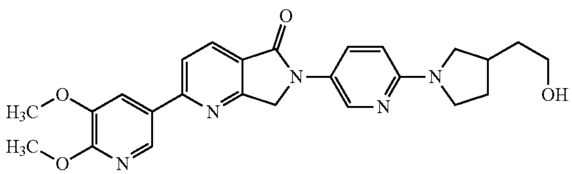 [SMILES: COc1cc(-c2ccc3c(n2)CN(c2ccc(N4CCC(CCO)C4)nc2)C3=O)cnc1OC] | 463 | |
| 192 | 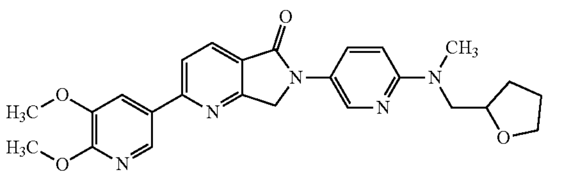 [SMILES: COc1cc(-c2ccc3c(n2)CN(c2ccc(N(C)CC4CCCO4)nc2)C3=O)cnc1OC] | 462.3 | |
| 193 | 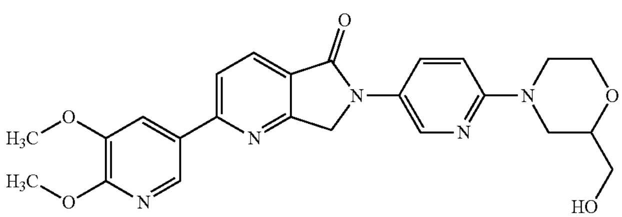 [SMILES: COc1cc(-c2ccc3c(n2)CN(c2ccc(N4CCOC(CO)C4)nc2)C3=O)cnc1OC] | 463.2 | |
| 194 | 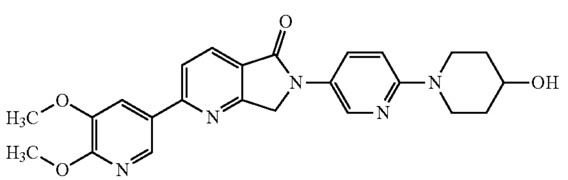 [SMILES: COc1cc(-c2ccc3c(n2)CN(c2ccc(N4CCC(O)CC4)nc2)C3=O)cnc1OC] | 448.2 | |
| 195 | 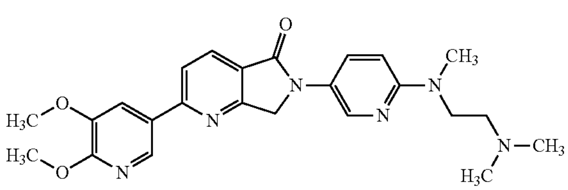 | 449.7 | |
| 196 | 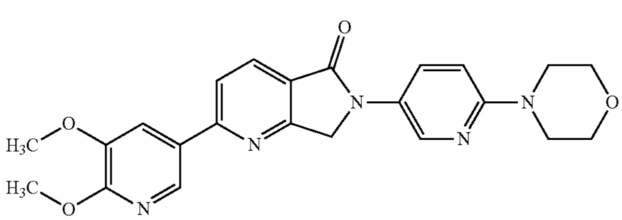 [SMILES: COc1cc(-c2ccc3c(n2)CN(c2ccc(N4CCOCC4)nc2)C3=O)cnc1OC] | 434.6 | |

TABLE 1-continued

| Cmpd No. | Structure | ESMS (M + H) | ¹H NMR (300 MHz, unless indicated otherwise) |
|---|---|---|---|
| 197 | 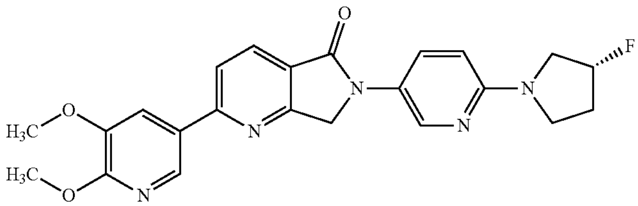 [SMILES: COc1cc(-c2ccc3c(n2)CN(c2ccc(N4CC[C@@H](F)C4)nc2)C3=O)cnc1OC] | 436.6 | |
| 198 | 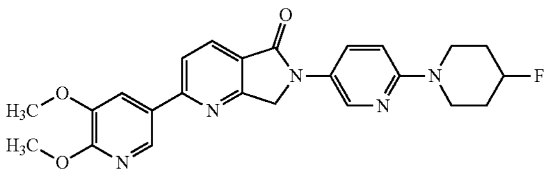 [SMILES: COc1cc(-c2ccc3c(n2)CN(c2ccc(N4CCC(F)CC4)nc2)C3=O)cnc1OC] | 450.6 | |
| 199 | 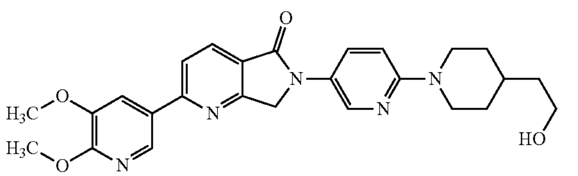 [SMILES: COc1cc(-c2ccc3c(n2)CN(c2ccc(N4CCC(CCO)CC4)nc2)C3=O)cnc1OC] | 476.7 | |
| 200 | 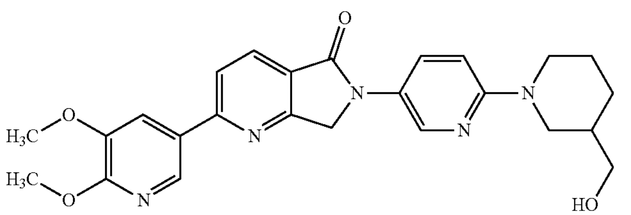 [SMILES: COc1cc(-c2ccc3c(n2)CN(c2ccc(N4CCCC(CO)C4)nc2)C3=O)cnc1OC] | 462.6 | |
| 201 | 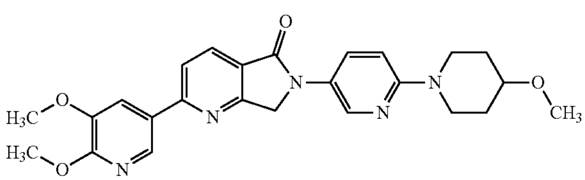 | 462.6 | |
| 202 | 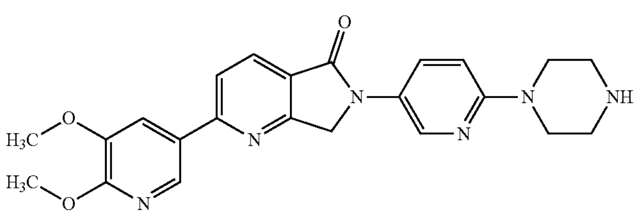 [SMILES: COc1cc(-c2ccc3c(n2)CN(c2ccc(N4CCNCC4)nc2)C3=O)cnc1OC] | 433.6 | |
| 203 | 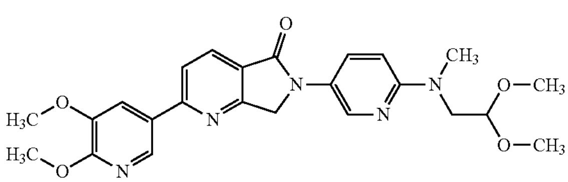 | 466.6 | |
| 204 | 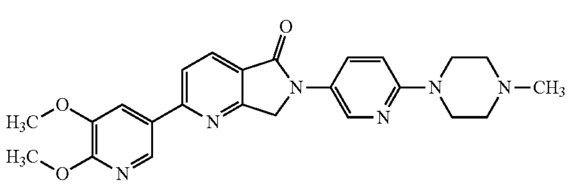 | 447.7 | |

TABLE 1-continued

| Cmpd No. | Structure | ESMS (M + H) | ¹H NMR (300 MHz, unless indicated otherwise) |
|---|---|---|---|
| 205 | 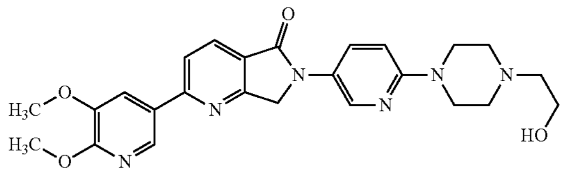 [SMILES: COc1cc(-c2ccc3c(n2)CN(c2ccc(N4CCN(CCO)CC4)nc2)C3=O)cnc1OC] | 477.6 | |
| 206 | 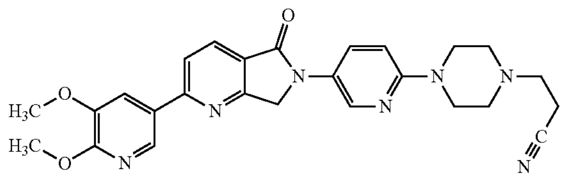 [SMILES: COc1cc(-c2ccc3c(n2)CN(c2ccc(N4CCN(CCC#N)CC4)nc2)C3=O)cnc1OC] | 486.7 | |
| 207 | 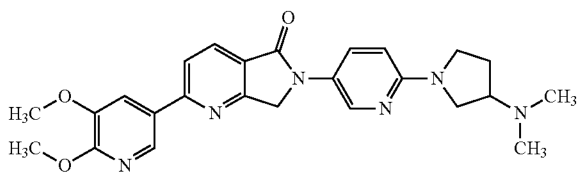 | 461.7 | |
| 208 | 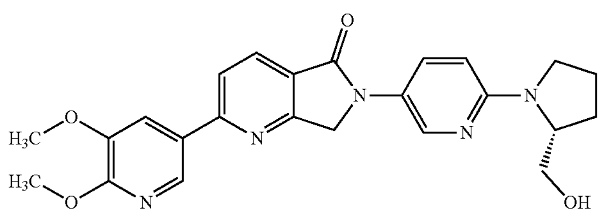 [SMILES: COc1cc(-c2ccc3c(n2)CN(c2ccc(N4CCC[C@@H]4CO)nc2)C3=O)cnc1OC] | 448.6 | |
| 209 | 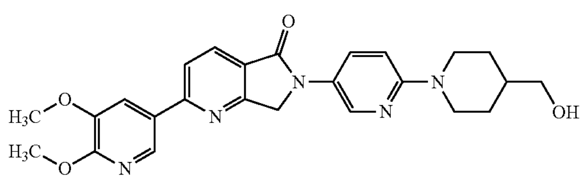 [SMILES: COc1cc(-c2ccc3c(n2)CN(c2ccc(N4CCC(CO)CC4)nc2)C3=O)cnc1OC] | 462.6 | |
| 210 | 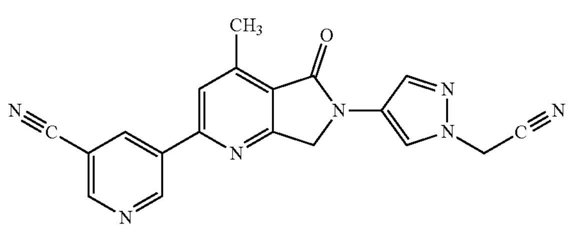 [SMILES: Cc1cc(-c2cncc(C#N)c2)nc2c1C(=O)N(c1cnn(CC#N)c1)C2] | 356.5 | (DMSO-d₆) δ 9.61 (d, J = 2.2 Hz, 1H), 9.14 (d, J = 1.9 Hz, 1H), 9.01 (t, J = 2.1 Hz, 1H), 8.38 (d, J = 0.5 Hz, 1H), 8.19 (s, 1H), 7.99 (d, J = 0.6 Hz, 1H), 5.56 (s, 2H), 4.95 (s, 2H), 2.74 (s, 3H) |
| 211 | 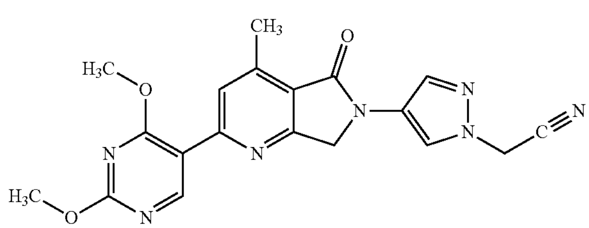 [SMILES: COc1ncc(-c2cc(C)c3c(n2)CN(c2cnn(CC#N)c2)C3=O)c(OC)n1] | 392.34 | (DMSO-d₆) δ 8.93 (s, 1H), 8.36 (s, 1H), 7.97 (s, 1H), 7.84 (s, 1H), 5.55 (s, 2H), 4.89 (s, 2H), 4.06 (s, 3H), 3.99 (s, 3H), 2.70 (s, 3H) |

TABLE 1-continued

| Cmpd No. | Structure | ESMS (M + H) | ¹H NMR (300 MHz, unless indicated otherwise) |
|---|---|---|---|
| 212 | 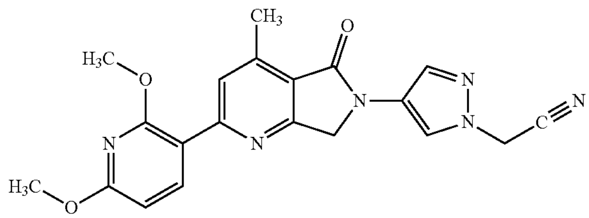 [SMILES: COc1ccc(-c2cc(C)c3c(n2)CN(c2cnn(CC#N)c2)C3=O)c(OC)n1] | 391.38 | (DMSO-d₆) δ 8.44-8.31 (m, 2H), 8.01-7.89 (m, 2H), 6.58 (d, J = 8.3 Hz, 1H), 5.55 (s, 2H), 4.87 (s, 2H), 4.04 (s, 3H), 3.96 (s, 3H), 2.69 (s, 3H) |
| 213 | 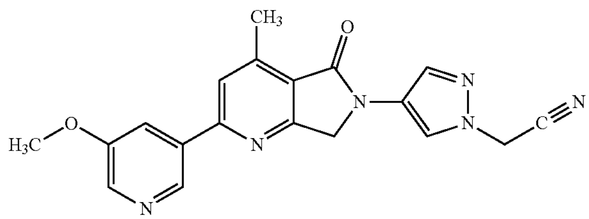 [SMILES: COc1cncc(-c2cc(C)c3c(n2)CN(c2cnn(CC#N)c2)C3=O)c1] | 361.05 | (DMSO-d₆) δ 8.96 (d, J = 1.7 Hz, 1H), 8.41 (d, J = 2.8 Hz, 1H), 8.37 (s, 1H), 8.10 (s, 1H), 8.05 (dd, J = 2.8, 1.9 Hz, 1H), 7.98 (d, J = 0.5 Hz, 1H), 5.56 (s, 2H), 4.97 (d, J = 16.1 Hz, 2H), 3.93 (d, J = 6.0 Hz, 3H), 2.76 (d, J = 12.4 Hz, 3H) |
| 214 | 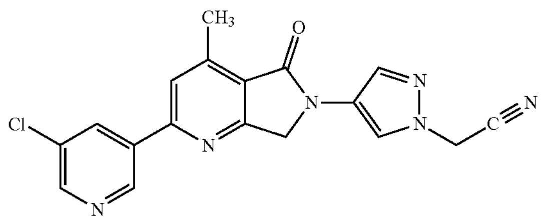 [SMILES: Cc1cc(-c2cncc(Cl)c2)nc2c1C(=O)N(c1cnn(CC#N)c1)C2] | 365.51 | (DMSO-d₆) δ 9.32 (d, J = 1.8 Hz, 1H), 8.75 (t, J = 3.2 Hz, 1H), 8.63 (t, J = 2.1 Hz, 1H), 8.37 (s, 1H), 8.16 (s, 1H), 7.98 (s, 1H), 5.52 (d, J = 25.4 Hz, 2H), 5.00-4.89 (m, 2H), 2.75 (d, J = 8.6 Hz, 3H) |
| 215 | 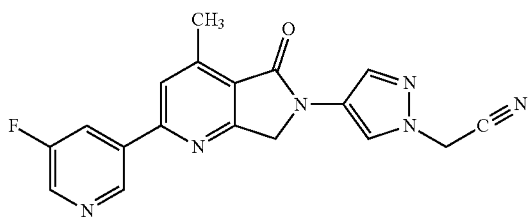 [SMILES: Cc1cc(-c2cncc(F)c2)nc2c1C(=O)N(c1cnn(CC#N)c1)C2] | 349 | (DMSO-d₆) δ 9.26 (d, J = 1.7 Hz, 1H), 8.71 (d, J = 2.7 Hz, 1H), 8.42 (ddd, J = 10.3, 2.7, 1.8 Hz, 1H), 8.37 (d, J = 0.6 Hz, 1H), 8.14 (s, 1H), 8.00-7.96 (m, 1H), 5.56 (s, 2H), 4.93 (d, J = 6.9 Hz, 2H), 2.74 (s, 3H) |
| 216 | 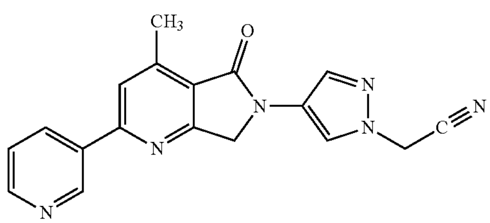 [SMILES: Cc1cc(-c2cccnc2)nc2c1C(=O)N(c1cnn(CC#N)c1)C2] | 330.98 | (DMSO-d₆) δ 9.36 (d, J = 1.7 Hz, 1H), 8.69 (dd, J = 4.8, 1.6 Hz, 1H), 8.57-8.47 (m, 1H), 8.37 (s, 1H), 8.07 (s, 1H), 7.98 (d, J = 0.5 Hz, 1H), 7.58 (dd, J = 8.0, 4.8 Hz, 1H), 5.56 (s, 2H), 4.93 (d, J = 8.1 Hz, 2H), 2.74 (s, 3H) |
| 217 | 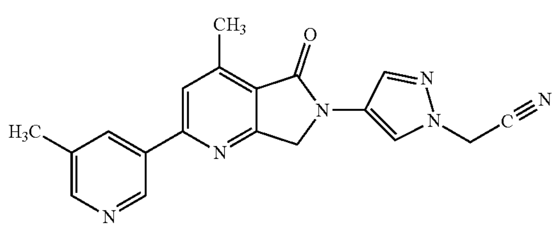 [SMILES: Cc1cncc(-c2cc(C)c3c(n2)CN(c2cnn(CC#N)c2)C3=O)c1] | 345.28 | (DMSO-d₆) δ 9.15 (d, J = 1.9 Hz, 1H), 8.52 (d, J = 1.4 Hz, 1H), 8.38-8.32 (m, 2H), 8.04 (s, 1H), 7.98 (d, J = 0.4 Hz, 1H), 5.55 (d, J = 3.9 Hz, 2H), 4.91 (s, 2H), 2.72 (s, 3H), 2.41 (s, 3H) |
| 218 | 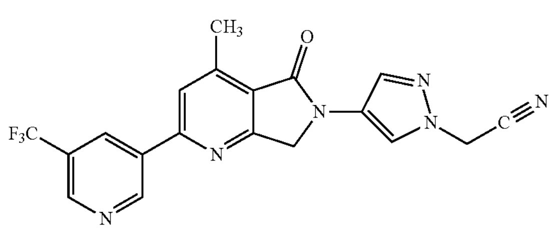 [SMILES: Cc1cc(-c2cncc(C(F)(F)F)c2)nc2c1C(=O)N(c1cnn(CC#N)c1)C2] | 398.93 | (DMSO-d₆) δ 9.65 (d, J = 1.6 Hz, 1H), 9.10 (d, J = 1.1 Hz, 1H), 8.86 (s, 1H), 8.37 (s, 1H), 8.23 (d, J = 16.1 Hz, 1H), 7.98 (s, 1H), 5.56 (s, 2H), 4.94 (d, J = 7.9 Hz, 2H), 2.75 (s, 3H) |

TABLE 1-continued

| Cmpd No. | Structure | ESMS (M + H) | ¹H NMR (300 MHz, unless indicated otherwise) |
|---|---|---|---|
| 219 | 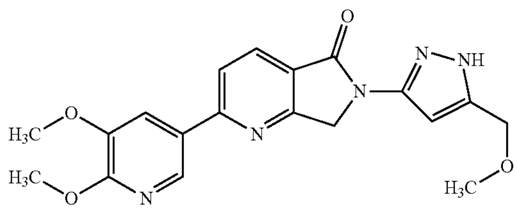 [SMILES: COCc1cc(N2Cc3nc(-c4cnc(OC)c(OC)c4)ccc3C2=O)n[nH]1] | 382.42 | |
| 220 | 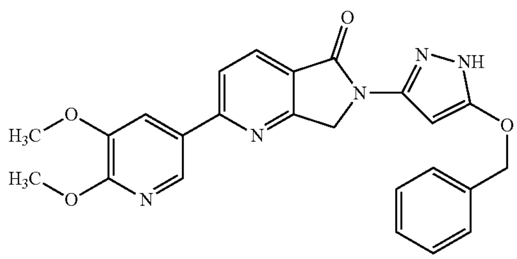 [SMILES: COc1cc(-c2ccc3c(n2)CN(c2cc(OCc4ccccc4)[nH]n2)C3=O)cnc1OC] | 444.49 | |
| 221 | 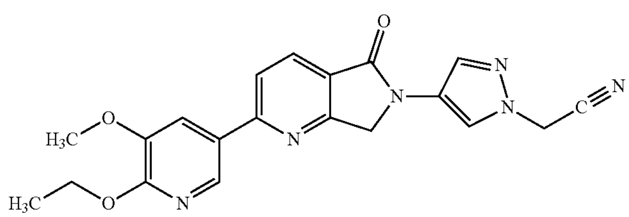 [SMILES: CCOc1ncc(-c2ccc3c(n2)CN(c2cnn(CC#N)c2)C3=O)cc1OC] | 391.38 | (CDCl₃) δ 8.46-8.29 (m, 2H), 8.22 (d, J = 8.2 Hz, 1H), 7.89 (dd, J = 6.7, 5.1 Hz, 2H), 7.79 (s, 1H), 5.14 (s, 2H), 4.87 (s, 2H), 4.57 (q, J = 7.1 Hz, 2H), 4.03 (s, 3H), 1.52 (t, J = 7.1 Hz, 3H) |
| 222 | 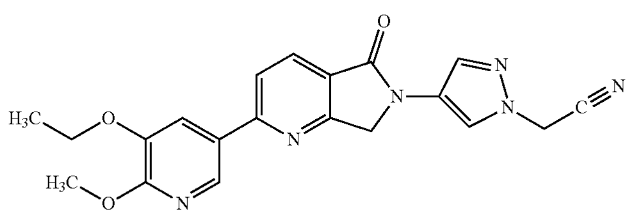 [SMILES: CCOc1cc(-c2ccc3c(n2)CN(c2cnn(CC#N)c2)C3=O)cnc1OC] | 391.44 | (CDCl₃) δ 8.38 (d, J = 9.8 Hz, 2H), 8.21 (d, J = 8.2 Hz, 1H), 7.88 (dd, J = 7.7, 5.1 Hz, 2H), 7.79 (s, 1H), 5.14 (s, 2H), 4.86 (s, 2H), 4.27 (d, J = 7.0 Hz, 2H), 4.15-4.11 (m, J = 2.4 Hz, 3H), 1.63-1.54 (m, 8H) |
| 223 | 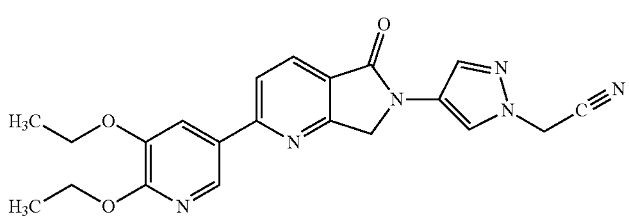 [SMILES: CCOc1cc(-c2ccc3c(n2)CN(c2cnn(CC#N)c2)C3=O)cnc1OCC] | 405.43 | (CDCl₃) δ 8.50-8.29 (m, 2H), 8.20 (d, J = 8.1 Hz, 1H), 7.87 (dd, J = 6.9, 5.1 Hz, 2H), 7.79 (s, 1H), 5.14 (s, 2H), 4.86 (s, 2H), 4.57 (q, J = 7.1 Hz, 2H), 4.26 (q, J = 7.0 Hz, 2H), 1.72- 1.44 (m, 6H) |
| 224 | 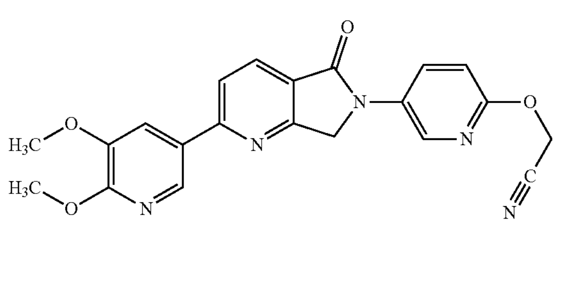 [SMILES: COc1cc(-c2ccc3c(n2)CN(c2ccc(OCC#N)nc2)C3=O)cnc1OC] | 404.43 | |

TABLE 1-continued
| Cmpd No. | Structure | ESMS (M + H) | ¹H NMR (300 MHz, unless indicated otherwise) |
|---|---|---|---|
| 225 | 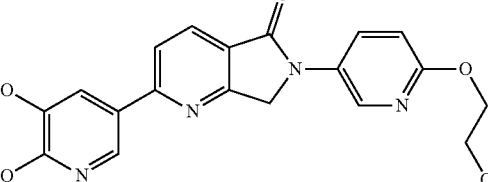 | 423.43 | |
| 226 | 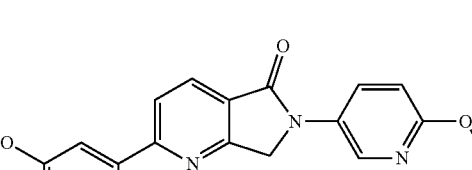 | 475.45 | |
| 227 | 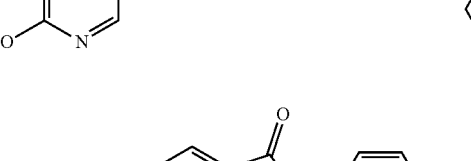 | 451.4 | |
| 228 | 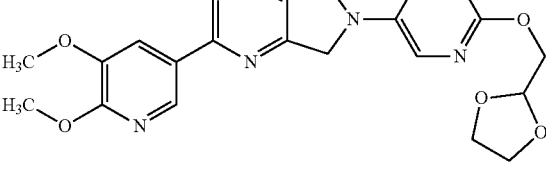 | 465.45 | |
| 229 | 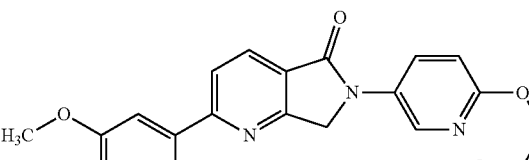 | 477.44 | |
| 230 | 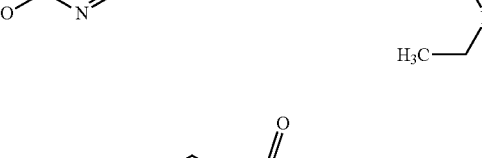 | 404.37 | |

TABLE 1-continued

| Cmpd No. | Structure | ESMS (M + H) | ¹H NMR (300 MHz, unless indicated otherwise) |
|---|---|---|---|
| 231 | 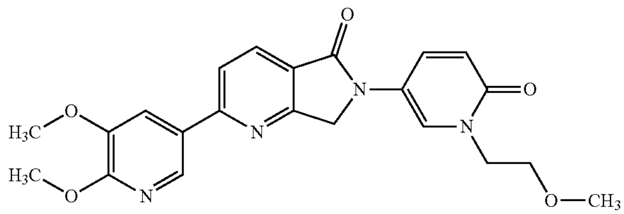 | 423.43 | |
| 232 | 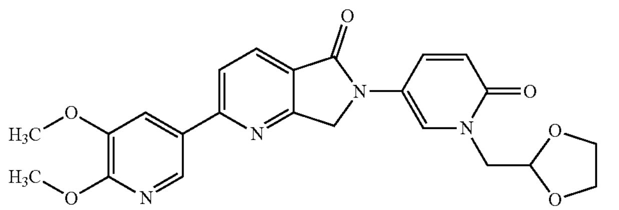 [SMILES: COc1cc(-c2ccc3c(n2)CN(c2ccc(=O)n(CC4OCCO4)c2)C3=O)cnc1OC] | 451.4 | |
| 233 | 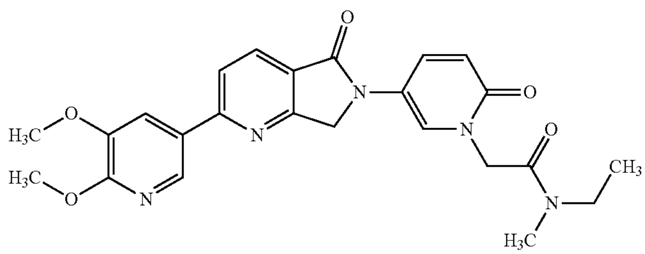 [SMILES: CCN(C)C(=O)Cn1cc(N2Cc3nc(-c4cnc(OC)c(OC)c4)ccc3C2=O)ccc1=O] | 464.45 | |
| 234 | 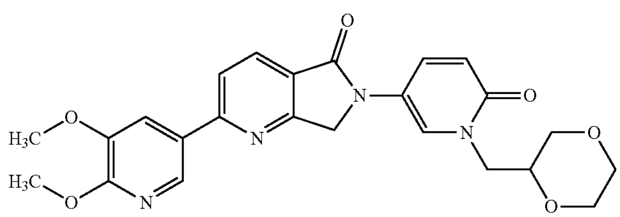 [SMILES: COc1cc(-c2ccc3c(n2)CN(c2ccc(=O)n(CC4COCCO4)c2)C3=O)cnc1OC] | 465.41 | |
| 235 | 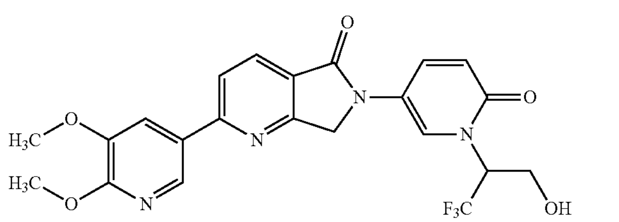 [SMILES: COc1cc(-c2ccc3c(n2)CN(c2ccc(=O)n(C(CO)C(F)(F)F)c2)C3=O)cnc1OC] | 477.44 | |
| 236 | 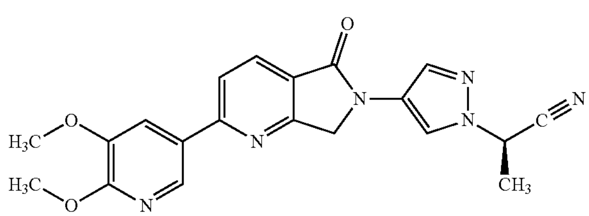 [SMILES: COc1cc(-c2ccc3c(n2)CN(c2cnn([C@H](C)C#N)c2)C3=O)cnc1OC] | 391.34 | (DMSO-d$_6$) δ 8.57 (d, J = 1.9 Hz, 1H), 8.43 (s, 1H), 8.22 (d, J = 3.8 Hz, 2H), 8.01 (m, 2H), 6.03-5.88 (m, 1H), 5.01 (s, 2H), 3.96 (s, 3H), 3.92 (s, 3H), 1.82 (d, J = 7.1 Hz, 3H) |
| 237 | 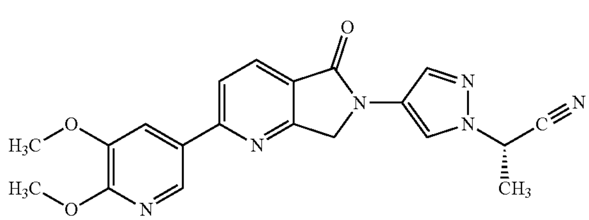 [SMILES: COc1cc(-c2ccc3c(n2)CN(c2cnn([C@@H](C)C#N)c2)C3=O)cnc1OC] | 391.34 | (DMSO-d$_6$) δ 8.56 (d, J = 1.6 Hz, 1H), 8.43 (s, 1H), 8.21 (q, J = 8.2 Hz, 2H), 8.11-7.89 (m, 2H), 5.96 (q, J = 7.0 Hz, 1H), 5.00 (s, 2H), 3.95 (s, 3H), 3.92 (s, 3H), 1.83 (d, J = 7.1 Hz, 3H) |

TABLE 1-continued

| Cmpd No. | Structure | ESMS (M + H) | ¹H NMR (300 MHz, unless indicated otherwise) |
|---|---|---|---|
| 238 | 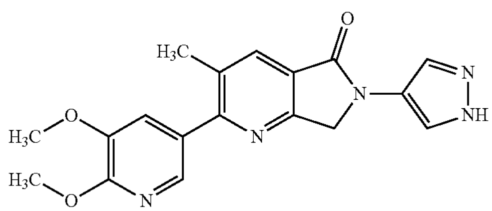 [SMILES: COc1cc(-c2nc3c(cc2C)C(=O)N(c2cn[nH]c2)C3)cnc1OC] | 352.26 | (CDCl₃) δ 8.10 (d, J = 11.8 Hz, 3H), 7.97 (d, J = 1.9 Hz, 1H), 7.34 (d, J = 1.8 Hz, 1H), 4.83 (s, 2H), 4.10 (s, 3H), 3.96 (s, 3H), 2.54 (s, 3H) |
| 239 | 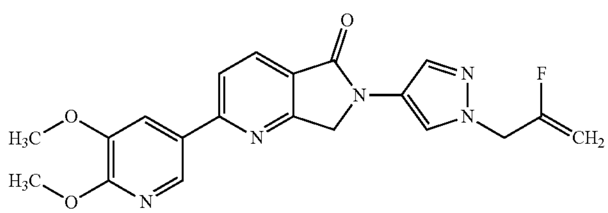 [SMILES: C=C(F)Cn1cc(N2Cc3nc(-c4cnc(OC)c(OC)c4)ccc3C2=O)cn1] | 396.5, 396.12 | (DMSO-d₆) δ 8.55 (d, J = 2.0 Hz, 1H), 8.29 (s, 1H), 8.25-8.10 (m, 2H), 7.99 (d, J = 1.9 Hz, 1H), 7.87 (s, 1H), 5.04 (s, 1H), 4.99 (s, 2H), 4.93-4.61 (m, 3H), 3.94 (d, J = 11.5 Hz, 6H) |
| 240 | 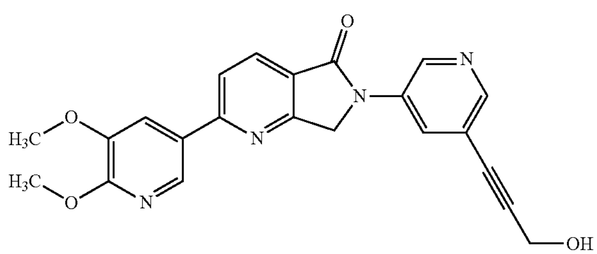 [SMILES: COc1cc(-c2ccc3c(n2)CN(c2cncc(C#CCO)c2)C3=O)cnc1OC] | 403.41 | (DMSO-d₆) δ 9.12 (dd, J = 5.5, 2.4 Hz, 1H), 8.58 (d, J = 1.8 Hz, 1H), 8.48 (dt, J = 20.1, 4.1 Hz, 1H), 8.26 (dd, J = 17.2, 8.3 Hz, 2H), 8.00 (d, J = 1.8 Hz, 1H), 5.21 (s, 2H), 4.37 (s, 2H), 3.94 (d, J = 10.0 Hz, 6H), 3.34 (s, 1H) |
| 241 | 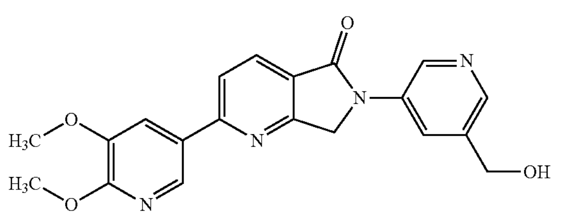 [SMILES: COc1cc(-c2ccc3c(n2)CN(c2cncc(CO)c2)C3=O)cnc1OC] | 379.15 | (DMSO-d₆) δ 9.11 (d, J = 2.5 Hz, 1H), 8.58 (d, J = 1.8 Hz, 1H), 8.52-8.48 (m, 1H), 8.45 (s, 1H), 8.26 (dd, J = 17.2, 8.3 Hz, 2H), 8.00 (d, J = 1.8 Hz, 1H), 5.21 (s, 2H), 4.37 (s, 2H), 3.94 (d, J = 10.0 Hz, 11H), 3.34 (s, 5H) |
| 242 | 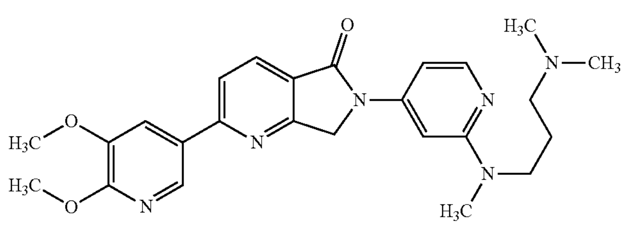 | 463.55 | |
| 243 | 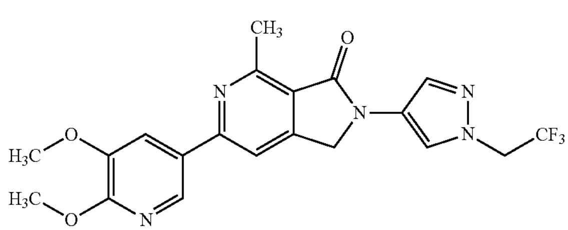 [SMILES: COc1cc(-c2cc3c(c(C)n2)C(=O)N(c2cnn(CC(F)(F)F)c2)C3)cnc1OC] | 434.02 | (DMSO-d₆) δ 8.54 (d, J = 1.9 Hz, 1H), 8.38 (s, 1H), 8.13 (s, 1H), 7.99 (d, J = 1.9 Hz, 1H), 7.94 (s, 1H), 5.19 (q, J = 9.1 Hz, 2H), 4.94 (s, 2H), 3.95 (s, 3H), 3.91 (s, 3H), 2.87 (s, 3H) |

TABLE 1-continued

| Cmpd No. | Structure | ESMS (M + H) | $^1$H NMR (300 MHz, unless indicated otherwise) |
|---|---|---|---|
| 244 | 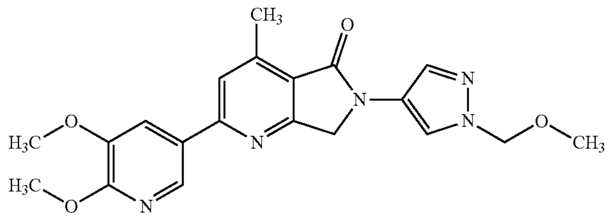 | 396.43 | (CDCl$_3$) δ 8.38 (d, J = 1.8 Hz, 1H), 8.30 (s, 1H), 7.87 (d, J = 1.8 Hz, 1H), 7.81 (s, 1H), 7.58 (s, 1H), 5.46 (d, J = 14.0 Hz, 2H), 4.78 (d, J = 13.8 Hz, 2H), 4.12 (s, 3H), 4.03 (s, 3H), 3.38 (s, 3H), 2.83 (s, 3H) |
| 245 | 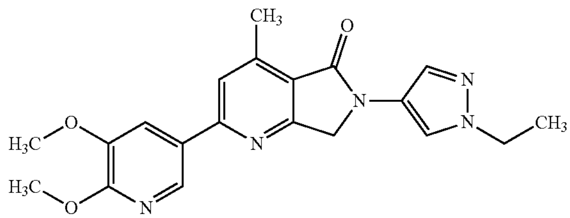 [SMILES: CCn1cc(N2Cc3nc(-c4cnc(OC)c(OC)c4)cc(C)c3C2=O)cn1] | 380.44 | (CDCl$_3$) δ 8.37 (d, J = 2.0 Hz, 1H), 8.20 (d, J = 0.5 Hz, 1H), 7.87 (d, J = 1.9 Hz, 1H), 7.64 (d, J = 0.6 Hz, 1H), 7.56 (s, 1H), 5.31 (s, 1H), 4.78 (s, 2H), 4.23 (q, J = 7.3 Hz, 2H), 4.12 (s, 3H), 4.03 (s, 3H), 2.82 (s, 3H), 1.55 (t, J = 7.3 Hz, 3H) |
| 246 | 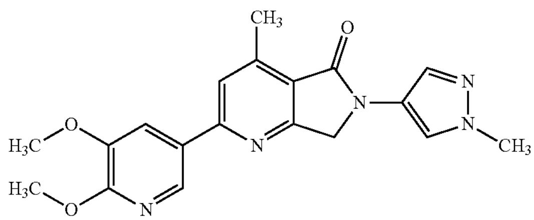 | 366.42 | (CDCl$_3$) δ 8.38 (d, J = 2.0 Hz, 1H), 8.15 (s, 1H), 7.87 (d, J = 1.9 Hz, 1H), 7.65 (d, J = 0.6 Hz, 1H), 7.57 (s, 1H), 4.78 (s, 2H), 4.12 (s, 3H), 4.05 (d, J = 8.9 Hz, 3H), 3.95 (d, J = 14.2 Hz, 3H), 2.83 (s, 3H) |
| 247 | 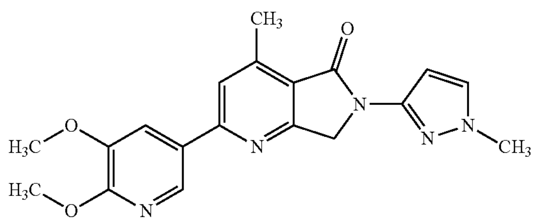 | 366.42 | (CDCl$_3$) δ 8.46-8.32 (m, 1H), 7.89 (s, 1H), 7.55 (s, 1H), 7.36 (d, J = 1.5 Hz, 1H), 6.97 (dd, J = 2.3, 1.1 Hz, 1H), 4.96 (s, 2H), 4.12 (d, J = 1.0 Hz, 3H), 4.03 (d, J = 0.7 Hz, 3H), 3.90 (d, J = 0.8 Hz, 3H), 2.83 (s, 3H) |
| 248 | 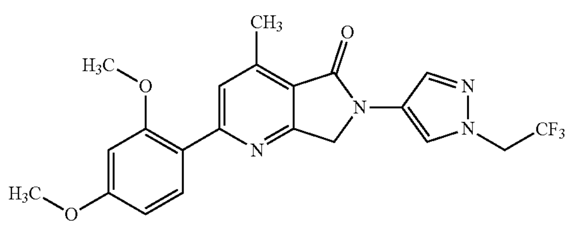 [SMILES: COc1ccc(-c2cc(C)c3c(n2)CN(c2cnn(CC(F)(F)F)c2)C3=O)c(OC)c1] | 433.22 | (CDCl$_3$) δ 8.28 (s, 1H), 7.82 (d, J = 8.6 Hz, 1H), 7.73 (d, J = 11.5 Hz, 2H), 6.78-6.42 (m, 2H), 4.91-4.53 (m, 4H), 4.04-3.62 (m, 6H), 2.76 (s, 3H) |
| 249 | 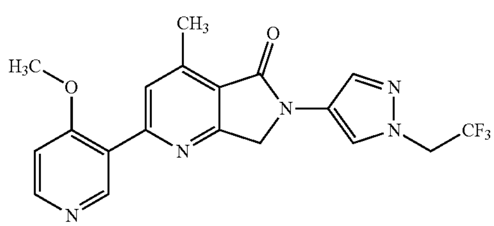 [SMILES: COc1ccncc1-c1cc(C)c2c(n1)CN(c1cnn(CC(F)(F)F)c1)C2=O] | 404.17 | |
| 250 | 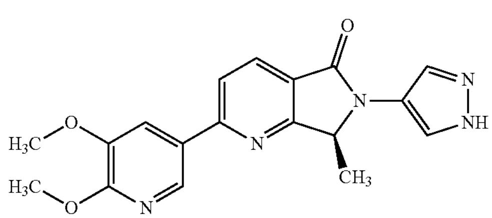 [SMILES: COc1cc(-c2ccc3c(n2)[C@H](C)N(c2cn[nH]c2)C3=O)cnc1OC] | 352.41 | |

TABLE 1-continued

| Cmpd No. | Structure | ESMS (M + H) | ¹H NMR (300 MHz, unless indicated otherwise) |
|---|---|---|---|
| 251 | 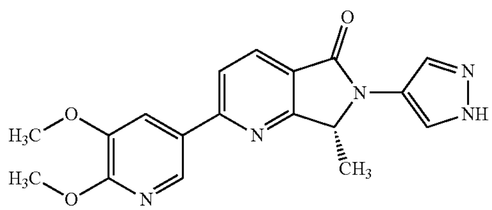 | 352.41 | |
| 252 | 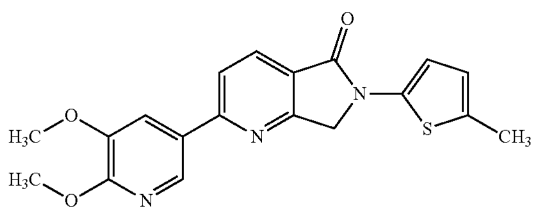 | 368.01 | (DMSO-d$_6$) δ 8.56 (d, J = 2.0 Hz, 1H), 8.30-8.12 (m, 2H), 7.99 (d, J = 2.0 Hz, 1H), 6.73 (d, J = 3.7 Hz, 1H), 6.67 (dd, J = 3.7, 1.1 Hz, 1H), 5.09 (s, 2H), 3.96 (s, 3H), 3.92 (s, 3H), 2.42 (d, J = 0.7 Hz, 3H) |
| 253 | 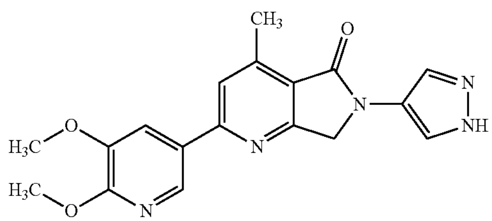 [SMILES: COc1cc(-c2cc(C)c3c(n2)CN(c2cn[nH]c2)C3=O)cnc1OC] | 352.35 | (DMSO-d$_6$) δ 12.57 (s, 1H), 8.53 (d, J = 1.9 Hz, 1H), 8.04-7.88 (m, 2H), 7.76 (d, J = 2.0 Hz, 1H), 6.82 (s, 1H), 4.94 (s, 2H), 3.93 (d, J = 9.7 Hz, 5H), 2.72 (s, 3H) |
| 254 | 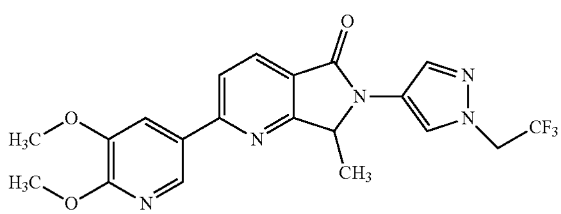 [SMILES: COc1cc(-c2ccc3c(n2)C(C)N(c2cnn(CC(F)(F)F)c2)C3=O)cnc1OC] | 434.44 | |
| 255 | 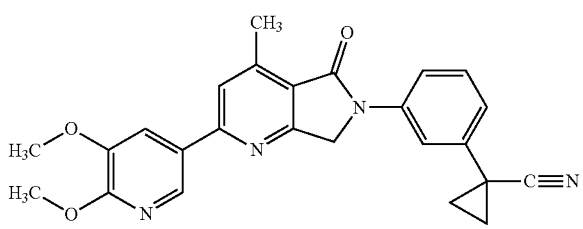 [SMILES: COc1cc(-c2cc(C)c3c(n2)CN(c2cccc(C4(C#N)CC4)c2)C3=O)cnc1OC] | 426.92 | (DMSO-d$_6$) δ 8.55 (s, 1H), 7.99 (m, 3H), 7.84 (d, J = 8.2 Hz, 1H), 7.46 (t, J = 7.6 Hz, 1H), 7.17 (d, J = 7.5 Hz, 1H), 5.08 (s, 2H), 3.95 (s, 3H), 3.91 (s, 3H), 2.70 (s, 3H), 1.79 (m, 2H), 1.58 (m, 2H) |
| 256 | 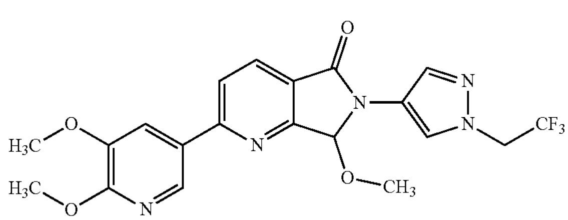 [SMILES: COc1cc(-c2ccc3c(n2)C(OC)N(c2cnn(CC(F)(F)F)c2)C3=O)cnc1OC] | 450.44 | |
| 257 | 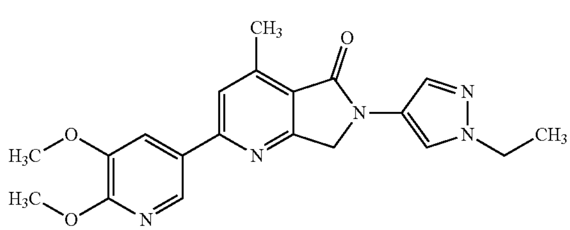 [SMILES: CCn1cc(N2Cc3nc(-c4cnc(OC)c(OC)c4)cc(C)c3C2=O)cn1] | 380.44 | |

TABLE 1-continued

| Cmpd No. | Structure | ESMS (M + H) | ¹H NMR (300 MHz, unless indicated otherwise) |
|---|---|---|---|
| 258 | 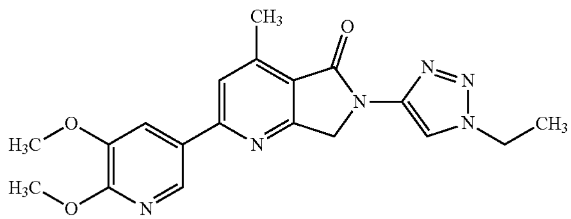 [SMILES: CCn1cc(N2Cc3nc(-c4cnc(OC)c(OC)c4)cc(C)c3C2=O)nn1] | 381 | |
| 259 | 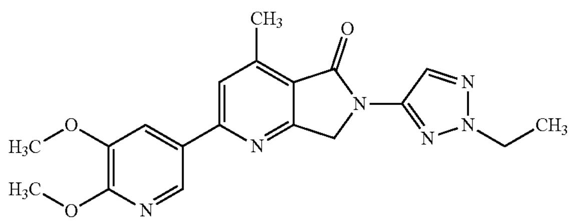 [SMILES: CCn1ncc(N2Cc3nc(-c4cnc(OC)c(OC)c4)cc(C)c3C2=O)n1] | 367 | |
| 260 | 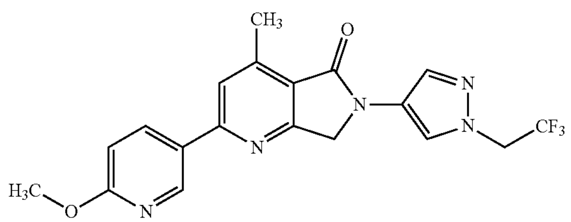 [SMILES: COc1ccc(-c2cc(C)c3c(n2)CN(c2cnn(CC(F)(F)F)c2)C3=O)cn1] | 404.54 | (DMSO-$d_6$) δ 8.98 (d, J = 2.1 Hz, 1H), 8.47 (dd, J = 8.7, 2.5 Hz, 1H), 8.37 (s, 1H), 7.95 (d, J = 3.2 Hz, 1H), 6.98 (d, J = 8.7 Hz, 1H), 5.19 (d, J = 9.1 Hz, 2H), 4.91 (s, 2H), 4.06-3.78 (m, 3H), 2.71 (s, 2H), 1.40-1.05 (m, 1H) |
| 261 | 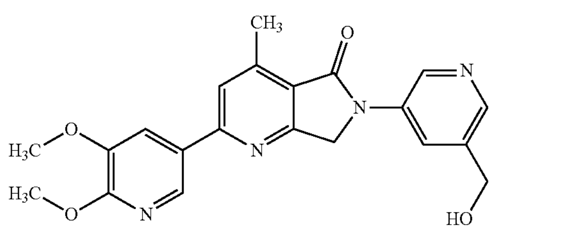 [SMILES: COc1cc(-c2cc(C)c3c(n2)CN(c2cncc(CO)c2)C3=O)cnc1OC] | 393.43 | |
| 262 | 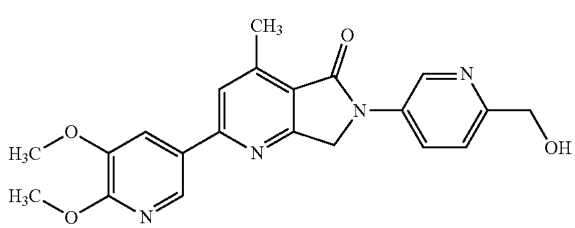 [SMILES: COc1cc(-c2cc(C)c3c(n2)CN(c2ccc(CO)nc2)C3=O)cnc1OC] | 393.11 | |
| 263 | 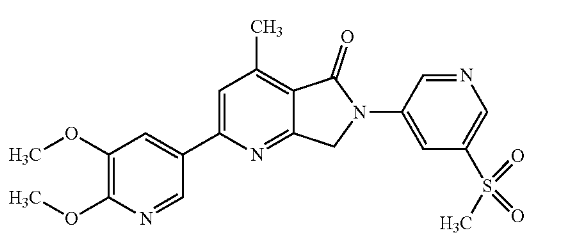 [SMILES: COc1cc(-c2cc(C)c3c(n2)CN(c2cncc(S(C)(=O)=O)c2)C3=O)cnc1OC] | 441.13 | |

TABLE 1-continued

| Cmpd No. | Structure | ESMS (M + H) | ¹H NMR (300 MHz, unless indicated otherwise) |
|---|---|---|---|
| 264 | 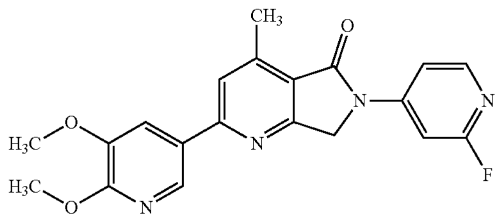 [SMILES: COc1cc(-c2cc(C)c3c(n2)CN(c2ccnc(F)c2)C3=O)cnc1OC] | 381.49 | (DMSO-d$_6$) δ 8.56 (d, J = 1.9 Hz, 1H), 8.23 (d, J = 5.8 Hz, 1H), 8.05 (s, 1H), 7.97 (d, J = 1.9 Hz, 1H), 7.90 (d, J = 5.8 Hz, 1H), 7.68 (d, J = 1.7 Hz, 1H), 5.08 (s, 2H), 3.94 (d, J = 11.0 Hz, 5H), 2.73 (s, 3H) |
| 265 | 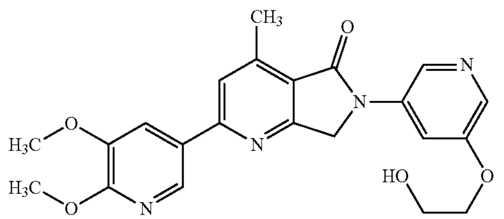 [SMILES: COc1cc(-c2cc(C)c3c(n2)CN(c2cncc(OCCO)c2)C3=O)cnc1OC] | 423.43 | |
| 266 | 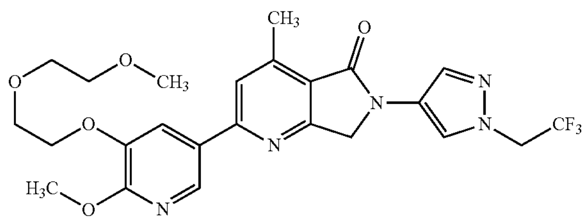 [SMILES: COCCOCCOc1cc(-c2cc(C)c3c(n2)CN(c2cnn(CC(F)(F)F)c2)C3=O)cnc1OC] | 521.94 | (DMSO-d$_6$) δ 8.55 (d, J = 1.9 Hz, 1H), 8.37 (s, 1H), 7.99 (s, 2H), 7.94 (s, 1H), 5.19 (d, J = 9.2 Hz, 2H), 4.92 (s, 2H), 4.25 (s, 2H), 3.96 (s, 3H), 3.81 (s, 2H), 3.62 (dd, J = 5.7, 3.7 Hz, 2H), 3.48 (dd, J = 5.6, 3.7 Hz, 5H), 2.72 (s, 3H) |
| 267 | 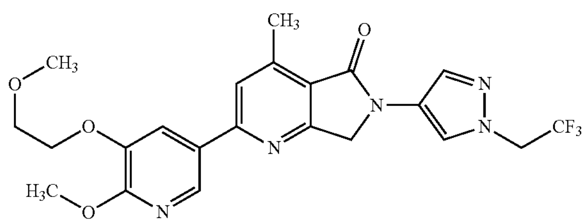 [SMILES: COCCOc1cc(-c2cc(C)c3c(n2)CN(c2cnn(CC(F)(F)F)c2)C3=O)cnc1OC] | 477.88 | (DMSO-d$_6$) δ 8.54 (d, J = 1.8 Hz, 1H), 8.37 (s, 1H), 7.98 (d, J = 2.3 Hz, 2H), 7.94 (s, 1H), 5.19 (d, J = 9.1 Hz, 2H), 4.91 (s, 2H), 4.25 (s, 2H), 3.96 (s, 3H), 3.73 (s, 2H), 3.34 (s, 3H), 2.72 (s, 3H) |
| 268 | 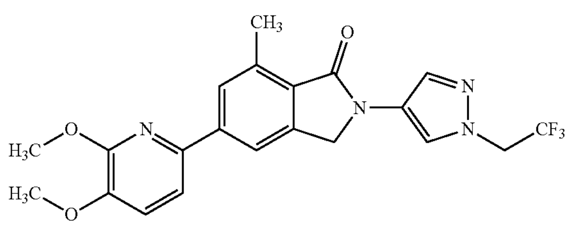 [SMILES: COc1ccc(-c2cc(C)c3c(c2)CN(c2cnn(CC(F)(F)F)c2)C3=O)nc1OC] | 432.86 | (DMSO-d$_6$) δ 8.35 (s, 1H), 8.07 (s, 1H), 7.92 (m, 2H), 7.66 (d, J = 8.1 Hz, 1H), 7.39 (d, J = 8.2 Hz, 1H), 5.18 (q, J = 9.1 Hz, 2H), 4.86 (s, 2H), 4.01 (s, 3H), 3.85 (s, 3H), 2.72 (s, 3H) |
| 269 | 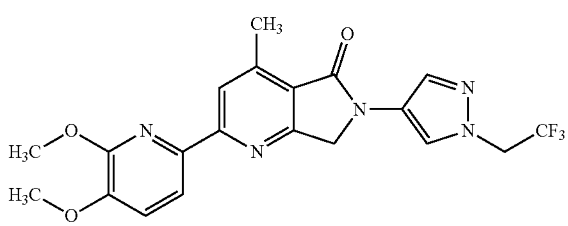 [SMILES: COc1ccc(-c2cc(C)c3c(n2)CN(c2cnn(CC(F)(F)F)c2)C3=O)nc1OC] | 433.88 | (DMSO-d$_6$) δ 8.37 (s, 1H), 8.19 (s, 1H), 8.05 (d, J = 8.1 Hz, 1H), 7.94 (s, 1H), 7.45 (d, J = 8.3 Hz, 1H), 5.19 (q, J = 9.2 Hz, 2H), 4.91 (s, 2H), 4.04 (s, 3H), 3.87 (s, 3H), 2.73 (s, 3H) |
| 270 | 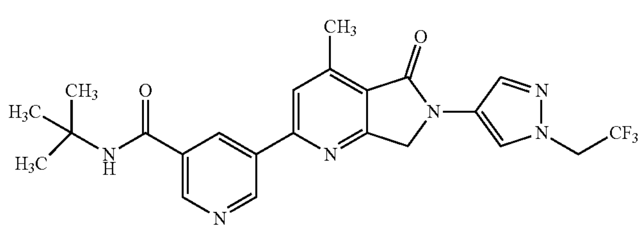 [SMILES: Cc1cc(-c2cncc(C(=O)NC(C)(C)C)c2)nc2c1C(=O)N(c1cnn(CC(F)(F)F)c1)C2] | 473.52 | (DMSO-d$_6$) δ 9.43 (d, J = 2.1 Hz, 1H), 9.02 (d, J = 2.0 Hz, 1H), 8.80 (t, J = 2.1 Hz, 1H), 8.51 (s, 1H), 8.38 (s, 1H), 8.17 (d, J = 16.7 Hz, 1H), 7.96 (s, 1H), 5.20 (dd, J = 18.2, 9.0 Hz, 2H), 4.97 (s, 2H), 2.76 (s, 3H), 1.41 (d, J = 12.8 Hz, 9H) |

TABLE 1-continued

| Cmpd No. | Structure | ESMS (M + H) | ¹H NMR (300 MHz, unless indicated otherwise) |
|---|---|---|---|
| 271 | 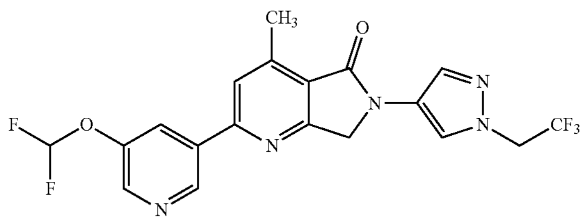 | 439.76 | (DMSO-d$_6$) δ 9.27 (d, J = 1.8 Hz, 1H), 8.62 (d, J = 2.7 Hz, 1H), 8.48-8.30 (m, 2H), 8.15 (s, 1H), 7.96 (s, 1H), 7.67 (d, J = 22.5 Hz, 1H), 7.46 (s, 1H), 7.21 (s, 1H), 5.20 (dd, J = 18.2, 9.2 Hz, 3H), 4.96 (s, 2H), 2.75 (s, 2H) |
| 272 | 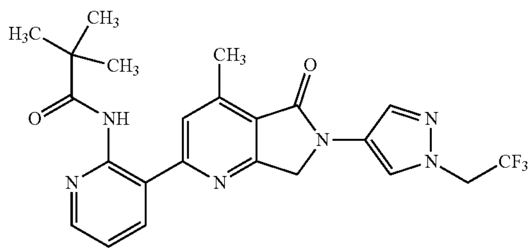 [SMILES: Cc1cc(-c2cccnc2NC(=O)C(C)(C)C)nc2c1C(=O)N(c1cnn(CC(F)(F)F)c1)C2] | 472.9 | (DMSO-d$_6$) δ 10.57 (s, 1H), 8.51 (dd, J = 4.7, 1.8 Hz, 1H), 8.38 (s, 1H), 8.31-8.14 (m, 1H), 7.97 (s, 1H), 7.76-7.49 (m, 5H), 7.39 (dd, J = 7.8, 4.7 Hz, 1H), 5.19 (d, J = 9.1 Hz, 2H), 4.91 (s, 2H), 2.69 (s, 3H), 1.15 (s, 9H) |
| 273 | 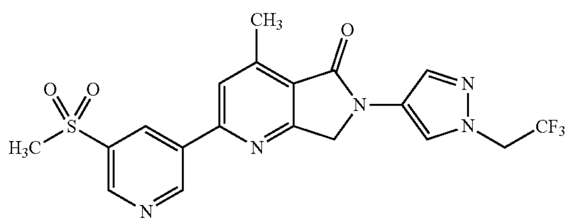 [SMILES: Cc1cc(-c2cncc(S(C)(=O)=O)c2)nc2c1C(=O)N(c1cnn(CC(F)(F)F)c1)C2] | 451.89 | (DMSO-d$_6$) δ 9.67 (d, J = 2.1 Hz, 1H), 9.19 (d, J = 2.2 Hz, 1H), 9.00 (t, J = 2.2 Hz, 1H), 8.46 (d, J = 43.9 Hz, 1H), 8.28 (d, J = 16.6 Hz, 1H), 7.96 (s, 1H), 5.21 (dd, J = 18.2, 9.1 Hz, 2H), 4.99 (s, 2H), 3.43 (s, 3H), 2.77 (s, 3H) |
| 274 | 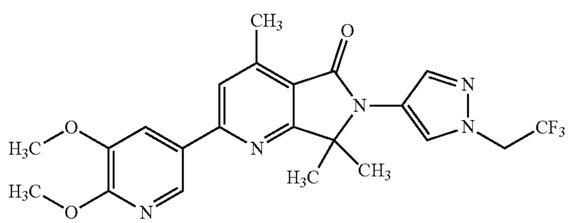 [SMILES: COc1cc(-c2cc(C)c3c(n2)C(C)(C)N(c2cnn(CC(F)(F)F)c2)C3=O)cnc1OC] | 450.44 | |
| 275 | 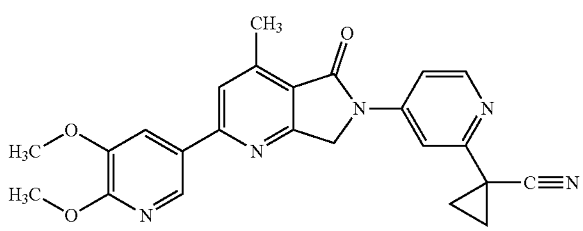 | 427.88 | (DMSO-d$_6$) δ = 8.57 (d, J = 2.0, 1H), 8.48 (d, J = 5.7, 1H), 8.34 (d, J = 1.9, 1H), 8.06 (s, 1H), 7.99 (d, J = 1.9, 1H), 7.70 (dd, J = 5.7, 2.1, 1H), 5.10 (s, 2H), 3.96 (s, 3H), 3.92 (s, 3H), 2.74 (s, 3H), 1.83 (dd, J = 7.8, 4.5, 2H), 1.74 (dd, J = 7.7, 4.5, 2H) |
| 276 | 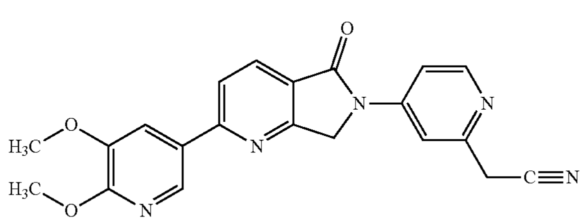 [SMILES: COc1cc(-c2ccc3c(n2)CN(c2ccnc(CC#N)c2)C3=O)cnc1OC] | 387.85 | (DMSO-d$_6$) δ 8.59 (d, J = 1.4, 1H), 8.56 (d, J = 5.8, 1H), 8.28 (m, 2H), 8.12 (s, 1H), 8.01 (d, J = 1.5, 1H), 7.87 (m, 1H), 5.15 (s, 2H), 4.26 (s, 2H), 3.96 (s, 3H), 3.93 (s, 2H) |

TABLE 1-continued

| Cmpd No. | Structure | ESMS (M + H) | ¹H NMR (300 MHz, unless indicated otherwise) |
|---|---|---|---|
| 277 | 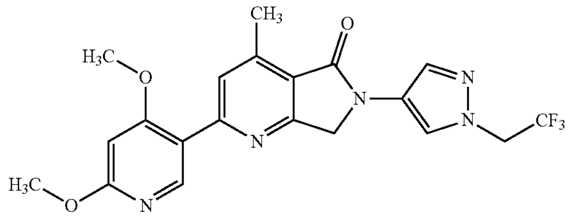 [SMILES: COc1cc(OC)c(-c2cc(C)c3c(n2)CN(c2cnn(CC(F)(F)F)c2)C3=O)cn1] | 433.95 | |
| 278 | 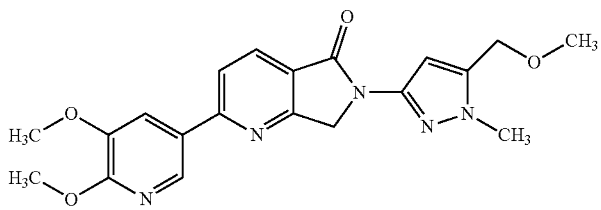 | 396.37 | (CDCl₃) δ 8.41 (d, J = 2.0 Hz, 1H), 8.23 (d, J = 8.1 Hz, 1H), 7.93 (d, J = 1.9 Hz, 1H), 7.85 (d, J = 8.2 Hz, 1H), 7.01 (s, 1H), 5.03 (s, 2H), 4.51 (s, 2H), 4.13 (s, 3H), 4.05 (s, 3H), 3.89 (s, 2H), 3.40 (s, 3H) |
| 279 | 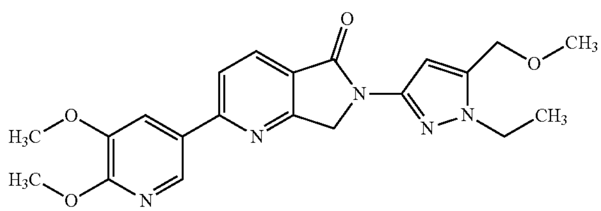 | 410.45 | (CDCl₃) δ 8.41 (d, J = 1.9 Hz, 1H), 8.21 (d, J = 8.1 Hz, 1H), 7.93 (d, J = 1.9 Hz, 1H), 7.84 (d, J = 8.1 Hz, 1H), 6.99 (s, 1H), 5.05 (s, 2H), 4.50 (s, 2H), 4.18 (q, J = 7.2 Hz, 2H), 4.13 (s, 2H), 4.04 (s, 2H), 3.39 (s, 2H), 1.48 (t, J = 7.2 Hz, 2H) |
| 280 | 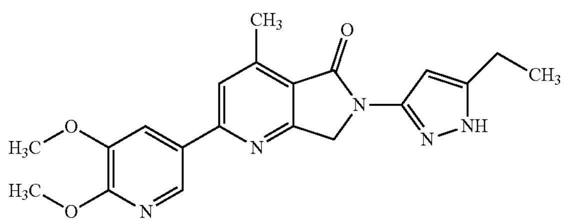 [SMILES: CCc1cc(N2Cc3nc(-c4cnc(OC)c(OC)c4)cc(C)c3C2=O)n[nH]1] | 380.37 | (DMSO-d₆) δ 12.29 (s, 1H), 8.54 (d, J = 1.9 Hz, 1H), 8.08-7.88 (m, 2H), 6.62 (s, 1H), 4.91 (s, 2H), 3.93 (d, J = 9.5 Hz, 6H), 2.72 (s, 3H), 2.64 (d, J = 7.4 Hz, 2H), 1.22 (t, J = 7.6 Hz, 3H) |
| 281 | 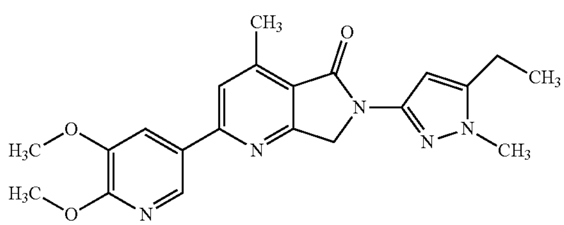 [SMILES: CCc1cc(N2Cc3nc(-c4cnc(OC)c(OC)c4)cc(C)c3C2=O)nn1C] | 394.45 | (CDCl₃) δ 8.37 (d, J = 1.9 Hz, 1H), 7.89 (d, J = 1.9 Hz, 1H), 7.59 (s, 1H), 6.83 (s, 1H), 4.99 (s, 2H), 4.13 (s, 3H), 4.04 (s, 3H), 3.80 (s, 3H), 2.84 (s, 3H), 2.67 (q, J = 7.6 Hz, 2H), 1.35 (t, J = 7.5 Hz, 3H) |
| 282 | 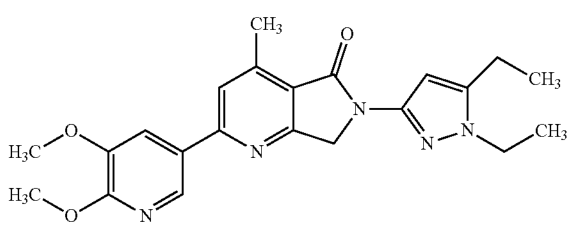 [SMILES: CCc1cc(N2Cc3nc(-c4cnc(OC)c(OC)c4)cc(C)c3C2=O)nn1CC] | 408.46 | (CDCl₃) δ 8.37 (d, J = 2.0 Hz, 1H), 7.89 (d, J = 1.9 Hz, 1H), 7.57 (s, 1H), 6.81 (s, 1H), 4.99 (s, 2H), 4.24-3.83 (m, 8H), 2.84 (s, 3H), 2.77-2.57 (m, 2H), 1.44 (t, J = 7.2 Hz, 3H), 1.35 (t, J = 7.5 Hz, 3H) |
| 283 | 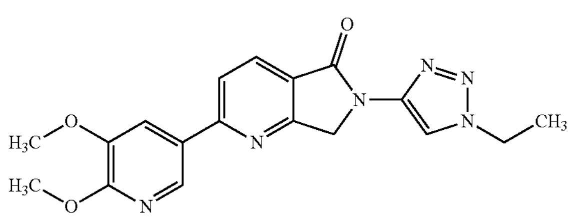 [SMILES: CCn1cc(N2Cc3nc(-c4cnc(OC)c(OC)c4)ccc3C2=O)nn1] | 367 | |

TABLE 1-continued

| Cmpd No. | Structure | ESMS (M + H) | $^1$H NMR (300 MHz, unless indicated otherwise) |
|---|---|---|---|
| 284 | 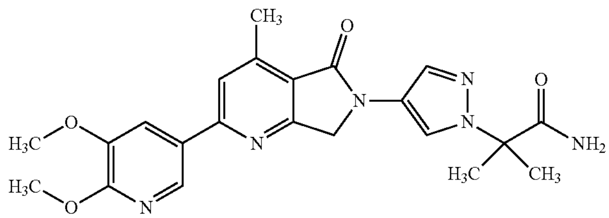 [SMILES: COc1cc(-c2cc(C)c3c(n2)CN(c2cnn(C(C)(C)C(N)=O)c2)C3=O)cnc1OC] | 437 | |
| 285 | 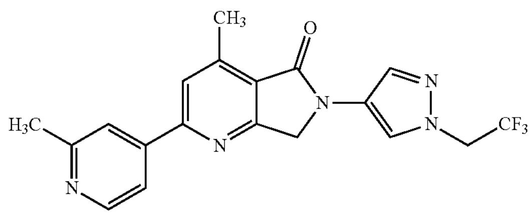 [SMILES: Cc1cc(-c2cc(C)c3c(n2)CN(c2cnn(CC(F)(F)F)c2)C3=O)ccn1] | 388.94 | (DMSO-d$_6$) δ 8.49 (d, J = 1.9 Hz, 1H), 8.38 (s, 1H), 8.21 (s, 0H), 8.02 (d, J = 2.6 Hz, 1H), 7.95 (s, 1H), 7.90 (s, 1H), 7.75-7.63 (m, 1H), 5.55 (s, 2H), 5.21 (d, J = 9.1 Hz, 2H), 4.91 (s, 2H), 2.72 (s, 3H) |
| 286 | 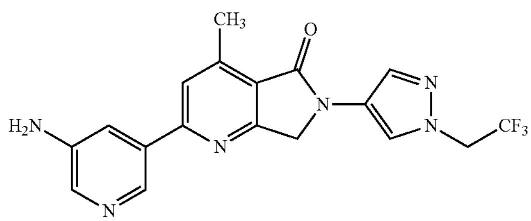 [SMILES: Cc1cc(-c2cncc(N)c2)nc2c1C(=O)N(c1cnn(CC(F)(F)F)c1)C2] | 388.13 | (DMSO-d$_6$) δ 8.61 (d, J = 5.2 Hz, 1H), 8.39 (s, 1H), 8.10 (s, 1H), 8.02 (s, 1H), 7.98-7.88 (m, 2H), 5.21 (q, J = 9.2 Hz, 2H), 4.95 (s, 2H), 2.75 (s, 3H), 2.59 (s, 2H) |
| 287 | 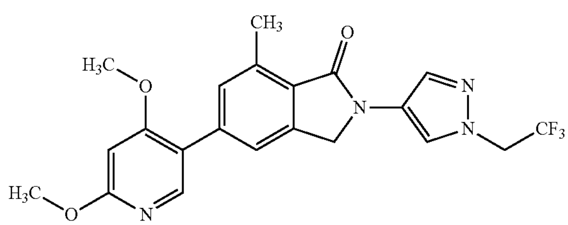 [SMILES: COc1cc(OC)c(-c2cc(C)c3c(c2)CN(c2cnn(CC(F)(F)F)c2)C3=O)cn1] | 432.93 | (DMSO-d$_6$) δ 8.35 (s, 1H), 8.03 (s, 1H), 7.90 (s, 1H), 7.50 (s, 1H), 7.35 (s, 1H), 6.55 (s, 1H), 5.19 (q, J = 9.0 Hz, 2H), 4.83 (s, 2H), 3.89 (s, 3H), 3.84 (s, 3H), 2.68 (s, 3H) |
| 288 | 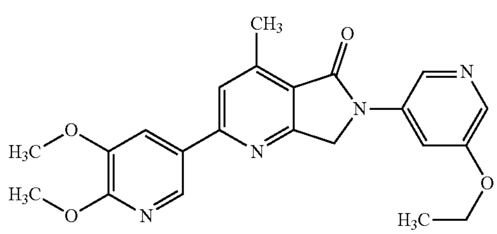 | 407.37 | |
| 289 | 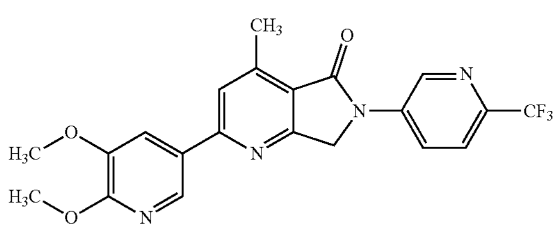 [SMILES: COc1cc(-c2cc(C)c3c(n2)CN(c2ccc(C(F)(F)F)nc2)C3=O)cnc1OC] | 431.16 | (DMSO-d$_6$) δ 9.30 (d, J = 2.4 Hz, 1H), 8.66 (dd, J = 8.7, 2.3 Hz, 1H), 8.58 (d, J = 1.9 Hz, 1H), 8.07 (s, 1H), 8.00 (dd, J = 7.0, 5.5 Hz, 2H), 5.18 (s, 2H), 3.94 (d, J = 9.7 Hz, 7H), 2.74 (s, 3H) |

TABLE 1-continued

| Cmpd No. | Structure | ESMS (M + H) | ¹H NMR (300 MHz, unless indicated otherwise) |
|---|---|---|---|
| 290 | 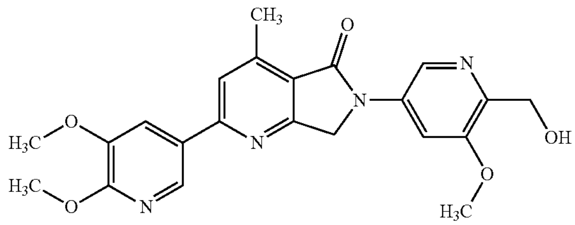 [SMILES: COc1cc(N2Cc3nc(-c4cnc(OC)c(OC)c4)cc(C)c3C2=O)cnc1CO] | 423.43 | |
| 291 | 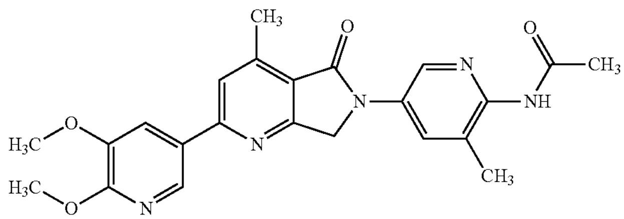 [SMILES: COc1cc(-c2cc(C)c3c(n2)CN(c2cnc(NC(C)=O)c(C)c2)C3=O)cnc1OC] | 434.27 | |
| 292 | 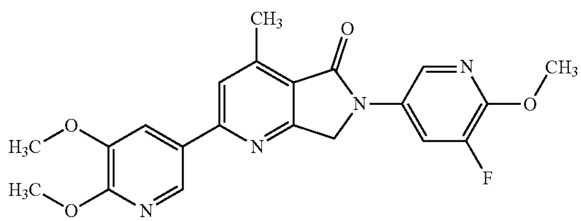 | 411.38 | |
| 293 | 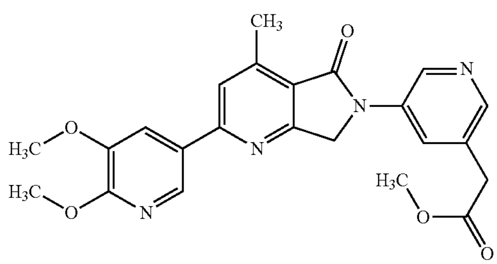 [SMILES: COC(=O)Cc1cncc(N2Cc3nc(-c4cnc(OC)c(OC)c4)cc(C)c3C2=O)c1] | 435.43 | |
| 294 | 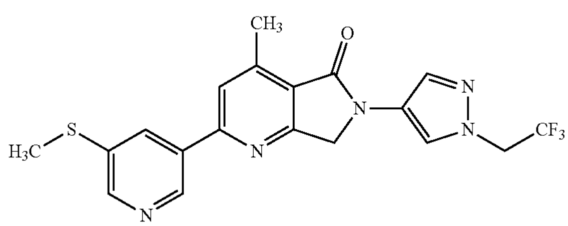 [SMILES: CSc1cncc(-c2cc(C)c3c(n2)CN(c2cnn(CC(F)(F)F)c2)C3=O)c1] | 419.77 | (DMSO-d$_6$) δ 9.12 (d, J = 1.9 Hz, 1H), 8.59 (d, J = 2.3 Hz, 1H), 8.46 (s, 1H), 8.38 (d, J = 6.2 Hz, 1H), 8.13 (s, 1H), 7.96(s, 1H), 5.21 (d, J = 9.1 Hz, 2H), 4.96 (s, 1H), 2.75 (t, J = 6.1 Hz, 2H), 2.64 (s, 2H) |
| 295 | 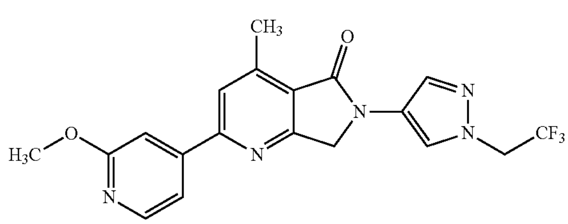 [SMILES: COc1cc(-c2cc(C)c3c(n2)CN(c2cnn(CC(F)(F)F)c2)C3=O)ccn1] | 403.88 | (DMSO-d$_6$) δ 8.50 (s, 1H), 8.39 (s, 1H), 8.34 (d, J = 5.4 Hz, 1H), 8.11 (s, 1H), 7.96 (s, 1H), 7.76 (s, 1H), 7.56 (s, 1H), 5.21 (d, J = 9.1 Hz, 2H), 4.95 (s, 2H), 3.93 (s, 3H), 2.74 (s, 3H) |

TABLE 1-continued

| Cmpd No. | Structure | ESMS (M + H) | ¹H NMR (300 MHz, unless indicated otherwise) |
|---|---|---|---|
| 296 | 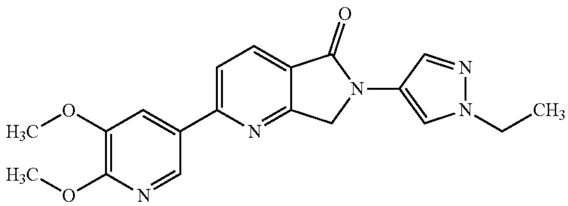 [SMILES: CCn1cc(N2Cc3nc(-c4cnc(OC)c(OC)c4)ccc3C2=O)cn1] | 366.42 | (CDCl$_3$) δ 8.40 (d, J = 2.0 Hz, 1H), 8.27-8.15 (m, 2H), 7.88 (dd, J = 14.6, 5.0 Hz, 2H), 7.66 (d, J = 0.5 Hz, 1H), 4.86 (s, 2H), 4.25 (q, J = 7.3 Hz, 2H), 4.13 (s, 3H), 4.04 (s, 3H), 1.56 (t, J = 7.3 Hz, 3H) |
| 297 | 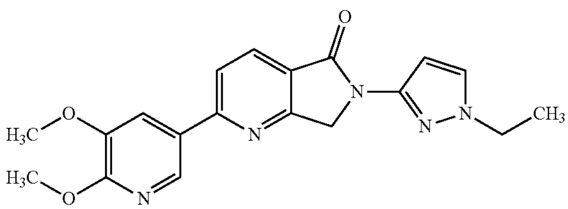 [SMILES: CCn1ccc(N2Cc3nc(-c4cnc(OC)c(OC)c4)ccc3C2=O)n1] | 366.42 | (CDCl$_3$) δ 8.41 (d, J = 2.0 Hz, 1H), 8.21 (d, J = 8.1 Hz, 1H), 7.93 (d, J = 1.9 Hz, 1H), 7.84 (d, J = 8.1 Hz, 1H), 7.41 (d, J = 2.3 Hz, 1H), 7.00 (d, J = 2.3 Hz, 1H), 5.05 (s, 2H), 4.17 (dd, J = 14.7, 7.4 Hz, 2H), 4.13 (s, 3H), 4.04 (s, 3H), 1.53 (t, J = 7.3 Hz, 3H) |
| 298 | 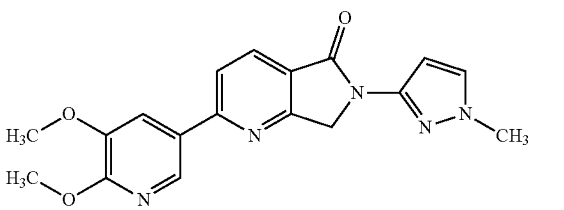 | 352.35 | (CDCl$_3$) δ 8.40 (d, J = 2.0 Hz, 1H), 8.21 (d, J = 8.1 Hz, 1H), 7.92 (d, J = 2.0 Hz, 1H), 7.84 (d, J = 8.1 Hz, 1H), 7.37 (d, J = 2.3 Hz, 1H), 6.99 (d, J = 2.3 Hz, 1H), 5.03 (s, 2H), 4.12 (s, 3H), 4.04 (s, 3H), 3.92 (d, J = 3.8 Hz, 3H) |
| 299 | 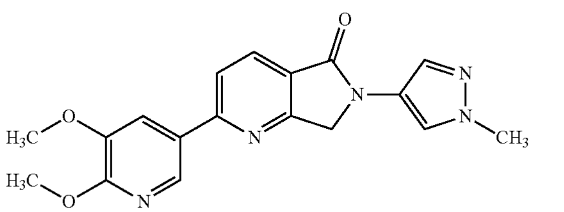 | 352.35 | (CDCl$_3$) δ 8.40 (d, J = 2.0 Hz, 1H), 8.24- 8.14 (m, 2H), 7.88 (dd, J = 13.9, 5.0 Hz, 2H), 7.65 (s, 1H), 4.85 (s, 2H), 4.12 (s, 3H), 4.04 (s, 3H), 3.98 (d, J = 4.1 Hz, 3H) |
| 300 | 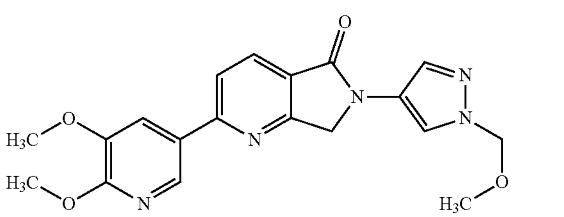 [SMILES: COCn1cc(N2Cc3nc(-c4cnc(OC)c(OC)c4)ccc3C2=O)cn1] | 382.42 | (CDCl$_3$) δ 8.40 (d, J = 2.0 Hz, 1H), 8.35-8.29 (m, 1H), 8.21 (d, J = 8.1 Hz, 1H), 7.88 (dd, J = 12.1, 5.0 Hz, 2H), 7.82-7.74 (m, 1H), 5.45 (s, 2H), 4.86 (s, 2H), 4.12 (s, 3H), 4.04 (s, 3H), 3.39 (s, 3H) |
| 301 | 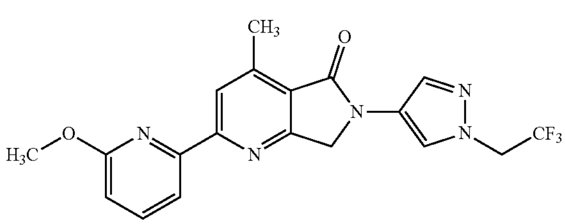 [SMILES: COc1cccc(-c2cc(C)c3c(n2)CN(c2cnn(CC(F)(F)F)c2)C3=O)n1] | 403.81 | |
| 302 | 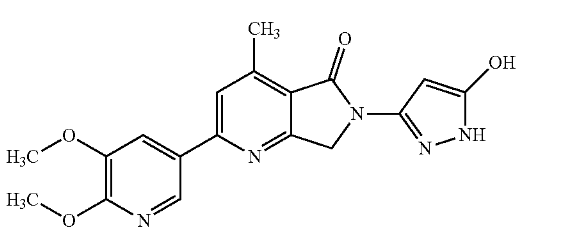 [SMILES: COc1cc(-c2cc(C)c3c(n2)CN(c2cc(O)[nH]n2)C3=O)cnc1OC] | 368.41 | |

TABLE 1-continued

| Cmpd No. | Structure | ESMS (M + H) | ¹H NMR (300 MHz, unless indicated otherwise) |
|---|---|---|---|
| 303 | 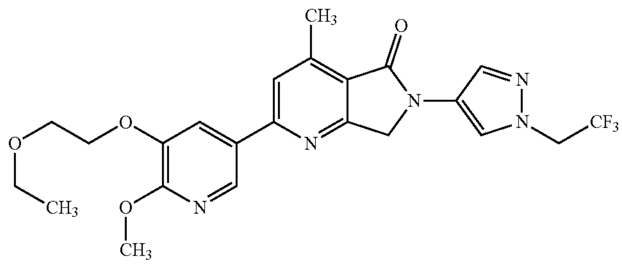 [SMILES: CCOCCOc1cc(-c2cc(C)c3c(n2)CN(c2cnn(CC(F)(F)F)c2)C3=O)cnc1OC] | 491.86 | (CDCl₃) δ 8.41 (s, 1H), 8.32 (s, 1H), 7.98 (s, 1H), 7.85 (s, 1H), 7.65 (s, 1H), 4.91 (s, 2H), 4.80 (q, J = 8.2 Hz, 2H), 4.34 (d, J = 4.2 Hz, 2H), 4.14 (s, 3H), 3.91 (d, J = 3.5 Hz, 2H), 3.66 (q, J = 7.0 Hz, 2H), 2.86 (s, 3H), 1.26 (t, J = 7.0 Hz, 3H) |
| 304 | 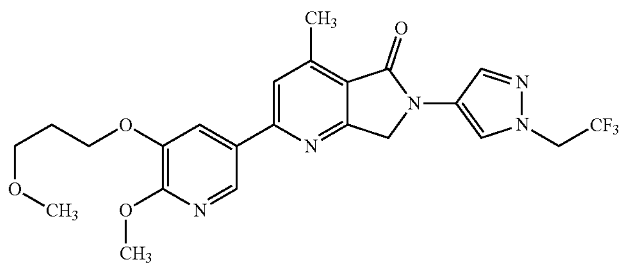 [SMILES: COCCCOc1cc(-c2cc(C)c3c(n2)CN(c2cnn(CC(F)(F)F)c2)C3=O)cnc1OC] | 491.93 | (CDCl₃) δ 8.39 (d, J = 1.5 Hz, 1H), 8.33 (s, 1H), 7.90 (d, J = 1.4 Hz, 1H), 7.81 (s, 1H), 7.60 (s, 1H), 4.84 (s, 2H), 4.77 (q, J = 8.3 Hz, 2H), 4.28 (t, J = 6.4 Hz, 2H), 4.12 (s, 3H), 3.64 (t, J = 6.0 Hz, 2H), 3.40 (s, 3H), 2.84 (s, 3H), 2.20 (p, J = 6.2 Hz, 2H) |
| 305 | 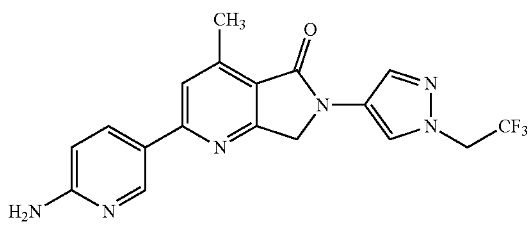 [SMILES: Cc1cc(-c2ccc(N)nc2)nc2c1C(=O)N(c1cnn(CC(F)(F)F)c1)C2] | 389.52 | |
| 306 | 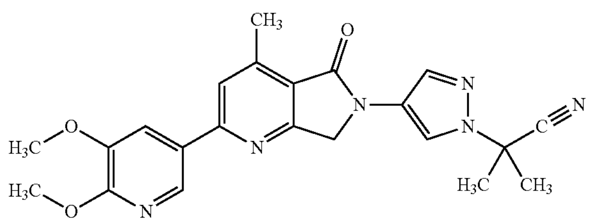 [SMILES: COc1cc(-c2cc(C)c3c(n2)CN(c2cnn(C(C)(C)C#N)c2)C3=O)cnc1OC] | 419 | |
| 307 | 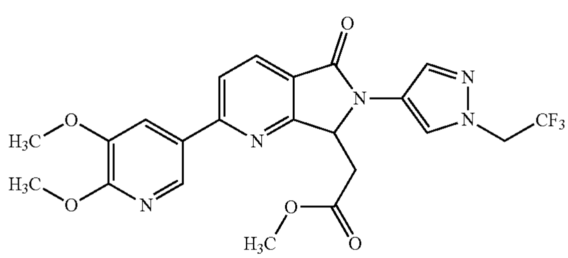 [SMILES: COC(=O)CC1c2nc(-c3cnc(OC)c(OC)c3)ccc2C(=O)N1c1cnn(CC(F)(F)F)c1] | 491.86 | |
| 308 | 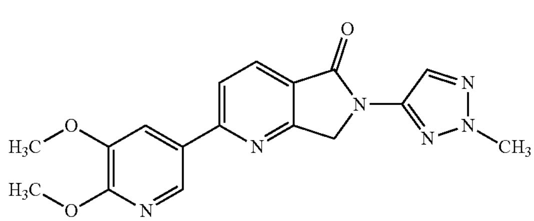 | 353 | |

TABLE 1-continued

| Cmpd No. | Structure | ESMS (M + H) | ¹H NMR (300 MHz, unless indicated otherwise) |
|---|---|---|---|
| 309 | 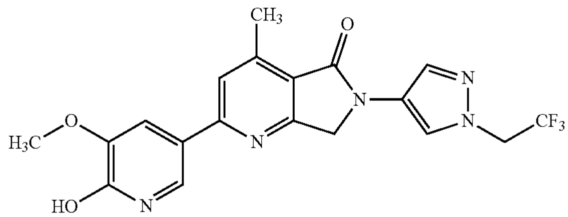 [SMILES: COc1cc(-c2cc(C)c3c(n2)CN(c2cnn(CC(F)(F)F)c2)C3=O)cnc1O] | 419.84 | (DMSO-d$_6$) δ 12.04 (s, 1H), 8.35 (s, 1H), 7.92 (s, 2H), 7.85 (s, 1H), 7.58 (d, J = 2.2 Hz, 1H), 5.19 (q, J = 9.1 Hz, 2H), 4.87 (s, 2H), 3.83 (s, 3H), 2.67 (s, 3H) |
| 310 | 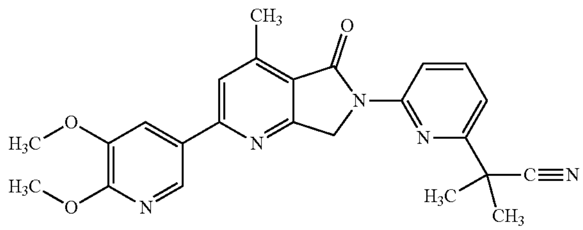 [SMILES: COc1cc(-c2cc(C)c3c(n2)CN(c2cccc(C(C)(C)C#N)n2)C3=O)cnc1OC] | 429.86 | (DMSO-d$_6$) δ = 8.56 (d, J = 1.9, 1H), 8.46 (d, J = 8.3, 1H), 8.02 (d, J = 7.5, 2H), 7.97 (d, J = 8.3, 1H), 7.40 (d, J = 7.6, 1H), 5.13 (s, 2H), 3.96 (s, 3H), 3.92 (s, 3H), 2.74 (s, 3H), 1.76 (s, 6H) |
| 311 | 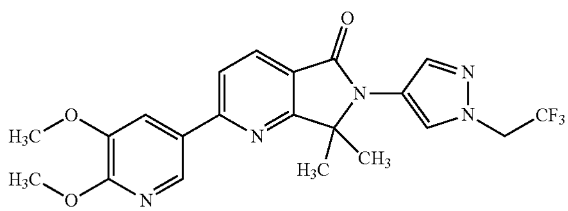 [SMILES: COc1cc(-c2ccc3c(n2)C(C)(C)N(c2cnn(CC(F)(F)F)c2)C3=O)cnc1OC] | 447.87 | (CDCl$_3$) δ 8.45 (d, J = 1.9 Hz, 1H), 8.24-8.08 (m, 2H), 7.84 (dd, J = 19.0, 4.1 Hz, 3H), 4.75 (q, J = 8.3 Hz, 2H), 4.08 (t, J = 17.3 Hz, 6H), 1.72 (s, 6H) |
| 312 | 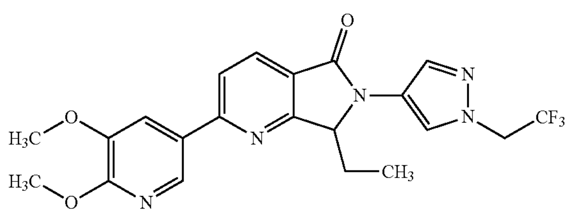 [SMILES: CCC1c2nc(-c3cnc(OC)c(OC)c3)ccc2C(=O)N1c1cnn(CC(F)(F)F)c1] | 448.45 | (CDCl$_3$) δ 8.43 (d, J = 2.0 Hz, 1H), 8.29 (s, 1H), 8.17 (d, J = 8.1 Hz, 1H), 7.86 (dd, J = 15.6, 5.0 Hz, 2H), 7.74 (s, 1H), 5.04 (dd, J = 6.0, 2.5 Hz, 1H), 4.75 (q, J = 8.3 Hz, 2H), 4.17-4.07 (m, 3H), 4.01 (s, 3H), 2.56-2.37 (m, 1H), 2.28-2.12 (m, 1H), 0.63 (t, J = 7.4 Hz, 3H) |
| 313 | 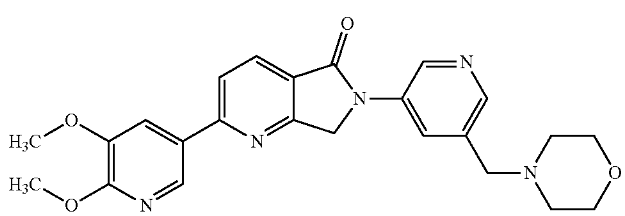 [SMILES: COc1cc(-c2ccc3c(n2)CN(c2cncc(CN4CCOCC4)c2)C3=O)cnc1OC] | 448.45 | (CDCl$_3$) δ 8.93 (d, J = 2.2 Hz, 1H), 8.46-8.37 (m, 3H), 8.22 (d, J = 8.2 Hz, 1H), 7.89 (t, J = 5.1 Hz, 2H), 4.99 (d, J = 13.3 Hz, 2H), 4.10 (s, 3H), 4.01 (s, 3H), 3.77-3.67 (m, 4H), 3.59 (s, 2H), 2.54-2.42 (m, 4H) |
| 314 | 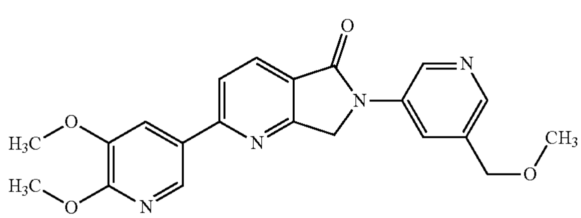 | 393.43 | |
| 315 | 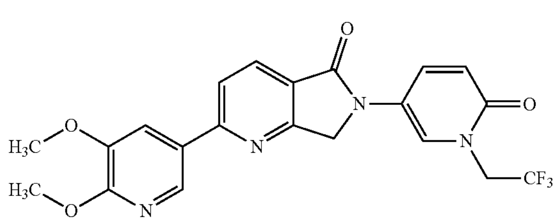 [SMILES: COc1cc(-c2ccc3c(n2)CN(c2ccc(=O)n(CC(F)(F)F)c2)C3=O)cnc1OC] | 447.36 | (CDCl$_3$) δ 8.42 (d, J = 1.9 Hz, 1H), 8.24 (dd, J = 12.5, 5.3 Hz, 2H), 7.89 (dd, J = 5.0, 3.1 Hz, 2H), 7.75 (dd, J = 9.9, 2.9 Hz, 1H), 6.80 (d, J = 10.0 Hz, 1H), 4.87 (s, 2H), 4.72 (q, J = 8.5 Hz, 2H), 4.13 (s, 3H), 4.04 (s, 3H) |

TABLE 1-continued

| Cmpd No. | Structure | ESMS (M + H) | ¹H NMR (300 MHz, unless indicated otherwise) |
|---|---|---|---|
| 316 | 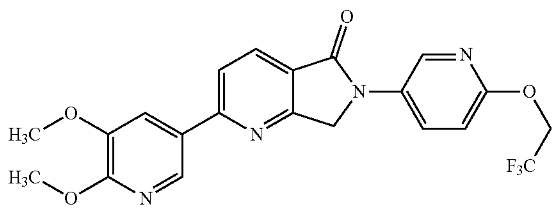 [SMILES: COc1cc(-c2ccc3c(n2)CN(c2ccc(OCC(F)(F)F)nc2)C3=O)cnc1OC] | 447.36 | (CDCl$_3$) δ 8.50 (d, J = 2.7 Hz, 1H), 8.46-8.34 (m, 2H), 8.24 (d, J = 8.1 Hz, 1H), 7.90 (t, J = 5.5 Hz, 2H), 7.00 (d, J = 9.0 Hz, 1H), 4.97 (s, 2H), 4.82 (q, J = 8.5 Hz, 2H), 4.09 (d, J = 26.6 Hz, 5H) |
| 317 | 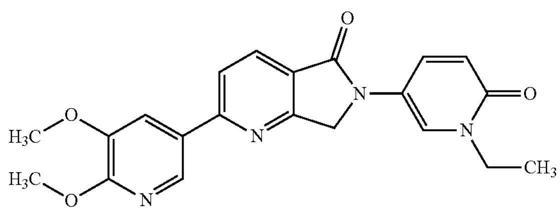 [SMILES: CCn1cc(N2Cc3nc(-c4cnc(OC)c(OC)c4)ccc3C2=O)ccc1=O] | 393.43 | |
| 318 | 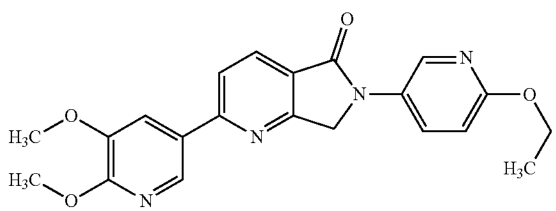 [SMILES: CCOc1ccc(N2Cc3nc(-c4cnc(OC)c(OC)c4)ccc3C2=O)cn1] | 393.18 | |
| 319 | 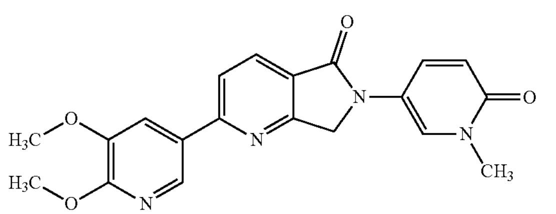 [SMILES: COc1cc(-c2ccc3c(n2)CN(c2ccc(=O)n(C)c2)C3=O)cnc1OC] | 379.41 | |
| 320 | 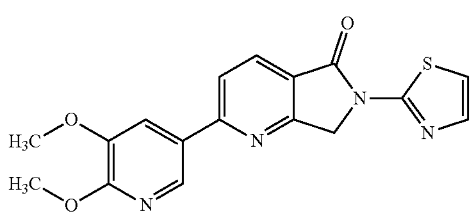 [SMILES: COc1cc(-c2ccc3c(n2)CN(c2nccs2)C3=O)cnc1OC] | 355.25 | (DMSO-d$_6$) δ 8.59 (d, J = 2.1 Hz, 1H), 8.34 (m, 1H), 8.26 (m, 1H), 8.02 (m, 1H), 7.62 (d, J = 3.5 Hz, 1H), 7.42 (d, J = 3.5 Hz, 1H), 5.25 (s, 2H), 3.97 (s, 3H), 3.93 (s, 3H) |
| 321 | 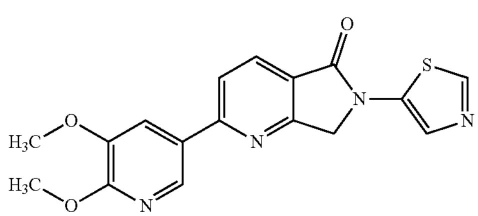 [SMILES: COc1cc(-c2ccc3c(n2)CN(c2cncs2)C3=O)cnc1OC] | 355.23 | (DMSO-d$_6$) δ 8.78 (s, 1H), 8.58 (d, J = 1.9 Hz, 1H), 8.26 (dd, J = 17.4, 8.2 Hz, 2H), 8.01 (d, J = 1.9 Hz, 1H), 7.91 (s, 1H), 5.19 (s, 2H), 3.96 (s, 3H), 3.93 (s, 3H) |
| 322 | 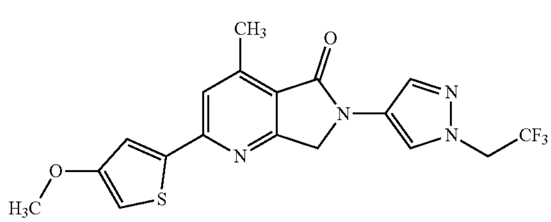 [SMILES: COc1csc(-c2cc(C)c3c(n2)CN(c2cnn(CC(F)(F)F)c2)C3=O)c1] | 408.79 | (DMSO-d$_6$) δ = 8.34 (s, 1H), 7.91 (s, 1H), 7.87 (s, 1H), 7.65 (d, J = 1.5 Hz, 1H), 6.82 (d, J = 1.4 Hz, 1H), 5.19 (q, J = 9.0, 2H), 4.87 (s, 2H), 3.80 (s, 3H), 2.67 (s, 3H) |

TABLE 1-continued

| Cmpd No. | Structure | ESMS (M + H) | ¹H NMR (300 MHz, unless indicated otherwise) |
|---|---|---|---|
| 323 | 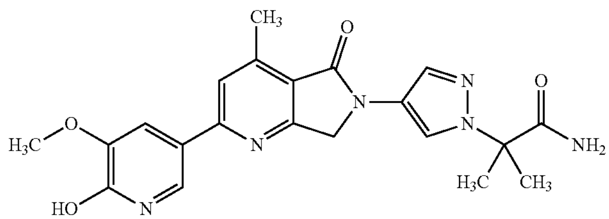 [SMILES: COc1cc(-c2cc(C)c3c(n2)CN(c2cnn(C(C)(C)C(N)=O)c2)C3=O)cnc1O] | 423 | |
| 324 | 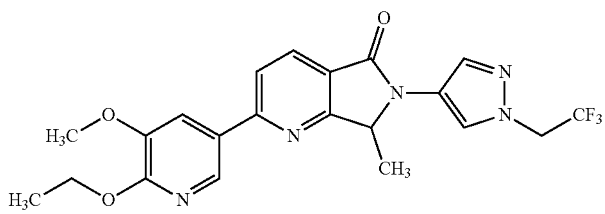 | 448.39 | |
| 325 | 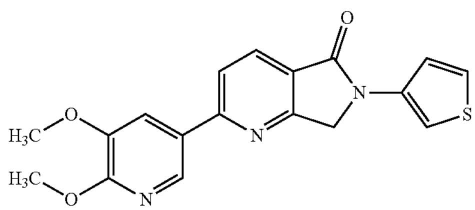 [SMILES: COc1cc(-c2ccc3c(n2)CN(c2ccsc2)C3=O)cnc1OC] | 354.14 | (DMSO-d$_6$) δ 8.56 (d, J = 2.0 Hz, 1H), 8.21 (q, J = 8.2 Hz, 2H), 7.99 (d, J = 1.9 Hz, 1H), 7.80-7.69 (m, 2H), 7.65 (dd, J = 5.1, 3.3 Hz, 1H), 5.11 (s, 2H), 3.96 (s, 3H), 3.92 (s, 3H) |
| 326 | 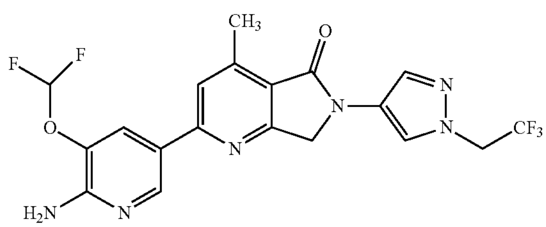 [SMILES: Cc1cc(-c2cnc(N)c(OC(F)F)c2)nc2c1C(=O)N(c1cnn(CC(F)(F)F)c1)C2] | 455.36 | (DMSO-d$_6$) δ 8.69 (d, J = 1.7 Hz, 1H), 8.37 (d, J = 5.3 Hz, 1H), 8.29 (s, 1H), 7.93 (t, J = 7.0 Hz, 2H), 7.61-7.01 (m, 3H), 5.19 (q, J = 9.2 Hz, 2H), 4.91 (s, 2H), 2.76-2.65 (m, 3H) |
| 327 | 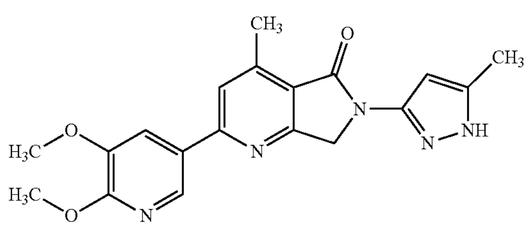 | 366.36 | (DMSO-d$_6$) δ 12.23 (s, 1H), 8.53 (d, J = 1.9 Hz, 1H), 7.96 (d, J = 2.1 Hz, 2H), 6.58 (s, 1H), 4.89 (s, 2H), 3.93 (d, J = 10.0 Hz, 5H), 2.72 (s, 2H), 2.27 (s, 3H) |
| 328 | 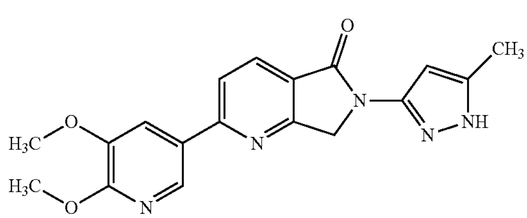 | 352.35 | (DMSO-d$_6$) δ 12.27 (s, 1H), 8.55 (d, J = 2.0 Hz, 1H), 8.19 (d, J = 5.3 Hz, 2H), 7.99 (d, J = 1.9 Hz, 1H), 6.60 (s, 1H), 4.98 (s, 2H), 3.94 (d, J = 10.4 Hz, 5H), 2.27 (s, 3H) |
| 329 | 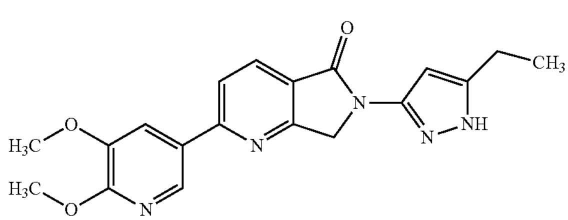 [SMILES: CCc1cc(N2Cc3nc(-c4cnc(OC)c(OC)c4)ccc3C2=O)n[nH]1] | 366.42 | (DMSO-d$_6$) δ 12.30 (s, 1H), 8.55 (d, J = 1.9 Hz, 1H), 8.20 (s, 2H), 7.99 (d, J = 1.9 Hz, 1H), 6.62 (s, 1H), 4.99 (s, 2H), 3.94 (d, J = 10.5 Hz, 5H), 2.77-2.56 (m, 2H), 1.24 (d, J = 7.6 Hz, 3H) |

TABLE 1-continued

| Cmpd No. | Structure | ESMS (M + H) | ¹H NMR (300 MHz, unless indicated otherwise) |
|---|---|---|---|
| 330 | 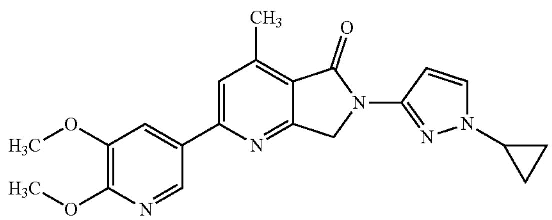 [SMILES: COc1cc(-c2cc(C)c3c(n2)CN(c2ccn(C4CC4)n2)C3=O)cnc1OC] | 392.47 | (CDCl$_3$) δ 8.37 (d, J = 2.0 Hz, 1H), 7.89 (d, J = 1.9 Hz, 1H), 7.58 (s, 1H), 7.46 (d, J = 2.4 Hz, 1H), 6.96 (d, J = 2.4 Hz, 1H), 5.02 (s, 2H), 4.13 (s, 3H), 4.04 (s, 3H), 3.60 (ddd, J = 11.0, 7.2, 3.8 Hz, 1H), 2.84 (s, 3H), 1.20-0.97 (m, 4H) |
| 331 | 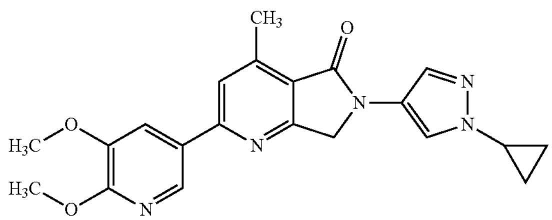 [SMILES: COc1cc(-c2cc(C)c3c(n2)CN(c2cnn(C4CC4)c2)C3=O)cnc1OC] | 392.4 | (CDCl$_3$) δ 8.38 (d, J = 1.9 Hz, 1H), 8.23 (s, 1H), 7.87 (d, J = 1.9 Hz, 1H), 7.64 (s, 1H), 7.57 (s, 1H), 4.77 (s, 2H), 4.12 (s, 3H), 4.03 (s, 3H), 3.76-3.55 (m, 1H), 2.82 (s, 3H), 1.24-0.96 (m, 5H) |
| 332 | 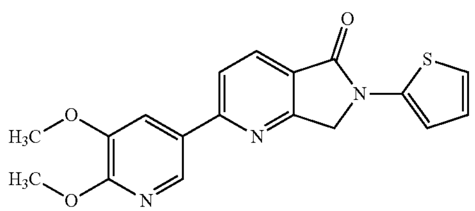 [SMILES: COc1cc(-c2ccc3c(n2)CN(c2cccs2)C3=O)cnc1OC] | 354.14 | (DMSO-d$_6$) δ 8.57 (d, J = 1.9 Hz, 1H), 8.24 (t, J = 6.4 Hz, 2H), 8.00 (d, J = 1.9 Hz, 1H), 7.17 (dd, J = 5.4, 1.1 Hz, 1H), 7.07-6.99 (m, 1H), 6.99-6.89 (m, 1H), 5.15 (s, 2H), 3.96 (s, 3H), 3.92 (s, 3H) |
| 333 | 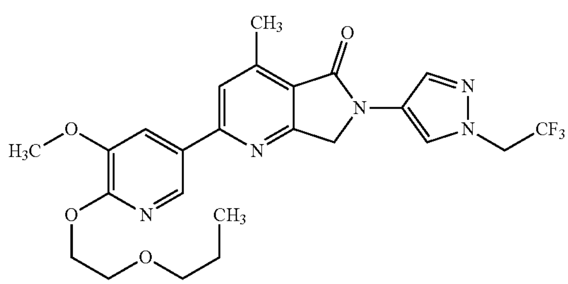 [SMILES: CCCOCCOc1ncc(-c2cc(C)c3c(n2)CN(c2cnn(CC(F)(F)F)c2)C3=O)cc1OC] | 506.55 | (DMSO-d$_6$) δ 8.35 (s, 1H), 8.25 (d, J = 2.2 Hz, 1H), 7.92 (s, 1H), 7.83 (s, 1H), 7.57 (d, J = 2.2 Hz, 1H), 5.19 (m, 2H), 4.87 (s, 2H), 4.20 (t, J = 5.3 Hz, 2H), 3.84 (s, 3H), 3.67 (t, J = 5.3 Hz, 2H), 3.36 (t, J = 6.5 Hz, 2H), 2.69 (s, 3H), 1.46 (dd, J = 13.9, 6.7 Hz, 2H), 0.79 (t, J = 7.4 Hz, 3H) |
| 334 | 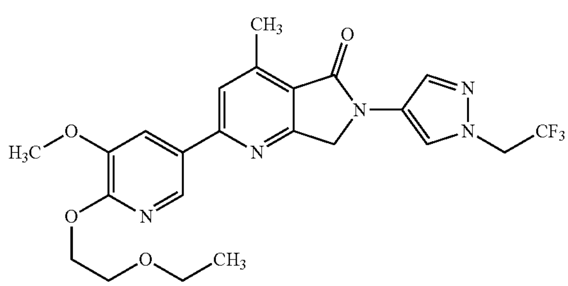 [SMILES: CCOCCOc1ncc(-c2cc(C)c3c(n2)CN(c2cnn(CC(F)(F)F)c2)C3=O)cc1OC] | 492.56 | (CDCl$_3$) δ 8.22 (s, 1H), 7.82 (d, J = 2.2 Hz, 1H), 7.68 (s, 1H), 7.35 (d, J = 2.2 Hz, 1H), 7.29 (s, 1H), 4.67 (s, 2H), 4.65 (m, 2H), 4.20 (m, 2H), 3.89 (s, 3H), 3.72 (m, 2H), 3.42 (q, J = 7.0 Hz, 2H), 2.71 (s, 3H), 1.08 (t, J = 7.0 Hz, 3H) |
| 335 | 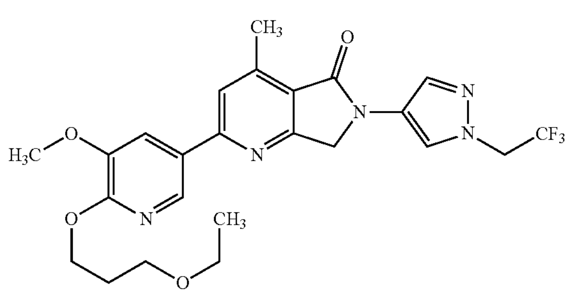 [SMILES: CCOCCCOc1ncc(-c2cc(C)c3c(n2)CN(c2cnn(CC(F)(F)F)c2)C3=O)cc1OC] | 505.91 | (CDCl$_3$) δ 8.32 (s, 1H), 7.91 (d, J = 2.2 Hz, 1H), 7.77 (s, 1H), 7.38 (s, 2H), 4.75 (m, 4H), 4.24 (m, 2H), 3.98 (s, 3H), 3.50 (m, 6H), 2.80 (s, 3H), 2.23-2.02 (m, 2H), 1.26 (t, J = 7.0 Hz, 3H) |

TABLE 1-continued

| Cmpd No. | Structure | ESMS (M + H) | ¹H NMR (300 MHz, unless indicated otherwise) |
|---|---|---|---|
| 336 | 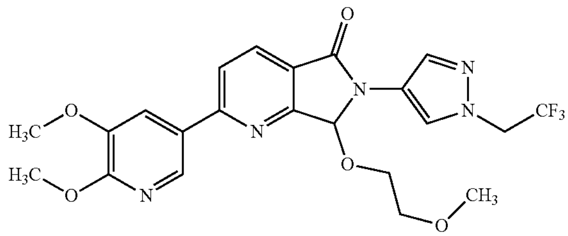 [SMILES: COCCOC1c2nc(-c3cnc(OC)c(OC)c3)ccc2C(=O)N1c1cnn(CC(F)(F)F)c1] | 494.39 | |
| 337 | 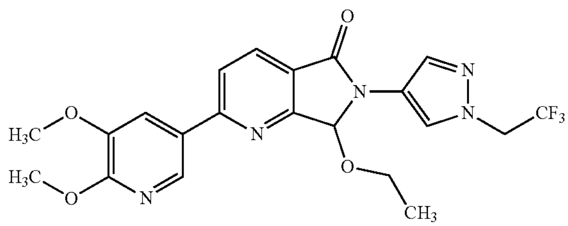 [SMILES: CCOC1c2nc(-c3cnc(OC)c(OC)c3)ccc2C(=O)N1c1cnn(CC(F)(F)F)c1] | 464.38 | |
| 338 | 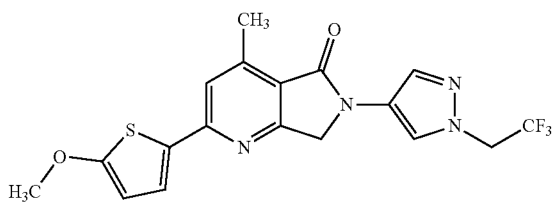 [SMILES: COc1ccc(-c2cc(C)c3c(n2)CN(c2cnn(CC(F)(F)F)c2)C3=O)s1] | 408.79 | (DMSO-$d_6$) δ = 8.32 (s, 1H), 7.90 (s, 1H), 7.76 (s, 1H), 7.67 (d, J = 4.2, 1H), 6.44 (d, J = 4.2, 1H), 5.18 (q, J = 9.2, 2H), 4.82 (s, 2H), 3.94 (s, 3H), 2.65 (s, 3H) |
| 339 | 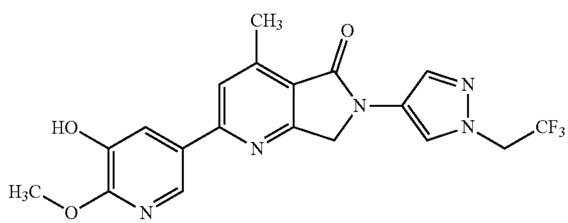 [SMILES: COc1ncc(-c2cc(C)c3c(n2)CN(c2cnn(CC(F)(F)F)c2)C3=O)cc1O] | 419.84 | (DMSO-$d_6$) δ 8.34 (s, 1H), 8.16 (s, 1H), 7.92 (d, J = 2.7 Hz, 1H), 7.74 (s, 1H), 7.64 (s, 1H), 5.18 (dd, J = 17.7, 8.8 Hz, 2H), 4.87 (s, 2H), 3.88 (s, 3H), 2.66 (s, 3H) |
| 340 | 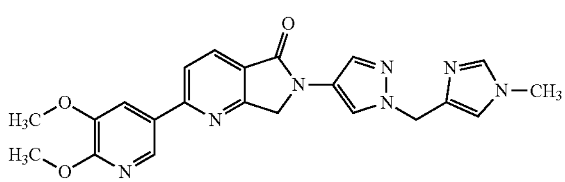 | 432.2 | (DMSO-$d_6$) δ 8.87 (s, 1H), 8.56 (d, J = 1.9 Hz, 1H), 8.39 (s, 1H), 8.20 (d, J = 1.8 Hz, 2H), 7.98 (d, J = 1.8 Hz, 1H), 7.86 (s, 1H), 7.65 (s, 1H), 5.46 (s, 2H), 4.97 (s, 2H), 3.96 (s, 3H), 3.92 (s, 3H), 3.82 (s, 3H) |
| 341 | 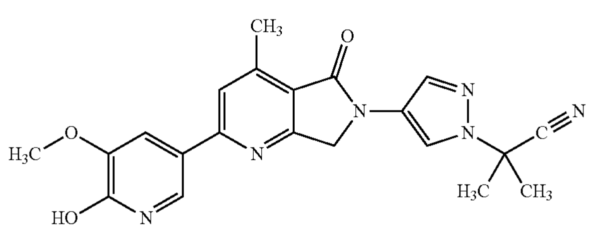 [SMILES: COc1cc(-c2cc(C)c3c(n2)CN(c2cnn(C(C)(C)C#N)c2)C3=O)cnc1O] | 405 | |
| 342 | 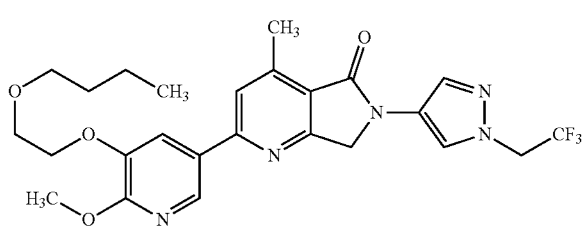 [SMILES: CCCCOCCOc1cc(-c2cc(C)c3c(n2)CN(c2cnn(CC(F)(F)F)c2)C3=O)cnc1OC] | 519.96 | |

TABLE 1-continued

| Cmpd No. | Structure | ESMS (M + H) | ¹H NMR (300 MHz, unless indicated otherwise) |
|---|---|---|---|
| 343 | 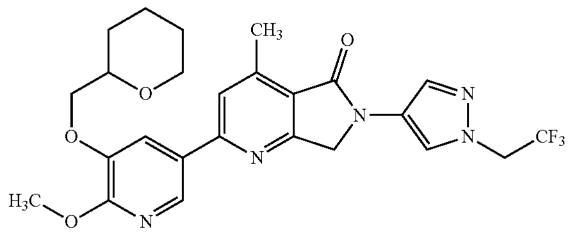 [SMILES: COc1ncc(-c2cc(C)c3c(n2)CN(c2cnn(CC(F)(F)F)c2)C3=O)cc1OCC1CCCCO1] | 517.92 | (CDCl$_3$) δ 8.41 (s, 1H), 8.33 (s, 1H), 7.90 (s, 1H), 7.84 (s, 1H), 7.61 (s, 1H), 4.87 (s, 2H), 4.80 (q, J = 8.3 Hz, 2H), 4.27-4.00 (m, 6H), 3.88 (s, 1H), 3.59 (d, J = 11.2 Hz, 1H), 2.85 (s, 3H), 2.01 (d, J = 35.6 Hz, 1H), 1.86-1.39 (m, 5H) |
| 344 | 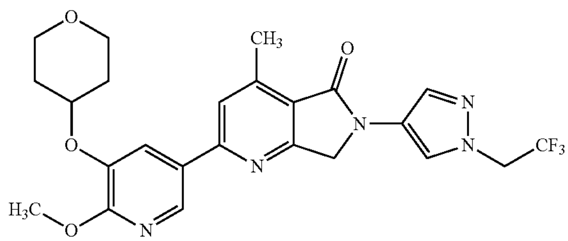 [SMILES: COc1ncc(-c2cc(C)c3c(n2)CN(c2cnn(CC(F)(F)F)c2)C3=O)cc1OC1CCOCC1] | 503.93 | (CDCl$_3$) δ 8.42 (d, J = 2.0 Hz, 1H), 8.33 (s, 1H), 7.90 (d, J = 1.9 Hz, 1H), 7.84 (s, 1H), 7.63 (s, 1H), 4.90 (s, 2H), 4.80 (q, J = 8.3 Hz, 2H), 4.72-4.61 (m, 1H), 4.20-3.98 (m, 5H), 3.68 (ddd, J = 11.6, 8.3, 3.1 Hz, 2H), 2.87 (s, 3H), 2.12 (dd, J = 9.6, 5.5 Hz, 2H), 2.02-1.70 (m, 2H) |
| 345 | 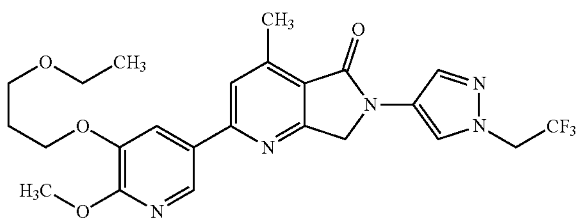 [SMILES: CCOCCCOc1cc(-c2cc(C)c3c(n2)CN(c2cnn(CC(F)(F)F)c2)C3=O)cnc1OC] | 505.91 | (CDCl$_3$) δ 8.39 (d, J = 1.9 Hz, 1H), 8.33 (s, 1H), 7.90 (d, J = 1.9 Hz, 1H), 7.82 (s, 1H), 7.61 (s, 1H), 4.86 (s, 2H), 4.77 (t, J = 8.3 Hz, 2H), 4.29 (t, J = 6.4 Hz, 2H), 4.13 (s, 3H), 3.69 (t, J = 6.1 Hz, 2H), 3.56 (q, J = 7.0 Hz, 2H), 2.85 (s, 3H), 2.19 (p, J = 6.3 Hz, 2H), 1.35-1.15 (m, 3H) |
| 346 | 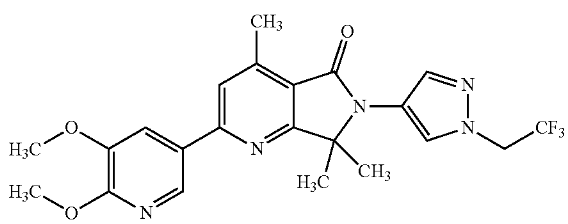 [SMILES: COc1cc(-c2cc(C)c3c(n2)C(C)(C)N(c2cnn(CC(F)(F)F)c2)C3=O)cnc1OC] | 461.85 | |
| 347 | 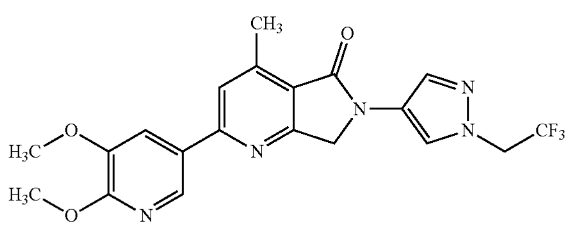 [SMILES: COc1cc(-c2cc(C)c3c(n2)CN(c2cnn(CC(F)(F)F)c2)C3=O)cnc1OC] | 433.82 | |
| 348 | 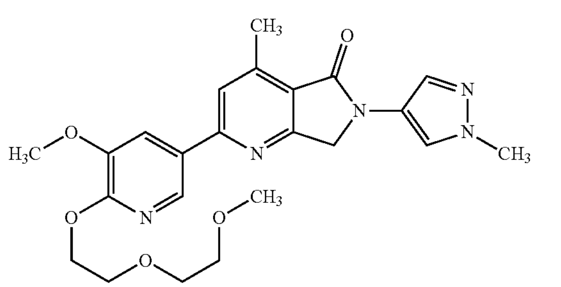 | 453.93 | (DMSO-d$_6$) δ 8.52 (d, J = 2.0 Hz, 1H), 8.07-7.89 (m, 2H), 7.70 (d, J = 2.2 Hz, 1H), 6.76 (d, J = 2.3 Hz, 1H), 4.90 (s, 2H), 4.54-4.38 (m, 2H), 3.92 (s, 3H), 3.83 (s, 3H), 3.81-3.73 (m, 2H), 3.60 (dd, J = 5.7, 3.7 Hz, 2H), 3.46 (dd, J = 5.7, 3.7 Hz, 2H), 3.30 (s, 3H), 2.71 (s, 3H) |

TABLE 1-continued

| Cmpd No. | Structure | ESMS (M + H) | ¹H NMR (300 MHz, unless indicated otherwise) |
|---|---|---|---|
| 349 | 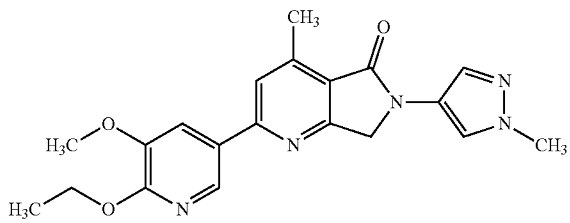 [SMILES: CCOc1ncc(-c2cc(C)c3c(n2)CN(c2cnn(C)c2)C3=O)cc1OC] | 379.87 | |
| 350 | 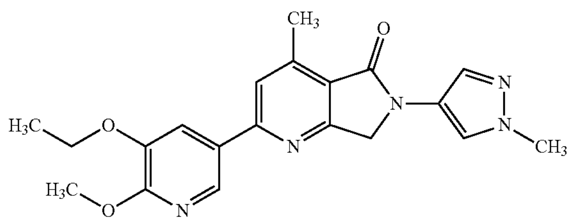 [SMILES: CCOc1cc(-c2cc(C)c3c(n2)CN(c2cnn(C)c2)C3=O)cnc1OC] | 379.87 | (DMSO-d$_6$) δ 8.52 (d, J = 1.9 Hz, 1H), 8.07-7.86 (m, 2H), 7.70 (d, J = 2.2 Hz, 1H), 6.76 (d, J = 2.3 Hz, 1H), 4.90 (s, 2H), 4.18 (q, J = 6.9 Hz, 2H), 3.95 (s, 2H), 3.83 (s, 2H), 2.71 (s, 3H), 1.40 (t, J = 7.0 Hz, 3H) |
| 351 | 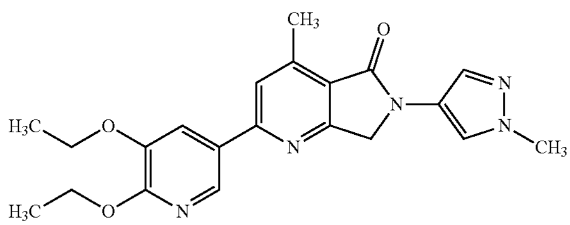 [SMILES: CCOc1cc(-c2cc(C)c3c(n2)CN(c2cnn(C)c2)C3=O)cnc1OCC] | 393.92 | (DMSO-d$_6$) δ 8.50 (d, J = 1.9 Hz, 1H), 8.07-7.82 (m, 2H), 7.70 (d, J = 2.2 Hz, 1H), 6.75 (d, J = 2.2 Hz, 1H), 4.88 (s, 2H), 4.42 (q, J = 7.0 Hz, 2H), 4.17 (q, J = 6.9 Hz, 2H), 3.83 (s, 3H), 2.70 (s, 2H), 1.38 (dt, J = 10.6, 7.0 Hz, 6H) |
| 352 | 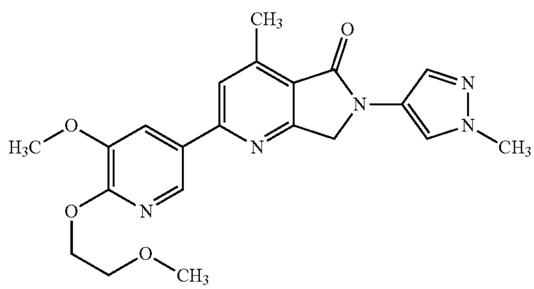 | 409.88 | |
| 353 | 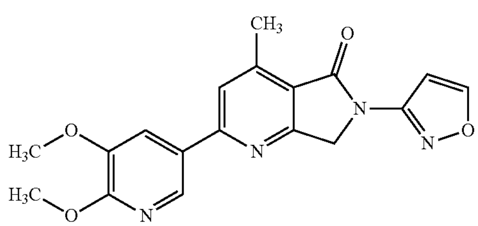 [SMILES: COc1cc(-c2cc(C)c3c(n2)CN(c2ccon2)C3=O)cnc1OC] | 353.37 | (CDCl$_3$) δ 8.30 (dd, J = 2.7, 2.0 Hz, 2H), 7.82 (d, J = 1.9 Hz, 1H), 7.51 (s, 1H), 7.27 (d, J = 1.8 Hz, 1H), 4.91 (s, 2H), 4.02 (s, 3H), 3.95 (s, 3H), 2.73 (s, 3H) |
| 354 | 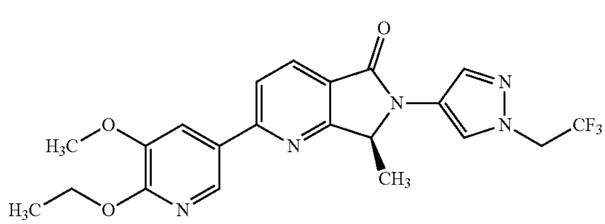 [SMILES: CCOc1ncc(-c2ccc3c(n2)[C@H](C)N(c2cnn(CC(F)(F)F)c2)C3=O)cc1OC] | 448.45 | |

TABLE 1-continued

| Cmpd No. | Structure | ESMS (M + H) | ¹H NMR (300 MHz, unless indicated otherwise) |
|---|---|---|---|
| 355 | 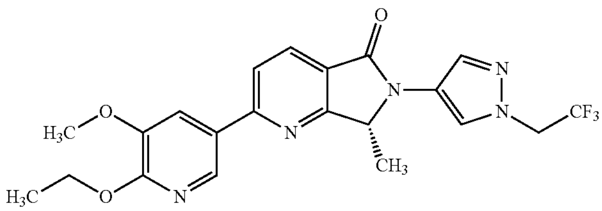 [SMILES: CCOc1ncc(-c2ccc3c(n2)[C@@H](C)N(c2cnn(CC(F)(F)F)c2)C3=O)cc1OC] | 448.45 | |
| 356 | 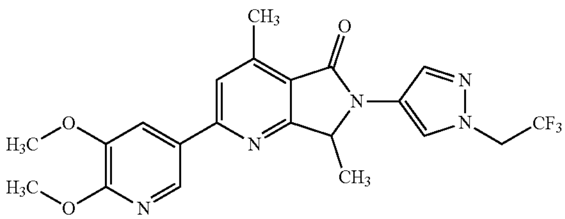 [SMILES: COc1cc(-c2cc(C)c3c(n2)C(C)N(c2cnn(CC(F)(F)F)c2)C3=O)cnc1OC] | 447.93 | (CDCl₃) δ 8.40 (d, J = 2.0 Hz, 1H), 8.28 (s, 1H), 7.90 (s, 1H), 7.74 (s, 1H), 7.58 (s, 1H), 4.97 (d, J = 6.7 Hz, 1H), 4.78-4.68 (m, 2H), 4.11 (d, J = 3.7 Hz, 2H), 4.03 (s, 3H), 2.82 (s, 3H), 1.73 (d, J = 6.7 Hz, 3H) |
| 357 | 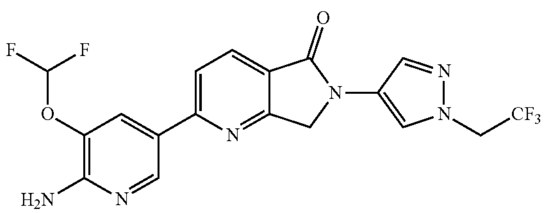 [SMILES: Nc1ncc(-c2ccc3c(n2)CN(c2cnn(CC(F)(F)F)c2)C3=O)cc1OC(F)F] | 440.78 | (DMSO-d₆) δ 8.70 (d, J = 1.9 Hz, 1H), 8.40 (s, 1H), 8.28 (s, 1H), 8.16 (dd, J = 28.2, 8.2 Hz, 2H), 7.94 (s, 1H), 7.39 (dd, J = 98.5, 47.3 Hz, 1H), 5.21 (q, J = 9.1 Hz, 2H), 4.99 (s, 2H) |
| 358 | 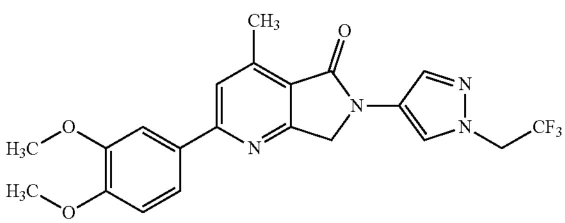 [SMILES: COc1ccc(-c2cc(C)c3c(n2)CN(c2cnn(CC(F)(F)F)c2)C3=O)cc1OC] | 432.86 | (CDCl₃) δ 8.32 (s, 1H), 7.78 (s, 1H), 7.72 (d, J = 2.0 Hz, 1H), 7.63 (dd, J = 8.4, 2.1 Hz, 1H), 7.58 (s, 1H), 7.00 (d, J = 8.4 Hz, 1H), 4.80 (s, 2H), 4.75 (m, 2H), 4.04 (s, 3H), 3.98 (s, 3H), 2.82 (s, 3H) |
| 359 | 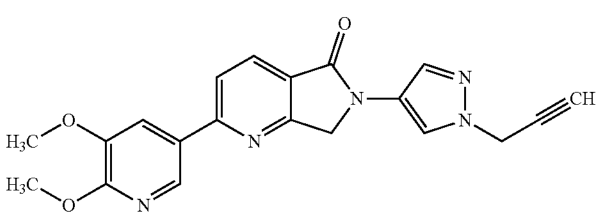 [SMILES: C#CCn1cc(N2Cc3nc(-c4cnc(OC)c(OC)c4)ccc3C2=O)cn1] | 375.92 | (DMSO-d₆) δ 8.55 (d, J = 1.9 Hz, 1H), 8.29 (s, 1H), 8.24-8.13 (m, 2H), 7.97 (t, J = 5.3 Hz, 1H), 7.86 (s, 1H), 5.09 (d, J = 2.5 Hz, 2H), 4.98 (s, 2H), 3.94 (d, J = 11.4 Hz, 6H), 3.51 (t, J = 2.5 Hz, 1H) |
| 360 | 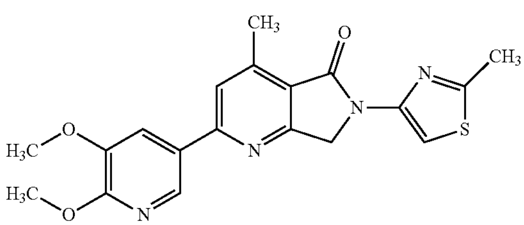 | 383.12 | (DMSO-d₆) δ 8.55 (d, J = 1.9 Hz, 1H), 8.01 (s, 1H), 7.97 (d, J = 1.9 Hz, 1H), 7.72 (s, 1H), 5.07 (s, 2H), 3.95 (s, 3H), 3.92 (s, 3H), 2.73 (s, 3H), 2.70 (s, 3H) |
| 361 | 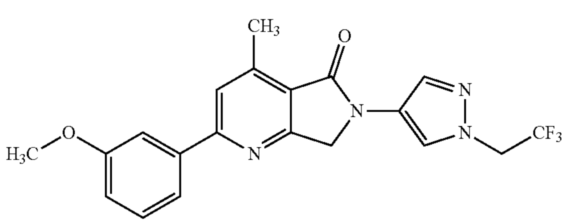 [SMILES: COc1cccc(-c2cc(C)c3c(n2)CN(c2cnn(CC(F)(F)F)c2)C3=O)c1] | 402.85 | (CDCl₃) δ 8.32 (s, 1H), 7.79 (s, 1H), 7.64 (m, 3H), 7.44 (t, J = 7.9 Hz, 1H), 7.04 (dd, J = 7.8, 2.2 Hz, 1H), 4.81 (s, 2H), 4.75 (q, J = 8.4 Hz, 2H), 3.94 (s, 3H), 2.83 (s, 3H) |

| Cmpd No. | Structure | ESMS (M + H) | ¹H NMR (300 MHz, unless indicated otherwise) |
|---|---|---|---|
| 362 | 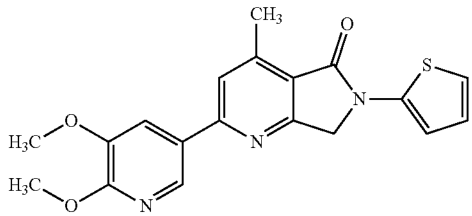 [SMILES: COc1cc(-c2cc(C)c3c(n2)CN(c2cccs2)C3=O)cnc1OC] | 368.15 | (DMSO-d₆) δ 8.56 (d, J = 2.0 Hz, 1H), 8.03 (s, 1H), 7.98 (d, J = 1.9 Hz, 1H), 7.15 (dd, J = 5.4, 1.4 Hz, 1H), 6.99 (dd, J = 5.4, 3.8 Hz, 1H), 6.92 (dd, J = 3.8, 1.4 Hz, 1H), 5.07 (s, 2H), 3.96 (s, 3H), 3.92 (s, 3H), 2.73 (s, 3H) |
| 363 | 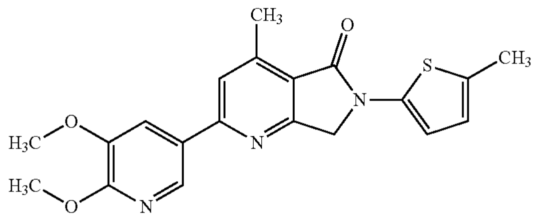 | 382.16 | (DMSO-d₆) δ 8.55 (d, J = 2.0 Hz, 1H), 8.01 (s, 1H), 7.97 (d, J = 1.9 Hz, 1H), 6.74-6.60 (m, 2H), 5.01 (s, 2H), 3.95 (s, 3H), 3.91 (s, 3H), 2.71 (s, 3H), 2.41 (d, J = 0.9 Hz, 3H) |
| 364 | 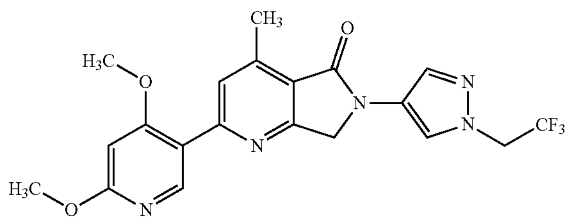 [SMILES: COc1cc(OC)c(-c2cc(C)c3c(n2)CN(c2cnn(CC(F)(F)F)c2)C3=O)cn1] | 448 | (CDCl₃) δ 8.68 (s, 1H), 8.29 (s, 1H), 7.83 (s, 1H), 7.71 (s, 1H), 6.39 (s, 1H), 4.91-4.65 (m, 4H), 4.24 (q, J = 7.0 Hz, 2H), 4.09 (s, 3H), 2.82 (s, 3H), 1.51 (t, J = 7.0 Hz, 3H) |
| 365 | 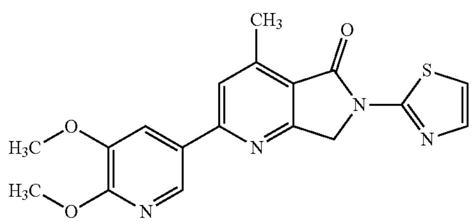 [SMILES: COc1cc(-c2cc(C)c3c(n2)CN(c2nccs2)C3=O)cnc1OC] | 368.88 | (CDCl₃) δ 8.41 (d, J = 1.9 Hz, 1H), 7.95 (d, J = 1.9 Hz, 1H), 7.64 (s, 1H), 7.60 (d, J = 3.6 Hz, 1H), 7.12 (d, J = 3.6 Hz, 1H), 5.24 (s, 2H), 4.14 (s, 3H), 4.06 (d, J = 2.7 Hz, 3H), 2.85 (d, J = 5.3 Hz, 3H) |
| 366 | 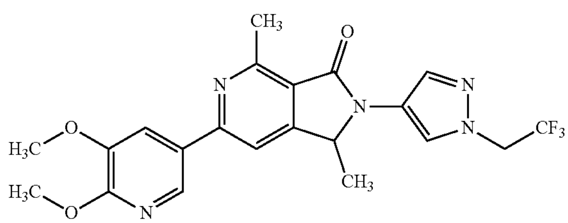 [SMILES: COc1cc(-c2cc3c(c(C)n2)C(=O)N(c2cnn(CC(F)(F)F)c2)C3C)cnc1OC] | 448.04 | (DMSO-d₆) δ 8.57 (d, J = 2.0 Hz, 2H), 8.36 (s, 2H), 8.22 (s, 2H), 8.00 (s, 2H), 7.96 (s, 2H), 5.20 (dd, J = 11.6, 6.6 Hz, 7H), 3.94 (d, J = 9.5 Hz, 10H), 2.87 (s, 5H), 1.56 (d, J = 6.6 Hz, 6H) |
| 367 | 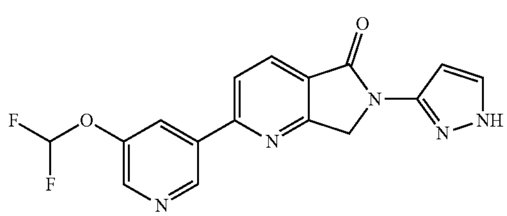 [SMILES: O=C1c2ccc(-c3cncc(OC(F)F)c3)nc2CN1c1cc[nH]n1] | 344.08 | |
| 368 | 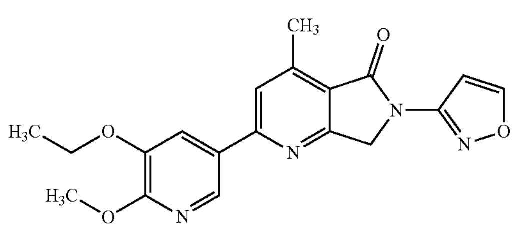 [SMILES: CCOc1cc(-c2cc(C)c3c(n2)CN(c2ccon2)C3=O)cnc1OC] | 366.91 | (CDCl₃) δ 8.39 (dd, J = 5.4, 1.9 Hz, 2H), 7.91 (d, J = 2.0 Hz, 1H), 7.60 (s, 1H), 7.37 (d, J = 1.8 Hz, 1H), 5.00 (s, 2H), 4.28 (q, J = 7.0 Hz, 2H), 4.12 (s, 3H), 2.82 (s, 3H), 1.57 (t, J = 7.0 Hz, 3H) |

TABLE 1-continued

| Cmpd No. | Structure | ESMS (M + H) | ¹H NMR (300 MHz, unless indicated otherwise) |
|---|---|---|---|
| 369 | 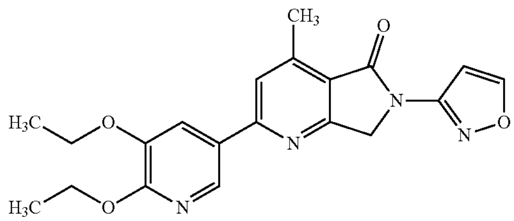 [SMILES: CCOc1cc(-c2cc(C)c3c(n2)CN(c2ccon2)C3=O)cnc1OCC] | 380.89 | (CDCl₃) δ 8.40 (dd, J = 5.7, 1.9 Hz, 2H), 7.91 (d, J = 1.9 Hz, 1H), 7.61 (s, 1H), 7.37 (d, J = 1.7 Hz, 1H), 5.01 (s, 2H), 4.57 (q, J = 7.1 Hz, 2H), 4.27 (q, J = 7.0 Hz, 2H), 2.83 (s, 3H), 1.54 (dt, J = 13.9, 7.0 Hz, 6H) |
| 370 | 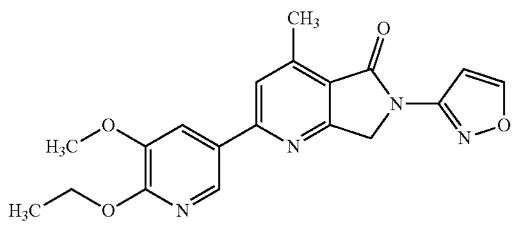 [SMILES: CCOc1ncc(-c2cc(C)c3c(n2)CN(c2ccon2)C3=O)cc1OC] | 366.91 | (CDCl₃) δ 8.40 (dd, J = 5.7, 1.9 Hz, 2H), 7.92 (d, J = 2.0 Hz, 1H), 7.62 (s, 1H), 7.37 (d, J = 1.8 Hz, 1H), 5.02 (s, 2H), 4.58 (q, J = 7.1 Hz, 2H), 4.04 (s, 3H), 2.83 (s, 3H), 1.52 (t, J = 7.1 Hz, 3H) |
| 371 | 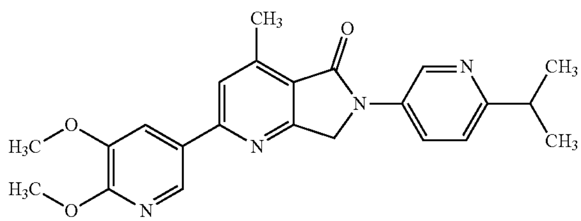 [SMILES: COc1cc(-c2cc(C)c3c(n2)CN(c2ccc(C(C)C)nc2)C3=O)cnc1OC] | 404.96 | (DMSO-d₆) δ 8.98 (s, 1H), 8.54 (s, 1H), 8.28 (d, J = 7.3 Hz, 1H), 7.98 (d, J = 13.0 Hz, 2H), 7.35 (d, J = 8.3 Hz, 1H), 5.07 (s, 2H), 3.93 (d, J = 10.1 Hz, 6H), 3.30 (s, 2H), 3.13-2.92 (m, 1H), 2.72 (s, 3H), 1.21 (t, J = 22.6 Hz, 6H) |
| 372 | 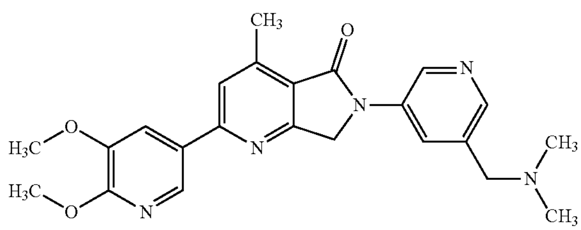 | 406.48 | |
| 373 | 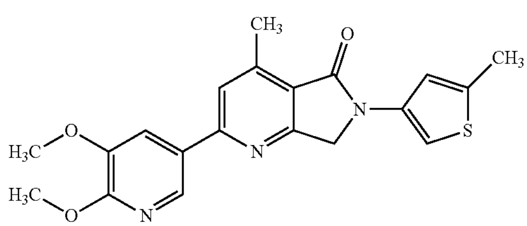 | 382.04 | (CDCl₃) δ 8.26 (d, J = 1.8 Hz, 1H), 7.74 (d, J = 1.9 Hz, 1H), 7.50 (s, 1H), 7.26 (d, J = 1.1 Hz, 1H), 7.14 (d, J = 1.6 Hz, 1H), 4.81 (s, 2H), 4.04 (s, 3H), 3.93 (s, 3H), 2.76 (s, 3H), 2.45 (d, J = 0.9 Hz, 3H) |
| 374 | 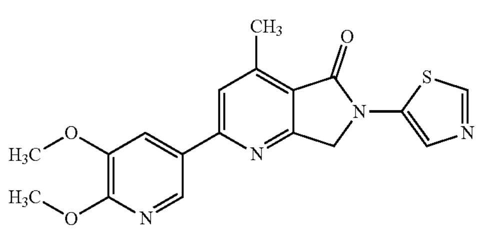 [SMILES: COc1cc(-c2cc(C)c3c(n2)CN(c2cncs2)C3=O)cnc1OC] | 369.11 | (CDCl₃) δ 8.50 (s, 1H), 8.31 (d, J = 1.8 Hz, 1H), 7.80 (d, J = 1.6 Hz, 1H), 7.70 (s, 1H), 7.55 (s, 1H), 4.87 (s, 2H), 4.03 (s, 3H), 3.94 (s, 3H), 2.74 (s, 3H) |

TABLE 1-continued

| Cmpd No. | Structure | ESMS (M + H) | ¹H NMR (300 MHz, unless indicated otherwise) |
|---|---|---|---|
| 375 | 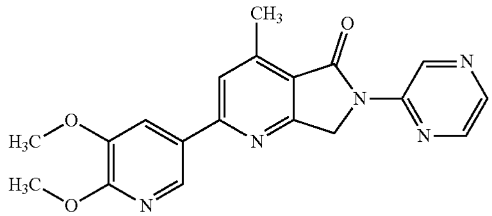 [SMILES: COc1cc(-c2cc(C)c3c(n2)CN(c2cnccn2)C3=O)cnc1OC] | 364.12 | (CDCl₃) δ 9.97 (s, 1H), 8.41 (m, 3H), 7.92 (d, J = 1.9 Hz, 1H), 7.62 (s, 1H), 5.12 (s, 2H), 4.13 (s, 3H), 4.05 (s, 3H), 2.86 (s, 3H) |
| 376 | 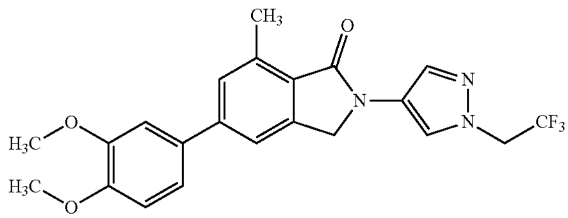 [SMILES: COc1ccc(-c2cc(C)c3c(c2)CN(c2cnn(CC(F)(F)F)c2)C3=O)cc1OC] | 432.14 | (DMSO-d₆) δ 8.35 (s, 1H), 7.91 (s, 1H), 7.70 (s, 1H), 7.57 (s, 1H), 7.38-7.23 (m, 2H), 7.07 (d, J = 9.0 Hz, 1H), 5.18 (q, J = 9.1 Hz, 2H), 4.84 (s, 2H), 3.84 (d, J = 17.5 Hz, 6H), 2.71 (s, 3H) |
| 377 | 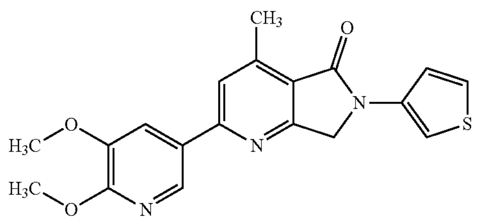 [SMILES: COc1cc(-c2cc(C)c3c(n2)CN(c2ccsc2)C3=O)cnc1OC] | 368.5 | (CDCl₃) δ 8.27 (d, J = 1.9 Hz, 1H), 7.76 (d, J = 1.8 Hz, 1H), 7.58-7.45 (m, 3H), 7.31 (dd, J = 5.2, 3.3 Hz, 1H), 4.85 (s, 2H), 4.04 (s, 3H), 3.94 (s, 3H), 2.76 (s, 3H) |
| 378 | 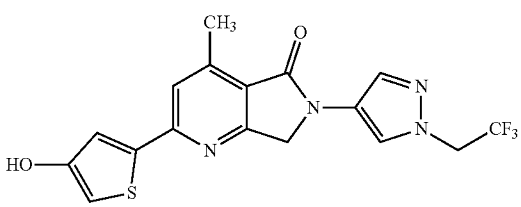 [SMILES: Cc1cc(-c2cc(O)cs2)nc2c1C(=O)N(c1cnn(CC(F)(F)F)c1)C2] | 394.81 | (DMSO-d₆) δ 8.34 (s, 1H), 7.91 (s, 1H), 7.78 (s, 1H), 7.47 (d, J = 1.6 Hz, 1H), 6.51 (d, J = 1.6 Hz, 1H), 5.19 (q, J = 9.1, 2H), 4.86 (s, 2H), 2.67 (s, 3H) |
| 379 | 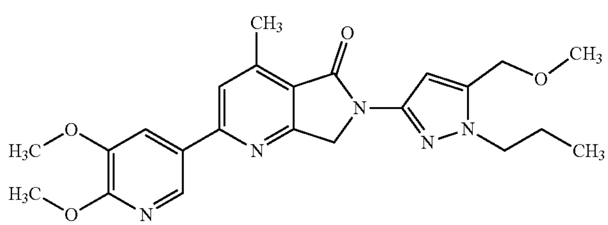 [SMILES: CCCn1nc(N2Cc3nc(-c4cnc(OC)c(OC)c4)cc(C)c3C2=O)cc1COC] | 423.86 | (CDCl₃) δ 8.39 (d, J = 1.9 Hz, 1H), 8.19 (d, J = 8.1 Hz, 1H), 7.91 (d, J = 1.9 Hz, 1H), 7.82 (d, J = 7.9 Hz, 1H), 6.97 (s, 1H), 5.02 (s, 2H), 4.48 (s, 2H), 4.11 (s, 3H), 4.02 (s, 3H), 3.36 (s, 3H), 2.63 (s, 2H), 1.90 (dd, J = 14.7, 7.3 Hz, 2H), 1.26 (s, 2H), 0.96 (t, J = 7.4 Hz, 3H) |
| 380 | 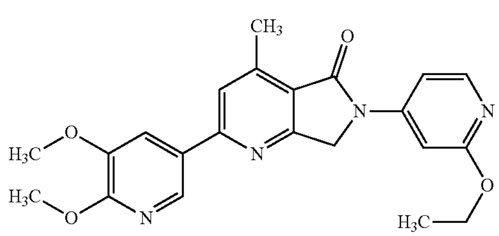 [SMILES: CCOc1cc(N2Cc3nc(-c4cnc(OC)c(OC)c4)cc(C)c3C2=O)ccn1] | 406.97 | (DMSO-d₆) δ 8.56 (d, J = 1.9 Hz, 1H), 8.13 (d, J = 5.9 Hz, 1H), 8.03 (s, 1H), 7.97 (d, J = 1.9 Hz, 1H), 7.61 (dd, J = 5.9, 1.9 Hz, 1H), 7.28 (d, J = 1.8 Hz, 1H), 5.04 (s, 2H), 4.33 (q, J = 7.0 Hz, 2H), 3.94 (d, J = 11.2 Hz, 4H), 2.73 (s, 2H), 1.33 (t, J = 7.0 Hz, 2H) |
| 381 | 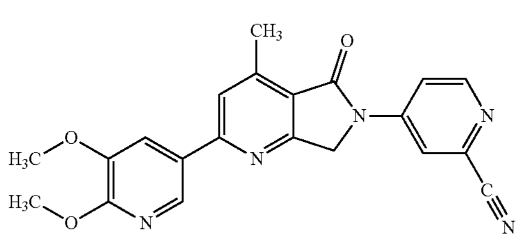 [SMILES: COc1cc(-c2cc(C)c3c(n2)CN(c2ccnc(C#N)c2)C3=O)cnc1OC] | 388.14 | |

TABLE 1-continued

| Cmpd No. | Structure | ESMS (M + H) | ¹H NMR (300 MHz, unless indicated otherwise) |
|---|---|---|---|
| 382 | 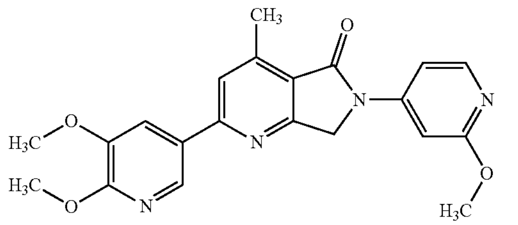 [SMILES: COc1cc(N2Cc3nc(-c4cnc(OC)c(OC)c4)cc(C)c3C2=O)ccn1] | 393.46 | (DMSO-d$_6$) δ 8.94-8.85 (m, 1H), 8.57 (d, J = 2.0 Hz, 1H), 8.36 (s, 1H), 8.31 (d, J = 2.1 Hz, 0H), 8.05 (s, 1H), 7.98 (d, J = 2.0 Hz, 1H), 5.24 (s, 1H), 5.13 (s, 2H), 4.00-3.92 (m, 5H), 2.74 (s, 3H) |
| 383 | 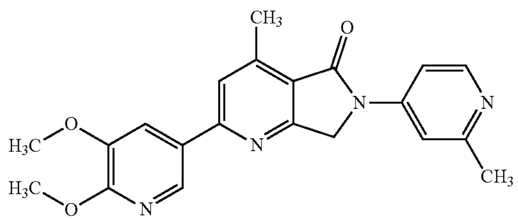 | 377.19 | (DMSO-d$_6$) δ 8.97 (d, J = 2.4 Hz, 1H), 8.60-8.48 (m, 1H), 8.25 (s, 1H), 8.20 (d, J = 1.8 Hz, 1H), 8.03 (s, 1H), 7.98 (d, J = 1.9 Hz, 1H), 5.09 (s, 2H), 3.94 (d, J = 10.8 Hz, 6H), 2.74 (s, 3H), 2.36 (s, 2H) |
| 384 | 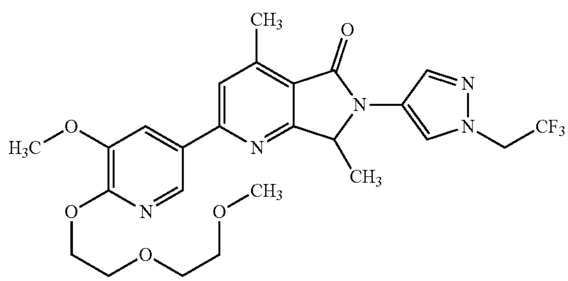 [SMILES: COCCOCCOc1ncc(-c2cc(C)c3c(n2)C(C)N(c2cnn(CC(F)(F)F)c2)C3=O)cc1OC] | 535.93 | |
| 385 | 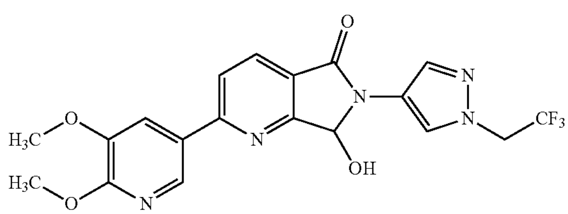 [SMILES: COc1cc(-c2ccc3c(n2)C(O)N(c2cnn(CC(F)(F)F)c2)C3=O)cnc1OC] | 436.42 | |
| 386 | 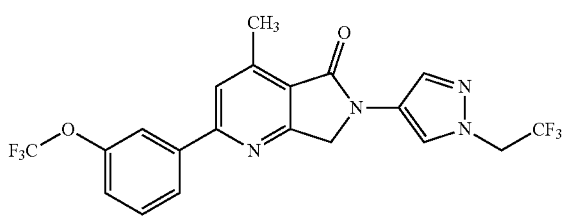 [SMILES: Cc1cc(-c2cccc(OC(F)(F)F)c2)nc2c1C(=O)N(c1cnn(CC(F)(F)F)c1)C2] | 456.87 | (CDCl$_3$) δ 8.32 (s, 1H), 8.00 (d, J = 7.7 Hz, 2H), 7.80 (s, 1H), 7.63 (s, 1H), 7.56 (t, J = 8.0 Hz, 1H), 7.35 (d, J = 8.3 Hz, 1H), 4.88-4.66 (m, 4H), 2.85 (s, 3H) |
| 387 | 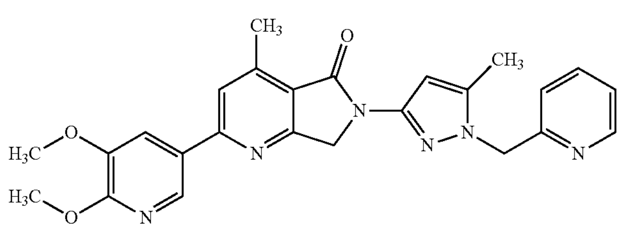 [SMILES: COc1cc(-c2cc(C)c3c(n2)CN(c2cc(C)n(Cc4ccccn4)n2)C3=O)cnc1OC] | 457.47 | (CDCl$_3$) δ 8.60 (d, J = 4.1 Hz, 1H), 8.38 (d, J = 1.9 Hz, 1H), 7.88 (d, J = 1.9 Hz, 1H), 7.65 (td, J = 7.8, 1.7 Hz, 1H), 7.56 (s, 1H), 7.23 (dd, J = 6.6, 4.9 Hz, 1H), 6.88 (t, J = 3.9 Hz, 2H), 5.41 (s, 2H), 4.97 (s, 2H), 4.12 (s, 3H), 4.03 (s, 3H), 2.83 (s, 3H), 2.29 (s, 3H) |

TABLE 1-continued

| Cmpd No. | Structure | ESMS (M + H) | ¹H NMR (300 MHz, unless indicated otherwise) |
|---|---|---|---|
| 388 | 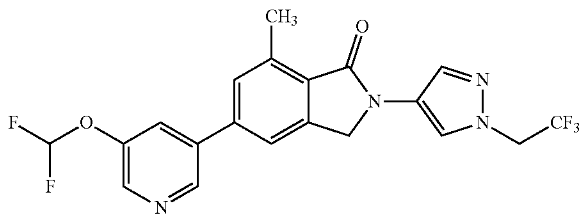 [SMILES: Cc1cc(-c2cncc(OC(F)F)c2)cc2c1C(=O)N(c1cnn(CC(F)(F)F)c1)C2] | 439.11 | (DMSO-d₆) δ 8.92 (d, J = 1.8 Hz, 1H), 8.92 (d, J = 1.8 Hz, 1H), 8.58 (d, J = 2.5 Hz, 1H), 8.38(s, 1H), 8.11 (t, J = 2.1 Hz, 1H), 7.94 (s, 1H), 7.88 (s, 1H), 7.74 (d, J = 4.4 Hz, 1H), 7.49 (s, 1H), 5.20 (q, J = 9.2 Hz, 2H), 4.89 (s, 2H), 2.74 (s, 3H) |
| 389 | 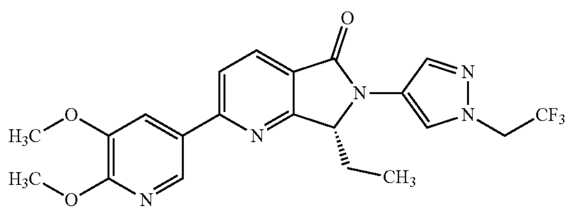 [SMILES: CC[C@@H]1c2nc(-c3cnc(OC)c(OC)c3)ccc2C(=O)N1c1cnn(CC(F)(F)F)c1] | 447.99 | |
| 390 | 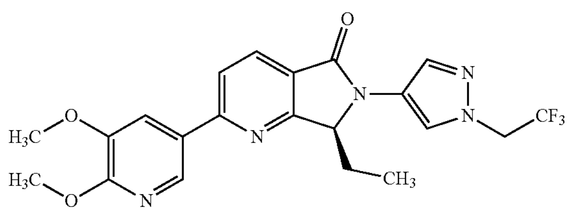 [SMILES: CC[C@H]1c2nc(-c3cnc(OC)c(OC)c3)ccc2C(=O)N1c1cnn(CC(F)(F)F)c1] | 447.99 | |
| 391 | 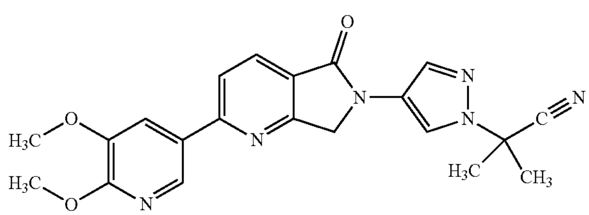 [SMILES: COc1cc(-c2ccc3c(n2)CN(c2cnn(C(C)(C)C#N)c2)C3=O)cnc1OC] | 405 | (DMSO-d₆) δ 8.56 (d, 1H, J = 2 Hz), 8.43 (s, 1H), 8.2 (s, 1H), 8.19 (s, 1H), 8.07 (s, 1H), 7.98 (d, 1H, J = 2 Hz), 4.99 (s, 2H), 3.95 (s, 3H), 3.92 (s, 3H), 1.99 (s, 6H) |
| 392 | 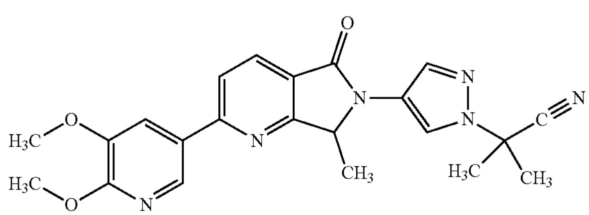 [SMILES: COc1cc(-c2ccc3c(n2)C(C)N(c2cnn(C(C)(C)C#N)c2)C3=O)cnc1OC] | 419 | (DMSO-d₆) δ 8.80(d, 1H, J = 2 Hz), 8.43 (s, 1H), 8.22 (s, 1H), 8.20 (s, 1H), 8.07 (s, 1H), 1.00 (d, 1H, J = 2 Hz), 5.23 (quart, 1H), 3.96(s, 3H), 3.93 (s, 3H), 2.03(s, 6H), 1.60 (d, 3H) |
| 393 | 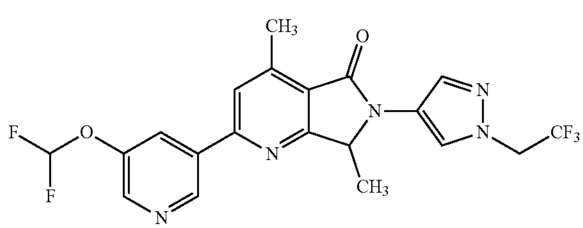 [SMILES: Cc1cc(-c2cncc(OC(F)F)c2)nc2c1C(=O)N(c1cnn(CC(F)(F)F)c1)C2C] | 453.93 | (DMSO-d₆) δ 9.29 (d, J = 1.7 Hz, 1H), 8.64 (d, J = 2.6 Hz, 1H), 8.40 (dd, J = 4.9, 2.7 Hz, 2H), 8.16 (s, 1H), 7.99 (d, J = 4.2 Hz, 1H), 7.48 (t, J = 73.2 Hz, 1H), 5.29-5.14 (m, 3H), 2.78 (d, J = 13.6 Hz, 3H), 1.59 (t, J = 7.6 Hz, 3H) |
| 394 | 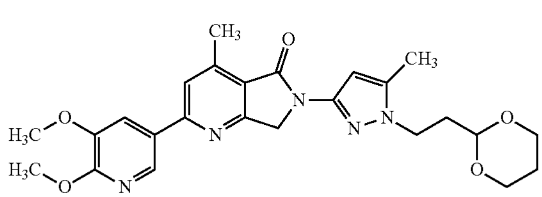 [SMILES: COc1cc(-c2cc(C)c3c(n2)CN(c2cc(C)n(CCC4OCCCO4)n2)C3=O)cnc1OC] | 480.51 | (CDCl₃) δ 8.37 (d, J = 1.9 Hz, 1H), 7.89 (d, J = 1.9 Hz, 1H), 7.56 (s, 1H), 6.75 (s, 1H), 4.96 (s, 1H), 4.47 (s, 1H), 4.13 (q, J = 3.8 Hz, 6H), 4.03 (d, J = 3.4 Hz, 3H), 3.85-3.65 (m, 3H), 2.83 (s, 3H), 2.68 (s, 1H), 2.36-2.27 (m, 3H), 2.14 (dt, J = 13.9, 7.1 Hz, 4H), 1.41 (dd, J = 19.7, 16.7 Hz, 3H) |

TABLE 1-continued

| Cmpd No. | Structure | ESMS (M + H) | ¹H NMR (300 MHz, unless indicated otherwise) |
|---|---|---|---|
| 395 | 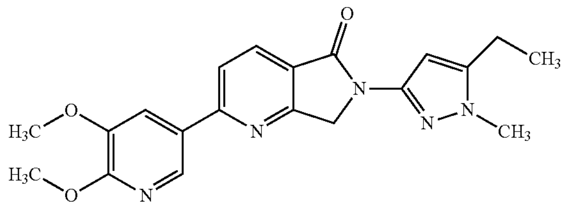 [SMILES: CCc1cc(N2Cc3nc(-c4cnc(OC)c(OC)c4)ccc3C2=O)nn1C] | 380.44 | (CDCl₃) δ 8.40 (d, J = 1.9 Hz, 1H), 8.22 (d, J = 8.1 Hz, 1H), 7.93 (d, J = 1.8 Hz, 1H), 7.84 (d, J = 8.0 Hz, 1H), 6.82 (s, 1H), 5.01 (s, 2H), 4.13 (s, 3H), 4.05 (s, 3H), 3.79 (s, 3H), 2.78-2.52 (m, 2H), 1.35 (t, J = 7.5 Hz, 3H) |
| 396 | 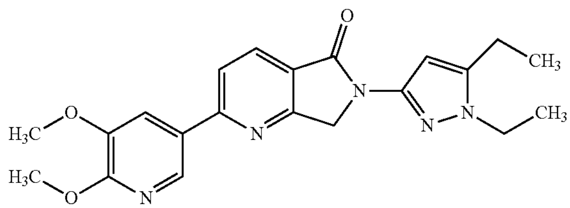 [SMILES: CCc1cc(N2Cc3nc(-c4cnc(OC)c(OC)c4)ccc3C2=O)nn1CC] | 394.45 | (CDCl₃) δ 8.41 (d, J = 2.0 Hz, 1H), 8.21 (d, J = 8.1 Hz, 1H), 7.93 (d, J = 1.9 Hz, 1H), 7.84 (d, J = 8.1 Hz, 1H), 6.80 (s, 1H), 5.03 (s, 2H), 4.12 (s, 3H), 4.08 (q, J = 7.2 Hz, 2H), 4.04 (s, 3H), 2.77-2.56 (m, 2H), 1.44 (t, J = 7.2 Hz, 3H), 1.35 (t, J = 7.5 Hz, 3H) |
| 397 | 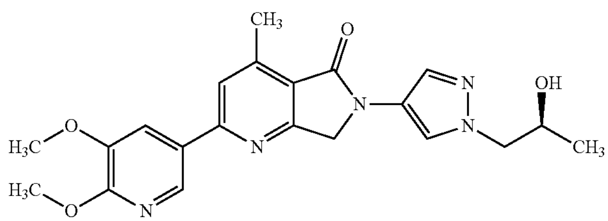 [SMILES: COc1cc(-c2cc(C)c3c(n2)CN(c2cnn(C[C@H](C)O)c2)C3=O)cnc1OC] | 410.45 | (CDCl₃) δ 8.37 (t, J = 2.6 Hz, 1H), 8.22 (s, 1H), 7.86 (d, J = 1.9 Hz, 1H), 7.72 (s, 1H), 7.58 (d, J = 4.3 Hz, 1H), 5.32 (s, 1H), 4.78 (s, 2H), 4.23 (dd, J = 18.2, 4.7 Hz, 2H), 4.12 (s, 3H), 4.11-4.04 (m, 1H), 4.03 (s, 3H), 2.82 (s, 3H), 1.28 (d, J = 6.3 Hz, 3H) |
| 398 | 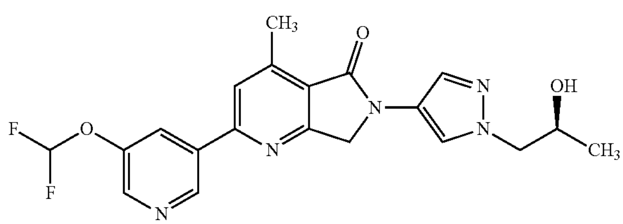 [SMILES: Cc1cc(-c2cncc(OC(F)F)c2)nc2c1C(=O)N(c1cnn(C[C@H](C)O)c1)C2] | 416.46 | |
| 399 | 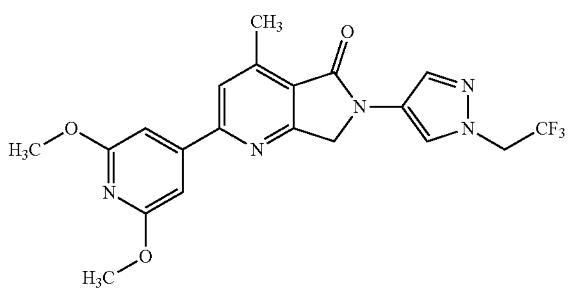 [SMILES: COc1cc(-c2cc(C)c3c(n2)CN(c2cnn(CC(F)(F)F)c2)C3=O)cc(OC)n1] | 433.38 | (DMSO-d₆) δ 8.39 (s, 1H), 8.08 (s, 1H), 7.95 (s, 1H), 7.13 (s, 3H), 5.28-5.14 (m, 2H), 4.94 (s, 2H), 3.93 (s, 3H), 2.73 (s, 6H) |
| 400 | 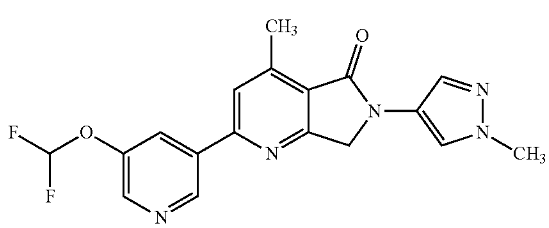 [SMILES: Cc1cc(-c2cncc(OC(F)F)c2)nc2c1C(=O)N(c1cnn(C)c1)C2] | 372.47 | (CDCl₃) δ 9.16 (d, J = 1.7 Hz, 1H), 8.60 (d, J = 2.5 Hz, 1H), 8.29 (s, 1H), 7.65 (s, 1H), 7.37 (d, J = 2.3 Hz, 1H), 6.98 (d, J = 2.3 Hz, 1H), 6.57 (d, J = 72.4 Hz, 1H), 5.00 (s, 2H), 3.91 (s, 3H), 2.87 (s, 3H) |

TABLE 1-continued

| Cmpd No. | Structure | ESMS (M + H) | ¹H NMR (300 MHz, unless indicated otherwise) |
|---|---|---|---|
| 401 | 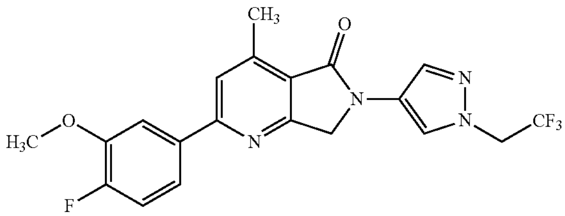 [SMILES: COc1cc(-c2cc(C)c3c(n2)CN(c2cnn(CC(F)(F)F)c2)C3=O)ccc1F] | 420.86 | (DMSO-d$_6$) δ 8.38 (s, 1H), 8.01 (s, 1H), 7.93 (m, 2H), 7.78 (m, 1H), 7.37 (dd, J = 11.2, 8.6 Hz, 1H), 5.30-5.08 (m, 2H), 4.93 (s, 2H), 3.97 (s, 3H), 2.73 (s, 3H) |
| 402 | 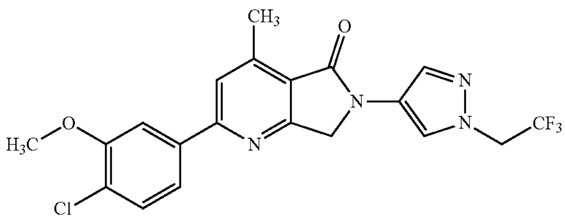 [SMILES: COc1cc(-c2cc(C)c3c(n2)CN(c2cnn(CC(F)(F)F)c2)C3=O)ccc1Cl] | 437.01 | (DMSO-d$_6$) δ 8.38 (s, 1H), 8.05 (s, 1H), 7.94 (s, 1H), 7.90 (d, J = 1.6 Hz, 1H), 7.83-7.75 (m, 1H), 7.59 (d, J = 8.3 Hz, 1H), 5.21 (q, J = 9.3 Hz, 2H), 4.94 (s, 2H), 3.99 (s, 3H), 2.73 (s, 3H) |
| 403 | 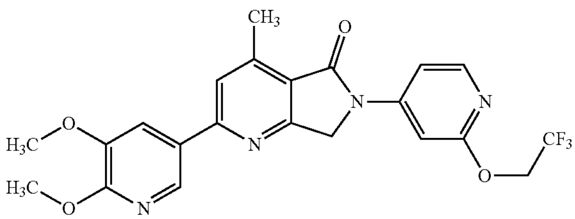 [SMILES: COc1cc(-c2cc(C)c3c(n2)CN(c2ccnc(OCC(F)(F)F)c2)C3=O)cnc1OC] | 461.44 | |
| 404 | 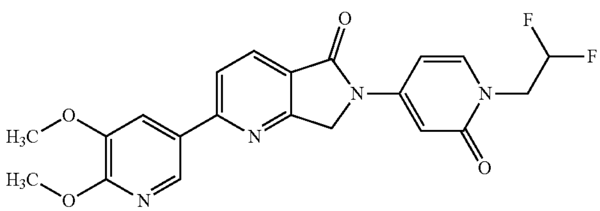 [SMILES: COc1cc(-c2ccc3c(n2)CN(c2ccn(CC(F)F)c(=O)c2)C3=O)cnc1OC] | 429.45 | |
| 405 | 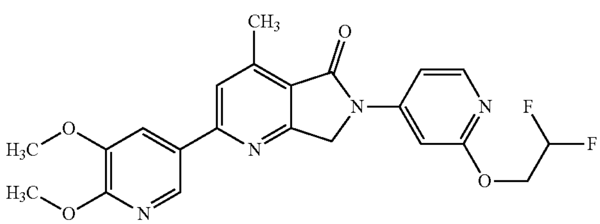 [SMILES: COc1cc(-c2cc(C)c3c(n2)CN(c2ccnc(OCC(F)F)c2)C3=O)cnc1OC] | 443.46 | |
| 406 | 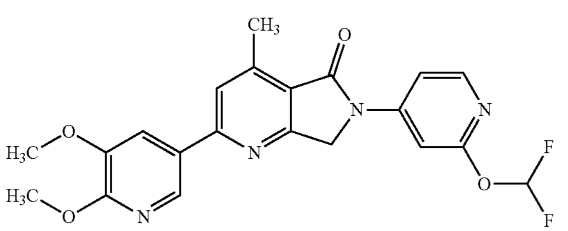 [SMILES: COc1cc(-c2cc(C)c3c(n2)CN(c2ccnc(OC(F)F)c2)C3=O)cnc1OC] | 429.38 | |
| 407 | 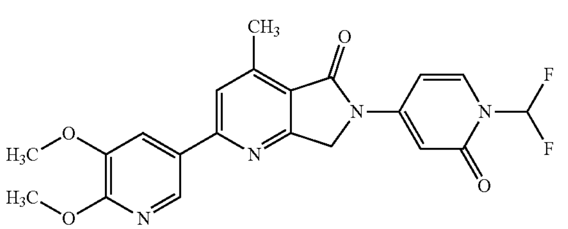 [SMILES: COc1cc(-c2cc(C)c3c(n2)CN(c2ccn(C(F)F)c(=O)c2)C3=O)cnc1OC] | 429.38 | |

TABLE 1-continued

| Cmpd No. | Structure | ESMS (M + H) | ¹H NMR (300 MHz, unless indicated otherwise) |
|---|---|---|---|
| 408 | 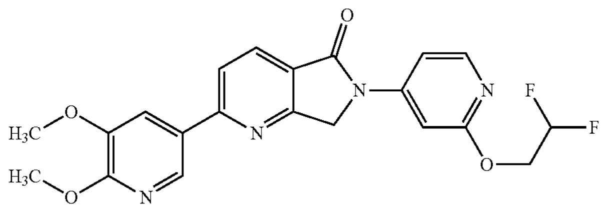 [SMILES: COc1cc(-c2ccc3c(n2)CN(c2ccnc(OCC(F)F)c2)C3=O)cnc1OC] | 429.38 | |
| 409 | 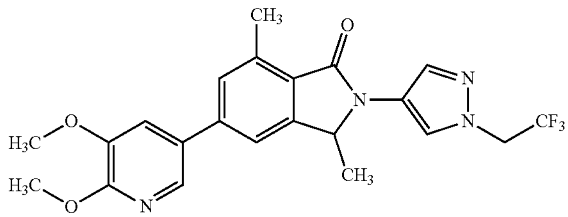 [SMILES: COc1cc(-c2cc(C)c3c(c2)C(C)N(c2cnn(CC(F)(F)F)c2)C3=O)cnc1OC] | 447.17 | |
| 410 | 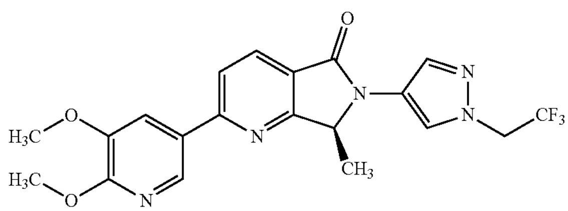 [SMILES: COc1cc(-c2ccc3c(n2)[C@H](C)N(c2cnn(CC(F)(F)F)c2)C3=O)cnc1OC] | 434.44 | |
| 411 | 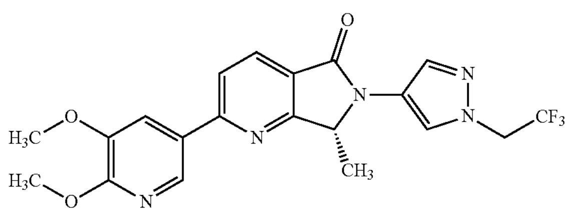 [SMILES: COc1cc(-c2ccc3c(n2)[C@@H](C)N(c2cnn(CC(F)(F)F)c2)C3=O)cnc1OC] | 434.44 | |
| 412 | 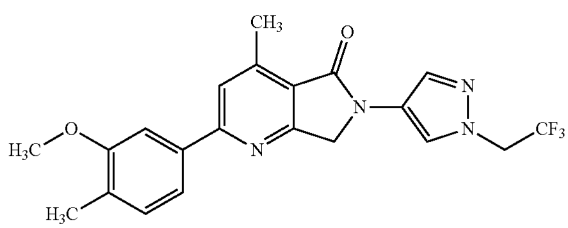 [SMILES: COc1cc(-c2cc(C)c3c(n2)CN(c2cnn(CC(F)(F)F)c2)C3=O)ccc1C] | 416.9 | (DMSO-d$_6$) δ 8.38 (s, 1H), 7.97 (s, 1H), 7.94 (s, 1H), 7.73 (s, 1H), 7.70 (d, J = 7.7 Hz, 1H), 7.29 (d, J = 7.8 Hz, 1H), 5.29- 5.12 (m, 2H), 4.93 (s, 2H), 3.91 (s, 3H), 2.72 (s, 3H), 2.22 (s, 3H) |
| 413 | 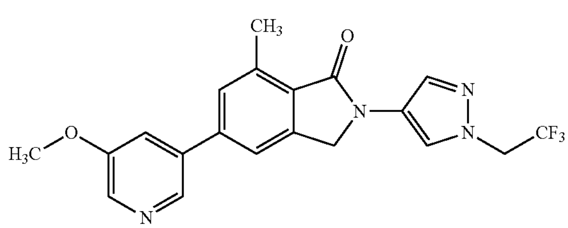 [SMILES: COc1cncc(-c2cc(C)c3c(c2)CN(c2cnn(CC(F)(F)F)c2)C3=O)c1] | 403.15 | |
| 414 | 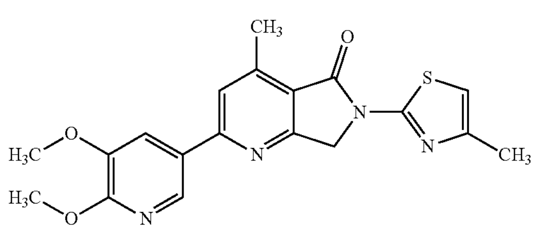 | 383.32 | (DMSO-d$_6$) δ 8.57 (d, J = 1.9 Hz, 1H), 8.06 (s, 1H), 7.97 (d, J = 1.9 Hz, 1H), 6.94 (d, J = 1.0 Hz, 1H), 5.12 (s, 2H), 3.95 (s, 3H), 3.92 (s, 3H), 2.73 (s, 3H), 2.34 (s, 3H) |

TABLE 1-continued

| Cmpd No. | Structure | ESMS (M + H) | ¹H NMR (300 MHz, unless indicated otherwise) |
|---|---|---|---|
| 415 | 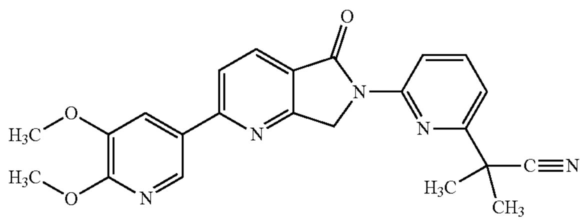 [SMILES: COc1cc(-c2ccc3c(n2)CN(c2cccc(C(C)(C)C#N)n2)C3=O)cnc1OC] | 416.52 | (CDCl₃) δ 8.60 (d, J = 8.4 Hz, 1H), 8.42 (d, J = 1.9 Hz, 1H), 8.24 (d, J = 8.2 Hz, 1H), 7.98 (d, J = 1.9 Hz, 1H), 7.86 (dd, J = 15.9, 8.2 Hz, 2H), 7.35 (d, J = 7.6 Hz, 1H), 5.26 (s, 2H), 4.13 (s, 3H), 4.06 (s, 3H), 1.82 (s, 6H) |
| 416 | 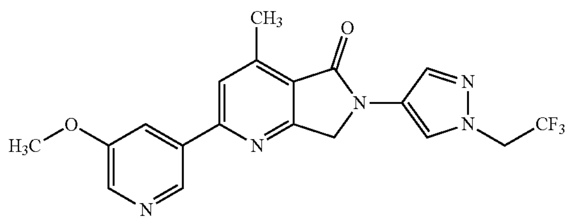 [SMILES: COc1cncc(-c2cc(C)c3c(n2)CN(c2cnn(CC(F)(F)F)c2)C3=O)c1] | 404 | |
| 417 | 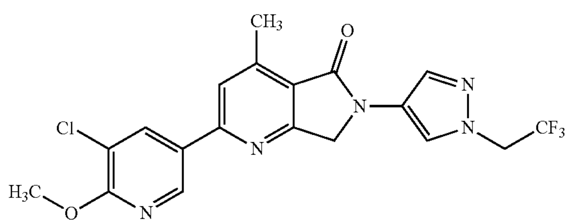 [SMILES: COc1ncc(-c2cc(C)c3c(n2)CN(c2cnn(CC(F)(F)F)c2)C3=O)cc1Cl] | 437.84 | (DMSO-d₆) δ 8.95 (d, J = 2.1 Hz, 1H), 8.62 (d, J = 2.1 Hz, 1H), 8.38 (s, 1H), 8.04 (s, 1H), 7.94 (s, 1H), 5.20 (q, J = 9.1 Hz, 2H), 4.92 (s, 2H), 4.03 (s, 3H), 2.72 (s, 3H) |
| 418 | 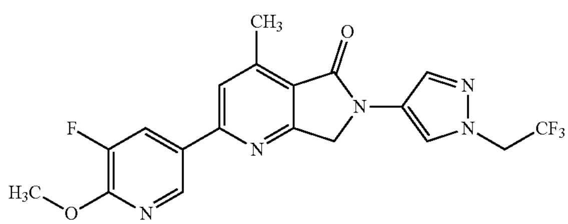 [SMILES: COc1ncc(-c2cc(C)c3c(n2)CN(c2cnn(CC(F)(F)F)c2)C3=O)cc1F] | 421.88 | (DMSO-d₆) δ 8.83 (d, J = 2.0 Hz, 1H), 8.38 (m, 2H), 8.02 (s, 1H), 7.95 (s, 1H), 5.20 (q, J = 9.2 Hz, 2H), 4.92 (s, 2H), 4.04 (s, 3H), 2.71 (s, 3H) |
| 419 | 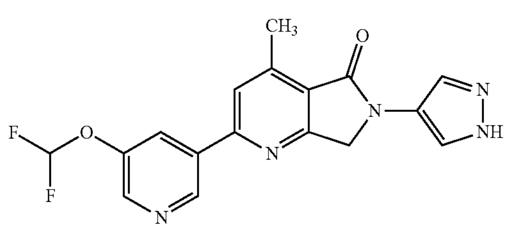 [SMILES: Cc1cc(-c2cncc(OC(F)F)c2)nc2c1C(=O)N(c1cn[nH]c1)C2] | 358.4 | |
| 420 | 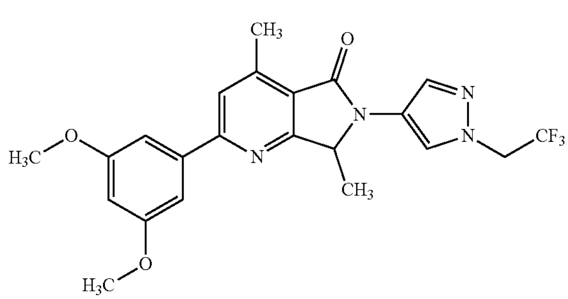 [SMILES: COc1cc(OC)cc(-c2cc(C)c3c(n2)C(C)N(c2cnn(CC(F)(F)F)c2)C3=O)c1] | 447.36 | (DMSO-d₆) δ 8.35 (d, J = 9.0 Hz, 1H), 7.96 (s, 2H), 7.35 (d, J = 2.3 Hz, 2H), 6.65 (t, J = 2.3 Hz, 1H), 5.76 (s, 1H), 5.18 (dd, J = 11.7, 6.6 Hz, 2H), 3.85 (s, 6H), 2.72 (s, 3H), 1.56 (d, J = 6.6 Hz, 3H) |

TABLE 1-continued

| Cmpd No. | Structure | ESMS (M + H) | ¹H NMR (300 MHz, unless indicated otherwise) |
|---|---|---|---|
| 421 | 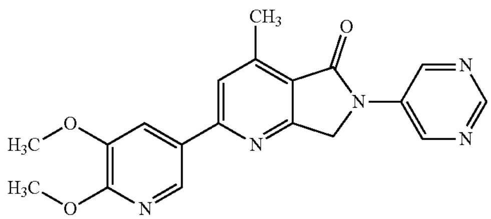 [SMILES: COc1cc(-c2cc(C)c3c(n2)CN(c2cncnc2)C3=O)cnc1OC] | 364.42 | (DMSO-d₆) δ 9.38 (s, 2H), 9.00 (s, 1H), 8.57 (d, J = 2.0 Hz, 1H), 8.06 (s, 1H), 7.98 (d, J = 1.9 Hz, 1H), 5.14 (s, 2H), 3.95 (s, 3H), 3.92 (s, 3H), 2.74 (s, 3H) |
| 422 | 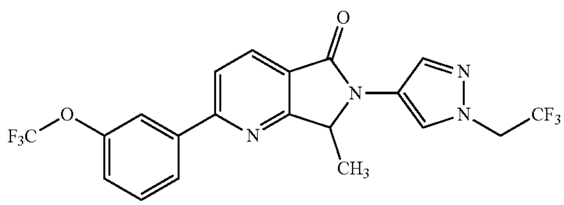 [SMILES: CC1c2nc(-c3cccc(OC(F)(F)F)c3)ccc2C(=O)N1c1cnn(CC(F)(F)F)c1] | 471.23 | (methanol-d₄) δ 8.32 (s, 1H), 8.17-8.04 (m, 2H), 7.99 (d, J = 2.3 Hz, 2H), 7.68 (t, J = 8.0 Hz, 1H), 7.49 (d, J = 8.3 Hz, 1H), 5.24 (q, J = 6.7 Hz, 1H), 4.98 (d, J = 8.7 Hz, 2H), 2.95-2.82 (m, 3H), 1.69 (d, J = 6.7 Hz, 3H) |
| 423 | 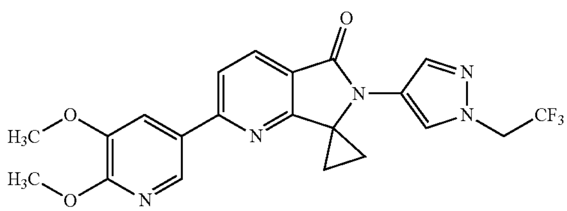 [SMILES: COc1cc(-c2ccc3c(n2)C2(CC2)N(c2cnn(CC(F)(F)F)c2)C3=O)cnc1OC] | 446.4 | (CDCl₃) δ 8.44 (d, J = 1.8 Hz, 1H), 8.24 (d, J = 8.1 Hz, 1H), 7.90 (s, 1H), 7.81 (t, J = 4.8 Hz, 2H), 7.62 (s, 1H), 4.88-4.67 (m, 2H), 4.13 (d, J = 9.1 Hz, 3H), 4.07-3.95 (m, 3H), 1.81 (dd, J = 8.0, 5.5 Hz, 2H), 1.56 (dd, J = 8.0, 5.4 Hz, 2H) |
| 424 | 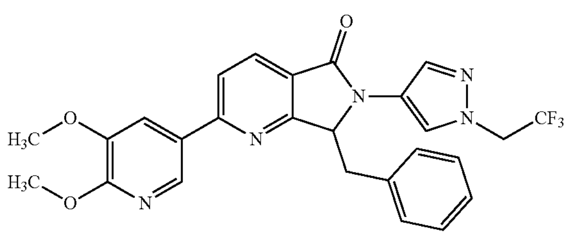 [SMILES: COc1cc(-c2ccc3c(n2)C(Cc2ccccc2)N(c2cnn(CC(F)(F)F)c2)C3=O)cnc1OC] | 510.28 | (CDCl₃) δ 8.47 (d, J = 1.9 Hz, 1H), 8.25 (s, 1H), 8.07-7.96 (m, 1H), 7.89 (d, J = 1.8 Hz, 1H), 7.86-7.75 (m, 2H), 7.12-6.95 (m, 3H), 6.66 (d, J = 6.8 Hz, 2H), 5.31 (dd, J = 5.2, 3.3 Hz, 1H), 4.78 (tt, J = 8.3, 4.2 Hz, 2H), 4.12 (d, J = 7.9 Hz, 3H), 4.03 (d, J = 5.9 Hz, 3H), 3.66 (dd, J = 14.1, 3.1 Hz, 1H), 3.51 (dd, J = 14.1, 5.4 Hz, 1H) |
| 425 | 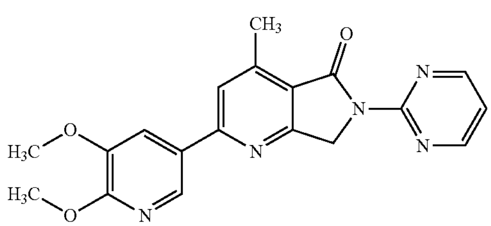 [SMILES: COc1cc(-c2cc(C)c3c(n2)CN(c2ncccn2)C3=O)cnc1OC] | 364.4 | (DMSO-d₆) δ 8.81 (d, J = 4.7 Hz, 2H), 8.57 (d, J = 1.9 Hz, 1H), 8.04 (s, 1H), 7.99 (d, J = 1.9 Hz, 1H), 7.30 (s, 1H), 5.10 (s, 2H), 3.96 (s, 3H), 3.92 (s, 3H), 2.74 (s, 3H) |
| 426 | 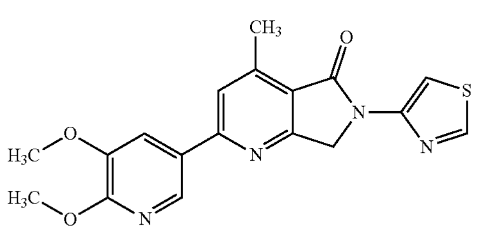 [SMILES: COc1cc(-c2cc(C)c3c(n2)CN(c2cscn2)C3=O)cnc1OC] | 369.36 | (DMSO-d₆) δ 9.13 (d, J = 2.3 Hz, 1H), 8.56 (d, J = 2.0 Hz, 1H), 8.03 (s, 1H), 7.98 (d, J = 2.3 Hz, 2H), 5.13 (s, 2H), 3.95 (s, 3H), 3.92 (s, 3H), 2.75 (s, 3H) |

TABLE 1-continued

| Cmpd No. | Structure | ESMS (M + H) | ¹H NMR (300 MHz, unless indicated otherwise) |
|---|---|---|---|
| 427 | 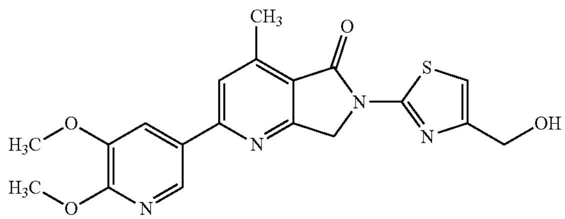 [SMILES: COc1cc(-c2cc(C)c3c(n2)CN(c2nc(CO)cs2)C3=O)cnc1OC] | 399.37 | (DMSO-d$_6$) δ 8.57 (d, J = 2.0 Hz, 1H), 8.07 (s, 1H), 7.98 (d, J = 1.9 Hz, 1H), 7.10 (s, 1H), 5.34 (s, 1H), 5.13 (s, 2H), 4.54 (d, J = 4.8 Hz, 2H), 3.95 (s, 3H), 3.92 (s, 3H), 2.74 (s, 3H) |
| 428 | 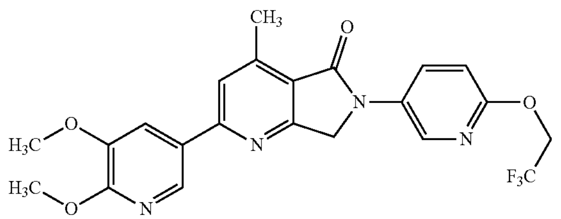 [SMILES: COc1cc(-c2cc(C)c3c(n2)CN(c2ccc(OCC(F)(F)F)nc2)C3=O)cnc1OC] | 461.51 | (DMSO-d$_6$) δ 8.67 (d, J = 2.7 Hz, 1H), 8.56 (d, J = 1.8 Hz, 1H), 8.42 (dd, J = 9.0, 2.7 Hz, 1H), 8.03 (s, 1H), 7.97 (d, J = 1.8 Hz, 1H), 7.12 (d, J = 9.0 Hz, 1H), 5.08 (s, 2H), 4.99 (s, J = 9.1 Hz, 2H), 3.93 (dd, J = 10.2 Hz, 2H), 2.73 (s, 3H) |
| 429 | 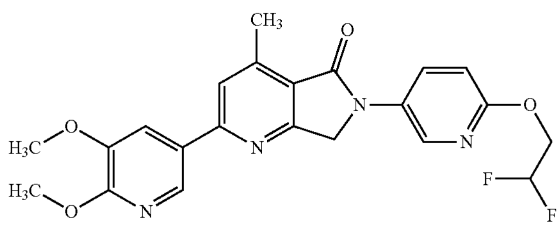 [SMILES: COc1cc(-c2cc(C)c3c(n2)CN(c2ccc(OCC(F)F)nc2)C3=O)cnc1OC] | 443.46 | (DMSO-d$_6$) δ 8.65 (d, J = 2.5 Hz, 1H), 8.56 (d, J = 2.0 Hz, 1H), 8.38 (dd, J = 9.0, 2.8 Hz, 1H), 8.07-7.92 (m, 2H), 7.05 (d, J = 9.0 Hz, 1H), 6.42 (tt, J = 54.7, 3.5 Hz, 1H), 5.07 (s, 2H), 4.59 (d, J = 3.6 Hz, 2H), 3.93 (d, J = 10.2 Hz, 6H), 2.73 (s, 3H) |
| 430 | 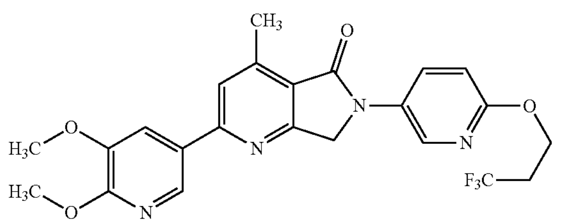 [SMILES: COc1cc(-c2cc(C)c3c(n2)CN(c2ccc(OCCC(F)(F)F)nc2)C3=O)cnc1OC] | 475.52 | |
| 431 | 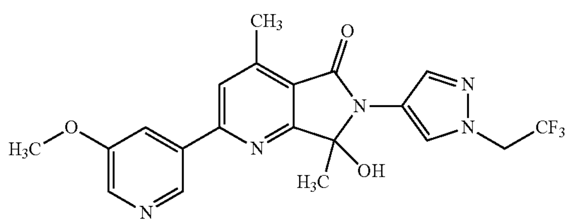 [SMILES: COc1cncc(-c2cc(C)c3c(n2)C(C)(O)N(c2cnn(CC(F)(F)F)c2)C3=O)c1] | 464.51 | |
| 432 | 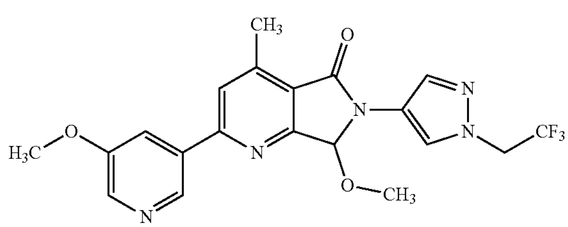 [SMILES: COc1cncc(-c2cc(C)c3c(n2)C(OC)N(c2cnn(CC(F)(F)F)c2)C3=O)c1] | 464.51 | |
| 433 | 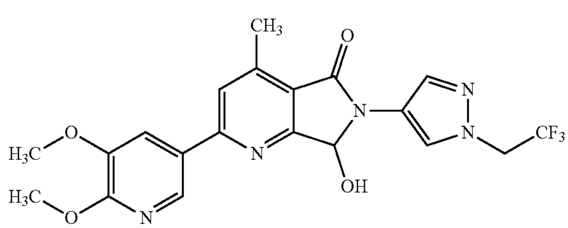 [SMILES: COc1cc(-c2cc(C)c3c(n2)C(O)N(c2cnn(CC(F)(F)F)c2)C3=O)cnc1OC] | 450.5 | |

TABLE 1-continued

| Cmpd No. | Structure | ESMS (M + H) | ¹H NMR (300 MHz, unless indicated otherwise) |
|---|---|---|---|
| 434 | 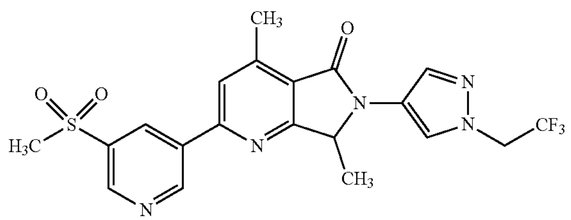 [SMILES: Cc1cc(-c2cncc(S(C)(=O)=O)c2)nc2c1C(=O)N(c1cnn(CC(F)(F)F)c1)C2C] | 466.32 | (DMSO-d₆) δ 9.68 (d, J = 2.1 Hz, 1H), 9.19 (d, J = 2.1 Hz, 1H), 9.00 (t, J = 2.0 Hz, 1H), 8.37 (d, J = 9.9 Hz, 1H), 8.25 (d, Jr 6.1 Hz, 1H), 7.97 (d, J = 9.6 Hz, 1H), 5.76 (s, 2H), 5.21 (dd, J = 18.8, 8.1 Hz, 2H), 3.49-3.39 (m, 2H), 2.89 (s, 1H), 2.75 (d, J = 13.2 Hz, 2H), 1.72-1.49 (m, 2H) |
| 435 | 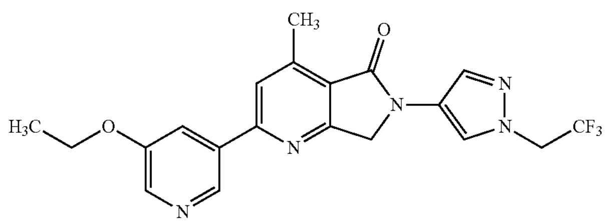 | 418.37 | (DMSO-d₆) δ 8.94 (d, J = 1.3 Hz, 1H), 8.38 (d, J = 3.1 Hz, 2H), 8.08 (s, 1H), 8.02 (s, 1H), 7.95 (s, 1H), 5.21 (q, J = 9.0 Hz, 2H), 4.93 (s, 2H), 4.22 (q, J = 6.9 Hz, 2H), 2.72 (s, 3H), 2.51 (s, 3H), 1.50-1.28 (m, 3H) |
| 436 | 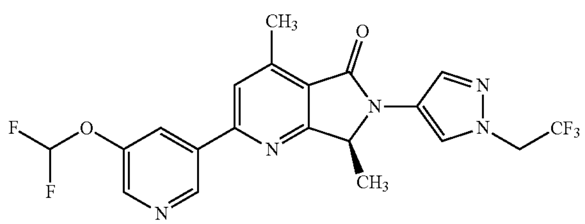 [SMILES: Cc1cc(-c2cncc(OC(F)F)c2)nc2c1C(=O)N(c1cnn(CC(F)(F)F)c1)[C@H]2C] | 454.32 | |
| 437 | 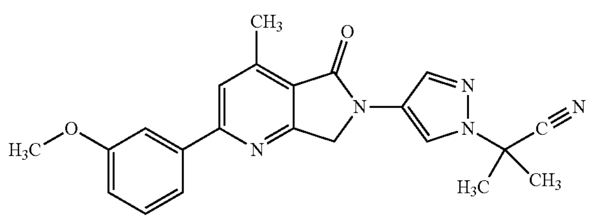 [SMILES: COc1cccc(-c2cc(C)c3c(n2)CN(c2cnn(C(C)(C)C#N)c2)C3=O)c1] | 388 | |
| 438 | 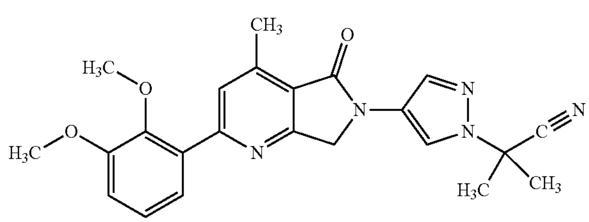 [SMILES: COc1cccc(-c2cc(C)c3c(n2)CN(c2cnn(C(C)(C)C#N)c2)C3=O)c1OC] | 418 | |
| 439 | 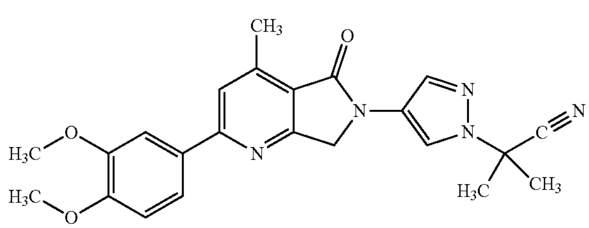 [SMILES: COc1ccc(-c2cc(C)c3c(n2)CN(c2cnn(C(C)(C)C#N)c2)C3=O)cc1OC] | 418 | |

TABLE 1-continued

| Cmpd No. | Structure | ESMS (M + H) | ¹H NMR (300 MHz, unless indicated otherwise) |
|---|---|---|---|
| 440 | 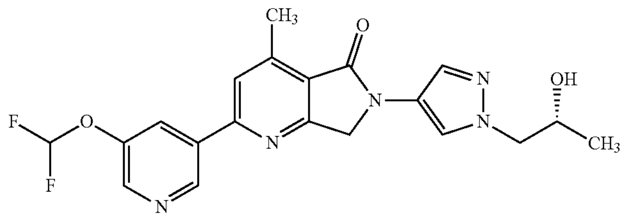 [SMILES: Cc1cc(-c2cncc(OC(F)F)c2)nc2c1C(=O)N(c1cnn(C[C@@H](C)O)c1)C2] | 416.46 | (CDCl$_3$) δ 8.63 (d, J = 2.0 Hz, 1H), 8.46 (s, 1H), 8.24 (s, 1H), 7.72 (d, J = 12.6 Hz, 2H), 6.74 (t, J = 71.6 Hz, 2H), 4.80 (s, 2H), 4.40-4.17 (m, 2H), 4.09 (dd, J = 14.0, 8.1 Hz, 1H), 2.86 (s, 3H), 1.30 (d, J = 6.3 Hz, 3H) |
| 441 | 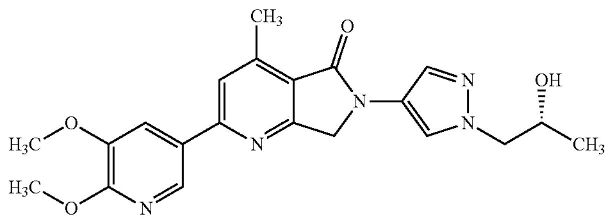 [SMILES: COc1cc(-c2cc(C)c3c(n2)CN(c2cnn(C[C@@H](C)O)c2)C3=O)cnc1OC] | 410.51 | (CDCl$_3$) δ 8.37 (d, J = 1.9 Hz, 1H), 8.24 (s, 1H), 7.86 (d, J = 1.9 Hz, 1H), 7.74 (s, 1H), 7.58 (s, 1H), 4.80 (s, 2H), 4.25 (d, J = 12.9 Hz, 2H), 4.11 (d, J = 10.1 Hz, 4H), 4.03 (s, 3H), 2.83 (s, 3H), 1.29 (d, J = 8.5 Hz, 3H) |
| 442 | 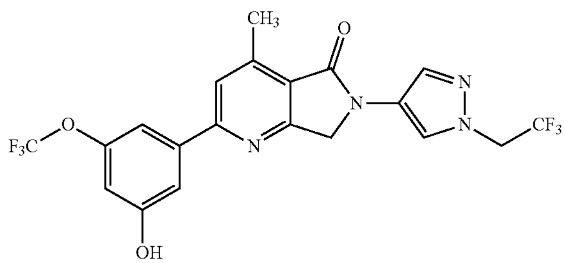 [SMILES: Cc1cc(-c2cc(O)cc(OC(F)(F)F)c2)nc2c1C(=O)N(c1cnn(CC(F)(F)F)c1)C2] | 473 | (CDCl$_3$) δ 8.28 (s, 1H), 7.94 (s, 1H), 7.64 (s, 1H), 7.41 (d, J = 5.9 Hz, 2H), 6.83 (s, 1H), 4.98-4.76 (m, 4H), 2.82 (s, 3H) |
| 443 | 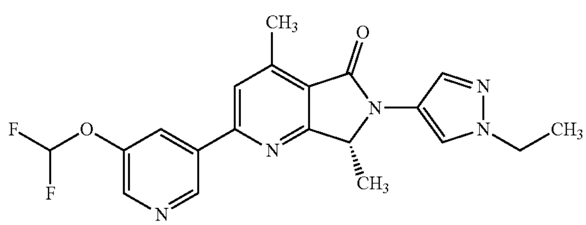 [SMILES: CCn1cc(N2C(=O)c3c(C)cc(-c4cncc(OC(F)F)c4)nc3[C@H]2C)cn1] | 454.38 | |
| 444 | 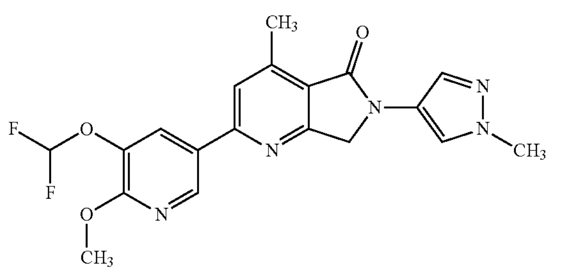 [SMILES: COc1ncc(-c2cc(C)c3c(n2)CN(c2cnn(C)c2)C3=O)cc1OC(F)F] | 402.45 | (DMSO-d$_6$) δ 8.88 (d, J = 2.0 Hz, 1H), 8.33 (s, 1H), 8.03 (s, 1H), 7.71 (d, J = 2.2 Hz, 1H), 7.32 (t, J = 73.7 Hz, 2H), 6.76 (d, J = 2.2 Hz, 1H), 4.92 (s, 2H), 4.02 (s, 3H), 3.83 (s, 3H), 2.72 (s, 3H) |
| 445 | 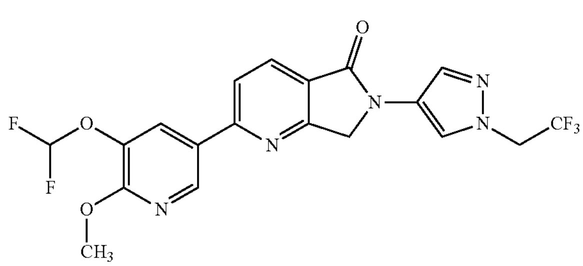 [SMILES: COc1ncc(-c2ccc3c(n2)CN(c2cnn(CC(F)(F)F)c2)C3=O)cc1OC(F)F] | 456.85 | (DMSO-d$_6$) δ 8.90 (d, J = 2.0 Hz, 1H), 8.42 (s, 1H), 8.35 (d, J = 1.8 Hz, 1H), 8.24 (q, J = 8.2 Hz, 2H), 7.95 (s, 1H), 7.34 (t, J = 73.6 Hz, 2H), 5.22 (q, J = 9.1 Hz, 2H), 5.02 (s, 2H), 4.02 (s, 3H) |

TABLE 1-continued

| Cmpd No. | Structure | ESMS (M + H) | ¹H NMR (300 MHz, unless indicated otherwise) |
|---|---|---|---|
| 446 | 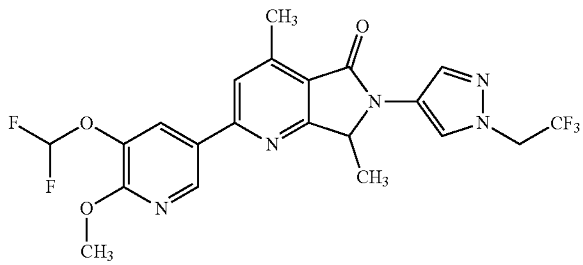 [SMILES: COc1ncc(-c2cc(C)c3c(n2)C(C)N(c2cnn(CC(F)(F)F)c2)C3=O)cc1OC(F)F] | 484.89 | (DMSO-d$_6$) δ 8.90 (d, J = 2.1 Hz, 1H), 8.43-8.26 (m, 2H), 8.04 (s, 1H), 7.96 (s, 1H) 7.32 (t, J = 73.6 Hz, 2H), 5.29-5.04 (m, 3H), 4.02 (s, 2H), 2.73 (s, 3H), 1.56 (d, J = 6.7 Hz, 3H) |
| 447 | 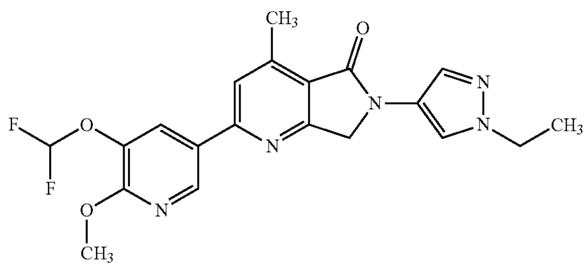 [SMILES: CCn1cc(N2Cc3nc(-c4cnc(OC)c(OC(F)F)c4)cc(C)c3C2=O)cn1] | | (DMSO-d$_6$) δ 8.87 (d, J = 2.0 Hz, 1H), 8.32 (d, J = 1.8 Hz, 1H), 8.19 (s, 1H), 8.02 (s, 1H), 7.81 (s, 1H), 7.32 (t, J = 73.6 Hz, 1H), 4.88 (s, 2H), 4.16 (q, J = 7.2 Hz, 2H), 4.01 (s, 3H), 2.71 (s, 3H), 1.39 (t, J = 7.3 Hz, 3H) |
| 448 | 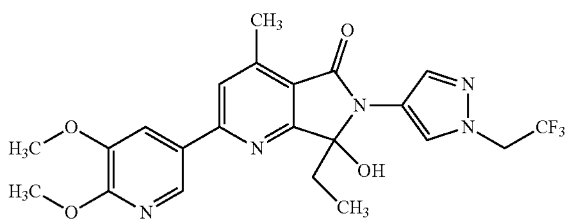 [SMILES: CCC1(O)c2nc(-c3cnc(OC)c(OC)c3)cc(C)c2C(=O)N1c1cnn(CC(F)(F)F)c1] | 478.46 | |
| 449 | 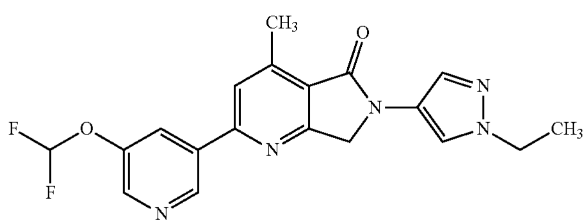 [SMILES: CCn1cc(N2Cc3nc(-c4cncc(OC(F)F)c4)cc(C)c3C2=O)cn1] | 386.45 | (DMSO-d$_6$) δ 9.27 (d, J = 1.7 Hz, 1H), 8.63 (d, J = 2.6 Hz, 1H), 8.39 (s, 1H), 8.18 (d, J = 15.8 Hz, 2H), 7.83 (s, 1H), 7.48 (t, J = 73.2 Hz, 1H), 4.92 (s, 2H), 4.17 (q, J = 7.3 Hz, 2H), 2.74 (s, 3H), 1.39 (t, J = 7.3 Hz, 3H) |
| 450 | 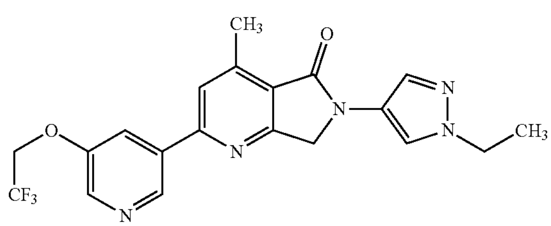 [SMILES: CCn1cc(N2Cc3nc(-c4cncc(OCC(F)(F)F)c4)cc(C)c3C2=O)cn1] | 418.43 | (DMSO-d$_6$) δ 9.10 (d, J = 1.7 Hz, 1H), 8.58 (d, J = 2.8 Hz, 1H), 8.34-8.27 (m, 1H), 8.18 (d, J = 19.9 Hz, 2H), 7.83 (d, J = 0.6 Hz, 1H), 5.05 (q, J = 8.8 Hz, 2H), 4.91 (s, 2H), 4.17 (q, J = 7.3 Hz, 2H), 2.71 (d, J = 24.8 Hz, 3H), 1.39 (t, J = 7.3 Hz, 3H) |
| 451 | 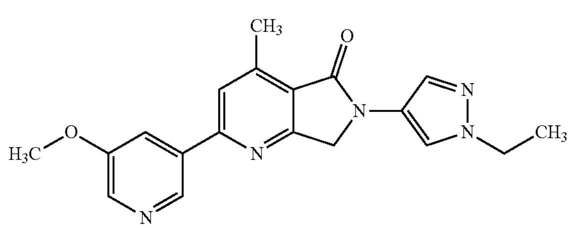 [SMILES: CCn1cc(N2Cc3nc(-c4cncc(OC)c4)cc(C)c3C2=O)cn1] | 350.49 | (DMSO-d$_6$) δ 9.07 (d, J = 1.7 Hz, 1H), 8.58 (d, J = 2.7 Hz, 1H), 8.36 (s, 1H), 8.20 (d, J = 7.1 Hz, 2H), 7.83 (d, J = 0.6 Hz, 1H), 4.92 (s, 2H), 4.17 (q, J = 7.3 Hz, 2H), 4.01 (s, 3H), 2.74 (d, J = 6.2 Hz, 3H), 1.39 (t, J = 7.3 Hz, 3H) |

TABLE 1-continued

| Cmpd No. | Structure | ESMS (M + H) | ¹H NMR (300 MHz, unless indicated otherwise) |
|---|---|---|---|
| 452 | 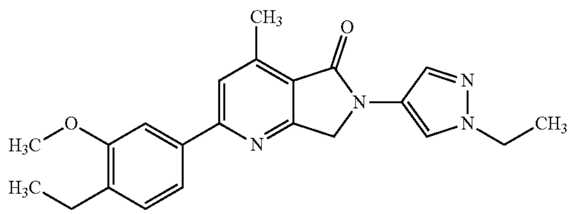 [SMILES: CCc1ccc(-c2cc(C)c3c(n2)CN(c2cnn(CC)c2)C3=O)cc1OC] | 379.43 | |
| 453 | 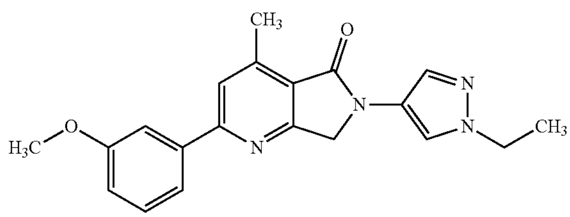 [SMILES: CCn1cc(N2Cc3nc(-c4cccc(OC)c4)cc(C)c3C2=O)cn1] | 349.17 | (DMSO-d$_6$) δ 8.19 (d, J = 0.5 Hz, 1H), 7.96 (s, 1H), 7.82 (d, J = 0.6 Hz, 1H), 7.78-7.70 (m, 2H), 7.45 (t, J = 8.0 Hz, 1H), 7.14-7.01 (m, 1H), 4.88 (s, 2H), 4.22-4.09 (m, 2H), 3.86 (s, 3H), 2.72 (s, 3H), 1.39 (t, J = 7.3 Hz, 3H) |
| 454 | 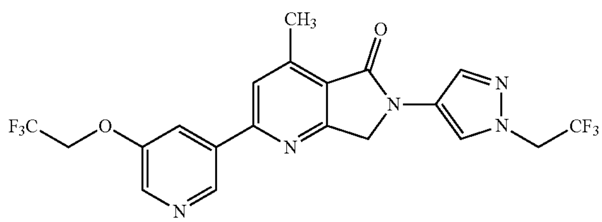 [SMILES: Cc1cc(-c2cncc(OCC(F)(F)F)c2)nc2c1C(=O)N(c1cnn(CC(F)(F)F)c1)C2] | 472.43 | (DMSO-d$_6$) δ 9.11 (d, J = 1.7 Hz, 1H), 8.60 (d, J = 2.8 Hz, 1H), 8.40 (s, 1H), 8.34 (dd, J = 2.7, 1.8 Hz, 1H), 8.17 (s, 1H), 7.95 (t, J = 3.9 Hz, 1H), 5.21 (q, J = 9.1 Hz, 2H), 5.05 (t, J = 7.8 Hz, 2H), 4.95 (s, 2H), 2.80-2.63 (m, 3H) |
| 455 | 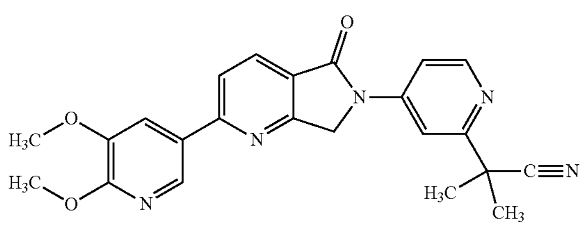 | 416 | (CDCl$_3$) δ 8.64 (d, J = 5.7 Hz, 1H), 8.44 (d, J = 2.0 Hz, 1H), 8.25 (d, J = 8.2 Hz, 1H), 8.08 (d, J = 1.8 Hz, 1H), 7.94 (ddd, J = 12.7, 7.2, 5.2 Hz, 3H), 5.02 (s, 2H), 4.13 (s, 3H), 4.05 (s, 3H), 1.84 (s, 6H) |
| 456 | 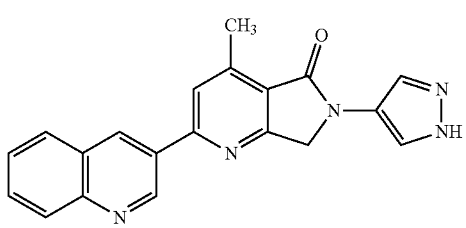 [SMILES: Cc1cc(-c2cnc3ccccc3c2)nc2c1C(=O)N(c1cn[nH]c1)C2] | 342.52 | (DMSO-d$_6$) δ 12.92 (s, 1H), 9.70 (d, J = 2.2 Hz, 1H), 9.15 (d, J = 1.9 Hz, 1H), 8.22 (s, 1H), 8.20-8.07 (m, 3H), 7.95 (s, 1H), 7.89-7.81 (m, 1H), 7.70 (t, J = 7.5 Hz, 1H), 4.96 (s, 2H), 2.78 (s, 3H) |
| 457 | 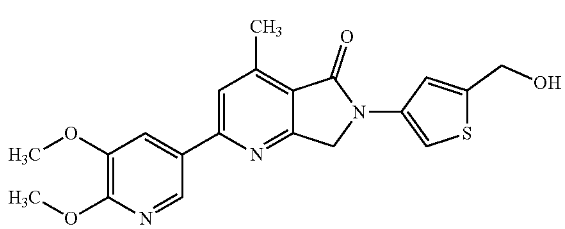 [SMILES: COc1cc(-c2cc(C)c3c(n2)CN(c2csc(CO)c2)C3=O)cnc1OC] | 398.34 | (DMSO-d$_6$) δ 8.55 (d, J = 1.9 Hz, 1H), 8.01 (s, 1H), 7.97 (d, J = 1.9 Hz, 1H), 7.59 (s, 1H), 7.52 (d, J = 1.5 Hz, 1H), 4.99 (s, 2H), 4.65 (s, 2H), 3.95 (s, 3H), 3.92 (s, 3H), 2.72 (s, 3H) |
| 458 | 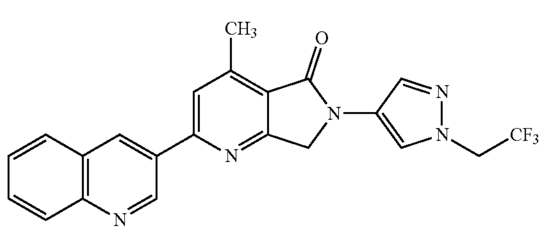 [SMILES: Cc1cc(-c2cnc3ccccc3c2)nc2c1C(=O)N(c1cnn(CC(F)(F)F)c1)C2] | 424.37 | (DMSO-d$_6$) δ 9.70 (d, J = 2.3 Hz, 1H), 9.15 (d, J = 2.0 Hz, 1H), 8.40 (s, 1H), 8.23 (s, 1H), 8.13 (m, 2H), 7.97 (s, 1H), 7.92-7.77 (m, 1H), 7.76-7.63 (m, 1H), 5.22 (q, J = 9.1 Hz, 2H), 4.99 (s, 2H), 2.78 (s, 3H) |

TABLE 1-continued

| Cmpd No. | Structure | ESMS (M + H) | ¹H NMR (300 MHz, unless indicated otherwise) |
|---|---|---|---|
| 459 | 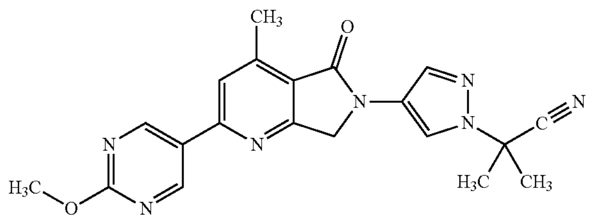 [SMILES: COc1ncc(-c2cc(C)c3c(n2)CN(c2cnn(C(C)(C)C#N)c2)C3=O)cn1] | 390 | (CDCl₃) δ 9.19 (s, 2H), 8.27 (s, 1H), 7.79 (s, 1H), 7.56 (s, 1H), 7.29 (s, 1H), 4.81 (s, 2H), 4.12 (s, 3H), 2.83 (s, 3H), 2.05 (s, 6H) |
| 460 | 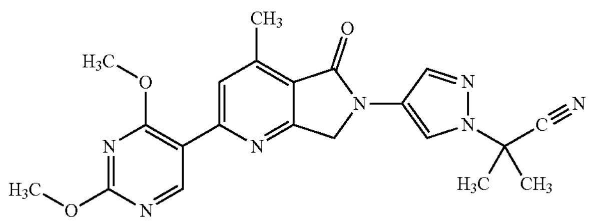 [SMILES: COc1ncc(-c2cc(C)c3c(n2)CN(c2cnn(C(C)(C)C#N)c2)C3=O)c(OC)n1] | 420 | (CDCl₃) δ 9.00 (s, 1H), 8.42 (s, 1H), 7.78 (s, 1H), 4.78 (s, 2H), 4.14 (s, 3H), 4.09 (s, 3H), 2.78 (s, 3H), 2.05 (s, 6H) |
| 461 | 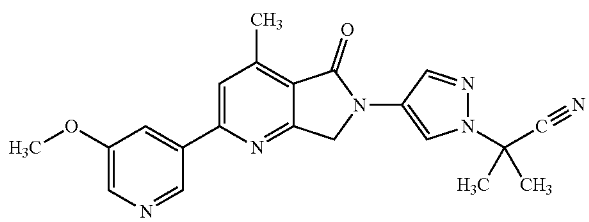 [SMILES: COc1cncc(-c2cc(C)c3c(n2)CN(c2cnn(C(C)(C)C#N)c2)C3=O)c1] | 389 | (CDCl₃) δ 8.44 (s, 2H), 7.98 (s, 1H), 7.78 (s, 1H), 7.65 (s, 1H), 7.26 (s, 1H), 4.81 (s, 2H), 3.99 (s, 3H), 2.84 (s, 3H), 2.05 (s, 6H) |
| 462 | 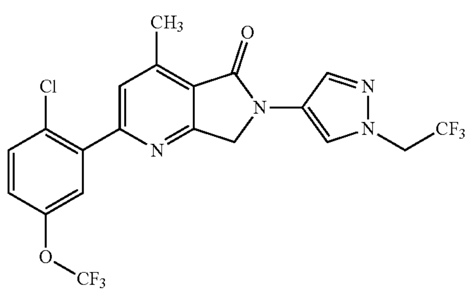 [SMILES: Cc1cc(-c2cc(OC(F)(F)F)ccc2Cl)nc2c1C(=O)N(c1cnn(CC(F)(F)F)c1)C2] | 490.91 | (CDCl₃) δ 8.32 (s, 1H), 8.00 (d, J = 7.9 Hz, 1H), 7.80 (s, 1H), 7.65-7.48 (m, 3H), 4.89-4.67 (m, 4H), 2.85 (s, 3H). |
| 463 | 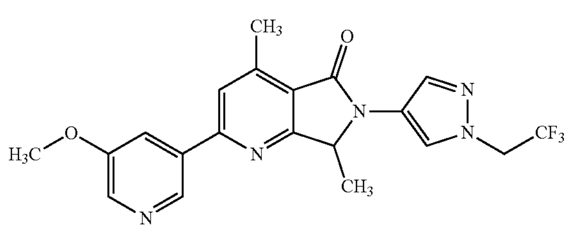 [SMILES: COc1cncc(-c2cc(C)c3c(n2)C(C)N(c2cnn(CC(F)(F)F)c2)C3=O)c1] | 418.54 | (DMSO-d₆) δ 9.10 (d, J = 1.4 Hz, 1H), 8.62 (d, J = 2.6 Hz, 1H), 8.41 (d, J = 12.9 Hz, 2H), 8.22 (s, 1H), 7.97 (d, J = 7.2 Hz, 1H), 5.29-5.12 (m, 3H), 4.03 (s, 3H), 2.76 (s, 3H), 1.60 (t, J = 7.4 Hz, 3H) |
| 464 | 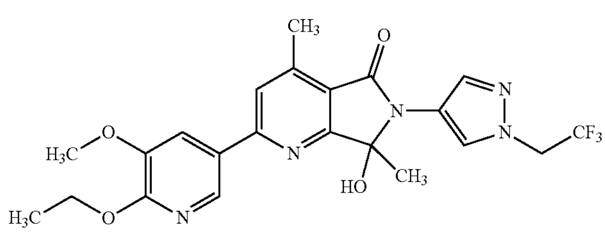 [SMILES: CCOc1ncc(-c2cc(C)c3c(n2)C(C)(O)N(c2cnn(CC(F)(F)F)c2)C3=O)cc1OC] | 478.59 | |

TABLE 1-continued

| Cmpd No. | Structure | ESMS (M + H) | ¹H NMR (300 MHz, unless indicated otherwise) |
|---|---|---|---|
| 465 | 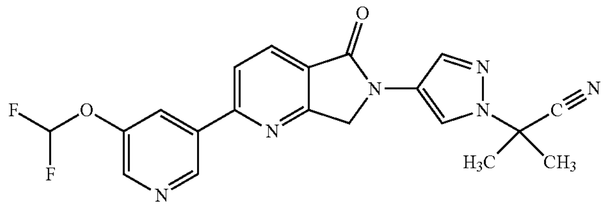 [SMILES: CC(C)(C#N)n1cc(N2Cc3nc(-c4cncc(OC(F)F)c4)ccc3C2=O)cn1] | 411 | (CDCl$_3$) δ 9.16 (s, 1H), 8.61 (s, 1H), 8.44 (s, 1H), 8.27 (d, 1H, J = 8 Hz), 7.96 (d, 1H, J = 8 Hz), 7.81 (d, 1H), 6.67 (t, 1H, J = 75 Hz - H-F coupling), 4.89 (s, 2H), 2.05 (s, 6H) |
| 466 | 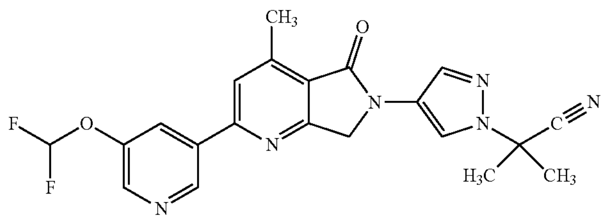 [SMILES: Cc1cc(-c2cncc(OC(F)F)c2)nc2c1C(=O)N(c1cnn(C(C)(C)C#N)c1)C2] | 425 | |
| 467 | 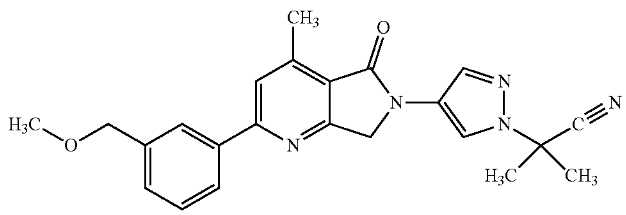 [SMILES: COCc1cccc(-c2cc(C)c3c(n2)CN(c2cnn(C(C)(C)C#N)c2)C3=O)c1] | 402 | 300 MHz; CDCl3-d: 8.42 (d, 1H, J = 2 Hz), 8.04 (s, 1H), 7.97 (d, 1H, J = 7 Hz), 7.75 (s, 1H), 7.62 (s, 1H), 7.53 (m, 2H), 7.26 (s, 1H), 4.8 (s, 2H), 4.57 (s, 2H), 3.45 (s, 3H), 2.82 (s, 3H), 2.05 (s, 6H) |
| 468 | 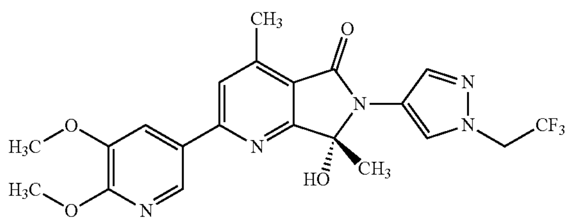 [SMILES: COc1cc(-c2cc(C)c3c(n2)[C@@](C)(O)N(c2cnn(CC(F)(F)F)c2)C3=O)cnc1OC] | 464.51 | |
| 469 | 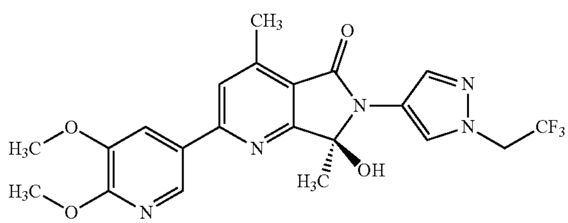 [SMILES: COc1cc(-c2cc(C)c3c(n2)[C@](C)(O)N(c2cnn(CC(F)(F)F)c2)C3=O)cnc1OC] | 464.51 | |
| 470 | 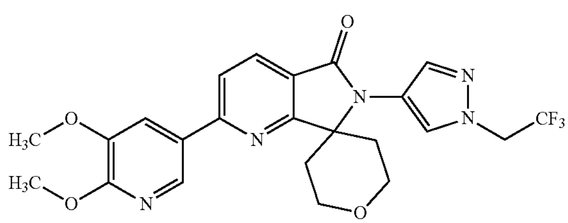 [SMILES: COc1cc(-c2ccc3c(n2)C2(CCOCC2)N(c2cnn(CC(F)(F)F)c2)C3=O)cnc1OC] | 490.14 | (CDCl$_3$) δ 8.55 (d, J = 2.0 Hz, 1H), 8.26 (d, J = 8.1 Hz, 1H), 7.91 (dd, J = 9.9, 1.6 Hz, 3H), 7.77 (s, 1H), 4.86-4.64 (m, 4H), 4.14 (s, 3H), 4.08 (dd, J = 11.5, 5.0 Hz, 2H), 4.03 (s, 3H), 2.44 (td, J = 12.9, 5.3 Hz, 2H), 1.70 (s, 2H) |
| 471 | 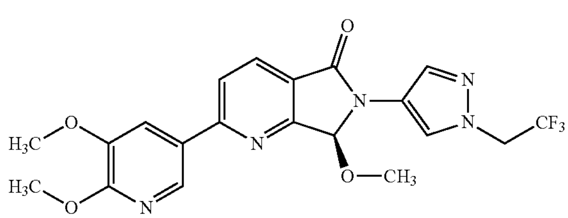 [SMILES: COc1cc(-c2ccc3c(n2)[C@H](OC)N(c2cnn(CC(F)(F)F)c2)C3=O)cnc1OC] | 450.5 | |

TABLE 1-continued

| Cmpd No. | Structure | ESMS (M + H) | ¹H NMR (300 MHz, unless indicated otherwise) |
|---|---|---|---|
| 472 | 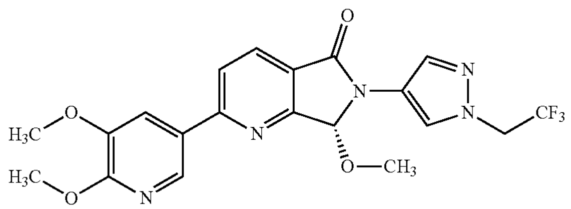 [SMILES: COc1cc(-c2ccc3c(n2)[C@@H](OC)N(c2cnn(CC(F)(F)F)c2)C3=O)cnc1OC] | 450.5 | |
| 473 | 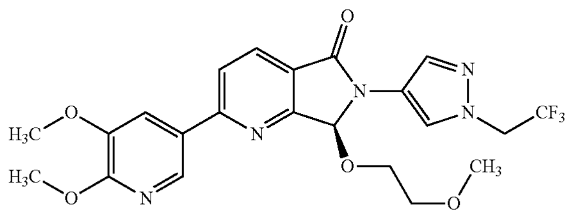 [SMILES: COCCO[C@H]1c2nc(-c3cnc(OC)c(OC)c3)ccc2C(=O)N1c1cnn(CC(F)(F)F)c1] | 494.52 | |
| 474 | 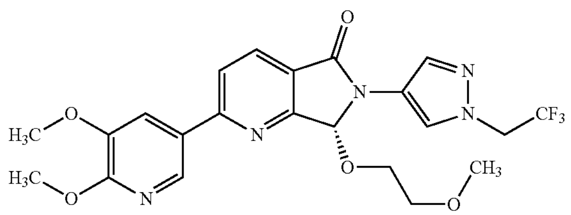 [SMILES: COCCO[C@@H]1c2nc(-c3cnc(OC)c(OC)c3)ccc2C(=O)N1c1cnn(CC(F)(F)F)c1] | 494.52 | |
| 475 | 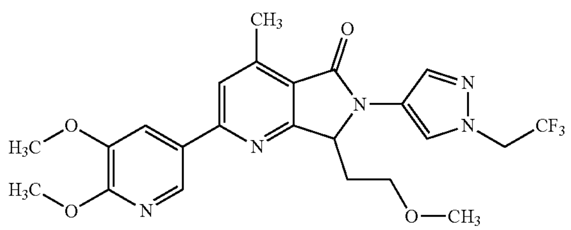 [SMILES: COCCC1c2nc(-c3cnc(OC)c(OC)c3)cc(C)c2C(=O)N1c1cnn(CC(F)(F)F)c1] | 492.54 | |
| 476 | 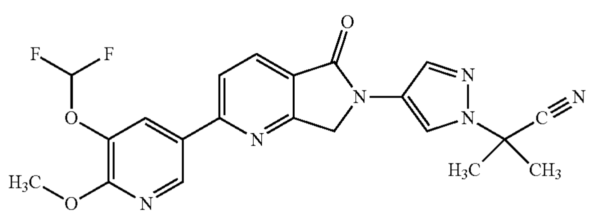 [SMILES: COc1ncc(-c2ccc3c(n2)CN(c2cnn(C(C)(C)C#N)c2)C3=O)cc1OC(F)F] | 441 | (CDCl$_3$) δ 8.72 (d, 1H, J = 2 Hz), 8.42 (s, 1H), 8.2 (s, 1H) 8.16 (d, 1H, J = 8 Hz), 7.85 (d, 1H, J = 8 Hz), 7.80 (s, 1H), 6.94-6.45 (t, 1H, J = 74 Hz H-F), 4.86 (s, 2H), 4.11 (s, 3H), 2.05 (s, 6H) |
| 477 | 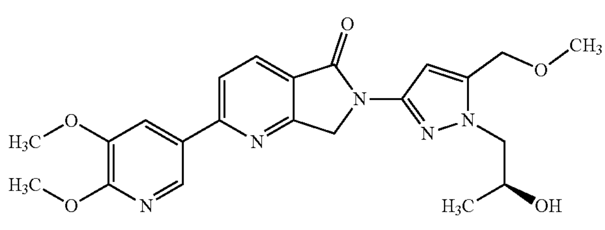 | 440.58 | (CDCl$_3$) δ 8.40 (d, J = 1.9 Hz, 1H), 8.22 (d, J = 8.1 Hz, 1H), 7.93 (d, J = 1.9 Hz, 1H), 7.86 (d, J = 8.1 Hz, 1H), 7.04 (s, 1H), 5.01 (s, 2H), 4.57-4.40 (m, 2H), 4.24 (td, J = 9.0, 2.1 Hz, 2H), 4.12 (s, 3H), 4.04 (s, 3H), 4.03-3.93 (m, 1H), 3.40 (s, 3H), 1.29 (d, J = 6.3 Hz, 3H). |
| 478 | 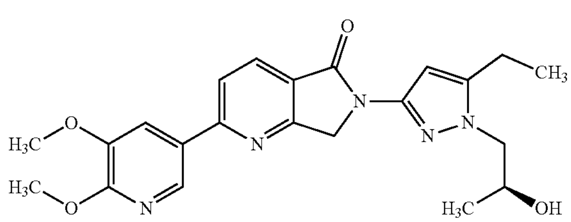 [SMILES: CCc1cc(N2Cc3nc(-c4cnc(OC)c(OC)c4)ccc3C2=O)nn1C[C@H](C)O] | 424.59 | (CDCl$_3$) δ 8.41 (d, J = 2.0 Hz, 1H), 8.24 (d, J = 8.1 Hz, 1H), 7.95 (d, J = 1.9 Hz, 1H), 7.87 (d, J = 8.2 Hz, 1H), 6.85 (s, 1H), 5.02 (s, 2H), 4.28 (dd, J = 10.4, 4.1 Hz, 1H), 4.20-4.10 (m, 3H), 4.07-4.02 (m, 3H), 3.91 (dd, J = 13.8, 8.0 Hz, 3H), 2.68 (q, J = 7.5 |

TABLE 1-continued

| Cmpd No. | Structure | ESMS (M + H) | ¹H NMR (300 MHz, unless indicated otherwise) |
|---|---|---|---|
| | | | Hz, 2H), 1.35 (t, J = 7.5 Hz, 3H), 1.32- 1.14 (d, 3H). |
| 479 | 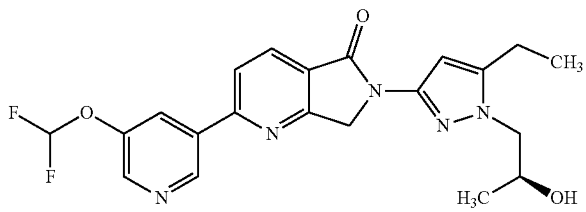 [SMILES: CCc1cc(N2Cc3nc(-c4cncc(OC(F)F)c4)ccc3C2=O)nn1C[C@H](C)O] | 430.54 | (CDCl₃) δ 8.65 (s, 1H), 8.47 (s, 1H), 8.32 (d, J = 8.1 Hz, 1H), 7.96 (d, J = 8.1 Hz, 1H), 6.84 (s, 1H), 7.03-6.36 (t, 1H), 5.04 (s, 2H), 4.35-4.19 (m, 1H), 4.08 (dd, J = 13.9, 2.4 Hz, 1H), 3.90 (dd, J = 13.9, 8.1 Hz, 1H), 2.68 (q, J = 7.5 Hz, 2H), 1.45- 1.12 (m, 6H). |
| 480 | 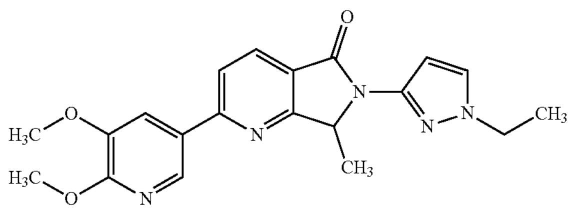 [SMILES: CCn1ccc(N2C(=O)c3ccc(-c4cnc(OC)c(OC)c4)nc3C2C)n1] | 394.51 | (CDCl₃) δ 8.39 (d, J = 2.0 Hz, 1H), 7.89 (d, J = 1.9 Hz, 1H), 7.58 (s, 1H), 7.42 (d, J = 2.4 Hz, 1H), 6.91 (d, J = 2.4 Hz, 1H), 5.32 (q, J 6.6 Hz, 1H), 4.19 (q, J = 7.3 Hz, 2H), 4.14 (s, 3H), 4.04 (s, 3H), 2.85 (s, 3H), 1.78 (d, J = 6.7 Hz, 3H), 1.53 (t, J = 7.3 Hz, 3H). |
| 481 | 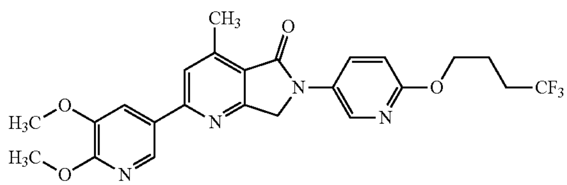 [SMILES: COc1cc(-c2cc(C)c3c(n2)CN(c2ccc(OCCCC(F)(F)F)nc2)C3=O)cnc1OC] | 489.29 | |
| 482 | 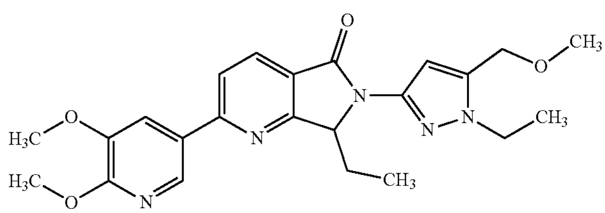 | 438.6 | (CDCl₃) δ 8.46 (d, J = 1.8 Hz, 1H), 8.22 (d, J = 8.1 Hz, 1H), 7.93 (d, J = 1.8 Hz, 1H), 7.84 (d, J = 8.1 Hz, 1H), 6.94 (s, 1H), 5.47-5.35 (m, 1H), 4.51 (s, 2H), 4.27-4.16 (q, 2H), 4.13 (s, 3H), 4.04 (s, 3H), 3.41 (s, 3H), 2.42 (m, 2H), 1.47 (t, J = 7.2 Hz, 3H), 0.60 (t, J = 7.4 Hz, 3H). |
| 483 | 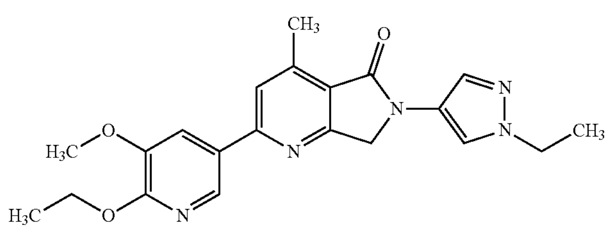 [SMILES: CCOc1ncc(-c2cc(C)c3c(n2)CN(c2cnn(CC)c2)C3=O)cc1OC] | 394.17 | (DMSO-d₆) δ 8.51 (d, J = 2.0 Hz, 1H), 8.17 (d, J = 6.6 Hz, 1H), 7.95 (dd, J = 9.9, 8.0 Hz, 2H), 7.80 (t, J = 3.1 Hz, 1H), 5.00 (s, 2H), 4.84 (d, J = 13.2 Hz, 2H), 4.40 (q, J = 7.0 Hz, 2H), 4.16 (q, J = 7.3 Hz, 2H), 3.91 (s, 3H), 2.70 (s, 3H), 1.37 (dt, J = 9.7, 7.2 Hz, 6H) |
| 484 | 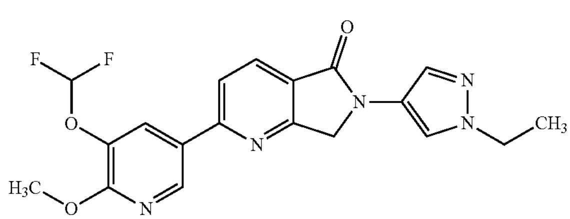 [SMILES: CCn1cc(N2Cc3nc(-c4cnc(OC)c(OC(F)F)c4)ccc3C2=O)cn1] | 402.68 | (DMSO-d₆) δ 8.90 (d, J = 2.0 Hz, 1H), 8.34 (d, J = 1.9 Hz, 1H), 8.27-8.11 (m, 3H), 7.82 (s, 1H), 7.33 (t, J = 73.6 Hz, 1H), 4.97 (s, 2H), 4.18 (q, J = 7.2 Hz, 2H), 4.03 (d, J = 5.4 Hz, 3H), 1.39 (t, J = 7.3 Hz, 3H) |

TABLE 1-continued

| Cmpd No. | Structure | ESMS (M + H) | ¹H NMR (300 MHz, unless indicated otherwise) |
|---|---|---|---|
| 485 | 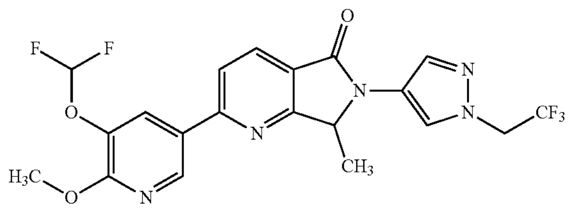 [SMILES: COc1ncc(-c2ccc3c(n2)C(C)N(c2cnn(CC(F)(F)F)c2)C3=O)cc1OC(F)F] | 470.65 | (DMSO-d$_6$) δ 8.92 (d, J = 2.0 Hz, 1H), 8.48-8.33 (m, 2H), 8.26 (t, J = 8.4 Hz, 2H), 7.98 (s, 1H), 7.33 (t, J = 73.6 Hz, 1H), 5.37-5.11 (m, 3H), 4.03 (s, 3H), 1.59 (d, J = 6.7 Hz, 3H) |
| 486 | 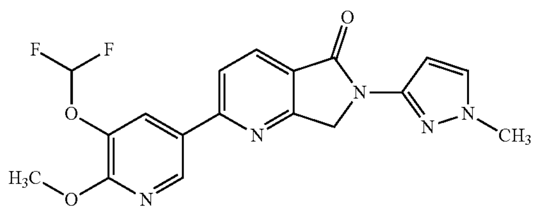 | 388.63 | |
| 487 | 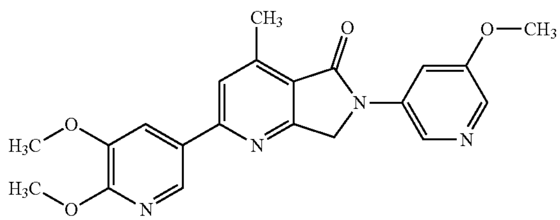 | 393.09 | (DMSO-d$_6$) δ 8.75 (d, J = 2.0 Hz, 1H), 8.53 (t, J = 8.9 Hz, 1H), 8.13 (d, J = 2.5 Hz, 1H), 8.02 (d, J = 4.6 Hz, 2H), 7.96 (d, J = 1.9 Hz, 1H), 5.09 (s, 2H), 3.98-3.84 (m, 9H), 2.72 (s, 3H) |
| 488 | 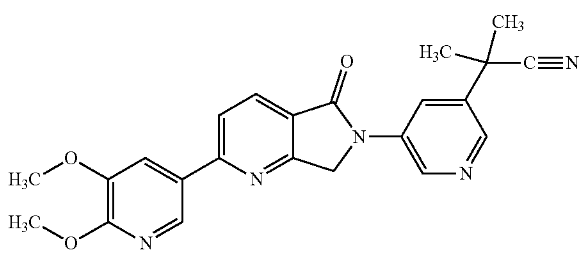 [SMILES: COc1cc(-c2ccc3c(n2)CN(c2cncc(C(C)(C)C#N)c2)C3=O)cnc1OC] | 416.13 | (CDCl$_3$) δ 8.96 (d, J = 2.4 Hz, 1H), 8.74 (t, J = 2.3 Hz, 1H), 8.66 (d, J = 2.1 Hz, 1H), 8.43 (d, J = 1.9 Hz, 1H), 8.25 (d, J = 8.2 Hz, 1H), 7.97-7.85 (m, 2H), 5.05 (s, 2H), 4.13 (s, 3H), 4.05 (s, 3H), 1.86 (s, 6H). |
| 489 | 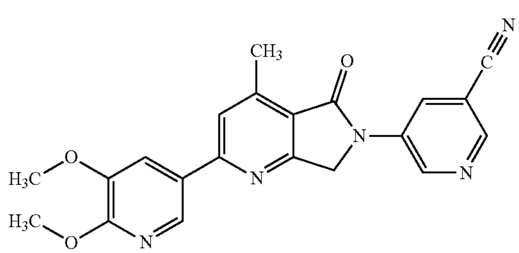 [SMILES: COc1cc(-c2cc(C)c3c(n2)CN(c2cncc(C#N)c2)C3=O)cnc1OC] | 388.04 | (DMSO-d$_6$) δ 9.46 (d, J = 2.5 Hz, 1H), 8.85-8.75 (m, 2H), 8.56 (d, J = 2.0 Hz, 1H), 8.06 (s, 1H), 7.95 (dd, J = 9.2, 2.0 Hz, 1H), 5.13 (s, 2H), 3.96-3.91 (m, 6H), 2.73 (s, 3H) |
| 490 | 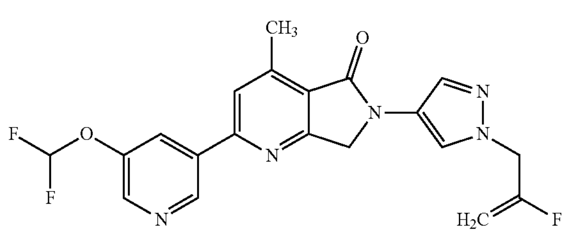 [SMILES: C=C(F)Cn1cc(N2Cc3nc(-c4cncc(OC(F)F)c4)cc(C)c3C2=O)cn1] | 416.13 | (DMSO-d$_6$) δ 9.27 (d, J = 1.7 Hz, 1H), 8.63 (d, J = 2.6 Hz, 1H), 8.39 (s, 1H), 8.27 (d, J = 8.7 Hz, 1H), 7.89 (s, 1H), 7.48 (t, J = 73.2 Hz, 1H), 5.06-4.62 (m, 6H), 2.76 (d, J = 9.1 Hz, 3H) |

TABLE 1-continued

| Cmpd No. | Structure | ESMS (M + H) | ¹H NMR (300 MHz, unless indicated otherwise) |
|---|---|---|---|
| 491 | 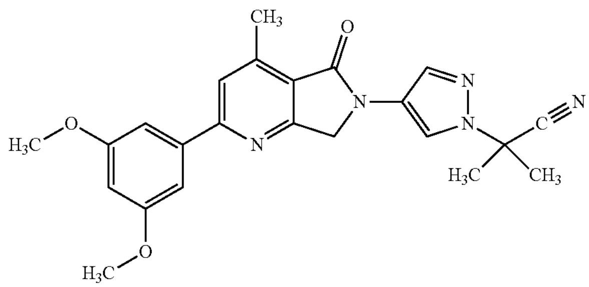 [SMILES: COc1cc(OC)cc(-c2cc(C)c3c(n2)CN(c2cnn(C(C)(C)C#N)c2)C3=O)c1] | 418 | (DMSO-d$_6$) δ 8.43 (s, 1H), 8.06 (s, 1H), 7.99 (s, 1H), 7.343 (2d, J = 2Hz, 2H), 6.63 (dd, J = 2Hz, 1H), 4.92 (s, 2H), 3.84 (s, 6H), 2.02 (s, 6H) |
| 492 | 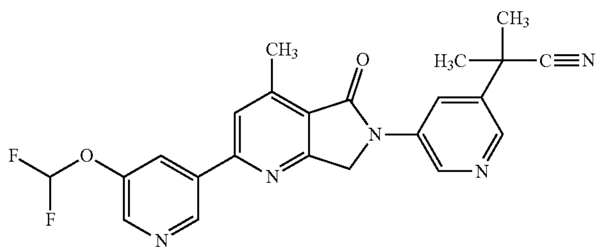 [SMILES: Cc1cc(-c2cncc(OC(F)F)c2)nc2c1C(=O)N(c1cncc(C(C)(C)C#N)c1)C2] | 436.12 | (CDCl$_3$) δ 9.15 (d, J = 1.8 Hz, 1H), 8.90 (d, J = 2.4 Hz, 1H), 8.78 (t, J = 2.3 Hz, 1H), 8.66 (d, J = 2.1 Hz, 1H), 8.62 (d, J = 2.6 Hz, 1H), 8.26 (s, 1H), 7.71 (s, 1H), 6.69 (t, 1H), 5.02 (s, 2H), 2.88 (s, 3H), 1.86 (s, 6H). |
| 493 | 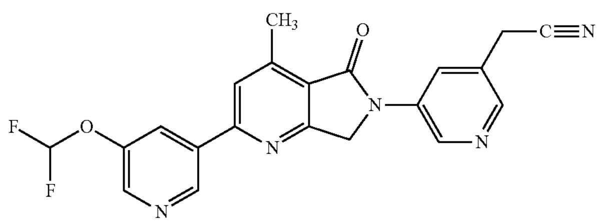 [SMILES: Cc1cc(-c2cncc(OC(F)F)c2)nc2c1C(=O)N(c1cncc(CC#N)c1)C2] | 408.46 | (DMSO-d$_6$) δ 9.29 (d, J = 1.6 Hz, 1H), 9.02 (d, J = 2.4 Hz, 1H), 8.64 (d, J = 2.6 Hz, 1H), 8.57 (s, 1H), 8.39 (d, J = 1.7 Hz, 2H), 8.21 (s, 1H), 7.72-7.23(F coupling) (t, 1H), 5.17 (s, 2H), 4.20 (s, 2H), 2.77 (s, 3H) |
| 494 | 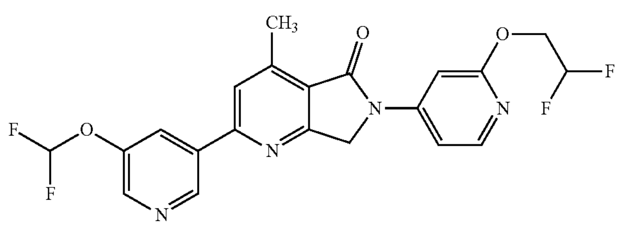 [SMILES: Cc1cc(-c2cncc(OC(F)F)c2)nc2c1C(=O)N(c1ccnc(OCC(F)F)c1)C2] | 449.48 | (DMSO-d$_6$) δ 9.28 (d, J = 1.7 Hz, 1H), 8.64 (d, J = 2.7 Hz, 1H), 8.42-8.33 (m, 1H), 8.19 (d, J = 6.1 Hz, 2H), 7.78-7.66 (m, 1H), 7.47 (s, 1H), 7.41 (d, J = 1.8 Hz, 1H), 7.23 (s, 1H), 6.60-6.24 (F coupling 1H) (t, J = 3.5 Hz, 1H), 6.42 (s, 1H), 6.24 (t, J = 3.5 Hz, 1H), 5.10 (s, 2H), 4.60 (td, J = 15.1, 3.5 Hz, 2H), 2.76 (s, 3H) |
| 495 | 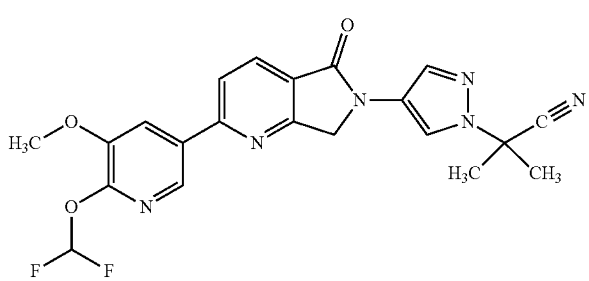 [SMILES: COc1cc(-c2ccc3c(n2)CN(c2cnn(C(C)(C)C#N)c2)C3=O)cnc1OC(F)F] | 441.03 | (DMSO-d$_6$) δ 8.42 (s, 1H), 8.28 (d, J = 2.0 Hz, 1H), 8.22 (s, 2H), 8.06 (s, 1H), 8.01 (t, J = 59.4 Hz, 1H), 7.66 (d, J = 2.0 Hz, 1H), 4.99 (s, 2H), 3.91 (s, 3H), 2.02 (s, 6H) |

TABLE 1-continued

| Cmpd No. | Structure | ESMS (M + H) | ¹H NMR (300 MHz, unless indicated otherwise) |
|---|---|---|---|
| 496 | 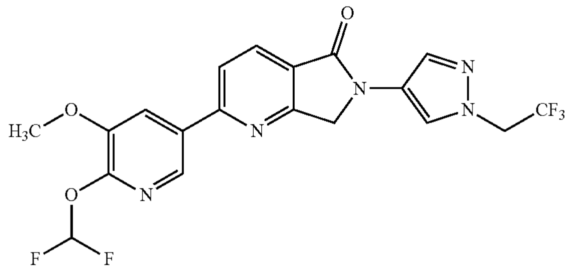 [SMILES: COc1cc(-c2ccc3c(n2)CN(c2cnn(CC(F)(F)F)c2)C3=O)cnc1OC(F)F] | 455.98 | (DMSO-d₆) δ 8.41 (m, 1H), 8.27 (s, 1H), 8.22 (s, 2H), 8.02 (t, J = 59.1 Hz), 7.93 (s, 1H), 7.66 (m, 1H), 5.22 (q, J = 9.1 Hz, 2H), 5.00 (s, 2H), 3.91 (s, 3H) |
| 497 | 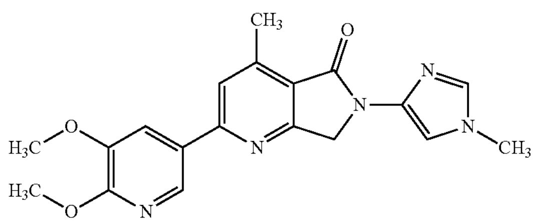 | 366.12 | (DMSO-d₆) δ 8.54 (d, J = 1.9 Hz, 1H), 8.07-7.95 (m, 2H), 7.53 (d, J = 10.6 Hz, 2H), 4.93 (s, 2H), 3.95 (s, 3H), 3.92 (s, 3H), 3.70 (s, 3H), 2.72 (s, 3H) |
| 498 | 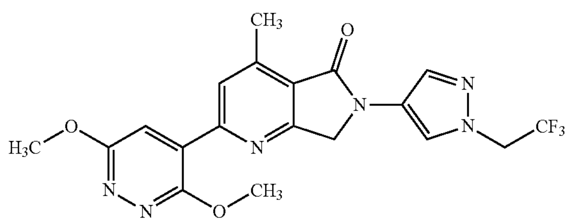 [SMILES: COc1cc(-c2cc(C)c3c(n2)CN(c2cnn(CC(F)(F)F)c2)C3=O)c(OC)nn1] | 435.16 | (DMSO-d₆) δ 8.40 (s, 1H), 7.97 (d, J = 6.6 Hz, 2H), 7.58 (s, 1H), 5.21 (dd, J = 18.2, 8.9 Hz, 2H), 4.94 (s, 2H), 4.08 (s, 3H), 4.02 (s, 3H), 2.74 (s, 3H) |
| 499 | 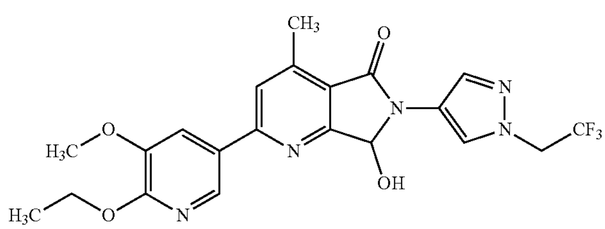 | 464.51 | |
| 500 | 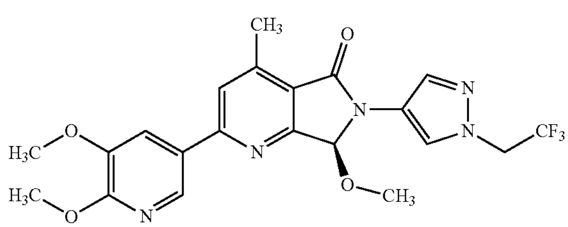 [SMILES: COc1cc(-c2cc(C)c3c(n2)[C@H](OC)N(c2cnn(CC(F)(F)F)c2)C3=O)cnc1OC] | 464.51 | |
| 501 | 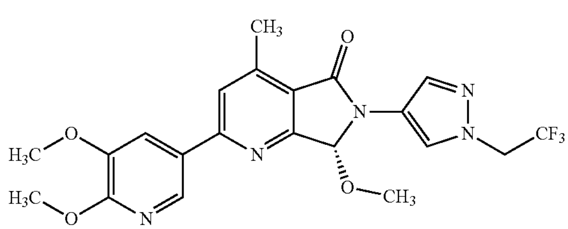 [SMILES: COc1cc(-c2cc(C)c3c(n2)[C@@H](OC)N(c2cnn(CC(F)(F)F)c2)C3=O)cnc1OC] | 464.58 | |

TABLE 1-continued

| Cmpd No. | Structure | ESMS (M + H) | ¹H NMR (300 MHz, unless indicated otherwise) |
|---|---|---|---|
| 502 | 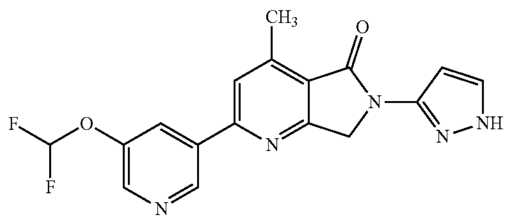 [SMILES: Cc1cc(-c2cncc(OC(F)F)c2)nc2c1C(=O)N(c1cc[nH]n1)C2] | 358.26 | (DMSO-d$_6$) δ 9.28 (s, 1H), 8.63 (d, J = 2.4 Hz, 1H), 8.39 (s, 1H), 8.16 (s, 1H), 7.78 (d, J = 2.3 Hz, 1H), 7.48 (t, J = 73.3 Hz, 1H), 6.83 (d, J = 2.3 Hz, 1H), 4.99 (s, 2H), 2.76 (s, 3H) |
| 503 | 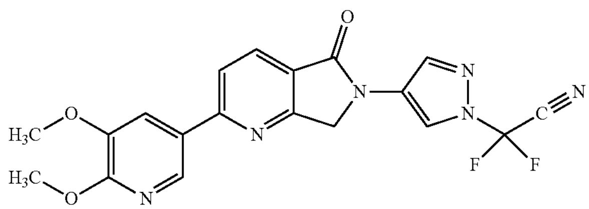 [SMILES: COc1cc(-c2ccc3c(n2)CN(c2cnn(C(F)(F)C#N)c2)C3=O)cnc1OC] | 413.15 | (DMSO-d$_6$) δ 8.83 (s, 1H), 8.56 (m, 2H), 8.35-8.12 (m, 2H), 7.98 (s, 1H), 5.03 (s, 2H), 3.95 (s, 3H), (3.92 (s, 3H) |
| 504 | 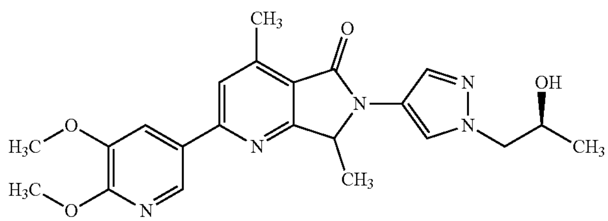 [SMILES: COc1cc(-c2cc(C)c3c(n2)C(C)N(c2cnn(C[C@H](C)O)c2)C3=O)cnc1OC] | 424.52 | |
| 505 | 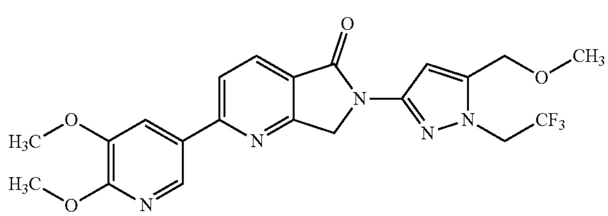 | 464.51 | (CDCl$_3$) δ 8.41 (d, J = 2.0 Hz, 1H), 8.22 (d, J = 8.1 Hz, 1H), 7.94 (d, J = 1.9 Hz, 1H), 7.86 (d, J = 8.2 Hz, 1H), 7.11 (s, 1H), 5.04 (s, 2H), 4.81 (q, J = 8.5 Hz, 2H), 4.57 (s, 2H), 4.13 (s, 2H), 4.04 (s, 3H), 3.40 (s, 3H). |
| 506 | 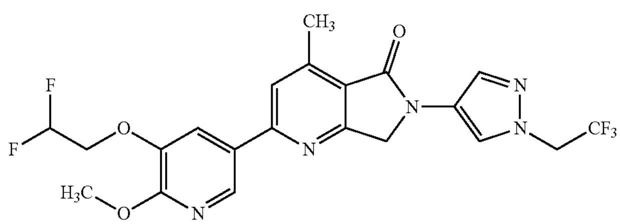 [SMILES: COc1ncc(-c2cc(C)c3c(n2)CN(c2cnn(CC(F)(F)F)c2)C3=O)cc1OCC(F)F] | 484.54 | |
| 507 | 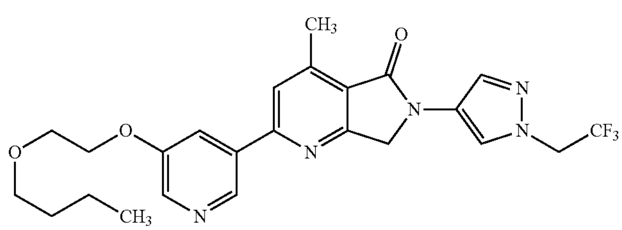 [SMILES: CCCCOCCOc1cncc(-c2cc(C)c3c(n2)CN(c2cnn(CC(F)(F)F)c2)C3=O)c1] | 490.62 | |
| 508 | 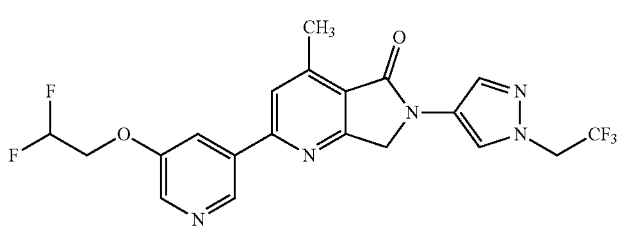 [SMILES: Cc1cc(-c2cncc(OCC(F)F)c2)nc2c1C(=O)N(c1cnn(CC(F)(F)F)c1)C2] | 454.47 | (DMSO-d$_6$) δ 9.10 (d, J = 1.6 Hz, 1H), 8.60 (d, J = 2.7 Hz, 1H), 8.40 (s, 1H), 8.36 (d, J = 1.9 Hz, 1H), 8.19 (s, 1H), 7.96 (s, 1H), 6.70-6.29 (m, 1H), 5.21 (q, J = 9.1 Hz, 2H), 4.96 (s, 2H), 4.62 (td, J = 14.7, 3.4 Hz, 2H), 2.74 (d, 3H) |

TABLE 1-continued

| Cmpd No. | Structure | ESMS (M + H) | ¹H NMR (300 MHz, unless indicated otherwise) |
|---|---|---|---|
| 509 | 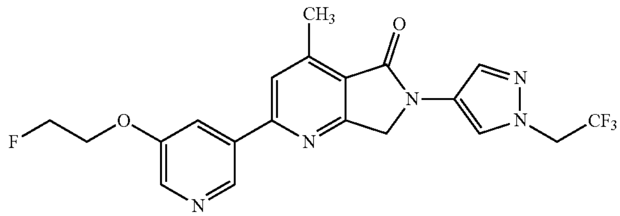 [SMILES: Cc1cc(-c2cncc(OCCF)c2)nc2c1C(=O)N(c1cnn(CC(F)(F)F)c1)C2] | 436.49 | |
| 510 | 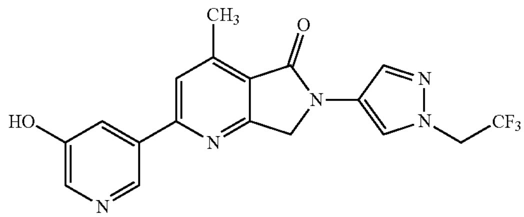 [SMILES: Cc1cc(-c2cncc(O)c2)nc2c1C(=O)N(c1cnn(CC(F)(F)F)c1)C2] | 390.42 | |
| 511 | 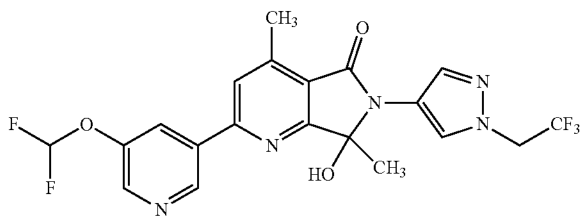 [SMILES: Cc1cc(-c2cncc(OC(F)F)c2)nc2c1C(=O)N(c1cnn(CC(F)(F)F)c1)C2(C)O] | 470.39 | (DMSO-d₆) δ 9.29 (s, 1H), 8.64 (s, 1H), 8.39 (d, J = 2.0 Hz, 1H), 8.29 (s, 1H), 8.19 (s, 1H), 7.97 (s, 1H), 7.47 (t, J = 73.3 Hz, 1H), 6.97 (s, 1H), 5.22 (q, J = 9.2 Hz, 2H), 2.74 (s, 3H), 1.72 (s, 3H) |
| 512 | 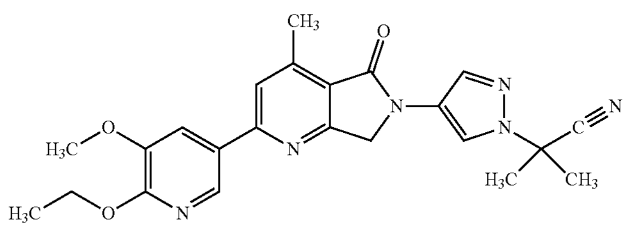 [SMILES: CCOc1ncc(-c2cc(C)c3c(n2)CN(c2cnn(C(C)(C)C#N)c2)C3=O)cc1OC] | 433 | (CDCl₃) δ 8.43 (s, 1H), 8.35 (d, 1H, J = 2 Hz), 7.86 (d, 1H, J = 2 Hz), 7.77 (s, 1H), 7.57 (s, 1H), 4.79 (s, 2H), 4.54 (quart, 2H), 4.01 (s, 3H), 2.81 (s, 3H), 2.05 (s, 6H), 1.49 (t, 3H) |
| 513 | 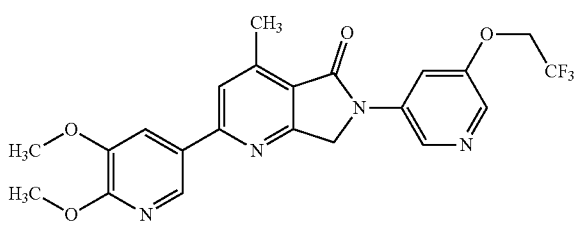 [SMILES: COc1cc(-c2cc(C)c3c(n2)CN(c2cncc(OCC(F)(F)F)c2)C3=O)cnc1OC] | 461.51 | (DMSO-d₆) δ 8.93 (d, J = 1.9 Hz, 1H), 8.56 (d, J = 1.9 Hz, 1H), 8.24 (t, J = 5.7 Hz, 1H), 8.15-7.93 (m, 3H), 5.11 (s, 2H), 4.95 (q, J = 8.8 Hz, 2H), 3.91 (dd, J = 12.2, 6.7 Hz, 6H), 2.76 (d, J = 20.1 Hz, 3H) |
| 514 | 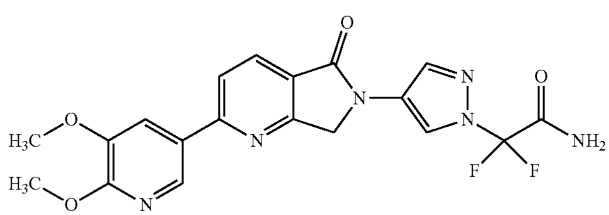 [SMILES: COc1cc(-c2ccc3c(n2)CN(c2cnn(C(F)(F)C(N)=O)c2)C3=O)cnc1OC] | 431.5 | (DMSO-d₆) δ 8.72 (s, 1H), 8.57 (s, 2H), 8.47 (s, 1H), 8.37-8.13 (m, 3H), 8.00 (s, 2H), 5.05 (s, 2H), 3.96 (s, 3H), 3.92 (s, 3H) |
| 515 | 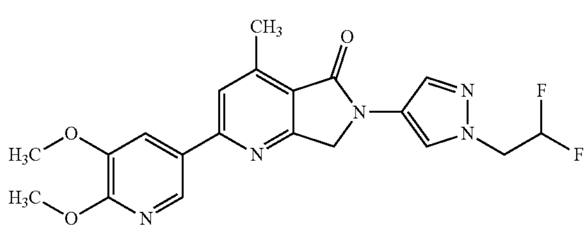 [SMILES: COc1cc(-c2cc(C)c3c(n2)CN(c2cnn(CC(F)F)c2)C3=O)cnc1OC] | 416.25 | (DMSO-d₆) δ 8.54 (d, J = 1.9 Hz, 1H), 8.30 (s, 1H), 8.05-7.93 (m, 2H), 7.89 (s, 1H), 6.38 (tt, J = 54.9, 3.6 Hz, 1H), 4.90 (s, 2H), 4.68 (d, J = 3.7 Hz, 2H), 3.95 (s, 3H), 3.91 (s, 3H), 2.71 (s, 3H) |

TABLE 1-continued

| Cmpd No. | Structure | ESMS (M + H) | ¹H NMR (300 MHz, unless indicated otherwise) |
|---|---|---|---|
| 516 | 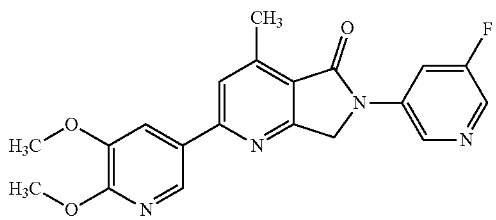 [SMILES: COc1cc(-c2cc(C)c3c(n2)CN(c2cncc(F)c2)C3=O)cnc1OC] | 381.41 | |
| 517 | 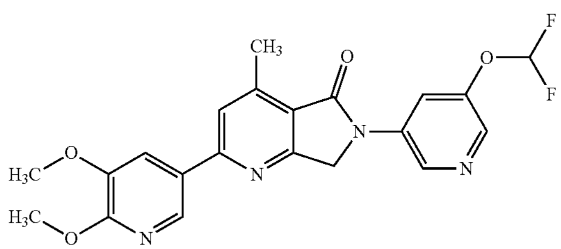 [SMILES: COc1cc(-c2cc(C)c3c(n2)CN(c2cncc(OC(F)F)c2)C3=O)cnc1OC] | 429.1 | |
| 518 | 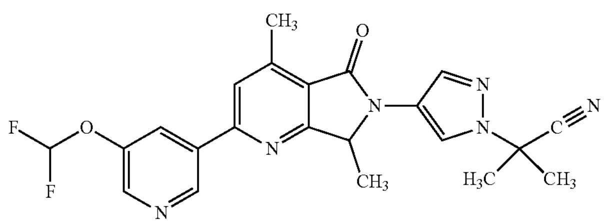 [SMILES: Cc1cc(-c2cncc(OC(F)F)c2)nc2c1C(=O)N(c1cnn(C(C)(C)C#N)c1)C2C] | 439 | |
| 519 | 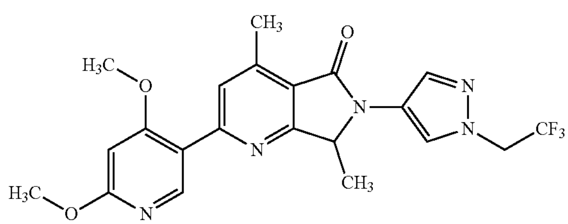 [SMILES: COc1cc(OC)c(-c2cc(C)c3c(n2)C(C)N(c2cnn(CC(F)(F)F)c2)C3=O)cn1] | 448.52 | (CDCl₃) δ 8.73 (s, 1H), 8.29 (s, 1H), 7.80 (s, 1H), 7.66 (s, 1H), 6.46 (s, 1H), 5.02 (q, J = 6.6 Hz, 1H), 4.78 (q, J = 8.3 Hz, 2H), 4.14 (s, 3H), 4.05 (s, 3H), 2.83 (s, 3H), 1.70 (d, J = 6.7 Hz, 3H) |
| 520 | 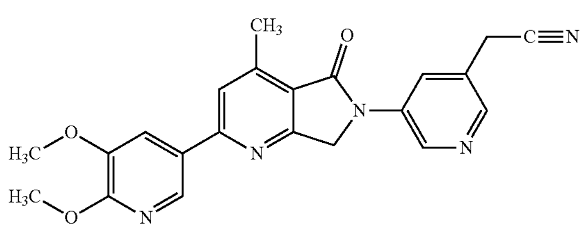 [SMILES: COc1cc(-c2cc(C)c3c(n2)CN(c2cncc(CC#N)c2)C3=O)cnc1OC] | 402.19 | (DMSO-d₆) δ 9.01 (d, J = 2.4 Hz, 1H), 8.57 (d, J = 1.8 Hz, 2H), 8.38 (d, J = 1.8 Hz, 1H), 8.17 (s, 1H), 8.05 (s, 1H), 7.98 (d, J = 1.9 Hz, 1H), 5.13 (s, 2H), 4.19 (s, 2H), 3.94 (d, J = 9.9 Hz, 6H), 2.74 (s, 3H) |
| 521 | 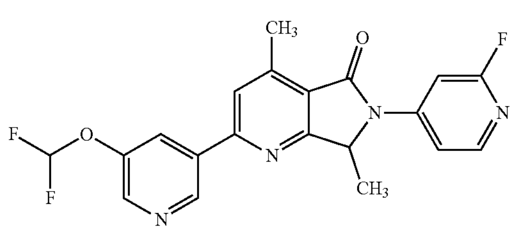 [SMILES: Cc1cc(-c2cncc(OC(F)F)c2)nc2c1C(=O)N(c1ccnc(F)c1)C2C] | 401.49 | (CDCl₃) δ 9.18 (d, J = 1.8 Hz, 1H), 8.62 (d, J = 2.6 Hz, 1H), 8.34-8.20 (m, 2H), 7.71 (s, 1H), 7.62-7.53 (m, 1H), 7.50 (d, J = 1.8 Hz, 1H), 6.93-6.45 (t, 1H F spliting), 5.24 (q, J = 6.6 Hz, 1H), 2.88 (s, 3H), 1.73 (d, J = 6.6 Hz, 3H) |

TABLE 1-continued

| Cmpd No. | Structure | ESMS (M + H) | ¹H NMR (300 MHz, unless indicated otherwise) |
|---|---|---|---|
| 522 | 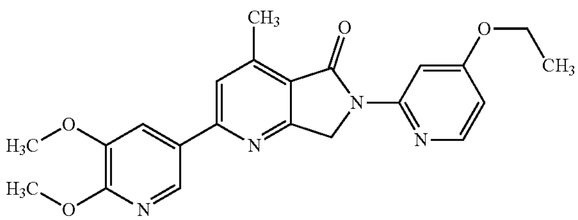 [SMILES: CCOc1ccnc(N2Cc3nc(-c4cnc(OC)c(OC)c4)cc(C)c3C2=O)c1] | 407.57 | |
| 523 | 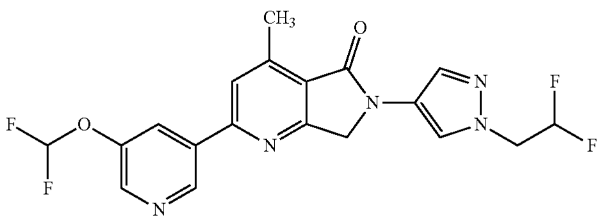 [SMILES: Cc1cc(-c2cncc(OC(F)F)c2)nc2c1C(=O)N(c1cnn(CC(F)F)c1)C2] | 422.33 | (DMSO-d₆) δ 9.27 (d, J = 1.7 Hz, 1H), 8.63 (d, J = 2.6 Hz, 1H), 8.43-8.36 (m, 1H), 8.32 (s, 1H), 8.17 (s, 1H), 7.91 (d, J = 0.5 Hz, 1H), 7.48 (t, J = 73.2 Hz, 1H), 6.40 (ddt, J = 58.6, 55.0, 3.7 Hz, 1H), 4.95 (s, 2H), 4.68 (td, J = 15.1, 3.6 Hz, 2H), 2.75 (s, 3H) |
| 524 | 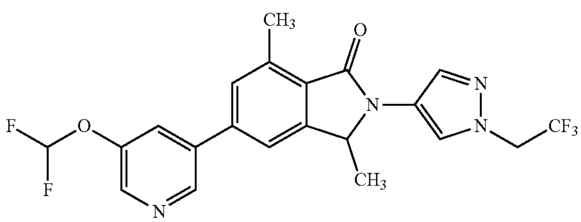 [SMILES: Cc1cc(-c2cncc(OC(F)F)c2)cc2c1C(=O)N(c1cnn(CC(F)(F)F)c1)C2C] | 453.25 | |
| 525 | 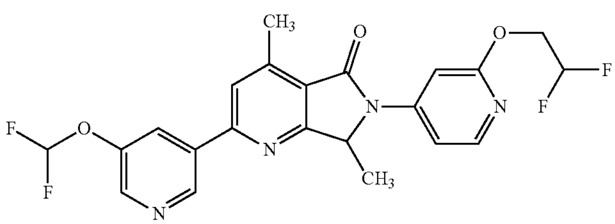 [SMILES: Cc1cc(-c2cncc(OC(F)F)c2)nc2c1C(=O)N(c1ccnc(OCC(F)F)c1)C2C] | 463.55 | (CDCl₃) δ 9.18 (s, 1H), 8.62 (d, J = 1.7 Hz, 1H), 8.30 (s, 1H), 8.20 (d, J = 5.9 Hz, 1H), 7.70 (s, 1H), 7.50 (dd, J = 5.9, 1.9 Hz, 1H), 7.18 (d, J = 1.8 Hz, 1H), 6.94 (s, 0H), 6.70 (s, 1H), 6.46 (s, 0H), 6.18 (tt, J = 55.6, 4.2 Hz, 1H), 5.22 (q, J = 6.6 Hz, 1H), 4.60 (td, J = 13.6, 4.2 Hz, 2H), 3.52 (s, 0H), 2.87 (s, 3H), 1.70 (d, J = 6.7 Hz, 3H) |
| 526 | 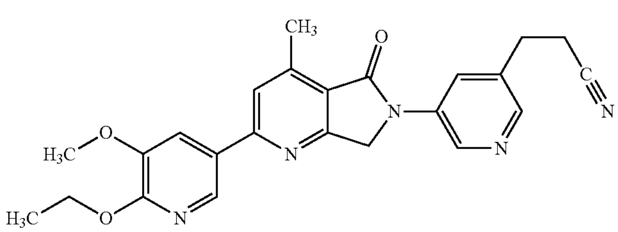 [SMILES: CCOc1ncc(-c2cc(C)c3c(n2)CN(c2cncc(CCC#N)c2)C3=O)cc1OC] | 416.59 | (CDCl₃) δ 8.93 (d, J = 2.2 Hz, 1H), 8.68 (s, 1H), 8.46 (s, 1H), 8.38 (d, J = 1.9 Hz, 1H), 7.88 (d, J = 1.9 Hz, 1H), 7.66-7.61 (m, 1H), 4.97 (s, 2H), 4.57 (q, J = 7.1 Hz, 2H), 4.04 (s, 3H), 3.87 (s, 2H), 2.83 (s, 3H), 1.52 (t, J = 7.1 Hz, 3H) |
| 527 | 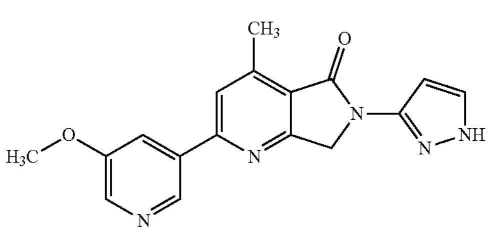 [SMILES: COc1cncc(-c2cc(C)c3c(n2)CN(c2cc[nH]n2)C3=O)c1] | 322.33 | (CDCl₃) δ 9.25 (s, 1H), 8.83 (s, 1H), 8.65 (d, J = 2.6 Hz, 1H), 8.05 (s, 1H), 7.76 (d, J = 2.6 Hz, 1H), 6.98 (d, J = 2.6 Hz, 1H), 5.07 (s, 2H), 4.19 (s, 3H), 2.90 (s, 3H) |

TABLE 1-continued

| Cmpd No. | Structure | ESMS (M + H) | ¹H NMR (300 MHz, unless indicated otherwise) |
|---|---|---|---|
| 528 | 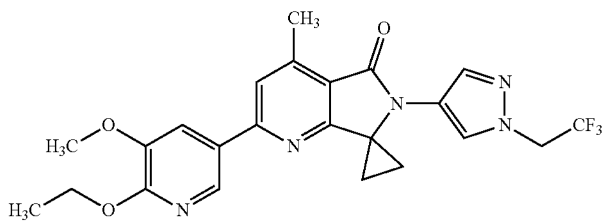 [SMILES: CCOc1ncc(-c2cc(C)c3c(n2)C2(CC2)N(c2cnn(CC(F)(F)F)c2)C3=O)cc1OC] | 474.47 | |
| 529 | 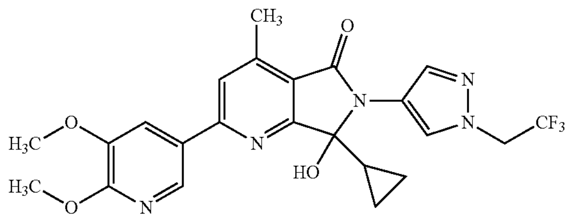 [SMILES: COc1cc(-c2cc(C)c3c(n2)C(O)(C2CC2)N(c2cnn(CC(F)(F)F)c2)C3=O)cnc1OC] | 490.55 | |
| 530 | 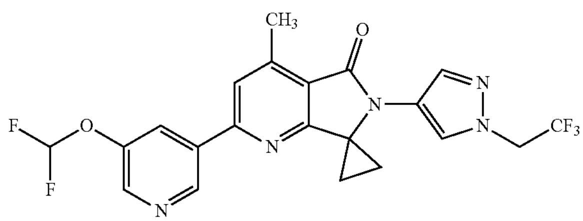 [SMILES: Cc1cc(-c2cncc(OC(F)F)c2)nc2c1C(=O)N(c1cnn(CC(F)(F)F)c1)C21CC1] | 466.44 | |
| 531 | 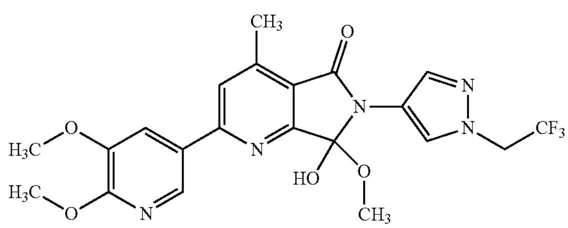 [SMILES: COc1cc(-c2cc(C)c3c(n2)C(O)(OC)N(c2cnn(CC(F)(F)F)c2)C3=O)cnc1OC] | 478.44 | |
| 532 | 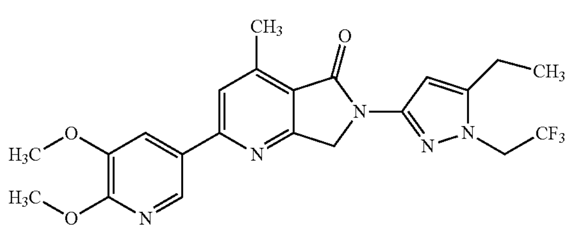 [SMILES: CCc1cc(N2Cc3nc(-c4cnc(OC)c(OC)c4)cc(C)c3C2=O)nn1CC(F)(F)F] | 462.59 | (CDCl$_3$) δ 8.43-8.31 (m, 1H), 7.96-7.82 (m, 1H), 7.60-7.50 (m, 1H), 6.94 (t, J = 3.1 Hz, 1H), 5.02-4.86 (m, 2H), 4.70-4.50 (m, 2H), 4.12 (s, 3H), 4.04 (s, 3H), 2.83 (s, 3H), 2.68 (tt, J = 7.7, 3.8 Hz, 2H), 1.45-1.32 (t, 3H) |
| 533 | 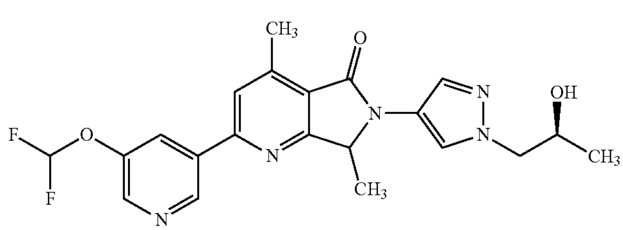 [SMILES: Cc1cc(-c2cncc(OC(F)F)c2)nc2c1C(=O)N(c1cnn(C[C@H](C)O)c1)C2C] | 430.54 | (CDCl$_3$) δ 9.11 (dd, J = 4.0, 1.8 Hz, 1H), 8.56 (s, 1H), 8.21 (d, J = 2.1 Hz, 1H), 8.14 (d, J = 8.0 Hz, 1H), 7.73-7.56 (m, 2H), 6.67 (dd, J = 72.9, 72.2 Hz, 1H), 5.02-4.82 (m, 1H), 4.35-4.14 (m, 2H), 4.04 (ddd, J = 13.7, 7.9, 1.6 Hz, 1H), 3.53 (dd, J = 28.4, 3.7 Hz, 1H), 2.83 (s, 3H), 1.72-1.59 (m, 3H), 1.27 (d, J = 6.3 Hz, 3H) |

TABLE 1-continued

| Cmpd No. | Structure | ESMS (M + H) | ¹H NMR (300 MHz, unless indicated otherwise) |
|---|---|---|---|
| 534 | 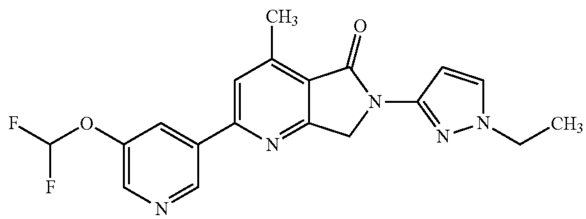 [SMILES: CCn1ccc(N2Cc3nc(-c4cncc(OC(F)F)c4)cc(C)c3C2=O)n1] | 386.52 | (CDCl₃) δ 8.59 (d, J = 2.6 Hz, 1H), 8.24 (s, 1H), 7.64 (s, 1H), 7.41 (d, J = 2.3 Hz, 1H), 6.98 (t, J = 3.5 Hz, 1H), 6.68 (t, J = 72.6 Hz, 1H), 5.02 (s,, 2H), 4.17 (q, J = 7.3 Hz, 2H), 2.88 (s, 3H), 1.53 (t, J = 7.3 Hz, 3H) |
| 535 | 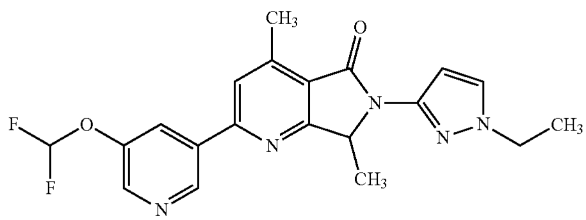 [SMILES: CCn1ccc(N2C(=O)c3c(C)cc(-c4cncc(OC(F)F)c4)nc3C2C)n1] | 400.53 | (CDCl₃) δ 8.59 (d, J = 2.6 Hz, 1H), 8.25 (dd, J = 2.5, 1.9 Hz, 1H), 7.63 (s, 1H), 7.41 (d, J = 2.3 Hz, 1H), 6.94 (d, J = 2.3 Hz, 1H), 6.68 (t, J = 72.6 Hz, 1H), 5.29 (q, J = 6.6 Hz, 1H), 4.18 (q, J = 7.3 Hz, 2H), 2.87 (s, 3H), 1.79 (d, J = 6.7 Hz, 3H), 1.53 (dd, J = 9.1, 5.5 Hz, 3H) |
| 536 | 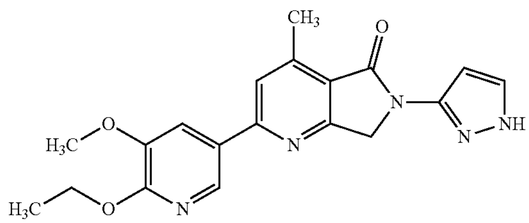 [SMILES: CCOc1ncc(-c2cc(C)c3c(n2)CN(c2cc[nH]n2)C3=O)cc1OC] | 366.49 | (DMSO-d₆) δ 12.59 (s, 1H), 8.53 (d, J = 1.9 Hz, 1H), 8.08-7.93 (m, 2H), 7.77 (s, 1H), 6.81 (d, J = 10.3 Hz, 1H), 4.95 (s, 2H), 4.41 (d, J = 7.0 Hz, 2H), 3.92 (s, 3H), 2.72 (s, 3H), 1.36 (t, J = 7.0 Hz, 3H) |
| 537 | 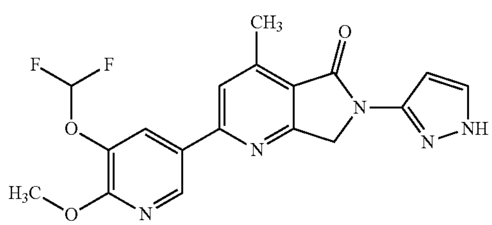 [SMILES: COc1ncc(-c2cc(C)c3c(n2)CN(c2cc[nH]n2)C3=O)cc1OC(F)F] | 388.5 | (DMSO-d₆) δ 12.60 (s, 1H), 8.88 (d, J = 2.0 Hz, 1H), 8.33 (d, J = 1.6 Hz, 1H), 8.03 (s, 1H), 7.77 (d, J = 2.0 Hz, 1H), 7.20 (d, J = 73.6 Hz, 1H), 6.82 (d, J = 1.8 Hz, 1H), 4.96 (s, 2H), 4.02 (s, 3H), 2.73 (s, 3H) |
| 538 | 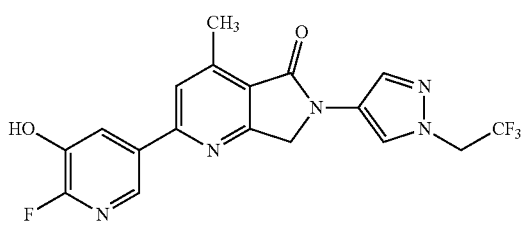 [SMILES: Cc1cc(-c2cnc(F)c(O)c2)nc2c1C(=O)N(c1cnn(CC(F)(F)F)c1)C2] | 407.4 | (DMSO-d₆) δ 8.37 (s, 1H), 7.95 (s, 1H), 7.85 (dd, J = 7.8, 3.0 Hz, 1H), 7.60 (ddd, J = 8.4, 4.2, 2.2 Hz, 1H), 7.28 (dd, J = 11.0, 8.6 Hz, 1H), 5.76 (s, 1H), 5.20 (q, J = 9.1 Hz, 2H), 4.89 (d, J = 10.6 Hz, 2H), 2.80-2.62 (m, 3H) |
| 539 | 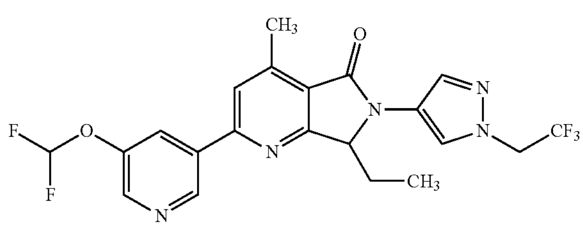 [SMILES: CCC1c2nc(-c3cncc(OC(F)F)c3)cc(C)c2C(=O)N1c1cnn(CC(F)(F)F)c1] | 468 | |

TABLE 1-continued

| Cmpd No. | Structure | ESMS (M + H) | ¹H NMR (300 MHz, unless indicated otherwise) |
|---|---|---|---|
| 540 | 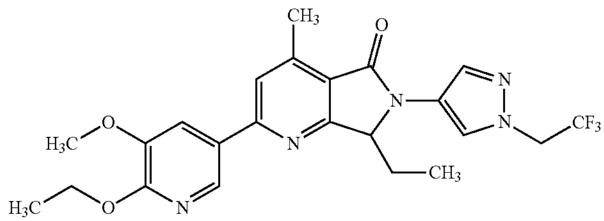 [SMILES: CCOc1ncc(-c2cc(C)c3c(n2)C(CC)N(c2cnn(CC(F)(F)F)c2)C3=O)cc1OC] | 476 | (DMSO-d$_6$) δ 8.55 (d, JJ = 2.0 Hz, 1H), 8.36 (s, 1H), 8.00 (s, 1H), 7.98 (d, J2Hz, 1H), 7.96 (s, 1H), 5.21 (m, 3H-methyne and the methylene of the CF3 ethyl), 4.40 (quart, 2H), 3.92 (s, 3H), 2.73 (s, 3H), 2.22 and 2.11 (m, 2H - methylene of C3), 1.36 (t, 3H), 0.47 (t, 3H) |
| 541 | 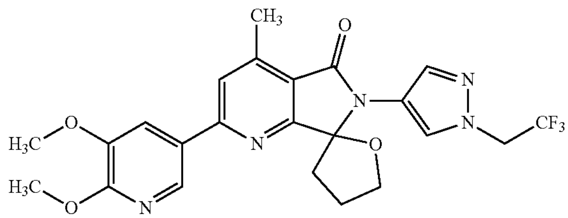 [SMILES: COc1cc(-c2cc(C)c3c(n2)C2(CCCO2)N(c2cnn(CC(F)(F)F)c2)C3=O)cnc1OC] | 490.55 | |
| 542 | 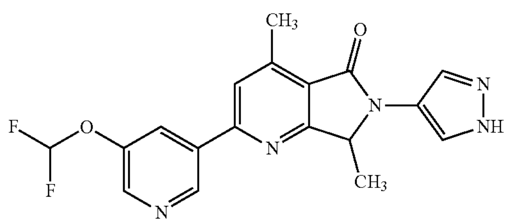 [SMILES: Cc1cc(-c2cncc(OC(F)F)c2)nc2c1C(=O)N(c1cn[nH]c1)C2C] | 372.25 | (DMSO-d$_6$) δ 12.94 (s, 1H), 9.28 (d, J = 1.7 Hz, 1H), 8.62 (d, J = 2.6 Hz, 1H), 8.38 (s, 1H), 8.15 (s, 2H), 7.92 (s, 1H), 7.47 (t, J = 73.3 Hz, 1H), 5.17 (q, J = 6.5 Hz, 1H), 2.75 (s, 3H), 1.56 (d, J = 6.6 Hz, 3H) |
| 543 | 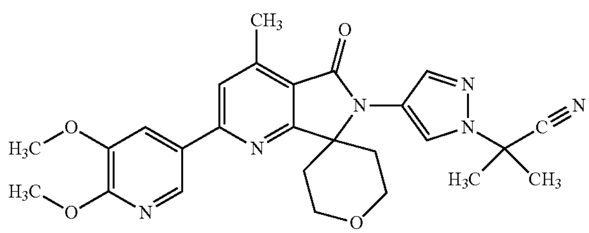 [SMILES: COc1cc(-c2cc(C)c3c(n2)C2(CCOCC2)N(c2cnn(C(C)(C)C#N)c2)C3=O)cnc1OC] | 489.55 | |
| 544 | 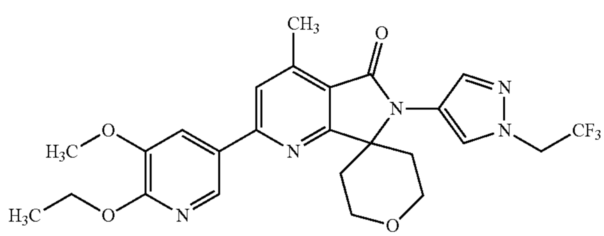 [SMILES: CCOc1ncc(-c2cc(C)c3c(n2)C2(CCOCC2)N(c2cnn(CC(F)(F)F)c2)C3=O)cc1OC] | 518.51 | |
| 545 | 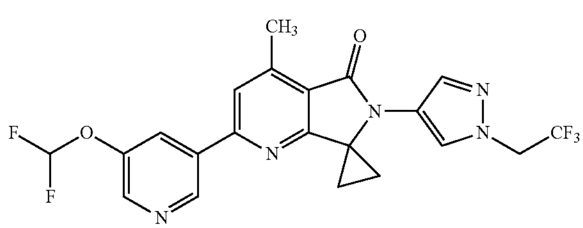 [SMILES: Cc1cc(-c2cncc(OC(F)F)c2)nc2c1C(=O)N(c1cnn(CC(F)(F)F)c1)C21CC1] | 412.49 | |

TABLE 1-continued

| Cmpd No. | Structure | ESMS (M + H) | ¹H NMR (300 MHz, unless indicated otherwise) |
|---|---|---|---|
| 546 | 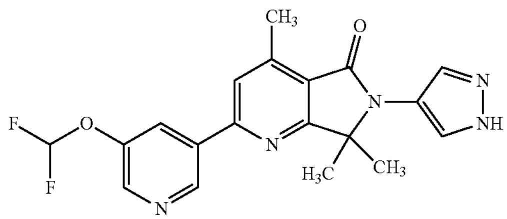 [SMILES: Cc1cc(-c2cncc(OC(F)F)c2)nc2c1C(=O)N(c1cn[nH]c1)C2(C)C] | 386.26 | (DMSO-d₆) δ 12.70 (br s, 1H), 9.30 (s, 1H), 8.62 (d, J = 2.4 Hz, 1H), 8.40 (s, 1H), 8.13 (s, 1H), 7.93 (s, 2H), 7.47 (t, J = 73.3 Hz, 1H), 2.74 (s, 3H), 1.57 (s, 6H) |
| 547 | 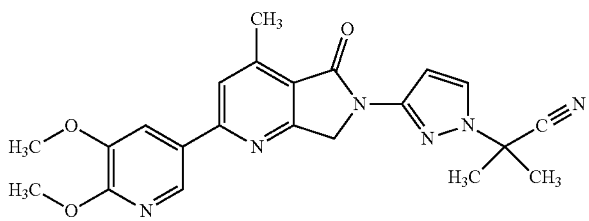 [SMILES: COc1cc(-c2cc(C)c3c(n2)CN(c2ccn(C(C)(C)C#N)n2)C3=O)cnc1OC] | 419 | (CDCl₃) δ 8.70 (d, J = 2 Hz, 1H), 7.91 (d, J = 2 Hz, 1H), 7.65 (d, J = 2.5 Hz, 1H), 7.57 (s, 1H), 7.08 (d, J = 2.5 Hz, 1H), 5.00 (s, 2H), 4.11 (s, 3H), 4.03 (s, 3H), 2.82 (s, 3H), 2.02 (s, 6H) |
| 548 | 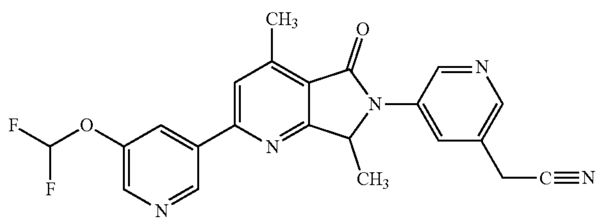 [SMILES: Cc1cc(-c2cncc(OC(F)F)c2)nc2c1C(=O)N(c1cncc(CC#N)c1)C2C] | 422.54 | (CDCl₃) δ 9.09 (d, J = 1.8 Hz, 1H), 8.70 (d, J = 2.4 Hz, 1H), 8.53 (d, J = 2.6 Hz, 1H), 8.41 (d, J = 2.0 Hz, 1H), 8.27 (t, J = 2.2 Hz, 1H), 8.18 (dd, J = 2.5, 2.0 Hz, 1H), 7.62 (s, 1H), 6.60 (t, J = 72.5 Hz, 1H), 5.25 (d, J = 6.7 Hz, 1H), 3.79 (s, 2H), 2.79 (s, 3H), 1.59 (d, J = 6.7 Hz, 3H), 1.52 (s, 5H). |
| 549 | 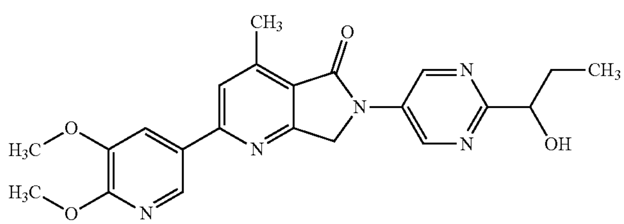 [SMILES: CCC(O)c1ncc(N2Cc3nc(-c4cnc(OC)c(OC)c4)cc(C)c3C2=O)cn1] | 422.6 | |
| 550 | 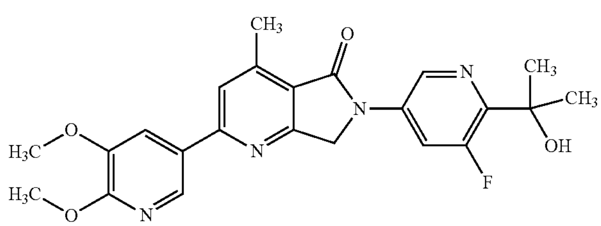 [SMILES: COc1cc(-c2cc(C)c3c(n2)CN(c2cnc(C(C)(C)O)c(F)c2)C3=O)cnc1OC] | 439.56 | (DMSO-d₆) δ 8.89 (s, 1H), 8.57 (d, J = 1.9 Hz, 1H), 8.34 (dd, J = 13.9, 2.0 Hz, 1H), 8.06 (s, 1H), 7.98 (d, J = 1.9 Hz, 1H), 5.26 (s, 1H), 5.13 (s, 2H), 3.94 (d, J = 10.3 Hz, 6H), 2.74 (s, 3H), 1.53 (s, 6H) |
| 551 | 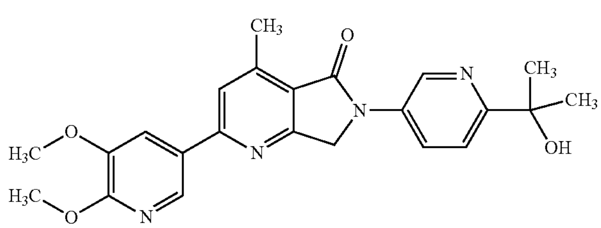 [SMILES: COc1cc(-c2cc(C)c3c(n2)CN(c2ccc(C(C)(C)O)nc2)C3=O)cnc1OC] | 421.42 | (DMSO-d₆) δ 8.98 (d, J = 2.3 Hz, 1H), 8.56 (d, J = 1.9 Hz, 1H), 8.36 (dd, J = 8.7, 2.7 Hz, 1H), 8.04 (s, 1H), 7.98 (d, J = 1.9 Hz, 1H), 7.72 (d, J = 8.7 Hz, 1H), 5.25 (s, 1H), 5.11 (s, 2H), 3.94 (d, J = 9.8 Hz, 6H), 2.74 (s, 3H), 1.46 (s, 6H) |

TABLE 1-continued

| Cmpd No. | Structure | ESMS (M + H) | ¹H NMR (300 MHz, unless indicated otherwise) |
|---|---|---|---|
| 552 | 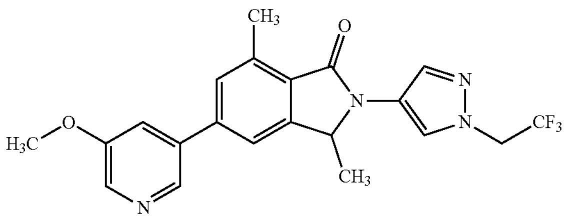 [SMILES: COc1cncc(-c2cc(C)c3c(c2)C(C)N(c2cnn(CC(F)(F)F)c2)C3=O)c1] | 417.29 | (methanol-d₄) d 8.75 (s, 1H), 8.53 (s, 1H), 8.28 (s, 2H), 7.94 (s, 1H), 7.85 (s, 1H), 7.70 s, 1H, 5.14 (q, J = 6.6 Hz, 1H), 5.00 (q, J = 8.7 Hz, 2H), 4.10 (s, 3H), 2.80 (d, J = 5.1 Hz, 3H), 1.61 (t, J = 5.4 Hz, 3H) |
| 553 | 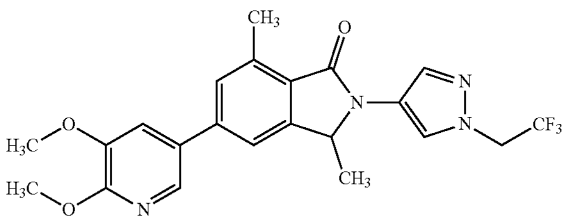 [SMILES: COc1cc(-c2cc(C)c3c(c2)C(C)N(c2cnn(CC(F)(F)F)c2)C3=O)cnc1OC] | 447.3 | |
| 554 | 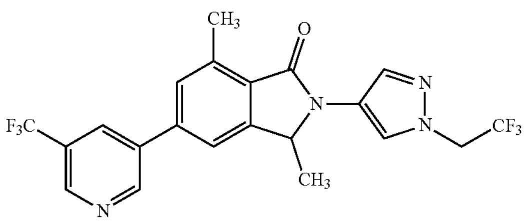 [SMILES: Cc1cc(-c2cncc(C(F)(F)F)c2)cc2c1C(=O)N(c1cnn(CC(F)(F)F)c1)C2C] | 455.23 | |
| 555 | 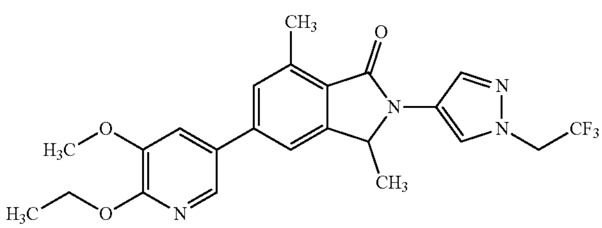 [SMILES: CCOc1ncc(-c2cc(C)c3c(c2)C(C)N(c2cnn(CC(F)(F)F)c2)C3=O)cc1OC] | 461.31 | (DMSO-d₆) δ 8.35 (s, 1H), 8.11 (d, J = 2.0 Hz, 1H), 7.94 (s, 1H), 7.84 (s, 1H), 7.72-7.54 (m, 2H), 5.16 (dt, J = 13.3, 7.9 Hz, 3H), 4.38 (q, J = 7.0 Hz, 2H), 3.92 (s, 3H), 2.71 (s, 3H), 1.53 (d, J = 6.5 Hz, 3H), 1.35 (t, J = 7.0 Hz, 3H) |
| 556 | 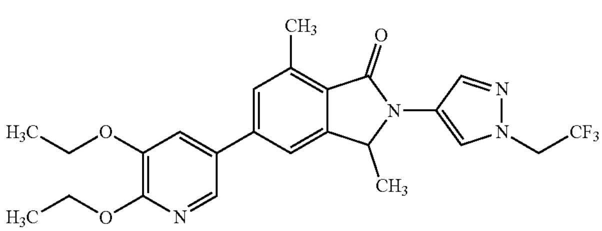 [SMILES: CCOc1cc(-c2cc(C)c3c(c2)C(C)N(c2cnn(CC(F)(F)F)c2)C3=O)cnc1OCC] | 475.33 | (DMSO-d₆) δ 8.35 (s, 1H), 8.10 (d, J = 2.0 Hz, 1H), 7.94 (s, 1H), 7.82 (s, 1H), 7.70-7.52 (m, 2H), 5.34-4.99 (m, 3H), 4.40 (q, J = 7.0 Hz, 2H), 4.19 (q, J = 6.9 Hz, 2H), 2.71 (s, 3H), 1.53 (d, J = 6.5 Hz, 3H), 1.37 (dt, J = 9.7, 7.0 Hz, 6H) |
| 557 | 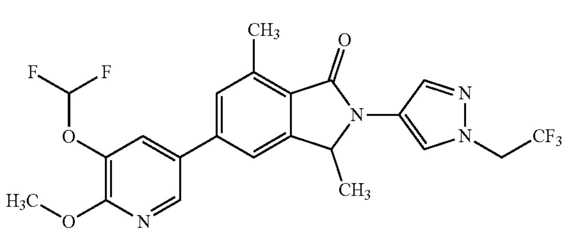 [SMILES: COc1ncc(-c2cc(C)c3c(c2)C(C)N(c2cnn(CC(F)(F)F)c2)C3=O)cc1OC(F)F] | 483.32 | |

TABLE 1-continued

| Cmpd No. | Structure | ESMS (M + H) | ¹H NMR (300 MHz, unless indicated otherwise) |
|---|---|---|---|
| 558 | 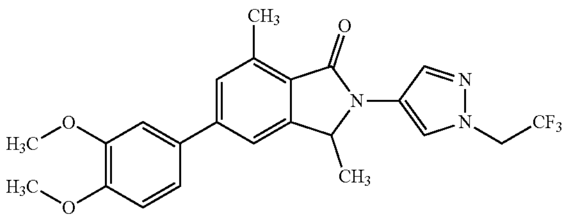 [SMILES: COc1ccc(-c2cc(C)c3c(c2)C(C)N(c2cnn(CC(F)(F)F)c2)C3=O)cc1OC] | 446.28 | |
| 559 | 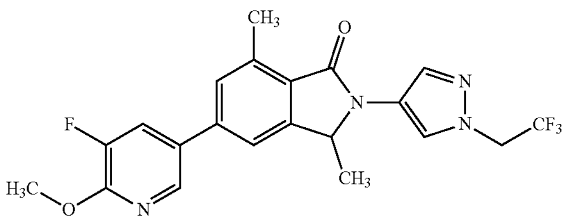 [SMILES: COc1ncc(-c2cc(C)c3c(c2)C(C)N(c2cnn(CC(F)(F)F)c2)C3=O)cc1F] | 435.27 | |
| 560 | 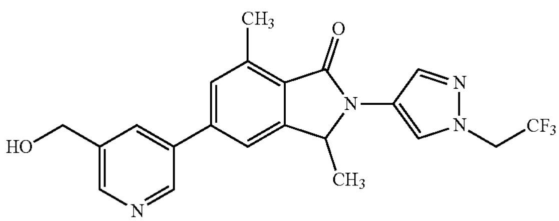 [SMILES: Cc1cc(-c2cncc(CO)c2)cc2c1C(=O)N(c1cnn(CC(F)(F)F)c1)C2C] | 417.29 | |
| 561 | 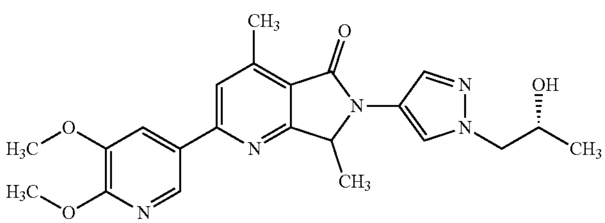 [SMILES: COc1cc(-c2cc(C)c3c(n2)C(C)N(c2cnn(C[C@@H](C)O)c2)C3=O)cnc1OC] | 424.59 | (CDCl$_3$) δ 8.40 (d, J = 1.6 Hz, 1H), 8.17 (s, 1H), 7.87 (s, 1H), 7.67 (s, 1H), 7.56 (s, 1H), 4.93 (q, J = 6.6 Hz, 1H), 4.23 (dd, J = 19.2, 5.4 Hz, 2H), 4.11 (s, J = 7.4 Hz, 3H), 4.03 (s, 3H), 3.48 (d, J = 3.4 Hz, 1H), 2.82 (s, 3H), 1.71 (d, J = 6.7 Hz, 3H), 1.28 (d, J = 6.2 Hz, 3H). |
| 562 | 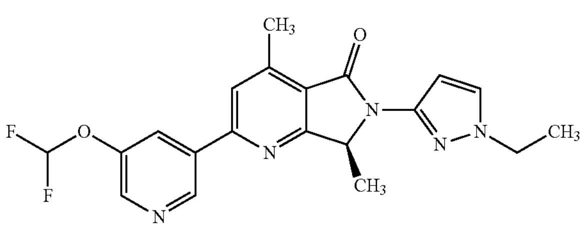 [SMILES: CCn1ccc(N2C(=O)c3c(C)cc(-c4cncc(OC(F)F)c4)nc3[C@@H]2C)n1] | 400.53 | |
| 563 | 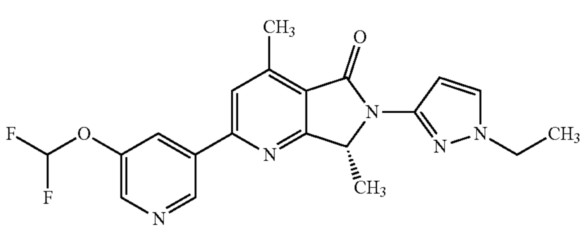 [SMILES: CCn1ccc(N2C(=O)c3c(C)cc(-c4cncc(OC(F)F)c4)nc3[C@H]2C)n1] | 400.53 | |

TABLE 1-continued

| Cmpd No. | Structure | ESMS (M + H) | ¹H NMR (300 MHz, unless indicated otherwise) |
|---|---|---|---|
| 564 | 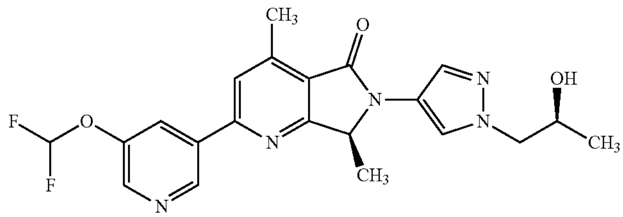 [SMILES: Cc1cc(-c2cncc(OC(F)F)c2)nc2c1C(=O)N(c1cnn(C[C@H](C)O)c1)[C@H]2C] | 430.6 | |
| 565 | 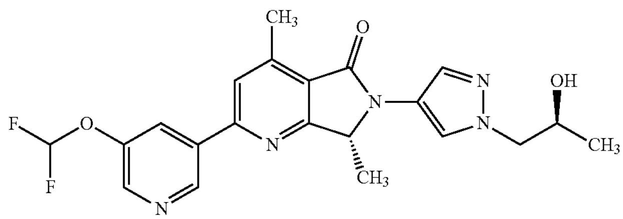 [SMILES: Cc1cc(-c2cncc(OC(F)F)c2)nc2c1C(=O)N(c1cnn(C[C@H](C)O)c1)[C@@H]2C] | 430.54 | |
| 566 | 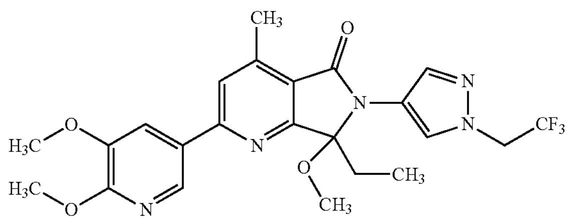 [SMILES: CCC1(OC)c2nc(-c3cnc(OC)c(OC)c3)cc(C)c2C(=O)N1c1cnn(CC(F)(F)F)c1] | 492.56 | |
| 567 | 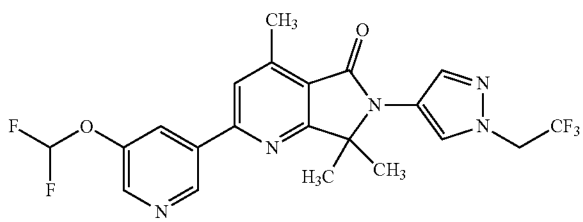 [SMILES: Cc1cc(-c2cncc(OC(F)F)c2)nc2c1C(=O)N(c1cnn(CC(F)(F)F)c1)C2(C)C] | 468.59 | (DMSO-d$_6$) δ 9.30 (d, J = 1.6 Hz, 1H), 8.63 (d, J = 2.6 Hz, 1H), 8.41 (d, J = 2.0 Hz, 1H), 8.35 (s, 1H), 8.14 (s, 1H), 7.95 (s, 1H), 7.76-7.18 (m, 2H), 5.20 (q, J = 9.1 Hz, 2H), 2.74 (s, 3H), 1.62 (s, 5H) |
| 568 | 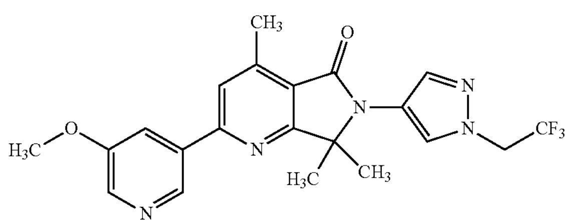 | 431.82 | (DMSO-d$_6$) δ 9.08 (d, J = 1.7 Hz, 1H), 8.55 (d, J = 2.7 Hz, 1H), 8.40-8.29 (m, 2H), 8.18 (d, J = 11.8 Hz, 1H), 5.20 (q, J = 9.1 Hz, 2H), 4.01 (s, 3H), 2.75 (s, 3H), 1.62 (s, 6H) |
| 569 | 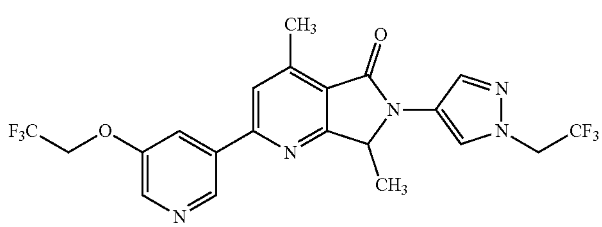 [SMILES: Cc1cc(-c2cncc(OCC(F)(F)F)c2)nc2c1C(=O)N(c1cnn(CC(F)(F)F)c1)C2C] | 485.77 | (DMSO-d$_6$) δ 9.17 (s, 1H), 8.69 (d, J = 2.0 Hz, 1H), 8.44 (d, J = 25.7 Hz, 2H), 8.21 (s, 1H), 7.97 (d, J = 9.0 Hz, 1H), 5.30-5.03 (m, 5H), 2.75 (d, J = 6.6 Hz, 3H), 1.59 (d, J = 6.5 Hz, 3H) |
| 570 | 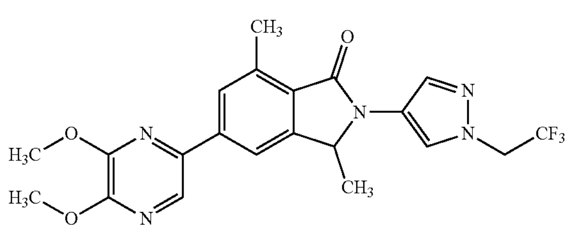 [SMILES: COc1ncc(-c2cc(C)c3c(c2)C(C)N(c2cnn(CC(F)(F)F)c2)C3=O)nc1OC] | 448.32 | (DMSO-d$_6$) δ 8.48 (d, J = 13.2 Hz, 1H), 8.33 (d, J = 8.6 Hz, 1H), 8.10 (s, 1H), 7.94 (d, J = 5.2 Hz, 2H), 5.33-4.99 (m, 3H), 4.02 (d, J = 26.1 Hz, 6H), 2.72 (s, 3H), 1.53 (d, J = 6.5 Hz, 3H) |

TABLE 1-continued

| Cmpd No. | Structure | ESMS (M + H) | ¹H NMR (300 MHz, unless indicated otherwise) |
|---|---|---|---|
| 571 | 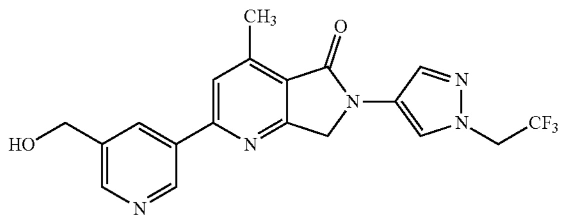 [SMILES: Cc1cc(-c2cncc(CO)c2)nc2c1C(=O)N(c1cnn(CC(F)(F)F)c1)C2] | 404.24 | (DMSO-d₆) δ 9.32 (s, 1H), 8.69 (d, J = 11.5 Hz, 2H), 8.39 (s, 1H), 8.12 (s, 1H), 7.96 (d, J = 0.5 Hz, 1H), 5.22 (dd, J = 18.2, 9.1 Hz, 2H), 4.96 (s, 2H), 4.70 (s, 2H), 2.75 (s, 3H) |
| 572 | 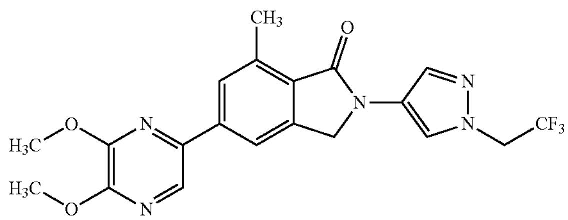 [SMILES: COc1ncc(-c2cc(C)c3c(c2)CN(c2cnn(CC(F)(F)F)c2)C3=O)nc1OC] | 435.27 | |
| 573 | 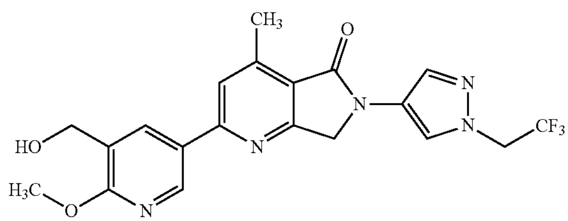 [SMILES: COc1ncc(-c2cc(C)c3c(n2)CN(c2cnn(CC(F)(F)F)c2)C3=O)cc1CO] | 434.25 | (DMSO-d₆) δ 8.85 (d, J = 2.3 Hz, 1H), 8.55 (s, 1H), 8.37 (s, 1H), 7.95 (d, J = 5.2 Hz, 2H), 5.41 (s, 1H), 5.21 (q, J = 9.0 Hz, 2H), 4.93 (s, 2H), 4.54 (s, 2H), 3.96 (s, 3H), 2.73 (d, J = 3.3 Hz, 3H) |
| 574 | 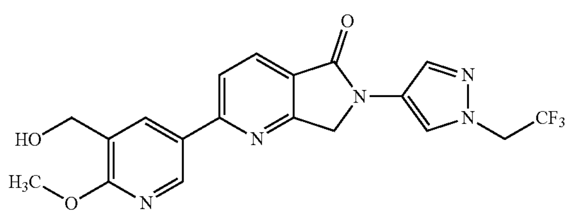 [SMILES: COc1ncc(-c2ccc3c(n2)CN(c2cnn(CC(F)(F)F)c2)C3=O)cc1CO] | 420.24 | (DMSO-d₆) δ 8.87 (d, J = 2.4 Hz, 1H), 8.56 (d, J = 2.3 Hz, 1H), 8.40 (s, 1H), 8.18 (dd, J = 25.1, 8.2 Hz, 2H), 7.95 (s, 1H), 5.41 (s, 1H), 5.22 (d, J = 9.1 Hz, 2H), 5.01 (s, 2H), 4.55 (s, 2H), 3.97 (s, 3H) |
| 575 | 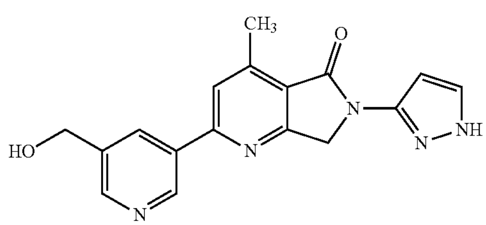 [SMILES: Cc1cc(-c2cncc(CO)c2)nc2c1C(=O)N(c1cc[nH]n1)C2] | 322.14 | |
| 576 | 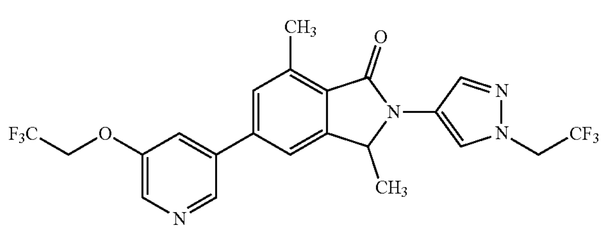 [SMILES: Cc1cc(-c2cncc(OCC(F)(F)F)c2)cc2c1C(=O)N(c1cnn(CC(F)(F)F)c1)C2C] | 485.42 | (DMSO-d₆) δ 8.81 (dd, J = 7.3, 1.6 Hz, 1H), 8.54 (d, J = 2.7 Hz, 1H), 8.35 (d, J = 10.8 Hz, 1H), 8.10-8.04 (m, 1H), 7.95 (t, J = 10.3 Hz, 2H), 7.78 (s, 1H), 5.26-5.12 (m, 2H), 5.12-4.98 (m, 2H), 2.73 (s, 3H), 1.63-1.50 (m, 3H). |

TABLE 1-continued

| Cmpd No. | Structure | ESMS (M + H) | ¹H NMR (300 MHz, unless indicated otherwise) |
|---|---|---|---|
| 577 | 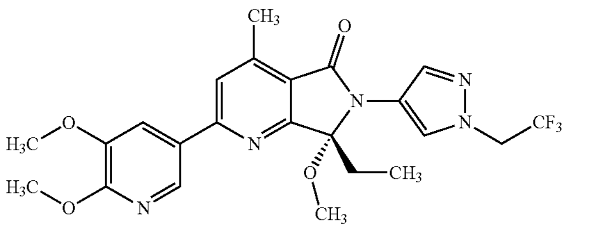 [SMILES: CC[C@@]1(OC)c2nc(-c3cnc(OC)c(OC)c3)cc(C)c2C(=O)N1c1cnn(CC(F)(F)F)c1] | 492.54 | |
| 578 | 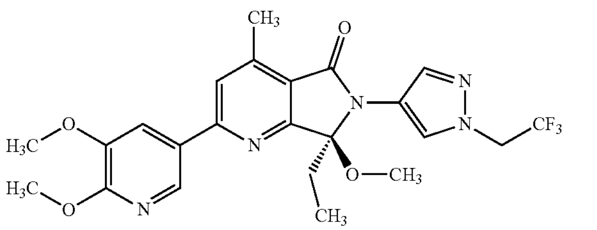 [SMILES: CC[C@]1(OC)c2nc(-c3cnc(OC)c(OC)c3)cc(C)c2C(=O)N1c1cnn(CC(F)(F)F)c1] | 492.54 | |
| 579 | 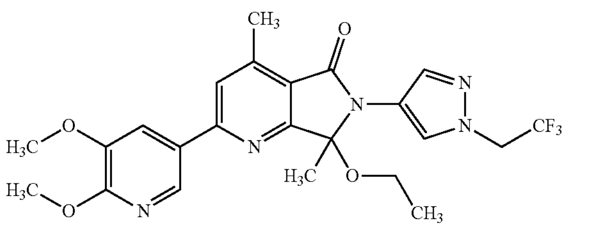 [SMILES: CCOC1(C)c2nc(-c3cnc(OC)c(OC)c3)cc(C)c2C(=O)N1c1cnn(CC(F)(F)F)c1] | 492.08 | (400 MHz, CDCl₃) δ 8.45 (d, J = 1.8 Hz, 1H), 8.27 (s, 1H), 8.12 (s, 1H), 7.96 (s, 1H), 7.63 (s, 1H), 4.77 (d, J = 8.5 Hz, 2H), 4.18 (s, 3H), 4.06 (s, 3H), 3.19 (d, J = 7.0 Hz, 1H), 3.04-2.95 (m, 1H), 2.83 (s, 3H), 1.87 (s, 3H), 1.16 (t, J = 7.0 Hz, 3H) |
| 580 | 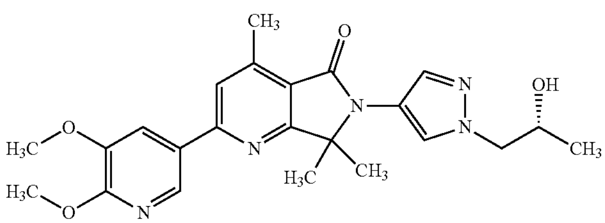 [SMILES: COc1cc(-c2cc(C)c3c(n2)C(C)(C)N(c2cnn(C[C@@H](C)O)c2)C3=O)cnc1OC] | 438.6 | (400 MHz, CDCl₃) δ 8.45 (d, J = 1.9 Hz, 1H), 7.96 (s, 1H), 7.89 (t, J = 5.1 Hz, 1H), 7.74 (d, J = 9.0 Hz, 1H), 7.56 (s, 1H), 4.40-4.21 (m, 2H), 4.11 (s, 3H), 4.08 (d, J = 5.7 Hz, 1H), 4.02 (s, 3H), 2.82 (s? 3H), 1.66 (s, 6H), 1.29 (t, J = 6.5 Hz, 3H) |
| 581 | 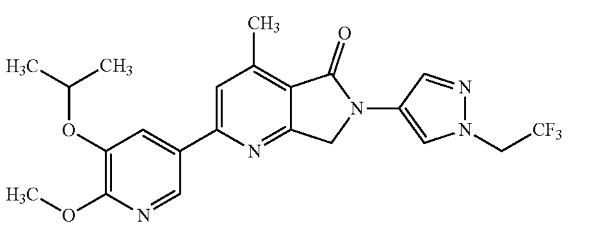 | 462.1 | (DMSO-d₆) δ 8.53 (s, 1H), 8.38 (s, 1H), 7.99 (s, 1H), 7.94 (s, 2H), 5.46-5.32 (m, 1H), 5.28-5.11 (m, 2H), 4.92 (s, 2H), 3.90 (s, 3H), 2.71 (s, 3H), 1.34 (d, J = 6.1 Hz, 6H) |
| 582 | 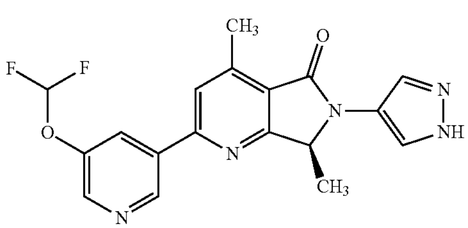 [SMILES: Cc1cc(-c2cncc(OC(F)F)c2)nc2c1C(=O)N(c1cn[nH]c1)[C@H]2C] | | (DMSO-d₆) δ 12.95 (s, 1H), 9.28 (d, J = 1.7 Hz, 4H), 8.62 (d, J = 2.6 Hz, 3H), 8.38 (s, 3H), 8.15 (s, 3H), 8.03 (s, 5H), 7.47 (t, J = 73.3 Hz, 7H), 5.23-5.13 (m, 3H), 2.75 (s, 8H), 1.56 (d, J = 6.7 Hz, 8H) |

TABLE 1-continued

| Cmpd No. | Structure | ESMS (M + H) | ¹H NMR (300 MHz, unless indicated otherwise) |
|---|---|---|---|
| 583 | 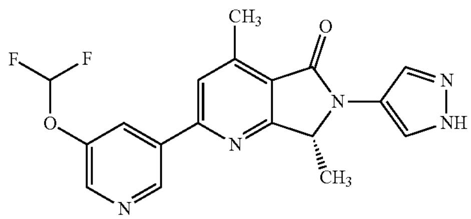 [SMILES: Cc1cc(-c2cncc(OC(F)F)c2)nc2c1C(=O)N(c1cn[nH]c1)[C@@H]2C] | | (DMSO-d₆) δ 13.06-12.81 (br s, 1H), 9.28 (d, J = 1.7 Hz, 1H), 8.62 (d, J = 2.6 Hz, 1H), 8.38 (s, 1H), 8.15 (s, 1H), 8.02 (br s, 2H), 7.47 (t, J = 73.3 Hz, 1H), 5.17 (q, J = 6.5 Hz, 1H), 2.75 (s, 3H), 1.56 (d, J = 6.6 Hz, 3H) |
| 584 | 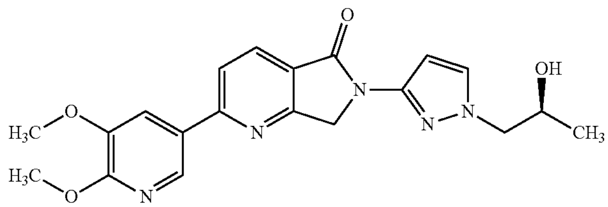 [SMILES: COc1cc(-c2ccc3c(n2)CN(c2ccn(C[C@H](C)O)n2)C3=O)cnc1OC] | 396.5 | |
| 585 | 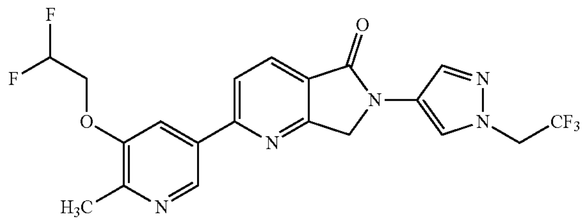 [SMILES: Cc1ncc(-c2ccc3c(n2)CN(c2cnn(CC(F)(F)F)c2)C3=O)cc1OCC(F)F] | 454.47 | |
| 586 | 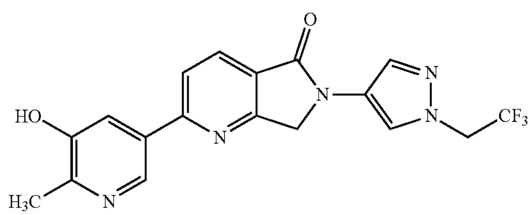 [SMILES: Cc1ncc(-c2ccc3c(n2)CN(c2cnn(CC(F)(F)F)c2)C3=O)cc1O] | 390.48 | |
| 587 | 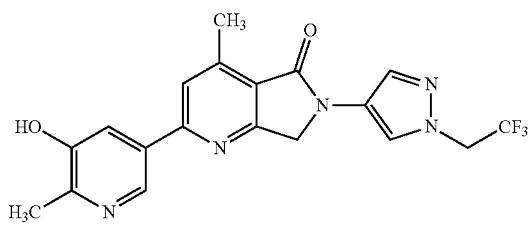 [SMILES: Cc1cc(-c2cnc(C)c(O)c2)nc2c1C(=O)N(c1cnn(CC(F)(F)F)c1)C2] | 404.49 | |
| 588 | 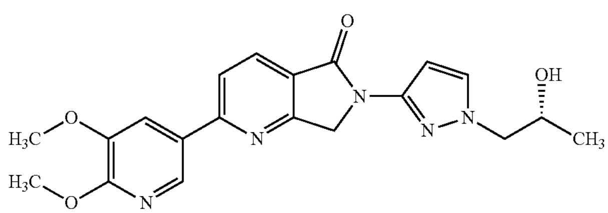 [SMILES: COc1cc(-c2ccc3c(n2)CN(c2ccn(C[C@@H](C)O)n2)C3=O)cnc1OC] | 396.5 | |
| 589 | 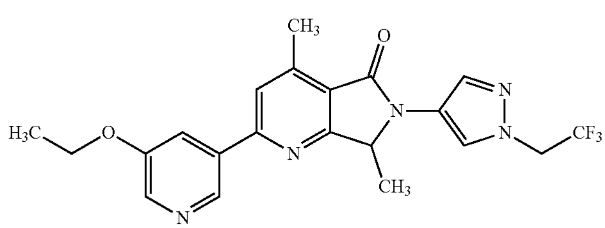 [SMILES: CCOc1cncc(-c2cc(C)c3c(n2)C(C)N(c2cnn(CC(F)(F)F)c2)C3=O)c1] | 432.52 | (DMSO-d₆) δ 9.04 (d, J = 1.5, 1H), 8.51 (d, J = 2.7, 1H), 8.38 (s, 1H), 8.25 (s, 1H), 8.16 (s, 1H), 7.98 (s, 1H), 5.29-5.12 (m, 3H), 4.28 (dd, J = 13.9, 6.9, 2H), 2.75 (s, 3H), 1.58 (d, J = 6.6, 3H), 1.42 (t, J = 6.9, 3H) |

TABLE 1-continued

| Cmpd No. | Structure | ESMS (M + H) | ¹H NMR (300 MHz, unless indicated otherwise) |
|---|---|---|---|
| 590 | 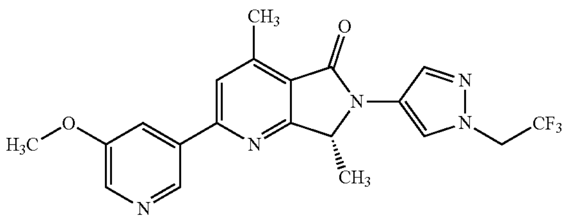 [SMILES: COc1cncc(-c2cc(C)c3c(n2)[C@@H](C)N(c2cnn(CC(F)(F)F)c2)C3=O)c1] | 418.09 | (DMSO-d₆) δ 9.10 (d, J = 1.4 Hz, 1H), 8.60 (t, J = 6.7 Hz, 1H), 8.43 (d, J = 1.7 Hz, 1H), 8.38 (d, J = 4.6 Hz, 1H), 8.21 (s, 1H), 7.98 (s, 1H), 5.20 (dt, J = 9.2, 7.2 Hz, 3H), 4.03 (s, 3H), 2.76 (s, 3H), 1.58 (t, J = 6.3 Hz, 3H) |
| 591 | 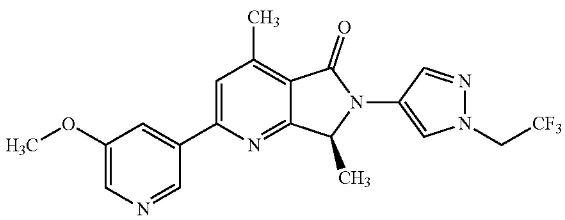 [SMILES: COc1cncc(-c2cc(C)c3c(n2)[C@H](C)N(c2cnn(CC(F)(F)F)c2)C3=O)c1] | 418.34 | (DMSO-d₆) δ 9.11 (d, J = 1.6 Hz, 1H), 8.60 (dd, J = 20.6, 2.2 Hz, 1H), 8.52-8.44 (m, 1H), 8.38 (d, J = 4.9 Hz, 1H), 8.26-8.18 (m, 1H), 8.02-7.94 (m, 1H), 5.26-5.12 (m, 3H), 4.04 (s, 3H), 2.76 (s, 3H), 1.57 (dd, J = 13.8, 7.5 Hz, 3H) |
| 592 | 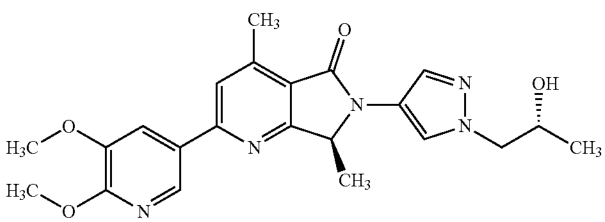 [SMILES: COc1cc(-c2cc(C)c3c(n2)[C@H](C)N(c2cnn(C[C@@H](C)O)c2)C3=O)cnc1OC] | 424.59 | |
| 593 | 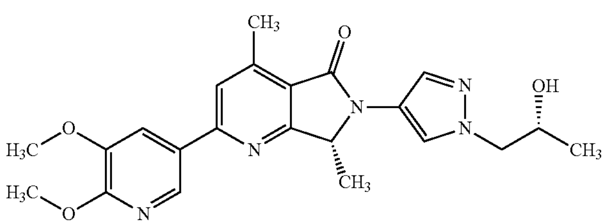 [SMILES: COc1cc(-c2cc(C)c3c(n2)[C@@H](C)N(c2cnn(C[C@@H](C)O)c2)C3=O)cnc1OC] | 424.59 | |
| 594 | 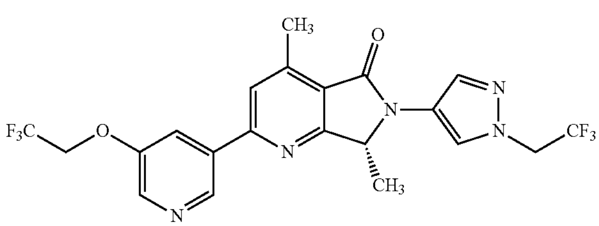 | 486.06 | (DMSO-d₆) δ 9.15 (s, 1H), 8.64 (s, 1H), 8.40 (d, J = 5.0 Hz, 2H), 8.19 (s, 1H), 7.99 (s, 1H), 5.29-5.16 (m, 3H), 5.08 (dd, J = 17.4, 8.7 Hz, 2H), 2.76 (s, 3H), 1.59 (d, J = 6.5 Hz, 3H) |
| 595 | 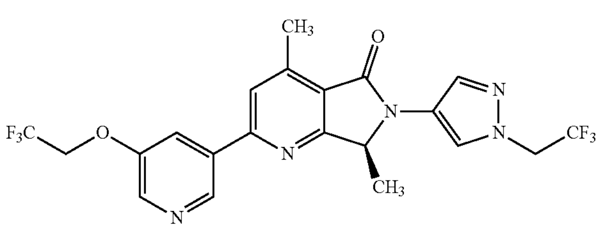 [SMILES: Cc1cc(-c2cncc(OCC(F)(F)F)c2)nc2c1C(=O)N(c1cnn(CC(F)(F)F)c1)[C@H]2C] | 485.9 | (DMSO-d₆) δ 9.13 (s, 1H), 8.60 (d, J = 2.0 Hz, 1H), 8.39 (s, 1H), 8.33 (s, 1H), 8.16 (s, 1H), 7.99 (s, 1H), 5.27-5.13 (m, 3H), 5.06 (q, J = 8.8 Hz, 2H), 2.75 (s, 3H), 1.59 (d, J = 6.6 Hz, 3H) |
| 596 | 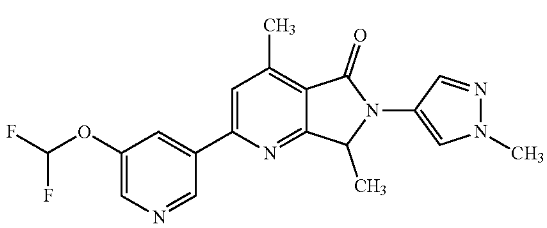 [SMILES: Cc1cc(-c2cncc(OC(F)F)c2)nc2c1C(=O)N(c1cnn(C)c1)C2C] | 386.63 | (DMSO-d₆) δ 9.28 (s, 1H), 8.62 (d, J = 2.4 Hz, 1H), 8.38 (s, 1H), 8.15 (d, J = 4.8 Hz, 2H), 7.80 (s, 1H), 7.47 (t, J = 73.3 Hz, 1H), 5.14 (q, J = 6.5 Hz, 1H), 3.89 (s, 3H), 2.75 (s, 3H), 1.56 (d, J = 6.6 Hz, 3H) |

TABLE 1-continued

| Cmpd No. | Structure | ESMS (M + H) | ¹H NMR (300 MHz, unless indicated otherwise) |
|---|---|---|---|
| 597 | 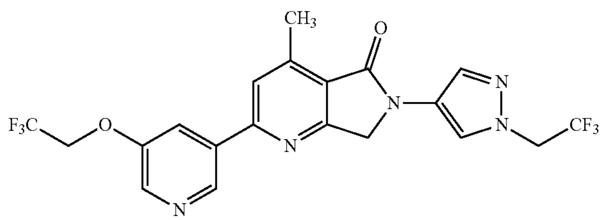 [SMILES: Cc1cc(-c2cncc(OCC(F)(F)F)c2)nc2c1C(=O)N(c1cnn(CC(F)(F)F)c1)C2] | 471.34 | (DMSO-d$_6$) δ 8.77 (d, J = 1.7 Hz, 1H), 8.55 (d, J = 2.7 Hz, 1H), 8.38 (s, 1H), 8.15-8.03 (m, 1H), 7.92 (d, J = 13.5 Hz, 2H), 7.77 (s, 1H), 5.20 (dd, J = 18.2, 9.1 Hz, 2H), 5.06 (dd, J = 17.7, 8.8 Hz, 2H), 4.89 (s, 2H), 2.74 (s, 3H) |
| 598 | 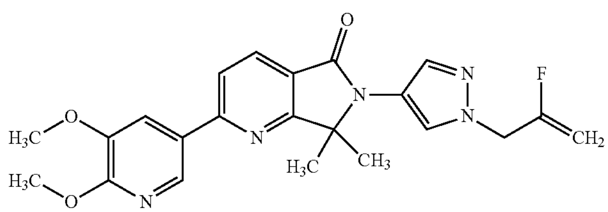 [SMILES: C=C(F)Cn1cc(N2C(=O)c3ccc(-c4cnc(OC)c(OC)c4)nc3C2(C)C)cn1] | 426.57 | (DMSO-d$_6$) δ 8.58 (d, J = 1.8 Hz, 1H), 8.19 (d, J = 8.3 Hz, 3H), 8.00 (d, J = 1.8 Hz, 1H), 7.87 (s, 1H), 6.97 (s, 1H), 5.04 (d, J = 15.1 Hz, 2H), 4.80 (ddd, J = 52.9, 33.1, 3.2 Hz, 2H), 3.95 (d, J = 8.9 Hz, 6H), 1.72 (s, 6H) |
| 599 | 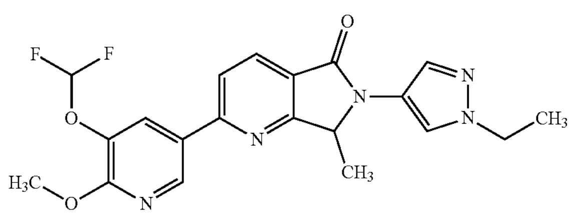 | | (DMSO-d$_6$) δ 8.91 (d, J = 2.0 Hz, 1H), 8.36 (d, J = 2.0 Hz, 1H), 8.29-8.13 (m, 3H), 7.82 (d, J = 0.4 Hz, 1H), 7.33 (t, J = 73.6 Hz, 2H), 5.21 (q, J = 6.6 Hz, 1H), 4.18 (q, J = 7.3 Hz, 2H), 4.03 (s, 3H), 1.58 (d, J = 6.7 Hz, 3H), 1.40 (t, J = 7.3 Hz, 3H) |
| 600 | 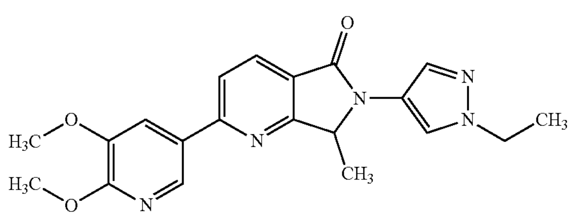 | 380.14 | (DMSO-d$_6$) δ 8.57 (d, J = 1.9 Hz, 1H), 8.28-8.13 (m, 3H), 7.98 (t, J = 7.3 Hz, 1H), 7.81 (s, 1H), 5.20 (q, J = 6.7 Hz, 1H), 4.18 (q, J = 7.2 Hz, 2H), 3.94 (d, J = 9.2 Hz, 6H), 1.58 (d, J = 6.7 Hz, 3H), 1.40 (t, J = 7.3 Hz, 3H) |
| 601 | 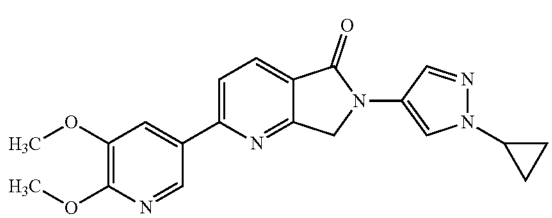 [SMILES: COc1cc(-c2ccc3c(n2)CN(c2cnn(C4CC4)c2)C3=O)cnc1OC] | 378.52 | (400 MHz, CDCl$_3$) δ 8.40 (d, J = 2.0 Hz, 1H), 8.29-8.15 (m, 2H), 7.88 (dd, J = 13.5, 5.1 Hz, 2H), 7.64 (d, J = 0.7 Hz, 1H), 4.84 (s, 2H), 4.12 (s, 3H), 4.04 (s, 3H), 3.78-3.55 (m, 1H), 1.30-0.99 (m, 4H) |
| 602 | 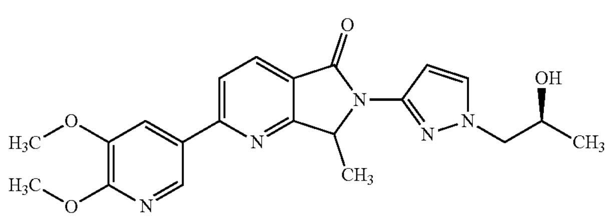 [SMILES: COc1cc(-c2ccc3c(n2)C(C)N(c2ccn(C[C@H](C)O)n2)C3=O)cnc1OC] | 410.57 | (400 MHz, CDCl$_3$) δ 8.43 (d, J = 1.9 Hz, 1H), 8.21 (d, J = 8.1 Hz, 1H), 7.93 (d, J = 1.8 Hz, 1H), 7.84 (d, J = 8.1 Hz, 1H), 7.44 (d, J = 2.3 Hz, 1H), 7.03 (t, J = 2.9 Hz, 1H), 5.32 (q, J = 6.6 Hz, 1H), 4.20 (ddd, J = 11.4, 8.3, 5.1 Hz, 2H), 4.16-4.09 (s, 3H), 4.08-3.93 (m, 4H), 3.61 (dd, J = 15.8, 3.6 Hz, 1H), 1.81 (d, J = 6.6 Hz, 3H), 1.28 (dd, J = 6.3, 3.2 Hz, 3H) |

TABLE 1-continued
| Cmpd No. | Structure | ESMS (M + H) | ¹H NMR (300 MHz, unless indicated otherwise) |
|---|---|---|---|
| 603 | 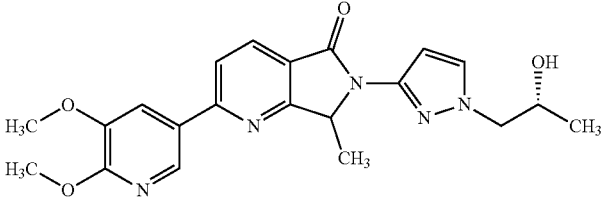 [SMILES: COc1cc(-c2ccc3c(n2)C(C)N(c2ccn(C[C@@H](C)O)n2)C3=O)cnc1OC] | 410.57 | (400 MHz, CDCl₃) δ 8.43 (d, J = 1.9 Hz, 1H), 8.21 (d, J = 8.1 Hz, 1H), 7.93 (d, J = 1.7 Hz, 1H), 7.84 (d, J = 8.1 Hz, 1H), 7.44 (d, J = 2.3 Hz, 1H), 7.03 (d, J = 1.9 Hz, 1H), 5.39-5.22 (m, 1H), 4.37-4.14 (m, 2H), 4.13 (s, 3H), 4.07-3.91 (m, 4H), 3.62 (dd, J = 15.5, 3.6 Hz, 1H), 1.81 (d, J = 6.7 Hz, 3H), 1.28 (dd, J = 6.3, 3.2 Hz, 3H) |
| 604 | 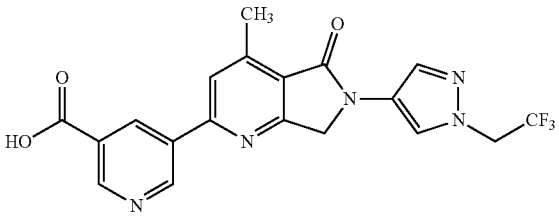 [SMILES: Cc1cc(-c2cncc(C(=O)O)c2)nc2c1C(=O)N(c1cnn(CC(F)(F)F)c1)C2] | 418.06 | (DMSO-d₆) δ 9.23 (d, J = 1.9 Hz, 1H), 9.03 (s, 1H), 8.84 (s, 1H), 8.37 (s, 1H), 8.03 (s, 1H), 7.93 (d, J = 17.7 Hz, 3H), 5.21 (q, J = 9.1 Hz, 2H), 4.96 (s, 2H), 2.55 (s, 3H) |
| 605 | 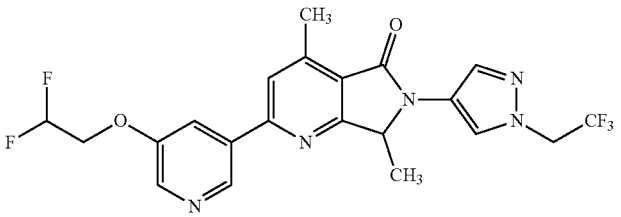 [SMILES: Cc1cc(-c2cncc(OCC(F)F)c2)nc2c1C(=O)N(c1cnn(CC(F)(F)F)c1)C2C] | 468.07 | (DMSO-d₆) δ 9.11 (d, J = 1.6 Hz, 1H), 8.59 (d, J = 2.7 Hz, 1H), 8.39 (s, 1H), 8.36-8.32 (m, 1H), 8.18 1H), 7.98 (s, 1H), 6.87-6.10 (m, 1H), 5.30-5.14 (m, 3H), 4.62 (td, J = 14.7, 3.3 Hz, 2H), 2.74 (d, J = 6.8 Hz, 3H), 1.59 (d, J = 6.7 Hz, 3H) |
| 606 | 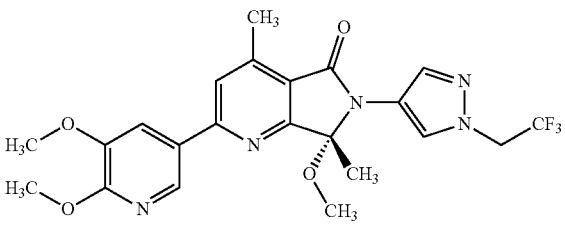 [SMILES: COc1cc(-c2cc(C)c3c(n2)[C@@](C)(OC)N(c2cnn(CC(F)(F)F)c2)C3=O)cnc1OC] | 478.12 | |
| 607 | 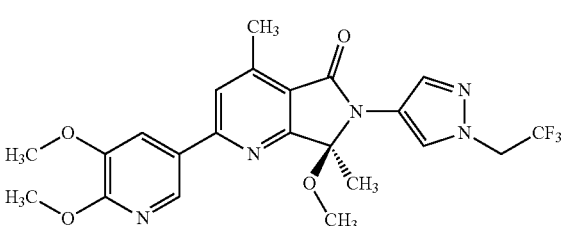 | 478.09 | |
| 608 | 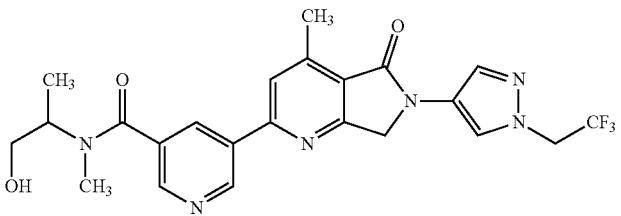 [SMILES: Cc1cc(-c2cncc(C(=O)N(C)C(C)CO)c2)nc2c1C(=O)N(c1cnn(CC(F)(F)F)c1)C2] | 489.13 | |

TABLE 1-continued

| Cmpd No. | Structure | ESMS (M + H) | ¹H NMR (300 MHz, unless indicated otherwise) |
|---|---|---|---|
| 609 | 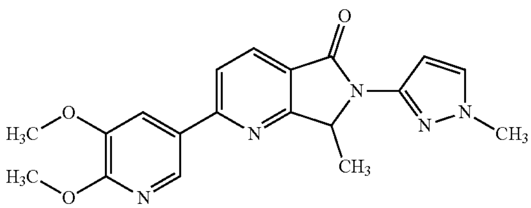 | 366 | (DMSO-d$_6$) δ 8.57 (d, 1HH, j = 2 Hz), 8.25 (d, 1H, J = 8 Hz), 8.18 (d, 1H, J = 8 Hz), 7.99 (d, 1H, J = 1.9 Hz), 7.72 (d, 1H, J = 1.9 Hz), 6.77 (d, 1H, J = 2.0 Hz), 5.25 (quart, 1H, J = 8 Hz), 3.96 (s, 3H), 3.93 (s, 3H), 3.86 (s, 3H), 1.72 (d, 3H, J = 8 Hz) |
| 610 | 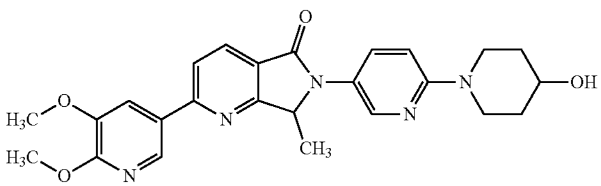 [SMILES: COc1cc(-c2ccc3c(n2)C(C)N(c2ccc(N4CCC(O)CC4)nc2)C3=O)cnc1OC] | 462.66 | (DMSO-d$_6$) δ 8.58 (d, J = 1.9 Hz, 1H), 8.34 (d, J = 2.7 Hz, 1H), 8.22 (d, J = 2.0 Hz, 2H), 8.01 (d, J = 1.8 Hz, 1H), 7.79 (dd, J = 9.1, 2.8 Hz, 1H), 6.96 (d, J = 9.0 Hz, 1H), 5.42 (d, J = 6.8 Hz, 1H), 4.71 (d, J = 4.3 Hz, 1H), 4.04 (d, J = 13.1 Hz, 1H), 3.94 (d, J = 9.9 Hz, 6H), 3.77-3.61 (m, 1H), 3.13 (dd, J = 21.8, 7.7 Hz, 3H), 1.80 (d, J = 9.4 Hz, 2H), 1.45 (d, J = 6.7 Hz, 3H), 1.38 (d, J = 9.4 Hz, 2H) |
| 611 | 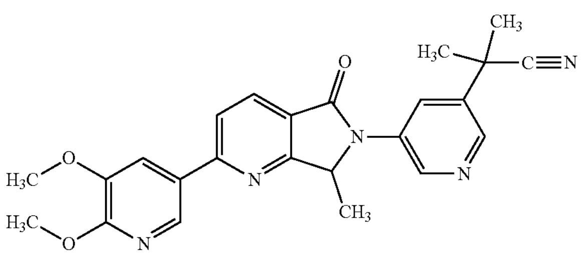 [SMILES: COc1cc(-c2ccc3c(n2)C(C)N(c2cncc(C(C)(C)C#N)c2)C3=O)cnc1OC] | 430.6 | (DMSO-d$_6$) δ 9.00 (d, J = 2.3 Hz, 1H), 8.63 (dd, J = 9.7, 2.0 Hz, 2H), 8.46-8.16 (m, 3H), 8.03 (d, J = 2.0 Hz, 1H), 5.76 (d, J = 6.7 Hz, 1H), 4.10 (d, J = 5.3 Hz, 1H), 3.93 (d, 6H), 3.17 (d, J = 5.3 Hz, 1H), 1.81 (t, J = 3.7 Hz, 6H), 1.53 (d, J = 6.7 Hz, 3H) |
| 612 | 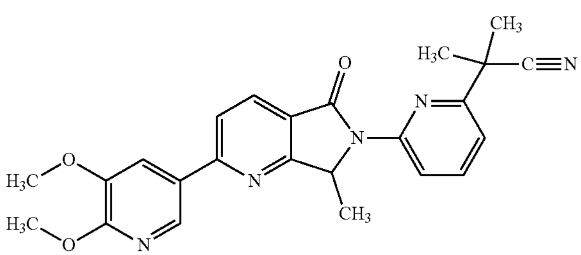 [SMILES: COc1cc(-c2ccc3c(n2)C(C)N(c2cccc(C(C)(C)C#N)n2)C3=O)cnc1OC] | 430.6 | (DMSO-d$_6$) δ 8.61 (d, J = 1.8 Hz, 1H), 8.42 (d, J = 8.3 Hz, 1H), 8.26 (dd, J = 21.0, 8.2 Hz, 2H), 8.13-7.92 (m, 2H), 7.41 (d, J = 7.6 Hz, 1H), 5.69 (q, J = 6.4 Hz, 1H), 3.95 (d, J = 8.2 Hz, 6H), 1.81-1.69 (m, 9H) |
| 613 | 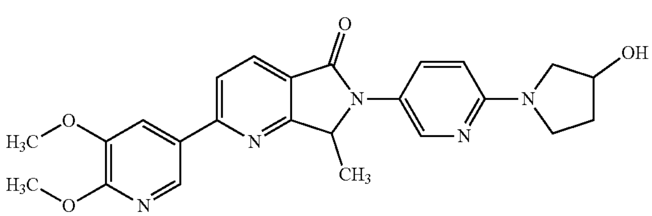 [SMILES: COc1cc(-c2ccc3c(n2)C(C)N(c2ccc(N4CCC(O)C4)nc2)C3=O)cnc1OC] | 448.64 | (DMSO-d$_6$) δ 8.58 (s, 1H), 8.29 (d, J = 2.2 Hz, 1H), 8.21 (s, 2H), 8.01 (s, 1H), 7.75 (d, J = 9.0 Hz, 1H), 6.54 (d, J = 8.7 Hz, 1H), 5.93-5.76 (m, 1H), 5.38 (d, J = 6.9 Hz, 1H), 4.98 (d, J = 3.3 Hz, 1H), 4.42 (m, 1H), 3.94 (d, J = 9.9 Hz, 6H), 3.49 (d, J = 4.8 Hz, 2H), 1.98 (d, J = 30.8 Hz, 4H), 1.44 (d, J = 6.8 Hz, 3H) |

TABLE 1-continued

| Cmpd No. | Structure | ESMS (M + H) | ¹H NMR (300 MHz, unless indicated otherwise) |
|---|---|---|---|
| 614 | 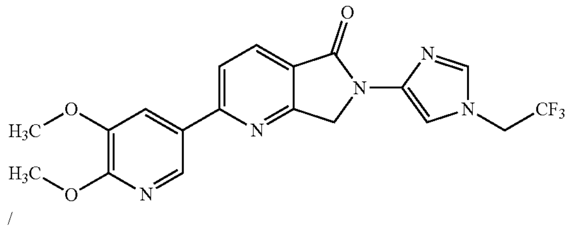 | 420.56 | (DMSO-d₆) δ 8.56 (s, 1H), 8.21 (m, 2H), 8.00 (s, 1H), 7.75 (s, 1H), 7.69 (s, 1H), 5.15 (q, J = 9.5 Hz, 2H), 5.04 (s, 2H), 3.96 (s, 3H), 3.92 (s, 3H) |
| 615 | 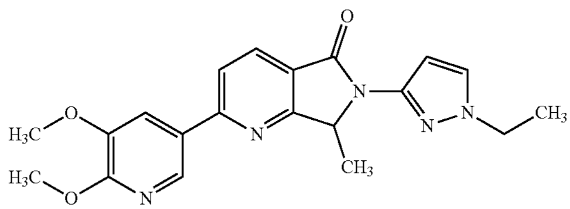 [SMILES: CCn1ccc(N2C(=O)c3ccc(-c4cnc(OC)c(OC)c4)nc3C2C)n1] | 380 | (400 MHz, CDCl₃) δ 8.42 (d, 1H, J = 1.9 Hz), 8.18 (d, 1H, J = 8.1 Hz), 7.8 (d, 1H, J = 1.8 Hz), 7.4 (d, 1H, J = 8.1 Hz), 6.94 (d, 1H, J = 1.8 Hz), 5.25 (quart, 1H), 4.17 (quart, 2H), 4.11 (s, 3H), 4.03 (s, 3H), 1.80 (d, 3H). 1.52 (t, 3H) |
| 616 | 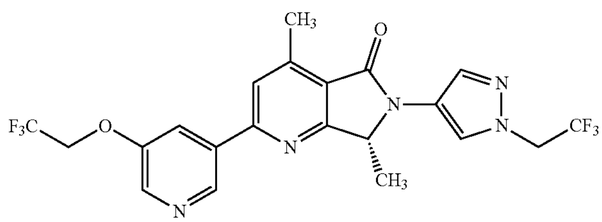 [SMILES: Cc1cc(-c2cncc(OCC(F)(F)F)c2)nc2c1C(=O)N(c1cnn(CC(F)(F)F)c1)[C@@H]2C] | 485.07 | |
| 617 | 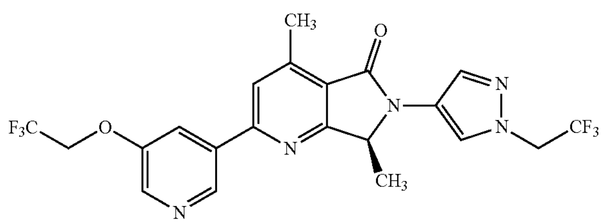 [SMILES: Cc1cc(-c2cncc(OCC(F)(F)F)c2)nc2c1C(=O)N(c1cnn(CC(F)(F)F)c1)[C@H]2C] | 485.1 | |
| 618 | 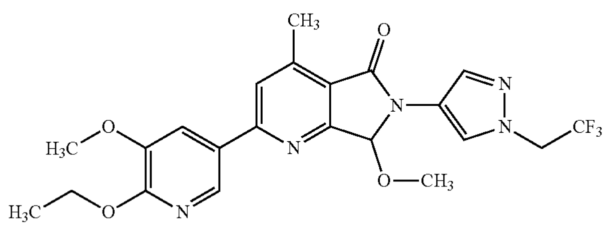 [SMILES: CCOc1ncc(-c2cc(C)c3c(n2)C(OC)N(c2cnn(CC(F)(F)F)c2)C3=O)cc1OC] | 478.33 | (400 MHz, CDCl₃) δ 8.39 (s, 1H), 8.27 (s, 1H), 8.03 (s, 1H), 7.90 (s, 1H), 7.64 (s, 1H), 6.11 (s, 1H), 4.76 (q, J = 8.2 Hz, 2H), 4.57 (q, J = 7.1 Hz, 2H), 4.03 (s, 3H), 3.16 (s, 3H), 2.82 (s, 3H), 1.51 (t, J = 7.1 Hz, 3H). |
| 619 | 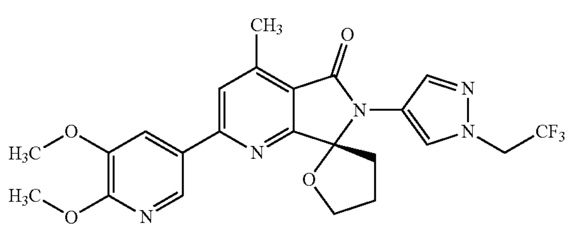 [SMILES: COc1cc(-c2cc(C)c3c(n2)[C@]2(CCCO2)N(c2cnn(CC(F)(F)F)c2)C3=O)cnc1OC] | 490.62 | |
| 620 | 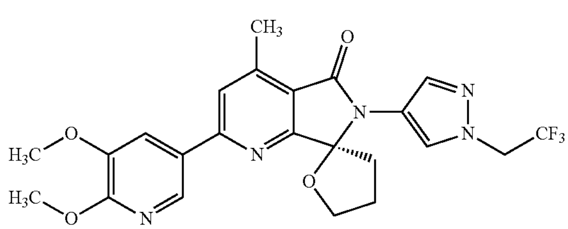 [SMILES: COc1cc(-c2cc(C)c3c(n2)[C@@]2(CCCO2)N(c2cnn(CC(F)(F)F)c2)C3=O)cnc1OC] | 490.62 | |

TABLE 1-continued

| Cmpd No. | Structure | ESMS (M + H) | ¹H NMR (300 MHz, unless indicated otherwise) |
|---|---|---|---|
| 621 | 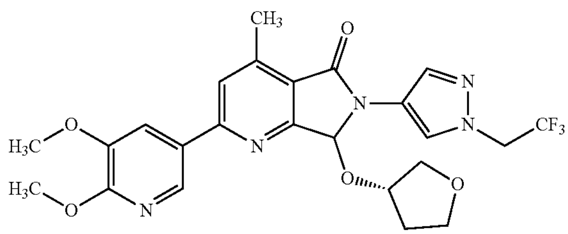 [SMILES: COc1cc(-c2cc(C)c3c(n2)C(O[C@H]2CCOC2)N(c2cnn(CC(F)(F)F)c2)C3=O)cnc1OC] | 520.63 | |
| 622 | 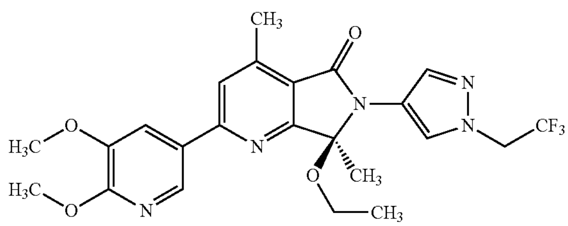 [SMILES: CCO[C@@]1(C)c2nc(-c3cnc(OC)c(OC)c3)cc(C)c2C(=O)N1c1cnn(CC(F)(F)F)c1] | 492.6 | |
| 623 | 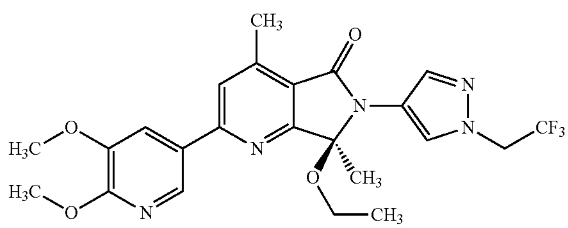 [SMILES: CCO[C@@]1(C)c2nc(-c3cnc(OC)c(OC)c3)cc(C)c2C(=O)N1c1cnn(CC(F)(F)F)c1] | 492.6 | |
| 624 | 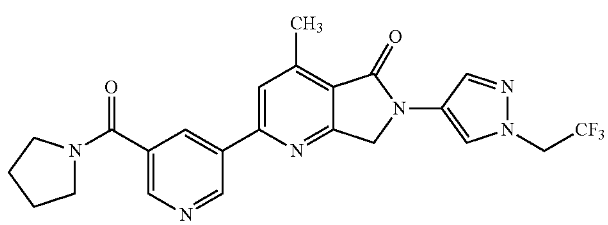 [SMILES: Cc1cc(-c2cncc(C(=O)N3CCCC3)c2)nc2c1C(=O)N(c1cnn(CC(F)(F)F)c1)C2] | 471.3 | |
| 625 | 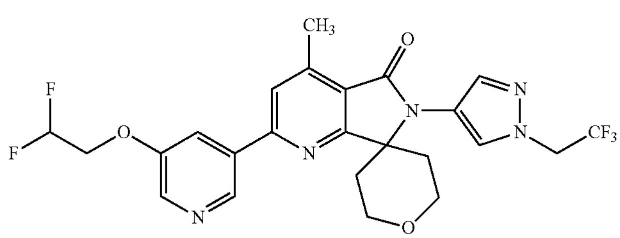 [SMILES: Cc1cc(-c2cncc(OCC(F)F)c2)nc2c1C(=O)N(c1cnn(CC(F)(F)F)c1)C21CCOCC1] | 524.14 | |
| 626 | 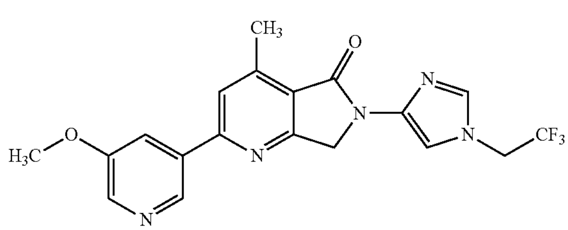 [SMILES: COc1cncc(-c2cc(C)c3c(n2)CN(c2cn(CC(F)(F)F)cn2)C3=O)c1] | 404.49 | (DMSO-d$_6$) δ 8.97 (d, J = 1.5 Hz, 1H), 8.41 (d, J = 2.8 Hz, 1H), 8.09 (s, 1H), 8.06 (s, 1H), 7.74 (s, 1H), 7.67 (s, 1H), 5.14 (q, J = 9.3 Hz, 2H), 4.99 (s, 2H), 3.95 (s, 3H), 2.74 (s, 3H) |

| Cmpd No. | Structure | ESMS (M + H) | ¹H NMR (300 MHz, unless indicated otherwise) |
|---|---|---|---|
| 627 | 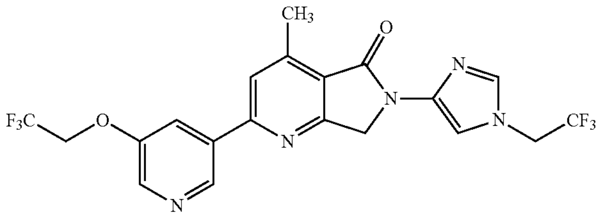 [SMILES: Cc1cc(-c2cncc(OCC(F)(F)F)c2)nc2c1C(=O)N(c1cn(CC(F)(F)F)cn1)C2] | 472.51 | (DMSO-d₆) δ 9.08 (s, 1H), 8.52 (s, 1H), 8.22 (s, 1H), 8.12 (s, 1H), 7.75 (s, 1H), 7.68 (s, 1H), 5.20-5.09 (m, 2H), 5.09-5.00 (m, 2H), 4.99 (s, 2H), 2.75 (s, 3H) |
| 628 | 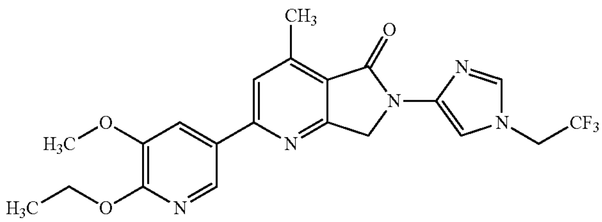 [SMILES: CCOc1ncc(-c2cc(C)c3c(n2)CN(c2cn(CC(F)(F)F)cn2)C3=O)cc1OC] | 448.58 | (DMSO-d₆) δ 8.52 (s, 1H), 7.99 (m, 2H), 7.73 (s, 1H), 7.66 (s, 1H), 5.14 (m, 2H), 4.96 (s, 2H), 4.40 (q, J = 6.9 Hz, 2H), 3.92 (s, 3H), 2.72 (s, 3H), 1.36 (t, J = 6.9 Hz, 3H) |
| 629 | 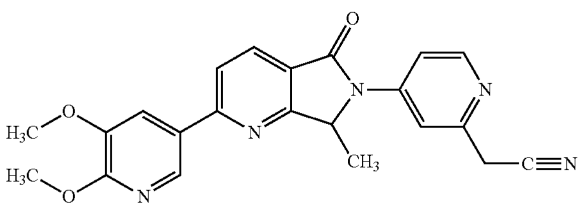 [SMILES: COc1cc(-c2ccc3c(n2)C(C)N(c2ccnc(CC#N)c2)C3=O)cnc1OC] | 402.58 | |
| 630 | 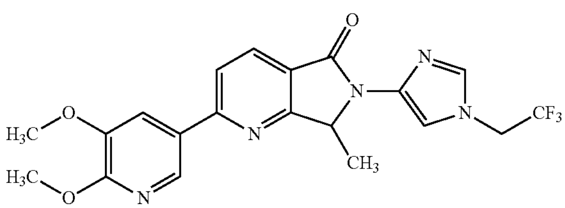 [SMILES: COc1cc(-c2ccc3c(n2)C(C)N(c2cn(CC(F)(F)F)cn2)C3=O)cnc1OC] | 434.4 | (DMSO-d₆) δ 8.57 (d, J = 1.9 Hz, 1H), 8.20 m, 2H), 8.01 (d, J = 1.9 Hz, 1H), 7.78 (s, 1H), 7.71 (s, 1H), 5.32 (q, J = 6.7 Hz, 1H), 5.15 (q, J = 9.3 Hz, 2H), 3.96 (s, 3H), 3.93 (s, 3H), 1.74 (d, J = 6.7 Hz, 3H) |
| 631 | 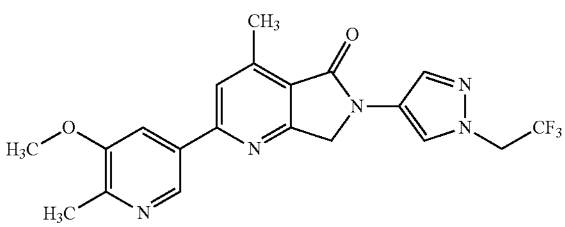 [SMILES: COc1cc(-c2cc(C)c3c(n2)CN(c2cnn(CC(F)(F)F)c2)C3=O)cnc1C] | 418.09 | (CDCl₃) δ 8.69 (d, J = 1.7 Hz, 1H), 8.34 (s, 1H), 7.88 (d, J = 1.5 Hz, 1H), 7.78 (s, 1H), 7.65 (s, 1H), 4.82 (s, 2H), 4.76 (d, J = 8.3 Hz, 2H), 4.00 (s, 3H), 2.85 (s, 3H), 2.57 (s, 3H). |
| 632 | 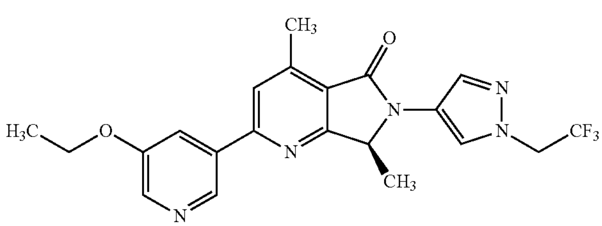 [SMILES: CCOc1cncc(-c2cc(C)c3c(n2)[C@H](C)N(c2cnn(CC(F)(F)F)c2)C3=O)c1] | 432.49 | (DMSO-d₆) δ 8.97 (d, J = 1.6, 1H), 8.40 (d, J = 2.7, 1H), 8.38 (s, 1H), 8.10 (s, 1H), 8.08-8.03 (m, 1H), 7.98 (s, 1H), 5.20 (dd, J = 12.0, 6.1, 3H), 4.24 (q, J = 7.0, 2H), 2.74 (s, 3H), 1.57 (d, J = 6.7 Hz, 3H), 1.40 (t, J = 7.0, 3H). |
| 633 | 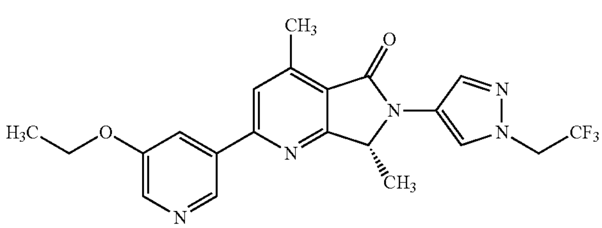 [SMILES: CCOc1cncc(-c2cc(C)c3c(n2)[C@@H](C)N(c2cnn(CC(F)(F)F)c2)C3=O)c1] | 432.49 | (DMSO-d₆) δ 8.97 (s, 1H), 8.40 (d, J = 2.6, 1H), 8.38 (s, 1H), 8.10 (s, 1H), 8.07-8.03 (m, 1H), 7.98 (s, 1H), 5.20 (dt, J = 8.9, 8.1, 3H), 4.24 (q, J = 7.0, 2H), 2.74 (s, 3H), 1.57 (d, J = 6.6 Hz, 3H), 1.40 (t, J = 7.0, 3H). |

TABLE 1-continued

| Cmpd No. | Structure | ESMS (M + H) | ¹H NMR (300 MHz, unless indicated otherwise) |
|---|---|---|---|
| 634 | 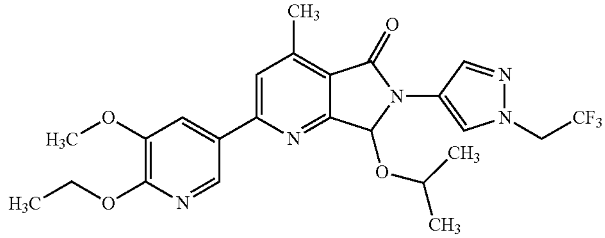 [SMILES: CCOc1ncc(-c2cc(C)c3c(n2)C(OC(C)C)N(c2cnn(CC(F)(F)F)c2)C3=O)cc1OC] | 505.96 | (400 MHz, DMSO-d₆) δ 8.56 (s, 1H), 8.28 (s, 1H), 8.08 (s, 1H), 7.98 (s, 1H), 7.90 (s, 1H), 6.34 (s, 1H), 5.30-5.13 (m, 2H), 4.41 (q, J = 6.9 Hz, 2H), 4.05-3.94 (m, 1H), 3.91 (s, 3H), 2.71 (s, 3H), 1.36 (t, J = 7.0 Hz, 3H), 1.12 (d, 3H), 1.10 (d, 3H). |
| 635 | 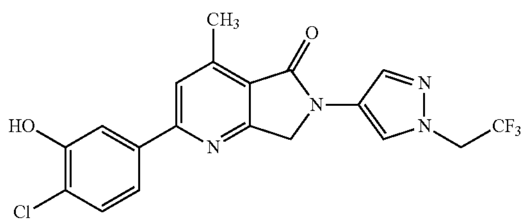 [SMILES: Cc1cc(-c2ccc(Cl)c(O)c2)nc2c1C(=O)N(c1cnn(CC(F)(F)F)c1)C2] | 423.02 | (DMSO-d₆) δ 8.37 (s, 1H), 7.95 (s, 1H), 7.88 (s, 1H), 7.60 (dd, J = 8.4, 2.0 Hz, 1H), 7.48 (d, J = 8.4 Hz, 1H), 5.21 (d, J = 9.1 Hz, 2H), 4.91 (s, 2H), 2.71 (s, 3H), |
| 636 | 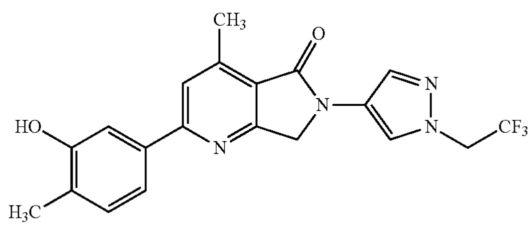 [SMILES: Cc1ccc(-c2cc(C)c3c(n2)CN(c2cnn(CC(F)(F)F)c2)C3=O)cc1O] | 403.3 | |
| 637 | 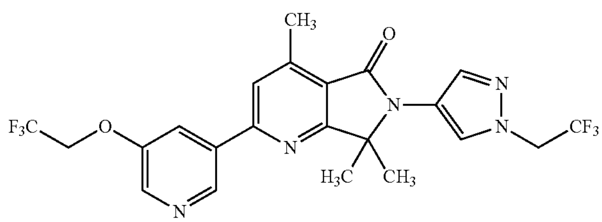 [SMILES: Cc1cc(-c2cncc(OCC(F)(F)F)c2)nc2c1C(=O)N(c1cnn(CC(F)(F)F)c1)C2(C)C] | 500.6 | (DMSO-d₆) δ 9.14 (d, J = 1.5 Hz, 1H), 8.59 (d, J = 2.8 Hz, 1H), 8.38-8.29 (m, 2H), 8.14 (s, 1H), 7.96 (s, 1H), 5.20 (q, J = 9.2 Hz, 2H), 5.06 (q, J = 8.9 Hz, 2H), 2.74 (d, J = 4.2 Hz, 3H), 1.62 (s, 6H) |
| 638 | 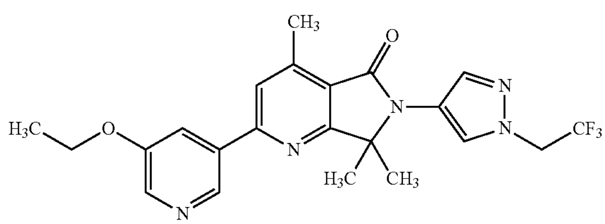 [SMILES: CCOc1cncc(-c2cc(C)c3c(n2)C(C)(C)N(c2cnn(CC(F)(F)F)c2)C3=O)c1] | 446.38 | (DMSO-d₆) δ 8.99 (d, J = 1.7 Hz, 1H), 8.47-8.37 (m, 1H), 8.34 (s, 1H), 8.18-8.01 (m, 1H), 7.95 (s, 1H), 5.20 (dd, J = 18.3, 9.2 Hz, 2H), 4.24 (q, J = 7.0 Hz, 2H), 2.73 (s, 2H), 1.61 (s, 3H), 1.40 (s, 2H) |
| 639 | 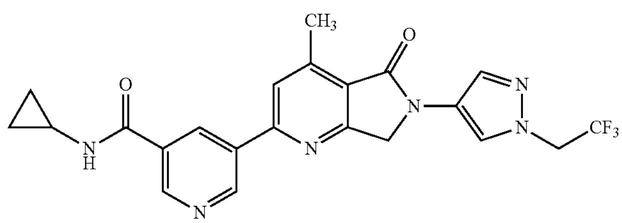 [SMILES: Cc1cc(-c2cncc(C(=O)NC3CC3)c2)nc2c1C(=O)N(c1cnn(CC(F)(F)F)c1)C2] | 457.1 | |

TABLE 1-continued

| Cmpd No. | Structure | ESMS (M + H) | ¹H NMR (300 MHz, unless indicated otherwise) |
|---|---|---|---|
| 640 | 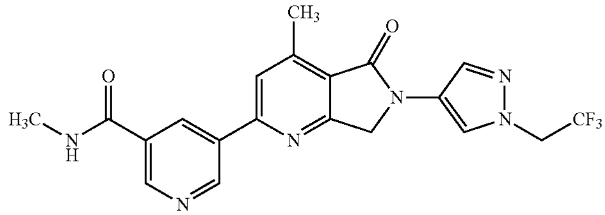 [SMILES: CNC(=O)c1cncc(-c2cc(C)c3c(n2)CN(c2cnn(CC(F)(F)F)c2)C3=O)c1] | 431.08 | |
| 641 | 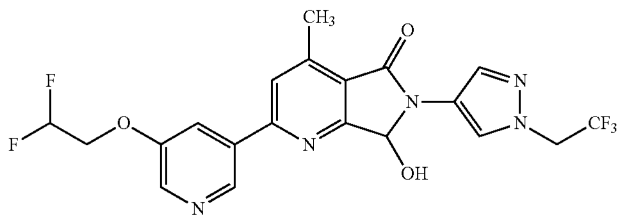 [SMILES: Cc1cc(-c2cncc(OCC(F)F)c2)nc2c1C(=O)N(c1cnn(CC(F)(F)F)c1)C2O] | 471.15 | (DMSO-d₆) δ 9.05 (s, 1H), 8.49 (d, J = 2.3 Hz, 1H), 8.33 (s, 1H), 8.18 (s, 1H), 8.15 (s, 1H), 7.95 (s, 1H), 7.16 (d, J = 9.9 Hz, 1H), 6.48 (t, J = 54.5 Hz, 1H), 6.22 (d, J = 9.9 Hz, 1H), 5.21 (q, J = 9.1 Hz, 2H), 4.57 (td, 2H), 2.74 (s, 3H) |
| 642 | 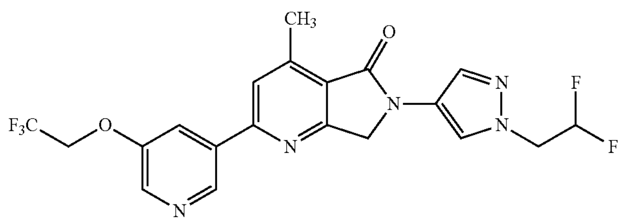 [SMILES: Cc1cc(-c2cncc(OCC(F)(F)F)c2)nc2c1C(=O)N(c1cnn(CC(F)F)c1)C2] | 454.51 | (DMSO-d₆) δ 9.09 (s, 1H), 8.55 (d, J = 2.7 Hz, 1H), 8.32 (s, 1H), 8.26 (s, 1H), 8.14 (s, 1H), 7.91 (s, 1H), 6.39 (t, J = 54.9 Hz, 1H), 5.04 (d, J = 8.8 Hz, 2H), 4.94 (s, 2H), 4.75-4.62 (m, 2H), 2.75 (s, 3H) |
| 643 | 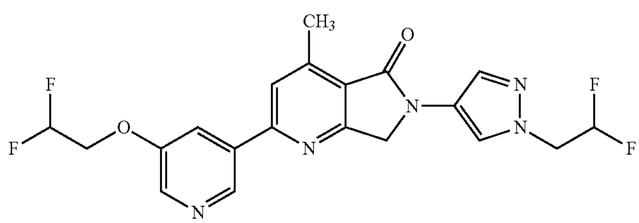 [SMILES: Cc1cc(-c2cncc(OCC(F)F)c2)nc2c1C(=O)N(c1cnn(CC(F)F)c1)C2] | 436.14 | (DMSO-d₆) δ 9.07 (s, 1H), 8.54 (d, J = 2.6 Hz, 1H), 8.32 (s, 1H), 8.26 (s, 1H), 8.16 (s, 1H), 7.91 (s, 1H), 6.48 (m, 2H), 4.94 (s, 2H), 4.78-4.30 (m, 4H), 2.75 (s, 3H) |
| 644 | 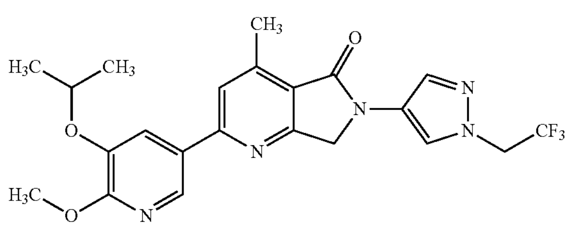 [SMILES: COc1ncc(-c2cc(C)c3c(n2)CN(c2cnn(CC(F)(F)F)c2)C3=O)cc1OC(C)C] | 462.38 | (DMSO-d₆) δ 8.53 (d, J = 1.9 Hz, 1H), 8.38 (s, 1H), 7.99 (s, 1H), 7.97 (d, J = 1.7 Hz, 1H), 7.94 (s, 1H), 5.20 (q, J = 9.1 Hz, 2H), 4.92 (s, 2H), 4.78 (dt, J = 11.9, 6.0 Hz, 1H), 3.94 (s, 3H), 2.72 (s, 3H), 1.33 (d, J = 6.0 Hz, 6H) |
| 645 | 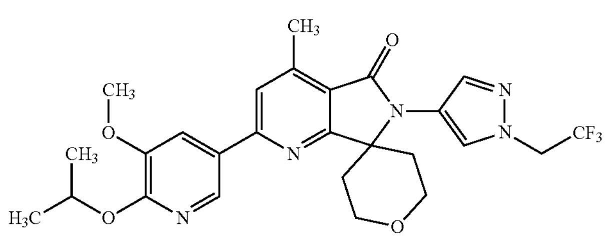 [SMILES: COc1cc(-c2cc(C)c3c(n2)C2(CCOCC2)N(c2cnn(CC(F)(F)F)c2)C3=O)cnc1OC(C)C] | 532.14 | |

TABLE 1-continued

| Cmpd No. | Structure | ESMS (M + H) | ¹H NMR (300 MHz, unless indicated otherwise) |
|---|---|---|---|
| 646 | 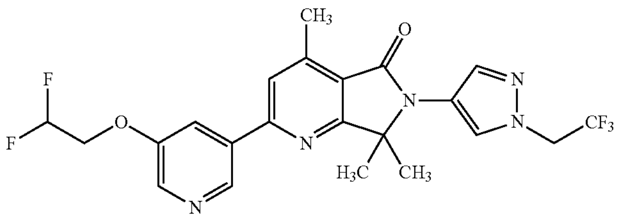 [SMILES: Cc1cc(-c2cncc(OCC(F)F)c2)nc2c1C(=O)N(c1cnn(CC(F)(F)F)c1)C2(C)C] | 482.38 | (DMSO-d₆) δ 9.11 (d, J = 1.7 Hz, 1H), 8.56 (d, J = 2.8 Hz, 1H), 8.35 (s, 1H), 8.33-8.26 (m, 1H), 8.15 (s, 1H), 7.96 (s, 1H), 6.49 (tt, J = 54.2, 3.4 Hz, 1H), 5.20 (q, J = 9.1 Hz, 2H), 4.61 (td, J = 14.7, 3.4 Hz, 2H), 2.74 (s, 3H), 1.62 (s, 6H) |
| 647 | 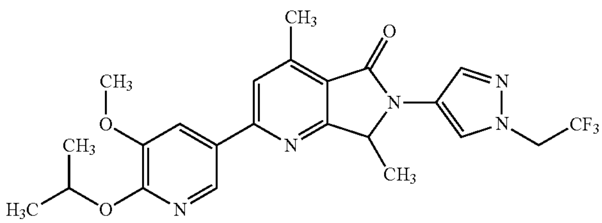 [SMILES: COc1cc(-c2cc(C)c3c(n2)C(C)N(c2cnn(CC(F)(F)F)c2)C3=O)cnc1OC(C)C] | 475.92 | (CDCl3) δ 8.41 (d, J = 2.0 Hz, 1H), 8.31 (s, 1H), 7.88 (d, J = 1.9 Hz, 1H), 7.75 (s, 1H), 7.58 (s, 1H), 5.61-5.41 (m, 1H), 4.97 (m, 1H), 4.76 (q, J = 8.3 Hz, 2H), 4.02 (s, 3H), 2.83 (s, 3H), 1.73 (d, J = 6.7 Hz, 3H), 1.48 (d, J = 6.2 Hz, 6H). |
| 648 | 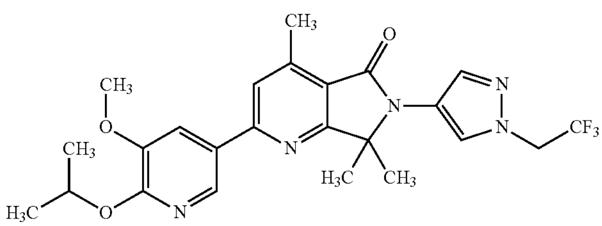 [SMILES: COc1cc(-c2cc(C)c3c(n2)C(C)(C)N(c2cnn(CC(F)(F)F)c2)C3=O)cnc1OC(C)C] | 490.38 | (CDCl3) δ 8.44 (d, J = 1.9 Hz, 1H), 8.17 (s, 1H), 7.85 (d, J = 1.9 Hz, 1H), 7.81 (s, 1H), 7.54 (s, 1H), 5.64-5.38 (m, 1H), 4.76 (q, J = 8.3 Hz, 2H), 4.01 (s, 3H), 2.81 (s, 3H), 1.72 (s, 6H), 1.47 (d, J = 6.2 Hz, 6H) |
| 649 | 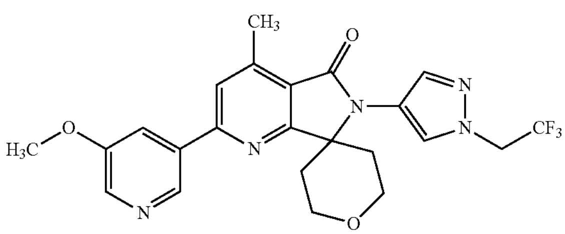 [SMILES: COc1cncc(-c2cc(C)c3c(n2)C2(CCOCC2)N(c2cnn(CC(F)(F)F)c2)C3=O)c1] | 474.12 | |
| 650 | 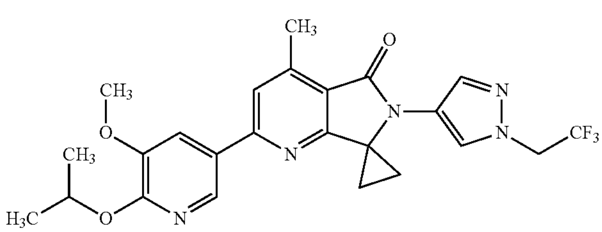 [SMILES: COc1cc(-c2cc(C)c3c(n2)C2(CC2)N(c2cnn(CC(F)(F)F)c2)C3=O)cnc1OC(C)C] | 488.11 | |
| 651 | 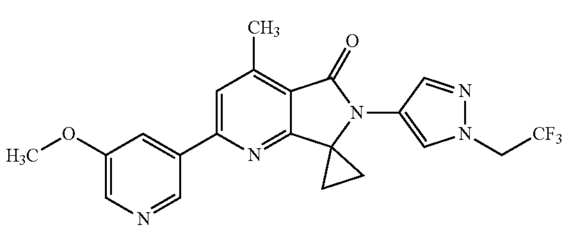 [SMILES: COc1cncc(-c2cc(C)c3c(n2)C2(CC2)N(c2cnn(CC(F)(F)F)c2)C3=O)c1] | 430.09 | |

| Cmpd No. | Structure | ESMS (M + H) | ¹H NMR (300 MHz, unless indicated otherwise) |
|---|---|---|---|
| 652 | 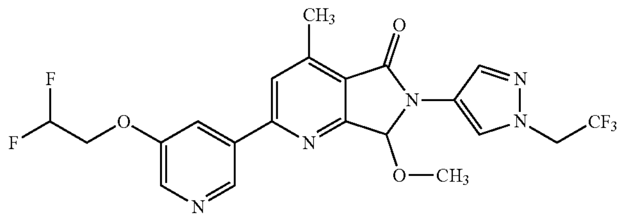 [SMILES: COC1c2nc(-c3cncc(OCC(F)F)c3)cc(C)c2C(=O)N1c1cnn(CC(F)(F)F)c1] | 484.35 | (DMSO-d$_6$) δ 9.05 (s, 1H), 8.51 (d, J = 2.6 Hz, 1H), 8.33 (s, 1H), 8.23 (s, 1H), 8.16 (s, 1H), 7.94 (s, 1H), 6.70-6.25 (tt, 2H), 6.32 (s, 1H), 5.22 (dd, J = 18.2, 9.0 Hz, 2H), 4.58 (dd, J = 14.7, 11.5 Hz, 2H), 3.12 (s, 3H), 2.75 (s, 3H) |
| 653 | 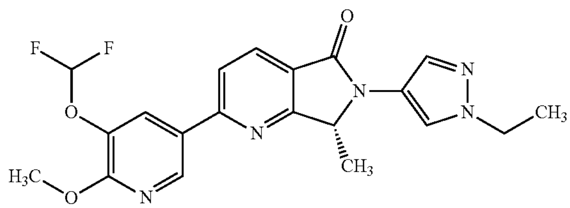 | 416.59 | (DMSO-d$_6$) δ 8.91 (d, J = 2.1 Hz, 1H), 8.36 (d, J = 2.0 Hz, 1H), 8.28-8.17 (m, 3H), 7.82 (d, J = 0.5 Hz, 1H), 7.33 (t, J = 73.6 Hz, 1H), 5.21 (q, J = 6.6 Hz, 1H), 4.18 (q, J = 7.3 Hz, 2H), 4.03 (s, 3H), 1.59 (t, J = 7.6 Hz, 3H), 1.40 (td, J = 7.2, 3.8 Hz, 3H) |
| 654 | 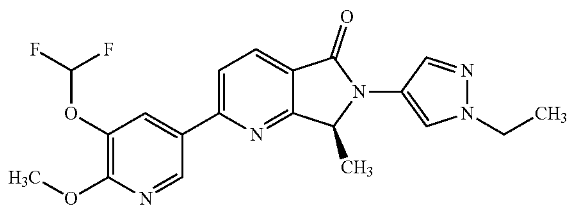 [SMILES: CCn1cc(N2C(=O)c3ccc(-c4cnc(OC)c(OC(F)F)c4)nc3[C@@H]2C)cn1] | | (DMSO-d$_6$) δ 8.91 (d, J = 2.1 Hz, 1H), 8.36 (d, J = 2.0 Hz, 1H), 8.30-8.13 (m, 3H), 7.82 (s, 1H), 7.33 (t, J = 73.6 Hz, 1H), 5.21 (q, J = 6.6 Hz, 1H), 4.18 (q, J = 7.3 Hz, 2H), 4.03 (s, 3H), 1.58 (d, J = 6.7 Hz, 3H), 1.40 (t, J = 7.3 Hz, 3H) |
| 655 | 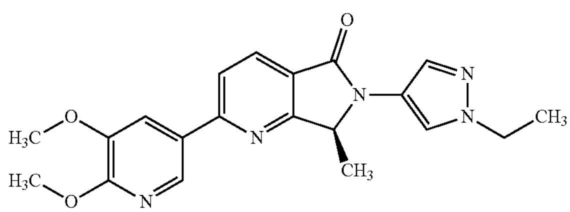 [SMILES: CCn1cc(N2C(=O)c3ccc(-c4cnc(OC)c(OC)c4)nc3[C@@H]2C)cn1] | 380.56 | (DMSO-d$_6$) δ 8.56 (t, J = 4.1 Hz, 1H), 8.20 (t, J = 4.6 Hz, 2H), 7.98 (t, J = 5.8 Hz, 1H), 7.81 (s, 1H), 5.20 (q, J = 6.6 Hz, 1H), 4.18 (q, J = 7.2 Hz, 2H), 3.94 (d, J = 9.2 Hz, 6H), 1.58 (d, J = 6.7 Hz, 3H), 1.47-1.34 (m, 3H) |
| 656 | 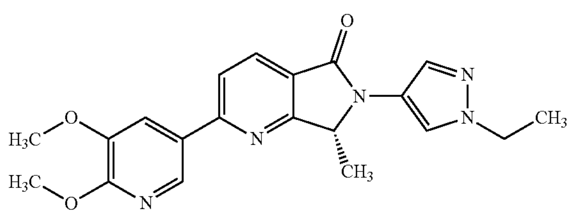 [SMILES: CCn1cc(N2C(=O)c3ccc(-c4cnc(OC)c(OC)c4)nc3[C@H]2C)cn1] | 380.56 | (DMSO-d$_6$) δ 8.57 (d, J = 1.9 Hz, 1H), 8.20 (dd, J = 6.3, 5.8 Hz, 2H), 7.98 (t, J = 6.5 Hz, 1H), 7.81 (s, 1H), 5.20 (q, J = 6.6 Hz, 1H), 4.18 (q, J = 7.3 Hz, 2H), 3.94 (d, J = 9.1 Hz, 6H), 1.58 (d, J = 6.7 Hz, 3H), 1.41 (t, J = 7.3 Hz, 3H) |
| 657 | 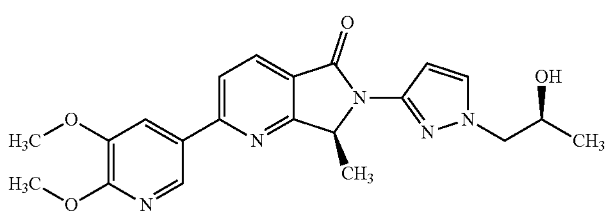 [SMILES: COc1cc(-c2ccc3c(n2)[C@H](C)N(c2ccn(C[C@H](C)O)n2)C3=O)cnc1OC] | 410.57 | |
| 658 | 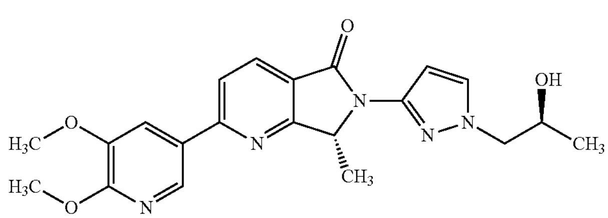 | 409.93 | |

TABLE 1-continued

| Cmpd No. | Structure | ESMS (M + H) | ¹H NMR (300 MHz, unless indicated otherwise) |
|---|---|---|---|
| 659 | 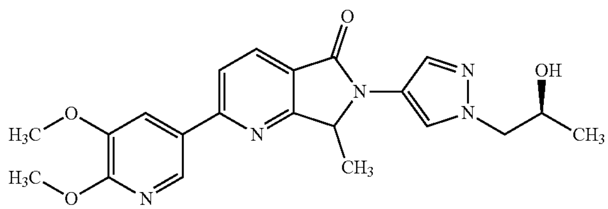 [SMILES: COc1cc(-c2ccc3c(n2)C(C)N(c2cnn(C[C@H](C)O)c2)C3=O)cnc1OC] | 410.51 | (methanol-d₄) δ 8.52 (d, J = 2.0 Hz, 1H), 8.33-8.25 (m, 3H), 8.09-8.06 (m, 2H), 4.05 (t, J = 24.7 Hz, 9H), 1.40-1.12 (m, 7H) |
| 660 | 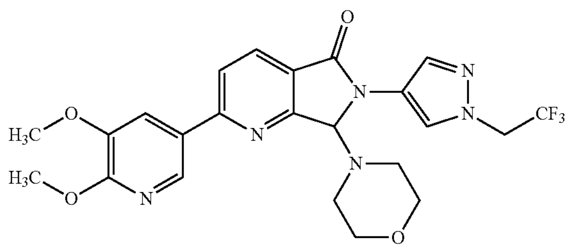 [SMILES: COc1cc(-c2ccc3c(n2)C(N2CCOCC2)N(c2cnn(CC(F)(F)F)c2)C3=O)cnc1OC] | 505.4 | |
| 661 | 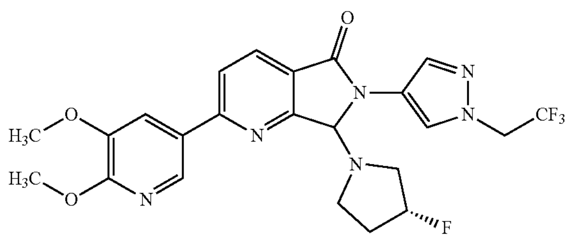 [SMILES: COc1cc(-c2ccc3c(n2)C(N2CC[C@@H](F)C2)N(c2cnn(CC(F)(F)F)c2)C3=O)cnc1OC] | 507.5 | |
| 662 | 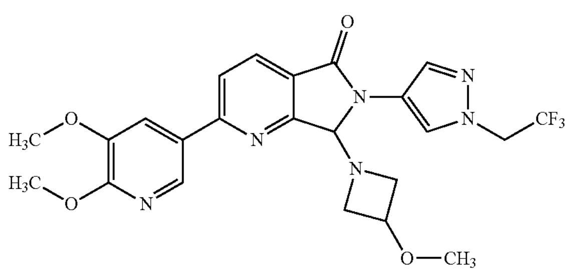 [SMILES: COc1cc(-c2ccc3c(n2)C(N2CC(OC)C2)N(c2cnn(CC(F)(F)F)c2)C3=O)cnc1OC] | 505.6 | |
| 663 | 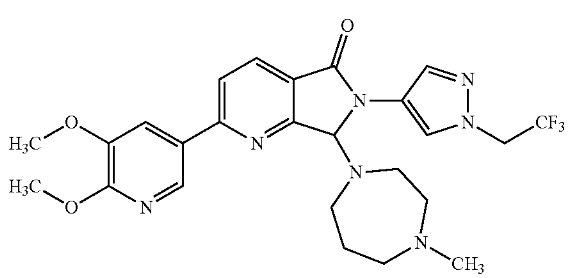 [SMILES: COc1cc(-c2ccc3c(n2)C(N2CCCN(C)CC2)N(c2cnn(CC(F)(F)F)c2)C3=O)cnc1OC] | 532.6 | |
| 664 | 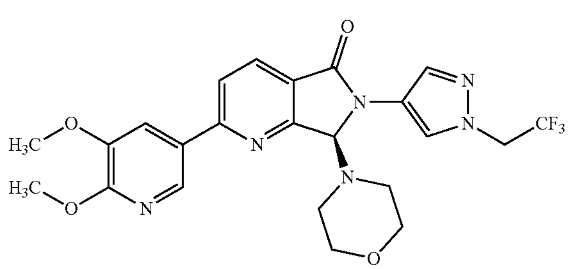 [SMILES: COc1cc(-c2ccc3c(n2)[C@H](N2CCOCC2)N(c2cnn(CC(F)(F)F)c2)C3=O)cnc1OC] | 505.46 | |

TABLE 1-continued

| Cmpd No. | Structure | ESMS (M + H) | ¹H NMR (300 MHz, unless indicated otherwise) |
|---|---|---|---|
| 665 | 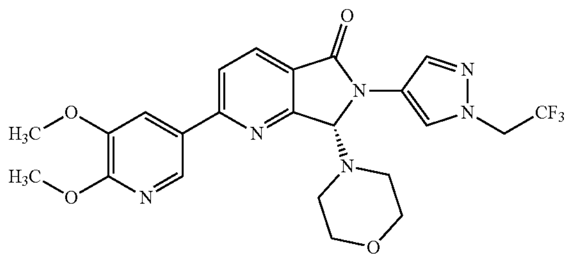 [SMILES: COc1cc(-c2ccc3c(n2)[C@@H](N2CCOCC2)N(c2cnn(CC(F)(F)F)c2)C3=O)cnc1OC] | 505.46 | |
| 666 | 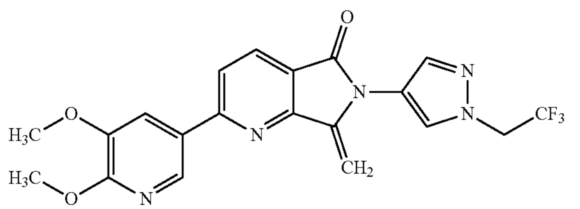 [SMILES: C=C1c2nc(-c3cnc(OC)c(OC)c3)ccc2C(=O)N1c1cnn(CC(F)(F)F)c1] | 432.52 | |
| 667 | 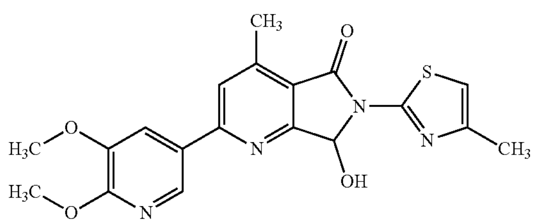 | 399.5 | (DMSO-d$_6$) δ 8.57 (d, J = 1.9 Hz, 1H), 8.11 (s, 1H), 7.97 (d, J = 1.9 Hz, 1H), 7.42-7.25 (m, 1H), 6.95 (s, 1H), 6.59 (s, 1H), 3.96 (s, 3H), 3.93 (s, 3H), 2.73 (s, 3H), 2.36 (s, 3H) |
| 668 | 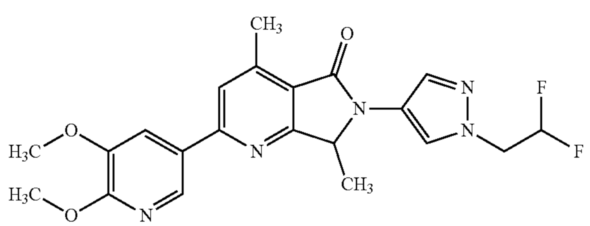 | 416.59 | (DMSO-d$_6$) δ 8.58 (d, J = 2.0 Hz, 1H), 8.32 (s, 1H), 8.21 (q, J = 8.2 Hz, 2H), 8.00 (d, J = 1.9 Hz, 1H), 7.91 (s, 1H), 6.40 (tt, 1H), 5.25 (d, J = 6.7 Hz, 1H), 4.69 (td, J = 15.1, 3.7 Hz, 2H), 3.96 (s, 3H), 3.93 (s, 3H), 1.59 (d, J = 6.7 Hz, 3H) |
| 669 | 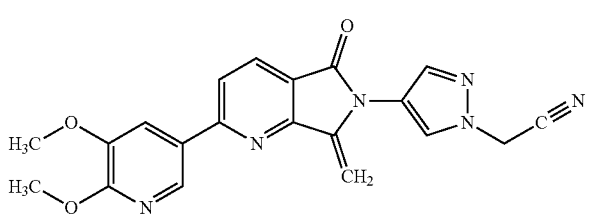 [SMILES: C=C1c2nc(-c3cnc(OC)c(OC)c3)ccc2C(=O)N1c1cnn(CC#N)c1] | 389.1 | (DMSO-d$_6$) δ 8.65 (d, J = 2.0 Hz, 1H), 8.31 (m, 3H), 8.08 (d, J = 1.9 Hz, 1H), 7.91 (s, 1H), 5.87 (d, J = 1.8 Hz, 1H), 5.59 (s, 2H), 5.15 (d, J = 1.8 Hz, 1H), 3.97 (s, 3H), 3.94 (s, 3H) |
| 670 | 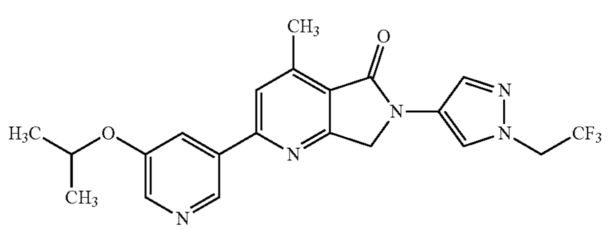 [SMILES: Cc1cc(-c2cncc(OC(C)C)c2)nc2c1C(=O)N(c1cnn(CC(F)(F)F)c1)C2] | 432.52 | (DMSO-d$_6$) δ 8.93 (d, J = 1.7 Hz, 1H), 8.45-8.33 (m, 2H), 8.10 (s, 1H), 8.08-8.01 (m, 1H), 7.95 (s, 1H), 5.21 (d, J = 9.1 Hz, 2H), 4.95 (s, 2H), 4.92-4.79 (m, 1H), 2.74 (s, 3H), 1.34 (d, J = 6.0 Hz, 6H) |

TABLE 1-continued

| Cmpd No. | Structure | ESMS (M + H) | ¹H NMR (300 MHz, unless indicated otherwise) |
|---|---|---|---|
| 671 | 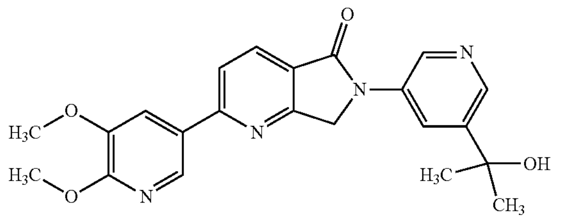 [SMILES: COc1cc(-c2ccc3c(n2)CN(c2cncc(C(C)(C)O)c2)C3=O)cnc1OC] | 421.32 | (DMSO-d$_6$) δ 8.94 (d, J = 2.4 Hz, 1H), 8.57 (d, J = 1.9 Hz, 1H), 8.51 (t, J = 2.6 Hz, 1H), 8.47 (t, J = 2.2 Hz, 1H), 8.04 (s, 1H), 7.98 (d, J = 1.9 Hz, 1H), 5.31 (s, 1H), 5.13 (s, 2H), 3.96-3.90 (m, 6H), 2.74 (s, 3H), 1.51 (s, 6H) |
| 672 | 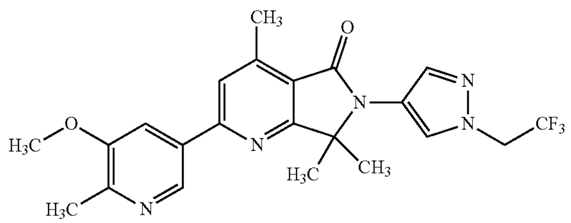 [SMILES: COc1cc(-c2cc(C)c3c(n2)C(C)(C)N(c2cnn(CC(F)(F)F)c2)C3=O)cnc1C] | 446.6 | (DMSO-d$_6$) δ 8.84 (d, J = 1.6 Hz, 1H), 8.34 (s, 1H), 8.06 (s, 1H), 8.00 (d, J = 1.6 Hz, 1H), 7.95 (s, 1H), 5.20 (q, J = 9.1 Hz, 2H), 3.96 (s, 3H), 2.73 (s, 3H), 2.44 (s, 3H), 1.61 (s, 6H) |
| 673 | 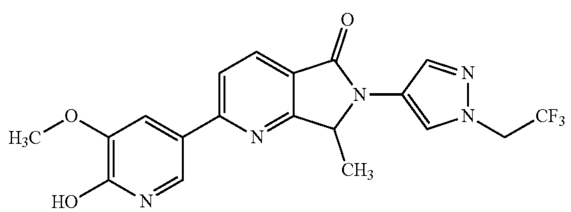 [SMILES: COc1cc(-c2ccc3c(n2)C(C)N(c2cnn(CC(F)(F)F)c2)C3=O)cnc1O] | 420.07 | (DMSO-d$_6$) δ 12.09 (s, 1H), 8.36 (d, J = 9.2, 1H), 8.15 (d, J = 8.3, 1H), 8.05 (dd, J = 8.2, 4.0, 1H), 8.00-7.92 (m, 2H), 7.62 (d, J = 2.1, 1H), 5.32-5.05 (m, 3H), 3.84 (s, 3H), 1.62-1.54 (m, 3H) |
| 674 | 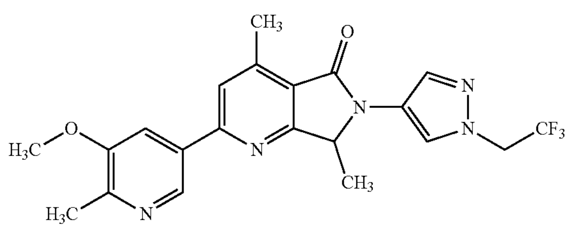 [SMILES: COc1cc(-c2cc(C)c3c(n2)C(C)N(c2cnn(CC(F)(F)F)c2)C3=O)cnc1C] | 432.11 | (DMSO-d$_6$) δ 8.83 (d, J = 1.7 Hz, 1H), 8.37 (s, 1H), 8.08 (s, 1H), 7.98 (d, J = 8.4 Hz, 2H), 5.32-5.11 (m, 3H), 3.96 (s, 3H), 2.74 (s, 3H), 2.44 (s, 3H), 1.57 (d, J = 6.6 Hz, 3H) |
| 675 | 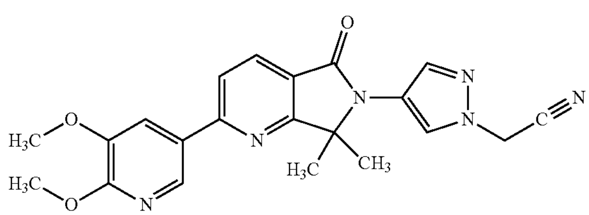 [SMILES: COc1cc(-c2ccc3c(n2)C(C)(C)N(c2cnn(CC#N)c2)C3=O)cnc1OC] | 405.13 | (DMSO-d$_6$) δ 8.59 (d, J = 1.9 Hz, 1H), 8.35 (s, 1H), 8.20 (m, 2H), 8.02 (d, J = 1.9 Hz, 1H), 7.97 (s, 1H), 5.56 (s, 2H), 3.96 (s, 3H), 3.93 (s, 3H), 1.63 (s, 6H) |
| 676 | 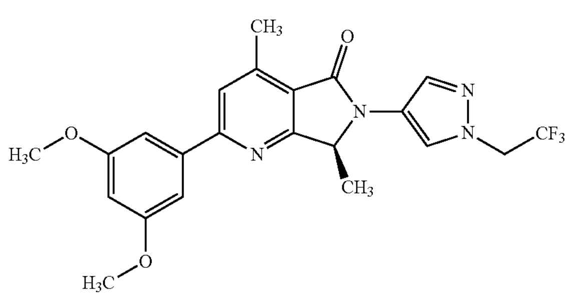 [SMILES: COc1cc(OC)cc(-c2cc(C)c3c(n2)[C@H](C)N(c2cnn(CC(F)(F)F)c2)C3=O)c1] | 447.43 | (DMSO-d$_6$) δ 8.37 (s, 1H), 7.97 (d, J = 4.9 Hz, 2H), 7.34 (d, J = 2.2 Hz, 2H), 6.65 (t, J = 2.2 Hz, 1H), 5.20 (d, J = 8.9 Hz, 2H), 3.82 (d, J = 13.8 Hz, 5H), 2.72 (s, 3H), 1.57 (t, J = 7.4 Hz, 3H) |

TABLE 1-continued

| Cmpd No. | Structure | ESMS (M + H) | ¹H NMR (300 MHz, unless indicated otherwise) |
|---|---|---|---|
| 677 | 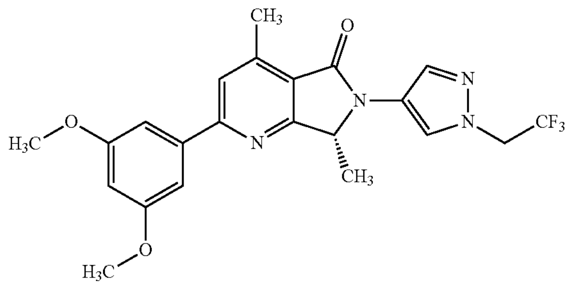 | 448.11 | (DMSO-d₆) δ 8.37 (s, 1H), 7.97 (d, J = 4.9 Hz, 2H), 7.34 (d, J = 2.2 Hz, 2H), 6.65 (t, J = 2.2 Hz, 1H), 5.18 (dd, J = 12.3, 5.8 Hz, 2H), 3.82 (d, J = 13.8 Hz, 6H), 2.72 (s, 3H), 1.57 (t, J = 7.4 Hz, 3H) |
| 678 | 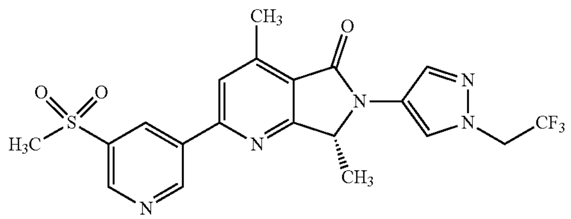 | 466.08 | (DMSO-d₆) δ 9.50 (s, 1H), 9.06 (s, 1H), 8.94 (s, 1H), 8.20 (s, 1H), 7.91 (d, J = 18.7 Hz, 2H), 5.04 (dd, J = 13.3, 6.6 Hz, 1H), 4.90 (d, J = 8.8 Hz, 2H), 2.73 (s, 3H), 1.56 (d, J = 6.6 Hz, 3H), 1.18 (s, 3H) |
| 679 | 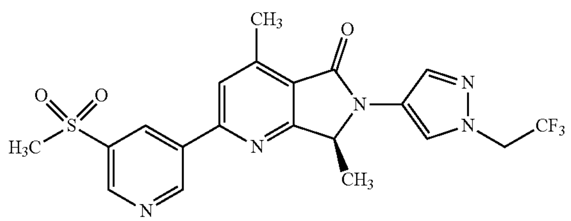 [SMILES: Cc1cc(-c2cncc(S(C)(=O)=O)c2)nc2c1C(=O)N(c1cnn(CC(F)(F)F)c1)[C@H]2C] | 466.03 | (methanol-d₄) δ 9.50 (s, 1H), 9.06 (s, 1H), 8.94 (s, 1H), 8.20 (s, 1H), 7.91 (d, J = 18.7 Hz, 2H), 5.04 (dd, J 13.3, 6.6 Hz, 1H), 4.90 (d, J = 8.8 Hz, 2H), 2.73 (s, 3H), 1.56 (d, J = 6.6 Hz, 3H), 1.18 (s, 3H) |
| 680 | 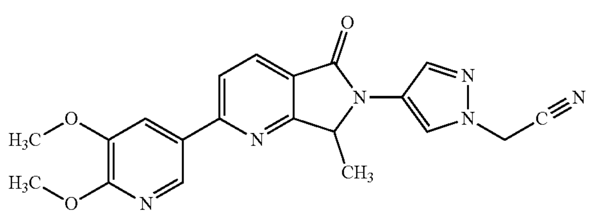 [SMILES: COc1cc(-c2ccc3c(n2)C(C)N(c2cnn(CC#N)c2)C3=O)cnc1OC] | 391.11 | (DMSO-d₆) δ 8.58 (d, J = 1.9 Hz, 1H), 8.39 (s, 1H), 8.22 m, 2H), 8.01 (d, J = 1.9 Hz, 1H), 7.99 (s, 1H), 5.56 (s, 2H), 5.26 (d, J = 6.7 Hz, 1H), 3.96 (s, 3H), 3.93 (s, 3H), 1.59 (d, J = 6.7 Hz, 3H) |
| 681 | 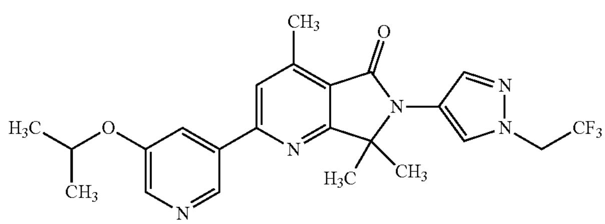 [SMILES: Cc1cc(-c2cncc(OC(C)C)c2)nc2c1C(=O)N(c1cnn(CC(F)(F)F)c1)C2(C)C] | 461.13 | (DMSO-d₆) δ 9.11 (d, J = 1.3 Hz, 1H), 8.62 (d, J = 2.5 Hz, 1H), 8.48 (s, 1H), 8.36 (s, 1H), 8.22 (s, 1H), 7.96 (s, 1H), 5.76 (s, 2H), 5.34-5.13 (m, 2H), 4.98 (ddd, J = 20.9, 13.4, 7.5 Hz, 3H), 4.03 (q, J = 7.1 Hz, 1H), 3.77 (dt, J = 12.2, 6.1 Hz, 1H), 2.75 (s, 2H), 1.37 (s, 3H), 1.04 (d, J = 6.1 Hz, 4H) |
| 682 | 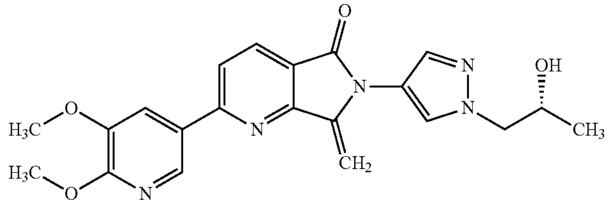 [SMILES: C=C1c2nc(-c3cnc(OC)c(OC)c3)ccc2C(=O)N1c1cnn(C[C@@H](C)O)c1] | 408 | (CDCl₃) δ 8.47 (d, J = 2.0 Hz, 1H), 8.23 (d, J = 8.1 Hz, 1H), 7.96 (d, J = 1.9 Hz, 1H), 7.90 (d, J = 8.2 Hz, 1H), 7.81 (s, 1H), 7.75 (s, 1H), 5.92 (d, J = 1.7 Hz, 1H), 5.18 (d, J = 1.7 Hz, 1H), 4.30 (ddd, J = 16.3, 10.9, 2.2 Hz, 2H), 4.17-3.99 (m, 6H), 3.40 (d, J = 3.7 Hz, 1H), 1.32 (d, J = 6.3 Hz, 3H) |

TABLE 1-continued

| Cmpd No. | Structure | ESMS (M + H) | ¹H NMR (300 MHz, unless indicated otherwise) |
|---|---|---|---|
| 683 | 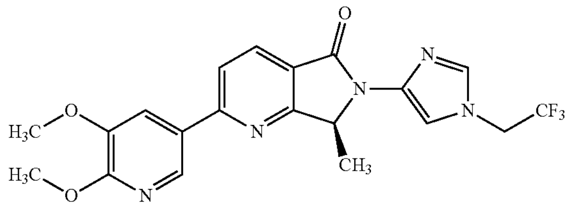 [SMILES: COc1cc(-c2ccc3c(n2)[C@H](C)N(c2cn(CC(F)(F)F)cn2)C3=O)cnc1OC] | | (DMSO-d₆) δ 8.57 (d, J = 2.0 Hz, 1H), 8.21 (m, 2H), 8.01 (d, J = 2.0 Hz, 1H), 7.77 (s, 1H), 7.71 (s, 1H), 5.76 (s, 2H), 5.32 (q, J = 6.7 Hz, 1H), 5.15 (q, J = 9.4 Hz, 2H), 3.96 (s, 3H), 3.93 (s, 3H), 1.74 (d, J = 6.7 Hz, 3H) |
| 684 | 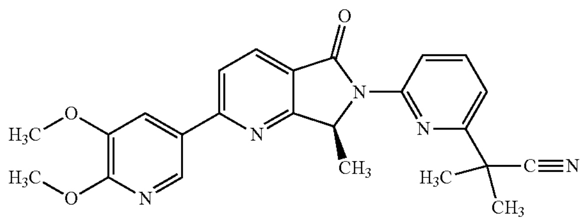 [SMILES: COc1cc(-c2ccc3c(n2)[C@H](C)N(c2cccc(C(C)(C)C#N)n2)C3=O)cnc1OC] | 430.6 | (DMSO-d₆) δ 8.61 (d, J = 1.9 Hz, 1H), 8.42 (d, J = 8.1 Hz, 1H), 8.27 (dd, J = 21.0, 8.2 Hz, 2H), 8.08-7.95 (m, 2H), 7.41 (d, J = 7.5 Hz, 1H), 5.70 (d, J = 6.7 Hz, 1H), 3.95 (d, J = 8.3 Hz, 6H), 1.76 (dd, J = 6.8, 3.9 Hz, 7H) |
| 685 | 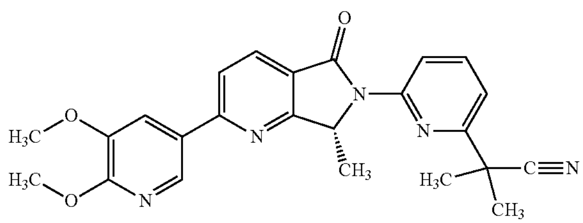 [SMILES: COc1cc(-c2ccc3c(n2)[C@@H](C)N(c2cccc(C(C)(C)C#N)n2)C3=O)cnc1OC] | 430.6 | (DMSO-d₆) δ 8.61 (d, J = 1.9 Hz, 1H), 8.42 (d, J = 8.3 Hz, 1H), 8.27 (dd, J = 21.0, 8.2 Hz, 2H), 8.11-7.97 (m, 2H), 7.41 (d, J = 7.6 Hz, 1H), 5.70 (d, J = 6.7 Hz, 1H), 3.95 (d, J = 8.3 Hz, 6H), 1.82- 1.65 (m, 7H) |
| 686 | 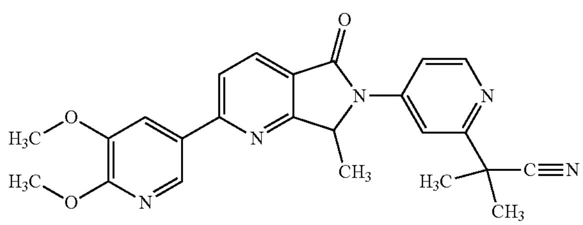 [SMILES: COc1cc(-c2ccc3c(n2)C(C)N(c2ccnc(C(C)(C)C#N)c2)C3=O)cnc1OC] | 430.6 | (DMSO-d₆) δ 8.62 (dd, J = 7.1, 3.8 Hz, 2H), 8.28 (dd, J = 17.2, 8.2 Hz, 2H), 8.14 (d, J = 1.8 Hz, 1H), 8.03 (d, J = 1.9 Hz, 1H), 7.81 (dd, J = 5.7, 1.9 Hz, 1H), 5.75 (d, J = 6.6 Hz, 1H), 3.95 (d, J = 10.1 Hz, 6H), 1.76 (d, J = 2.7 Hz, 6H), 1.58 (d, J = 6.6 Hz, 3H) |
| 687 | 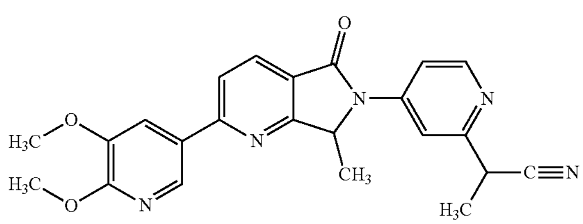 [SMILES: COc1cc(-c2ccc3c(n2)C(C)N(c2ccnc(C(C)C#N)c2)C3=O)cnc1OC] | 416.59 | (DMSO-d₆) δ 8.62 (t, J = 3.6 Hz, 2H), 8.28 (dd, J = 19.3, 8.2 Hz, 2H), 8.02 (d, J = 2.0 Hz, 2H), 7.81 (d, J = 5.7 Hz, 1H), 5.67 (d, J = 6.6 Hz, 1H), 4.49 (dd, J = 7.2, 4.7 Hz, 1H), 3.95 (d, J = 9.6 Hz, 6H), 1.69-1.44 (m, 6H) |
| 688 | 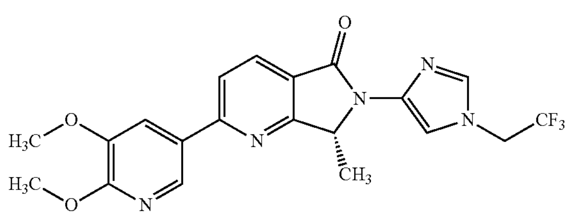 [SMILES: COc1cc(-c2ccc3c(n2)[C@@H](C)N(c2cn(CC(F)(F)F)cn2)C3=O)cnc1OC] | | (DMSO-d₆) δ 8.57 (d, J = 1.9 Hz, 1H), 8.20 (m, 2H), 8.01 (d, J = 1.9 Hz, 1H), 7.77 (s, 1H), 7.71 (s, 1H), 5.76 (s, 2H), 5.32 (q, J = 6.7 Hz, 1H), 5.15 (q, J = 9.4 Hz, 2H), 3.96 (s, 3H), 3.93 (s, 3H), 1.74 (d, J = 6.7 Hz, 3H) |
| 689 | 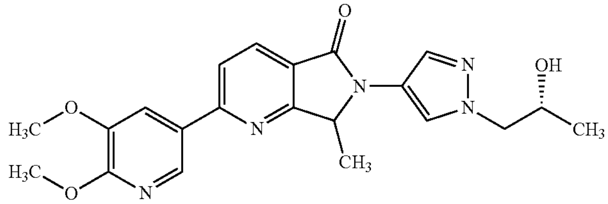 [SMILES: COc1cc(-c2ccc3c(n2)C(C)N(c2cnn(C[C@@H](C)O)c2)C3=O)cnc1OC] | 410.12 | (CDCl₃) δ 8.33 (t, J = 1.8 Hz, 1H), 8.09 (dd, J = 5.9, 2.2 Hz, 2H), 7.87-7.70 (m, 2H), 7.58 (d, J = 4.3 Hz, 1H), 4.89 (qd, J = 6.7, 3.3 Hz, 1H), 4.25-4.08 (m, 2H), 4.03 (s, 3H), 3.95 (s, 3H), 3.49 (d, J = 23.0 Hz, 1H), 1.63 (dd, J = 6.7, 0.6 Hz, 3H), 1.20 (d, J = 6.2 Hz, 3H) |

TABLE 1-continued

| Cmpd No. | Structure | ESMS (M + H) | ¹H NMR (300 MHz, unless indicated otherwise) |
|---|---|---|---|
| 690 | 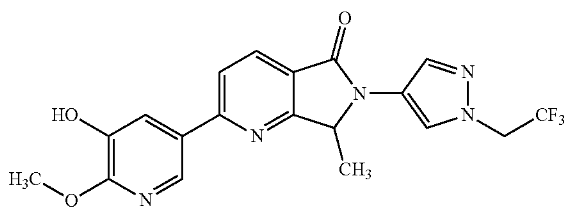 [SMILES: COc1ncc(-c2ccc3c(n2)C(C)N(c2cnn(CC(F)(F)F)c2)C3=O)cc1O] | 420.49 | (400 MHz, DMSO-d₆) δ 9.89 (s, 1H), 8.46 (d, J = 1.9, 1H), 8.39 (s, 1H), 8.19 (d, J = 8.1, 1H), 8.08 (d, J = 8.1, 1H), 7.97 (s, 1H), 7.91 (d, J = 1.9, 1H), 5.32-5.13 (m, 3H), 3.96 (s, 3H), 1.58 (d, J = 6.7, 3H) |
| 691 | 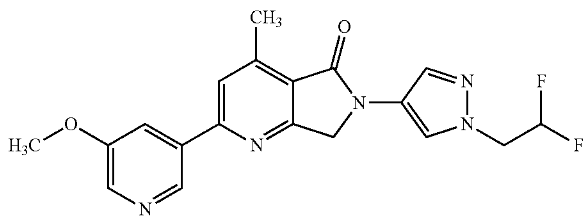 [SMILES: COc1cncc(-c2cc(C)c3c(n2)CN(c2cnn(CC(F)F)c2)C3=O)c1] | 386.15 | (400 MHz, DMSO-d₆) δ 8.97 (s, 1H), 8.41 (d, J = 2.7 Hz, 1H), 8.32 (s, 1H), 8.10 (s, 1H), 8.06 (s, 1H), 7.90 (s, 1H), 6.54-6.22 (tt, 1H), 4.94 (s, 2H), 4.68 (dd, J = 3.6 Hz, 2H), 3.95 (s, 3H), 2.74 (s, 3H) |
| 692 | 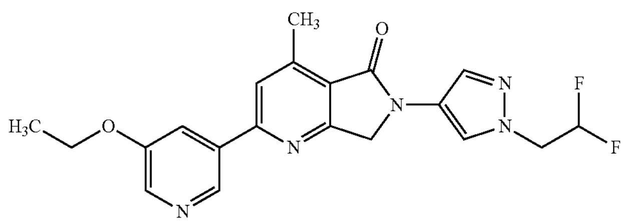 [SMILES: CCOc1cncc(-c2cc(C)c3c(n2)CN(c2cnn(CC(F)F)c2)C3=O)c1] | 400.17 | (400 MHz, DMSO-d₆) δ 8.94 (s, 1H), 8.38 (t, J = 4.3 Hz, 1H), 8.31 (s, 1H), 8.07 (s, 1H), 8.02 (s, 1H), 7.90 (s, 1H), 6.39 (tt, J = 55.0, 3.6 Hz, 1H), 4.91 (s, 2H), 4.68 (td, J = 15.1, 3.6 Hz, 2H), 4.22 (q, J = 6.9 Hz, 2H), 2.72 (s, 3H), 1.40 (t, J = 6.9 Hz, 3H) |
| 693 | 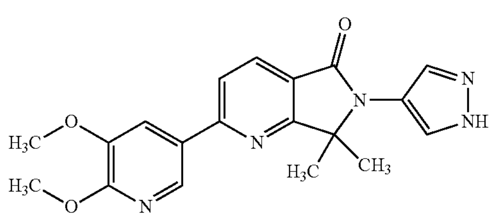 [SMILES: COc1cc(-c2ccc3c(n2)C(C)(C)N(c2cn[nH]c2)C3=O)cnc1OC] | 365.99 | (400 MHz, DMSO-d₆) δ 8.59 (s, 1H), 8.18 (m, 2H), 8.02 (s, 1H), 7.94 (m, 2H), 3.96 (s, 3H), 3.93 (s, 3H), 1.59 (s, 6H) |
| 694 | 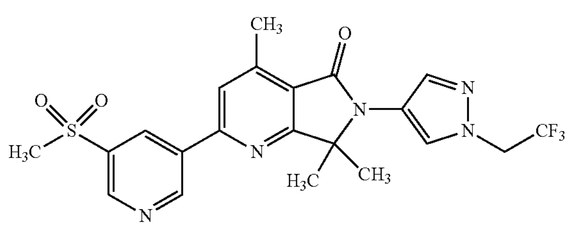 [SMILES: Cc1cc(-c2cncc(S(C)(=O)=O)c2)nc2c1C(=O)N(c1cnn(CC(F)(F)F)c1)C2(C)C] | 480.57 | (DMSO-d₆) δ 9.19 (d, J = 1.9 Hz, 1H), 9.09 (d, J = 2.4 Hz, 1H), 8.99 (s, 1H), 8.91 (d, J = 3.4 Hz, 1H), 8.33 (d, J = 7.9 Hz, 2H), 5.27-5.12 (m, 2H), 3.44 (s, 3H), 2.75 (d, J = 11.0 Hz, 3H), 1.63 (s, 6H) |
| 695 | 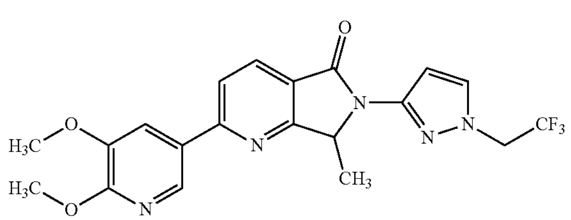 | 433.83 | (400 MHz, DMSO-d₆) δ 8.58 (d, J = 1.7 Hz, 1H), 8.22 (dd, J = 23.0, 8.1 Hz, 2H), 8.01 (s, 1H), 7.90 (d, J = 2.3 Hz, 1H), 6.93 (d, J = 2.4 Hz, 1H), 5.25 (q, J = 6.6 Hz, 1H), 5.16 (dd, J = 8.9, 5.1 Hz, 2H), 3.96 (s, 3H), 3.93 (s, 3H), 1.72 (d, J = 6.7 Hz, 3H) |
| 696 | 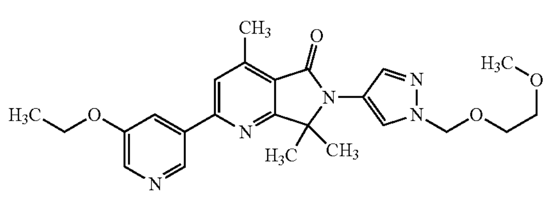 [SMILES: CCOc1cncc(-c2cc(C)c3c(n2)C(C)(C)N(c2cnn(COCCOC)c2)C3=O)c1] | 452.52 | (CDCl₃) δ 8.89 (d, J = 1.7 Hz, 1H), 8.40 (d, J = 2.8 Hz, 1H), 8.12 (s, 1H), 8.01-7.90 (m, 1H), 7.80 (s, 1H), 7.62 (s, 1H), 5.56 (s, 2H), 3.40 (s, 3H), 2.84 (s, 3H), 1.70 (s, 6H), 1.52 (t, J = 7.0 Hz, 3H) |

TABLE 1-continued

| Cmpd No. | Structure | ESMS (M + H) | ¹H NMR (300 MHz, unless indicated otherwise) |
|---|---|---|---|
| 697 | 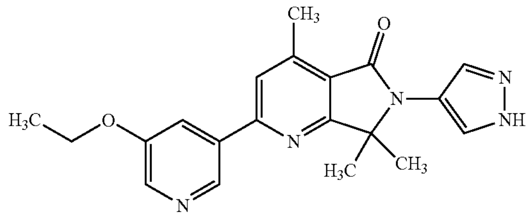 [SMILES: CCOc1cncc(-c2cc(C)c3c(n2)C(C)(C)N(c2cn[nH]c2)C3=O)c1] | 364.58 | (CDCl₃) δ 8.89 (d, J = 1.7 Hz, 1H), 8.41 (d, J = 2.8 Hz, 1H), 7.95 (dd, J = 8.3, 6.3 Hz, 2H), 7.62 (s, 1H), 4.23 (q, J = 7.0 Hz, 2H), 2.84 (s, 3H), 1.70 (s, 6H), 1.52 (t, J = 7.0 Hz, 3H) |
| 698 | 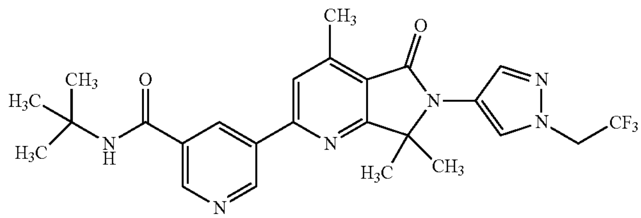 [SMILES: Cc1cc(-c2cncc(C(=O)NC(C)(C)C)c2)nc2c1C(=O)N(c1cnn(CC(F)(F)F)c1)C2(C)C] | 501.71 | (DMSO-d₆) δ 9.46 (d, J = 2.2 Hz, 1H), 9.04 (d, J = 2.0 Hz, 1H), 8.79 (t, J = 2.1 Hz, 1H), 8.35 (s, 1H), 7.96 (d, J = 0.4 Hz, 2H), 5.18 (t, J = 9.1 Hz, 2H), 1.63 (s, 6H), 1.41 (d, J = 13.8 Hz, 12H) |
| 699 | 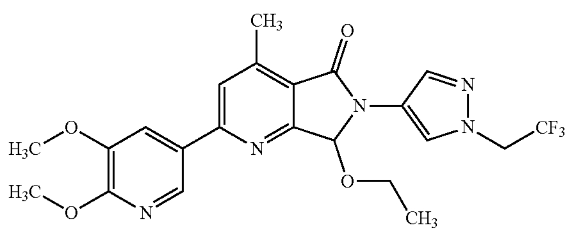 [SMILES: CCOC1c2nc(-c3cnc(OC)c(OC)c3)cc(C)c2C(=O)N1c1cnn(CC(F)(F)F)c1] | | (400 MHz, DMSO-d₆) δ 8.56 (s, 1H), 8.31 (s, 1H), 8.08 (s, 1H), 7.96 (s, 1H), 7.93 (s, 1H), 6.30 (s, 1H), 5.22 (q, J = 9.1 Hz, 2H), 3.96 (s, 3H), 3.92 (s, 3H), 3.59-3.46 (m, 1H), 3.42-3.34 (m, 1H), 2.72 (s, 3H), 1.10 (t, J = 7.0 Hz, 3H) |
| 700 | 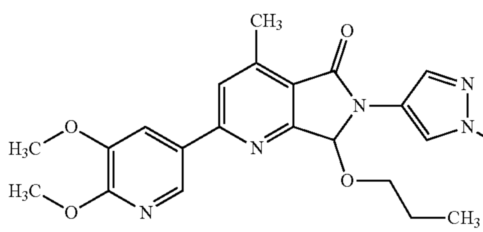 | | (400 MHz, DMSO-d₆) δ 8.56 (s, 1H), 8.31 (s, 1H), 8.09 (s, 1H), 7.97 (s, 1H), 7.93 (s, 1H), 6.34 (s, 1H), 5.22 (q, J = 9.1 Hz, 2H), 3.96 (s, 3H), 3.92 (s, 3H), 3.37 (dd, J = 9.2, 3.4 Hz, 1H), 3.18 (dd, J = 15.3, 6.3 Hz, 1H), 2.72 (s, 3H), 1.48 (dd, J = 14.2, 7.0 Hz, 2H), 0.79 (t, J = 7.3 Hz, 3H) |
| 701 | 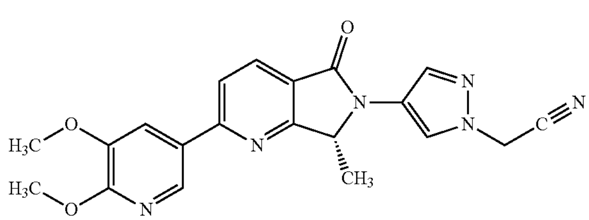 | 391.05 | (DMSO-d₆) δ 8.57 (d, J = 2.0 Hz, 1H), 8.38 (s, 1H), 8.21 (m, 2H), 8.07-7.92 (m, 2H), 5.56 (s, 2H), 5.26 (q, J = 6.7 Hz, 1H), 3.96 (s, 3H), 3.93 (s, 3H), 1.59 (d, J = 6.7 Hz, 3H) |
| 702 | 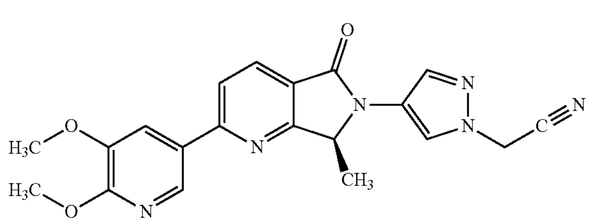 [SMILES: COc1cc(-c2ccc3c(n2)[C@H](C)N(c2cnn(CC#N)c2)C3=O)cnc1OC] | 391.27 | (DMSO-d₆) δ 8.58 (d, J = 1.8 Hz, 1H), 8.38 (s, 1H), 8.21 m, 2H), 8.06-7.93 (m, 2H), 5.56 (s, 2H), 5.26 (q, J = 6.7 Hz, 1H), 3.96 (s, 3H), 3.93 (s, 3H), 1.60 (d, J = 6.7 Hz, 3H) |

TABLE 1-continued

| Cmpd No. | Structure | ESMS (M + H) | ¹H NMR (300 MHz, unless indicated otherwise) |
|---|---|---|---|
| 703 | 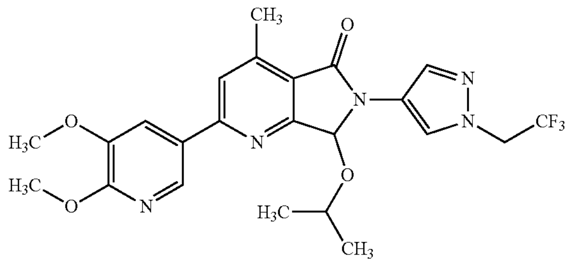 [SMILES: COc1cc(-c2cc(C)c3c(n2)C(OC(C)C)N(c2cnn(CC(F)(F)F)c2)C3=O)cnc1OC] | 492.58 | (400 MHz, DMSO-d₆) δ 8.58 (s, 1H), 8.28 (s, 1H), 8.09 (s, 1H), 7.99 (s, 1H), 7.90 (s, 1H), 6.34 (s, 1H), 5.22 (q, J = 9.0 Hz, 2H), 4.00-3.97 (m, 1H), 3.96 (s, 3H), 3.91 (s, 3H), 2.69 (s, 3H), 1.13 (d, J = 6.1 Hz, 3H), 1.10 (d, J = 6.2 Hz, 3H) |
| 704 | 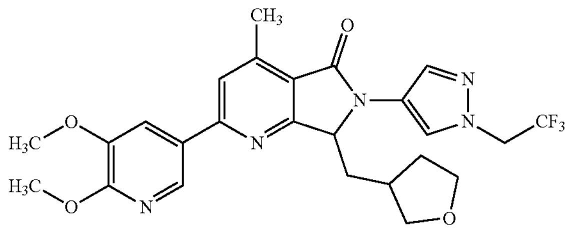 [SMILES: COc1cc(-c2cc(C)c3c(n2)C(CC2CCOC2)N(c2cnn(CC(F)(F)F)c2)C3=O)cnc1OC] | 518.56 | |
| 705 | 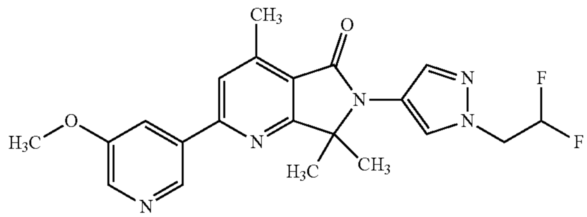 [SMILES: COc1cncc(-c2cc(C)c3c(n2)C(C)(C)N(c2cnn(CC(F)F)c2)C3=O)c1] | 414.18 | (400 MHz, DMSO-d₆) δ 9.00 (s, 1H), 8.42 (d, J = 2.7 Hz, 1H), 8.25 (s, 1H), 8.08 (s, 2H), 7.88 (s, 1H), 6.42 (s, 1H), 4.69 (td, J = 15.1, 3.7 Hz, 2H), 3.96 (s, 3H), 2.73 (s, 3H), 1.60 (s, 6H) |
| 706 | 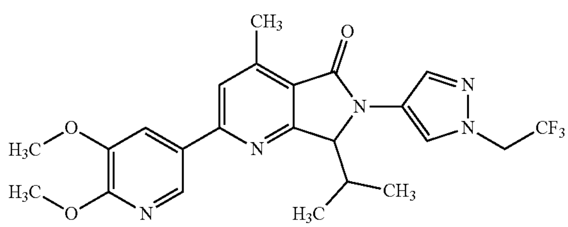 [SMILES: COc1cc(-c2cc(C)c3c(n2)C(C(C)C)N(c2cnn(CC(F)(F)F)c2)C3=O)cnc1OC] | 476.62 | |
| 707 | 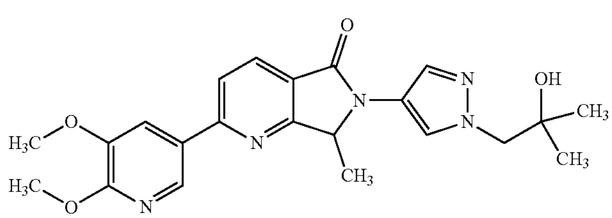 [SMILES: COc1cc(-c2ccc3c(n2)C(C)N(c2cnn(CC(C)(C)O)c2)C3=O)cnc1OC] | 424.59 | |
| 708 | 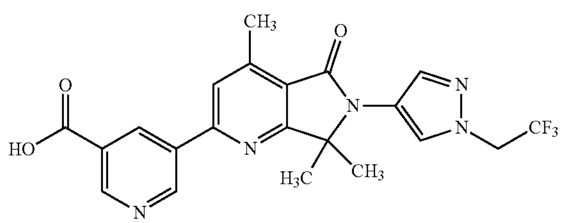 [SMILES: Cc1cc(-c2cncc(C(=O)O)c2)nc2c1C(=O)N(c1cnn(CC(F)(F)F)c1)C2(C)C] | 446.51 | (DMSO-d₆) δ 9.56 (d, J = 2.0 Hz, 1H), 9.17 (d, J = 1.8 Hz, 1H), 8.97 (d, J = 1.9 Hz, 1H), 8.34 (s, 1H), 8.16 (s, 1H), 7.95 (s, 2H), 5.19 (q, J = 9.1 Hz, 2H), 2.89 (s, 3H), 1.62 (s, 6H) |

TABLE 1-continued

| Cmpd No. | Structure | ESMS (M + H) | ¹H NMR (300 MHz, unless indicated otherwise) |
|---|---|---|---|
| 709 | 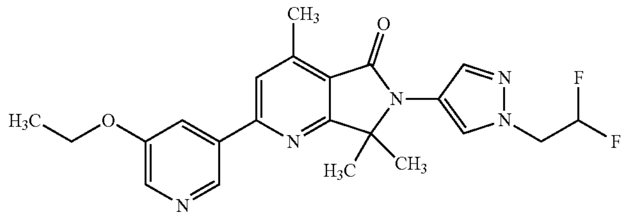 [SMILES: CCOc1cncc(-c2cc(C)c3c(n2)C(C)(C)N(c2cnn(CC(F)F)c2)C3=O)c1] | 428.2 | (400 MHz, DMSO-d$_6$) δ 8.99 (s, 1H), 8.40 (s, 1H), 8.26 (s, 1H), 8.08 (s, 2H), 7.88 (s, 1H), 6.43 (t, J = 54.8 Hz, 1H), 4.69 (t, J = 15.1 Hz, 2H), 4.30-4.15 (q, 2H), 2.73 (s, 3H), 1.60 (s, 6H), 1.40 (t, J = 6.9 Hz, 3H) |
| 710 | 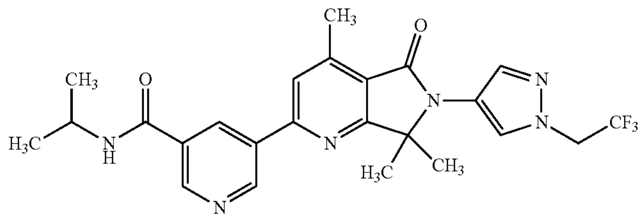 [SMILES: Cc1cc(-c2cncc(C(=O)NC(C)C)c2)nc2c1C(=O)N(c1cnn(CC(F)(F)F)c1)C2(C)C] | 487.66 | (DMSO-d$_6$) δ 9.58 (d, J = 2.0 Hz, 1H), 9.22 (d, J = 1.9 Hz, 1H), 9.14 (t, J = 1.8 Hz, 1H), 8.85 (d, J = 7.5 Hz, 1H), 8.36 (s, 1H), 8.24 (s, 1H), 7.96 (s, 1H), 5.20 (q, J = 9.1 Hz, 2H), 2.51 (dt, J = 3.6, 1.8 Hz, 3H), 1.23 (t, J = 8.0 Hz, 6H), 1.04 (d, J = 6.1 Hz, 6H) |
| 711 | 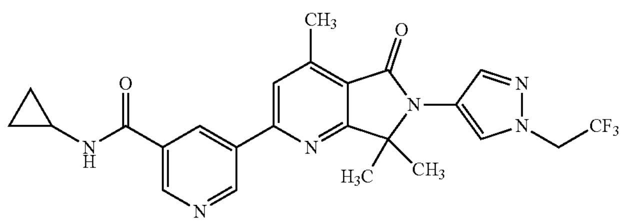 [SMILES: Cc1cc(-c2cncc(C(=O)NC3CC3)c2)nc2c1C(=O)N(c1cnn(CC(F)(F)F)c1)C2(C)C] | 485.68 | (DMSO-d$_6$) δ 9.47 (d, J = 2.1 Hz, 1H), 9.05 (d, J = 2.0 Hz, 1H), 8.82 (dd, J = 6.5, 4.4 Hz, 1H), 8.34 (s, 1H), 8.10 (s, 1H), 7.95 (s, 2H), 5.19 (d, J = 9.1 Hz, 2H), 4.02 (t, J = 7.1 Hz, 1H), 2.69 (s, 2H), 1.63 (s, 5H), 0.73 (dd, J = 19.8, 17.1 Hz, 2H), 0.70-0.57 (m, 2H) |
| 712 | 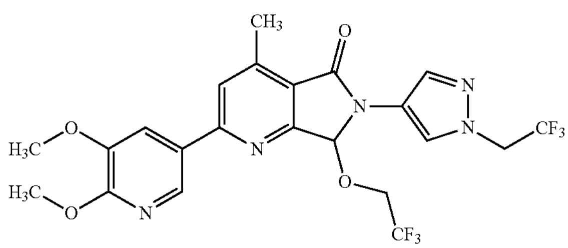 [SMILES: COc1cc(-c2cc(C)c3c(n2)C(OCC(F)(F)F)N(c2cnn(CC(F)(F)F)c2)C3=O)cnc1OC] | | (400 MHz, DMSO-d$_6$) δ 8.58 (s, 1H), 8.31 (s, 1H), 8.13 (s, 1H), 7.97 (s, 1H), 7.91 (s, 1H), 6.51 (s, 1H), 5.22 (q, J = 9.0 Hz, 2H), 4.16 (dt, J = 20.9, 11.9 Hz, 2H), 3.96 (s, 3H), 3.92 (s, 3H), 2.72 (s, 3H) |
| 713 | 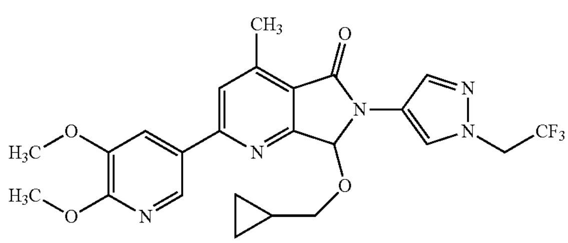 [SMILES: COc1cc(-c2cc(C)c3c(n2)C(OCC2CC2)N(c2cnn(CC(F)(F)F)c2)C3=O)cnc1OC] | | (400 MHz, DMSO-d$_6$) δ 8.56 (s, 1H), 8.31 (s, 1H), 8.08 (s, 1H), 7.95 (s, 2H), 6.33 (s, 1H), 5.22 (q, J = 9.1 Hz, 2H), 3.96 (s, 3H), 3.92 (s, 3H), 3.21 (dt, J = 16.9, 10.0 Hz, 2H), 2.71 (s, 3H), 0.97 (s, 1H), 0.40 (d, J = 8.0 Hz, 2H), 0.10 (d, J = 4.4 Hz, 1H), 0.06-0.01 (m, 1H) |
| 714 | 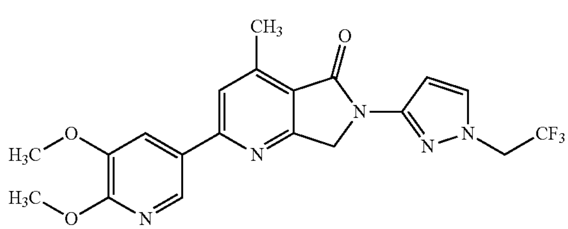 [SMILES: COc1cc(-c2cc(C)c3c(n2)CN(c2ccn(CC(F)(F)F)n2)C3=O)cnc1OC] | 434.15 | (400 MHz, DMSO-d$_6$) δ 8.55 (s, 1H), 8.01 (s, 1H), 7.98 (s, 1H), 7.89 (d, J = 2.2 Hz, 1H), 6.93 (d, J = 2.3 Hz, 1H), 5.14 (d, J = 9.1 Hz, 2H), 4.91 (s, 2H), 3.95 (s, 3H), 3.92 (s, 3H), 2.72 (s, 3H) |

TABLE 1-continued

| Cmpd No. | Structure | ESMS (M + H) | ¹H NMR (300 MHz, unless indicated otherwise) |
|---|---|---|---|
| 715 | 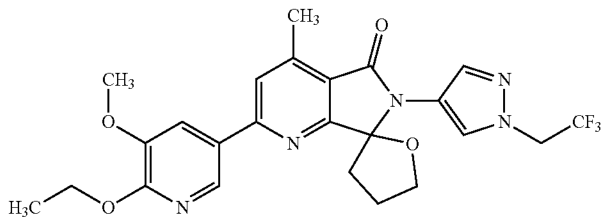 [SMILES: CCOc1ncc(-c2cc(C)c3c(n2)C2(CCCO2)N(c2cnn(CC(F)(F)F)c2)C3=O)cc1OC] | 504.63 | |
| 716 | 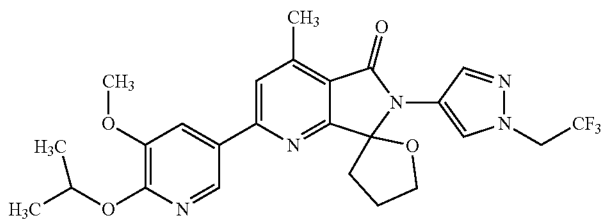 [SMILES: COc1cc(-c2cc(C)c3c(n2)C2(CCCO2)N(c2cnn(CC(F)(F)F)c2)C3=O)cnc1OC(C)C] | 518.64 | |
| 717 | 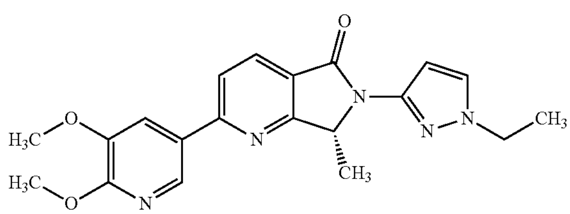 [SMILES: CCn1ccc(N2C(=O)c3ccc(-c4cnc(OC)c(OC)c4)nc3[C@H]2C)n1] | 380 | |
| 718 | 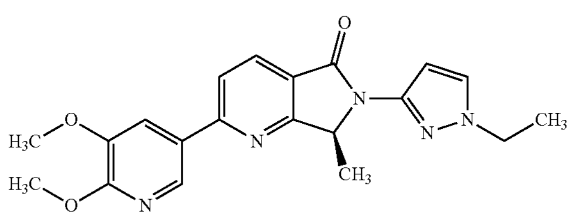 [SMILES: CCn1ccc(N2C(=O)c3ccc(-c4cnc(OC)c(OC)c4)nc3[C@@H]2C)n1] | 380 | |
| 719 | 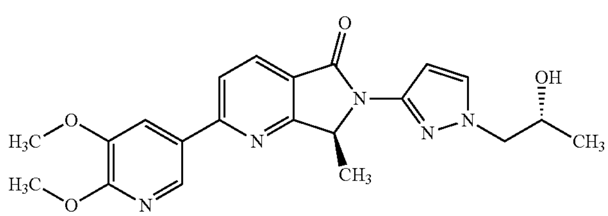 [SMILES: COc1cc(-c2ccc3c(n2)[C@H](C)N(c2ccn(C[C@@H](C)O)n2)C3=O)cnc1OC] | 410.31 | (DMSO-d$_6$) δ 8.56 (d, J = 1.9 Hz, 1H), 8.23-8.13 (m, 3H), 8.00 (d, J = 1.9 Hz, 1H), 7.81 (s, 1H), 5.20 (q, J = 6.6 Hz, 1H), 4.92 (d, J = 4.4 Hz, 1H), 4.04 (t, J = 7.8 Hz, 2H), 3.99-3.89 (m, 6H), 1.58 (d, J = 6.7 Hz, 3H), 1.06 (d, J = 5.7 Hz, 3H) |
| 720 | 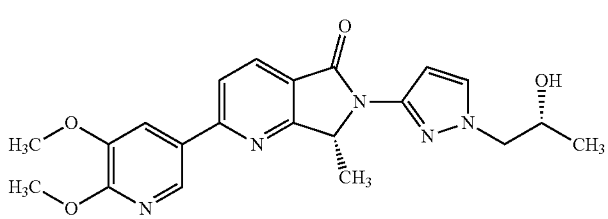 [SMILES: COc1cc(-c2ccc3c(n2)[C@@H](C)N(c2ccn(C[C@@H](C)O)n2)C3=O)cnc1OC] | 410.31 | (DMSO-d$_6$) δ 8.56 (d, J = 1.9 Hz, 1H), 8.25-8.13 (m, 3H), 7.99 (d, J = 1.9 Hz, 1H), 7.81 (s, 1H), 5.20 (q, J = 6.6 Hz, 1H), 4.93 (d, J = 4.4 Hz, 1H), 4.08-4.02 (m, 2H), 3.94 (d, J = 9.9 Hz, 6H), 1.59 (d, J = 6.7 Hz, 3H), 1.07 (d, J = 5.8 Hz, 3H) |
| 721 | 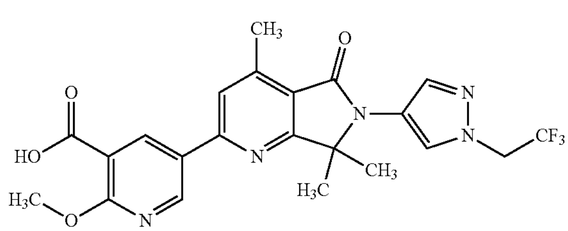 [SMILES: COc1ncc(-c2cc(C)c3c(n2)C(C)(C)N(c2cnn(CC(F)(F)F)c2)C3=O)cc1C(=O)O] | 476.27 | (DMSO-d$_6$) δ 9.16 (d, J = 2.4 Hz, 1H), 8.85 (d, J = 2.4 Hz, 1H), 8.32 (s, 1H), 8.03 (s, 1H), 7.94 (d, J = 5.3 Hz, 1H), 5.19 (q, J = 9.1 Hz, 2H), 4.03 (d, J = 7.0 Hz, 3H), 2.73 (d, J = 3.0 Hz, 3H), 1.60 (s, 6H) |

TABLE 1-continued

| Cmpd No. | Structure | ESMS (M + H) | ¹H NMR (300 MHz, unless indicated otherwise) |
|---|---|---|---|
| 722 | 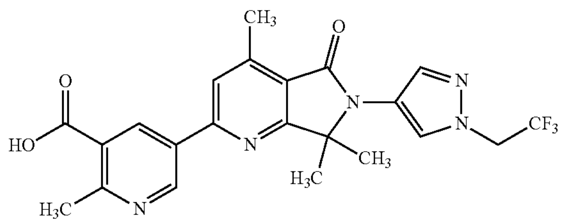 [SMILES: Cc1cc(-c2cnc(C)c(C(=O)O)c2)nc2c1C(=O)N(c1cnn(CC(F)(F)F)c1)C2(C)C] | 460.27 | (DMSO-d$_6$) δ 9.39 (d, J = 2.3 Hz, 1H), 8.92 (d, J = 2.1 Hz, 1H), 8.33 (s, 1H), 8.11 (s, 1H), 7.94 (s, 1H), 5.19 (d, J = 9.1 Hz, 2H), 2.82 (s, 3H), 2.74 (d, J = 3.3 Hz, 3H), 1.61 (s, 6H) |
| 723 | 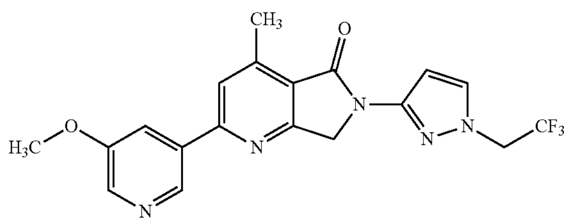 | 404.13 | (400 MHz, DMSO-d$_6$) δ 8.97 (s, 1H), 8.41 (d, J = 2.7 Hz, 1H), 8.10 (s, 1H), 8.05 (s, 1H), 7.89 (d, J = 2.3 Hz, 1H), 6.94 (d, J = 2.4 Hz, 1H), 5.14 (q, J = 9.0 Hz, 2H), 4.93 (s, 2H), 3.94 (s, 3H), 2.74 (s, 3H) |
| 724 | 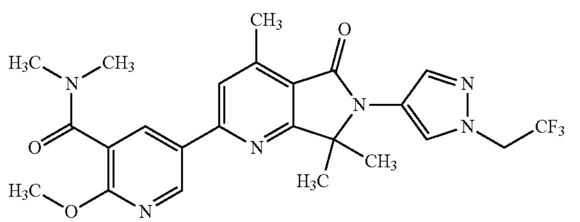 [SMILES: COc1ncc(-c2cc(C)c3c(n2)C(C)(C)N(c2cnn(CC(F)(F)F)c2)C3=O)cc1C(=O)N(C)C] | 503.63 | (DMSO-d$_6$) δ 9.08 (d, J = 2.2 Hz, 1H), 8.45 (d, J = 2.2 Hz, 1H), 8.32 (s, 1H), 8.02 (s, 1H), 7.94 (s, 1H), 5.18 (d, J = 9.1 Hz, 2H), 4.00 (s, 3H), 3.02 (s, 3H), 2.84 (s, 3H), 2.69 (s, 3H), 1.60 (s, 5H) |
| 725 | 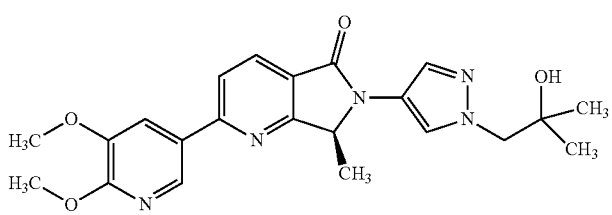 [SMILES: COc1cc(-c2ccc3c(n2)[C@H](C)N(c2cnn(CC(C)(C)O)c2)C3=O)cnc1OC] | 424.59 | |
| 726 | 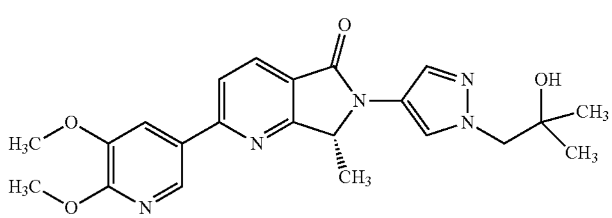 [SMILES: COc1cc(-c2ccc3c(n2)[C@@H](C)N(c2cnn(CC(C)(C)O)c2)C3=O)cnc1OC] | 424.59 | |
| 727 | 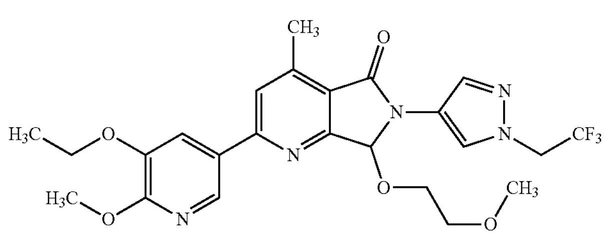 [SMILES: CCOc1cc(-c2cc(C)c3c(n2)C(OCCOC)N(c2cnn(CC(F)(F)F)c2)C3=O)cnc1OC] | 508.61 | (400 MHz, DMSO-d$_6$) δ 8.56 (s, 1H), 8.32 (s, 1H), 8.09 (s, 1H), 7.96 (s, 1H), 7.94 (s, 1H), 6.31 (s, 1H), 5.29-5.13 (m, 2H), 3.96 (s, 3H), 3.92 (s, 3H), 3.66-3.64 (m, 1H), 3.51-3.49 (m, 1H), 3.48-3.41 (m, 2H), 3.19 (s, 3H), 2.72 (s, 3H) |

TABLE 1-continued

| Cmpd No. | Structure | ESMS (M + H) | ¹H NMR (300 MHz, unless indicated otherwise) |
|---|---|---|---|
| 728 | 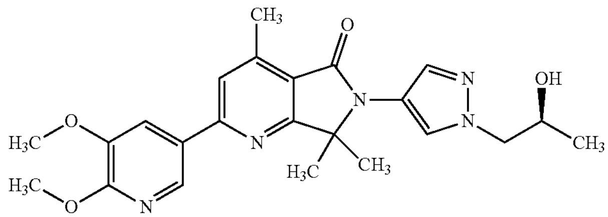 [SMILES: COc1cc(-c2cc(C)c3c(n2)C(C)(C)N(c2cnn(C[C@H](C)O)c2)C3=O)cnc1OC] | 438.6 | (DMSO-d₆) δ 8.56 (d, J = 1.9 Hz, 1H), 8.08 (s, 1H), 8.04-7.92 (m, 2H), 7.72 (s, 1H), 4.94 (s, 1H), 4.08-3.99 (m, 3H), 3.94 (d, J = 8.7 Hz, 6H), 2.71 (s, 3H), 1.58 (s, 6H), 1.06 (d, J = 5.8 Hz, 3H) |
| 729 | 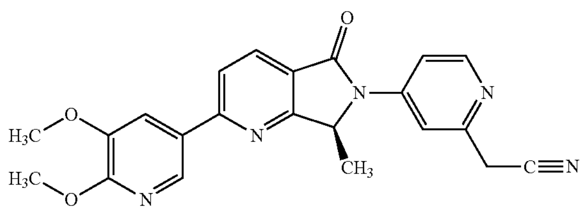 | 402.58 | |
| 730 | 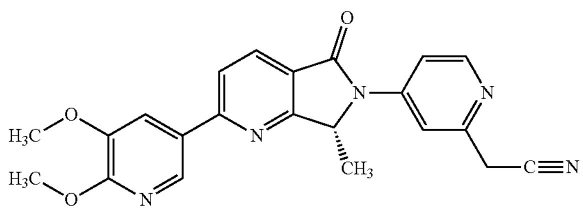 [SMILES: COc1cc(-c2ccc3c(n2)[C@@H](C)N(c2ccnc(CC#N)c2)C3=O)cnc1OC] | 402.64 | |
| 731 | 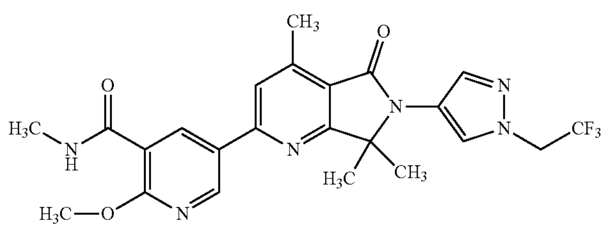 [SMILES: CNC(=O)c1cc(-c2cc(C)c3c(n2)C(C)(C)N(c2cnn(CC(F)(F)F)c2)C3=O)cnc1OC] | 489.29 | (DMSO-d₆) δ 9.08 (d, J = 2.2 Hz, 1H), 8.45 (d, J = 2.2 Hz, 1H), 8.32 (s, 1H), 8.02 (s, 1H), 7.94 (s, 1H), 5.18 (d, J = 9.1 Hz, 2H), 4.00 (s, 3H), 3.02 (s, 3H), 2.84 (s, 3H), 1.60 (s, 5H) |
| 732 | 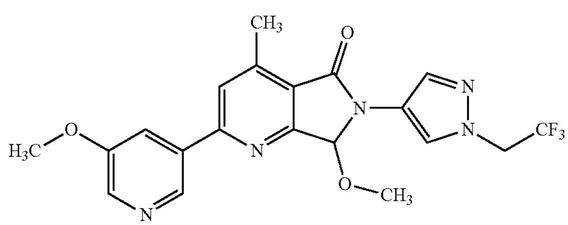 [SMILES: COc1cncc(-c2cc(C)c3c(n2)C(OC)N(c2cnn(CC(F)(F)F)c2)C3=O)c1] | 434.57 | |
| 733 | 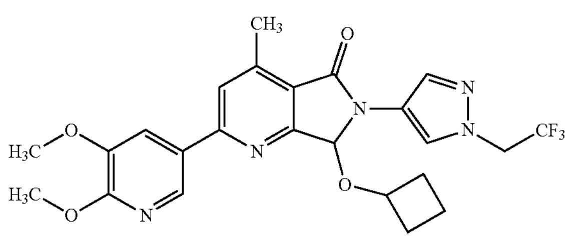 [SMILES: COc1cc(-c2cc(C)c3c(n2)C(OC2CCC2)N(c2cnn(CC(F)(F)F)c2)C3=O)cnc1OC] | 503.87 | (400 MHz, DMSO-d₆) δ 8.57 (s, 1H), 8.28 (s, 1H), 8.08 (s, 1H), 7.97 (s, 1H), 7.90 (s, 1H), 6.29 (s, 1H), 5.29-5.12 (m, 2H), 4.10-3.99 (m, 1H), 3.96 (s, 3H), 3.92 (s, 3H), 2.72 (s, 3H), 2.07-1.80 (m, 3H), 1.75-1.73 (m, 1H), 1.51-1.47 (m, 1H), 1.33-1.27 (m, 1H) |
| 734 | 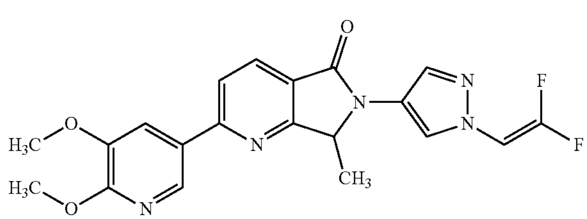 [SMILES: COc1cc(-c2ccc3c(n2)C(C)N(c2cnn(C=C(F)F)c2)C3=O)cnc1OC] | 414.47 | (DMSO-d₆) δ 8.57 (d, J = 1.8 Hz, 1H), 8.37 (s, 1H), 8.21 (d, J = 6.6 Hz, 2H), 8.09 (s, 1H), 8.00 (d, J = 1.7 Hz, 1H), 7.20 (d, J = 19.5 Hz, 1H), 5.28 (d, J = 6.7 Hz, 1H), 3.94 (d, J = 10.0 Hz, 6H), 1.60 (d, J = 6.6 Hz, 3H) |

TABLE 1-continued

| Cmpd No. | Structure | ESMS (M + H) | ¹H NMR (300 MHz, unless indicated otherwise) |
|---|---|---|---|
| 735 | 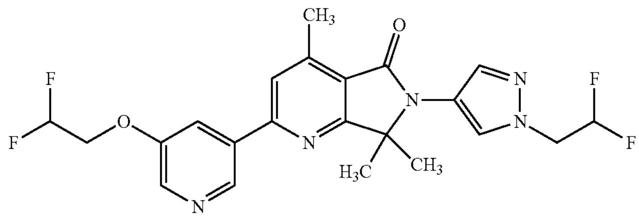 [SMILES: Cc1cc(-c2cncc(OCC(F)F)c2)nc2c1C(=O)N(c1cnn(CC(F)F)c1)C2(C)C] | 464.55 | (400 MHz, DMSO-d$_6$) δ 9.11 (s, 1H), 8.57 (d, J = 2.5 Hz, 1H), 8.32 (s, 1H), 8.26 (s, 1H), 8.15 (s, 1H), 7.88 (s, 1H), 6.64-6.25 (m, 2H), 4.65 (dtd, J = 17.9, 14.8, 3.4 Hz, 4H), 2.74 (s, 3H), 1.61 (s, 6H) |
| 736 | 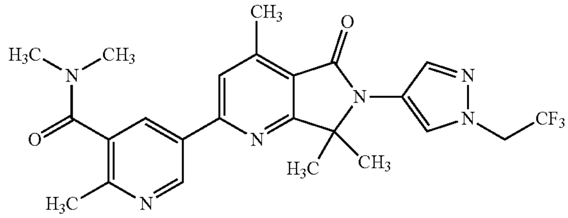 [SMILES: Cc1cc(-c2cnc(C)c(C(=O)N(C)C)c2)nc2c1C(=O)N(c1cnn(CC(F)(F)F)c1)C2(C)C] | 487.02 | |
| 737 | 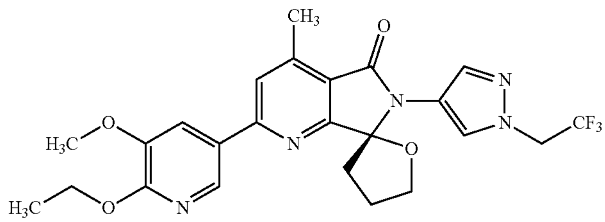 [SMILES: CCOc1ncc(-c2cc(C)c3c(n2)[C@]2(CCCO2)N(c2cnn(CC(F)(F)F)c2)C3=O)cc1OC] | 504.63 | |
| 738 | 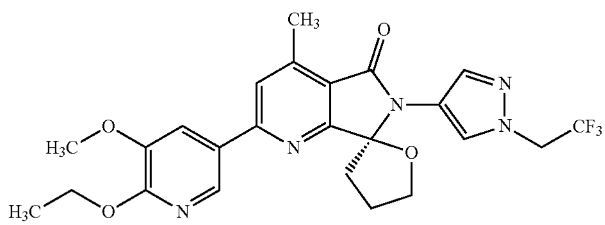 [SMILES: CCOc1ncc(-c2cc(C)c3c(n2)[C@@]2(CCCO2)N(c2cnn(CC(F)(F)F)c2)C3=O)cc1OC] | 504.63 | |
| 739 | 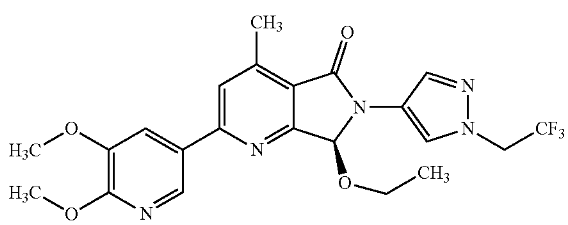 [SMILES: CCO[C@H]1c2nc(-c3cnc(OC)c(OC)c3)cc(C)c2C(=O)N1c1cnn(CC(F)(F)F)c1] | | (400 MHz, DMSO-d$_6$) δ 8.56 (s, 1H), 8.31 (s, 1H), 8.09 (s, 1H), 7.96 (s, 1H), 7.93 (s, 1H), 6.31 (s, 1H), 5.24-5.20 (m, 2H), 3.96 (s, 3H), 3.92 (s, 3H), 3.52-3.50 (m, 1H), 3.39-3.35 (m, 1H), 2.72 (s, 3H), 1.09 (t, J = 6.9 Hz, 3H) |
| 740 | 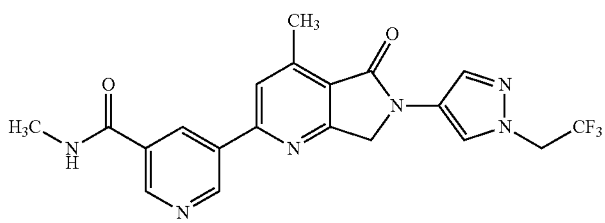 [SMILES: CNC(=O)c1cncc(-c2cc(C)c3c(n2)CN(c2cnn(CC(F)(F)F)c2)C3=O)c1] | | (400 MHz, DMSO-d$_6$) δ 8.56 (s, 1H), 8.31 (s, 1H), 8.09 (s, 1H), 7.96 (s, 1H), 7.93 (s, 1H), 6.31 (s, 1H), 5.22 (q, J = 8.9 Hz, 2H), 3.96 (s, 3H), 3.92 (s, 3H), 3.57-3.47 (m, 1H), 3.38-3.34 (m, 1H), 2.72 (s, 3H), 1.09 (t, J = 6.9 Hz, 3H) |

TABLE 1-continued

| Cmpd No. | Structure | ESMS (M + H) | ¹H NMR (300 MHz, unless indicated otherwise) |
|---|---|---|---|
| 741 | 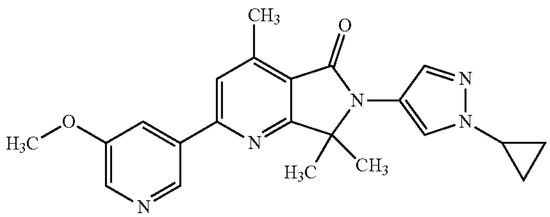 [SMILES: COc1cncc(-c2cc(C)c3c(n2)C(C)(C)N(c2cnn(C4CC4)c2)C3=O)c1] | 390.55 | (CDCl$_3$) δ 8.89 (d, J = 1.7 Hz, 1H), 8.41 (d, J = 2.8 Hz, 1H), 7.96 (dd, J = 5.0, 2.4 Hz, 2H), 7.63 (d, J = 10.2 Hz, 2H), 3.99 (s, 3H), 3.75-3.59 (m, 1H), 2.83 (s, 3H), 1.68 (s, 6H), 1.21 (dt, J = 5.0, 3.5 Hz, 2H), 1.07 (dt, J = 7.4, 3.7 Hz, 2H) |
| 742 | 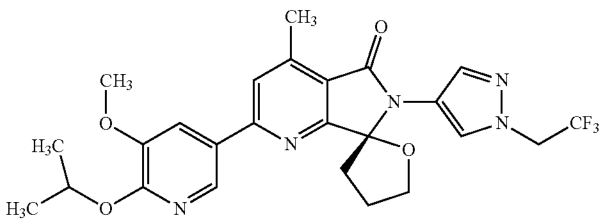 [SMILES: COc1cc(-c2cc(C)c3c(n2)[C@]2(CCCO2)N(c2cnn(CC(F)(F)F)c2)C3=O)cnc1OC(C)C] | 518.64 | |
| 743 | 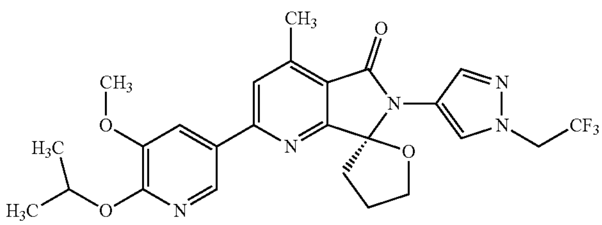 [SMILES: COc1cc(-c2cc(C)c3c(n2)[C@@]2(CCCO2)N(c2cnn(CC(F)(F)F)c2)C3=O)cnc1OC(C)C] | 518.64 | |
| 744 | 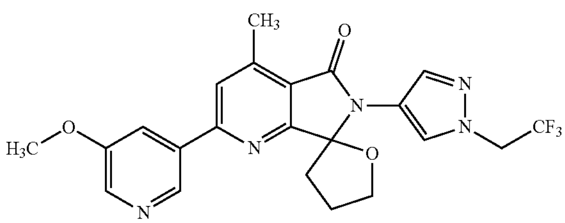 [SMILES: COc1cncc(-c2cc(C)c3c(n2)C2(CCCO2)N(c2cnn(CC(F)(F)F)c2)C3=O)c1] | 460.55 | |
| 745 | 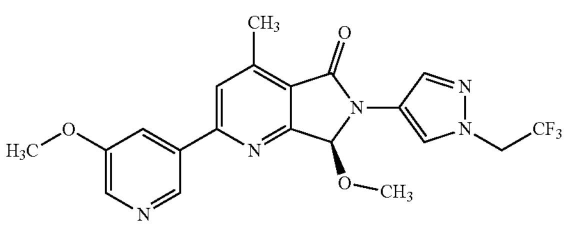 [SMILES: COc1cncc(-c2cc(C)c3c(n2)[C@H](OC)N(c2cnn(CC(F)(F)F)c2)C3=O)c1] | 434.57 | |
| 746 | 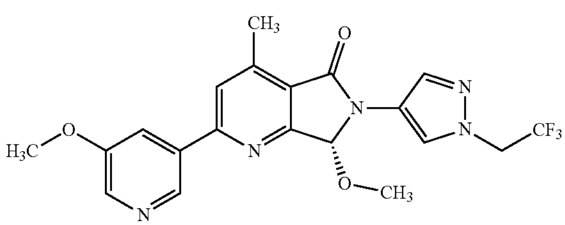 [SMILES: COc1cncc(-c2cc(C)c3c(n2)[C@@H](OC)N(c2cnn(CC(F)(F)F)c2)C3=O)c1] | 434.57 | |

TABLE 1-continued

| Cmpd No. | Structure | ESMS (M + H) | ¹H NMR (300 MHz, unless indicated otherwise) |
|---|---|---|---|
| 747 | 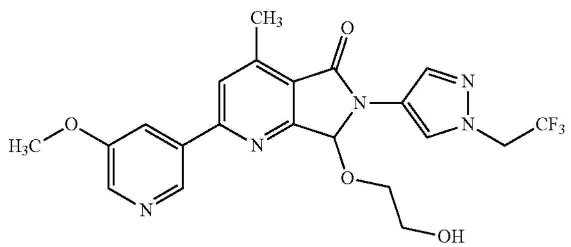 [SMILES: COc1cncc(-c2cc(C)c3c(n2)C(OCCO)N(c2cnn(CC(F)(F)F)c2)C3=O)c1] | 495.14 | (400 MHz, DMSO-d$_6$) δ 8.56 (s, 1H), 8.34 (s, 1H), 8.09 (s, 1H), 7.98-7.96 (m, 2H), 6.31 (s, 1H), 5.28-5.12 (m, 2H), 4.75 (t, J = 5.5 Hz, 1H), 3.96 (s, 3H), 3.92 (s, 3H), 3.61-3.37 (m, 4H), 2.72 (s, 3H) |
| 748 | 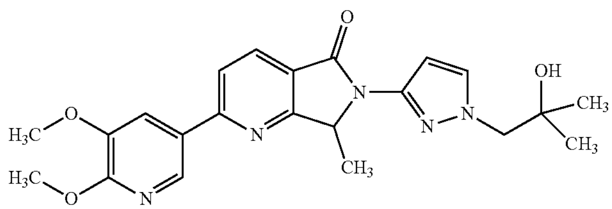 [SMILES: COc1cc(-c2ccc3c(n2)C(C)N(c2ccn(CC(C)(C)O)n2)C3=O)cnc1OC] | 424.59 | |
| 749 | 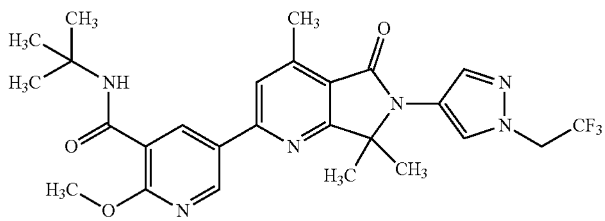 [SMILES: COc1ncc(-c2cc(C)c3c(n2)C(C)(C)N(c2cnn(CC(F)(F)F)c2)C3=O)cc1C(=O)NC(C)(C)C] | 531.6 | |
| 750 | 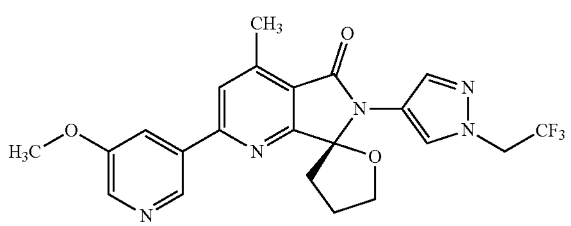 [SMILES: COc1cncc(-c2cc(C)c3c(n2)[C@]2(CCCO2)N(c2cnn(CC(F)(F)F)c2)C3=O)c1] | 460.55 | |
| 751 | 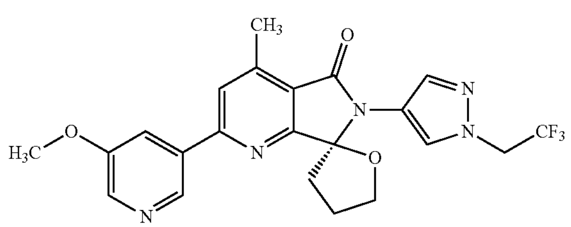 [SMILES: COc1cncc(-c2cc(C)c3c(n2)[C@@]2(CCCO2)N(c2cnn(CC(F)(F)F)c2)C3=O)c1] | 460.61 | |
| 752 | 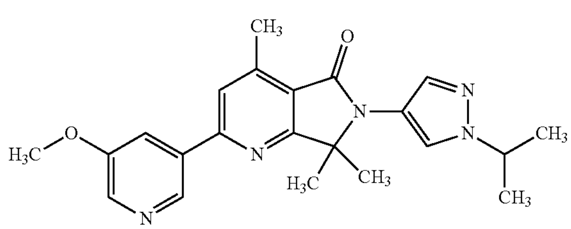 [SMILES: COc1cncc(-c2cc(C)c3c(n2)C(C)(C)N(c2cnn(C(C)C)c2)C3=O)c1] | 392.59 | (CDCl$_3$) δ 8.89 (s, 1H), 8.41 (s, 1H), 8.03-7.92 (m, 2H), 7.72-7.56 (m, 2H), 4.70-4.43 (m, 1H), 3.99 (s, 3H), 2.83 (s, 3H), 1.66 (d, J = 16.4 Hz, 6H), 1.57 (d, J = 6.7 Hz, 6H) |

| Cmpd No. | Structure | ESMS (M + H) | ¹H NMR (300 MHz, unless indicated otherwise) |
|---|---|---|---|
| 753 | 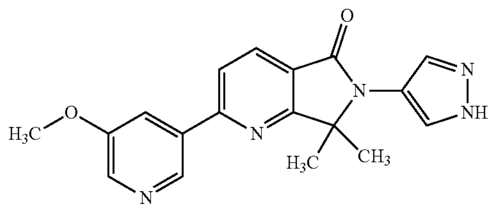 [SMILES: COc1cncc(-c2ccc3c(n2)C(C)(C)N(c2cn[nH]c2)C3=O)c1] | 350.47 | |
| 754 | 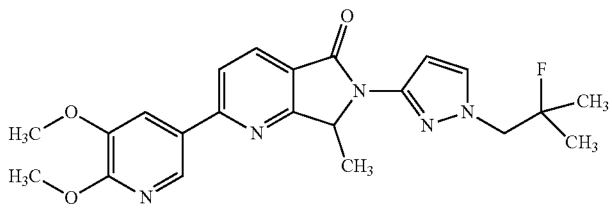 [SMILES: COc1cc(-c2ccc3c(n2)C(C)N(c2ccn(CC(C)(C)F)n2)C3=O)cnc1OC] | 426.57 | |
| 755 | 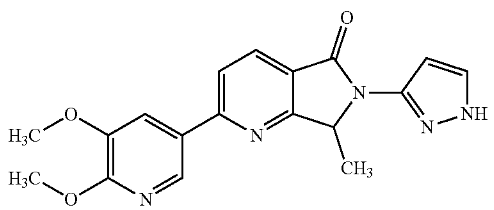 [SMILES: COc1cc(-c2ccc3c(n2)C(C)N(c2cc[nH]n2)C3=O)cnc1OC] | 352 | (400 MHz, DMSO-d6) 12.67(s, exch, 1H), 8.74 (d, J = 1.6 Hz, 1H), 8.22 (d, J = 8.2 Hz, 1H), 8.190 (d, J = 8.2 Hz, 1H), 8.00 (d, J = 1.6 Hz, 1H), 7.78 (s, 1H), 6.83 (s, 1H), 5.30 (quart, J = 6.7 Hz, 1H), 3.96 (s, 3H), 3.93(s, 3H), 1.72 (d, J = 6.7 Hz, 3H) |
| 756 | 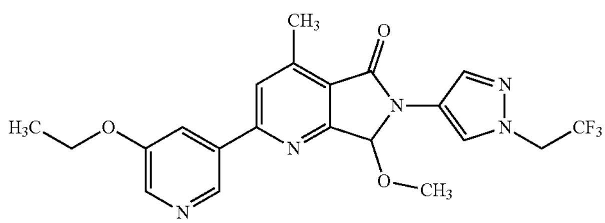 [SMILES: CCOc1cncc(-c2cc(C)c3c(n2)C(OC)N(c2cnn(CC(F)(F)F)c2)C3=O)c1] | 448.16 | (400 MHz, DMSO-$d_6$) δ 8.97 (s, 1H), 8.41 (d, J = 2.7 Hz, 1H), 8.33 (s, 1H), 8.20 (s, 1H), 8.05 (s, 1H), 7.93 (s, 1H), 6.34 (s, 1H), 5.22 (d, J = 9.2 Hz, 2H), 4.24 (d, J = 7.0 Hz, 2H), 3.11 (s, 3H), 2.74 (s, 3H), 1.40 (t, J = 6.9 Hz, 3H) |
| 757 | 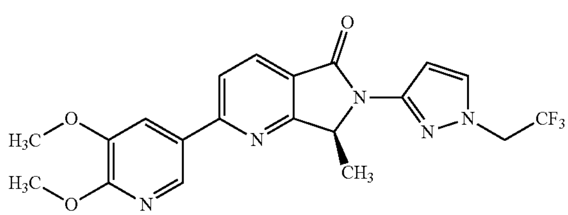 [SMILES: COc1cc(-c2ccc3c(n2)[C@H](C)N(c2ccn(CC(F)(F)F)n2)C3=O)cnc1OC] | 434.12 | (400 MHz, DMSO-$d_6$) δ 8.58 (d, J = 1.2 Hz, 1H), 8.22 (dd, J = 22.9, 8.1 Hz, 2H), 8.01 (s, 1H), 7.90 (d, J = 2.3 Hz, 1H), 6.93 (d, J = 2.4 Hz, 1H), 5.26 (d, J = 6.7 Hz, 1H), 5.16 (dd, J = 9.1, 4.9 Hz, 2H), 3.96 (s, 3H), 3.93 (s, 3H), 1.72 (d, J = 6.7 Hz, 3H) |
| 758 | 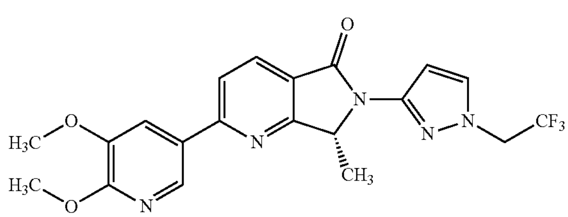 | 434.12 | (400 MHz, DMSO-$d_6$) δ 8.58 (s, 1H), 8.22 (dd, J = 22.9, 8.2 Hz, 2H), 8.01 (s, 1H), 7.90 (d, J = 2.2 Hz, 1H), 6.93 (d, J = 2.3 Hz, 1H), 5.26 (d, J = 6.7 Hz, 1H), 5.16 (dd, J = 9.0, 5.1 Hz, 2H), 3.96 (s, 3H), 3.93 (s, 3H), 1.72 (d, J = 6.7 Hz, 3H) |
| 759 | 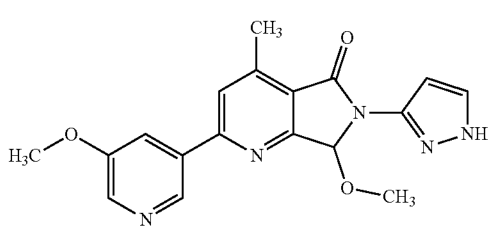 [SMILES: COc1cncc(-c2cc(C)c3c(n2)C(OC)N(c2cc[nH]n2)C3=O)c1] | 352.22 | (400 MHz, DMSO-$d_6$) δ 12.70 (s, 1H), 8.99 (s, 1H), 8.43 (d, J = 2.6 Hz, 1H), 8.19 (s, 1H), 8.07 (s, 1H), 7.79 (s, 1H), 6.69 (s, 1H), 6.40 (s, 1H), 3.96 (s, 3H), 3.29 (s, 3H), 2.74 (s, 3H) |

TABLE 1-continued

| Cmpd No. | Structure | ESMS (M + H) | ¹H NMR (300 MHz, unless indicated otherwise) |
|---|---|---|---|
| 760 | 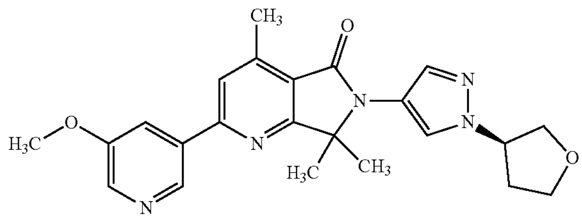 [SMILES: COc1cncc(-c2cc(C)c3c(n2)C(C)(C)N(c2cnn([C@@H]4CCOC4)c2)C3=O)c1] | 420.62 | (CDCl$_3$) δ 8.90 (d, J = 1.7 Hz, 1H), 8.42 (d, J = 2.8 Hz, 1H), 8.04 (s, 1H), 7.96 (dd, J = 2.8, 1.8 Hz, 1H), 7.70 (s, 1H), 7.62 (s, 1H), 5.03 (ddd, J = 9.7, 7.7, 3.7 Hz, 1H), 4.15 (ddd, J = 15.8, 11.3, 7.6 Hz, 3H), 4.04-3.90 (m, 4H), 2.84 (s, 3H), 2.65-2.28 (m, 2H), 1.69 (d, J = 3.8 Hz, 6H) |
| 761 | 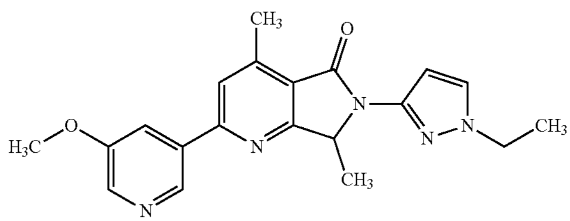 [SMILES: CCn1ccc(N2C(=O)c3c(C)cc(-c4cncc(OC)c4)nc3C2C)n1] | 364.5 | (CDCl$_3$) δ 8.87 (d, J = 1.8 Hz, 1H), 8.42 (d, J = 2.9 Hz, 1H), 7.97 (dd, J = 2.8, 1.8 Hz, 1H), 7.62 (s, 1H), 7.41 (d, J = 2.3 Hz, 1H), 6.94 (d, J = 2.3 Hz, 1H), 5.29 (q, J = 6.7 Hz, 1H), 4.17 (q, J = 7.3 Hz, 2H), 4.00 (s, 3H), 2.85 (s, 3H), 1.79 (d, J = 6.7 Hz, 3H), 1.53 (t, J = 7.3 Hz, 3H) |
| 762 | 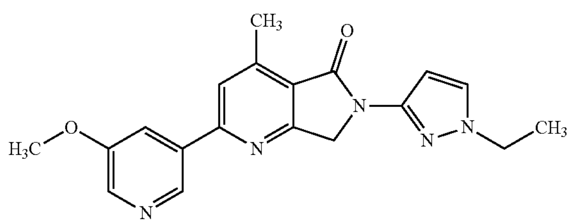 [SMILES: CCn1ccc(N2Cc3nc(-c4cncc(OC)c4)cc(C)c3C2=O)n1] | 350.56 | (CDCl$_3$) δ 8.97 (d, J = 1.7 Hz, 1H), 8.41 (d, J = 2.8 Hz, 1H), 8.12-8.02 (m, 2H), 7.77 (d, J = 2.3 Hz, 1H), 6.78 (d, J = 2.3 Hz, 1H), 4.94 (s, 2H), 4.12 (q, J = 7.2 Hz, 2H), 3.95 (s, 3H), 2.74 (s, 3H), 1.40 (t, J = 7.3 Hz, 3H) |
| 763 | 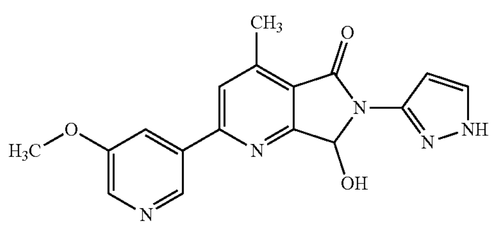 [SMILES: COc1cncc(-c2cc(C)c3c(n2)C(O)N(c2cc[nH]n2)C3=O)c1] | 338.08 | (400 MHz, DMSO-d$_6$) δ 12.65 (s, 1H), 8.97 (s, 1H), 8.42 (d, J = 2.7 Hz, 1H), 8.14 (s, 1H), 8.06 (s, 1H), 7.77 (s, 1H), 7.01 (d, J = 8.5 Hz, 1H), 6.68 (s, 1H), 6.42 (d, J = 8.6 Hz, 1H), 3.95 (s, 3H), 2.73 (s, 3H) |
| 764 | 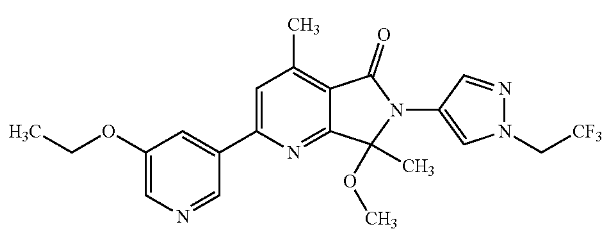 [SMILES: CCOc1cncc(-c2cc(C)c3c(n2)C(C)(OC)N(c2cnn(CC(F)(F)F)c2)C3=O)c1] | 462.15 | (400 MHz, DMSO-d$_6$) δ 8.97 (s, 1H), 8.42 (d, J = 2.7 Hz, 1H), 8.28 (s, 1H), 8.19 (s, 1H), 8.06 (s, 1H), 7.95 (s, 1H), 5.22 (m, 2H), 4.25 (q, 2H), 2.85 (s, 3H), 2.75 (s, 3H), 1.73 (s, 3H), 1.40 (t, J = 6.9 Hz, 3H) |
| 765 | 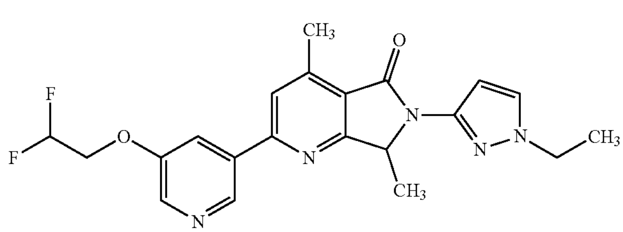 [SMILES: CCn1ccc(N2C(=O)c3c(C)cc(-c4cncc(OCC(F)F)c4)nc3C2C)n1] | | (CDCl$_3$) δ 8.95 (d, J = 1.7 Hz, 1H), 8.45 (d, J = 2.9 Hz, 1H), 8.03 (dd, J = 2.9, 1.8 Hz, 1H), 7.63 (s, 1H), 7.41 (d, J = 2.3 Hz, 1H), 6.94 (d, J = 2.3 Hz, 1H), 6.19 (tt, J = 54.9, 4.1 Hz, 1H), 5.29 (dd, J = 12.7, 6.1 Hz, 1H), 4.39 (td, J = 12.9, 4.0 Hz, 2H), 4.18 (q, J = 7.3 Hz, 2H), 2.86 (s, 3H), 1.80 (d, J = 6.7 Hz, 3H), 1.53 (t, J = 7.3 Hz, 3H) |

TABLE 1-continued

| Cmpd No. | Structure | ESMS (M + H) | ¹H NMR (300 MHz, unless indicated otherwise) |
|---|---|---|---|
| 766 | 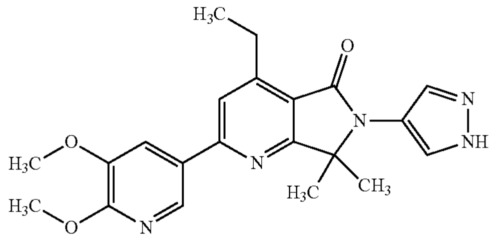 [SMILES: CCc1cc(-c2cnc(OC)c(OC)c2)nc2c1C(=O)N(c1cn[nH]c1)C2(C)C] | 394.58 | (CDCl₃) δ 9.60 (s, 1H), 8.45 (t, J = 2.6 Hz, 1H), 8.02 (s, 2H), 7.88 (d, J = 1.9 Hz, 1H), 7.61 (s, 1H), 4.10 (d, J = 12.5 Hz, 3H), 4.04 (s, 3H), 3.26 (q, J = 7.5 Hz, 2H), 1.69 (s, 6H), 1.39 (t, J = 13.8, 6.2 Hz, 3H) |
| 767 | 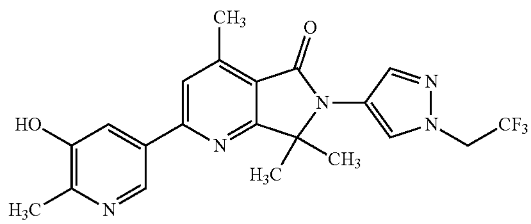 [SMILES: Cc1cc(-c2cnc(C)c(O)c2)nc2c1C(=O)N(c1cnn(CC(F)(F)F)c1)C2(C)C] | 432.58 | (CDCl₃) δ 8.71 (d, J = 20.5 Hz, 2H), 8.13 (s, 1H), 7.80 (s, 1H), 7.64 (s, 1H), 4.78 (q, J = 8.3 Hz, 2H), 2.84 (s, 3H), 2.62 (s, 3H), 1.69 (s, 6H) |
| 768 | 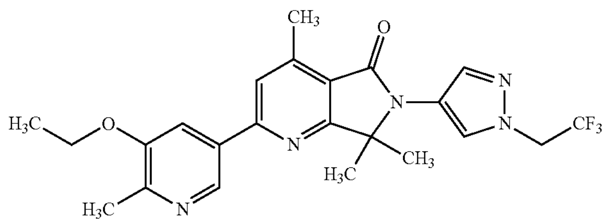 [SMILES: CCOc1cc(-c2cc(C)c3c(n2)C(C)(C)N(c2cnn(CC(F)(F)F)c2)C3=O)cnc1C] | 460.55 | (CDCl₃) δ 9.04 (d, J = 1.6 Hz, 1H), 8.42 (d, J = 1.4 Hz, 1H), 8.17 (s, 1H), 7.81 (s, 1H), 7.74 (s, 1H), 4.78 (q, J = 8.3 Hz, 2H), 4.38 (q, J = 6.9 Hz, 2H), 2.87 (s, 3H), 2.81 (s, 3H), 1.73 (s, 6H), 1.63 (t, J = 8.8, 5.1 Hz, 3H) |
| 769 | 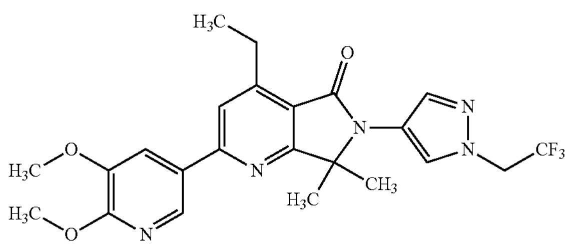 [SMILES: CCc1cc(-c2cnc(OC)c(OC)c2)nc2c1C(=O)N(c1cnn(CC(F)(F)F)c1)C2(C)C] | 476.61 | (DMSO-d₆) δ 8.59 (d, J = 1.9 Hz, 1H), 8.35 (s, 1H), 7.99 (dd, Jr 11.9, 8.9 Hz, 3H), 5.20 (q, J = 9.1 Hz, 2H), 3.94 (d, J = 7.1 Hz, 6H), 3.14 (q, J = 7.4 Hz, 2H), 1.61 (s, 6H), 1.31 (t, J = 7.5 Hz, 3H) |
| 770 | 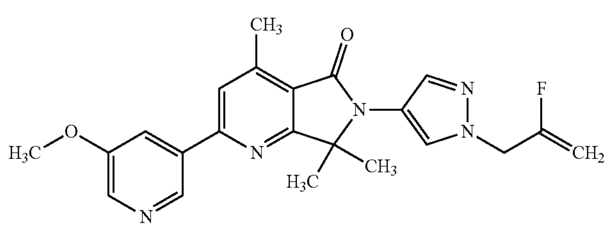 [SMILES: C=C(F)Cn1cc(N2C(=O)c3c(C)cc(-c4cncc(OC)c4)nc3C2(C)C)cn1] | 408.53 | (400 MHz, DMSO-d₆) δ 9.00 (s, 1H), 8.41 (t, J = 8.8 Hz, 1H), 8.22 (s, 1H), 8.08 (s, 2H), 7.83 (s, 1H), 5.02 (d, J = 14.9 Hz, 2H), 4.80 (ddd, J = 52.8, 33.1, 3.2 Hz, 2H), 3.94 (d, J = 8.1 Hz, 3H), 2.73 (s, 3H), 1.60 (s, 6H) |
| 771 | 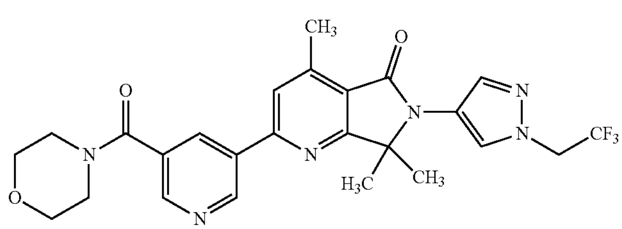 [SMILES: Cc1cc(-c2cncc(C(=O)N3CCOCC3)c2)nc2c1C(=O)N(c1cnn(CC(F)(F)F)c1)C2(C)C] | 515.63 | (DMSO-d₆) δ 9.46 (d, J = 2.2 Hz, 1H), 8.74 (d, J = 2.0 Hz, 1H), 8.59 (t, J = 2.1 Hz, 1H), 8.35 (s, 1H), 8.14 (s, 1H), 7.95 (d, J = 0.5 Hz, 1H), 5.20 (d, J = 9.1 Hz, 2H), 3.65 (d, J = 30.2 Hz, 8H), 2.74 (s, 3H), 1.62 (s, 6H) |

TABLE 1-continued

| Cmpd No. | Structure | ESMS (M + H) | ¹H NMR (300 MHz, unless indicated otherwise) |
|---|---|---|---|
| 772 | 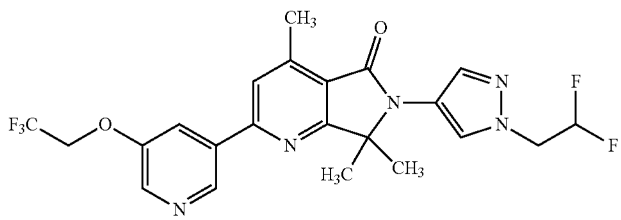 [SMILES: Cc1cc(-c2cncc(OCC(F)(F)F)c2)nc2c1C(=O)N(c1cnn(CC(F)F)c1)C2(C)C] | 482.15 | (400 MHz, DMSO-d$_6$) δ 9.11 (s, 1H), 8.53 (d, J = 2.7 Hz, 1H), 8.25 (m, 2H), 8.11 (s, 1H), 7.88 (s, 1H), 6.60-6.25 (m, 1H), 5.03 (d, J = 8.8 Hz, 2H), 4.68 (d, J = 3.7 Hz, 2H), 2.74 (s, 3H), 1.61 (s, 6H) |
| 773 | 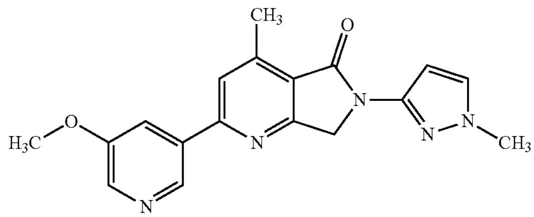 | 336.4 | (DMSO-d$_6$) δ 8.97 (d, J = 1.7 Hz, 1H), 8.41 (d, J = 2.8 Hz, 1H), 8.07 (dd, J = 8.2, 6.4 Hz, 2H), 7.72 (d, J = 2.2 Hz, 1H), 6.78 (d, J = 2.3 Hz, 1H), 4.94 (s, 2H), 3.95 (s, 3H), 3.84 (s, 3H), 2.74 (s, 3H) |
| 774 | 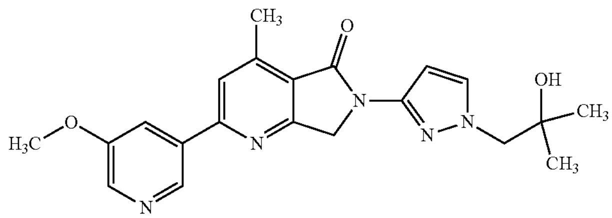 [SMILES: COc1cncc(-c2cc(C)c3c(n2)CN(c2ccn(CC(C)(C)O)n2)C3=O)c1] | 394.28 | (CDCl$_3$) δ 8.84 (d, J = 1.7 Hz, 1H), 8.42 (d, J = 2.8 Hz, 1H), 8.02-7.93 (m, 1H), 7.64 (s, 1H), 7.43 (d, J = 2.4 Hz, 1H), 7.05 (d, J = 2.4 Hz, 1H), 4.99 (s, 2H), 4.06 (s, 3H), 3.99 (s, 3H), 2.85 (s, 3H), 1.22 (s, 6H) |
| 775 | 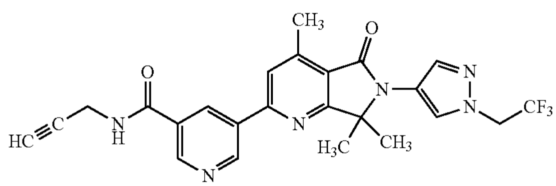 [SMILES: C#CCNC(=O)c1cncc(-c2cc(C)c3c(n2)C(C)(C)N(c2cnn(CC(F)(F)F)c2)C3=O)c1] | 483.53 | (DMSO-d$_6$) δ 9.51 (d, J = 2.1 Hz, 1H), 9.33 (t, J = 5.4 Hz, 1H), 9.10 (d, J = 2.1 Hz, 1H), 8.91 (s, 1H), 8.35 (s, 1H), 8.13 (d, J = 0.6 Hz, 1H), 7.96 (d, J = 0.5 Hz, 1H), 5.20 (d, J = 9.1 Hz, 2H), 4.23-4.10 (m, 2H), 3.22 (s, 1H), 2.76 (s, 3H), 1.63 (s, 6H) |
| 776 | 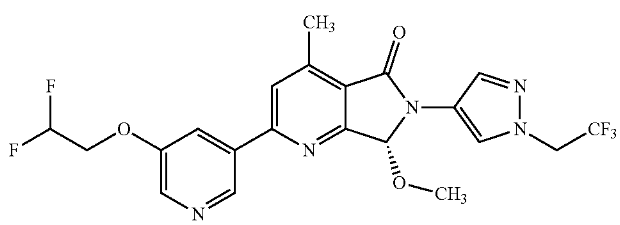 [SMILES: CO[C@@H]1c2nc(-c3cncc(OCC(F)F)c3)cc(C)c2C(=O)N1c1cnn(CC(F)(F)F)c1] | 484.54 | |
| 777 | 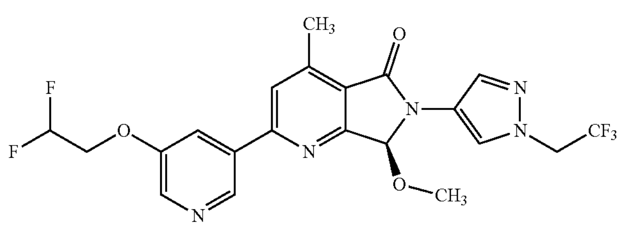 [SMILES: CO[C@H]1c2nc(-c3cncc(OCC(F)F)c3)cc(C)c2C(=O)N1c1cnn(CC(F)(F)F)c1] | 484.54 | |
| 778 | 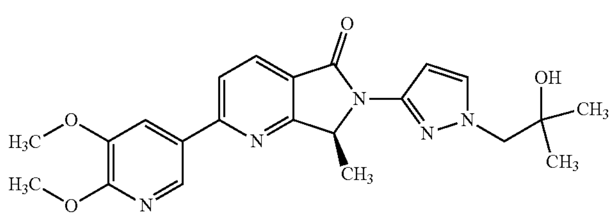 [SMILES: COc1cc(-c2ccc3c(n2)[C@H](C)N(c2ccn(CC(C)(C)O)n2)C3=O)cnc1OC] | 424.59 | |

TABLE 1-continued

| Cmpd No. | Structure | ESMS (M + H) | ¹H NMR (300 MHz, unless indicated otherwise) |
|---|---|---|---|
| 779 | 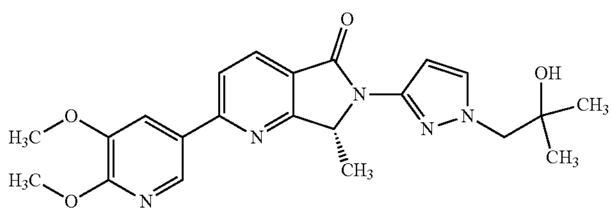 [SMILES: COc1cc(-c2ccc3c(n2)[C@@H](C)N(c2ccn(CC(C)(C)O)n2)C3=O)cnc1OC] | 424.59 | |
| 780 | 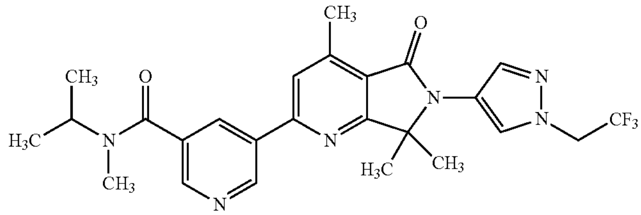 [SMILES: Cc1cc(-c2cncc(C(=O)N(C)C(C)C)c2)nc2c1C(=O)N(c1cnn(CC(F)(F)F)c1)C2(C)C] | 502.35 | (DMSO-d₆) δ 9.45 (d, J = 1.7 Hz, 1H), 8.70 (s, 1H), 8.56 (s, 1H), 8.35 (s, 1H), 8.15 (s, 1H), 7.95 (d, J = 0.5 Hz, 1H), 5.20 (q, J = 9.1 Hz, 2H), 4.77 (s, 1H), 3.78 (dd, J = 38.2, 31.4 Hz, 1H), 2.90 (s, 1H), 2.80 (s, 1H), 2.74 (s, 2H), 1.62 (s, 4H), 1.37-1.10 (m, 5H) |
| 781 | 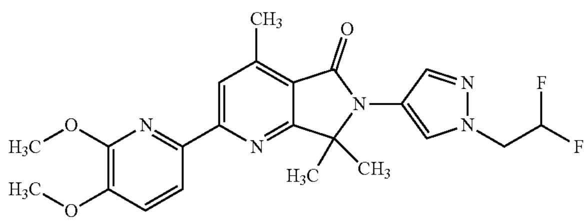 [SMILES: COc1ccc(-c2cc(C)c3c(n2)C(C)(C)N(c2cnn(CC(F)F)c2)C3=O)nc1OC] | 444.16 | (400 MHz, DMSO-d₆) δ 8.24 (s, 1H), 8.17 (s, 1H), 8.12 (d, J = 8.1 Hz, 1H), 7.87 (s, 1H), 7.46 (d, J = 8.3 Hz, 1H), 6.42 (tt, J = 56.8, 53.1 Hz, 1H), 4.68 (td, J = 3.6 Hz, 2H), 4.03 (s, 3H), 3.87 (s, 3H), 2.73 (s, 3H), 1.59 (s, 6H) |
| 782 | 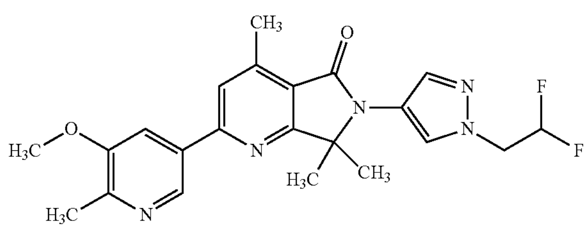 [SMILES: COc1cc(-c2cc(C)c3c(n2)C(C)(C)N(c2cnn(CC(F)F)c2)C3=O)cnc1C] | 428.17 | (400 MHz, DMSO-d₆) δ 8.83 (s, 1H), 8.25 (s, 1H), 8.05 (s, 1H), 8.00 (s, 1H), 7.88 (s, 1H), 6.42 (tt, 1H), 4.68 (td, J = 15.1, 3.8 Hz, 2H), 3.96 (s, 3H), 2.73 (s, 3H), 2.44 (s, 4H), 1.60 (s, 6H) |
| 783 | 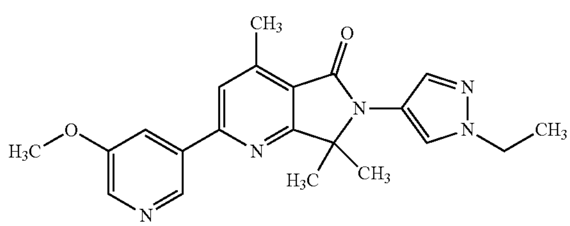 [SMILES: CCn1cc(N2C(=O)c3c(C)cc(-c4cncc(OC)c4)nc3C2(C)C)cn1] | 378.52 | (CDCl₃) δ 9.20 (s, 1H), 8.59 (s, 1H), 8.50 (s, 1H), 7.99 (s, 1H), 7.72 (s, 2H), 4.28 (dt, J = 7.4, 6.0 Hz, 2H), 4.13 (s, 3H), 2.86 (s, 3H), 1.69 (s, 6H), 1.58 (td, J = 7.3, 2.1 Hz, 3H) |
| 784 | 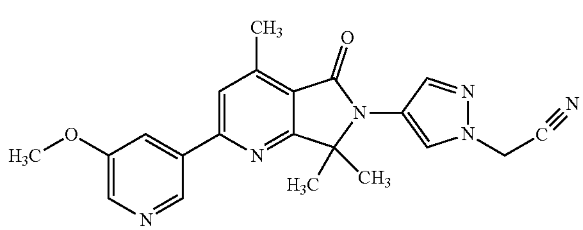 [SMILES: COc1cncc(-c2cc(C)c3c(n2)C(C)(C)N(c2cnn(CC#N)c2)C3=O)c1] | 389.52 | (DMSO-d₆) δ 9.00 (d, J = 1.7 Hz, 1H), 8.42 (d, J = 2.8 Hz, 1H), 8.33 (s, 1H), 8.08 (m, 2H), 7.96 (s, 1H), 5.55 (s, 2H), 3.96 (s, 3H), 2.74 (s, 3H), 1.61 (s, 6H) |

| Cmpd No. | Structure | ESMS (M + H) | ¹H NMR (300 MHz, unless indicated otherwise) |
|---|---|---|---|
| 785 | 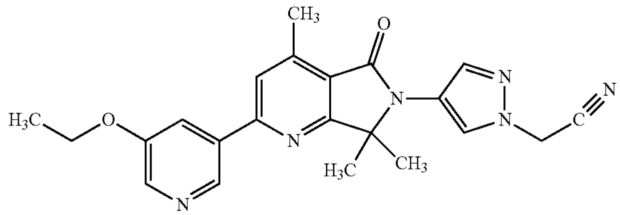 [SMILES: CCOc1cncc(-c2cc(C)c3c(n2)C(C)(C)N(c2cnn(CC#N)c2)C3=O)c1] | 403.6 | (DMSO-d₆) δ 8.99 (d, J = 1.6 Hz, 1H), 8.40 (d, J = 2.7 Hz, 1H), 8.33 (s, 1H), 8.08 (m, 2H), 7.96 (s, 1H), 5.55 (s, 2H), 4.24 (q, J = 6.9 Hz, 2H), 2.73 (s, 3H), 1.61 (s, 6H), 1.40 (t, J = 7.0 Hz, 3H) |
| 786 | 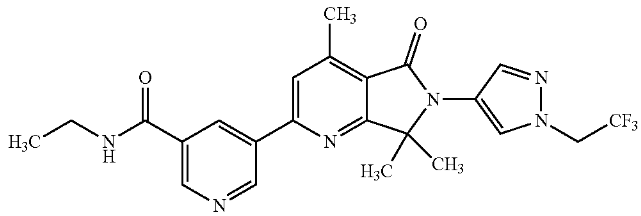 [SMILES: CCNC(=O)c1cncc(-c2cc(C)c3c(n2)C(C)(C)N(c2cnn(CC(F)(F)F)c2)C3=O)c1] | 474.31 | (DMSO-d₆) δ 9.48 (d, J = 2.1 Hz, 1H), 9.09 (d, J = 2.0 Hz, 1H), 8.86 (dd, J = 5.1, 3.0 Hz, 1H), 8.35 (s, 1H), 8.12 (s, 1H), 7.96 (s, 1H), 5.20 (q, J = 9.1 Hz, 2H), 3.50-3.35 (m, 2H), 2.76 (s, 3H), 1.63 (s, 6H), 1.18 (s, 3H) |
| 787 | 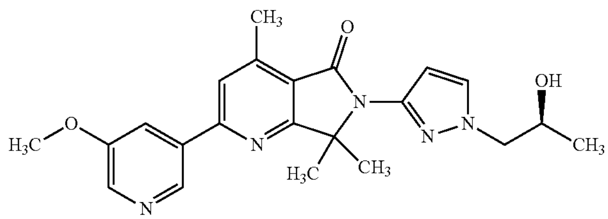 [SMILES: COc1cncc(-c2cc(C)c3c(n2)C(C)(C)N(c2ccn(C[C@H](C)O)n2)C3=O)c1] | 380.3 | (DMSO-d₆) δ 8.97 (d, J = 1.6 Hz, 1H), 8.41 (d, J = 2.8 Hz, 1H), 8.09 (s, 1H), 8.06-8.02 (m, 1H), 7.71 (d, J = 2.3 Hz, 1H), 6.77 (t, J = 4.2 Hz, 1H), 4.93 (s, 3H), 4.01 (m, 3H), 3.94 (s, 3H), 2.74 (s, 3H), 1.09 (s, 3H) |
| 788 | 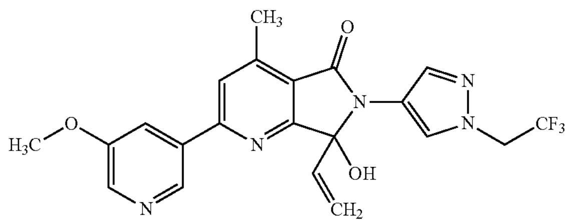 [SMILES: C=CC1(O)c2nc(-c3cncc(OC)c3)cc(C)c2C(=O)N1c1cnn(CC(F)(F)F)c1] | 446.53 | (DMSO-d₆) δ 8.94 (d, J = 1.7 Hz, 1H), 8.42 (d, J = 2.8 Hz, 1H), 8.25 (s, 1H), 8.13 (s, 1H), 8.04-7.99 (m, 1H), 7.91 (s, 1H), 7.36 (s, 1H), 5.94 (dd, J = 17.1, 10.2 Hz, 1H), 5.73-5.57 (m, 1H), 5.43 (d, J = 10.4 Hz, 1H), 5.19 (dd, J = 18.1, 9.1 Hz, 3H), 3.94 (s, 3H), 2.75 (s, 3H) |
| 789 | 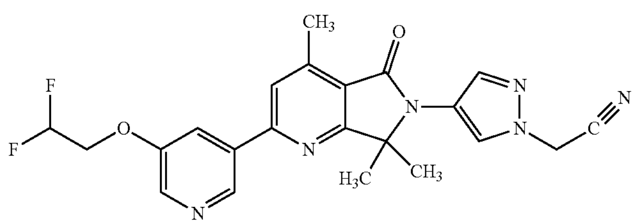 [SMILES: Cc1cc(-c2cncc(OCC(F)F)c2)nc2c1C(=O)N(c1cnn(CC#N)c1)C2(C)C] | 439.56 | (CDCl₃) δ 8.48 (d, J = 2.8 Hz, 1H), 8.23 (s, 1H), 8.19 (s, 1H), 7.82 (s, 1H), 7.68 (s, 1H), 6.21 (m, 1H), 5.15 (s, 2H), 4.44 (td, J = 12.8, 3.9 Hz, 2H), 2.86 (s, 3H), 1.73 (s, 6H) |
| 790 | 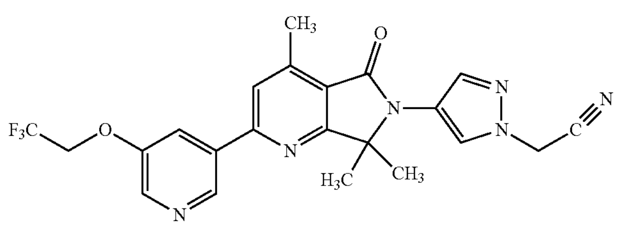 [SMILES: Cc1cc(-c2cncc(OCC(F)(F)F)c2)nc2c1C(=O)N(c1cnn(CC#N)c1)C2(C)C] | 457.54 | (CDCl₃) δ 8.51 (d, J = 2.8 Hz, 1H), 8.20 (m, 2H), 7.82 (s, 1H) 7.68 (s, 1H), 5.15 (s, 2H), 4.59 (q, J = 7.9 Hz, 2H), 2.86 (s, 3H), 1.74 (s, 6H) |

TABLE 1-continued

| Cmpd No. | Structure | ESMS (M + H) | ¹H NMR (300 MHz, unless indicated otherwise) |
|---|---|---|---|
| 791 | 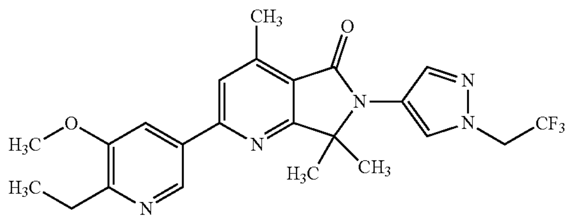 [SMILES: CCc1ncc(-c2cc(C)c3c(n2)C(C)(C)N(c2cnn(CC(F)(F)F)c2)C3=O)cc1OC] | 460.61 | (DMSO-d₆) δ 8.87 (s, 1H), 8.34 (s, 1H), 8.05 (s, 1H), 8.01 (s, 1H), 7.95 (s, 1H), 5.20 (dd, J = 18.4, 9.2 Hz, 2H), 3.96 (s, 3H), 2.82 (dd, J = 14.9, 7.5 Hz, 2H), 2.73 (s, 3H), 1.61 (s, 6H), 1.23 (d, J = 7.5 Hz, 3H) |
| 792 | 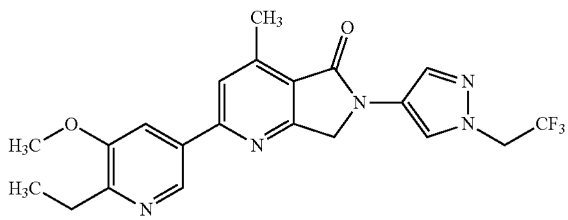 [SMILES: CCc1ncc(-c2cc(C)c3c(n2)CN(c2cnn(CC(F)(F)F)c2)C3=O)cc1OC] | 432.47 | (DMSO-d₆) δ 8.85 (d, J = 1.6 Hz, 1H), 8.39 (s, 1H), 8.08 (s, 1H), 7.99 (d, J = 1.6 Hz, 1H), 7.94 (s, 1H), 5.21 (q, J = 9.1 Hz, 2H), 4.95 (s, 2H), 3.95 (s, 3H), 2.81 (q, J = 7.4 Hz, 2H), 2.74 (s, 3H), 1.22 (s, 3H) |
| 793 | 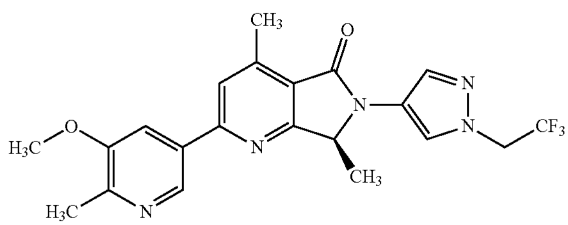 [SMILES: COc1cc(-c2cc(C)c3c(n2)[C@H](C)N(c2cnn(CC(F)(F)F)c2)C3=O)cnc1C] | 432.58 | (DMSO-d₆) δ 8.83 (d, J = 1.7 Hz, 1H), 8.37 (s, 1H), 8.08 (s, 1H), 8.00 (d, J = 1.6 Hz, 1H), 7.97 (s, 1H), 5.20 (dd, J = 12.3, 5.9 Hz, 3H), 3.96 (s, 3H), 2.74 (s, 3H), 2.44 (s, 3H), 1.57 (d, J = 6.6 Hz, 3H) |
| 794 | 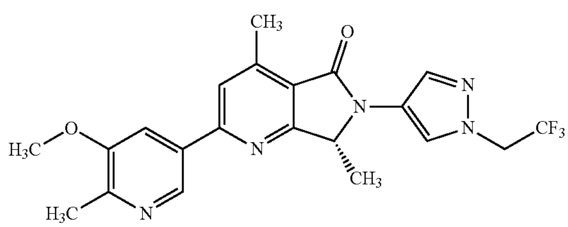 [SMILES: COc1cc(-c2cc(C)c3c(n2)[C@@H](C)N(c2cnn(CC(F)(F)F)c2)C3=O)cnc1C] | 432.58 | (DMSO-d₆) δ 8.83 (d, J = 1.7 Hz, 1H), 8.37 (s, 1H), 8.07 (s, 1H), 8.00 (d, J = 1.7 Hz, 1H), 7.97 (s, 1H), 5.32-5.11 (m, 3H), 3.96 (s, 3H), 2.74 (s, 3H), 2.44 (s, 3H), 1.57 (d, J = 6.6 Hz, 3H) |
| 795 | 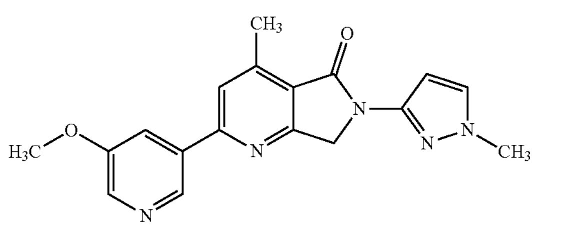 | 336.4 | (DMSO-d₆) δ 8.97 (d, J = 1.7 Hz, 1H), 8.41 (d, J = 2.8 Hz, 1H), 8.07 (dd, J = 8.2, 6.4 Hz, 2H), 7.72 (d, J = 2.2 Hz, 1H), 6.78 (d, J = 2.3 Hz, 1H), 4.94 (s, 2H), 3.95 (s, 3H), 3.84 (s, 3H), 2.74 (s, 3H) |
| 796 | 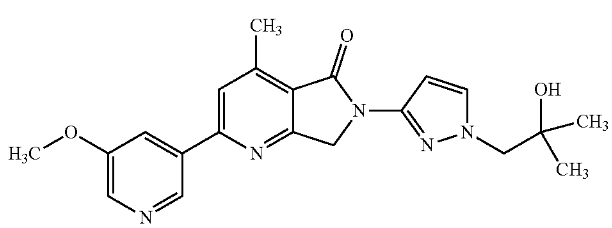 [SMILES: COc1cncc(-c2cc(C)c3c(n2)CN(c2ccn(CC(C)(C)O)n2)C3=O)c1] | 394.28 | (CDCl₃) δ 8.84 (d, J = 1.7 Hz, 1H), 8.42 (d, J = 2.8 Hz, 1H), 8.02-7.93 (m, 1H), 7.64 (s, 1H), 7.43 (d, J = 2.4 Hz, 1H), 7.05 (d, J = 2.4 Hz, 1H), 4.99 (s, 2H), 4.06 (s, 3H), 3.99 (s, 3H), 2.85 (s, 3H), 1.22 (s, 6H) |
| 797 | 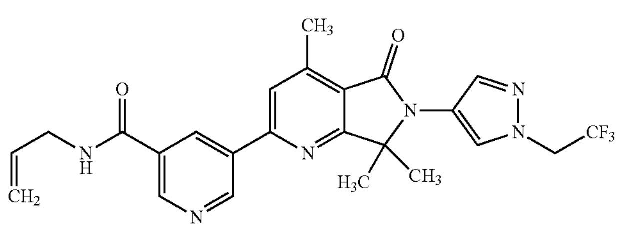 [SMILES: C=CCNC(=O)c1cncc(-c2cc(C)c3c(n2)C(C)(C)N(c2cnn(CC(F)(F)F)c2)C3=O)c1] | 483.53 | (DMSO-d₆) δ 9.51 (d, J = 2.1 Hz, 1H), 9.33 (t, J = 5.4 Hz, 1H), 9.10 (d, J = 2.1 Hz, 1H), 8.91 (s, 1H), 8.35 (s, 1H), 8.13 (d, J = 0.6 Hz, 1H), 7.96 (d, J = 0.5 Hz, 1H), 5.20 (d, J = 9.1 Hz, 2H), 4.23-4.10 (m, 2H), 3.22 (s, 1H), 2.76 (s, 3H), 1.63 (s, 6H) |

TABLE 1-continued

| Cmpd No. | Structure | ESMS (M + H) | ¹H NMR (300 MHz, unless indicated otherwise) |
|---|---|---|---|
| 798 | 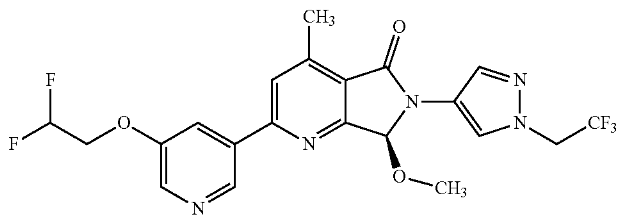 [SMILES: CO[C@H]1c2nc(-c3cncc(OCC(F)F)c3)cc(C)c2C(=O)N1c1cnn(CC(F)(F)F)c1] | 484.54 | |
| 799 | 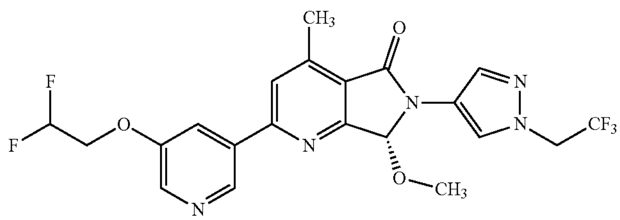 [SMILES: CO[C@@H]1c2nc(-c3cncc(OCC(F)F)c3)cc(C)c2C(=O)N1c1cnn(CC(F)(F)F)c1] | 484.54 | |
| 800 | 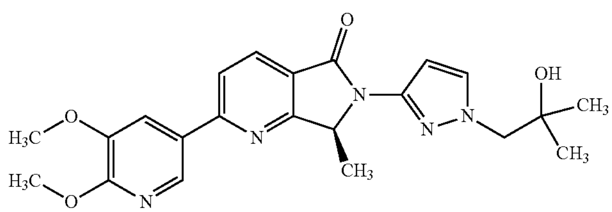 [SMILES: COc1cc(-c2ccc3c(n2)[C@H](C)N(c2ccn(CC(C)(C)O)n2)C3=O)cnc1OC] | 424.59 | |
| 801 | 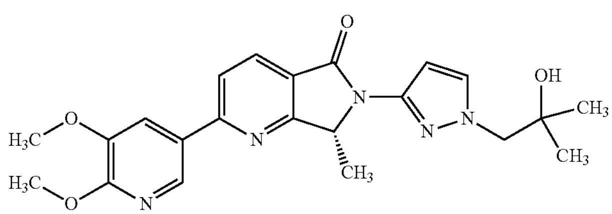 [SMILES: COc1cc(-c2ccc3c(n2)[C@@H](C)N(c2ccn(CC(C)(C)O)n2)C3=O)cnc1OC] | 424.59 | |
| 802 | 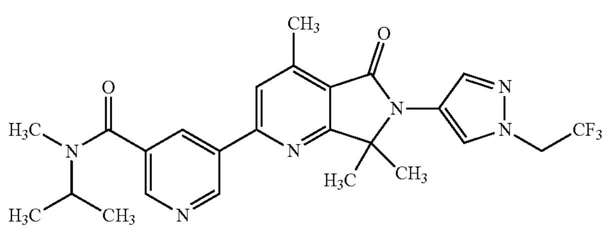 [SMILES: Cc1cc(-c2cncc(C(=O)N(C)C(C)C)c2)nc2c1C(=O)N(c1cnn(CC(F)(F)F)c1)C2(C)C] | 502.35 | (DMSO-d$_6$, 400 MHz) δ 9.45 (d, J = 1.7 Hz, 1H), 8.70 (s, 1H), 8.56 (s, 1H), 8.35 (s, 1H), 8.15 (s, 1H), 7.95 (d, J = 0.5 Hz, 1H), 5.20 (q, J = 9.1 Hz, 2H), 4.77 (s, 1H), 3.78 (dd, J = 38.2, 31.4 Hz, 1H), 2.90 (s, 1H), 2.80 (s, 1H), 2.74 (s, 2H), 1.62 (s, 4H), 1.37- 1.10 (m, 5H) |
| 803 | 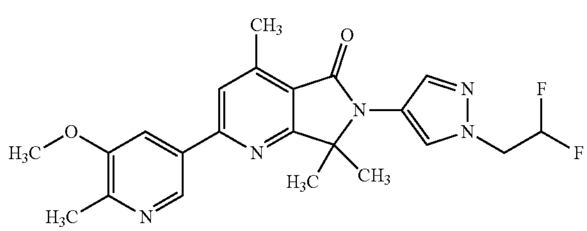 [SMILES: COc1cc(-c2cc(C)c3c(n2)C(C)(C)N(c2cnn(CC(F)F)c2)C3=O)cnc1C] | 428.17 | (DMSO-d$_6$, 400 MHz) δ 8.83 (s, 1H), 8.25 (s, 1H), 8.05 (s, 1H), 8.00 (s, 1H), 7.88 (s, 1H), 6.42 (tt, 1H), 4.68 (td, J = 15.1, 3.8 Hz, 2H), 3.96 (s, 3H), 2.73 (s, 3H), 2.44 (s, 4H), 1.60 (s, 6H) |

TABLE 1-continued

| Cmpd No. | Structure | ESMS (M + H) | ¹H NMR (300 MHz, unless indicated otherwise) |
|---|---|---|---|
| 804 | 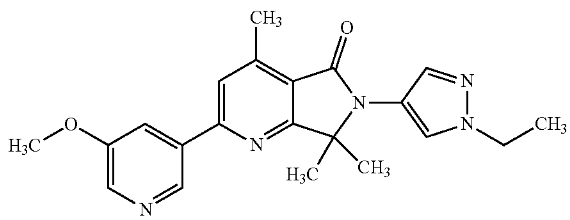 [SMILES: CCn1cc(N2C(=O)c3c(C)cc(-c4cncc(OC)c4)nc3C2(C)C)cn1] | 378.52 | (CDCl$_3$) δ 9.20 (s, 1H), 8.59 (s, 1H), 8.50 (s, 1H), 7.99 (s, 1H), 7.72 (s, 2H), 4.28 (dt, J = 7.4, 6.0 Hz, 2H), 4.13 (s, 3H), 2.86 (s, 3H), 1.69 (s, 6H), 1.58 (td, J = 7.3, 2.1 Hz, 3H) |
| 805 | 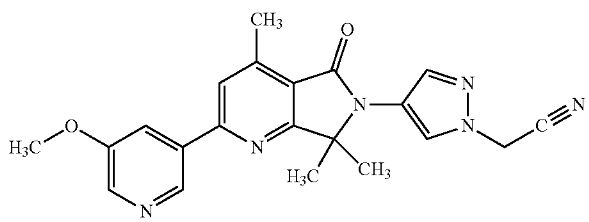 [SMILES: COc1cncc(-c2cc(C)c3c(n2)C(C)(C)N(c2cnn(CC#N)c2)C3=O)c1] | 389.52 | (DMSO-d$_6$) δ 9.00 (d, J = 1.7 Hz, 1H), 8.42 (d, J = 2.8 Hz, 1H), 8.33 (s, 1H), 8.08 (m, 2H), 7.96 (s, 1H), 5.55 (s, 2H), 3.96 (s, 3H), 2.74 (s, 3H), 1.61 (s, 6H) |
| 806 | 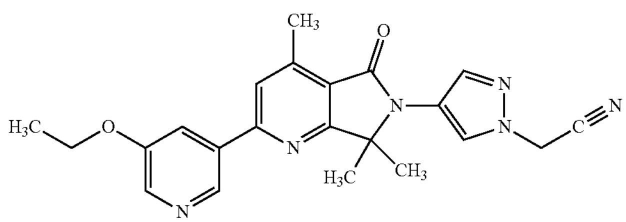 [SMILES: CCOc1cncc(-c2cc(C)c3c(n2)C(C)(C)N(c2cnn(CC#N)c2)C3=O)c1] | 403.6 | (DMSO-d$_6$) δ 8.99 (d, J = 1.6 Hz, 1H), 8.40 (d, J = 2.7 Hz, 1H), 8.33 (s, 1H), 8.08 (m, 2H) 7.96 (s, 1H), 5.55 (s, 2H), 4.24 (q, J = 6.9 Hz, 2H), 2.73 (s, 3H), 1.61 (s, 6H), 1.40 (t, J = 7.0 Hz, 3H) |
| 807 | 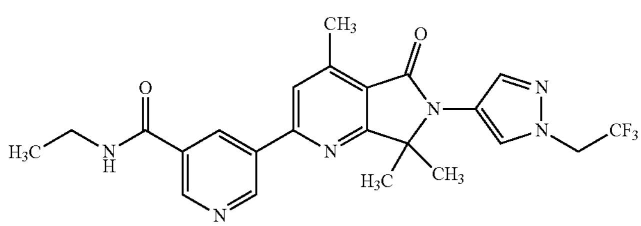 [SMILES: CCNC(=O)c1cncc(-c2cc(C)c3c(n2)C(C)(C)N(c2cnn(CC(F)(F)F)c2)C3=O)c1] | 474.31 | (DMSO-d$_6$) δ 9.48 (d, J = 2.1 Hz, 1H), 9.09 (d, J = 2.0 Hz, 1H), 8.86 (dd, J = 5.1, 3.0 Hz, 1H), 8.35 (s, 1H), 8.12 (s, 1H), 7.96 (s, 1H), 5.20 (q, J = 9.1 Hz, 2H), 3.50-3.35 (m, 2H), 2.76 (s, 3H), 1.63 (s, 6H), 1.18 (s, 3H) |
| 808 | 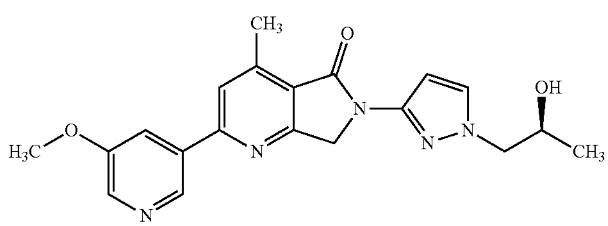 [SMILES: COc1cncc(-c2cc(C)c3c(n2)CN(c2ccn(C[C@H](C)O)n2)C3=O)c1] | 380.3 | (DMSO-d$_6$) δ 8.97 (d, J = 1.6 Hz, 1H), 8.41 (d, J = 2.8 Hz, 1H), 8.09 (s, 1H), 8.06-8.02 (m, 1H), 7.71 (d, J = 2.3 Hz, 1H), 6.77 (t, J = 4.2 Hz, 1H), 4.93 (s, 3H), 4.01 (m, 3H), 3.94 (s, 3H), 2.74 (s, 3H), 1.09 (s, 3H) |
| 809 | 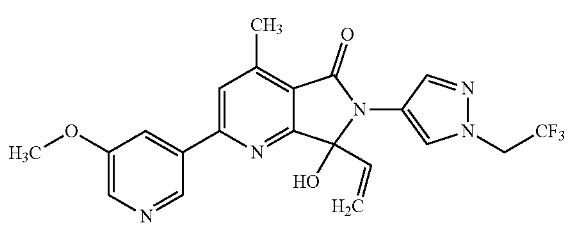 [SMILES: C=CC1(O)c2nc(-c3cncc(OC)c3)cc(C)c2C(=O)N1c1cnn(CC(F)(F)F)c1] | 446.53 | (DMSO-d$_6$) δ 8.94 (d, J = 1.7 Hz, 1H), 8.42 (d, J = 2.8 Hz, 1H), 8.25 (s, 1H), 8.13 (s, 1H), 8.04-7.99 (m, 1H), 7.91 (s, 1H), 7.36 (s, 1H), 5.94 (dd, J = 17.1, 10.2 Hz, 1H), 5.73-5.57 (m, 1H), 5.43 (d, J = 10.4 Hz, 1H), 5.19 (dd, J = 18.1, 9.1 Hz, 3H), 3.94 (s, 3H), 2.75 (s, 3H) |

TABLE 1-continued

| Cmpd No. | Structure | ESMS (M + H) | ¹H NMR (300 MHz, unless indicated otherwise) |
|---|---|---|---|
| 810 | 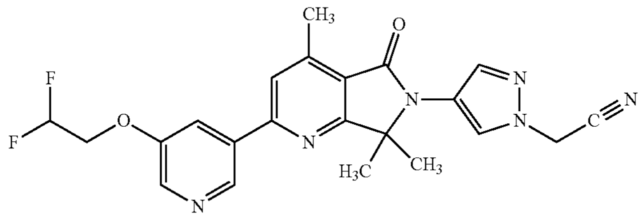 [SMILES: Cc1cc(-c2cncc(OCC(F)F)c2)nc2c1C(=O)N(c1cnn(CC#N)c1)C2(C)C] | 439.56 | (CDCl$_3$) δ 8.48 (d, J = 2.8 Hz, 1H), 8.23 (s, 1H), 8.19 (s, 1H), 7.82 (s, 1H), 7.68 (s, 1H), 6.21 (m, 1H), 5.15 (s, 2H), 4.44 (td, J = 12.8, 3.9 Hz, 2H), 2.86 (s, 3H), 1.73 (s, 6H) |
| 811 | 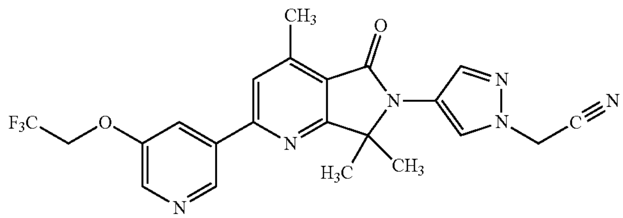 [SMILES: Cc1cc(-c2cncc(OCC(F)(F)F)c2)nc2c1C(=O)N(c1cnn(CC#N)c1)C2(C)C] | 457.54 | (CDCl$_3$) δ 8.51 (d, J = 2.8 Hz, 1H), 8.20 (m, 2H), 7.82 (s, 1H), 7.68 (s, 1H), 5.15 (s, 2H), 4.59 (q, J = 7.9 Hz, 2H), 2.86 (s, 3H), 1.74 (s, 6H) |
| 812 | 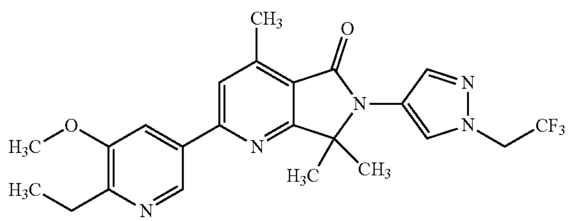 [SMILES: CCc1ncc(-c2cc(C)c3c(n2)C(C)(C)N(c2cnn(CC(F)(F)F)c2)C3=O)cc1OC] | 460.61 | (DMSO-d$_6$) δ 8.87 (s, 1H), 8.34 (s, 1H), 8.05 (s, 1H), 8.01 (s, 1H), 7.95 (s, 1H), 5.20 (dd, J = 18.4, 9.2 Hz, 2H), 3.96 (s, 3H), 2.82 (dd, J = 14.9, 7.5 Hz, 2H), 2.73 (s, 3H), 1.61 (s, 6H), 1.23 (d, J = 7.5 Hz, 3H) |
| 813 | 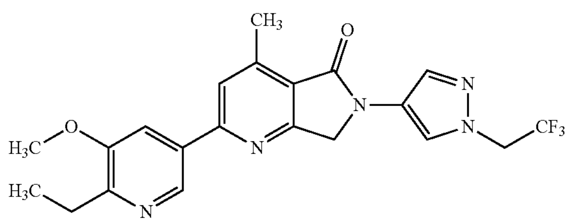 [SMILES: CCc1ncc(-c2cc(C)c3c(n2)CN(c2cnn(CC(F)(F)F)c2)C3=O)cc1OC] | 432.47 | (DMSO-d$_6$) δ 8.85 (d, J = 1.6 Hz, 1H), 8.39 (s, 1H), 8.08 (s, 1H), 7.99 (d, J = 1.6 Hz, 1H), 7.94 (s, 1H), 5.21 (q, J = 9.1 Hz, 2H), 4.95 (s, 2H), 3.95 (s, 3H), 2.81 (q, J = 7.4 Hz, 2H), 2.74 (s, 3H), 1.22 (s, 3H) |
| 814 | 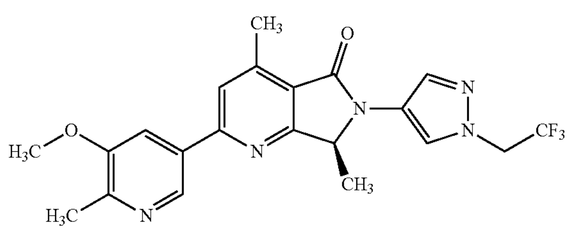 [SMILES: COc1cc(-c2cc(C)c3c(n2)[C@H](C)N(c2cnn(CC(F)(F)F)c2)C3=O)cnc1C] | 432.58 | (DMSO-d$_6$) δ 8.83 (d, J = 1.7 Hz, 1H), 8.37 (s, 1H), 8.08 (s, 1H), 8.00 (d, J = 1.6 Hz, 1H), 7.97 (s, 1H), 5.20 (dd, J = 12.3, 5.9 Hz, 3H), 3.96 (s, 3H), 2.74 (s, 3H), 2.44 (s, 3H), 1.57 (d, J = 6.6 Hz, 3H) |
| 815 | 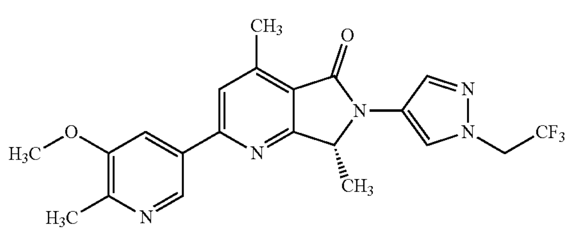 | 432.58 | (DMSO-d$_6$) δ 8.83 (d, J = 1.7 Hz, 1H), 8.37 (s, 1H), 8.07 (s, 1H), 8.00 (d, J = 1.7 Hz, 1H), 7.97 (s, 1H), 5.32-5.11 (m, 3H), 3.96 (s, 3H), 2.74 (s, 3H), 2.44 (s, 3H), 1.57 (d, J = 6.6 Hz, 3H) |

TABLE 1-continued

| Cmpd No. | Structure | ESMS (M + H) | ¹H NMR (300 MHz, unless indicated otherwise) |
|---|---|---|---|
| 816 | 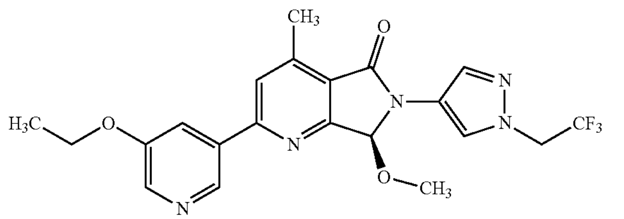 [SMILES: CCOc1cncc(-c2cc(C)c3c(n2)[C@H](OC)N(c2cnn(CC(F)(F)F)c2)C3=O)c1] | 448.16 | (DMSO-d₆, 400 MHz) δ 8.97 (s, 1H), 8.42 (d, J = 2.5 Hz, 1H), 8.33 (s, 1H), 8.21 (s, 1H), 8.05 (s, 1H), 7.93 (s, 1H), 6.34 (s, 1H), 5.22 (q, J = 9.0 Hz, 2H), 4.24 (q, J = 6.8 Hz, 2H), 3.11 (s, 3H), 2.74 (s, 3H), 1.40 (t, J = 6.9 Hz, 3H) |
| 817 | 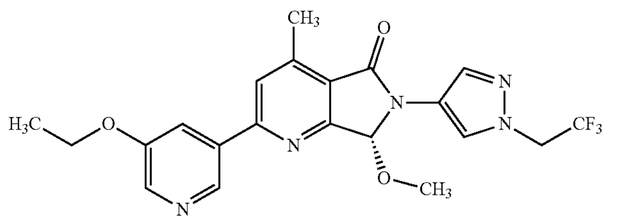 [SMILES: CCOc1cncc(-c2cc(C)c3c(n2)[C@@H](OC)N(c2cnn(CC(F)(F)F)c2)C3=O)c1] | 448.16 | (DMSO-d₆, 400 MHz) δ 8.97 (s, 1H), 8.42 (d, J = 2.3 Hz, 1H), 8.33 (s, 1H), 8.21 (s, 1H), 8.05 (s, 1H), 7.93 (s, 1H), 6.34 (s, 1H), 5.22 (d, J = 9.1 Hz, 2H), 4.24 (d, J = 7.0 Hz, 2H), 3.11 (s, 3H), 2.74 (s, 3H), 1.40 (t, J = 6.9 Hz, 3H) |
| 818 | 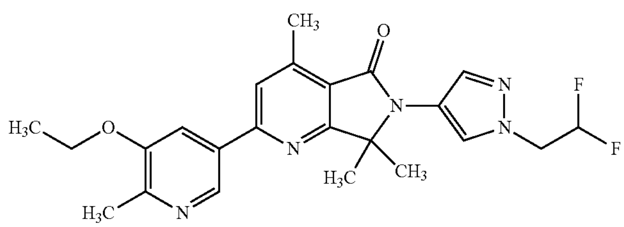 [SMILES: CCOc1cc(-c2cc(C)c3c(n2)C(C)(C)N(c2cnn(CC(F)F)c2)C3=O)cnc1C] | 442.21 | (DMSO-d₆, 400 MHz) δ 8.83 (s, 1H), 8.25 (s, 1H), 8.04 (s, 1H), 7.99 (s, 1H), 7.87 (s, 1H), 6.42 (tt, 1H), 4.68 (td, J = 15.0, 3.7 Hz, 2H), 4.23 (q, J = 6.9 Hz, 2H), 2.72 (s, 3H), 2.44 (s, 3H), 1.60 (s, 6H), 1.42 (t, J = 6.9 Hz, 3H) |
| 819 | 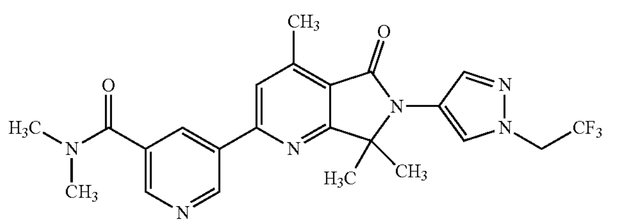 [SMILES: Cc1cc(-c2cncc(C(=O)N(C)C)c2)nc2c1C(=O)N(c1cnn(CC(F)(F)F)c1)C2(C)C] | 472.66 | (DMSO-d₆) δ 9.45 (d, J = 2.1 Hz, 1H), 8.73 (d, J = 1.9 Hz, 1H), 8.58 (t, J = 2.1 Hz, 1H), 8.35 (s, 1H), 8.15 (s, 1H), 7.95 (s, 1H), 5.20 (dd, J = 18.3, 9.1 Hz, 3H), 3.06 (s, 3H), 2.99 (s, 3H), 2.74 (s, 3H), 1.62 (s, 6H) |
| 820 | 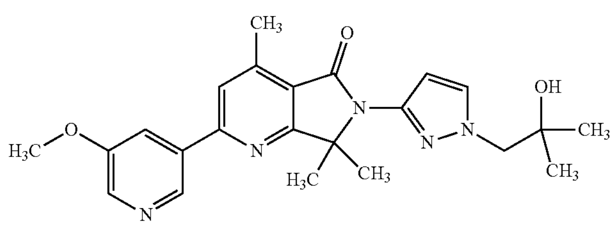 [SMILES: COc1cncc(-c2cc(C)c3c(n2)C(C)(C)N(c2ccn(CC(C)(C)O)n2)C3=O)c1] | 422.6 | (CDCl₃) δ 9.23 (d, J = 1.4 Hz, 1H), 8.61 (dd, J = 7.9, 2.1 Hz, 2H), 7.75 (s, 1H), 7.48 (d, J = 2.4 Hz, 1H), 6.97 (d, J = 2.3 Hz, 1H), 4.13 (d, J = 6.7 Hz, 5H), 2.90 (s, 3H), 1.85 (s, 6H), 1.26 (s, 6H) |
| 821 | 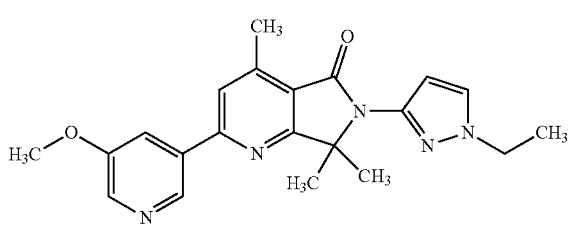 [SMILES: CCn1ccc(N2C(=O)c3c(C)cc(-c4cncc(OC)c4)nc3C2(C)C)n1] | 378.58 | (CDCl₃) δ 8.90 (d, J = 1.7 Hz, 1H), 8.41 (d, J = 2.8 Hz, 1H), 7.98 (dd, J = 2.8, 1.8 Hz, 1H), 7.60 (s, 1H), 7.41 (d, J = 2.3 Hz, 1H), 6.87 (d, J = 2.3 Hz, 1H), 4.19 (q, J = 7.3 Hz, 2H), 4.00 (s, 3H), 2.85 (s, 3H), 1.86 (s, 6H), 1.54 (t, J = 7.3 Hz, 3H) |
| 822 | 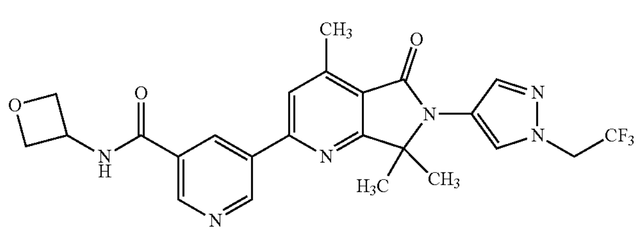 [SMILES: Cc1cc(-c2cncc(C(=O)NC3COC3)c2)nc2c1C(=O)N(c1cnn(CC(F)(F)F)c1)C2(C)C] | 501.32 | (DMSO-d₆) δ 9.51 (d, J = 2.1 Hz, 2H), 9.13 (d, J = 2.0 Hz, 1H), 8.89 (s, 1H), 8.35 (s, 1H), 8.13 (s, 1H), 7.96 (s, 1H), 5.20 (d, J = 9.1 Hz, 2H), 5.06 (dt, J = 13.9, 7.1 Hz, 1H), 4.83 (t, J = 6.9 Hz, 2H), 4.65 (t, J = 6.4 Hz, 2H), 2.76 (s, 3H), 1.63 (s, 5H) |

TABLE 1-continued

| Cmpd No. | Structure | ESMS (M + H) | ¹H NMR (300 MHz, unless indicated otherwise) |
|---|---|---|---|
| 823 | 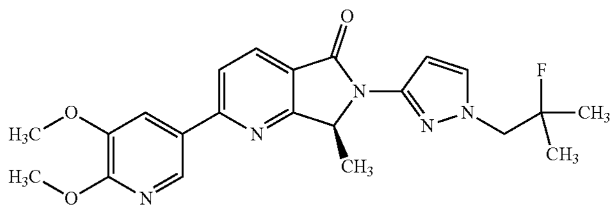 [SMILES: COc1cc(-c2ccc3c(n2)[C@H](C)N(c2ccn(CC(C)(C)F)n2)C3=O)cnc1OC] | 426.57 | |
| 824 | 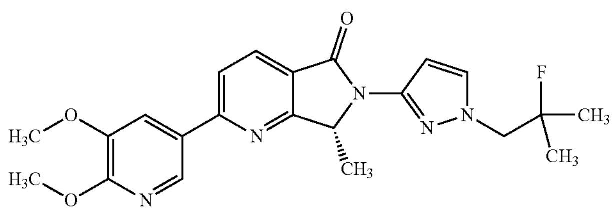 [SMILES: COc1cc(-c2ccc3c(n2)[C@@H](C)N(c2ccn(CC(C)(C)F)n2)C3=O)cnc1OC] | 426.57 | |
| 825 | 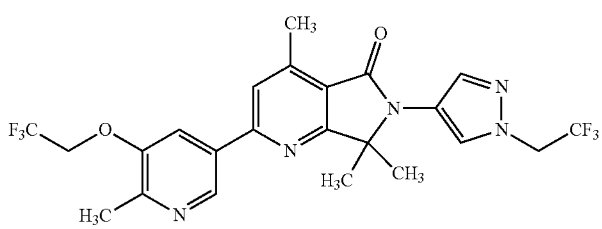 [SMILES: Cc1cc(-c2cnc(C)c(OCC(F)(F)F)c2)nc2c1C(=O)N(c1cnn(CC(F)(F)F)c1)C2(C)C] | 514.61 | |
| 826 | 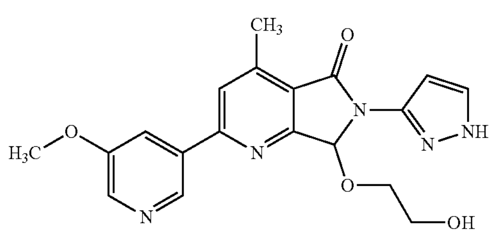 [SMILES: COc1cncc(-c2cc(C)c3c(n2)C(OCCO)N(c2cc[nH]n2)C3=O)c1] | 382.15 | (DMSO-d₆, 400 MHz) δ 12.75 (s, 1H), 8.98 (s, 1H), 8.44 (d, J = 2.6 Hz, 1H), 8.19 (s, 1H), 8.07 (s, 1H), 7.79 (s, 1H), 6.73 (s, 1H), 6.45 (s, 1H), 4.89 (s, 1H), 3.95 (s, 3H), 3.93-3.83 (m, 1H), 3.74 (s, 1H), 3.58 (s, 2H), 2.74 (s, 3H) |
| 827 | 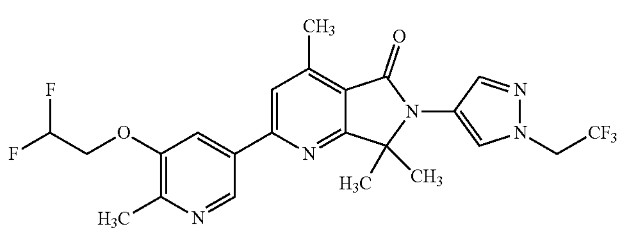 [SMILES: Cc1cc(-c2cnc(C)c(OCC(F)F)c2)nc2c1C(=O)N(c1cnn(CC(F)(F)F)c1)C2(C)C] | 496.57 | (DMSO-d₆) δ 8.91 (d, J = 1.6 Hz, 1H), 8.34 (s, 1H), 8.10 (d, J = 1.5 Hz, 1H), 8.07 (s, 1H), 7.95 (s, 1H), 6.50 (s, 1H), 5.20 (d, J = 9.1 Hz, 2H), 4.56 (d, J = 3.5 Hz, 2H), 2.74 (s, 3H), 2.47 (s, 3H), 1.62 (s, 6H) |
| 828 | 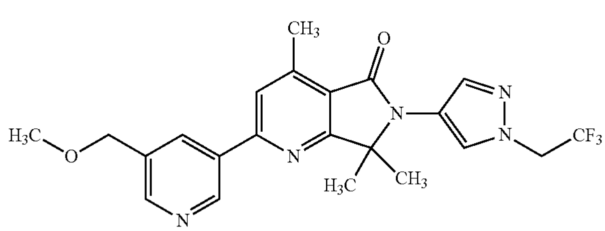 [SMILES: COCc1cncc(-c2cc(C)c3c(n2)C(C)(C)N(c2cnn(CC(F)(F)F)c2)C3=O)c1] | 446.63 | (DMSO-d₆) δ = 9.31 (s, 1H), 8.66 (s, 1H), 8.49 (s, 1H), 8.35 (s, 1H), 8.07 (s, 1H), 7.96 (s, 1H), 5.21 (q, J = 9.0, 2H), 4.58 (s, 2H), 2.74 (s, 3H), 1.62 (s, 6H) |

TABLE 1-continued

| Cmpd No. | Structure | ESMS (M + H) | ¹H NMR (300 MHz, unless indicated otherwise) |
|---|---|---|---|
| 829 | 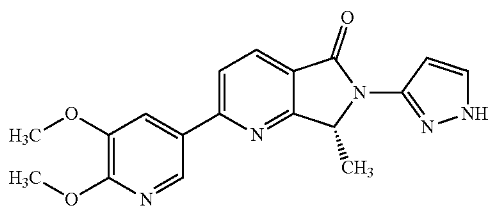 [SMILES: COc1cc(-c2ccc3c(n2)[C@@H](C)N(c2cc[nH]n2)C3=O)cnc1OC] | 352 | |
| 830 | 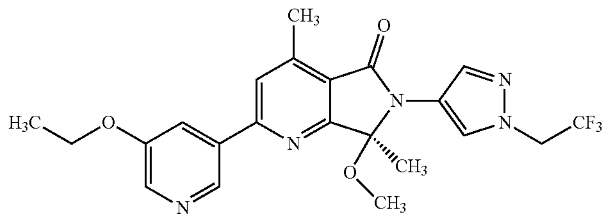 [SMILES: CCOc1cncc(-c2cc(C)c3c(n2)[C@](C)(OC)N(c2cnn(CC(F)(F)F)c2)C3=O)c1] | 462.18 | (DMSO-d$_6$, 400 MHz) δ 8.97 (s, 1H), 8.42 (d, J = 2.7 Hz, 1H), 8.29 (s, 1H), 8.19 (s, 1H), 8.06 (s, 1H), 7.95 (s, 1H), 5.22 (q, J = 9.1 Hz, 2H), 4.25 (q, J = 6.9 Hz, 2H), 2.85 (s, 3H), 2.75 (s, 3H), 1.73 (s, 3H), 1.41 (t, J = 6.9 Hz, 3H) |
| 831 | 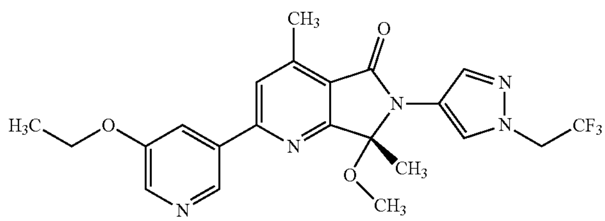 [SMILES: CCOc1cncc(-c2cc(C)c3c(n2)[C@@](C)(OC)N(c2cnn(CC(F)(F)F)c2)C3=O)c1] | 462.15 | (DMSO-d$_6$, 400 MHz) δ 8.97 (s, 1H), 8.42 (d, J = 2.7 Hz, 1H), 8.29 (s, 1H), 8.19 (s, 1H), 8.06 (s, 1H), 7.95 (s, 1H), 5.22 (q, J = 9.1 Hz, 2H), 4.25 (q, J = 6.9 Hz, 2H), 2.85 (s, 3H), 2.75 (s, 3H), 1.73 (s, 3H), 1.41 (t, J = 6.9 Hz, 3H) |
| 832 | 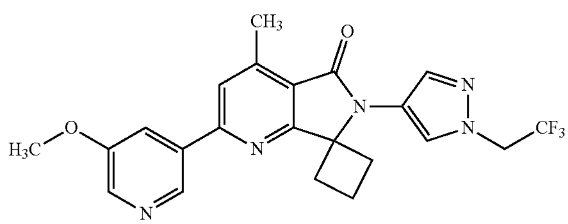 [SMILES: COc1cncc(-c2cc(C)c3c(n2)C2(CCC2)N(c2cnn(CC(F)(F)F)c2)C3=O)c1] | 444.49 | (CDCl$_3$) δ 8.97 (d, J = 1.6 Hz, 1H), 8.43 (d, J = 2.8 Hz, 1H), 8.25 (s, 1H), 8.10-8.01 (m, 1H), 7.95 (s, 1H), 7.65 (s, 1H), 4.80 (q, J = 8.4 Hz, 2H), 4.05-3.95 (m, 3H), 3.02-2.88 (m, 2H), 2.88-2.76 (m, 3H), 2.76-2.49 (m, 3H), 2.17-2.04 (m, 1H) |
| 833 | 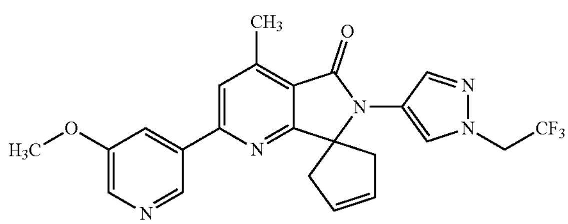 [SMILES: COc1cncc(-c2cc(C)c3c(n2)C2(CC=CC2)N(c2cnn(CC(F)(F)F)c2)C3=O)c1] | 456.68 | (CDCl$_3$) δ 8.90 (d, J = 1.8 Hz, 1H), 8.47-8.35 (m, 2H), 7.95 (d, J = 1.9 Hz, 1H), 7.84 (s, 1H), 7.65 (s, 1H), 6.04 (s, 2H), 4.77 (d, J = 8.4 Hz, 2H), 4.00 (s, 3H), 3.07 (d, J = 31.5 Hz, 4H), 2.87 (s, 3H) |
| 834 | 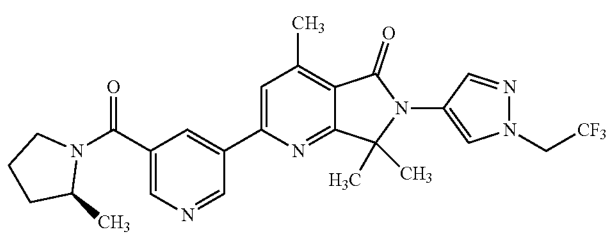 [SMILES: Cc1cc(-c2cncc(C(=O)N3CCC[C@@H]3C)c2)nc2c1C(=O)N(c1cnn(CC(F)(F)F)c1)C2(C)C] | 513.58 | (DMSO-d$_6$) δ 9.46 (s, 1H), 8.80 (d, J = 1.9 Hz, 1H), 8.62 (s, 1H), 8.35 (s, 1H), 8.16 (s, 1H), 7.95 (s, 1H), 5.20 (d, J = 9.2 Hz, 2H), 4.25-4.17 (m, 1H), 3.62-3.50 (m, 2H), 2.74 (s, 3H), 2.11 (dd, J = 11.6, 6.6 Hz, 1H), 1.92 (d, J = 5.1 Hz, 1H), 1.76 (dd, J = 13.1, 6.2 Hz, 1H), 1.62 (d, J = 1.1 Hz, 6H), 1.31 (d, J = 6.3 Hz, 3H), 0.90 (d, J = 6.3 Hz, 1H) |

TABLE 1-continued

| Cmpd No. | Structure | ESMS (M + H) | ¹H NMR (300 MHz, unless indicated otherwise) |
|---|---|---|---|
| 835 | 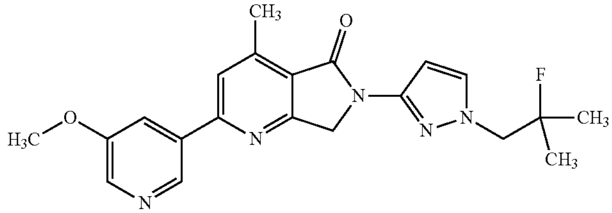 [SMILES: COc1cncc(-c2cc(C)c3c(n2)CN(c2ccn(CC(C)(C)F)n2)C3=O)c1] | 396.62 | (CDCl₃) δ 8.85 (d, J = 1.7 Hz, 1H), 8.42 (d, J = 2.9 Hz, 1H), 7.95 (dd, J = 2.8, 1.8 Hz, 1H), 7.63 (s, 1H), 7.50 (dd, J = 2.3, 1.5 Hz, 1H), 7.05 (d, J = 2.4 Hz, 1H), 4.99 (s, 2H), 4.24 (d, J = 20.7 Hz, 2H), 3.99 (s, 3H), 2.86 (s, 3H), 1.39 (d, J = 21.3 Hz, 6H) |
| 836 | 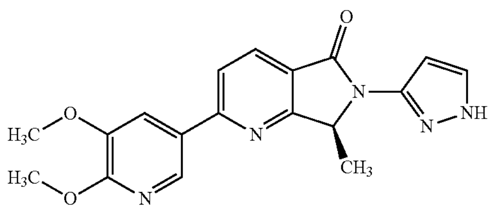 [SMILES: COc1cc(-c2ccc3c(n2)[C@H](C)N(c2cc[nH]n2)C3=O)cnc1OC] | 352 | |
| 837 | 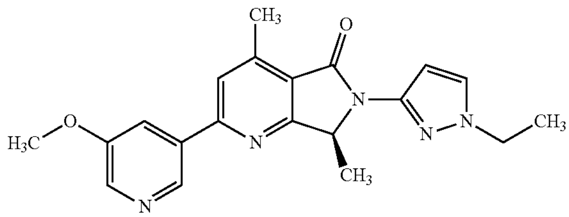 [SMILES: CCn1ccc(N2C(=O)c3c(C)cc(-c4cncc(OC)c4)nc3[C@@H]2C)n1] | 364.29 | (CDCl₃) δ 8.87 (d, J = 1.7 Hz, 1H), 8.42 (d, J = 2.8 Hz, 1H), 7.97 (dd, J = 2.8, 1.8 Hz, 1H), 7.62 (s, 1H), 7.41 (d, J = 2.3 Hz, 1H), 7.28 (s, 2H), 6.94 (d, J = 2.3 Hz, 1H), 5.29 (q, J = 6.6 Hz, 1H), 4.18 (q, J = 7.3 Hz, 2H), 4.00 (s, 3H), 2.85 (s, 3H), 1.79 (d, J = 6.7 Hz, 3H), 1.53 (t, J = 7.3 Hz, 3H) |
| 838 | 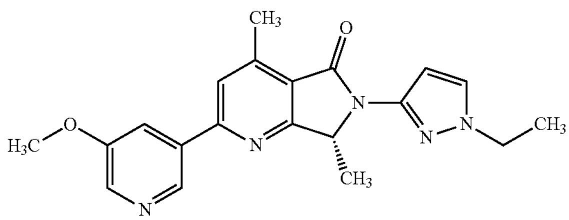 [SMILES: CCn1ccc(N2C(=O)c3c(C)cc(-c4cncc(OC)c4)nc3[C@H]2C)n1] | 364.33 | (CDCl₃) δ 8.87 (d, J = 1.7 Hz, 1H), 8.42 (d, J = 2.8 Hz, 1H), 8.03-7.92 (m, 1H), 7.62 (s, 1H), 7.41 (d, J = 2.3 Hz, 1H), 6.94 (d, J = 2.3 Hz, 1H), 5.29 (q, J = 6.6 Hz, 1H), 4.18 (q, J = 7.3 Hz, 2H), 4.00 (s, 3H), 3.51 (d, J = 5.5 Hz, 1H), 2.85 (s, 3H), 1.79 (d, J = 6.7 Hz, 3H), 1.53 (t, J = 7.3 Hz, 3H) |
| 839 | 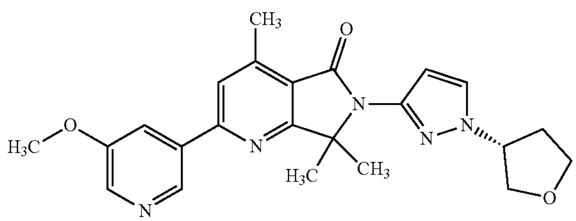 [SMILES: COc1cncc(-c2cc(C)c3c(n2)C(C)(C)N(c2ccn([C@@H]4CCOC4)n2)C3=O)c1] | 420.56 | (CDCl₃) δ 9.22 (d, J = 1.4 Hz, 1H), 8.62 (d, J = 2.6 Hz, 1H), 8.56 (d, J = 1.5 Hz, 1H), 7.72 (d, J = 0.6 Hz, 2H), 7.51 (d, J = 2.4 Hz, 1H), 6.93 (d, J = 2.4 Hz, 1H), 5.05-4.88 (m, 1H), 4.28-4.09 (m, 6H), 4.04 (td, J = 8.2, 5.3 Hz, 1H), 2.89 (s, 3H), 2.59-2.32 (m, 2H), 1.86 (s, 6H) |
| 840 | 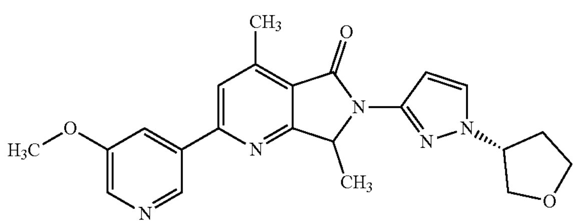 [SMILES: COc1cncc(-c2cc(C)c3c(n2)C(C)N(c2ccn([C@@H]4CCOC4)n2)C3=O)c1] | 406.61 | (CDCl₃) δ 9.20 (s, 1H), 8.59 (d, J = 2.7 Hz, 2H), 7.74 (s, 1H), 7.50 (d, J = 2.3 Hz, 1H), 7.00-6.91 (m, 1H), 5.30 (dd, J = 6.6, 2.5 Hz, 1H), 4.97 (dd, J = 7.9, 4.0 Hz, 1H), 4.25-4.09 (m, 6H), 4.07-3.92 (m, 1H), 2.88 (s, 3H), 2.58-2.29 (m, 2H), 1.84-1.69 (m, 3H) |

TABLE 1-continued

| Cmpd No. | Structure | ESMS (M + H) | ¹H NMR (300 MHz, unless indicated otherwise) |
|---|---|---|---|
| 841 | 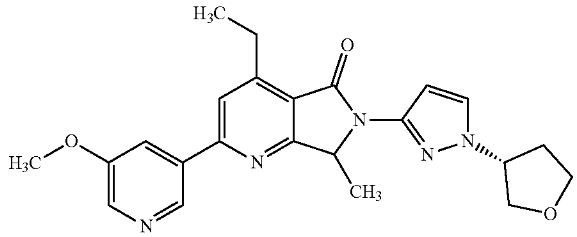 [SMILES: CCc1cc(-c2cncc(OC)c2)nc2c1C(=O)N(c1ccn([C@@H]3CCOC3)n1)C2C] | 420.56 | (CDCl$_3$) δ 9.19 (s, 1H), 8.60 (d, J = 2.8 Hz, 2H), 7.76 (s, 1H), 7.56-7.44 (m, 1H), 7.02-6.91 (m, 1H), 5.30 (dd, J = 6.3, 2.2 Hz, 1H), 4.97 (dd, J = 7.9, 3.9 Hz, 1H), 4.25-4.09 (m, 6H), 4.08-3.89 (m, 1H), 3.42-3.21 (m, 2H), 2.57-2.29 (m, 2H), 1.87-1.72 (m, 3H), 1.41 (t, J = 7.6 Hz, 3H) |
| 842 | 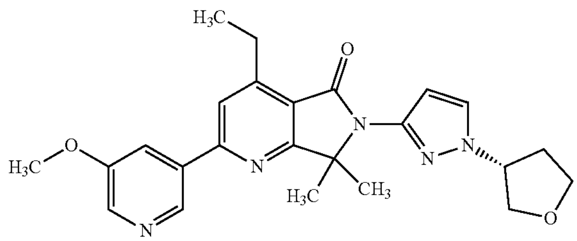 [SMILES: CCc1cc(-c2cncc(OC)c2)nc2c1C(=O)N(c1ccn([C@@H]3CCOC3)n1)C2(C)C] | 434.63 | (CDCl$_3$) δ 9.22 (s, 1H), 8.63 (d, J = 2.6 Hz, 1H), 8.57 (s, 1H), 7.74 (s, 1H), 7.51 (d, J = 2.4 Hz, 1H), 6.94 (d, J = 2.4 Hz, 1H), 5.05-4.89 (m, 1H), 4.24-4.10 (m, 6H), 4.04 (td, J = 8.3, 5.3 Hz, 1H), 3.33 (q, J = 7.5 Hz, 2H), 2.59-2.34 (m, 2H), 1.87 (s, 6H), 1.42 (t, J = 7.6 Hz, 3H) |
| 843 | 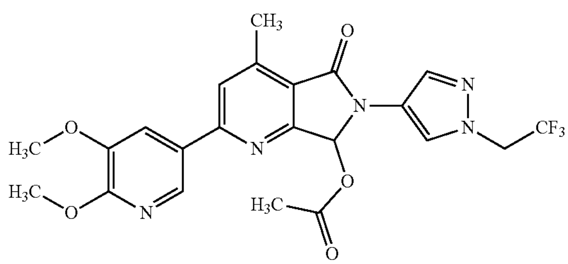 [SMILES: COc1cc(-c2cc(C)c3c(n2)C(OC(C)=O)N(c2cnn(CC(F)(F)F)c2)C3=O)cnc1OC] | 493.09 | (DMSO-d$_6$, 400 MHz) δ 8.54 (s, 1H), 8.20 (s, 1H), 8.11 (s, 1H), 7.93 (s, 1H), 7.75 (s, 1H), 7.43 (s, 1H), 5.22 (q, J = 9.3 Hz, 2H), 3.95 (s, 3H), 3.91 (s, 3H), 2.72 (s, 3H), 2.16 (s, 3H) |
| 844 | 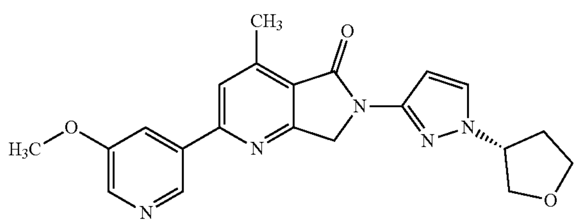 [SMILES: COc1cncc(-c2cc(C)c3c(n2)CN(c2ccn([C@@H]4CCOC4)n2)C3=O)c1] | 392.53 | (CDCl$_3$) δ 9.15 (s, 1H), 7.74 (s, 1H), 7.51 (d, J = 2.4 Hz, 1H), 7.00 (d, J = 2.4 Hz, 1H), 5.05-4.90 (m, 3H), 4.26-4.08 (m, 5H), 4.00 (td, J = 8.4, 5.4 Hz, 1H), 2.88 (s? 3H), 2.44 (dtd, J = 20.6, 7.7, 5.0 Hz, 2H) |
| 845 | 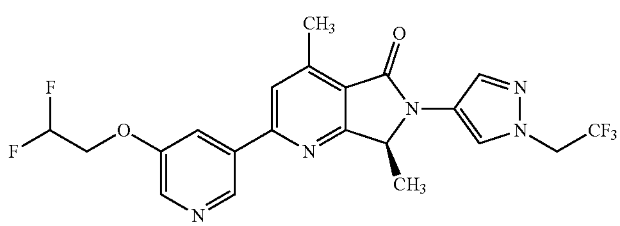 [SMILES: Cc1cc(-c2cncc(OCC(F)F)c2)nc2c1C(=O)N(c1cnn(CC(F)(F)F)c1)[C@H]2C] | 468.59 | (CDCl$_3$) δ 8.95 (d, J = 1.6 Hz, 1H), 8.46 (d, J = 2.8 Hz, 1H), 8.31 (s, 1H), 8.07-7.98 (m, 1H), 7.76 (s, 1H), 7.66 (s, 1H), 6.39-5.95 (m, 1H), 4.98 (d, J = 6.7 Hz, 1H), 4.76 (q, J = 8.3 Hz, 2H), 4.39 (td, J = 12.9, 4.0 Hz, 2H), 2.86 (s, 3H), 1.74 (d, J = 6.7 Hz, 3H) |
| 846 | 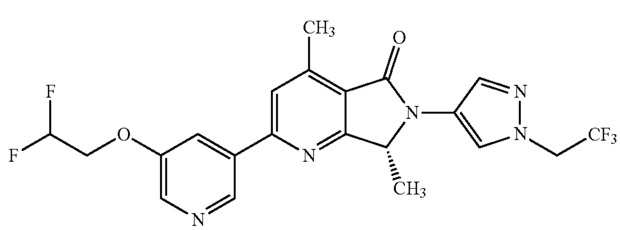 | 468.62 | (CDCl$_3$) δ 8.95 (d, J = 1.6 Hz, 1H), 8.46 (d, J = 2.8 Hz, 1H), 8.31 (s, 1H), 8.07-7.98 (m, 1H), 7.76 (s, 1H), 7.66 (s, 1H), 6.39-5.95 (m, 1H), 4.98 (d, J = 6.7 Hz, 1H), 4.76 (q, J = 8.3 Hz, 2H), 4.39 (td, J = 12.9, 4.0 Hz, 2H), 2.86 (s, 3H), 1.74 (d, J = 6.7 Hz, 3H) |

TABLE 1-continued

| Cmpd No. | Structure | ESMS (M + H) | ¹H NMR (300 MHz, unless indicated otherwise) |
|---|---|---|---|
| 847 | 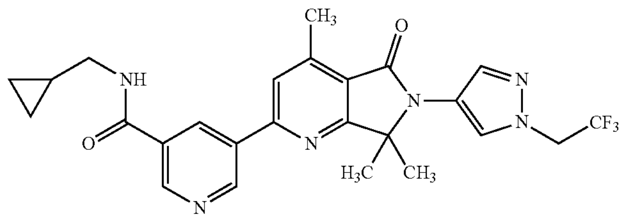 [SMILES: Cc1cc(-c2cncc(C(=O)NCC3CC3)c2)nc2c1C(=O)N(c1cnn(CC(F)(F)F)c1)C2(C)C] | 499.64 | (DMSO-d₆) δ 9.49 (d, J = 2.0 Hz, 1H), 9.11 (d, J = 2.0 Hz, 1H), 8.88 (t, J = 2.1 Hz, 1H), 8.35 (s, 1H), 8.13 (s, 1H), 7.96 (s, 1H), 5.20 (dd, J = 18.4, 9.2 Hz, 2H), 3.29-3.18 (m, 2H), 2.76 (s, 3H), 2.27 (s, 1H), 1.63 (s, 6H), 1.08 (s, 1H), 0.52-0.43 (m, 2H), 0.33-0.23 (m, 2H) |
| 848 | 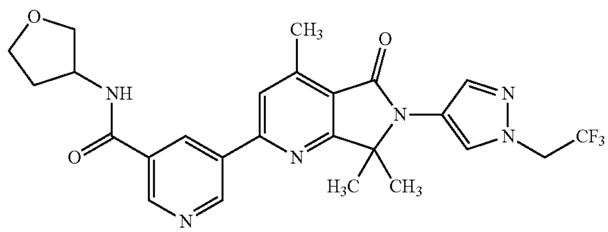 [SMILES: Cc1cc(-c2cncc(C(=O)NC3CCOC3)c2)nc2c1C(=O)N(c1cnn(CC(F)(F)F)c1)C2(C)C] | 515.63 | (DMSO-d₆) δ 9.49 (d, J = 2.1 Hz, 1H), 9.10 (d, J = 2.0 Hz, 1H), 8.93 (d, J = 6.3 Hz, 1H), 8.86 (t, J = 2.1 Hz, 1H), 8.35 (s, 1H), 8.12 (s, 1H), 7.96 (s, 1H), 5.20 (dd, J = 18.3, 9.1 Hz, 2H), 4.51 (s, 1H), 3.94-3.85 (m, 2H), 3.38 (dd, J = 14.0, 7.0 Hz, 1H), 2.76 (s, 3H), 2.61 (d, J = 17.1 Hz, 1H), 2.29-2.14 (m, 2H), 2.03-1.90 (m, 1H), 1.63 (s, 6H), 1.09 (t, J = 7.0 Hz, 1H) |
| 849 | 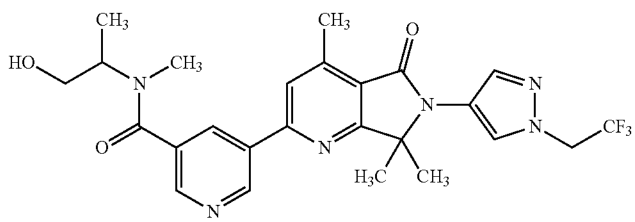 [SMILES: Cc1cc(-c2cncc(C(=O)N(C)C(C)CO)c2)nc2c1C(=O)N(c1cnn(CC(F)(F)F)c1)C2(C)C] | 517.62 | (DMSO-d₆) δ 9.42 (s, 1H), 8.70 (s, 1H), 8.57 (s, 1H), 8.35 (s, 1H), 8.12 (s, 1H), 7.95 (s, 1H), 5.20 (dd, J = 18.1, 9.0 Hz, 2H), 3.72 (s, 1H), 2.89 (s, 3H), 2.82 (s, 1H), 2.74 (s, 3H), 2.27 (s, 1H), 1.61 (s, 6H), 1.13-1.01 (m, 3H) |
| 850 | 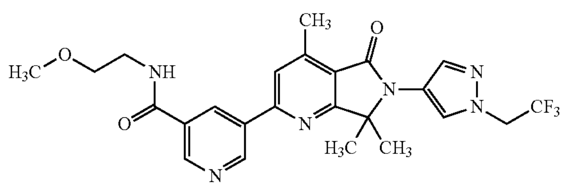 [SMILES: COCCNC(=O)c1cncc(-c2cc(C)c3c(n2)C(C)(C)N(c2cnn(CC(F)(F)F)c2)C3=O)c1] | 503.67 | (DMSO-d₆) δ 9.49 (s, 1H), 9.10 (s, 1H), 8.92 (d, J = 15.0 Hz, 1H), 8.35 (s, 1H), 8.12 (s, 1H), 7.96 (s, 1H), 5.20 (dd, J = 18.4, 9.3 Hz, 2H), 3.51 (s, 3H), 3.29 (s, 3H), 2.76 (s, 2H), 2.27 (s, 2H), 1.63 (s, 6H) |
| 851 | 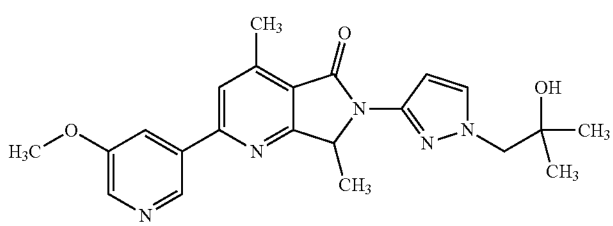 [SMILES: COc1cncc(-c2cc(C)c3c(n2)C(C)N(c2ccn(CC(C)(C)O)n2)C3=O)c1] | 408.52 | (CDCl₃) δ 8.86 (d, J = 1.8 Hz, 1H), 8.41 (d, J = 2.9 Hz, 1H), 7.97 (dd, J = 2.8, Hz, 1H), 7.63 (s, 1H), 7.43 (d, J = 2.4 Hz, 1H), 7.03 (d, J = 2.4 Hz, 1H), 5.27 (q, J = 6.6 Hz, 1H), 4.08 (d, J = 5.4 Hz, 3H), 3.99 (s, 3H), 2.85 (s, 3H), 1.78 (d, J = 6.7 Hz, 3H), 1.22 (d, J = 8.4 Hz, 6H) |
| 852 | 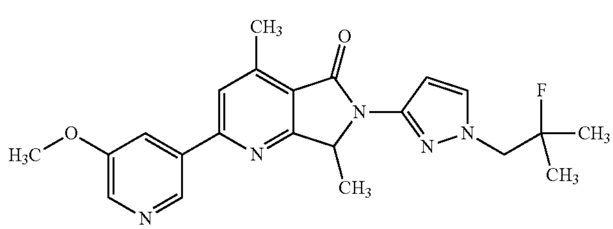 [SMILES: COc1cncc(-c2cc(C)c3c(n2)C(C)N(c2ccn(CC(C)(C)F)n2)C3=O)c1] | 410.6 | (CDCl₃) δ 8.88 (d, J = 1.7 Hz, 1H), 8.42 (d, J = 2.8 Hz, 1H), 8.02-7.91 (m, 1H), 7.62 (s, 1H), 7.54-7.47 (m, 1H), 7.02 (d, J = 2.4 Hz, 1H), 5.27 (q, J = 6.7 Hz, 1H), 4.26 (d, J = 20.7 Hz, 2H), 4.00 (s, 3H), 2.85 (s, 3H), 1.78 (d, J = 6.7 Hz, 3H), 1.49-1.31 (m, 6H) |

TABLE 1-continued

| Cmpd No. | Structure | ESMS (M + H) | ¹H NMR (300 MHz, unless indicated otherwise) |
|---|---|---|---|
| 853 | 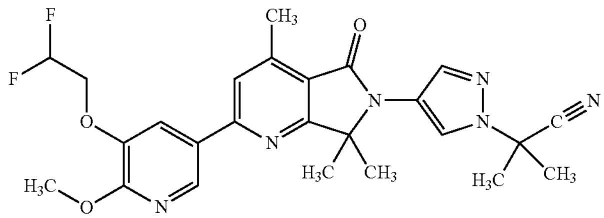 [SMILES: COc1ncc(-c2cc(C)c3c(n2)C(C)(C)N(c2cnn(C(C)(C)C#N)c2)C3=O)cc1OCC(F)F] | 497 | |
| 854 | 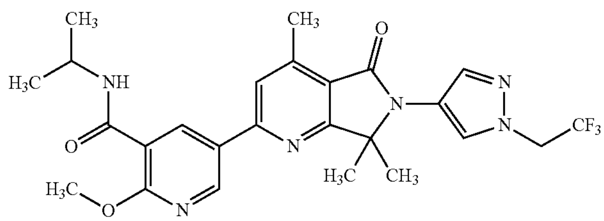 [SMILES: COc1ncc(-c2cc(C)c3c(n2)C(C)(C)N(c2cnn(CC(F)(F)F)c2)C3=O)cc1C(=O)NC(C)C] | 517.32 | (DMSO-d$_6$) δ 9.09 (d, J = 2.5 Hz, 1H), 8.76 (d, J = 2.5 Hz, 1H), 8.34 (s, 1H), 8.12 (d, J = 7.6 Hz, 1H), 8.02 (s, 1H), 7.95 (s, 1H), 5.20 (q, J = 9.1 Hz, 2H), 4.16-4.06 (m, 1H), 4.06 (d, J = 4.2 Hz, 3H), 2.72 (s, 3H), 1.60 (s, 6H), 1.20 (d, J = 6.6 Hz, 6H) |
| 855 | 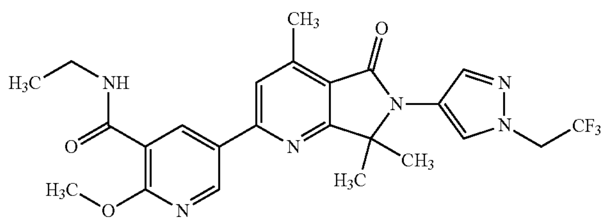 [SMILES: CCNC(=O)c1cc(-c2cc(C)c3c(n2)C(C)(C)N(c2cnn(CC(F)(F)F)c2)C3=O)cnc1OC] | 503.28 | (DMSO-d$_6$) δ 9.10 (d, J = 2.5 Hz, 1H), 8.83 (d, J = 2.5 Hz, 1H), 8.39 (t, J = 5.6 Hz, 1H), 8.34 (s, 1H), 8.02 (s, 1H), 7.95 (s, 1H), 5.20 (q, J = 9.1 Hz, 2H), 4.04 (d, J = 12.2 Hz, 3H), 3.39-3.29 (m, 2H), 2.71 (d, J = 10.1 Hz, 3H), 1.60 (s, 6H), 1.20- 1.07 (m, 3H) |
| 856 | 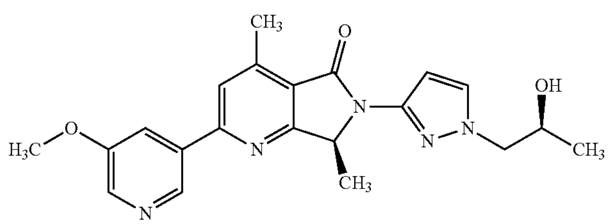 [SMILES: COc1cncc(-c2cc(C)c3c(n2)[C@H](C)N(c2ccn(C[C@H](C)O)n2)C3=O)c1] | 394.6 | (DMSO-d$_6$) δ 8.98 (d, J = 1.7 Hz, 1H), 8.42 (d, J = 2.8 Hz, 1H), 8.13-8.01 (m, 2H), 7.71 (t, J = 2.2 Hz, 1H), 6.82-6.73 (m, 1H), 5.19 (q, J = 6.5 Hz, 1H), 4.95-4.90 (m, 1H), 4.01 (s, 3H), 3.94 (d, J = 8.3 Hz, 3H), 2.75 (s, 3H), 1.69 (dd, J = 6.6, 3.4 Hz, 3H), 1.07 (t, J = 6.3 Hz, 3H) |
| 857 | 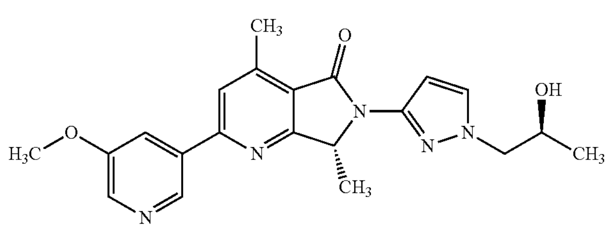 [SMILES: COc1cncc(-c2cc(C)c3c(n2)[C@@H](C)N(c2ccn(C[C@H](C)O)n2)C3=O)c1] | 394.31 | (DMSO-d$_6$) δ 8.98 (d, J = 1.7 Hz, 1H), 8.40 (t, J = 10.0 Hz, 1H), 8.13-8.00 (m, 2H), 7.76-7.66 (m, 1H), 6.77 (t, J = 1.9 Hz, 1H), 5.19 (q, J = 6.6 Hz, 1H), 4.99-4.91 (m, 1H), 4.00 (s, 3H), 3.94 (d, J = 8.1 Hz, 3H), 2.74 (s, 3H), 1.69 (dd, J = 6.7, 3.3 Hz, 3H), 1.07 (t, J = 6.3 Hz, 3H) |
| 858 | 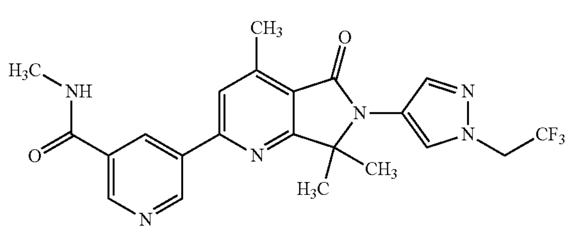 [SMILES: CNC(=O)c1cncc(-c2cc(C)c3c(n2)C(C)(C)N(c2cnn(CC(F)(F)F)c2)C3=O)c1] | 459.53 | (DMSO-d$_6$) δ 9.49 (d, J = 2.1 Hz, 1H), 9.08 (d, J = 2.0 Hz, 1H), 8.88 (t, J = 2.1 Hz, 1H), 8.82 (d, J = 4.5 Hz, 1H), 8.35 (s, 1H), 8.12 (s, 1H), 7.96 (s, 1H), 5.20 (d, J = 9.1 Hz, 2H), 2.86 (d, J = 4.5 Hz, 3H), 2.75 (s, 3H), 1.63 (s, 6H) |

TABLE 1-continued

| Cmpd No. | Structure | ESMS (M + H) | ¹H NMR (300 MHz, unless indicated otherwise) |
|---|---|---|---|
| 859 | 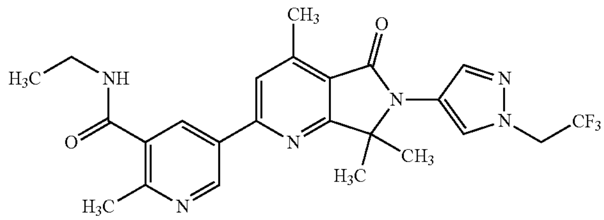 [SMILES: CCNC(=O)c1cc(-c2cc(C)c3c(n2)C(C)(C)N(c2cnn(CC(F)(F)F)c2)C3=O)cnc1C] | 487.56 | (DMSO-d₆) δ 9.28 (d, J = 2.2 Hz, 1H), 8.57 (d, J = 5.5 Hz, 1H), 8.41 (d, J = 2.2 Hz, 1H), 8.34 (s, 1H), 8.09 (s, 1H), 7.95 (s, 1H), 5.20 (q, J = 9.1 Hz, 2H), 3.30 (dd, J = 10.0, 4.4 Hz, 2H), 2.73 (s, 3H), 2.59 (s, 3H), 1.61 (s, 6H), 1.16 (t, J = 7.2 Hz, 3H) |
| 860 | 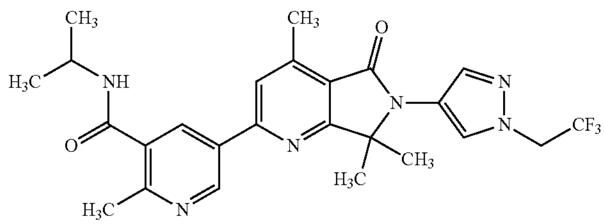 [SMILES: Cc1cc(-c2cnc(C)c(C(=O)NC(C)C)c2)nc2c1C(=O)N(c1cnn(CC(F)(F)F)c1)C2(C)C] | 501.58 | (DMSO-d₆) δ 9.28 (d, J = 2.3 Hz, 1H), 8.45 (d, J = 7.6 Hz, 1H), 8.39-8.32 (m, 2H), 8.08 (s, 1H), 7.95 (s, 1H), 5.20 (q, J = 9.1 Hz, 2H), 4.15-3.97 (m, 1H), 2.74 (s, 3H), 2.56 (d, J = 11.2 Hz, 3H), 1.61 (s, 6H), 1.18 (dd, J = 8.7, 6.9 Hz, 6H) |
| 861 | 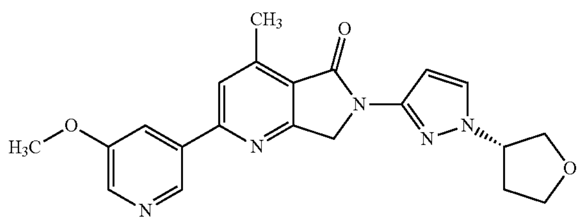 [SMILES: COc1cncc(-c2cc(C)c3c(n2)CN(c2ccn([C@H]4CCOC4)n2)C3=O)c1] | 392.53 | (CDCl₃) δ 9.14 (s, 1H), 8.56 (s, 2H), 7.74 (s, 1H), 7.50 (d, J = 2.3 Hz, 1H), 6.97 (d, J = 2.3 Hz, 1H), 5.13-4.85 (m, 3H), 4.28-4.07 (m, 6H), 3.99 (td, J = 8.4, 5.4 Hz, 1H), 2.87 (s, 3H), 2.59-2.27 (m, 2H) |
| 862 | 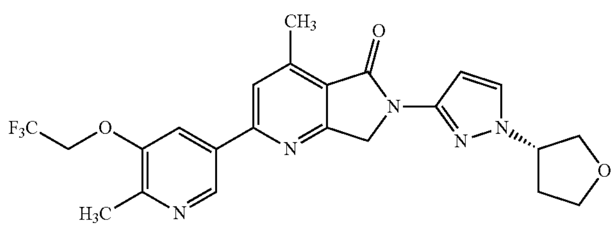 [SMILES: Cc1cc(-c2cnc(C)c(OCC(F)(F)F)c2)nc2c1C(=O)N(c1ccn([C@H]3CCOC3)n1)C2] | 474.56 | (CDCl₃) δ 9.09 (d, J = 0.9 Hz, 1H), 8.48 (s, 1H), 7.75 (s, 1H), 7.49 (d, J = 2.4 Hz, 1H), 6.97 (d, J = 2.4 Hz, 1H), 5.05-4.85 (m, 3H), 4.70 (q, J = 7.7 Hz, 2H), 4.25-4.07 (m, 3H), 3.99 (td, J = 8.4, 5.4 Hz, 1H), 2.86 (s, 3H), 2.79 (s, 3H), 2.42 (dddd, J = 13.3, 7.9, 5.9, 3.9 Hz, 2H) |
| 863 | 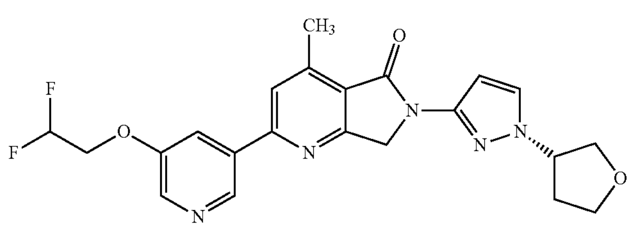 | 442.57 | (CDCl₃) δ 9.14 (s, 1H), 8.60 (s, 1H), 8.52 (s, 1H), 7.73 (s, 1H), 7.50 (d, J = 2.4 Hz, 1H), 6.98 (d, J = 2.4 Hz, 1H), 6.22 (tt, J = 54.4, 3.8 Hz, 1H), 5.10-4.86 (m, 3H), 4.49 (td, J = 12.8, 3.8 Hz, 2H), 4.29-3.90 (m, 4H), 2.87 (s, 3H), 2.60-2.24 (m, 2H) |
| 864 | 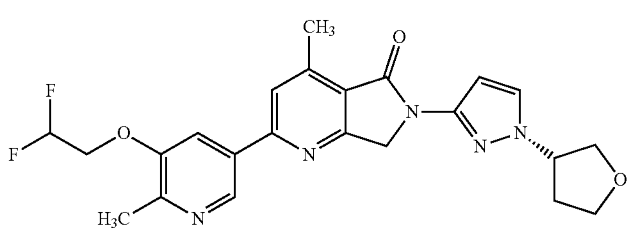 | 456.58 | (CDCl₃) δ 9.09 (s, 1H), 8.54 (s, 1H), 7.77 (s, 1H), 7.49 (d, J = 2.4 Hz, 1H), 6.97 (d, J = 2.4 Hz, 1H), 6.26 (tt, J = 54.4, 3.8 Hz, 1H), 5.09-4.87 (m, 3H), 4.54 (td, J = 12.7, 3.8 Hz, 2H), 4.24-4.07 (m, 3H), 4.00 (td, J = 8.4, 5.4 Hz, 1H), 2.86 (s, 3H), 2.80 (s, 3H), 2.56-2.29 (m, 2H) |

TABLE 1-continued

| Cmpd No. | Structure | ESMS (M + H) | ¹H NMR (300 MHz, unless indicated otherwise) |
|---|---|---|---|
| 865 | 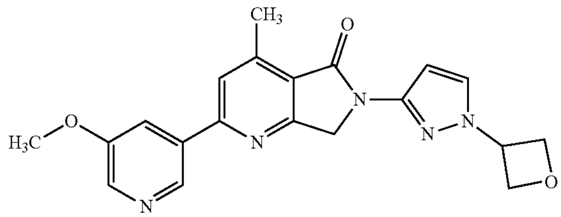 [SMILES: COc1cncc(-c2cc(C)c3c(n2)CN(c2ccn(C4COC4)n2)C3=O)c1] | 378.52 | (CDCl₃) δ 9.13 (s, 1H), 8.56 (s, 2H), 7.75 (s, 1H), 7.57 (d, J = 2.4 Hz, 1H), 7.06 (t, J = 3.9 Hz, 1H), 5.43 (dd, J = 14.3, 7.1 Hz, 1H), 5.24-5.02 (m, 6H), 4.12 (s, 3H), 2.87 (s, 3H) |
| 866 | 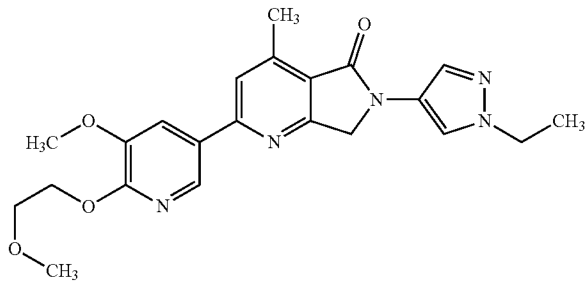 [SMILES: CCn1cc(N2Cc3nc(-c4cnc(OCCOC)c(OC)c4)cc(C)c3C2=O)cn1] | 424.5 | (DMSO-d₆) δ 8.51 (d, J = 1.9 Hz, 1H), 8.19 (s, 1H), 7.99 (s, 1H), 7.97 (d, J = 1.9 Hz, 1H), 7.81 (s, 1H), 4.87 (s, 2H), 4.58-4.38 (m, 2H), 4.16 (q, J = 7.3 Hz, 2H), 3.92 (s, 3H), 3.80-3.61 (m, 2H), 3.31 (s, 3H), 2.71 (s, 3H), 1.39 (t, J = 7.3 Hz, 3H) |
| 867 | 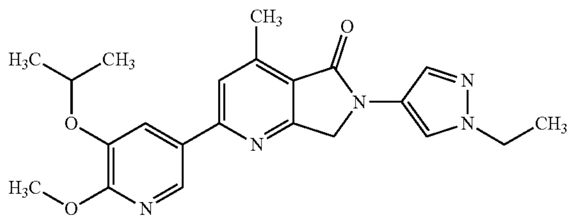 [SMILES: CCn1cc(N2Cc3nc(-c4cnc(OC)c(OC(C)C)c4)cc(C)c3C2=O)cn1] | 408.03 | (DMSO-d₆) δ 8.51 (d, J = 1.8 Hz, 1H), 8.18 (s, 1H), 7.95 (s, 2H), 7.80 (s, 1H), 4.85 (s, 2H), 4.77 (dt, J = 12.0, 6.0 Hz, 1H), 4.16 (q, J = 7.2 Hz, 2H), 3.93 (s, 3H), 2.70 (s, 3H), 1.39 (t, J = 7.2 Hz, 3H), 1.33 (d, J = 6.0 Hz, 6H) |
| 868 | 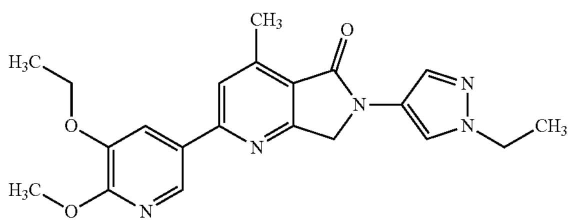 [SMILES: CCOc1cc(-c2cc(C)c3c(n2)CN(c2cnn(CC)c2)C3=O)cnc1OC] | 394.6 | (DMSO-d₆) δ 8.52 (d, J = 1.9 Hz, 1H), 8.18 (s, 1H), 7.97 (s, 1H), 7.94 (d, J = 1.9 Hz, 1H), 7.80 (s, 1H), 4.86 (s, 2H), 4.28-4.04 (m, 4H), 3.95 (s, 3H), 2.70 (s, 3H), 1.50-1.19 (m, J = 7.0, 1.7 Hz, 6H) |
| 869 | 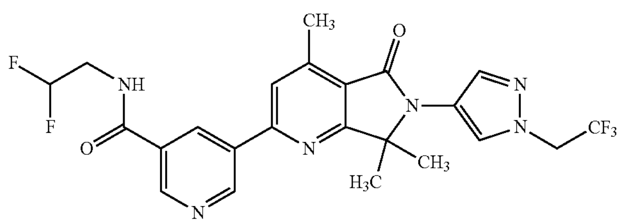 [SMILES: Cc1cc(-c2cncc(C(=O)NCC(F)F)c2)nc2c1C(=O)N(c1cnn(CC(F)(F)F)c1)C2(C)C] | 509.46 | (DMSO-d₆) δ 9.53 (d, J = 2.1 Hz, 1H), 9.25 (t, J = 5.9 Hz, 1H), 9.13 (d, J = 1.9 Hz, 1H), 8.92 (t, J = 2.1 Hz, 1H), 8.35 (s, 1H), 8.13 (s, 1H), 7.96 (s, 1H), 6.19 (t, J = 3.8 Hz, 1H), 5.20 (dd, J = 18.2, 9.1 Hz, 2H), 3.83-3.71 (m, 2H), 2.76 (s, 3H), 1.63 (s, 6H) |
| 870 | 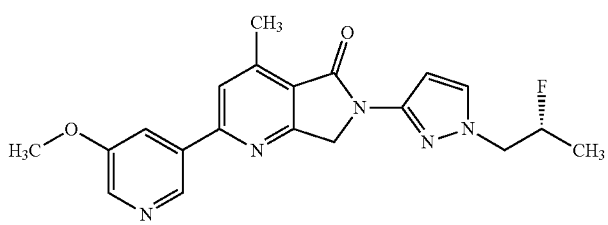 [SMILES: COc1cncc(-c2cc(C)c3c(n2)CN(c2ccn(C[C@@H](C)F)n2)C3=O)c1] | 382.57 | (DMSO-d₆) δ 8.97 (d, J = 1.7 Hz, 1H), 8.41 (d, J = 2.8 Hz, 1H), 8.10 (s, 1H), 8.06 (dd, J = 2.7, 1.9 Hz, 1H), 7.77 (d, J = 2.3 Hz, 1H), 6.83 (d, J = 2.3 Hz, 1H), 5.23-5.03 (m, 1H), 4.96 (d, J = 8.4 Hz, 2H), 4.32 (ddd, J = 11.9, 6.2, 2.8 Hz, 2H), 3.95 (s, 3H), 2.74 (s, 3H), 1.34 (dd, J = 23.9, 6.3 Hz, 3H) |

TABLE 1-continued

| Cmpd No. | Structure | ESMS (M + H) | ¹H NMR (300 MHz, unless indicated otherwise) |
|---|---|---|---|
| 871 | 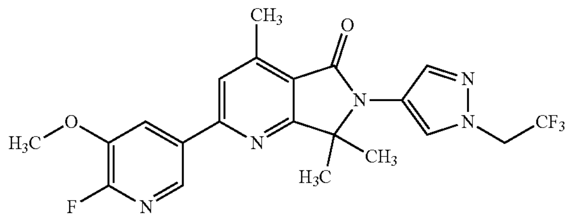 [SMILES: COc1cc(-c2cc(C)c3c(n2)C(C)(C)N(c2cnn(CC(F)(F)F)c2)C3=O)cnc1F] | 450.41 | (DMSO-d$_6$) δ = 8.56 (t, J = 1.8, 1H), 8.33 (d, J = 6.4, 1H), 8.32-8.22 (m, 1H), 8.09 (s, 1H), 7.95 (s, 1H), 5.20 (q, J = 9.1, 2H), 4.03 (s, 3H), 2.74 (s, 3H), 1.62 (s, 6H) |
| 872 | 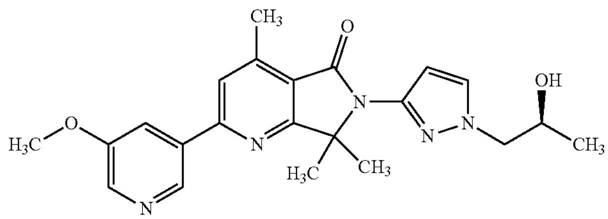 [SMILES: COc1cncc(-c2cc(C)c3c(n2)C(C)(C)N(c2ccn(C[C@H](C)O)n2)C3=O)c1] | 408.65 | (DMSO-d$_6$) δ 8.99 (d, J = 1.6 Hz, 1H), 8.42 (d, J = 2.8 Hz, 1H), 8.07 (d, J = 4.4 Hz, 2H), 7.69 (t, J = 9.3 Hz, 1H), 6.75 (d, J = 2.3 Hz, 1H), 4.95 (d, J = 4.7 Hz, 1H), 4.04 (d, J = 11.5 Hz, 2H), 4.00-3.90 (m, 3H), 2.75 (s, 3H), 1.77 (d, J = 3.7 Hz, 6H), 1.12-1.01 (m, 3H) |
| 873 | 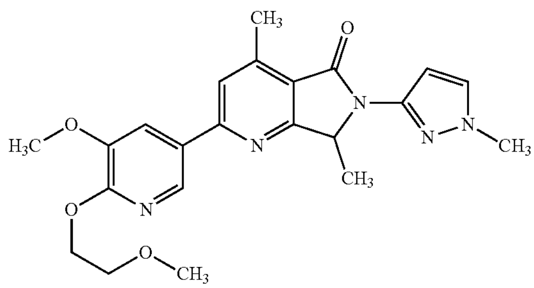 | 424.55 | (CDCl$_3$) δ 8.39 (d, J = 2.0 Hz, 1H), 7.87 (d, J = 2.0 Hz, 1H), 7.54 (s, 1H), 7.36 (d, J = 2.3 Hz, 1H), 6.94 (d, J = 2.3 Hz, 1H), 5.24 (q, J = 6.8 Hz, 1H), 4.71-4.58 (m, 2H), 4.01 (s, 3H), 3.92 (s, 3H), 3.89-3.80 (m, 2H), 3.48 (s, 3H), 2.83 (s, 3H), 1.78 (d, J = 6.7 Hz, 3H) |
| 874 | 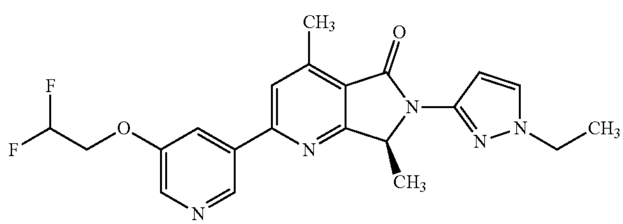 [SMILES: CCn1ccc(N2C(=O)c3c(C)cc(-c4cncc(OCC(F)F)c4)nc3[C@@H]2C)n1] | 414.6 | (CDCl$_3$) δ 8.94 (d, J = 1.6 Hz, 1H), 8.45 (d, J = 2.8 Hz, 1H), 8.12-7.95 (m, 1H), 7.63 (s, 1H), 7.41 (d, J = 2.3 Hz, 1H), 6.94 (d, J = 2.3 Hz, 1H), 6.19 (tt, J = 54.8, 4.0 Hz, 1H), 5.29 (q, J = 6.6 Hz, 1H), 4.39 (td, J = 12.9, 4.0 Hz, 2H), 4.18 (q, J = 7.3 Hz, 2H), 2.86 (s, 3H), 1.79 (d, J = 6.7 Hz, 3H), 1.53 (t, J = 7.3 Hz, 3H) |
| 875 | 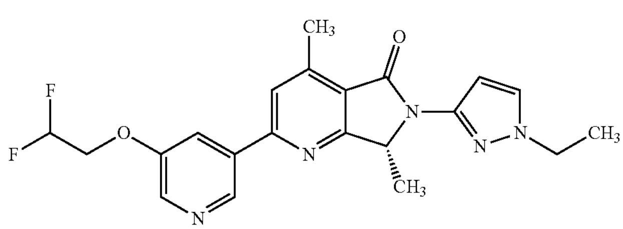 [SMILES: CCn1ccc(N2C(=O)c3c(C)cc(-c4cncc(OCC(F)F)c4)nc3[C@H]2C)n1] | 414.6 | (CDCl$_3$) δ 8.94 (s, 1H), 8.45 (d, J = 2.7 Hz, 1H), 8.03 (s, 1H), 7.63 (s, 1H), 7.41 (d, J = 2.0 Hz, 1H), 6.94 (d, J = 2.1 Hz, 1H), 6.41-5.96 (m, 1H), 5.29 (q, J = 6.7 Hz, 1H), 4.39 (td, J = 12.9, 4.0 Hz, 2H), 4.18 (q, J = 7.2 Hz, 2H), 2.86 (s, 3H), 1.79 (d, J = 6.7 Hz, 3H), 1.53 (t, J = 7.3 Hz, 3H) |
| 876 | 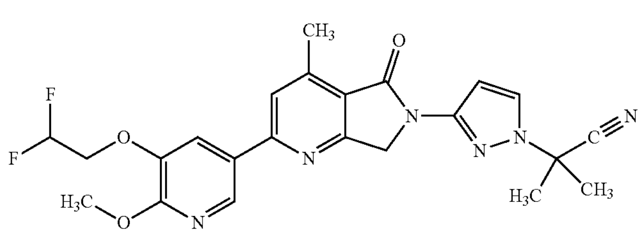 [SMILES: COc1ncc(-c2cc(C)c3c(n2)CN(c2ccn(C(C)(C)C#N)n2)C3=O)cc1OCC(F)F] | 469 | |

TABLE 1-continued

| Cmpd No. | Structure | ESMS (M + H) | $^1$H NMR (300 MHz, unless indicated otherwise) |
|---|---|---|---|
| 877 | 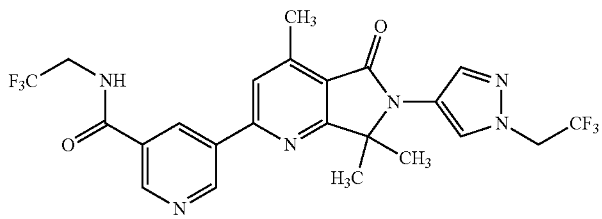 [SMILES: Cc1cc(-c2cncc(C(=O)NCC(F)(F)F)c2)nc2c1C(=O)N(c1cnn(CC(F)(F)F)c1)C2(C)C] | 527.53 | (DMSO-d$_6$) δ 9.55 (s, 1H), 9.15 (s, 1H), 8.94 (t, J = 2.0 Hz, 1H), 8.35 (s, 1H), 8.14 (s, 1H), 7.96 (s, 1H), 5.20 (d, J = 9.1 Hz, 2H), 4.23-4.18 (m, 2H), 2.76 (s, 3H), 1.63 (s, 6H) |
| 878 | 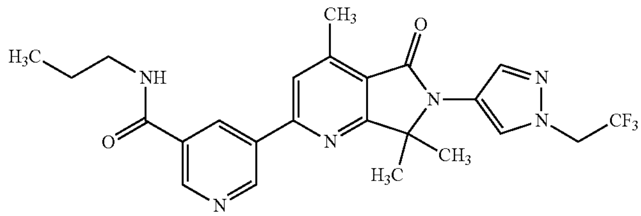 [SMILES: CCCNC(=O)c1cncc(-c2cc(C)c3c(n2)C(C)(C)N(c2cnn(CC(F)(F)F)c2)C3=O)c1] | 487.28 | (DMSO-d$_6$) δ 9.49 (d, J = 2.1 Hz, 1H), 9.09 (d, J = 2.1 Hz, 1H), 8.87 (t, J = 2.2 Hz, 1H), 8.35 (s, 1H), 8.12 (s, 1H), 7.96 (s, 1H), 5.25-5.15 (m, 2H), 3.30 (dd, J = 13.6, 6.6 Hz, 2H), 2.76 (s, 3H), 2.08 (s, 1H), 1.63 (s, 6H), 1.61-1.54 (m, 2H), 0.93 (s, 3H) |
| 879 | 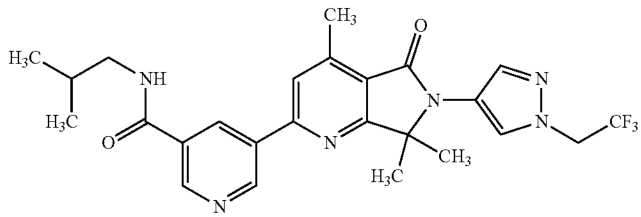 [SMILES: Cc1cc(-c2cncc(C(=O)NCC(C)C)c2)nc2c1C(=O)N(c1cnn(CC(F)(F)F)c1)C2(C)C] | 501.04 | (DMSO-d$_6$) δ 9.49 (d, J = 2.1 Hz, 1H), 9.10 (d, J = 2.0 Hz, 1H), 8.90-8.84 (m, 1H), 8.35 (s, 1H), 8.12 (s, 1H), 7.96 (s, 1H), 5.20 (dd, J = 18.3, 9.2 Hz, 2H), 3.21-3.12 (m, 2H), 2.76 (s, 3H), 1.91 (dd, J = 13.5, 6.7 Hz, 1H), 1.63 (s, 6H), 0.93 (d, J = 6.7 Hz, 6H) |
| 880 | 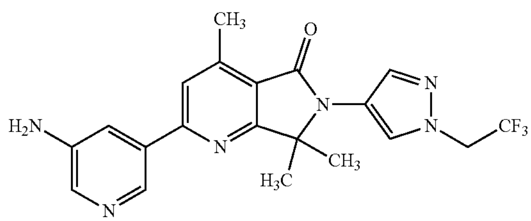 [SMILES: Cc1cc(-c2cncc(N)c2)nc2c1C(=O)N(c1cnn(CC(F)(F)F)c1)C2(C)C] | 417.26 | (DMSO-d$_6$) δ 8.50 (d, J = 1.9 Hz, 1H), 8.33 (s, 1H), 8.04 (d, J = 2.6 Hz, 1H), 7.94 (s, 1H), 7.88 (s, 1H), 7.74-7.66 (m, 1H), 5.55 (s, 2H), 5.20 (q, J = 9.2 Hz, 2H), 2.72 (d, J = 5.6 Hz, 3H), 1.60 (s, 6H) |
| 881 | 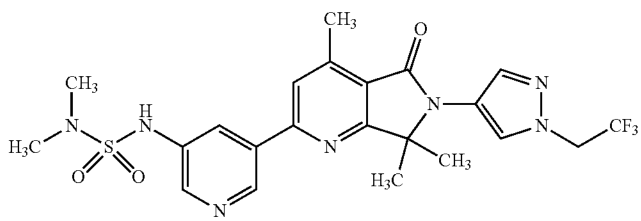 [SMILES: Cc1cc(-c2cncc(NS(=O)(=O)N(C)C)c2)nc2c1C(=O)N(c1cnn(CC(F)(F)F)c1)C2(C)C] | 524.52 | (CDCl$_3$) δ 10.79 (s, 1H), 9.41 (s, 1H), 9.15 (d, J = 5.9 Hz, 2H), 8.16 (s, 1H), 7.82 (s, 1H), 7.75 (s, 1H), 4.78 (d, J = 8.3 Hz, 2H), 3.11 (s, 6H), 2.90 (s, 3H), 1.73 (s, 6H) |
| 882 | 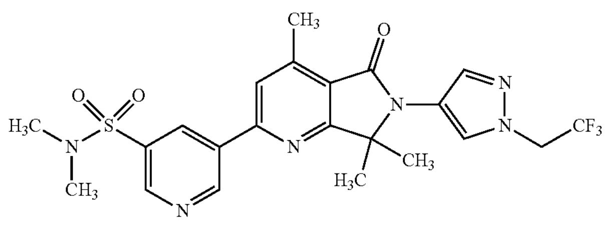 [SMILES: Cc1cc(-c2cncc(S(=O)(=O)N(C)C)c2)nc2c1C(=O)N(c1cnn(CC(F)(F)F)c1)C2(C)C] | 509.48 | (CDCl$_3$) δ 9.58 (s, 1H), 9.09 (d, J = 1.7 Hz, 1H), 8.80 (s, 1H), 8.17 (s, 1H), 7.83 (s, 1H), 7.71 (s, 1H), 4.78 (d, J = 8.4 Hz, 2H), 2.88 (d, J = 2.1 Hz, 9H), 1.74 (s, 6H) |
| 883 | 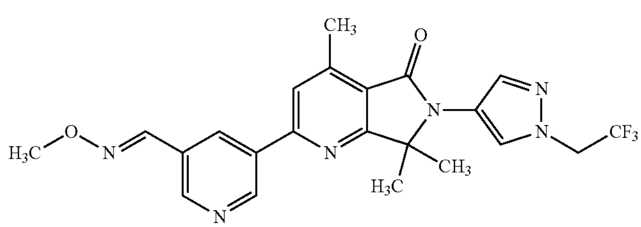 [SMILES: CO/N=C/c1cncc(-c2cc(C)c3c(n2)C(C)(C)N(c2cnn(CC(F)(F)F)c2)C3=O)c1] | 459.59 | (DMSO-d$_6$) δ 9.38 (d, J = 2.2 Hz, 2H), 8.88 (t, J = 5.0 Hz, 2H), 8.72 (t, J = 2.1 Hz, 2H), 8.44 (s, 2H), 8.35 (s, 2H), 8.09 (s, 2H), 7.96 (d, J = 7.7 Hz, 2H), 5.20 (q, J = 9.1 Hz, 4H), 4.04-3.93 (m, 6H), 2.74 (d, J = 4.6 Hz, 6H), 1.62(s, 11H) |

TABLE 1-continued

| Cmpd No. | Structure | ESMS (M + H) | ¹H NMR (300 MHz, unless indicated otherwise) |
| --- | --- | --- | --- |
| 884 | 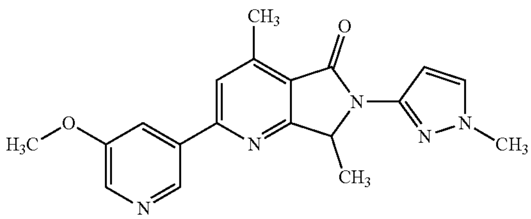 | 350.4 | (CDCl₃) δ 8.87 (d, J = 1.7 Hz, 1H), 8.42 (d, J = 2.9 Hz, 1H), 7.97 (dd, J = 2.8, 1.8 Hz, 1H), 7.62 (s, 1H), 6.95 (d, J = 2.3 Hz, 1H), 5.26 (q, J = 6.6 Hz, 1H), 4.00 (s, 3H), 3.92 (s, 3H), 2.85 (s, 3H), 1.79 (d, J = 6.7 Hz, 3H) |
| 885 | 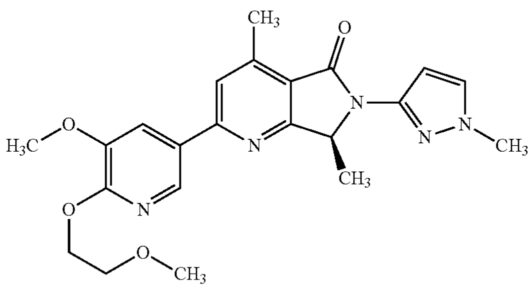 | 423.81 | (CDCl₃) δ 8.38 (d, J = 2.0 Hz, 1H), 7.87 (d, J = 1.9 Hz, 1H), 7.54 (s, 1H), 7.36 (d, J = 2.3 Hz, 1H), 6.94 (d, J = 2.3 Hz, 1H), 5.24 (q, J = 6.7 Hz, 1H), 4.75-4.56 (m, 2H), 4.01 (s, 3H), 3.92 (s, 3H), 3.90-3.79 (m, 2H), 3.48 (s, 3H), 2.83 (s, 3H), 1.78 (d, J = 6.7 Hz, 3H) |
| 886 | 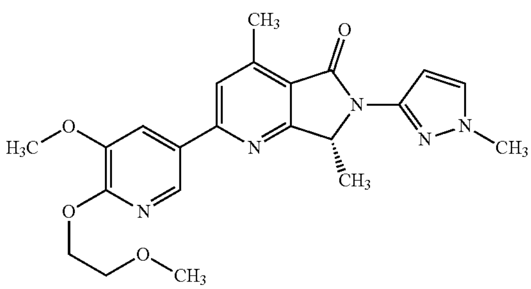 | 423.81 | (CDCl₃) δ 8.38 (d, J = 1.6 Hz, 1H), 7.87 (d, J = 1.5 Hz, 1H), 7.54 (s, 1H), 7.36 (d, J = 2.1 Hz, 1H), 6.94 (d, J = 2.1 Hz, 1H), 5.24 (q, J = 6.6 Hz, 1H), 4.79-4.50 (m, 2H), 4.01 (s, 3H), 3.91 (s, 3H), 3.89-3.78 (m, 2H), 3.48 (s, 3H), 2.82 (s, 3H), 1.78 (d, J = 6.6 Hz, 3H) |
| 887 | 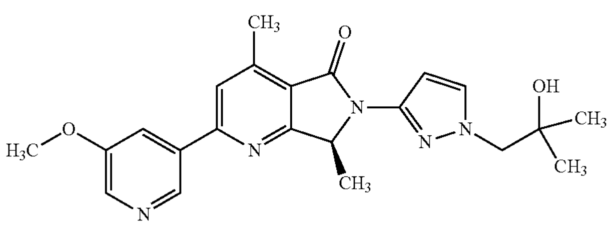 [SMILES: COc1cncc(-c2cc(C)c3c(n2)[C@H](C)N(c2ccn(CC(C)(C)O)n2)C3=O)c1] | 408.04 | (CDCl₃) δ 8.86 (d, J = 1.7 Hz, 1H), 8.42 (d, J = 2.8 Hz, 1H), 7.98 (dd, J = 2.8, 1.8 Hz, 1H), 7.63 (s, 1H), 7.44 (d, J = 2.4 Hz, 1H), 7.04 (d, J = 2.4 Hz, 1H), 5.27 (q, J = 6.6 Hz, 1H), 4.08 (s, 2H), 4.00 (s, 3H), 2.86 (s, 3H), 1.79 (d, J = 6.7 Hz, 3H), 1.22 (d, J = 8.5 Hz, 6H) |
| 888 | 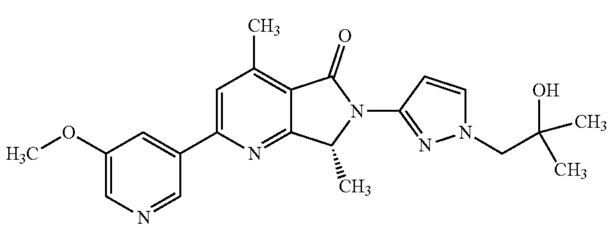 [SMILES: COc1cncc(-c2cc(C)c3c(n2)[C@@H](C)N(c2ccn(CC(C)(C)O)n2)C3=O)c1] | 407.72 | (CDCl₃) δ 8.86 (d, J = 1.7 Hz, 1H), 8.42 (d, J = 2.8 Hz, 1H), 7.98 (dd, J = 2.8, 1.8 Hz, 1H), 7.63 (s, 1H), 7.44 (t, J = 3.5 Hz, 1H), 7.04 (d, J = 2.4 Hz, 1H), 5.27 (q, J = 6.7 Hz, 1H), 4.08 (s, 2H), 4.00 (s, 3H), 2.86 (s, 3H), 1.79 (d, J = 6.7 Hz, 3H), 1.22 (d, J = 8.5 Hz, 6H) |
| 889 | 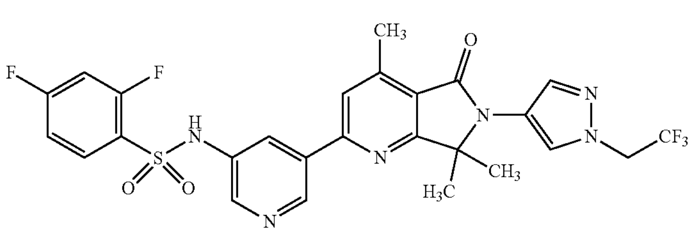 [SMILES: Cc1cc(-c2cncc(NS(=O)(=O)c3ccc(F)cc3F)c2)nc2c1C(=O)N(c1cnn(CC(F)(F)F)c1)C2(C)C] | 593.26 | (CDCl₃) δ 9.10 (d, J = 1.9 Hz, 1H), 8.43 (d, J = 2.6 Hz, 1H), 8.32 (d, J = 2.3 Hz, 1H), 8.17 (s, 1H), 7.98-7.91 (m, 1H), 7.82 (s, 1H), 7.59 (s, 1H), 7.00 (d, J = 4.1 Hz, 2H), 6.94 (d, J = 3.7 Hz, 1H), 4.77 (d, J = 8.3 Hz, 2H), 2.84 (s, 3H), 1.72 (s, 6H) |

| Cmpd No. | Structure | ESMS (M + H) | ¹H NMR (300 MHz, unless indicated otherwise) |
|---|---|---|---|
| 890 | 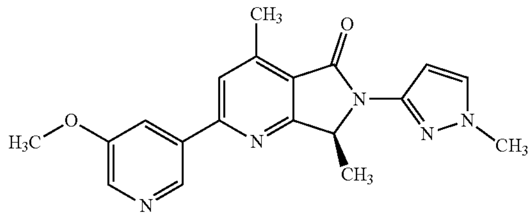 | 350.43 | (CDCl₃) δ 8.87 (s, 1H), 8.42 (s, 1H), 7.97 (s, 1H), 7.62 (s, 1H), 7.37 (d, J = 2.3 Hz, 1H), 6.95 (d, J = 2.3 Hz, 1H), 5.27 (q, J = 6.7 Hz, 1H), 4.00 (s, 3H), 3.92 (s, 3H), 2.85 (s, 3H), 1.79 (d, J = 6.7 Hz, 3H) |
| 891 | 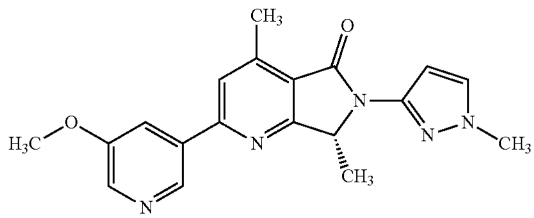 | 350.43 | (CDCl₃) δ 8.87 (s, 1H), 8.42 (s, 1H), 7.97 (s, 1H), 7.62 (s, 1H), 7.37 (d, J = 2.3 Hz, 1H), 6.95 (d, J = 2.3 Hz, 1H), 5.26 (q, J = 6.6 Hz, 1H), 4.00 (s, 3H), 3.92 (s, 3H), 2.85 (s, 3H), 1.79 (d, J = 6.7 Hz, 3H) |
| 892 | 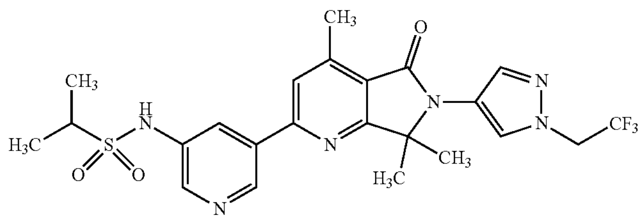 [SMILES: Cc1cc(-c2cncc(NS(=O)(=O)C(C)C)c2)nc2c1C(=O)N(c1cnn(CC(F)(F)F)c1)C2(C)C] | 523.31 | (CDCl₃) δ 9.04 (s, 1H), 8.47 (d, J = 14.2 Hz, 1H), 8.32 (s, 1H), 8.08 (s, 1H), 7.73 (s, 1H), 7.54 (s, 1H), 6.72 (s, 1H), 4.68 (dd, J = 16.6, 8.4 Hz, 2H), 3.33 (dd, J = 21.2, 14.5 Hz, 1H), 2.76 (s, 3H), 1.63 (s, 5H), 1.40 (d, J = 6.8 Hz, 5H) |
| 893 | 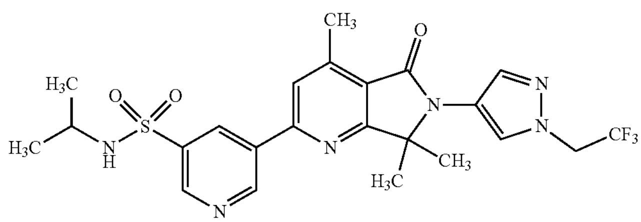 [SMILES: Cc1cc(-c2cncc(S(=O)(=O)NC(C)C)c2)nc2c1C(=O)N(c1cnn(CC(F)(F)F)c1)C2(C)C] | 523.21 | (CDCl₃) δ 9.51 (d, J = 2.0 Hz, 1H), 9.17 (d, J = 2.2 Hz, 1H), 8.87 (d, J = 2.1 Hz, 1H), 8.17 (s, 1H), 7.83 (s, 1H), 7.70 (s, 1H), 4.77 (d, J = 8.4 Hz, 2H), 4.48 (d, J = 7.4 Hz, 1H), 3.66 (dd, J = 14.2, 6.6 Hz, 1H), 2.87 (s, 3H), 1.74 (s, 6H), 1.20 (d, J = 6.5 Hz, 6H) |
| 894 | 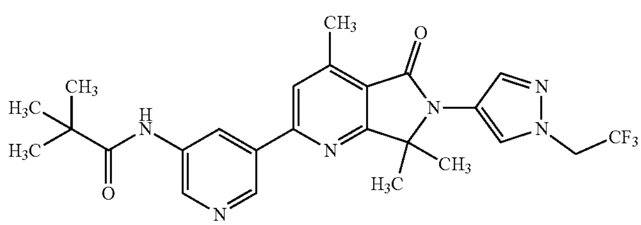 [SMILES: Cc1cc(-c2cncc(NC(=O)C(C)(C)C)c2)nc2c1C(=O)N(c1cnn(CC(F)(F)F)c1)C2(C)C] | 501.3 | (DMSO-d₆) δ = 9.66 (s, 1H), 9.03 (d, J = 8.8 Hz, 1H), 8.82 (s, 1H), 8.34 (s, 1H), 7.99 (s, 1H), 7.95 (s, 1H), 5.19 (m, 2H), 2.74 (s, 3H), 1.62 (s, 6H), 1.28 (s, 9H) |
| 895 | 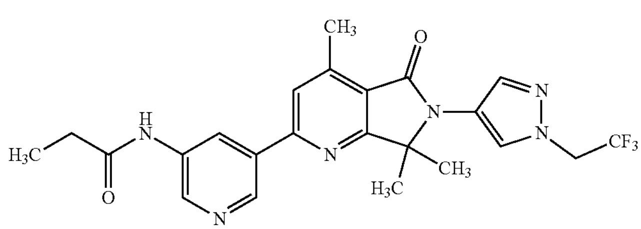 [SMILES: CCC(=O)Nc1cncc(-c2cc(C)c3c(n2)C(C)(C)N(c2cnn(CC(F)(F)F)c2)C3=O)c1] | 473.34 | (DMSO-d₆) δ 10.35 (s, 1H), 9.05 (d, J = 1.9 Hz, 1H), 8.95 (d, J = 2.3 Hz, 1H), 8.83 (s, 1H), 8.34 (s, 1H), 8.01 (s, 1H), 7.95 (s, 1H), 5.20 (d, J = 9.1 Hz, 2H), 2.74 (s, 3H), 2.42 (d, J = 7.5 Hz, 2H), 1.61 (s, 6H), 1.12 (t, J = 7.5 Hz, 3H) |
| 896 | 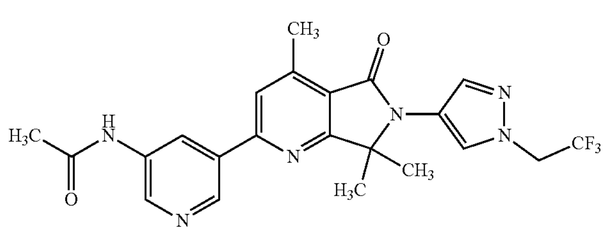 [SMILES: CC(=O)Nc1cncc(-c2cc(C)c3c(n2)C(C)(C)N(c2cnn(CC(F)(F)F)c2)C3=O)c1] | 459.24 | (DMSO-d₆) δ 10.39 (s, 1H), 8.98 (d, J = 32.2 Hz, 1H), 8.78 (s, 1H), 8.34 (s, 1H), 8.00 (s, 1H), 7.95 (s, 1H), 5.20 (dd, J = 18.2, 9.1 Hz, 2H), 2.74 (s, 3H), 2.13 (s, 3H), 1.61 (s, 6H) |

TABLE 1-continued

| Cmpd No. | Structure | ESMS (M + H) | ¹H NMR (300 MHz, unless indicated otherwise) |
|---|---|---|---|
| 897 | 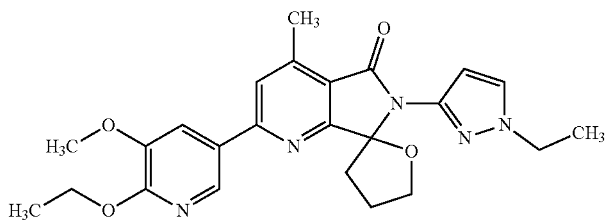 | 450.6 | (CDCl₃) δ 8.43 (d, J = 2.0 Hz, 1H), 7.83 (d, J = 2.0 Hz, 1H), 7.53 (d, J = 0.6 Hz, 1H), 7.42 (d, J = 2.3 Hz, 1H), 6.63 (d, J = 2.3 Hz, 1H), 4.54 (q, J = 7.1 Hz, 2H), 4.43-4.25 (m, 2H), 4.18 (q, J = 7.3 Hz, 2H), 3.99 (s, 3H), 2.85-2.67 (m, 4H), 2.62-2.37 (m, 2H), 2.29-2.09 (m, 1H), 1.51 (dt, J = 8.9, 7.2 Hz, 6H) |
| 898 | 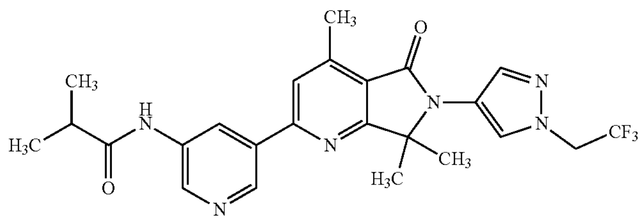 [SMILES: Cc1cc(-c2cncc(NC(=O)C(C)C)c2)nc2c1C(=O)N(c1cnn(CC(F)(F)F)c1)C2(C)C] | 487.6 | (DMSO-d₆) δ 10.37 (s, 1H), 9.07 (s, 1H), 8.88 (t, J = 2.1 Hz, 1H), 8.34 (s, 1H), 8.02 (s, 1H), 7.95 (s, 1H), 5.20 (q, J = 9.1 Hz, 2H), 2.75 (s, 3H), 2.71-2.62 (m, 1H), 1.62 (s, 6H), 1.16 (d, J = 6.8 Hz, 6H) |
| 899 | 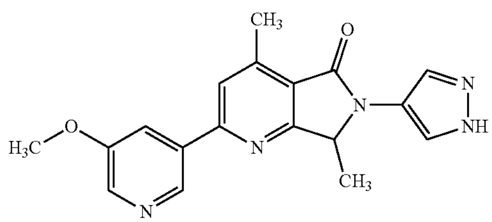 [SMILES: COc1cncc(-c2cc(C)c3c(n2)C(C)N(c2cn[nH]c2)C3=O)c1] | 336.24 | (DMSO-d₆) δ 12.94 (s, 1H), 8.98 (d, J = 1.7 Hz, 1H), 8.41 (d, J = 2.8 Hz, 1H), 8.14 (s, 1H), 8.09 (s, 1H), 8.07 (dd, J = 2.8, 1.9 Hz, 1H), 7.91 (s, 1H), 5.16 (d, J = 6.6 Hz, 1H), 3.95 (s, 3H), 2.74 (s, 3H), 1.55 (d, J = 6.7 Hz, 3H) |
| 900 | 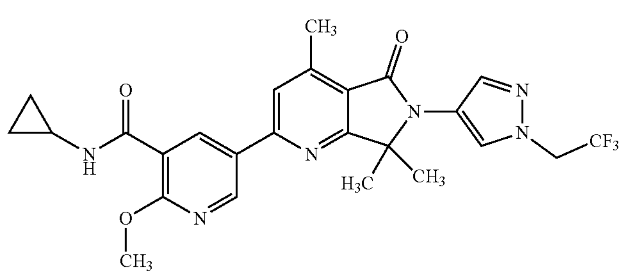 [SMILES: COc1ncc(-c2cc(C)c3c(n2)C(C)(C)N(c2cnn(CC(F)(F)F)c2)C3=O)cc1C(=O)NC1CC1] | 515.25 | (DMSO-d₆) δ 9.09 (d, J = 2.4 Hz, 1H), 8.72 (d, J = 2.4 Hz, 1H), 8.33 (s, 1H), 8.02 (s, 1H), 7.95 (s, 1H), 5.19 (d, J = 9.1 Hz, 2H), 4.02 (s, 3H), 2.87 (td, J = 7.1, 3.8 Hz, 1H), 2.72 (s, 3H), 1.60 (s, 6H), 0.73 (d, J = 4.7 Hz, 2H), 0.59 (d, J = 3.1 Hz, 2H) |
| 901 | 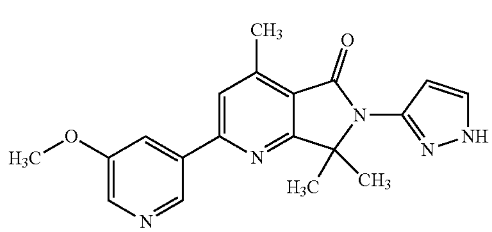 [SMILES: COc1cncc(-c2cc(C)c3c(n2)C(C)(C)N(c2cc[nH]n2)C3=O)c1] | 350.43 | (DMSO-d₆) δ 12.71 (s, 1H), 8.99 (d, J = 1.6 Hz, 1H), 8.41 (t, J = 6.2 Hz, 1H), 8.08 (s, 2H), 7.80-7.73 (m, 1H), 6.82 (t, J = 2.2 Hz, 1H), 3.96 (s, 3H), 2.74 (d, J = 6.6 Hz, 3H), 1.86- 1.67 (m, 6H) |
| 902 | 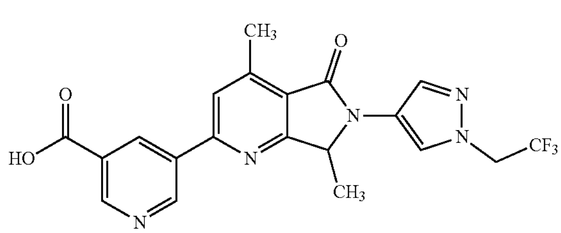 [SMILES: Cc1cc(-c2cncc(C(=O)O)c2)nc2c1C(=O)N(c1cnn(CC(F)(F)F)c1)C2C] | 432.2 | (DMSO-d₆) δ 13.68 (s, 1H), 9.57 (d, J = 2.2 Hz, 1H), 9.17 (d, J = 2.0 Hz, 1H), 8.98 (t, J = 2.1 Hz, 1H), 8.38 (s, 1H), 8.32 (d, J = 8.1 Hz, 0H), 8.20 (s, 1H), 8.02-7.93 (m, 1H), 5.27-5.19 (m, 2H), 4.97 (s, 0H), 3.10 (s, 0H), 2.89 (s, 0H), 2.74 (d, J = 7.6 Hz, 3H), 1.58 (d, J = 6.7 Hz, 3H) |

TABLE 1-continued

| Cmpd No. | Structure | ESMS (M + H) | ¹H NMR (300 MHz, unless indicated otherwise) |
|---|---|---|---|
| 903 | 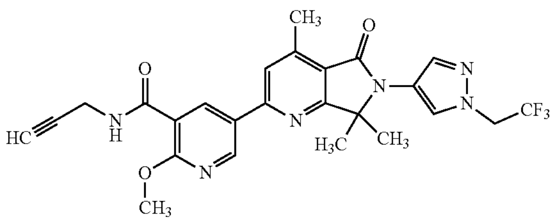 [SMILES: C#CCNC(=O)c1cc(-c2cc(C)c3c(n2)C(C)(C)N(c2cnn(CC(F)(F)F)c2)C3=O)cnc1OC] | 513.2 | (DMSO-d$_6$) δ 9.13 (d, J = 2.5 Hz, 1H), 8.87 (d, J = 2.5 Hz, 1H), 8.78 (s, 1H), 8.34 (s, 1H), 8.03 (s, 1H), 7.95 (s, 1H), 5.18 (t, J = 9.1 Hz, 2H), 4.07 (s, 3H), 3.16 (t, J = 2.5 Hz, 1H), 2.72 (s, 3H), 1.61 (s, 6H) |
| 904 | 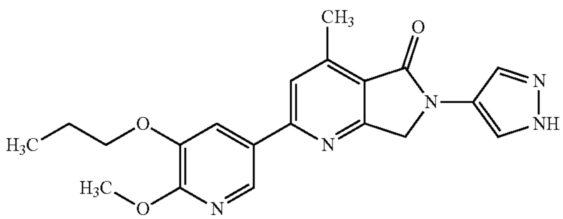 [SMILES: CCCOc1cc(-c2cc(C)c3c(n2)CN(c2cn[nH]c2)C3=O)cnc1OC] | 380.23 | (DMSO-d$_6$) δ 8.53 (d, J = 1.9 Hz, 1H), 8.02 (s, 2H), 7.99 (s, 1H), 7.96 (d, J = 1.8 Hz, 1H), 4.89 (s, 2H), 4.07 (t, J = 6.6 Hz, 2H), 3.95 (s, 3H), 2.71 (s, 3H), 1.87-1.71 (m, 2H), 1.02 (t, J = 7.4 Hz, 3H) |
| 905 | 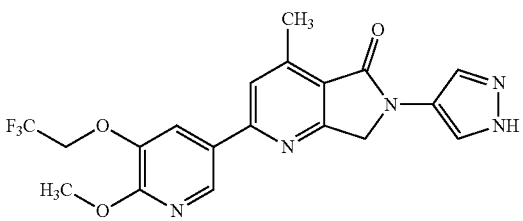 [SMILES: COc1ncc(-c2cc(C)c3c(n2)CN(c2cn[nH]c2)C3=O)cc1OCC(F)(F)F] | 420.17 | (DMSO-d$_6$) δ 8.66 (d, J = 1.8 Hz, 1H), 8.12 (d, J = 1.8 Hz, 1H), 8.03 (s, 2H), 7.99 (s, 1H), 5.02-4.90 (m, 2H), 4.89 (s, 2H), 3.99 (s, 3H), 2.72 (s, 3H) |
| 906 | 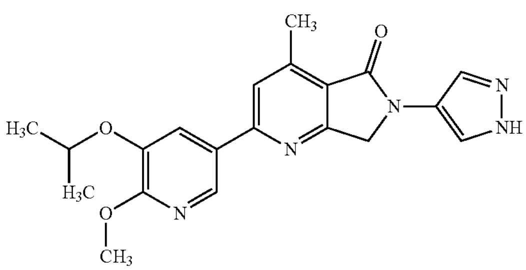 [SMILES: COc1ncc(-c2cc(C)c3c(n2)CN(c2cn[nH]c2)C3=O)cc1OC(C)C] | 380.23 | (DMSO-d$_6$) δ 8.53 (d, J = 1.8 Hz, 1H), 8.04 (s, 2H), 7.97 (d, J = 2.1 Hz, 2H), 4.89 (s, 2H), 4.85-4.71 (m, 1H), 3.94 (s, 3H), 2.71 (s, 3H), 1.33 (d, J = 6.0 Hz, 6H) |
| 907 | 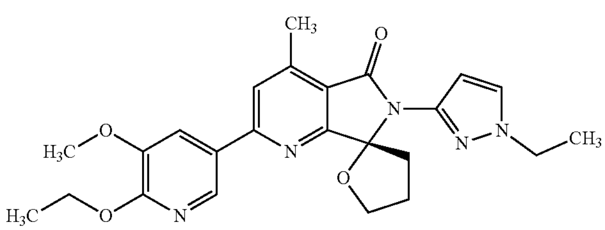 [SMILES: CCOc1ncc(-c2cc(C)c3c(n2)[C@]2(CCCO2)N(c2ccn(CC)n2)C3=O)cc1OC] | 450.47 | (CDCl$_3$) δ 8.43 (d, J = 2.0 Hz, 1H), 7.83 (d, J = 2.0 Hz, 1H), 7.53 (d, J = 0.6 Hz, 1H), 7.42 (d, J = 2.3 Hz, 1H), 6.63 (d, J = 2.3 Hz, 1H), 4.54 (q, J = 7.1 Hz, 2H), 4.43-4.25 (m, 2H), 4.18 (q, J = 7.3 Hz, 2H), 3.99 (s, 3H), 2.85-2.67 (m, 4H), 2.62-2.37 (m, 2H), 2.29-2.09 (m, 1H), 1.51 (dt, J = 8.9, 7.2 Hz, 6H) |
| 908 | 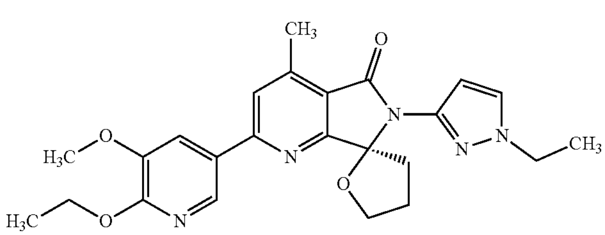 [SMILES: CCOc1ncc(-c2cc(C)c3c(n2)[C@@]2(CCCO2)N(c2ccn(CC)n2)C3=O)cc1OC] | 450.47 | (CDCl$_3$) δ 8.43 (d, J = 2.0 Hz, 1H), 7.83 (d, J = 2.0 Hz, 1H), 7.53 (d, J = 0.6 Hz, 1H), 7.42 (d, J = 2.3 Hz, 1H), 6.63 (d, J = 2.3 Hz, 1H), 4.54 (q, J = 7.1 Hz, 2H), 4.43-4.25 (m, 2H), 4.18 (q, J = 7.3 Hz, 2H), 3.99 (s, 3H), 2.85-2.67 (m, 4H), 2.62-2.37 (m, 2H), 2.29-2.09 (m, 1H), 1.51 (dt, J = 8.9, 7.2 Hz, 6H) |

TABLE 1-continued

| Cmpd No. | Structure | ESMS (M + H) | ¹H NMR (300 MHz, unless indicated otherwise) |
|---|---|---|---|
| 909 | 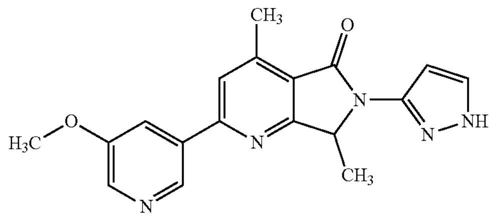 | 336.36 | (DMSO-d₆) δ 12.66 (s, 1H), 8.98 (d, J = 1.7 Hz, 1H), 8.42 (d, J = 2.8 Hz, 1H), 8.13-8.02 (m, 2H), 7.84-7.73 (m, 1H), 6.83 (t, J = 2.2 Hz, 1H), 5.23 (q, J = 6.6 Hz, 1H), 3.95 (s, 3H), 2.75 (s, 3H), 1.70 (d, J = 6.7 Hz, 3H) |
| 910 | 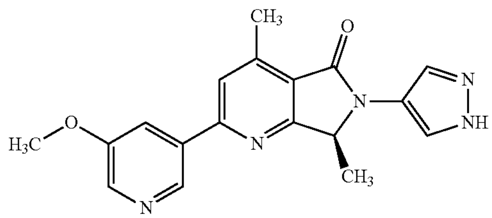 [SMILES: COc1cncc(-c2cc(C)c3c(n2)[C@H](C)N(c2cn[nH]c2)C3=O)c1] | 336 | |
| 911 | 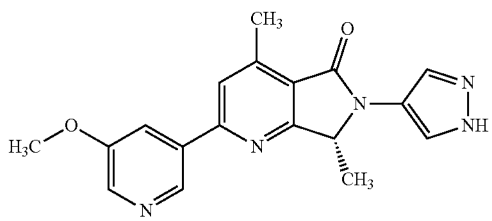 [SMILES: COc1cncc(-c2cc(C)c3c(n2)[C@@H](C)N(c2cn[nH]c2)C3=O)c1] | 336.1 | |
| 912 | 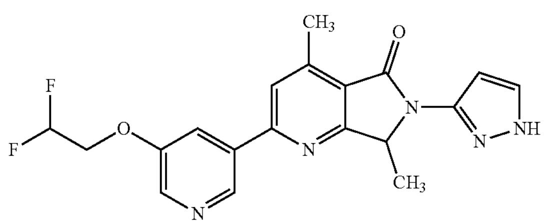 [SMILES: Cc1cc(-c2cncc(OCC(F)F)c2)nc2c1C(=O)N(c1cc[nH]n1)C2C] | 386.18 | (DMSO-d₆) δ 12.66 (s, 1H), 9.05 (d, J = 1.6 Hz, 1H), 8.49 (d, J = 2.8 Hz, 1H), 8.20-8.15 (m, 1H), 8.12 (s, 1H), 7.84-7.72 (m, 1H), 6.83 (t, J = 2.2 Hz, 1H), 6.48 (tt, J = 54.3, 3.4 Hz, 1H), 5.23 (q, J = 6.5 Hz, 1H), 4.57 (td, J = 14.7, 3.4 Hz, 2H), 2.75 (s, 3H), 1.68 (t, J = 13.3 Hz, 3H) |
| 913 | 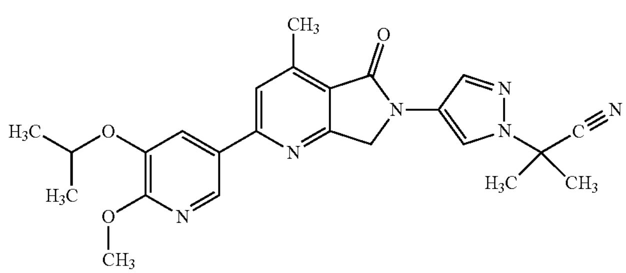 [SMILES: COc1ncc(-c2cc(C)c3c(n2)CN(c2cnn(C(C)(C)C#N)c2)C3=O)cc1OC(C)C] | 447 | |
| 914 | 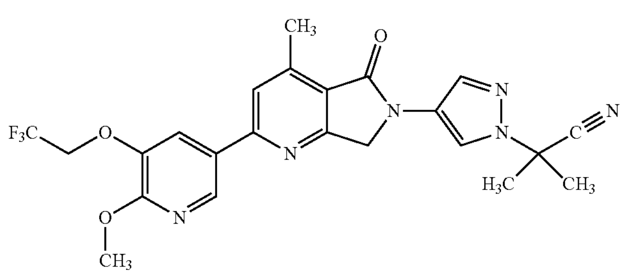 [SMILES: COc1ncc(-c2cc(C)c3c(n2)CN(c2cnn(C(C)(C)C#N)c2)C3=O)cc1OCC(F)(F)F] | 487 | |

TABLE 1-continued

| Cmpd No. | Structure | ESMS (M + H) | ¹H NMR (300 MHz, unless indicated otherwise) |
|---|---|---|---|
| 915 | 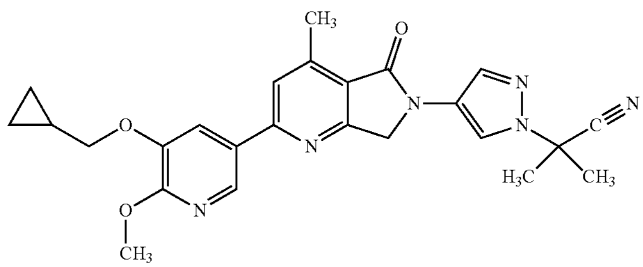 [SMILES: COc1ncc(-c2cc(C)c3c(n2)CN(c2cnn(C(C)(C)C#N)c2)C3=O)cc1OCC1CC1] | 459 | |
| 916 | 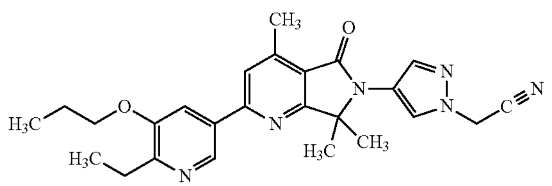 [SMILES: CCCOc1cc(-c2cc(C)c3c(n2)C(C)(C)N(c2cnn(CC#N)c2)C3=O)cnc1CC] | 447 | |
| 917 | 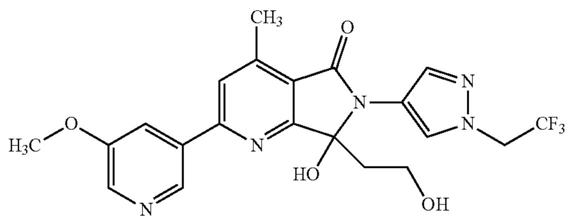 [SMILES: COc1cncc(-c2cc(C)c3c(n2)C(O)(CCO)N(c2cnn(CC(F)(F)F)c2)C3=O)c1] | 464.23 | (methanol-d₄) δ 9.18 (d, J = 1.4 Hz, 1H), 8.82-8.75 (m, 1H), 8.62 (d, J = 2.6 Hz, 1H), 8.27 (s, 1H), 8.12 (s, 1H), 8.04 (s, 1H), 5.00 (q, J = 8.7 Hz, 2H), 4.14 (s, 3H), 3.51-3.39 (m, 1H), 3.29-3.18 (m, 1H), 2.83 (s, 2H), 2.72 (dt, J = 14.4, 7.3 Hz, 1H), 2.46-2.32 (m, 1H) |
| 918 | 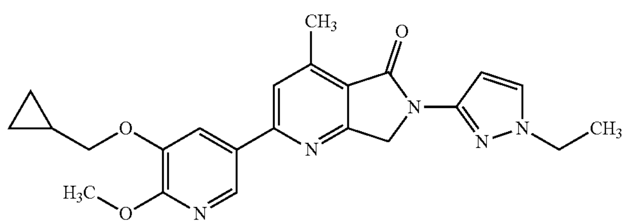 [SMILES: CCn1ccc(N2Cc3nc(-c4cnc(OC)c(OCC5CC5)c4)cc(C)c3C2=O)n1] | 420.23 | (DMSO-d₆) δ 8.52 (d, J = 1.9 Hz, 1H), 8.15 (s, 1H), 7.96 (s, 1H), 7.91 (d, J = 1.9 Hz, 1H), 7.80 (s, 1H), 4.84 (s, 2H), 4.16 (q, J = 7.3 Hz, 2H), 3.96 (m, 5H), 2.71 (s, 3H), 1.39 (t, J = 7.3 Hz, 3H), 1.26 (m, 1H), 0.67-0.52 (m, 2H), 0.44-0.31 (m, 2H) |
| 919 | 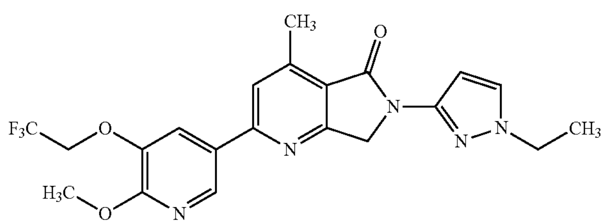 [SMILES: CCn1ccc(N2Cc3nc(-c4cnc(OC)c(OCC(F)(F)F)c4)cc(C)c3C2=O)n1] | 448.2 | (DMSO-d₆) δ 8.66 (d, J = 1.9 Hz, 1H), 8.18 (s, 1H), 8.12 (d, J = 1.9 Hz, 1H), 7.98 (s, 1H), 7.81 (s, 1H), 4.93 (q, J = 8.9 Hz, 2H), 4.87 (s, 2H), 4.16 (q, J = 7.3 Hz, 2H), 3.99 (s, 3H), 2.72 (s, 3H), 1.39 (t, J = 7.3 Hz, 3H) |
| 920 | 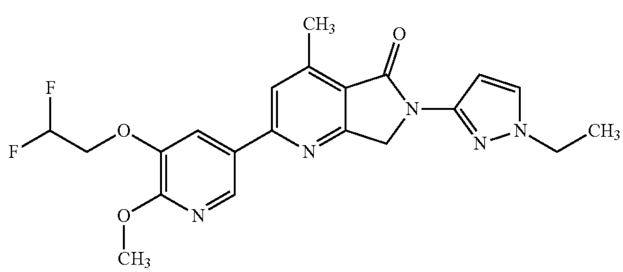 | 430.22 | (DMSO-d₆) δ 8.61 (d, J = 1.9 Hz, 1H), 8.18 (s, 1H), 8.05 (d, J = 1.9 Hz, 1H), 7.99 (s, 1H), 7.81 (d, J = 0.5 Hz, 1H), 6.55 (tt, J = 54.2, 3.5 Hz, 1H), 4.87 (s, 2H), 4.49 (td, J = 14.6, 3.6 Hz, 2H), 4.16 (q, J = 7.2 Hz, 2H), 3.98 (s, 3H), 2.72 (s, 3H), 1.39 (t, J = 7.2 Hz, 3H) |

TABLE 1-continued

| Cmpd No. | Structure | ESMS (M + H) | ¹H NMR (300 MHz, unless indicated otherwise) |
|---|---|---|---|
| 921 | 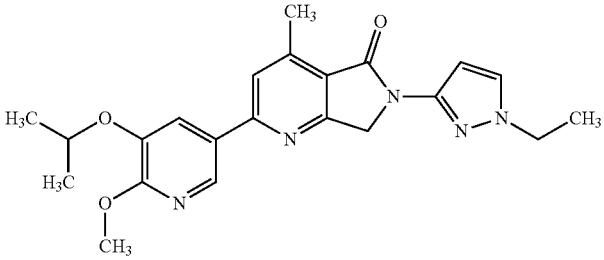 [SMILES: CCn1ccc(N2Cc3nc(-c4cnc(OC)c(OC(C)C)c4)cc(C)c3C2=O)n1] | 408.3 | (DMSO-d₆) δ 8.52 (s, 1H), 8.18 (s, 1H), 7.96 (s, 2H), 7.81 (s, 1H), 4.87 (s, 2H), 4.77 (m, 1H), 4.16 (q, J = 7.3 Hz, 2H), 3.94 (s, 3H), 2.71 (s, 3H), 1.39 (t, J = 7.3 Hz, 3H), 1.33 (d, J = 6.0 Hz, 6H) |
| 922 | 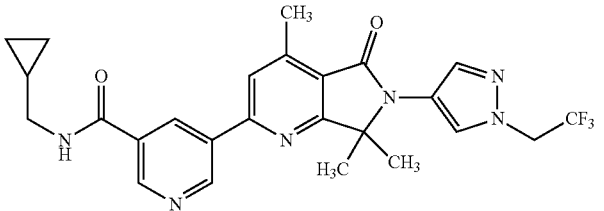 [SMILES: Cc1cc(-c2cncc(C(=O)NCC3CC3)c2)nc2c1C(=O)N(c1cnn(CC(F)(F)F)c1)C2(C)C] | 529.23 | (DMSO-d₆) δ 9.10 (s, 1H), 8.85 (s, 1H), 8.32 (s, 1H), 8.01 (s, 1H), 7.94 (s, 1H), 5.18 (q, J = 9.1 Hz, 2H), 4.07 (s, 3H), 3.27-3.19 (m, 2H), 2.72 (s, 3H), 1.60 (s, 6H), 1.07 (s, 1H), 0.51-0.40 (m, 2H), 0.33-0.23 (m, 2H) |
| 923 | 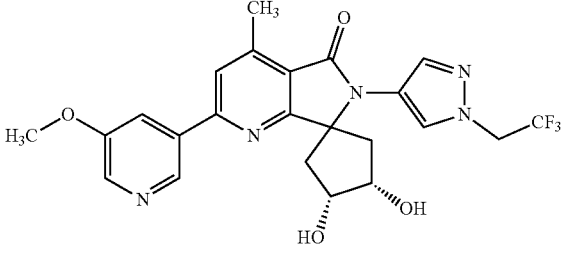 [SMILES: COc1cncc(-c2cc(C)c3c(n2)C2(C[C@@H](O)[C@@H](O)C2)N(c2cnn(CC(F)(F)F)c2)C3=O)c1] | 490.57 | (CDCl₃) δ 8.84 (d, J = 1.6 Hz, 1H), 8.49 (d, J = 10.9 Hz, 2H), 8.33 (d, J = 2.8 Hz, 1H), 7.82-7.71 (m, 1H), 7.54 (s, 1H), 4.81 (s, 2H), 4.68 (q, J = 8.3 Hz, 2H), 3.90 (s, 3H), 2.83 (d, J = 3.4 Hz, 2H), 2.76 (s, 3H), 2.58 (dd, J = 14.0, 5.2 Hz, 2H), 2.19 (dd, J = 14.0, 6.0 Hz, 2H) |
| 924 | 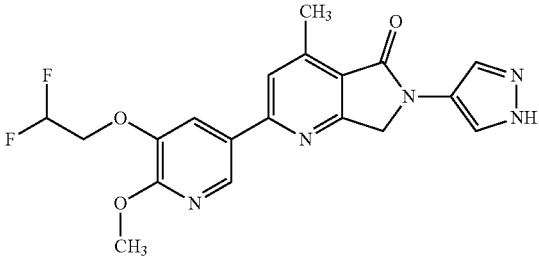 [SMILES: COc1ncc(-c2cc(C)c3c(n2)CN(c2cn[nH]c2)C3=O)cc1OCC(F)F] | 402.38 | (DMSO-d₆) δ 8.62 (d, J = 1.8 Hz, 1H), 8.06 (d, J = 1.7 Hz, 1H), 8.02 (s, 2H), 7.99 (s, 1H), 6.46 (s, 2H), 4.89 (s, 2H), 4.49 (dd, J = 14.5, 11.0 Hz, 3H), 3.98 (s, 3H), 2.72 (s, 3H) |
| 925 | 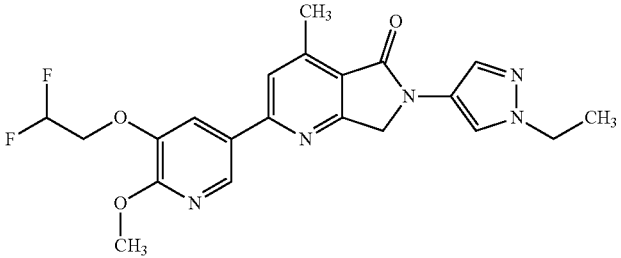 [SMILES: CCn1cc(N2Cc3nc(-c4cnc(OC)c(OCC(F)F)c4)cc(C)c3C2=O)cn1] | 430.41 | (DMSO-d₆) δ 8.61 (d, J = 1.8 Hz, 1H), 8.18 (s, 1H), 8.05 (d, J = 1.8 Hz, 1H), 7.99 (s, 1H), 7.81 (s, 1H), 6.67-6.23 (m, 1H), 4.86 (s, 2H), 4.49 (td, J = 14.5, 3.6 Hz, 2H), 4.16 (q, J = 7.2 Hz, 2H), 3.98 (s, 3H), 2.72 (s, 3H), 1.39 (t, J = 7.2 Hz, 3H) |
| 926 | 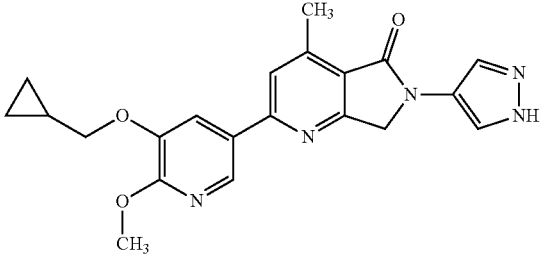 [SMILES: COc1ncc(-c2cc(C)c3c(n2)CN(c2cn[nH]c2)C3=O)cc1OCC1CC1] | 392.4 | (DMSO-d₆) δ 8.53 (d, J = 1.9 Hz, 1H), 8.02 (s, 2H), 7.96 (s, 1H), 7.92 (d, J = 1.9 Hz, 1H), 4.88 (s, 2H), 4.00-3.92 (m, J = 5.2 Hz, 5H), 2.71 (s, 3H), 1.33-1.24 (m, 1H), 0.66-0.55 (m, 2H), 0.38 (d, J = 4.9 Hz, 2H) |

TABLE 1-continued

| Cmpd No. | Structure | ESMS (M + H) | ¹H NMR (300 MHz, unless indicated otherwise) |
|---|---|---|---|
| 927 | 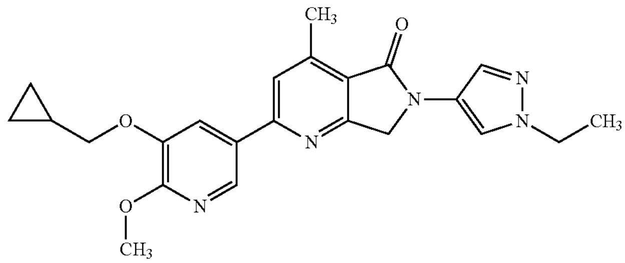 [SMILES: CCn1cc(N2Cc3nc(-c4cnc(OC)c(OCC5CC5)c4)cc(C)c3C2=O)cn1] | 420.43 | (DMSO-d₆) δ 8.52 (d, J = 1.9 Hz, 1H), 8.17 (s, 1H), 7.95 (s, 1H), 7.90 (d, J = 1.9 Hz, 1H), 7.80 (s, 1H), 4.85 (s, 2H), 4.16 (dd, J = 14.5, 7.3 Hz, 2H), 3.99-3.93 (m, 5H), 2.70 (s, 3H), 1.39 (t, J = 7.3 Hz, 3H), 1.32-1.19 (m, 1H), 0.70-0.55 (m, 2H), 0.42-0.30 (m, 2H) |
| 928 | 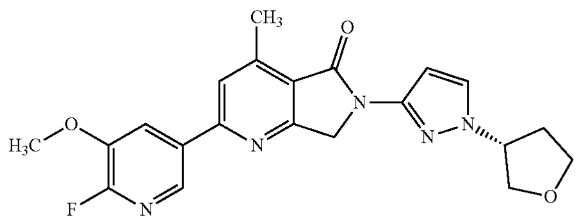 [SMILES: COc1cc(-c2cc(C)c3c(n2)CN(c2ccn([C@@H]4CCOC4)n2)C3=O)cnc1F] | 410.38 | (DMSO-d₆) δ = 8.53 (t, J = 1.8, 1H), 8.29 (dd, J = 10.1, 2.1, 1H), 8.09 (s, 1H), 7.82 (d, J = 2.4, 1H), 6.81 (d, J = 2.4, 1H), 5.05-4.97 (m, 1H), 4.95 (s, 2H), 4.02 (s, 3H), 4.01-3.78 (m, 4H), 2.74 (s, 3H), 2.41-2.27 (m, 2H) |
| 929 | 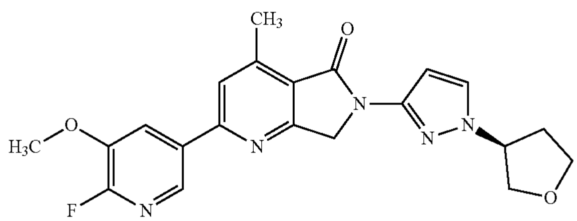 [SMILES: COc1cc(-c2cc(C)c3c(n2)CN(c2ccn([C@H]4CCOC4)n2)C3=O)cnc1F] | 410.38 | (DMSO-d₆) δ = 8.52 (t, J = 1.8, 1H), 8.27 (dd, J = 10.1, 2.0, 1H), 8.08 (s, 1H), 7.81 (d, J = 2.4, 1H), 6.80 (d, J = 2.4, 1H), 5.06-4.96 (m, 1H), 4.93 (s, 2H), 4.05 (s, 0H), 4.02 (s, 3H), 4.01-3.72 (m, 3H), 2.73 (s, 3H), 2.43-2.25 (m, 2H) |
| 930 | 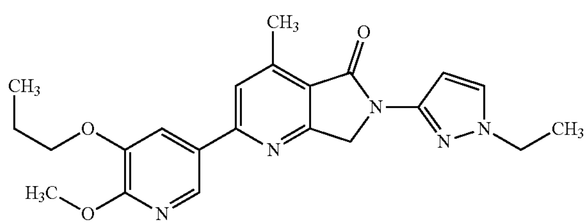 [SMILES: CCCOc1cc(-c2cc(C)c3c(n2)CN(c2ccn(CC)n2)C3=O)cnc1OC] | 408.46 | (DMSO-d₆) δ 8.53 (d, J = 1.6 Hz, 1H), 8.18 (s, 1H), 7.96 (m, 2H), 7.81 (s, 1H), 4.87 (s, 2H), 4.16 (q, J = 7.1 Hz, 2H), 4.08 (t, J = 6.6 Hz, 2H), 3.96 (s, 3H), 2.72 (s, 3H), 1.80 (dd, J = 14.1, 7.1 Hz, 2H), 1.39 (t, J = 7.3 Hz, 3H), 1.02 (t, J = 7.4 Hz, 3H) |
| 931 | 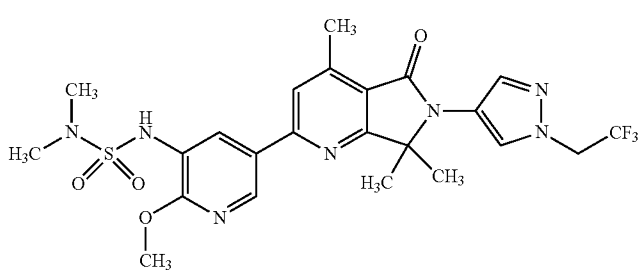 [SMILES: COc1ncc(-c2cc(C)c3c(n2)C(C)(C)N(c2cnn(CC(F)(F)F)c2)C3=O)cc1NS(=O)(=O)N(C)C] | 554.35 | (CDCl₃) δ 8.63 (d, J = 1.9 Hz, 1H), 8.45 (d, J = 2.0 Hz, 1H), 8.16 (s, 1H), 7.81 (s, 1H), 7 53 (s, 1H) 6.85 (s, 1H), 4.76 (q, J = 8.3. Hz, 2H), 4.12 (s, 3H), 2.93 (s, 6H), 2.82 (s, 3H), 1.70 (s, 6H) |
| 932 | 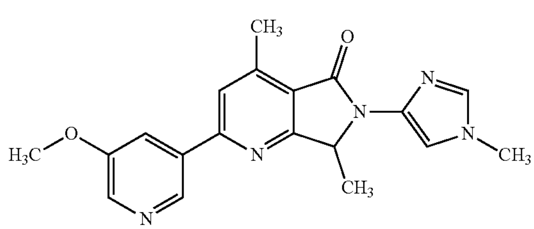 | 350.09 | |

TABLE 1-continued

| Cmpd No. | Structure | ESMS (M + H) | ¹H NMR (300 MHz, unless indicated otherwise) |
|---|---|---|---|
| 933 | 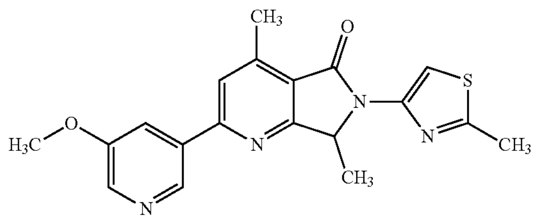 | 367.26 | |
| 934 | 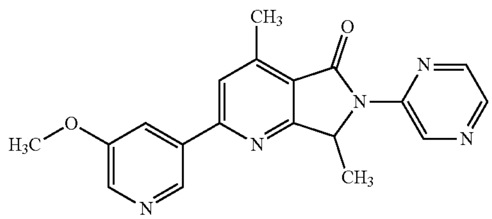 [SMILES: COc1cncc(-c2cc(C)c3c(n2)C(C)N(c2cnccn2)C3=O)c1] | 348.19 | |
| 935 | 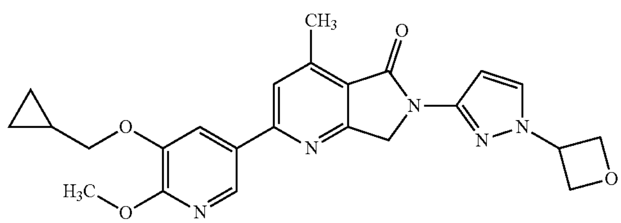 [SMILES: COc1ncc(-c2cc(C)c3c(n2)CN(c2ccn(C4COC4)n2)C3=O)cc1OCC1CC1] | 448 | |
| 936 | 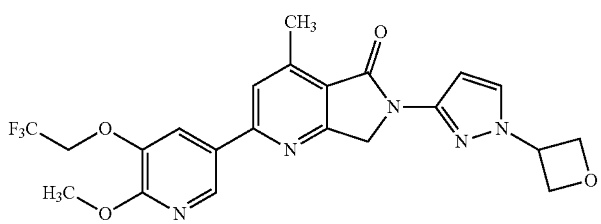 [SMILES: COc1ncc(-c2cc(C)c3c(n2)CN(c2ccn(C4COC4)n2)C3=O)cc1OCC(F)(F)F] | 476 | |
| 937 | 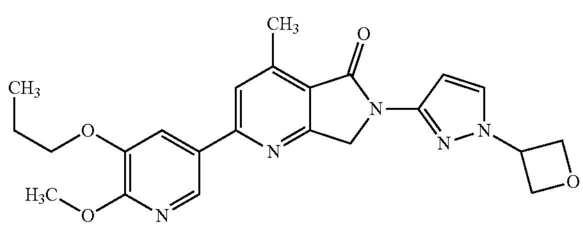 [SMILES: CCCOc1cc(-c2cc(C)c3c(n2)CN(c2ccn(C4COC4)n2)C3=O)cnc1OC] | 436 | |
| 938 | 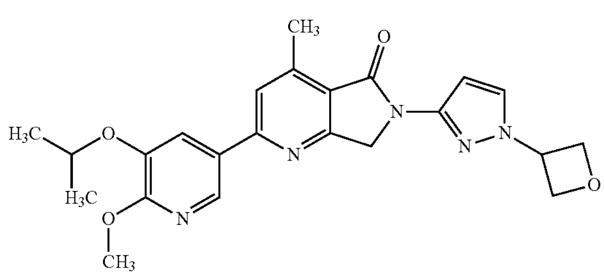 [SMILES: COc1ncc(-c2cc(C)c3c(n2)CN(c2ccn(C4COC4)n2)C3=O)cc1OC(C)C] | 436 | |

TABLE 1-continued

| Cmpd No. | Structure | ESMS (M + H) | ¹H NMR (300 MHz, unless indicated otherwise) |
|---|---|---|---|
| 939 | 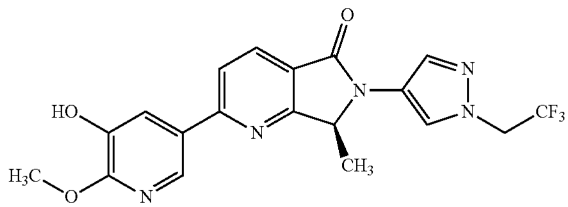 [SMILES: COc1ncc(-c2ccc3c(n2)[C@H](C)N(c2cnn(CC(F)(F)F)c2)C3=O)cc1O] | 420 | |
| 940 | 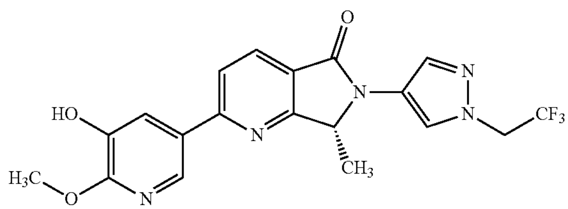 | 420 | |
| 941 | 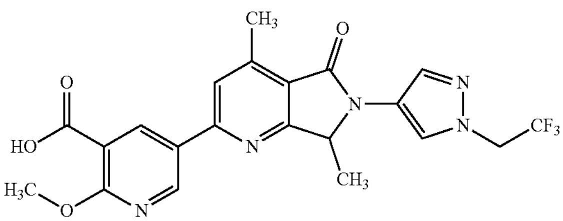 [SMILES: COc1ncc(-c2cc(C)c3c(n2)C(C)N(c2cnn(CC(F)(F)F)c2)C3=O)cc1C(=O)O] | 462.19 | (DMSO-d$_6$) δ 13.21 (s, 1H), 9.14 (d, J = 2.5 Hz, 1H), 8.86 (d, J = 2.5 Hz, 1H), 8.35 (s, 1H), 8.04 (s, 1H), 7.96 (s, 1H), 5.19 (dd, J = 7.9, 4.3 Hz, 2H), 4.02 (s, 3H), 2.73 (s, 3H), 1.56 (d, J = 6.6 Hz, 3H) |
| 942 | 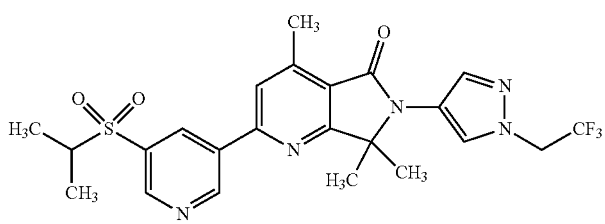 [SMILES: Cc1cc(-c2cncc(S(=O)(=O)C(C)C)c2)nc2c1C(=O)N(c1cnn(CC(F)(F)F)c1)C2(C)C] | 508.4 | (CDCl$_3$) δ 9.52 (d, J = 2.1 Hz, 1H), 9.08 (d, J = 2.1 Hz, 1H), 8.76 (t, J = 2.1 Hz, 1H), 8.07 (s, 1H), 7.74 (s, 1H), 7.62 (s, 1H), 4.69 (q, J = 8.3 Hz, 2H), 3.34-3.15 (m, 1H), 2.79 (s, 3H), 1.65 (s, 6H), 1.33 (d, J = 6.9 Hz, 6H) |
| 943 | 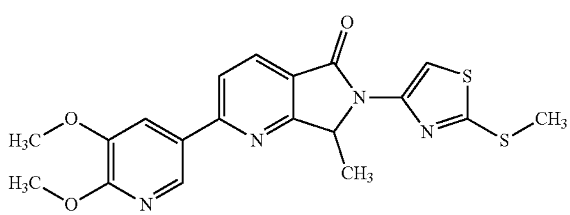 | 415.24 | (CDCl$_3$) δ 8.44 (d, J = 2.0 Hz, 1H), 8.21 (d, J = 8.1 Hz, 1H), 7.93 (d, J = 1.9 Hz, 1H), 7.84 (t, J = 4.0 Hz, 2H), 5.51 (q, J = 6.7 Hz, 1H), 4.13 (s, 3H), 4.04 (s, 3H), 2.76 (s, 3H), 1.83 (d, J = 6.7 Hz, 3H) |
| 944 | 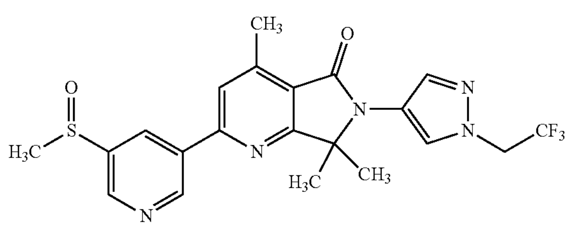 [SMILES: Cc1cc(-c2cncc(S(C)=O)c2)nc2c1C(=O)N(c1cnn(CC(F)(F)F)c1)C2(C)C] | 464.43 | (CDCl$_3$) δ 9.48 (d, J = 1.7 Hz, 1H), 8.85 (d, J = 1.8 Hz, 1H), 8.80 (s, 1H), 8.16 (s, 1H), 7.83 (s, 1H), 7.73 2H), 2.94 (d, J = 18.0 Hz, 3H), 2.86 (s, 3H), 1.74 (s, 6H) |
| 945 | 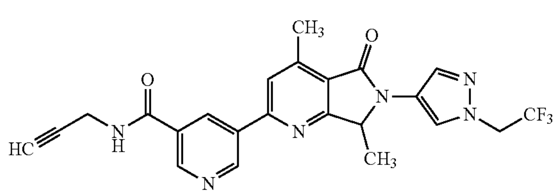 [SMILES: C#CCNC(=O)c1cncc(-c2cc(C)c3c(n2)C(C)N(c2cnn(CC(F)(F)F)c2)C3=O)c1] | 469.31 | (DMSO-d$_6$) δ 9.49 (d, J = 2.1 Hz, 1H), 9.10 (d, J = 2.1 Hz, 1H), 8.91 (t, J = 2.1 Hz, 1H), 8.37 (s, 1H), 8.14 (s, 1H), 7.98 (s, 1H), 5.21 (dd, J = 7.9, 4.8 Hz, 2H), 4.15 (dd, J = 5.4, 2.5 Hz, 2H), 3.72-3.52 (m, 2H), 3.19 (d, J = 2.5 Hz, 1H), 2.77 (s, 3H), 1.59 (d, J = 6.7 Hz, 3H) |

TABLE 1-continued

| Cmpd No. | Structure | ESMS (M + H) | ¹H NMR (300 MHz, unless indicated otherwise) |
|---|---|---|---|
| 946 | 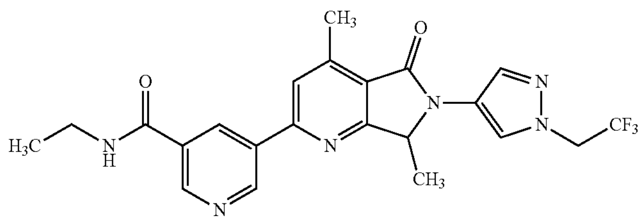 [SMILES: CCNC(=O)c1cncc(-c2cc(C)c3c(n2)C(C)N(c2cnn(CC(F)(F)F)c2)C3=O)c1] | 459.5 | (DMSO-d₆) δ 9.47 (d, J = 2.1 Hz, 1H), 9.09 (d, J = 2.0 Hz, 1H), 8.87 (s, 1H), 8.37 (s, 1H), 8.13 (s, 1H), 7.98 (s, 1H), 5.21 (dd, J = 7.9, 3.9 Hz, 2H), 3.35 (d, J = 6.9 Hz, 2H), 2.89 (s, 1H), 2.77 (s, 3H), 1.59 (d, J = 6.6 Hz, 3H), 1.18 (t, J = 7.2 Hz, 3H) |
| 947 | 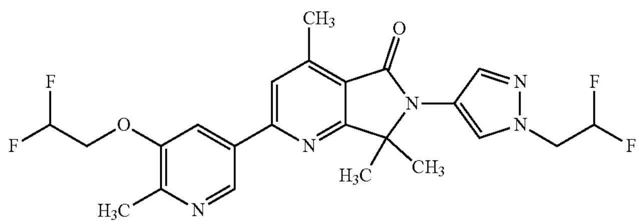 [SMILES: Cc1cc(-c2cnc(C)c(OCC(F)F)c2)nc2c1C(=O)N(c1cnn(CC(F)F)c1)C2(C)C] | 478.15 | (DMSO-d₆, 400 MHz) δ 8.91 (s, 1H), 8.25 (s, 1H), 8.10 (s, 1H), 8.06 (s, 1H), 7.88 (s, 1H), 6.46 (m, 2H), 4.68 (td, J = 15.1, 3.7 Hz, 2H), 4.56 (td, J = 14.7, 3.2 Hz, 2H), 2.73 (s, 3H), 2.46 (s, 3H), 1.61 (s, 6H) |
| 948 | 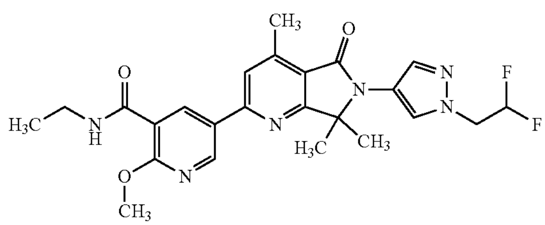 [SMILES: CCNC(=O)c1cc(-c2cc(C)c3c(n2)C(C)(C)N(c2cnn(CC(F)F)c2)C3=O)cnc1OC] | 485.15 | (DMSO-d₆, 400 MHz) δ 9.09 (d, J = 2.4 Hz, 1H), 8.83 (d, J = 2.4 Hz, 1H), 8.39 (t, 1H), 8.25 (s, 1H), 8.01 (s, 1H), 7.88 (s, 1H), 6.42 (tt, 1H), 4.67 (dt, J = 15.1, 7.5 Hz, 2H), 4.06 (s, 3H), 3.35 (m, 2H), 2.72 (s, 3H), 1.59 (s, 6H), 1.15 (t, J = 7.2 Hz, 3H) |
| 949 | 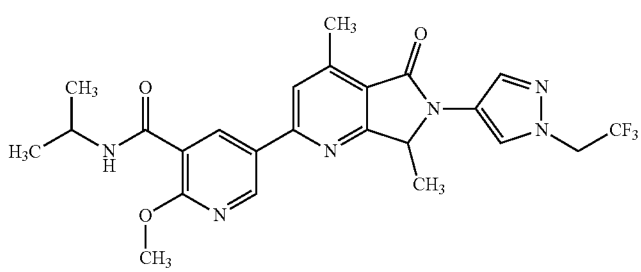 [SMILES: COc1ncc(-c2cc(C)c3c(n2)C(C)N(c2cnn(CC(F)(F)F)c2)C3=O)cc1C(=O)NC(C)C] | 503.28 | (DMSO-d₆) δ 9.08 (d, J = 2.5 Hz, 1H), 8.77 (d, J = 2.5 Hz, 1H), 8.35 (s, 1H), 8.03 (s, 1H), 7.96 (s, 1H), 5.22-5.14 (m, 2H), 4.15-4.08 (m, 1H), 4.05 (s, 3H), 2.73 (s, 3H), 1.56 (d, J = 6.7 Hz, 3H), 1.20 (d, J = 6.6 Hz, 6H) |
| 950 | 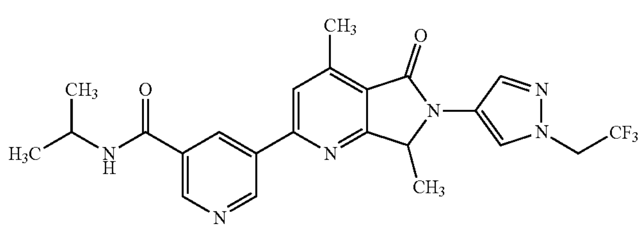 [SMILES: Cc1cc(-c2cncc(C(=O)NC(C)C)c2)nc2c1C(=O)N(c1cnn(CC(F)(F)F)c1)C2C] | | (DMSO-d₆) δ 9.46 (d, J = 2.2 Hz, 1H), 9.08 (d, J = 2.1 Hz, 1H), 8.85 (t, J = 2.1 Hz, 1H), 8.37 (s, 1H), 8.12 (s, 1H), 7.98 (s, 1H), 5.21 (dt, J = 18.3, 7.5 Hz, 3H), 4.16 (dd, J = 14.0, 6.7 Hz, 1H), 2.77 (s, 3H), 1.59 (d, J = 6.7 Hz, 3H), 1.22 (d, J = 6.6 Hz, 6H) |
| 951 | 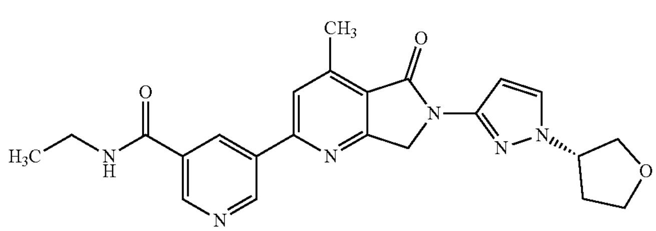 [SMILES: CCNC(=O)c1cncc(-c2cc(C)c3c(n2)CN(c2ccn([C@H]4CCOC4)n2)C3=O)c1] | 433.26 | (DMSO-d₆) δ 9.45 (d, J = 2.1 Hz, 1H), 9.08 (d, J = 2.1 Hz, 1H), 8.88 (t, J = 2.1 Hz, 1H), 8.82 (t, J = 5.6 Hz, 1H), 8.12 (s, 1H), 7.82 (d, J = 2.4 Hz, 1H), 6.82 (d, J = 2.4 Hz, 1H), 5.10-4.85 (m, 3H), 4.11-3.90 (m, 3H), 3.84 (td, J = 8.2, 5.5 Hz, 1H), 3.45-3.31 (m, 2H), 2.76 (s, 3H), 2.43-2.21 (m, 2H), 1.18 (t, J = 7.2 Hz, 3H) |

TABLE 1-continued

| Cmpd No. | Structure | ESMS (M + H) | ¹H NMR (300 MHz, unless indicated otherwise) |
|---|---|---|---|
| 952 | 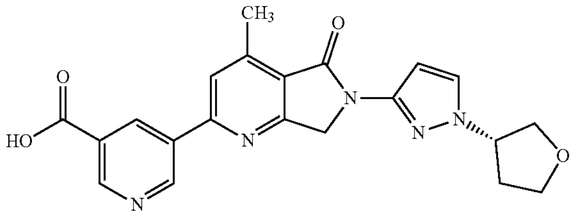 [SMILES: Cc1cc(-c2cncc(C(=O)O)c2)nc2c1C(=O)N(c1ccn([C@H]3CCOC3)n1)C2] | 406.22 | (DMSO-d₆) δ 9.54 (s, 1H), 9.15 (s, 1H), 8.98 (s, 1H), 8.18 (s, 1H), 7.82 (d, J = 2.3 Hz, 1H), 6.82 (d, J = 2.3 Hz, 1H), 5.11-4.89 (m, 3H), 4.11-3.90 (m, 3H), 3.84 (td, J = 8.2, 5.5 Hz, 1H), 2.75 (s, 3H), 2.45-2.18 (m, 3H) |
| 953 | 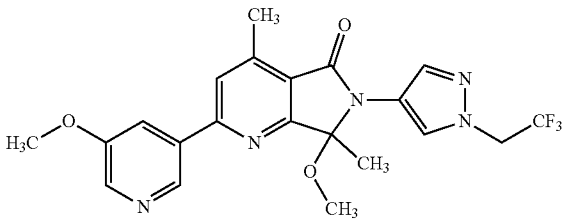 [SMILES: COc1cncc(-c2cc(C)c3c(n2)C(C)(OC)N(c2cnn(CC(F)(F)F)c2)C3=O)c1] | 448.07 | |
| 954 | 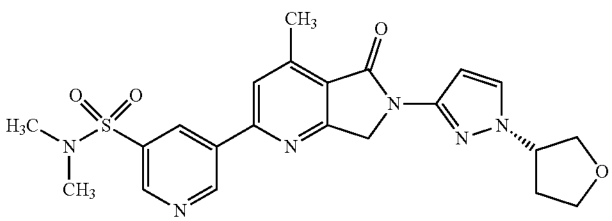 | 469.19 | (DMSO-d₆) δ 9.66 (d, J = 2.0 Hz, 1H), 9.04 (d, J = 2.1 Hz, 1H), 8.80 (t, J = 2.0 Hz, 1H), 8.26 (s, 1H), 7.84 (d, J = 2.3 Hz, 1H) 6.82 (d, J = 2.4 Hz, 1H), 5.10-4.89 (m, 3H), 4.10-3.71 (m, 4H), 2.75 (d, J = 9.6 Hz, 9H), 2.35 (ddd, J = 24.9, 11.9, 5.6 Hz, 2H) |
| 955 | 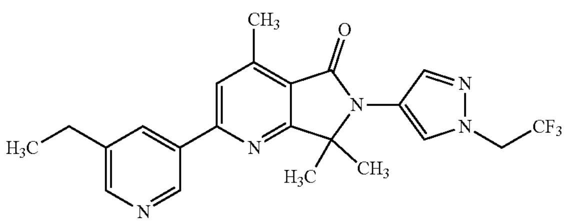 [SMILES: CCc1cncc(-c2cc(C)c3c(n2)C(C)(C)N(c2cnn(CC(F)(F)F)c2)C3=O)c1] | 430.57 | (DMSO-d₆) δ 9.20 (d, J = 2.1 Hz, 1H), 8.57 (d, J = 2.1 Hz, 1H), 8.38 (t, J = 2.1 Hz, 1H), 8.32 (d, J = 8.7 Hz, 1H), 8.04 (d, J = 0.6 Hz, 1H), 7.94 (s, 1H), 5.19 (q, J = 9.1 Hz, 2H), 3.30 (s, 3H), 2.80-2.69 (m, 5H), 1.61 (s, 6H), 1.28 (t, J = 7.6 Hz, 3H) |
| 956 | 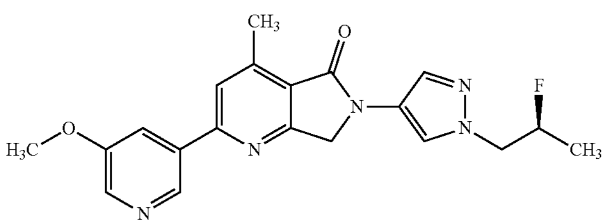 [SMILES: COc1cncc(-c2cc(C)c3c(n2)CN(c2cnn(C[C@H](C)F)c2)C3=O)c1] | 382.5 | (DMSO-d₆) δ 8.96 (d, J = 1.7 Hz, 1H), 8.40 (d, J = 2.8 Hz, 1H), 8.22 (s, 1H), 8.08 (s, 1H), 8.05 (dd, J = 2.8, 1.8 Hz, 1H), 7.86 (d, J = 0.5 Hz, 1H), 5.16-4.94 (m, 1H), 4.91 (s, 2H), 4.49-4.26 (m, 2H), 3.94 (s, 3H), 2.74 (s, 3H), 1.32 (dd, J = 23.8, 6.3 Hz, 3H) |
| 957 | 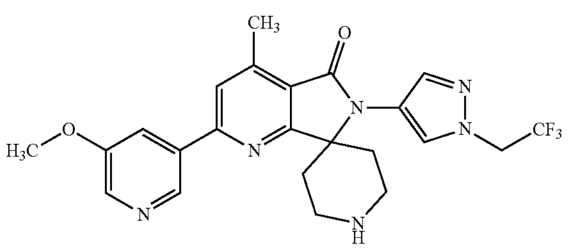 [SMILES: COc1cncc(-c2cc(C)c3c(n2)C2(CCNCC2)N(c2cnn(CC(F)(F)F)c2)C3=O)c1] | 473.41 | |

| Cmpd No. | Structure | ESMS (M + H) | ¹H NMR (300 MHz, unless indicated otherwise) |
|---|---|---|---|
| 958 | 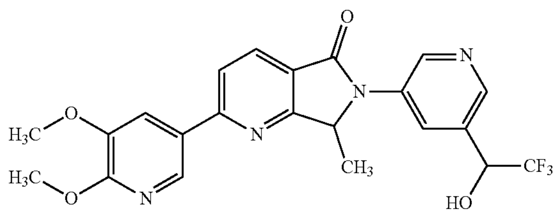 [SMILES: COc1cc(-c2ccc3c(n2)C(C)N(c2cncc(C(O)C(F)(F)F)c2)C3=O)cnc1OC] | 461.31 | (CDCl$_3$) δ 8.95 (dd, J = 14.0, 2.4 Hz, 1H), 8.56 (s, 1H), 8.45 (t, J = 2.2 Hz, 1H), 8.32 (d, J = 21.7 Hz, 1H), 8.25-8.16 (m, 1H), 7.96-7.83 (m, 2H), 5.34 (dd, J = 6.7, 4.9 Hz, 1H), 5.21 (d, J = 6.5 Hz, 1H), 4.41-4.16 (m, 1H), 4.13 (s, 3H), 4.04 (s, 3H), 1.67 (dd, J = 6.7, 2.8 Hz, 3H) |
| 959 | 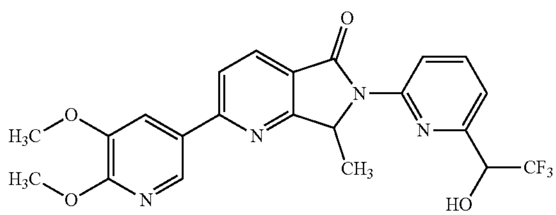 [SMILES: COc1cc(-c2ccc3c(n2)C(C)N(c2cccc(C(O)C(F)(F)F)n2)C3=O)cnc1OC] | 461.31 | (CDCl$_3$) δ 8.63 (d, J = 8.4 Hz, 1H), 8.49 (d, J = 1.9 Hz, 1H), 8.27 (d, J = 8.1 Hz, 1H), 8.00 (s, 1H), 7.97-7.88 (m, 2H), 7.31-7.23 (m, 1H), 5.77 (t, J = 6.6 Hz, 1H), 5.10 (dd, J = 8.8, 6.6 Hz, 1H), 4.16 (s, 3H), 4.06 (s, 3H), 1.80 (dd, J = 6.6, 4.5 Hz, 3H) |
| 960 | 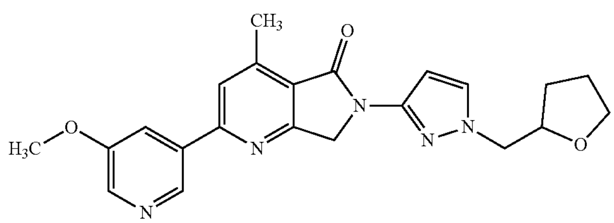 [SMILES: COc1cncc(-c2cc(C)c3c(n2)CN(c2ccn(CC4CCCO4)n2)C3=O)c1] | 406.25 | (CDCl$_3$) δ 8.85 (d, J = 1.7 Hz, 1H), 8.42 (d, J = 2.8 Hz, 1H), 8.03-7.89 (m, 1H), 7.62 (s, 1H), 7.50 (d, J = 2.4 Hz, 1H), 6.99 (d, J = 2.4 Hz, 1H), 4.99 (s, 2H), 4.38-4.07 (m, 3H), 3.99 (s, 3H), 3.94-3.72 (m, 2H), 2.85 (s, 3H), 2.13-1.66 (m, 4H) |
| 961 | 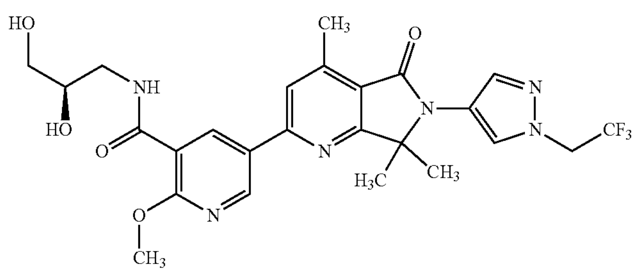 [SMILES: COc1ncc(-c2cc(C)c3c(n2)C(C)(C)N(c2cnn(CC(F)(F)F)c2)C3=O)cc1C(=O)NC[C@@H](O)CO] | 549.23 | (DMSO-d$_6$) δ 9.11 (d, J = 2.5 Hz, 1H), 8.93 (d, J = 2.5 Hz, 1H), 8.42 (t, J = 5.6 Hz, 1H), 8.33 (s, 1H), 8.01 (s, 1H), 7.94 (s, 1H), 5.18 (q, J = 9.1 Hz, 2H), 4.93 (d, J = 5.0 Hz, 1H), 4.67 (t, J = 5.7 Hz, 1H), 4.08 (s, 3H), 3.65 (dt, J = 10.8, 5.4 Hz, 1H), 3.56-3.44 (m, 1H), 3.44-3.34 (m, 2H), 3.30 (s, 1H), 2.73 (s, 3H), 1.61 (s, 6H) |
| 962 | 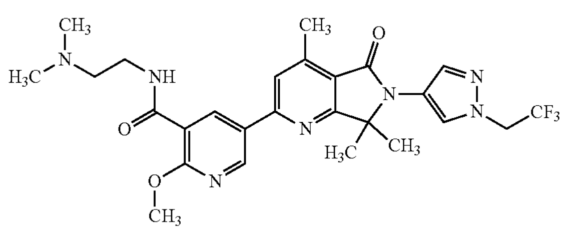 [SMILES: COc1ncc(-c2cc(C)c3c(n2)C(C)(C)N(c2cnn(CC(F)(F)F)c2)C3=O)cc1C(=O)NCCN(C)C] | 546.61 | (DMSO-d$_6$) δ 9.14 (d, J = 2.5 Hz, 1H), 8.95 (d, J = 2.5 Hz, 1H), 8.60 (t, J = 5.7 Hz, 1H), 8.33 (s, 1H), 8.01 (s, 1H), 7.94 (s, 1H), 5.19 q, J = 9.1 Hz, 2H), 4.09 (s, 3H), 3.67 (d, J = 5.8 Hz, 2H), 3.24 (s, 2H), 2.83 (s, 6H), 2.73 (s, 3H), 1.60 (s, 6H) |
| 963 | 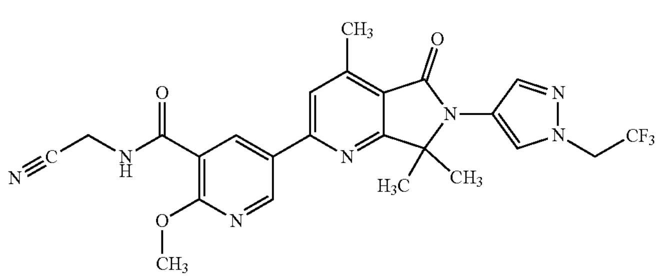 [SMILES: COc1ncc(-c2cc(C)c3c(n2)C(C)(C)N(c2cnn(CC(F)(F)F)c2)C3=O)cc1C(=O)NCC#N] | 514.22 | (DMSO-d$_6$) δ 9.16 (d, J = 2.5 Hz, 1H), 9.00 (t, J = 5.6 Hz, 1H), 8.95 (d, J = 2.5 Hz, 1H), 8.33 (s, 1H), 8.04 (s, 1H), 7.94 (d, J = 0.5 Hz, 1H), 5.19 (q, J = 9.1 Hz, 2H), 4.36 (d, J = 5.6 Hz, 2H), 4.09 (s, 3H), 2.73 (s, 3H), 1.61 (s, 6H) |

TABLE 1-continued

| Cmpd No. | Structure | ESMS (M + H) | ¹H NMR (300 MHz, unless indicated otherwise) |
|---|---|---|---|
| 964 | 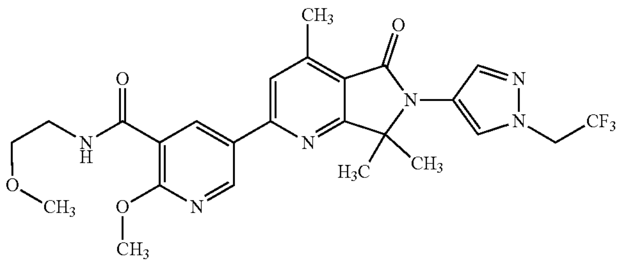 [SMILES: COCCNC(=O)c1cc(-c2cc(C)c3c(n2)C(C)(C)N(c2cnn(CC(F)(F)F)c2)C3=O)cnc1OC] | 533.23 | (DMSO-d₆) δ 9.11 (d, J = 2.5 Hz, 1H), 8.88 (d, J = 2.5 Hz, 1H), 8.40 (s, 1H), 8.33 (s, 1H), 8.02 (s, 1H), 7.94 (d, J = 0.6 Hz, 1H), 5.19 (q, J = 9.1 Hz, 2H), 4.08 (s, 3H), 3.50 (d, J = 2.6 Hz, 4H), 3.31 (d, J = 1.6 Hz, 3H), 2.73 (s, 3H), 1.61 (s, 6H) |
| 965 | 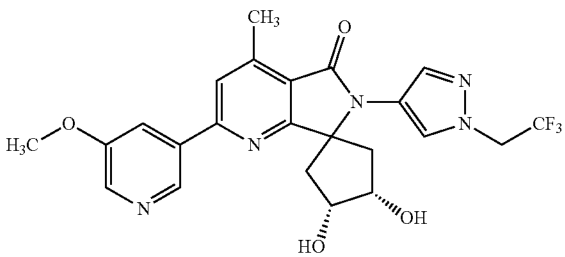 [SMILES: COc1cncc(-c2cc(C)c3c(n2)C2(C[C@@H](O)[C@@H](O)C2)N(c2cnn(CC(F)(F)F)c2)C3=O)c1] | 490 | |
| 966 | 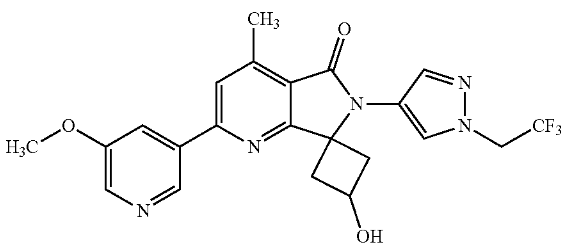 [SMILES: COc1cncc(-c2cc(C)c3c(n2)C2(CC(O)C2)N(c2cnn(CC(F)(F)F)c2)C3=O)c1] | 460.27 | (CDCl₃) δ 8.82 (d, J = 1.8 Hz, 1H), 8.47 (d, J = 2.8 Hz, 1H), 8.08 (s, 1H), 7.89-7.79 (m, 2H), 7.70 (d, J = 0.7 Hz, 1H), 6.37 (d, J = 12.4 Hz, 1H), 4.80 (q, J = 8.3 Hz, 2H), 4.55-4.36 (m, 1H), 3.98 (d, J = 9.5 Hz, 3H), 3.32- 3.13 (m, 2H), 2.86 (d, J = 0.6 Hz, 3H), 2.58-2.41 (m, 3H) |
| 967 | 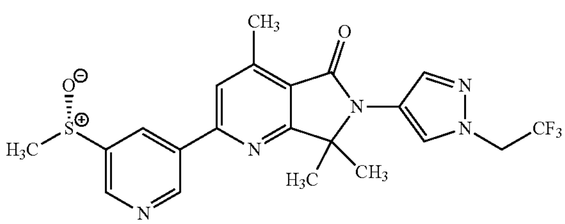 [SMILES: Cc1cc(-c2cncc([S@+](C)[O-])c2)nc2c1C(=O)N(c1cnn(CC(F)(F)F)c1)C2(C)C] | 464.23 | (CDCl₃) δ 9.48 (d, J = 1.7 Hz, 1H), 8.85 (d, J = 1.8 Hz, 1H), 8.80 (s, 1H), 8.16 (s, 1H), 7.83 (s, 1H), 7.73 (s, 1H), 4.77 (q, J = 8.3 Hz, 2H), 2.94 (d, J = 18.0 Hz, 3H), 2.86 (s, 3H), 1.74 (s, 6H) |
| 968 | 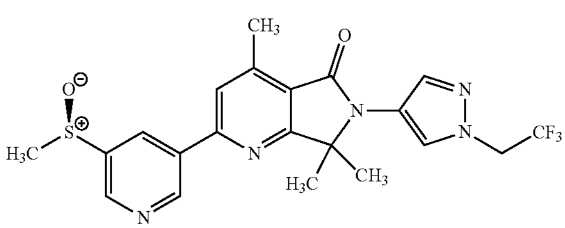 [SMILES: Cc1cc(-c2cncc([S@@+](C)[O-])c2)nc2c1C(=O)N(c1cnn(CC(F)(F)F)c1)C2(C)C] | 464.23 | (CDCl₃) δ 9.48 (d, J = 1.7 Hz, 1H), 8.85 (d, J = 1.8 Hz, 1H), 8.80 (s, 1H), 8.16 (s 1H), 7.83 (s, 1H), 7.73 (s, 1H), 4.77 (q, J = 8.3 Hz, 2H), 2.94 (d, J = 18.0 Hz, 3H), 2.86 (s, 3H), 1.74 (s, 6H) |
| 969 | 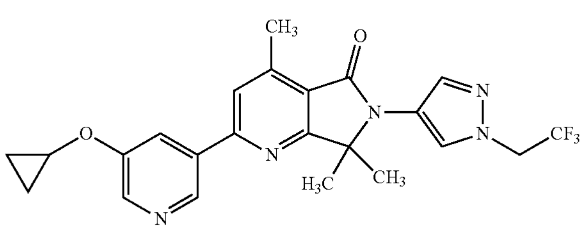 [SMILES: Cc1cc(-c2cncc(OC3CC3)c2)nc2c1C(=O)N(c1cnn(CC(F)(F)F)c1)C2(C)C] | 458.6 | (DMSO-d₆) δ 9.02 (d, J = 1.6 Hz, 1H), 8.51 (d, J = 2.7, 1H), 8.35 (s, 1H), 8.24-8.17 (m, 1H), 8.05 (s, 1H), 7.95 (s, 1H), 7.67-7.52 (m, 2H), 5.20 (q, J = 9.1, 2H), 4.11 (dt, J = 11.0, 4.1, 1H), 2.74 (s, 3H), 1.62 (s, 6H), 0.87 (t, J = 5.6, 2H), 0.80-0.70 (m, 2H) |

TABLE 1-continued

| Cmpd No. | Structure | ESMS (M + H) | ¹H NMR (300 MHz, unless indicated otherwise) |
|---|---|---|---|
| 970 | 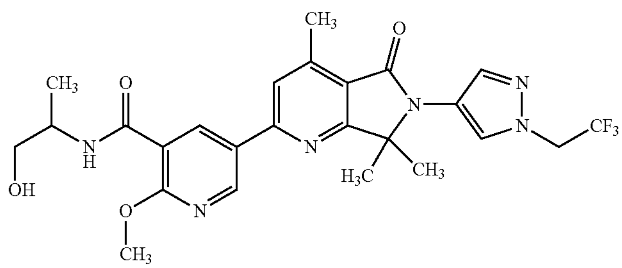 [SMILES: COc1ncc(-c2cc(C)c3c(n2)C(C)(C)N(c2cnn(CC(F)(F)F)c2)C3=O)cc1C(=O)NC(C)CO] | 533.23 | (DMSO-d$_6$) δ 9.10 (d, J = 2.5 Hz, 1H), 8.87 (d, J = 2.5 Hz, 1H), 8.33 (s, 1H), 8.01 (s, 1H), 7.94 (s, 1H), 5.75 (s, 3H), 5.18 (d, J = 9.1 Hz, 2H), 4.85 (t, J = 5.5 Hz, 1H), 4.07 (s, 4H), 3.56-3.37 (m, 2H), 2.73 (s, 3H), 1.61 (s, 6H), 1.18 (d, J = 6.7 Hz, 3H) |
| 971 | 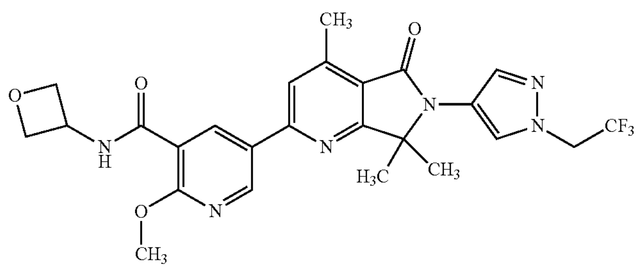 [SMILES: COc1ncc(-c2cc(C)c3c(n2)C(C)(C)N(c2cnn(CC(F)(F)F)c2)C3=O)cc1C(=O)NC1COC1] | 531.21 | (DMSO-d$_6$) δ 9.11 (d, J = 2.5 Hz, 1H), 8.77 (d, J = 2.5 Hz, 1H), 8.32 (s, 1H), 8.01 (s, 1H), 7.94 (s, 1H), 5.18 (q, J = 9.1 Hz, 2H), 5.07-4.95 (m, 1H), 4.79 (t, J = 6.9 Hz, 2H), 4.60 (t, J = 6.5 Hz, 2H), 4.06 (s, 3H), 2.72 (s, 3H), 1.60 (s, 6H) |
| 972 | 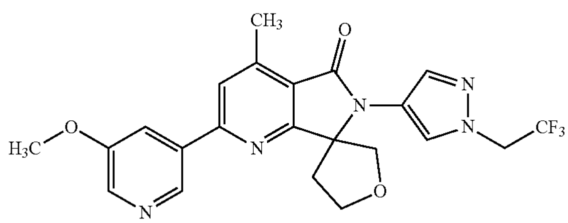 [SMILES: COc1cncc(-c2cc(C)c3c(n2)C2(CCOC2)N(c2cnn(CC(F)(F)F)c2)C3=O)c1] | 460.35 | |
| 973 | 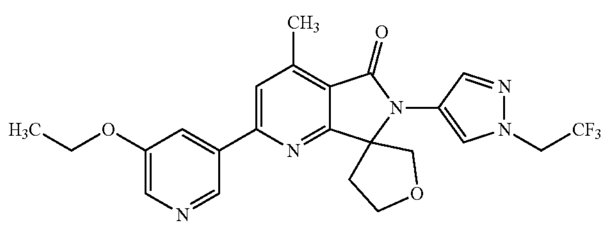 [SMILES: CCOc1cncc(-c2cc(C)c3c(n2)C2(CCOC2)N(c2cnn(CC(F)(F)F)c2)C3=O)c1] | 474.37 | |
| 974 | 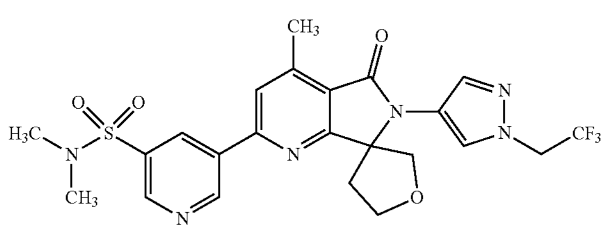 [SMILES: Cc1cc(-c2cncc(S(=O)(=O)N(C)C)c2)nc2c1C(=O)N(c1cnn(CC(F)(F)F)c1)C21CCOC1] | 537.26 | |
| 975 | 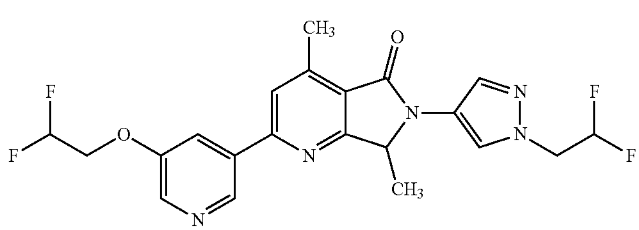 [SMILES: Cc1cc(-c2cncc(OCC(F)F)c2)nc2c1C(=O)N(c1cnn(CC(F)F)c1)C2C] | 450.51 | (DMSO-d$_6$) δ 9.05 (d, J = 1.7, 1H), 8.48 (d, J = 2.8, 1H), 8.30 (s, 1H), 8.19-8.13 (m, 1H), 8.11 (s, 1H), 7.92 (s, 1H), 6.68-6.25 (m, 1H), 6.43 (dt, 1H), 5.17 (m, 1H), 4.78-4.45 (m, 4H), 2.75 (s, 3H), 1.58 (d, J = 6.7 Hz, 3H) |

TABLE 1-continued

| Cmpd No. | Structure | ESMS (M + H) | ¹H NMR (300 MHz, unless indicated otherwise) |
|---|---|---|---|
| 976 | 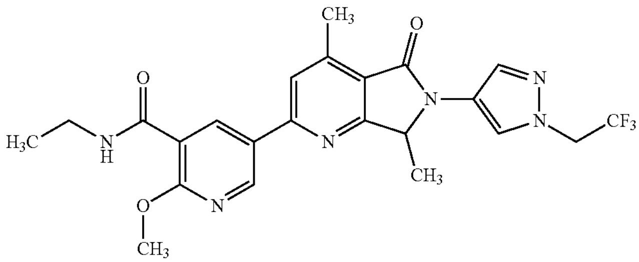 [SMILES: CCNC(=O)c1cc(-c2cc(C)c3c(n2)C(C)N(c2cnn(CC(F)(F)F)c2)C3=O)cnc1OC] | 489.27 | (DMSO-d$_6$) δ 9.09 (d, J = 2.5 Hz, 1H), 8.84 (d, J = 2.5 Hz, 1H), 8.39 (dd, J = 9.6, 3.5 Hz, 1H), 8.04 (s, 1H), 8.00-7.94 (m, 1H), 5.20 (dt, J = 9.4, 7.6 Hz, 3H), 4.06 (s, 3H), 3.40-3.28 (m, 2H), 2.73 (s, 3H), 1.58 (t, J = 7.1 Hz, 3H), 1.15 (t, J = 7.2 Hz, 3H) |
| 977 | 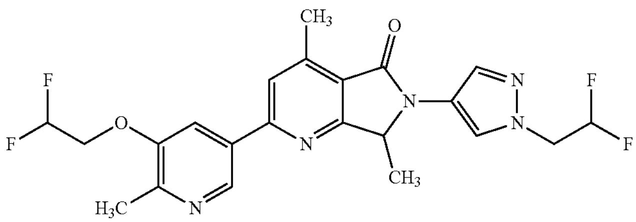 [SMILES: Cc1cc(-c2cnc(C)c(OCC(F)F)c2)nc2c1C(=O)N(c1cnn(CC(F)F)c1)C2C] | 464.52 | (DMSO-d$_6$) δ 8.91 (d, J = 1.6 Hz, 1H), 8.30 (s, 1H), 8.09 (s, 2H), 7.92 (s, 1H), 6.72-6.18 (m, 2H), 5.17 (q, J = 6.7 Hz, 2H), 4.68 (td, J = 15.1, 3.7 Hz, 2H), 4.55 (td, J = 14.5, 3.4 Hz, 2H), 2.74 (s, 3H), 2.46 (s, 3H), 1.57 (d, J = 6.7 Hz, 3H) |
| 978 | 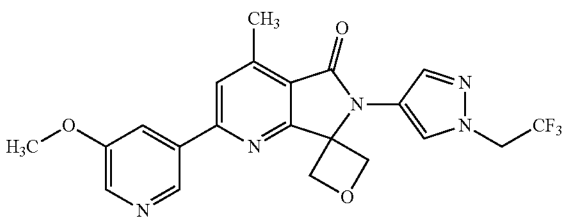 [SMILES: COc1cncc(-c2cc(C)c3c(n2)C2(COC2)N(c2cnn(CC(F)(F)F)c2)C3=O)c1] | 446.28 | |
| 979 | 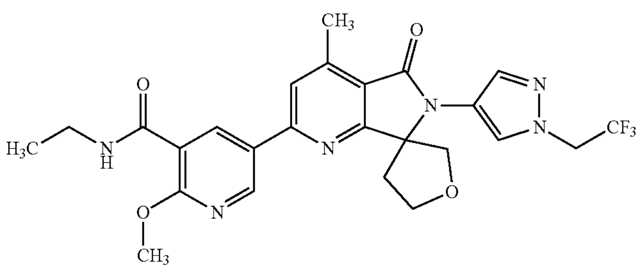 [SMILES: CCNC(=O)c1cc(-c2cc(C)c3c(n2)C2(CCOC2)N(c2cnn(CC(F)(F)F)c2)C3=O)cnc1OC] | 531.31 | |
| 980 | 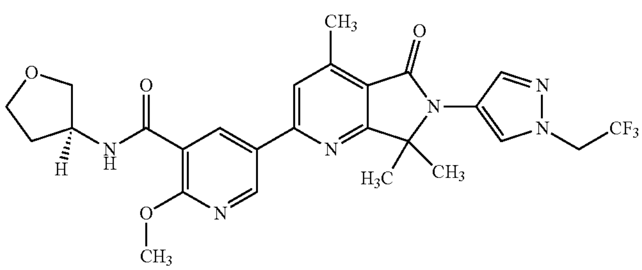 [SMILES: COc1ncc(-c2cc(C)c3c(n2)C(C)(C)N(c2cnn(CC(F)(F)F)c2)C3=O)cc1C(=O)N[C@H]1CCOC1] | 545.2 | (DMSO-d$_6$) δ 9.10 (d, J = 2.5 Hz, 1H), 8.73 (d, J = 2.5 Hz, 1H), 8.47 (d, J = 6.7 Hz, 1H), 8.34 (s, 1H), 8.02 (s, 1H), 7.95 (s, 1H), 5.20 (q, J = 9.1 Hz, 2H), 4.60-4.39 (m, 1H), 4.04 (s, 3H), 3.91-3.80 (m, 2H), 3.73 (td, J = 8.1, 5.7 Hz, 1H), 3.62 (dd, J = 8.9, 3.9 Hz, 1H), 2.72 (s, 3H), 2.31-2.11 (m, 1H), 2.02-1.80 (m, 1H), 1.60 (s, 6H) |
| 981 | 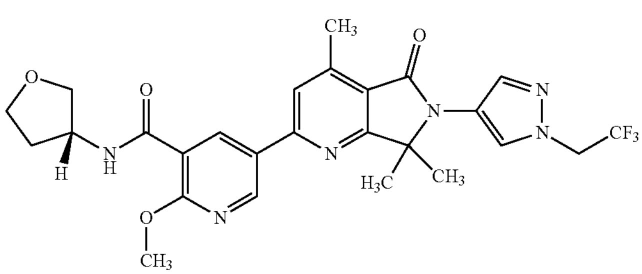 [SMILES: COc1ncc(-c2cc(C)c3c(n2)C(C)(C)N(c2cnn(CC(F)(F)F)c2)C3=O)cc1C(=O)N[C@@H]1CCOC1] | 545.2 | (DMSO-d$_6$) δ 9.10 (d, J = 2.5 Hz, 1H), 8.73 (d, J = 2.5 Hz, 1H), 8.47 (d, J = 6.7 Hz, 1H), 8.34 (s, 1H), 8.02 (s, 1H), 7.95 (s, 1H), 5.20 (q, J = 9.1 Hz, 2H), 4.58-4.41 (m, 1H), 4.04 (s, 3H), 3.92-3.80 (m, 2H), 3.73 (td, J = 8.1, 5.8 Hz, 1H), 3.63 (dd, J = 8.9, 3.9 Hz, 1H), 2.72 (s, 3H), 2.30-2.11 (m, 1H), 2.01-1.79 (m, 1H), 1.60 (s, 6H) |

TABLE 1-continued

| Cmpd No. | Structure | ESMS (M + H) | ¹H NMR (300 MHz, unless indicated otherwise) |
|---|---|---|---|
| 982 | 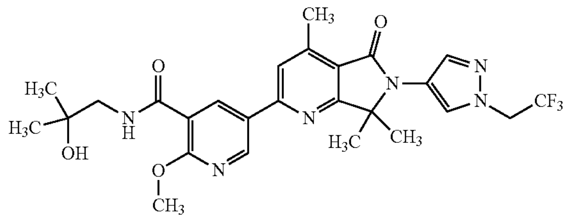 [SMILES: COc1ncc(-c2cc(C)c3c(n2)C(C)(C)N(c2cnn(CC(F)(F)F)c2)C3=O)cc1C(=O)NCC(C)(C)O] | 547.21 | (DMSO-d$_6$) δ 9.12 (d, J = 2.5 Hz, 1H), 8.91 (d, J = 2.5 Hz, 1H), 8.34 (s, 1H), 8.30 (t, J = 5.8 Hz, 1H), 8.03 (s, 1H), 7.95 (d, J = 0.5 Hz, 1H), 5.20 (q, J = 9.1 Hz, 2H), 4.08 (s, 3H), 3.31 (d, J = 5.8 Hz, 2H), 2.73 (s, 3H), 1.61 (s, 6H), 1.16 (s, 6H) |
| 983 | 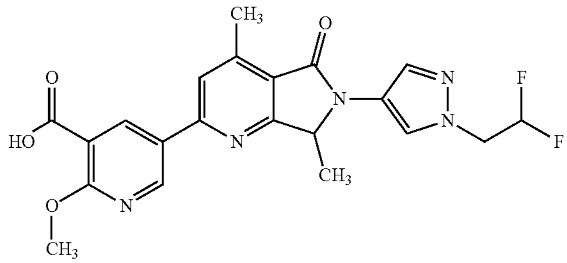 [SMILES: COc1ncc(-c2cc(C)c3c(n2)C(C)N(c2cnn(CC(F)F)c2)C3=O)cc1C(=O)O] | 444.17 | (DMSO-d$_6$) δ 13.25 (s, 1H), 9.16 (d, J = 2.4 Hz, 1H), 8.87 (d, J = 2.5 Hz, 1H), 8.29 (s, 1H), 8.05 (s, 1H), 7.91 (s, 1H), 6.40 (t, J = 55.0 Hz, 1H), 5.16 (d, J = 6.6 Hz, 1H), 4.68 (dd, J = 15.1, 11.7 Hz, 2H), 4.02 (s, 3H), 2.73 (s, 3H), 1.56 (d, J = 6.5 Hz, 3H) |
| 984 | 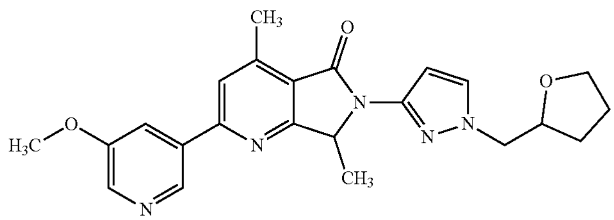 [SMILES: COc1cncc(-c2cc(C)c3c(n2)C(C)N(c2ccn(CC4CCCO4)n2)C3=O)c1] | 420.23 | (methanol-d$_4$) δ 8.90 (s, 1H), 8.41 (s, 1H), 8.15 (s, 1H), 7.68 (s, 1H), 7.51 (d, J = 2.4 Hz, 1H), 6.89 (d, J = 2.4 Hz, 1H), 5.28 (q, J = 6.6 Hz, 1H), 4.41-4.06 (m, 2H), 4.02 (s, 2H), 3.82 (qd, J = 14.6, 8.2 Hz, 1H), 2.83 (s, 2H), 2.19-1.79 (m, 2H), 1.73 (dd, J = 12.6, 4.8 Hz, 2H) |
| 985 | 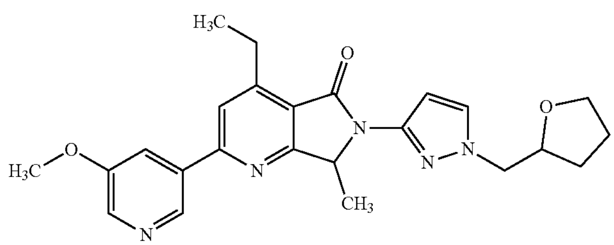 [SMILES: CCc1cc(-c2cncc(OC)c2)nc2c1C(=O)N(c1ccn(CC3CCCO3)n1)C2C] | 434.25 | (CDCl$_3$) δ 9.12 (s, 1H), 8.56 (s, 1H), 8.47 (s, 1H), 7.72 (s, 1H), 7.51 (s, 1H), 6.97 (s, 1H), 5.29 (d, J = 6.7 Hz, 1H), 4.37-4.15 (m, 3H), 4.11 (s, 3H), 3.83 (dd, J = 15.7, 7.1 Hz, 2H), 3.31 (d, J = 7.6 Hz, 2H), 1.88 (dd, J = 54.6, 25.9 Hz, 7H), 1.42 (t, J = 7.7 Hz, 3H) |
| 986 | 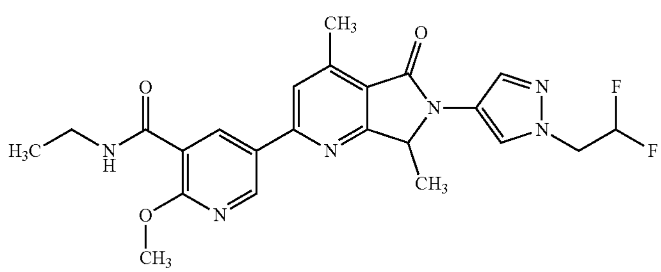 [SMILES: CCNC(=O)c1cc(-c2cc(C)c3c(n2)C(C)N(c2cnn(CC(F)F)c2)C3=O)cnc1OC] | 471.21 | (DMSO-d$_6$) δ 9.09 (d, J = 2.5 Hz, 1H), 8.84 (d, J = 2.4 Hz, 1H), 8.40 (s, 1H), 8.29 (s, 1H), 8.03 (s, 1H), 7.91 (s, 1H), 6.40 (t, J = 55.0 Hz, 1H), 5.16 (d, J = 6.5 Hz, 1H), 4.68 (dd, J = 15.2, 11.6 Hz, 2H), 4.06 (s, 3H), 2.73 (s, 3H), 1.56 (d, J = 6.7 Hz, 3H), 1.15 (t, J = 7.2 Hz, 3H) |
| 987 | 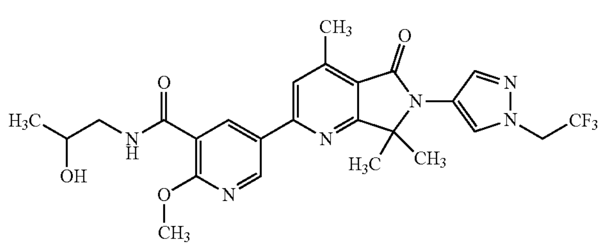 [SMILES: COc1ncc(-c2cc(C)c3c(n2)C(C)(C)N(c2cnn(CC(F)(F)F)c2)C3=O)cc1C(=O)NCC(C)O] | 533.2 | (DMSO-d$_6$) δ 9.12 (d, J = 2.5 Hz, 1H), 8.89 (d, J = 2.5 Hz, 1H), 8.37 (s, 1H), 8.34 (s, 1H), 5.20 (d, J = 9.1 Hz, 2H), 4.07 (s, 3H), 3.81 (dd, J = 11.7, 6.3 Hz, 1H), 3.39-3.17 (m, 2H), 2.72 (s, 3H), 1.60 (s, 6H), 1.11 (d, J = 6.2 Hz, 3H) |

TABLE 1-continued

| Cmpd No. | Structure | ESMS (M + H) | ¹H NMR (300 MHz, unless indicated otherwise) |
|---|---|---|---|
| 988 | 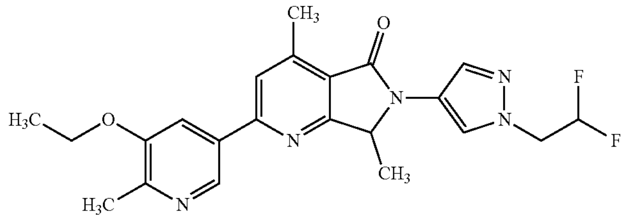 [SMILES: CCOc1cc(-c2cc(C)c3c(n2)C(C)N(c2cnn(CC(F)F)c2)C3=O)cnc1C] | 428.23 | (DMSO-d₆) δ 8.82 (d, J = 1.7 Hz, 1H), 8.30 (s, 1H), 8.06 (s, 1H), 7.98 (d, J = 1.7 Hz, 1H), 7.91 (s, 1H), 6.41 (ddt, J = 58.6, 54.9, 3.8 Hz, 1H), 5.17 (q, J = 6.6 Hz, 1H), 4.68 (td, J = 15.1, 3.7 Hz, 1H), 4.22 (q, J = 6.9 Hz, 1H), 2.73 (s, 3H), 2.44 (s, 3H), 1.56 (d, J = 6.7 Hz, 3H), 1.48-1.37 (m, 3H) |
| 989 | 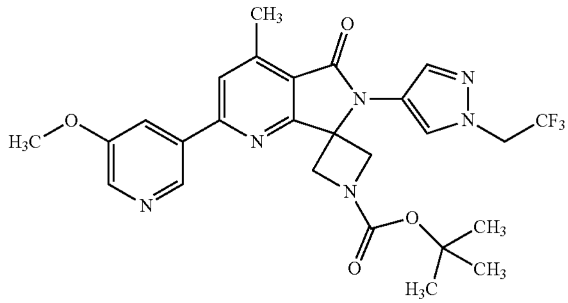 [SMILES: COc1cncc(-c2cc(C)c3c(n2)C2(CN(C(=O)OC(C)(C)C)C2)N(c2cnn(CC(F)(F)F)c2)C3=O)c1] | 545.26 | |
| 990 | 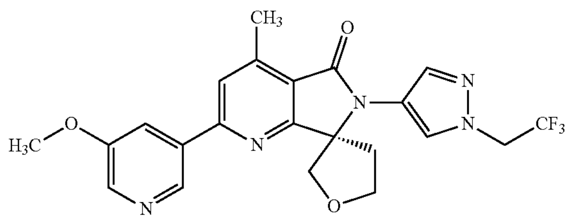 [SMILES: COc1cncc(-c2cc(C)c3c(n2)[C@@]2(CCOC2)N(c2cnn(CC(F)(F)F)c2)C3=O)c1] | 460.29 | |
| 991 | 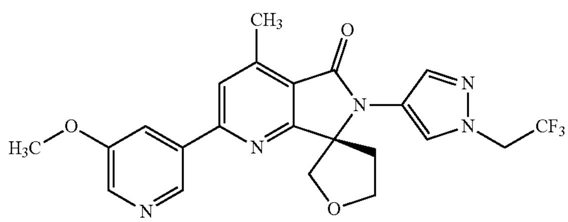 [SMILES: COc1cncc(-c2cc(C)c3c(n2)[C@]2(CCOC2)N(c2cnn(CC(F)(F)F)c2)C3=O)c1] | 460.29 | |
| 992 | 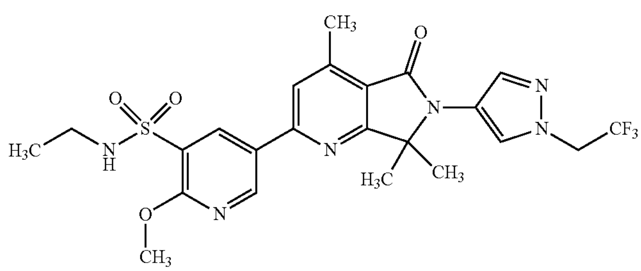 [SMILES: CCNS(=O)(=O)c1cc(-c2cc(C)c3c(n2)C(C)(C)N(c2cnn(CC(F)(F)F)c2)C3=O)cnc1OC] | 539.5 | (CDCl₃) δ 9.13 (d, J = 2.4 Hz, 1H), 8.88 (d, J = 2.4 Hz, 1H), 8.16 (s, 1H), 7.82 (s, 1H), 7.59 (s, 1H), 4.91 (s, 1H), 4.77 (q, J = 8.4 Hz, 2H), 4.21 (s, 3H), 3.16-2.96 (m, 2H), 2.84 (s, 3H), 1.72 (s, 6H), 1.17 (t, J = 7.2 Hz, 3H) |
| 993 | 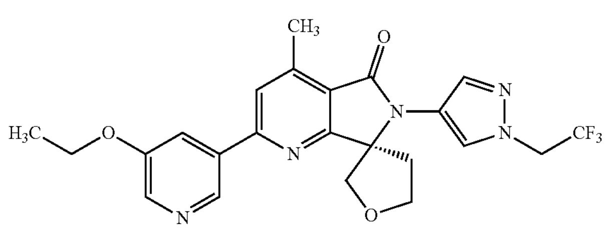 [SMILES: CCOc1cncc(-c2cc(C)c3c(n2)[C@@]2(CCOC2)N(c2cnn(CC(F)(F)F)c2)C3=O)c1] | 474.3 | |

TABLE 1-continued

| Cmpd No. | Structure | ESMS (M + H) | ¹H NMR (300 MHz, unless indicated otherwise) |
|---|---|---|---|
| 994 | 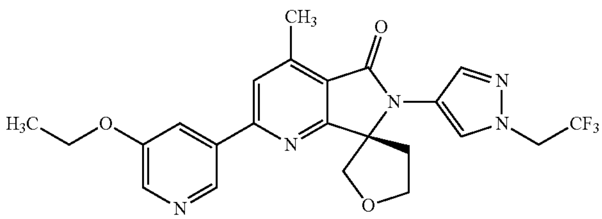 [SMILES: CCOc1cncc(-c2cc(C)c3c(n2)[C@]2(CCOC2)N(c2cnn(CC(F)(F)F)c2)C3=O)c1] | 474.3 | |
| 995 | 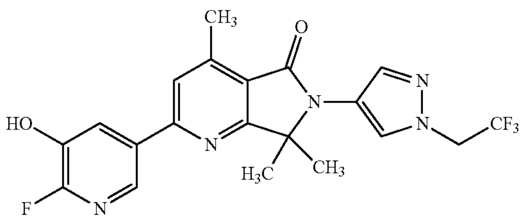 [SMILES: Cc1cc(-c2cnc(F)c(O)c2)nc2c1C(=O)N(c1cnn(CC(F)(F)F)c1)C2(C)C] | 436.3 | |
| 996 | 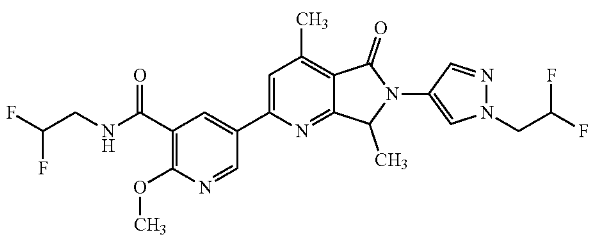 [SMILES: COc1ncc(-c2cc(C)c3c(n2)C(C)N(c2cnn(CC(F)F)c2)C3=O)cc1C(=O)NCC(F)F] | 507.15 | (DMSO-d$_6$) δ 9.13 (d, J = 2.5 Hz, 1H), 8.90 (d, J = 2.5 Hz, 1H), 8.71 (t, J = 6.0 Hz, 1H), 8.29 (s, 1H), 8.04 (s, 1H), 7.91 (s, 1H), 6.62-5.95 (m, 2H), 5.17 (q, J = 6.7 Hz, 1H), 4.68 (td, J = 15.1, 3.7 Hz, 2H), 4.06 (d, J = 10.3 Hz, 3H), 3.87-3.65 (m, 2H), 2.73 (s, 3H), 1.56 (d, J = 6.7 Hz, 3H) |
| 997 | 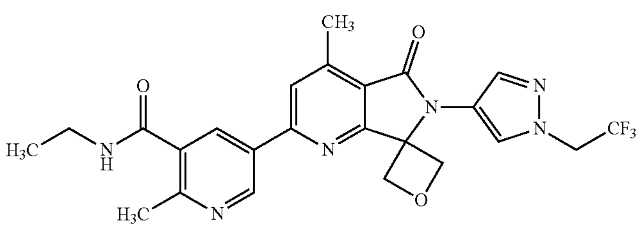 [SMILES: CCNC(=O)c1cc(-c2cc(C)c3c(n2)C2(COC2)N(c2cnn(CC(F)(F)F)c2)C3=O)cnc1C] | 517.3 | |
| 998 | 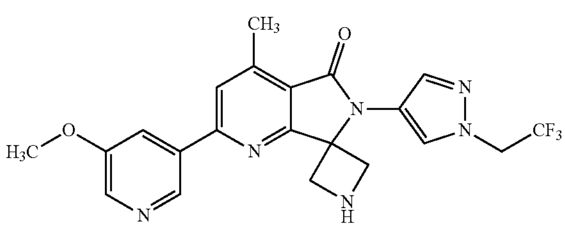 [SMILES: COc1cncc(-c2cc(C)c3c(n2)C2(CNC2)N(c2cnn(CC(F)(F)F)c2)C3=O)c1] | 445.32 | |
| 999 | 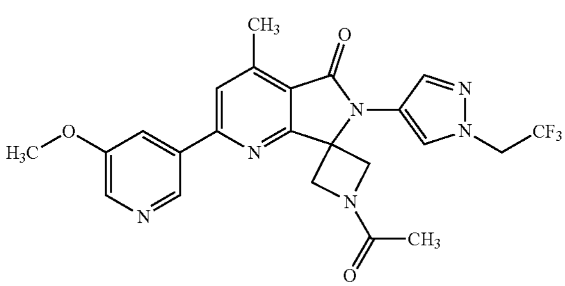 [SMILES: COc1cncc(-c2cc(C)c3c(n2)C2(CN(C(C)=O)C2)N(c2cnn(CC(F)(F)F)c2)C3=O)c1] | 487.36 | |

TABLE 1-continued

| Cmpd No. | Structure | ESMS (M + H) | $^1$H NMR (300 MHz, unless indicated otherwise) |
|---|---|---|---|
| 1000 | 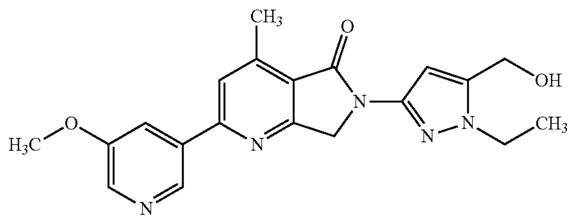 [SMILES: CCn1nc(N2Cc3nc(-c4cncc(OC)c4)cc(C)c3C2=O)cc1CO] | 380.37 | (methanol-$d_4$) δ 9.12 (s, 1H), 8.68 (s, 1H), 8.58 (s, 1H), 8.05 (s, 1H), 6.81 (s, 1H), 4.96 (s, 2H), 4.64 (s, 2H), 4.20 (q, J = 7.2 Hz, 2H), 4.12 (s, 3H), 2.82 (s, 3H), 1.45 (t, J = 7.2 Hz, 3H) |
| 1001 | 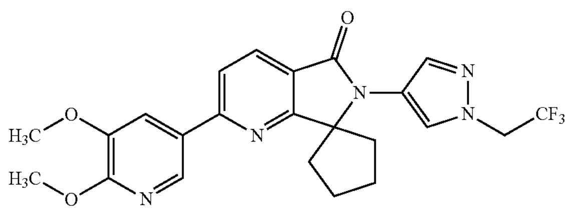 [SMILES: COc1cc(-c2ccc3c(n2)C2(CCCC2)N(c2cnn(CC(F)(F)F)c2)C3=O)cnc1OC] | 474.47 | (DMSO-$d_6$) δ 8.59 (d, J = 1.9 Hz, 1H), 8.29 (s, 1H), 8.21-8.14 (m, 2H), 7.99 (d, J = 1.9 Hz, 1H), 7.87 (s, 1H), 5.23 (q, J = 9.1 Hz, 2H), 3.94 (d, J = 11.6 Hz, 6H), 2.15 (d, J = 16.1 Hz, 6H), 1.83 (d, J = 3.4 Hz, 2H) |
| 1002 | 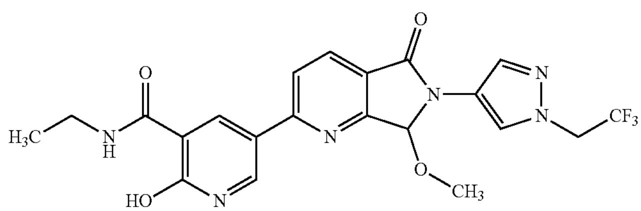 [SMILES: CCNC(=O)c1cc(-c2ccc3c(n2)C(OC)N(c2cnn(CC(F)(F)F)c2)C3=O)cnc1O] | 491.26 | (methanol-$d_4$) δ 9.81 (s, NH), 9.16 (d, J = 2.8 Hz, 1H), 8.55 (d, J = 2.8 Hz, 1H), 8.26 (s, 1H), 8.03 (s, 1H), 7.71 (s, 1H), 6.09 (s, 1H), 4.82 (q, J = 8.4 Hz, 2H), 3.57-3.45 (m, 2H), 3.13 (s, 3H), 2.82 (s, H) |
| 1003 | 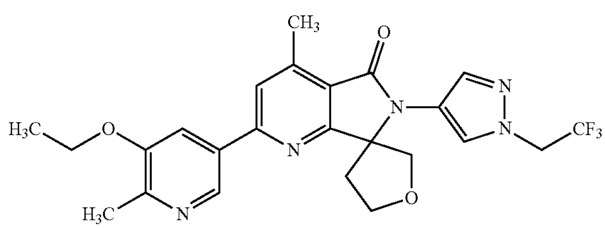 [SMILES: CCOc1cc(-c2cc(C)c3c(n2)C2(CCOC2)N(c2cnn(CC(F)(F)F)c2)C3=O)cnc1C] | 488.25 | (CDCl$_3$) δ 8.73 (d, J = 1.8 Hz, 1H), 8.38 (s, 1H), 8.19 (s, 1H), 7.84 (d, J = 1.8 Hz, 1H), 7.64 (d, J = 0.6 Hz, 1H), 4.77 (q, J = 8.3 Hz, 2H), 4.45 (dt, J = 8.4, 4.2 Hz, 1H), 4.40-4.30 (m, 2H), 4.30-4.07 (m, 3H), 2.84 (s, 3H), 2.68-2.58 (m, 1H), 2.57 (s, 3H), 2.49-2.38 (m, 1H), 1.59-1.50 (t, 3H) |
| 1004 | 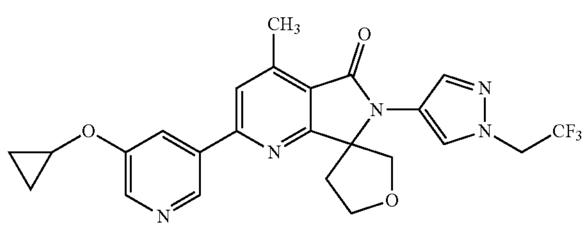 [SMILES: Cc1cc(-c2cncc(OC3CC3)c2)nc2c1C(=O)N(c1cnn(CC(F)(F)F)c1)C21CCOC1] | 486.27 | (CDCl$_3$) δ 8.93 (d, J = 1.8 Hz, 1H), 8.56 (d, J = 2.8 Hz, 1H), 8.38 (s, 1H), 8.20 (s, 1H), 8.14-8.06 (m, 1H), 7.66 (s, 1H), 4.77 (q, J = 8.3 Hz, 2H), 4.46 (t, J = 7.7 Hz, 1H), 4.40-4.20 (m, 3H), 4.02-3.82 (m, 1H), 2.85 (s, 3H), 2.72-2.51 (m, 1H), 2.51-2.32 (m, 1H), 1.03-0.74 (m, 4H) |
| 1005 | 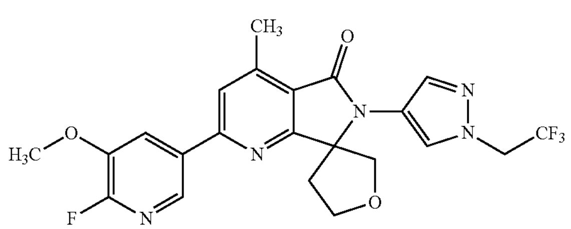 [SMILES: COc1cc(-c2cc(C)c3c(n2)C2(CCOC2)N(c2cnn(CC(F)(F)F)c2)C3=O)cnc1F] | 478.27 | (CDCl$_3$) δ 8.42 (t, J = 1.8 Hz, 1H), 8.37 (s, 1H), 8.19 (s, 1H), 8.07 (dd, J = 9.7, 2.0 Hz, 1H), 7.64 (s, 1H), 4.77 (q, J = 8.3 Hz, 2H), 4.46 (td, J = 8.4, 2.1 Hz, 1H), 4.41-4.18 (m, 3H), 4.06 (s, 3H), 2.85 (s, 3H), 2.62 (ddd, J = 13.2, 10.7, 8.3 Hz, 1H), 2.43 (ddd, J = 13.2, 6.7, 2.2 Hz, 1H) |

TABLE 1-continued

| Cmpd No. | Structure | ESMS (M + H) | ¹H NMR (300 MHz, unless indicated otherwise) |
|---|---|---|---|
| 1006 | 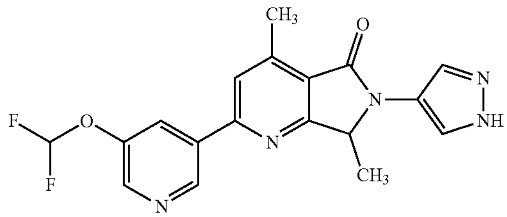 [SMILES: Cc1cc(-c2cncc(OC(F)F)c2)nc2c1C(=O)N(c1cn[nH]c1)C2C] | 386.18 | (DMSO-d$_6$) δ 12.94 (s, 1H), 9.05 (d, J = 1.7 Hz, 1H), 8.48 (d, J = 2.8 Hz, 1H), 8.19-8.08 (m, 3H), 7.90 (d, J = 6.5 Hz, 1H), 6.48 (tt, J = 54.3, 3.4 Hz, 1H) 5.15 (q, J = 6.6 Hz, 1H), 4.57 (td, J = 14.7, 3.4 Hz, 2H), 2.77 (d, J = 14.3 Hz, 3H), 1.57 (t, J = 7.7 Hz, 3H) |
| 1007 | 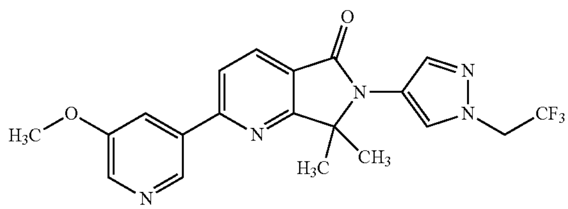 [SMILES: COc1cncc(-c2ccc3c(n2)C(C)(C)N(c2cnn(CC(F)(F)F)c2)C3=O)c1] | 418.63 | (DMSO-d$_6$) δ 9.01 (d, J = 1.7 Hz, 1H), 8.44 (d, J = 2.8 Hz, 1H), 8.37 (s, 1H), 8.33-8.23 (m, 2H), 8.10 (dd, J = 2.8, 1.9 Hz, 1H), 7.97 (d, J = 0.5 Hz, 1H), 5.22 (q, J = 9.1 Hz, 2H), 3.96 (s, 3H), 1.65 (s, 6H) |
| 1008 | 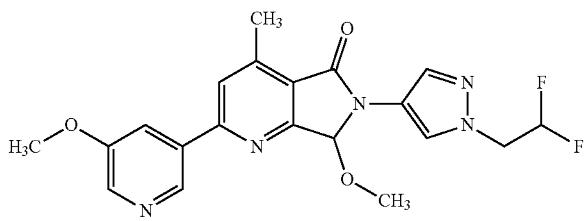 [SMILES: COc1cncc(-c2cc(C)c3c(n2)C(OC)N(c2cnn(CC(F)F)c2)C3=O)c1] | 416.2 | (CDCl$_3$) δ 8.87 (d, J = 1.6 Hz, 1H), 8.44 (d, J = 2.8 Hz, 1H), 8.21 (s, 1H), 7.99 (dd, J = 7.3, 5.5 Hz, 2H), 7.72 (s, 1H), 6.37-5.91 (m, 2H), 4.52 (td, J = 13.5, 4.3 Hz, 2H), 4.00 (s, 3H), 3.18 (s, 3H), 2.85 (s, 3H) |
| 1009 | 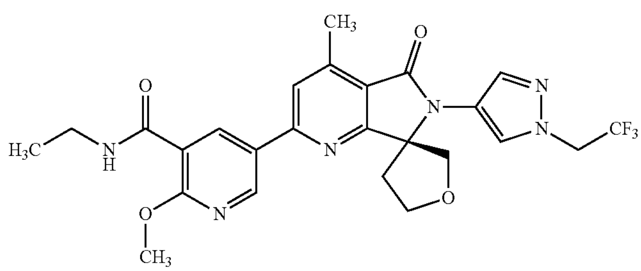 [SMILES: CCNC(=O)c1cc(-c2cc(C)c3c(n2)[C@@]2(CCOC2)N(c2cnn(CC(F)(F)F)c2)C3=O)cnc1OC] | | (DMSO-d$_6$) δ 9.12 (s, 1H), 8.84 (s, 1H), 8.40 (s, 1H), 8.33 (s, 1H), 8.06 (s, 1H), 7.94 (s, 1H), 5.23 (d, J = 8.9 Hz, 2H), 4.25 (d, J = 9.7 Hz, 1H), 4.13-4.09 (m, 3H), 2.72 (s, 3H), 2.47-2.35 (m, 2H), 1.15 (t, J = 7.0 Hz, 3H) |
| 1010 | 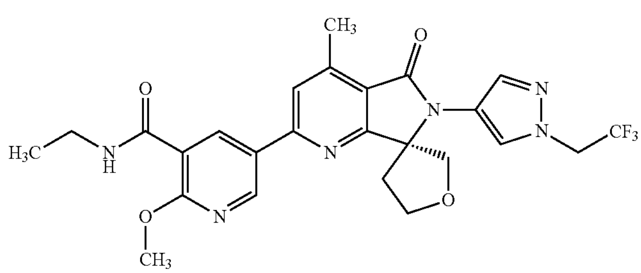 [SMILES: CCNC(=O)c1cc(-c2cc(C)c3c(n2)[C@]2(CCOC2)N(c2cnn(CC(F)(F)F)c2)C3=O)cnc1OC] | | (DMSO-d$_6$) δ 9.12 (s, 1H), 8.84 (s, 1H), 8.40 (s, 1H), 8.33 (s, 1H), 8.06 (s, 1H), 7.94 (s, 1H), 5.23 (d, J = 8.9 Hz, 2H), 4.25 (d, J = 9.7 Hz, 1H), 4.13-4.09 (m, 3H), 2.72 (s, 3H), 2.47-2.35 (m, 2H), 1.15 (t, J = 7.0 Hz, 3H) |
| 1011 | 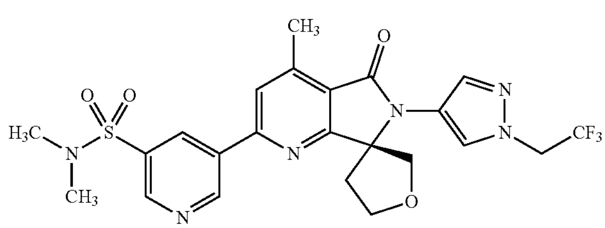 [SMILES: Cc1cc(-c2cncc(S(=O)(=O)N(C)C)c2)nc2c1C(=O)N(c1cnn(CC(F)(F)F)c1)[C@]21CCOC1] | | (DMSO-d$_6$) δ 9.69 (s, 1H), 9.05 (s, 1H), 8.80 (s, 1H), 8.35 (s, 1H), 8.28 (s, 1H), 7.96 (s, 1H), 5.24 (dd, J = 18.1, 8.9 Hz, 2H), 4.27 (d, J = 10.3 Hz, 1H), 4.12-4.08 (m 3H), 2.76 (s, 3H), 2.74 (s, 6H), 2.48-2.41 (m, 2H) |

| Cmpd No. | Structure | ESMS (M + H) | ¹H NMR (300 MHz, unless indicated otherwise) |
|---|---|---|---|
| 1012 | 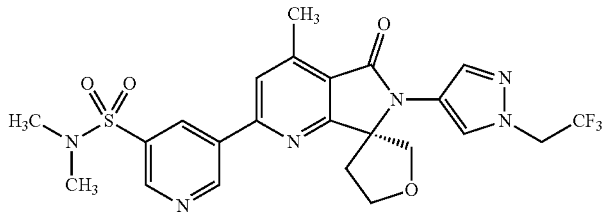 [SMILES: Cc1cc(-c2cncc(S(=O)(=O)N(C)C)c2)nc2c1C(=O)N(c1cnn(CC(F)(F)F)c1)[C@@]21CCOC1] | | (DMSO-d₆) δ 9.69 (s, 1H), 9.05 (s, 1H), 8.80 (s, 1H), 8.35 (s, 1H), 8.28 (s, 1H), 7.96 (s, 1H), 5.24 (dd, J = 18.1, 8.9 Hz, 2H), 4.27 (d, J = 10.3 Hz, 1H), 4.12-4.08 (m 3H), 2.76 (s, 3H), 2.74 (s, 6H), 2.48-2.41 (m, 2H) |
| 1013 | 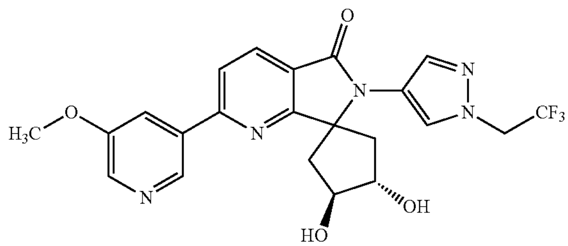 [SMILES: COc1cncc(-c2ccc3c(n2)C2(C[C@H](O)[C@@H](O)C2)N(c2cnn(CC(F)(F)F)c2)C3=O)c1] | 490.16 | |

Biological Assay of Compounds of the Invention

Example 25. PI3K Inhibition Assay

Using a Biomek FX from Beckman Coulter, 1.5 µL of each of ten 2.5-fold serial dilutions of a compound of the invention in 100% DMSO was added to an individual well (hereafter, "test well") in a 96 well polystyrene plate [Corning, Costar Item No. 3697]. One test well also contained 1.5 µL of DMSO with no compound. Another well contained an inhibitor in DMSO at a concentration known to completely inhibit the enzyme, (hereafter "background well"). Using a Titertek Multidrop, 50 µL of Reaction Mix [100 mM HEPES pH 7.5, 50 mM NaCl, 10 mM DTT, 0.2 mg/mL BSA, 60 µM phosphatidylinositol(4,5)bisphosphate diC16 (PI(4,5)P$_2$; Avanti Polar Lipids, Cat. No. 840046P) and PI3K isoform of interest (see Table 3 for isoform concentrations)] was added to each well. To initiate the reaction, 50 µL of ATP Mix [20 mM MgCl$_2$, 6 µM ATP (100 µCi/µmole $^{33}$P-ATP)] was added each well, followed by incubating the wells for 30 min. at 25° C. Final concentrations in each well were 50 mM HEPES 7.5, 10 mM MgCl$_2$, 25 mM NaCl, 5 mM DTT, 0.1 mg/mL BSA, 30 µM PI(4,5)P$_2$, 3 µM ATP, and the PI3K isoform of interest (see Table 2). Final compound concentrations in each well ranged from 10 µM to 1 nM.

TABLE 2

| PI3K Isoform Concentrations | PI3K-α | PI3K-β | PI3K-γ | PI3K-δ |
|---|---|---|---|---|
| Enzyme concentration in Reaction Mix | 4 nM | 20 nM | 4 nM | 4 nM |
| Final enzyme concentration | 2 nM | 10 nM | 2 nM | 2 nM |

After incubation, the reactions in each well were quenched by addition of 50 µL of stop solution [30% TCA/Water, 10 mM ATP]. Each quenched reaction mixture was then transferred to a 96 well glass fiber filter plate [Corning, Costar Item No. 3511]. The plate was vacuum-filtered and washed three times with 150 µL of 5% TCA/water in a modified Bio-Tek Instruments ELX-405 Auto Plate Washer. 50 µL of scintillation fluid was added to each well and the plate read on a Perkin-Elmer TopCount™ NXT liquid scintillation counter to obtain $^{33}$P-counts representing inhibition values.

The value for the background well was subtracted from the value obtained for each test well and the data were fit to the competitive tight binding Ki equation described by Morrison and Stone, *Comments Mol. Cell Biophys.* 2: 347-368, 1985.

Each of the following compounds has a Ki of less than 0.1 micromolar for the inhibition of PI3K-gamma: 1, 3, 6, 10, 12, 16, 18-20, 24-26, 34-36, 38, 44, 46-48, 51-59, 64, 66-68, 70-73, 77-82, 85-109, 113-119, 122-124, 126, 128-133, 135-136, 138-141, 143-156, 158, 161, 165-166, 170, 172, 174-176, 178, 181-187, 194, 198-201, 204-219, 221-223, 225-227, 229-230, 234, 236-237, 239, 241, 243-247, 250-273, 275-285, 287-312, 315, 317, 320-322, 324-328, 330-332, 336-340, 342-347, 363, 365-366, 368-388, 388-389, 391-407, and 409-411, 412-424, 426-437, 439-455, 457-461, 463-464, 466, 468-472, 474-478, 480-481, 483-495, 497, 499-506, 508-573, 576-584, 587-607, 609, 612, 614-616, 618-623, 625-658, 661, 664, 666-672, 674-681, 683-685, 687-688, 690-695, 698-706, 708-710, 712-730, 732-740, 742-749, 754-758, 760-762, 764-770, 772-779, 781-787, 789-801, 802-803, 810-818, 822-825, 829-833, 835-838, 840, 843-871, 873, 875-893, 896, 899-900, 902-906, 909-911, 913-916, 918-933, 935-943, 945-950, 952-956, 958-984, 986-999.

Each of the following compounds has a Ki of 0.1 micromolar to 0.49 micromolar for the inhibition of PI3K-gamma: 2, 5, 7, 9, 13-15, 17, 22, 23, 27-33, 37, 39-43, 45, 49-50, 60-63, 65, 69, 74-76, 83, 110, 112, 120, 125, 127, 134, 137, 142, 157, 159-160, 162, 164, 167-168, 171, 173, 177, 179-180, 188-193, 196-197, 202-203, 224, 228, 231-232, 240, 242, 248, 286, 313, 316, 318-319, 329, 333-335, 341, 348, 364, 367, 390, 408, 425, 456, 462, 465, 467, 473, 479, 482, 496, 507, 574-575, 585-586, 608, 611, 613, 617, 624, 660, 662, 686, 689, 696, 697, 707, 711, 731, 741, 750, 771, 780, 802, 809, 819, 820-821, 834, 839, 872, 874, 894-895, 897-898, 901, 907-908, 912, 934, 944, 951, and 957.

Each of the following compounds has a Ki of 0.5 micromolar to 2.5 micromolar for the inhibition of PI3K-gamma:

4, 11, 21, 84, 111, 121, 163, 169, 195, 220, 233, 235, 238, 249, 274, 314, 323, 610, 659, 663, 665, 673, 682, 751, 759, 763, 826, 841, 842, 917, and 985.

Example 26. Microglia Activation Assay

Female C57Bl/6J mice (7 weeks old) were purchased from Jackson Laboratory (Maine, US). Animals were acclimated for a week at standard laboratory conditions (12 hrs light cycles) with free access to rodent chow and water. All procedures were in accordance with the National Institute of Health Guidelines for the care and Use of Laboratory Animals and were approved by IACUCC. The endotoxin Lipopolysaccharide (LPS) (E. coli 011:B4, cat #437627) was purchased from Calbiochem. LPS was dissolved in PBS buffer at a concentration of 0.05 mg/ml and stored in frozen aliquots. At the start of the study, mice received an intraperitoneal (i.p.) injection of LPS (0.5 mg/kg) for three consecutive days. Therapeutic treatment with VRT compounds was started together with the 2$^{nd}$ LPS administration and maintained throughout the study. Compound was dosed twice a day orally by gavage for a total of 4 doses. 24 h following the last LPS injection, and 2 hrs following the last VRT dose, animals were sacrificed by CO$_2$ asphyxiation.

Following sacrifice, brains were rapidly removed and fixed overnight in 10% neutral buffered formalin. Brains were then processed for routine histology in an automated processor (Shandon Excelsior ES, Thermo Scientific) and embedded in paraffin. IHC analysis was performed on 5 μm sections in the Ventana Benchmark System (Ventana Medical Systems Inc, Tucson, Ariz.) using prediluted antibodies to Iba1 (Wako chemical USA) at a dilution of 1:800. 3,3'-Diaminobenzidine (DAB) was used as a chromogenic substrate, and the slides were counterstained with haematoxylin.

Digital images were captured using the Aperio ScanScope Slide Scanner (Aperio Technologies, Vista, Calif.). Images were captured at 20× optical magnification, and analyzed using the software Definiens Developer XD. Algorithms were created to count activated microglial cells taking into account distinct morphological characteristics of activated cells when compared to resting microglia. Compound efficacy was calculated as percent decrease in number of activated microglia relative to vehicle control. For compound 271, a 39 percent decrease was observed at 10 mg/kg b.i.d. dosing. For compound 568 a range of 44 to 60 percent decrease in the number of activated microglia at 10 mg/kg b.i.d. dosing was observed in three separate experiments. For compound 410 a range of 23 to 33 percent decrease in the number of activated microglia at 5 mg/kg b.i.d. dosing was observed in three separate experiments.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound having the formula:

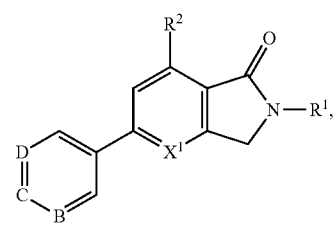

(II)

or a pharmaceutically acceptable salt thereof, wherein:
$X^1$ is CH or N;
$R^1$ is selected from a phenyl ring or a pyridinyl ring, wherein the phenyl ring or pyridinyl ring is optionally substituted with 1 or 2 independent occurrences of $R^{1a}$;
$R^{1a}$ is chloro, fluoro, $C_{1-6}$aliphatic, $C_{3-6}$cycloaliphatic, —CN, —C(O)$R^{1b}$, —C(O)N($R^{1b}$)$_2$, —C(O)O($R^{1b}$), heterocycloalkyl or —O$R^{1b}$, wherein each of said aliphatic, heterocycloalkyl, or cycloaliphatic is optionally substituted with up to 3 occurrences of $J^R$;
each $J^R$ is independently fluoro, oxo, —CN, —C(O)$R^{1b}$, —C(O)N($R^{1b}$)$_2$, —C(O)O($R^{1b}$), —N($R^{1b}$)$_2$, —N($R^{1b}$)C(O)$R^{1b}$, —O$R^{1b}$, or a 5-membered heteroaryl or heterocyclyl having up to 3 atoms selected from nitrogen, oxygen, or sulfur;
each $R^{1b}$ is independently selected from hydrogen, $C_{1-4}$ aliphatic, or $C_{3-6}$cycloaliphatic, wherein each of said aliphatic or cycloaliphatic is optionally substituted with up to 3 occurrences of F;
$R^2$ is hydrogen, F, Cl, CF$_3$, or CH$_3$;
B is N;
C is CR$^C$, wherein R$^C$ is hydrogen, fluoro, chloro, $C_{1-3}$aliphatic, CF$_3$, —OCF$_3$, or —OC$_{1-2}$aliphatic; and
D is CR$^D$, wherein R$^D$ is fluoro, chloro, $C_{1-3}$aliphatic, CF$_3$, —OCF$_3$, or —OC$_{1-2}$aliphatic.
2. The compound according to claim 1, or a pharmaceutically acceptable salt thereof, wherein $X^1$ is N.
3. The compound according to claim 2, or a pharmaceutically acceptable salt thereof, wherein $R^2$ is CH$_3$.
4. The compound according to claim 1, or a pharmaceutically acceptable salt thereof, wherein:
$R^1$ is

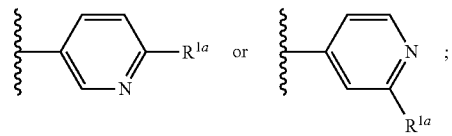

$R^2$ is CH$_3$;
$R^C$ is hydrogen, F, Cl, $C_{1-3}$aliphatic, (CH$_2$)$_{0-1}$CF$_3$, —OCF$_3$, or —OC$_{1-8}$aliphatic; and
$R^D$ is —C(O)NHC$_{1-8}$aliphatic.
5. The compound according to claim 4, or a pharmaceutically acceptable salt thereof, wherein $R^1$ is selected from

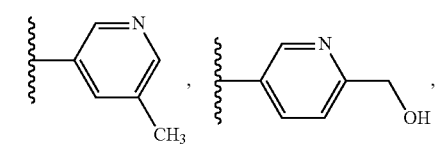

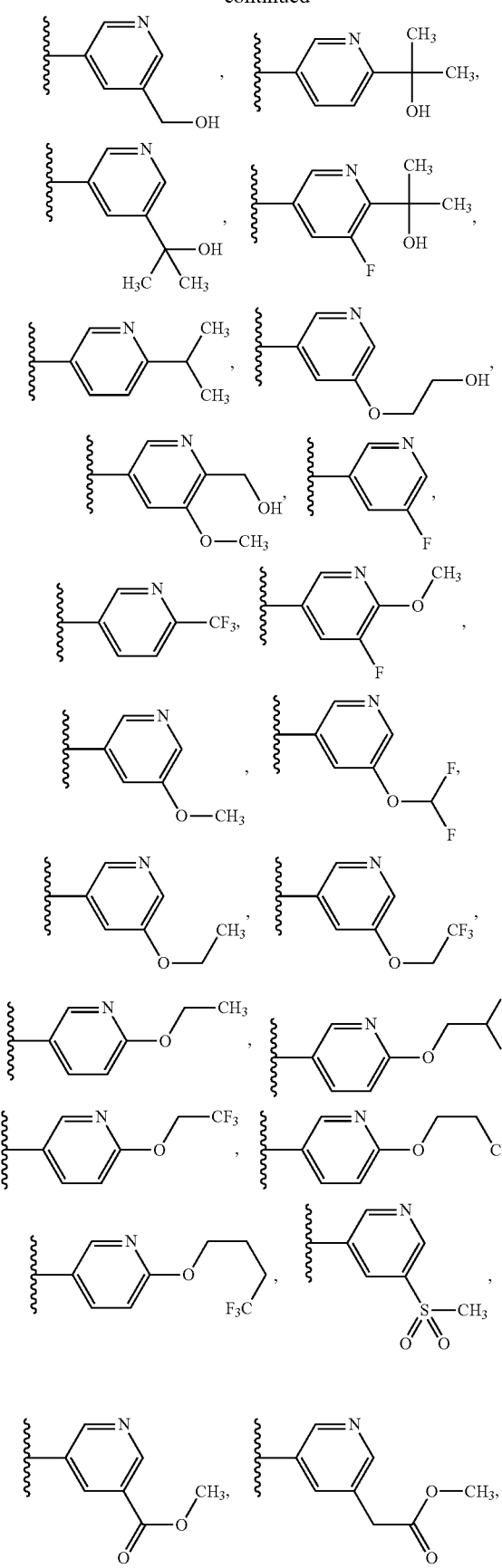
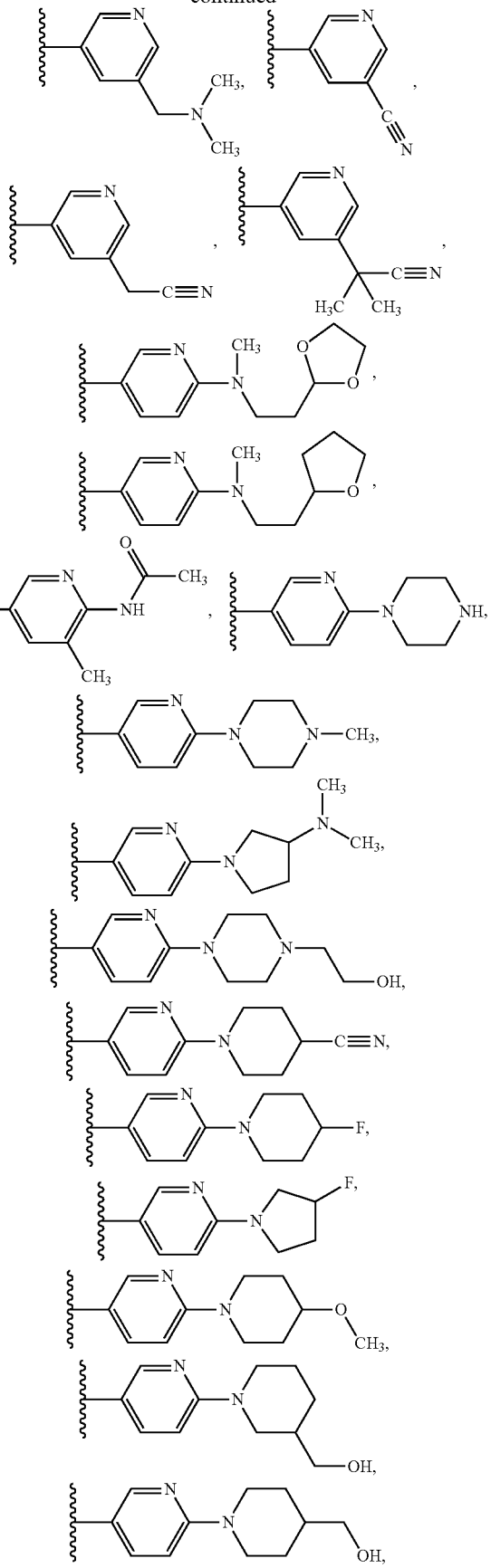

415
-continued
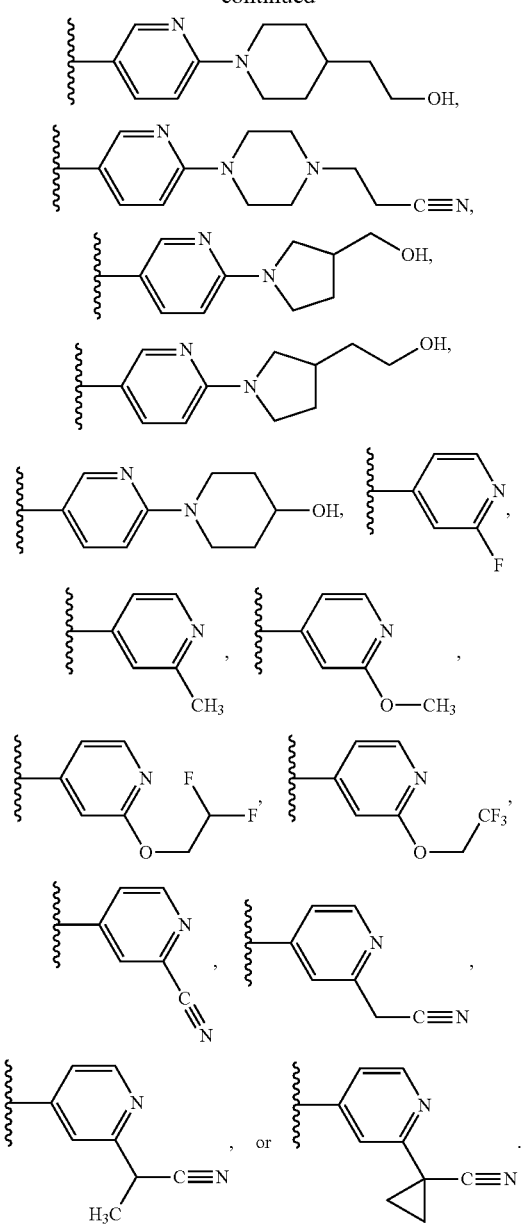
6. The compound according to claim 1, or a pharmaceutically acceptable salt thereof, wherein each of $R^C$ and $R^D$ is —OCH$_3$.
7. A compound selected from
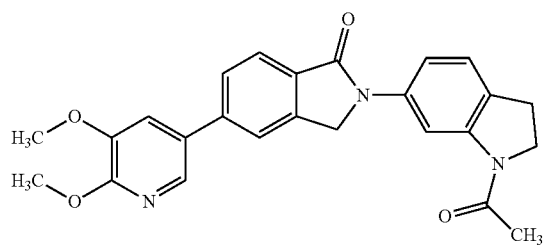
416
-continued
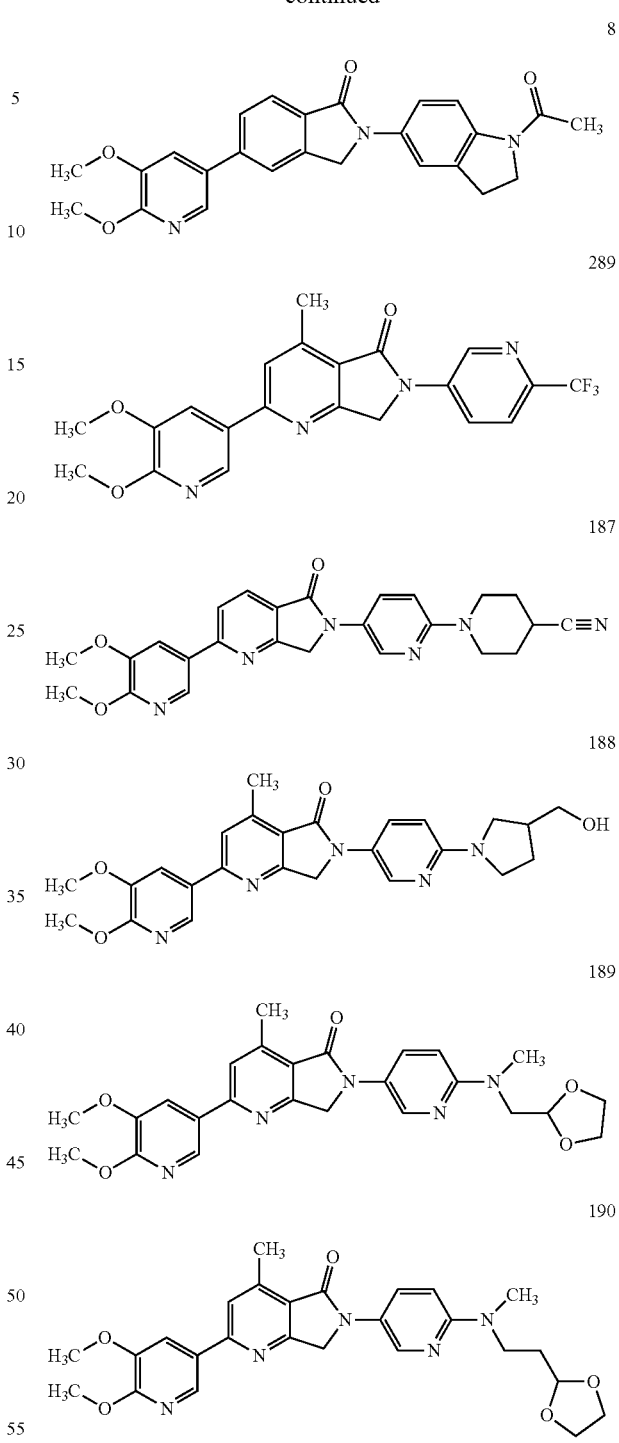
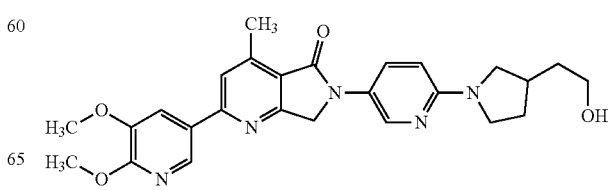

192
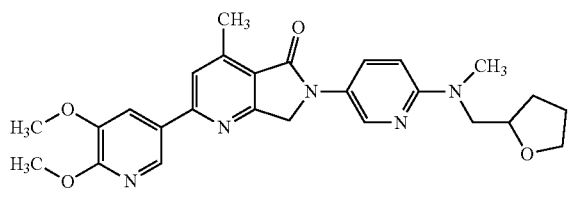
193
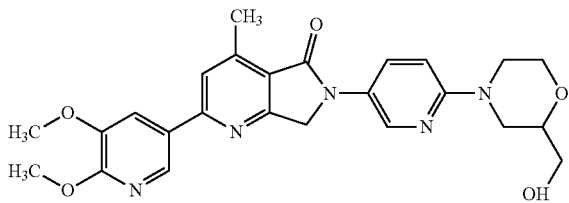
194
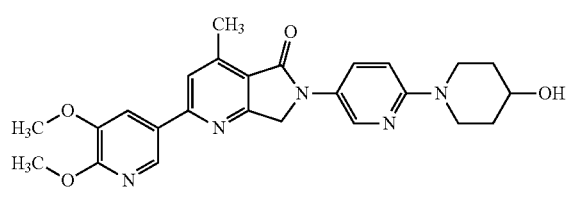
195
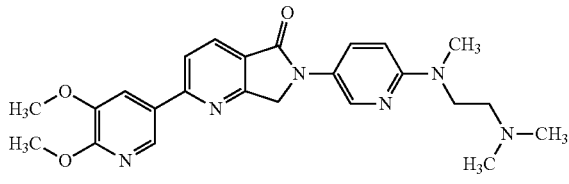
196
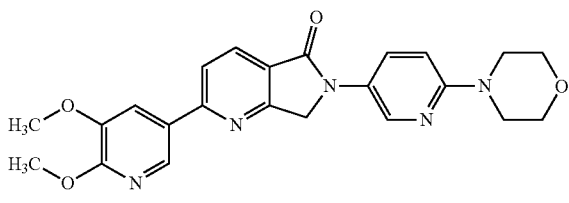
197
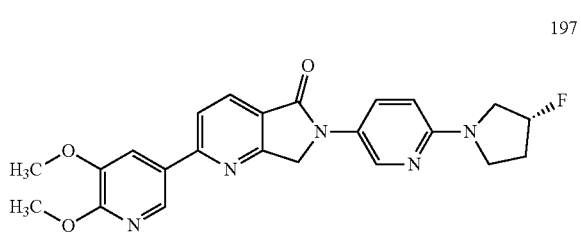
198
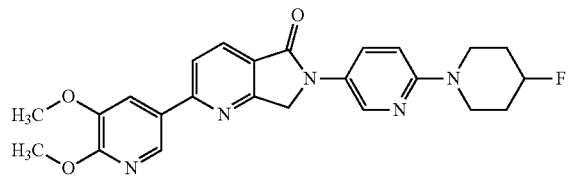
199
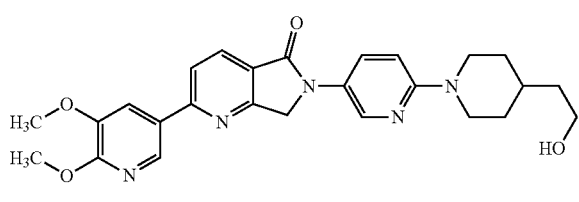
200
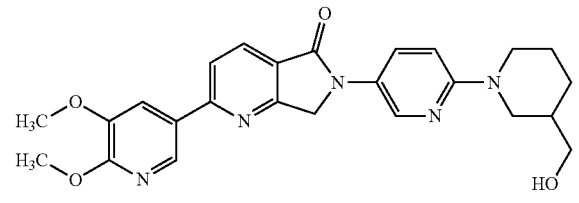
201
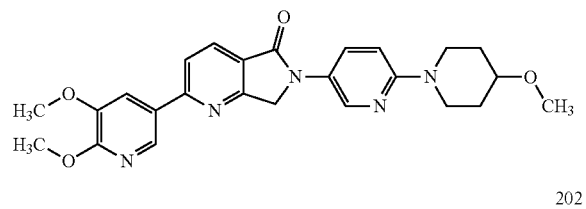
202
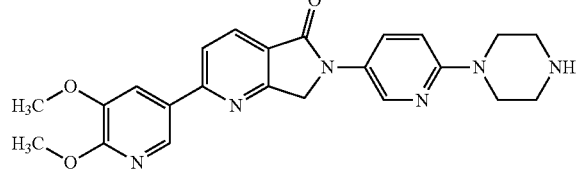
203
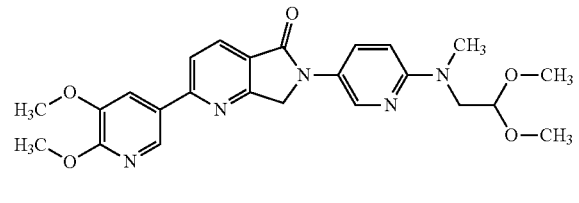
204
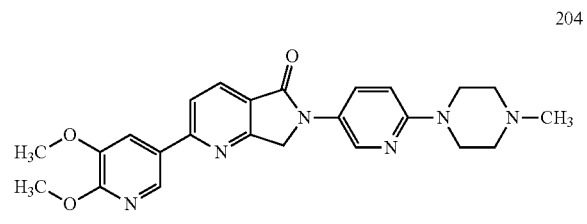
205
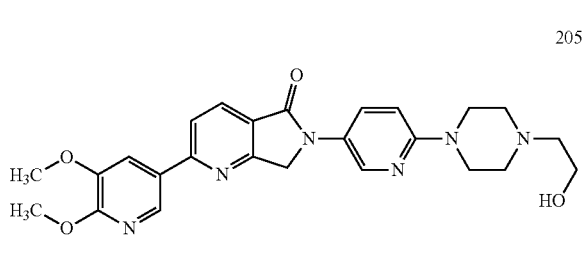

206
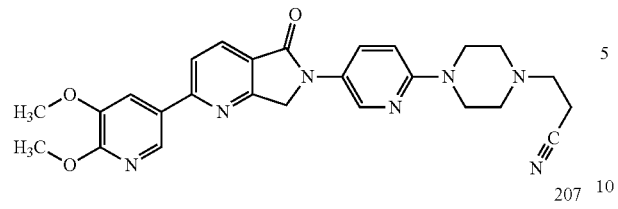
207
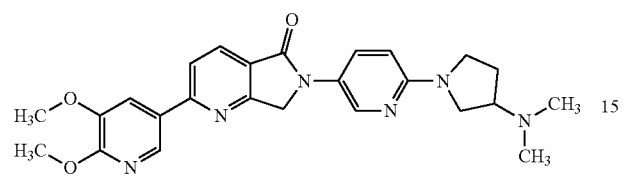
208
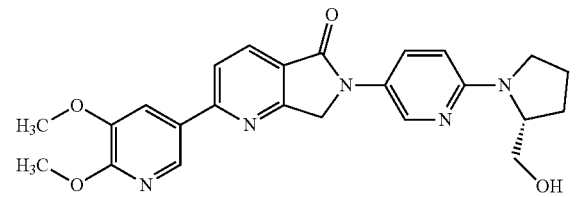
209
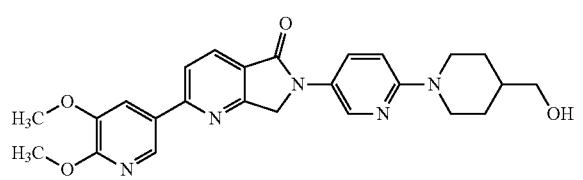
224
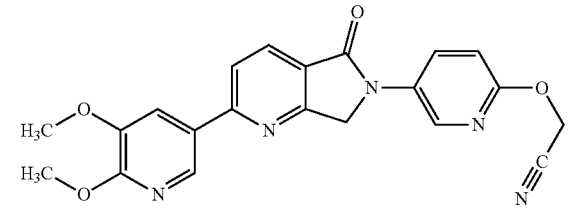
225
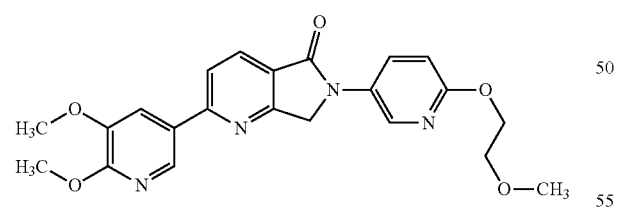
226
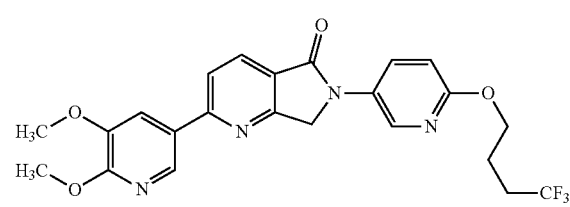
227
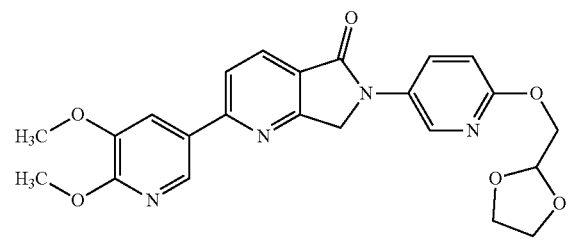
291
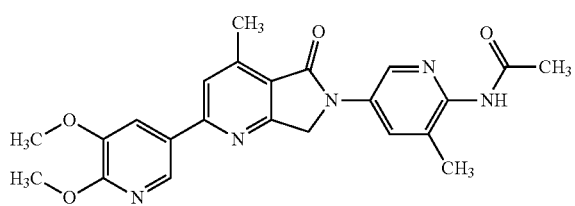
316
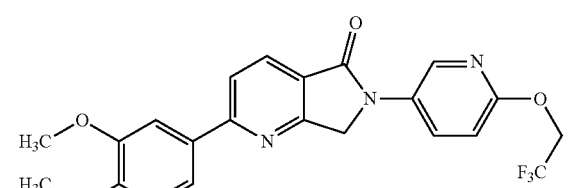
403
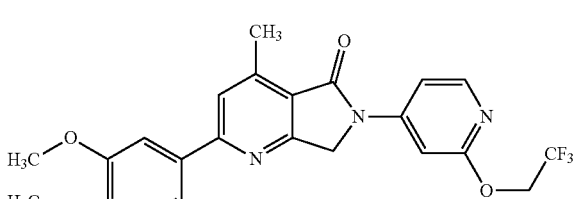
406
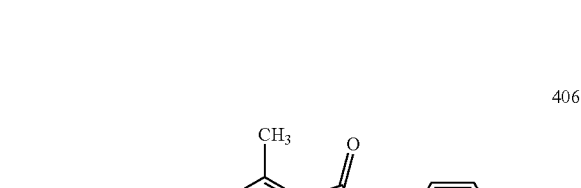
408
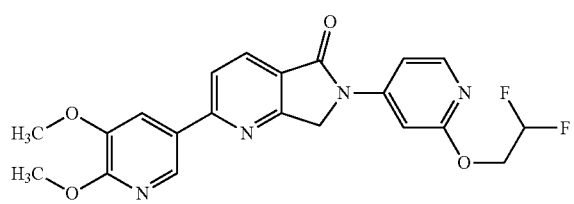
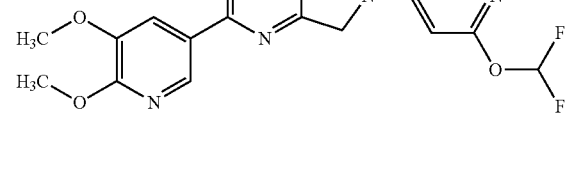

421
-continued

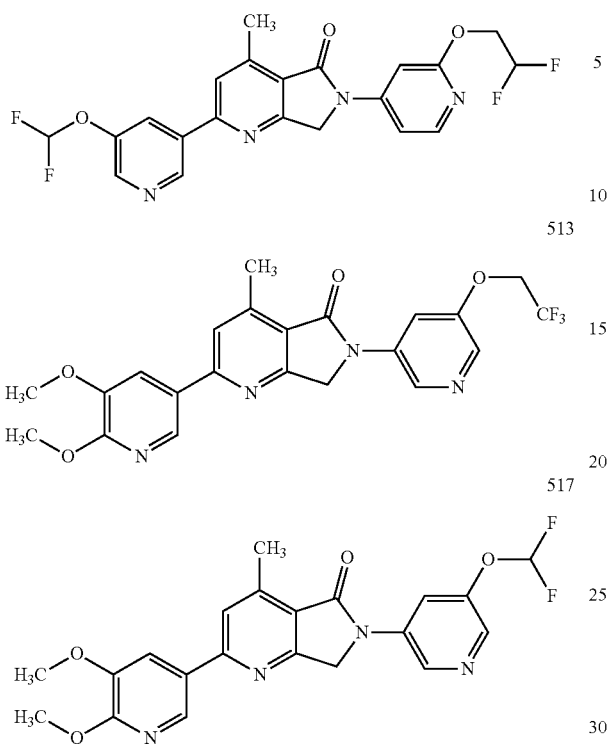

422
-continued

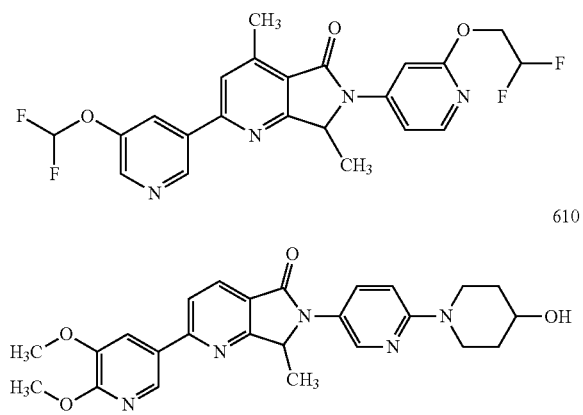

or a pharmaceutically acceptable salt thereof.

8. A pharmaceutical composition comprising a compound according to claim 1 and a pharmaceutically acceptable carrier, adjuvant, or vehicle.

9. A method of treating or lessening the severity of multiple sclerosis in a patient comprising the step of administering to said patient a compound or salt thereof according to claim 1, or a pharmaceutical composition thereof.

10. A method of inhibiting PI3K-gamma kinase activity in a biological sample comprising contacting said biological sample with a compound according to claim 1, or a composition comprising said compound.

* * * * *